(12) United States Patent
Cook et al.

(10) Patent No.: US 11,084,874 B2
(45) Date of Patent: Aug. 10, 2021

(54) IL-11 ANTIBODIES

(71) Applicants: Singapore Health Services Pte. Ltd., Singapore (SG); National University of Singapore, Singapore (SG); Enleofen Bio Ptd. Ltd., Singapore (SG)

(72) Inventors: Stuart Alexander Cook, Singapore (SG); Sebastian Schaefer, Singapore (SG)

(73) Assignees: Singapore Health Services PTE LTD., Singapore (SG); National University of Singapore, Singapore (SG); Boehringer Ingelheim International GmbH, Ingelheim Am Rhein (DE)

( * ) Notice: Subject to any disclaimer, the term of this patent is extended or adjusted under 35 U.S.C. 154(b) by 0 days.

(21) Appl. No.: 16/440,840

(22) Filed: Jun. 13, 2019

(65) Prior Publication Data

US 2020/0031918 A1 Jan. 30, 2020

(30) Foreign Application Priority Data

Jun. 13, 2018 (GB) .................................... 1809699

(51) Int. Cl.
*C07K 16/24* (2006.01)

(52) U.S. Cl.
CPC ...... *C07K 16/244* (2013.01); *C07K 2317/565* (2013.01)

(58) Field of Classification Search
None
See application file for complete search history.

(56) References Cited

FOREIGN PATENT DOCUMENTS

| RU | 2016125115 A | 12/2017 |
|---|---|---|
| RU | 2016151730 A | 6/2018 |
| WO | WO 2017/103108 A1 | 6/2017 |
| WO | WO 2018/109174 A2 | 6/2018 |

OTHER PUBLICATIONS

International Search Report and Written Opinion for Application No. PCT/EP2019/065598, dated Oct. 14, 2019.
International Preliminary Report on Patentability for Application No. PCT/EP2019/065598, dated Dec. 24, 2020.
[No Author Listed] Human IL-11 Antibody. Monoclonal Mouse IgG2A. Clone No. 22626. Cat. No. MAB218. R& D Systems: A Biotechne Brand. Rev. Feb. 7, 2018. 1 page.
Affo et al., The Role of Cancer-Associated Fibroblasts and Fibrosis in Liver Cancer. Annu Rev Pathol. Jan. 24, 2017;12:153-186. Author manuscript, 39 pgs.
Angal et al., A Single Amino acid Substitution Abolishes the Heterogeneity of Chimeric Mouse/Human (IgG4) Antibody. Molecular Immunology. 1993;30(1):105-108.
Arunkumar et al., Science Behind Cisplatin-induced Nephrotoxicity in Humans: A Clinical Study. Asian Pacific journal of Tropical Biomedicine. 2012;2(8):640-644. Epub Aug. 28, 2012.
Baena et al., Fructose, but not glucose, impairs insulin signaling in the three major insulin-sensitive tissues. Scientific Reports. May 2016;6(26149):1-15. Epub May 19, 2016.
Bamba et al., Regulation of IL-11 expression in intestinal myofibroblasts: role of c-Jun AP-1- and MAPK-dependent pathways. American Journal of Physiology Gastrointestinal and Liver Physiology. May 21, 2003;285:529-538.
Boersma et al., Bispecific Designed Ankyrin Repeat Proteins (DARPins) Targeting Epidermal Growth Factor Receptor Inhibit A431 Cell Proliferation and Receptor Recycling. Journal of Biological Chemistry. Dec. 2, 2011;286(48):41273-41285.
Bonner-Weir et al., Islets in Type 2 Diabetes: In Honor of Dr. Robert C. Turner. Perspectives in Diabetes. Nov. 2008;57(11):2899-2904.
Brinkmann et al., The Making of Bispecific Antibodies. mAbs. 2017;9(2):182-212.
Buck et al., Detection of S-phase cell cycle progression using 5-ethynyl-2′-deoxyuridine incorporation with click chemistry, an alternative to using 5-bromo-2?-deoxyuridine antibodies. BioTechniques. Jun. 2008;44(7):927-929.
Caballero et al., Anti-sphingosine-1-phosphate monoclonal antibodies inhibit angiogenesis and sub-retinal fibrosis in a murine model of laser-induced choroidal neovascularization. Exp Eye Res. Mar. 2009;88(3):367-77. doi: 10.1016/j.exer.2008.07.012. Epub Aug. 6, 2008.
Chandrudu et al., Chemical Methods for Peptide and Protein Production. Molecules. Apr. 12, 2013;18:4373-4388.
Chen et al., Fusion Protein Linkers: Property, Design and Functionality. Adv Drug Deliv Rev. Oct. 15, 2013;65(10):1357-1369. Author Manuscript, 32 pages.
Chen et al., IL-11 receptor alpha in the pathogenesis of IL-13-induced inflammation and remodeling. J Immunol. Feb. 15, 2005;174(4):2305-13.
Cheng et al., Cross-reactivity of antibody against SARS-coronavirus nucleocapsid protein with IL-11. Biochem Biophys Res Commun. Dec. 23, 2005;338(3):1654-60. Epub Oct. 25, 2005.
Chothia et al., Canonical Structures for the Hypervariable Regions of Immunoglobulins. Journal of Molecular Biology. 1987;196:901-917.
Ciliberto et al. Cytokine Inhibitors: Chapter 8. Marcel Dekker, Inc. 2001.
Concepcion et al., Label-free detection of biomolecular interactions using BioLayer interferometry for kinetic characterization. Comb Chem High Throughput Screen. Sep. 2009;12(8):791-800. doi: 10.2174/138620709789104915.
Curtis et al., Recombinant Soluble interleukin-11 (IL-11) Receptor Alpha-Chain Can Act as an IL-11 Antagonist. Blood. Dec. 1, 1997;90(11):4403-12.
Daba et al., Drug-induced pulmonary fibrosis. Saudi Med J. 2004;25(6):700-706.

(Continued)

*Primary Examiner* — Gary B Nickol
*Assistant Examiner* — Jegatheesan Seharaseyon
(74) *Attorney, Agent, or Firm* — Wolf, Greenfield & Sacks, P.C.

(57) ABSTRACT

Provided are antigen-binding molecules capable of binding to IL-11, and methods of medical treatment and prophylaxis using the same.

6 Claims, 99 Drawing Sheets

Specification includes a Sequence Listing.

(56) References Cited

OTHER PUBLICATIONS

Davies et al., Human IgG4: a structural perspective. Immunological Reviews. 2015;268:139-159.

Deguchi et al., Generation of and characterization of anti-IL-11 antibodies using newly established I11 1-deficient mice. Biochem Biophys Res Commun. Oct. 28, 2018;505(2):453-459. doi: 10.1016/j.bbrc.2018.09.128. Epub Sep. 26, 2018.

Dotti et al., Design and Development of Therapies using Chimeric Antigen Receptor-Expressing T cells. Immunol Rev. Jan. 2014;257(1)107-26, Author Manuscript. 35 pages.

Du et al., Interleukin-11: review of molecular, cell biology, and clinical use. Blood. Jun. 1, 1997;89(11):3897-908.

Emanuel et al., A fibronectin scaffold approach to bispecific inhibitors of epidermal growth factor receptor and insulin-like growth factor-I receptor. mAbs. 2011;3(1):38-48.

Ernst et al., STAT3 and STAT1 mediate IL-11-dependent and inflammation-associated gastric tumorigenesis in gp130 receptor mutant mice. The Journal of Clinical Investigation. May 2008;118(5):1727-1738.

Fearon et al., Definition and classification of cancer cachexia: an international consensus. Lancet Oncol. May 2011;12:489-495.

Fearon et al., Myopenia—a new universal term for muscle wasting. Journal of Cachexia, Sarcopenia and Muscle. 2011;2:1-3.

Frank et al., High-performance signal peptide prediction based on sequence alignment techniques. Bioinformatics. 2008;24(19):2172-2176.

French, How to make bispecific antibodies. Methods Mol Med. 2000;40:333-339.

Frenzel et al., Expression of recombinant antibodies. Frontiers in Immunology. Jul. 29, 2013;4(217):1-20.

Fulcher et al., Carboxyfluorescein succinimidyl ester-based proliferative assays for assessment of T cell function in the diagnostic laboratory. Immunology and Cell Biology. 1999;77:559-564.

Garbers et al., Interleukin-6 and interleukin-11: same same but different. Biol Chem. Sep. 2013;394(9):1145-61. doi: 10.1515/hsz-2013-0166.

Gräslund et al., Structural Genomics Consortium, Protein production and purification. Nat Methods. Feb. 2008;5(2):135-146, Author Manuscript. 25 pages.

Ha et al., Immunoglobulin Fc Heterodimer Platform Technology: from Design to Applications in Therapeutic Antibodies and Proteins. Frontiers in Immunology. Oct. 6, 2016;7(394):1-16.

Haverick et al., Separation of mAbs molecular variants by analytical hydrophobic interaction chromatography HPLC. mAbs. 2014;6(4):852-858. Epub Apr. 1, 2014.

Haynes et al., Redirecting mouse CTL against colon carcinoma: superior signaling efficacy of single-chain variable domain chimeras containing TCR-zeta vs Fc epsilon RI-gamma. J Immunol. Jan. 1, 2001;166(1):182-7. doi: 10.4049/jimmunol.166.1.182.

Hearty et al., Measuring antibody-antigen binding kinetics using surface plasmon resonance. Methods Mol Biol. 2012;907:411-42. doi: 10.1007/978-1-61779-974-7_24.

Hilton et al., Cloning of a Murine IL-11 Receptor Alpha-Chain; Requirement for gp130 for High Affinity Binding and Signal Transduction. EMBO J. Oct. 17, 1994;13(20):4765-75.

Hornbeck, Enzyme-Linked Immunosorbent Assays. Curr Protoc Immunol. 2015;110:2.1.1-2.1.23.

Hornig et al., Chapter 40: Production of bispecific antibodies: diabodies and tandem scFv. Methods Mol Biol. 2012;907:713-727. doi:10.1007/978-1-61779-974-7_40.

Hunter et al., IL-6 as a keystone cytokine in health and disease. Nature Immunology. May 2015;16(5)448-457. Epub Apr. 21, 2015.

Hurrell, Monoclonal Hybridoma Antibodies: Techniques and Applications. CRC Press. 1982.

Jansen et al., The Ascending Pathophysiology of Cholestatic Liver Disease. Hepatology. Feb. 2017;65(2):722-738.

Jerabek-Willemsen et al., Molecular interaction studies using microscale thermophoresis. Assay and Drug Development Technologies. Aug. 2011;9(4):342-353.

Johnstone et al., Emerging roles for IL-11 signaling in cancer development and progression: Focus on breast cancer. Cytokine Growth Factor Rev. Oct. 2015;26(5):489-98. doi: 10.1016/j.cytogfr.2015.07.015. Epub Jul. 14, 2015.

Karpovich et al., Expression and Function of interleukin-11 and Its Receptor Alpha in the Human Endometrium. Mol Hum Reprod. Feb. 2003;9(2):75-80. doi: 10.1093/molehr/gag012.

Katoh et al., MAFFT Multiple Sequence Alignment Software Version 7: Improvements in Performance and Usability. Molecular Biology and Evolution. Apr. 2013;30(4):772-780. Epub Jan. 16, 2013.

Khaw et al., Modulation of wound healing after glaucoma surgery. Curr Opin Ophthalmol. Apr. 2001;12(2):143-8.

Khoury et al., Drug Induced Liver Injury: Review With a Focus on Genetic Factors, Tissue Diagnosis, and Treatment Options. J Clin Transl Hepatol. Jun. 28, 2015;3(2):99-108. doi: 10.14218/JCTH.2015.00007.

Kunert et al., Advances in recombinant antibody manufacturing. Applied Microbiology and Biotechnology. 2016;100:3451-3461. Epub Mar. 3, 2016.

Lacob et al., Investigating monoclonal antibody aggregation using a combination of H/DX-MS and other biophysical measurements. J Pharm Sci., Dec. 2013;102(12):4315-4329, Author Manuscript, 25 pages.

Lad et al., High-Throughput Kinetic Screening of Hybridomas to Identify High-Affinity Antibodies Using Bio-Layer Interferometry. Journal of Biomolecular Screening. 2015;20(4):498-507.

Lassman et al., Kalign—an accurate and fast multiple sequence alignment algorithm. BMC Bioinformatics. Dec. 2005;6(298) https://doi.org/10.1186/1471-2105, 9 pages.

Lokau et al., Proteolytic Cleavage Governs Interleukin-11 Trans-signaling. Cell Rep. 2016; 14(7): 1761-1773.

Machado et al., Mouse Models of Diet-Induced Nonalcoholic Steatohepatitis Reproduce the Heterogeneity of the Human Disease. PLoS ONE. May 27, 2015;10(5)e0127991(1-16).

Marks et al., By-passing immunization: building high affinity human antibodies by chain shuffling. Biotechnology (N Y). 1992;10(7):779-783.

Martineau P., Affinity Measurements by Competition ELISA. Antibody Engineering. 2010;1:657-665.

Mead et al., Evaluation of Anti-TGF- 2 Antibody as a New Postoperative Anti-scarring Agent in Glaucoma Surgery. IOVS. Aug. 2003;44(8):3394-3401.

Menzen et al., High-Throughput Melting-Temperature Analysis of a Monoclonal Antibody by Differential Scanning Fluorimetry in the Presence of Surfactants. Journal of Pharmaceutical Sciences. Feb. 2013;102(2):415-428.

Morrison et al., Chimeric human antibody molecules: mouse antigen-binding domains with human constant region domains. Proc Natl Acad Sci U S A. 1984;81(21):6851-6855.

Nandurkar et al., The Human IL-11 Receptor Requires gp130 for Signalling: Demonstration by Molecular Cloning of the Receptor. Oncogene. Feb. 1, 1996;12(3):585-93.

Neuberger et al. Antibody Engineering. 8th International Biotechnology Symposium Part 2. 1988:792-799.

Notredame et al., T-Coffee: A Novel Method for Fast and Accurate Multiple Sequence Alignment. Journal of Molecular Biology. 2000;302:205-217.

Obana et al., Therapeutic activation of signal transducer and activator of transcription 3 by interleukin-11 ameliorates cardiac fibrosis after myocardial infarction. Circulation. Feb. 9, 2010;121(5):684-91. doi: 10.1161/CIRCULATIONAHA.109.893677. Epub Jan. 25, 2010.

Obana et al., Therapeutic administration of IL-11 exhibits the postconditioning effects against ischemia-reperfusion injury via STAT3 in the heart. Am J Physiol Heart Circ Physiol. Sep. 1, 2012;303(5):H569-77. doi: 10.1152/ajpheart.00060.2012.

Oh et al., Cisplatin-induced Kidney Dysfunction and Perspectives on Improving Treatment Strategies. Electrolyte Blood Press. Dec. 2014;12(2):55-65. Epub Dec. 31, 2014.

Park et al., Monoclonal antibody therapy. Advances in Protein Chemistry. 2001;56:369-421. https://doi.org/10.1016/S0065-3233(01)56010-6.

(56) References Cited

OTHER PUBLICATIONS

Parslow et al., Antibody-Drug Conjugates for Cancer Therapy. Biomedicines. Jul. 11, 2016;4(14): 17 pgs.
Petersen et al., SignalP 4.0: discriminating signal peptides from transmembrane regions. Nat Methods. Sep. 29, 2011;8(10):785-6. doi: 10.1038/nmeth.1701.
Pflanz et al., A Fusion Protein of interleukin-11 and Soluble interleukin-11 Receptor Acts as a Superagonist on Cells Expressing gp130. FEBS Lett. Apr. 30, 1999;450(1-2):117-22. doi: 10.1016/s0014-5793(99)00477-9.
Pollock et al., Diagnostic considerations for cholestatic liver disease. Journal of Gastroenterology and Hepatology. 2017;32:1303-1309.
Putoczki et al., More Than a Sidekick: The IL-6 Family Cytokine IL-11 Links Inflammation to Cancer. J Leukoc Biol. Dec. 2010;88(6):1109-17. doi: 10.1189/jlb.0410226.
Retter et al., VBASE2, an integrative V gene database. Nucleic Acids Research. 2005;33:D671-D674.
Reverdatto et al., Peptide Aptamers: Development and Applications. Curr Top Med Chem. 2015;15(12):1082-1101. Author Manuscript, 38 pages.
Rich et al., Extracting kinetic rate constants from surface plasmon resonance array systems. Analytical Biochemistry. 2008;373(1):112-120. Epub Aug. 19, 2007.
Rowe et al., Hepatocyte-derived Snail1 propagates liver fibrosis progression. Mol Cell Biol. Jun. 2011;31(12):2392-403. doi: 10.1128/MCB.01218-10.
Salic et al., A chemical method for fast and sensitive detection of DNA synthesis in vivo. PNAS. Feb. 19, 2008;105(7):2415-2420.
Schaefer et al., IL-11 is a crucial determinant of cardiovascular fibrosis. Nature. 2017; 552(7683): 110-115.
Schroeder et al., Structure and Function of Immunoglobulins. J Allergy Clin Immunol. Feb. 2010;125(202):S41-s52. Author Manuscript, 24 pages.
Seet et al., Validation of the Glaucoma Filtration Surgical Mouse Model for Antifibrotic Drug Evaluation. Mol Med. 2011;17(5-6):557-567. Epub Jan. 11, 2011.
Segal et al., Production of bispecific antibodies. Curr Protoc Immunol. 2001;Chapter 2:. doi:10.1002/0471142735.im0213s14.
Sittampalam et al., Assay Guidance Manual, Eli Lilly & Company and the National Center for Advancing Translational Sciences. 2004 (last updated Jul. 1, 2016), 10 pages.
Szendroi et al., Polarization colours of collagen fibres: a sign of collagen production activity in fibrotic processes. Acta Morphol Hung. 1984;32(1):47-55.
Söding J., Protein homology detection by HMM-HMM comparison. Bioinformatics. 2005;21(7):951-960. Epub Nov. 5, 2004.
Tang et al., Transforming Growth Factor-b Stimulates Interleukin-11 Transcription via Complex Activating Protein-1-dependent Pathways. J. Biol. Chem. 1998; 273(10): 5506-5513.
Tao et al., Cancer-associated fibroblasts treated with cisplatin facilitates chemoresistance of lung adenocarcinoma through IL-11/IL-11R/STAT3 signaling pathway. Sci Rep. Dec. 6, 2016;6:38408. doi: 10.1038/srep38408. 24 pages.
Tarnavski et al., Mouse cardiac surgery: comprehensive techniques for the generation of mouse models of human diseases and their application for genomic studies. Physiol Genomics. 2004;16:349-360. Epub Dec. 16, 2003.
Tisdale M.J., Cachexia in Cancer Patients. Nature. Nov. 2002;2:862-871.
Toda et al., Polarized in vivo expression of IL-11 and IL-17 between acute and chronic skin lesions. J Allergy Clin Immunol. Apr. 2003;111(4):875-81.
Trepicchio et al., Protective effect of rhIL-11 in a murine model of acetaminophen-induced hepatotoxicity. Toxicol Pathol. Mar.-Apr. 2001;29(2):242-9.
Unverdorben et al., Pharmacokinetic properties of IgG and various Fc fusion proteins in mice. MAbs. 2016;8(1):120-128.
Wong et al., Endogenous IL-11 is pro-inflammatory in acute methylated bovine serum albumin/interleukin-1-induced (mBSA/IL-1)arthritis. Cytokine. Jan. 21, 2005;29(2):72-6.
Wong et al., Matrix Metalloproteinase Inhibition Modulates Postoperative Scarring after Experimental Glaucoma Filtration Surgery. Investigative Ophthalmology & Visual Science. Mar. 2003;44(3):1097-1103.
Wong et al., Prolonged Antiscarring Effects of Ilomastat and MMC after Experimental Glaucoma Filtration Surgery. Investigative Ophthalmology & Visual Science. Jun. 2005;46(6):2018-2022.
Wynn et al., Mechanisms of fibrosis: therapeutic translation for fibrotic disease. Nat Med. 2012;18(7):1028-1040.
Wynn, Cellular and molecular mechanisms of fibrosis. J Pathol. Jan. 2008;214(2):199-210. Author Manuscript.
Xu et al., The role of IL-11 in immunity and cancer. Cancer Letters. 2016;373:156-163.
Yashiro et al., Transforming growth factor-beta stimulates interleukin-11 production by human periodontal ligament and gingival fibroblasts. J Clin Periodontol. Mar. 2006;33(3):165-71.
Zemella et al., Cell-Free Protein Synthesis: Pros and Cons of Prokaryotic and Eukaryotic Systems. ChemBioChem. 2015;16:2420-2431.
Zhang et al., IL-11 in multiple sclerosis. Oncotarget. Oct. 7, 2015;6(32):32297-32298.
Zhou et al., Aptamers as targeted therapeutics: current potential and challenges. Nat Rev Drug Discov. Mar. 2017;16(3):181-202. Author Manuscript, 52 pages.
Zhu et al., IL-11 Attenuates Liver Ischemia/Reperfusion Injury (IRI) through STAT3 Signaling Pathway in Mice. PLoS One. May 6, 2015;10(5):e0126296. doi: 10.1371/journal.pone.0126296.
Zola, Monoclonal Antibodies: A Manual of Techniques. CRC Press. 1988.

| Strategy No | Round 1 | Round 2 | Round 3 | biotinylated | No first hits |
|---|---|---|---|---|---|
| 1 | h-IL11 | m-IL11 | h-IL11 | Yes | 1 |
| 2 | h-IL11 | h-IL11 | h-IL11 | Yes | - |
| 3 | h-IL11 | h-IL11 | m-IL11 | Yes | - |
| 4 | m-IL11 | m-IL11 | m-IL11 | Yes | 5 |
| 5 | m-IL11 | h-IL11 | m-IL11 | Yes | - |
| 6 | m-IL11 | h-IL11 | h-IL11 | Yes | - |
| 7 | h-IL11 | h-IL11 | h-IL11 | No | 11 |
| 8 | h-IL11 | m-IL11 | h-IL11 | No | 14 |
| 9 | h-IL11 | m-IL11 | h-IL11 | Round 2 | 17 |
| 10 | h-IL11 | h-IL11 | m-IL11 | No | 19 |
| 11 | h-IL11 | h-IL11 | m-IL11 | Round 3 | 5 |
| 12 | m-IL11 | h-IL11 | m-IL11 | Round 3 | 10 |
| 13 | m-IL11 | m-IL11 | h-IL11 | Round 1, 2 | 6 |
| 14 | m-IL11 | m-IL11 | m-IL11 | No | 36 |
| 15 | m-IL11 | h-IL11 | m-IL11 | No | 15 |
| 16 | m-IL11 | m-IL11 | h-IL11 | No | 36 |

Figure 1

| Identical Sequence | Clone ID | Fc-part | Identical Sequence | Clone ID | Fc-part |
|---|---|---|---|---|---|
| 1 | YU33-A2 | hIgG1-Fc (IgG) | 20 | YU45-H8 | hIgG1-Fc |
| 2 | YU33-B3 | hIgG1-Fc (IgG) | 21 | YU45-F9 | hIgG1-Fc |
|   | YU33-H3 | hIgG1-Fc (IgG) | 22 | YU45-H10 | hIgG1-Fc |
|   | YU33-B4 | hIgG1-Fc (IgG) | 23 | YU46-A10 | hIgG1-Fc |
| 3 | YU45-G2 | hIgG1-Fc | 24 | YU45-F2 | hIgG1-Fc |
|   | YU45-A3 | hIgG1-Fc | 25 | YU45-H3 | hIgG1-Fc |
| 4 | YU33-E3 | hIgG1-Fc (IgG) | 26 | YU45-A1 | hIgG1-Fc |
| 5 | YU33-E6 | hIgG1-Fc (IgG) | 27 | YU45-A8 | hIgG1-Fc |
| 6 | YU45-C11 | hIgG1-Fc |   | YU45-C6 | hIgG1-Fc |
|   | YU45-A10 | hIgG1-Fc | 28 | YU45-B5 | hIgG1-Fc |
| 7 | YU45-D11 | hIgG1-Fc |   | YU45-A4 | hIgG1-Fc |
|   | YU45-F11 | hIgG1-Fc | 29 | YU45-C3 | hIgG1-Fc |
| 8 | YU45-E11 | hIgG1-Fc |   | YU45-A6 | hIgG1-Fc |
|   | YU45-E12 | hIgG1-Fc | 30 | YU45-D1 | hIgG1-Fc |
| 9 | YU45-H11 | hIgG1-Fc | 31 | YU45-D9 | hIgG1-Fc |
|   | YU45-D12 | hIgG1-Fc |   | YU45-D3 | hIgG1-Fc |
| 10 | YU45-A12 | hIgG1-Fc | 32 | YU45-E5 | hIgG1-Fc |
|   | YU45-G10 | hIgG1-Fc | 33 | YU45-G7 | hIgG1-Fc |
| 11 | YU45-G1 | hIgG1-Fc | 34 | YU45-B4 | hIgG1-Fc |
| 12 | YU45-B2 | hIgG1-Fc | 35 | YU45-H4 | hIgG1-Fc |
|   | YU45-C2 | hIgG1-Fc | 36 | YU45-B6 | hIgG1-Fc |
| 13 | YU45-A7 | hIgG1-Fc | 37 | YU45-D6 | hIgG1-Fc |
|   | YU45-B10 | hIgG1-Fc | 38 | YU45-E7 | hIgG1-Fc |
|   | YU45-D2 | hIgG1-Fc | 39 | YU45-F5 | hIgG1-Fc |
|   | YU45-H2 | hIgG1-Fc | 40 | YU45-H7 | hIgG1-Fc |
|   | YU45-C7 | hIgG1-Fc |   | YU46-B9 | hIgG1-Fc |
|   | YU45-F3 | hIgG1-Fc | 41 | YU45-B8 | hIgG1-Fc |
|   | YU45-C9 | hIgG1-Fc | 42 | YU45-C1 | hIgG1-Fc |
|   | YU45-E1 | hIgG1-Fc | 43 | YU46-G1 | hIgG1-Fc |
| 14 | YU45-E9 | hIgG1-Fc | 44 | YU46-A2 | hIgG1-Fc |
|   | YU45-C10 | hIgG1-Fc | 45 | YU46-A8 | hIgG1-Fc |
|   | YU45-G3 | hIgG1-Fc | 46 | YU46-B2 | hIgG1-Fc |
|   | YU45-H9 | hIgG1-Fc | 47 | YU46-B6 | hIgG1-Fc |
|   | YU45-C5 | hIgG1-Fc | 48 | YU46-C1 | hIgG1-Fc |
|   | YU45-A2 | hIgG1-Fc | 49 | YU46-D7 | hIgG1-Fc |
|   | YU45-A5 | hIgG1-Fc | 50 | YU46-E3 | hIgG1-Fc |
| 15 | YU45-B3 | hIgG1-Fc | 51 | YU46-E7 | hIgG1-Fc |
| 16 | YU45-E3 | hIgG1-Fc | 52 | YU46-H8 | hIgG1-Fc |
| 17 | YU45-C8 | hIgG1-Fc | 53 | YU46-G9 | hIgG1-Fc |
|   | YU45-E8 | hIgG1-Fc | 54 | YU46-G8 | hIgG1-Fc |
| 18 | YU45-F6 | hIgG1-Fc | 55 | YU46-B7 | hIgG1-Fc |
| 19 | YU45-G8 | hIgG1-Fc | 56 | YU46-D3 | hIgG1-Fc |
|   | YU45-H6 | hIgG1-Fc |   |   |   |

Figure 3

| Antibody Candidate | Human IL11 Activated fibroblasts (norm.) | Mouse IL11 Activated atrial fibroblasts (norm.) | Trans IL11 Activated fibroblasts (norm.) | Mouse IL11 Activated dermal fibroblasts (norm.) |
|---|---|---|---|---|
| - | 1.91 | 2.16 | 2.13 | 1.95 |
| Industry Standard | | | | |
| 1 | 1.91 | 1.76 | 2.16 | 1.98 |
| 2 | 1.95 | 1.83 | 2.09 | 1.91 |
| 3 | | | | 1.84 |
| 4 | 1.85 | 1.85 | 2.13 | 1.83 |
| 5 | 1.78 | 1.73 | 2.13 | 1.82 |
| 6 | | | 2.29 | |
| 7 | | 1.79 | 2.19 | 1.93 |
| 8 | | 1.83 | 2.05 | 1.85 |
| 9 | | | 1.71 | 1.54 |
| 10 | 1.67 | 1.75 | | 1.86 |
| 11 | | | 2.51 | |
| 12 | | 1.83 | 1.83 | 1.94 |
| 13 | 1.76 | 1.91 | 1.95 | 2.09 |
| 14 | | | 2.04 | |
| 15 | 1.57 | | 1.95 | |
| 16 | | 1.59 | | 1.76 |
| 17 | 1.55 | 1.70 | | 1.76 |
| 18 | | | 1.95 | |
| 19 | | | 1.77 | 1.53 |
| 20 | 1.65 | 1.79 | | 1.76 |
| 21 | | 1.83 | 2.06 | 1.83 |
| 22 | | | 2.02 | 1.56 |
| 23 | 1.69 | | 2.27 | 1.72 |
| 24 | | 1.87 | | 1.89 |
| 25 | | | 2.04 | |
| 26 | 1.68 | 1.92 | 2.50 | 1.94 |
| 27 | | | 2.15 | |
| 28 | | 2.19 | 2.12 | 1.79 |
| 29 | 1.65 | | 2.10 | 1.81 |
| 30 | 1.63 | 1.89 | 1.86 | 1.89 |
| 31 | | | 1.75 | |
| 32 | 1.68 | 2.03 | 2.00 | 1.89 |
| 33 | | 1.86 | 1.94 | 1.79 |
| 34 | 1.59 | 1.88 | 1.94 | 1.83 |
| 35 | 1.76 | 1.86 | 2.06 | 1.73 |
| 36 | | | 1.99 | |
| 37 | 1.61 | 1.92 | 1.82 | 1.75 |
| 38 | 1.54 | 1.91 | 1.96 | 1.91 |
| 39 | | | | 1.82 |
| 40 | | 1.79 | 1.97 | 1.85 |
| 41 | 1.57 | 1.79 | 1.87 | 1.89 |
| 42 | | | 2.04 | |
| 43 | 1.54 | 1.76 | 2.06 | 1.72 |
| 44 | 1.57 | 1.71 | 2.13 | 1.81 |
| 45 | | | 2.16 | 1.79 |
| 46 | 1.67 | 1.72 | 2.11 | 1.77 |
| 47 | | 1.81 | 1.80 | 1.76 |
| 48 | 1.58 | 1.85 | 1.84 | 1.81 |
| 49 | 1.60 | 1.70 | 1.89 | 1.70 |
| 50 | | 1.81 | 1.83 | 1.82 |
| 51 | 1.55 | 1.46 | 2.09 | 1.66 |
| 52 | 1.62 | | 2.02 | 1.85 |
| 53 | 1.47 | 1.57 | 1.99 | 1.80 |
| 54 | | | 2.16 | 1.82 |
| 55 | 1.56 | 1.61 | 2.15 | 1.80 |
| 56 | | | 1.87 | |

Figure 7

| Sequence Group | Clone | Format | EC50 |
|---|---|---|---|
| 3 | YU45-A3 | hIgG-Fc | 14.22 |
| 6 | YU45-A10 | hIgG-Fc | 67.67 |
| 7 | YU45-D11 | hIgG-Fc | 186.5 |
| 8 | YU45-E11 | hIgG-Fc | 15.66 |
| 9 | YU45-D12 | hIgG-Fc | 14.55 |
| 11 | YU45-G1 | hIgG-Fc | 42.75 |
| 12 | YU45-B2 | hIgG-Fc | 6.409 |
| 14 | YU45-A5 | hIgG-Fc | 6.543 |
| 16 | YU45-E3 | hIgG-Fc | 33.19 |
| 18 | YU45-F8 | hIgG-Fc | 7.786 |
| 19 | YU45-G8 | hIgG-Fc | 6.288 |
| 21 | YU45-F9 | hIgG-Fc | 4.016 |
| 22 | YU45-H10 | hIgG-Fc | 24.8 |
| 24 | YU45-F2 | hIgG-Fc | 4.239 |
| 25 | YU45-H3 | hIgG-Fc | 126.1 |
| 27 | YU45-A8 | hIgG-Fc | 710 |
| 31 | YU45-D9 | hIgG-Fc | 709.8 |
| 33 | YU45-G7 | hIgG-Fc | 10.15 |
| 36 | YU45-B6 | hIgG-Fc | 4984 |
| 39 | YU45-F5 | hIgG-Fc | 10.07 |
| 40 | YU46-B5 | hIgG-Fc | 234.1 |
| 42 | YU45-C1 | hIgG-Fc | 217 |
| 45 | YU46-A8 | hIgG-Fc | 351.2 |
| 47 | YU46-B6 | hIgG-Fc | 222.3 |
| 50 | YU46-E3 | hIgG-Fc | 706.7 |
| 54 | YU46-G8 | hIgG-Fc | 32.27 |
| 56 | YU46-D3 | hIgG-Fc | 654.8 |
| 3 | Yu33-B4 | hIgG-Fc | 197.6 |

Figure 11

| ID | Clone |
|---|---|
| A1 | BSN-1H2 |
| A2 | BSN-1H7 |
| A3 | BSN-2E1 |
| A4 | BSN-2F5 |
| A5 | BSN-2G6 |
| A6 | BSN-3C6 |
| A7 | BSN-3C11 |
| A8 | BSN-5A6 |
| A9 | BSN-5B8 |
| A10 | BSN-5F6 |
| A11 | BSN-6F3 |
| A12 | BSN-7D4 |
| A13 | BSN-7E4 |
| A14 | BSN-7F9 |
| A15 | BSN-8C4 |
| A16 | BSN-8H11 |

| No | Clone | GMFI | % positive | isotype |
|---|---|---|---|---|
| 1 | BSN-1H2 | 197496 | 157% | IgG1/kappa |
| 2 | BSN-1H7 | 247434 | 197% | IgG2a&IgG2c/kappa |
| 3 | BSN-2E1 | 206192 | 164% | IgG1/kappa |
| 4 | BSN-2F5 | 238332 | 190% | IgG1/kappa |
| 5 | BSN-2G6 | | | IgG2b/kappa |
| 6 | BSN-3C6 | 271636 | 176% | IgG1/kappa |
| 7 | BSN-3C11 | | | n.d./kappa |
| 8 | BSN-5A6 | 182487 | 145% | IgG1/kappa |
| 9 | BSN-5B6 | | | IgG1/kappa |
| 10 | BSN-5F6 | 199029 | 158% | IgG1/kappa |
| 11 | BSN-6F3 | 156008 | 124% | IgG2a&IgG2c/kappa |
| 12 | BSN-7D4 | 220736 | 176% | IgG2a&IgG2c/kappa |
| 13 | BSN-7E4 | 263377 | 209% | IgG1/kappa |
| 14 | BSN-7F9 | | | IgG1/kappa |
| 15 | BSN-8C4 | 275552 | 219% | IgG1/kappa |
| 16 | BSN-8H11 | 238663 | 190% | IgG2b/kappa |
| positive control | | 125733 | 100% | |
| negative control | | 1028 | 1% | |

| Strategy No | Round 1 | Round 2 | soluble competition with | No of first hits (lambda sublibrary) | No of first hits (kappa sublibrary) |
|---|---|---|---|---|---|
| 1 | h-IL11 | h-IL11 | h-IL11 | 27 | 14 |
| 2 | m-IL11 | m-IL11 | m-IL11 | 103 | 36 |
| 3 | h-IL11 | m-IL11 | h-IL11/m-IL11 | 11 | 21 |

Figure 19

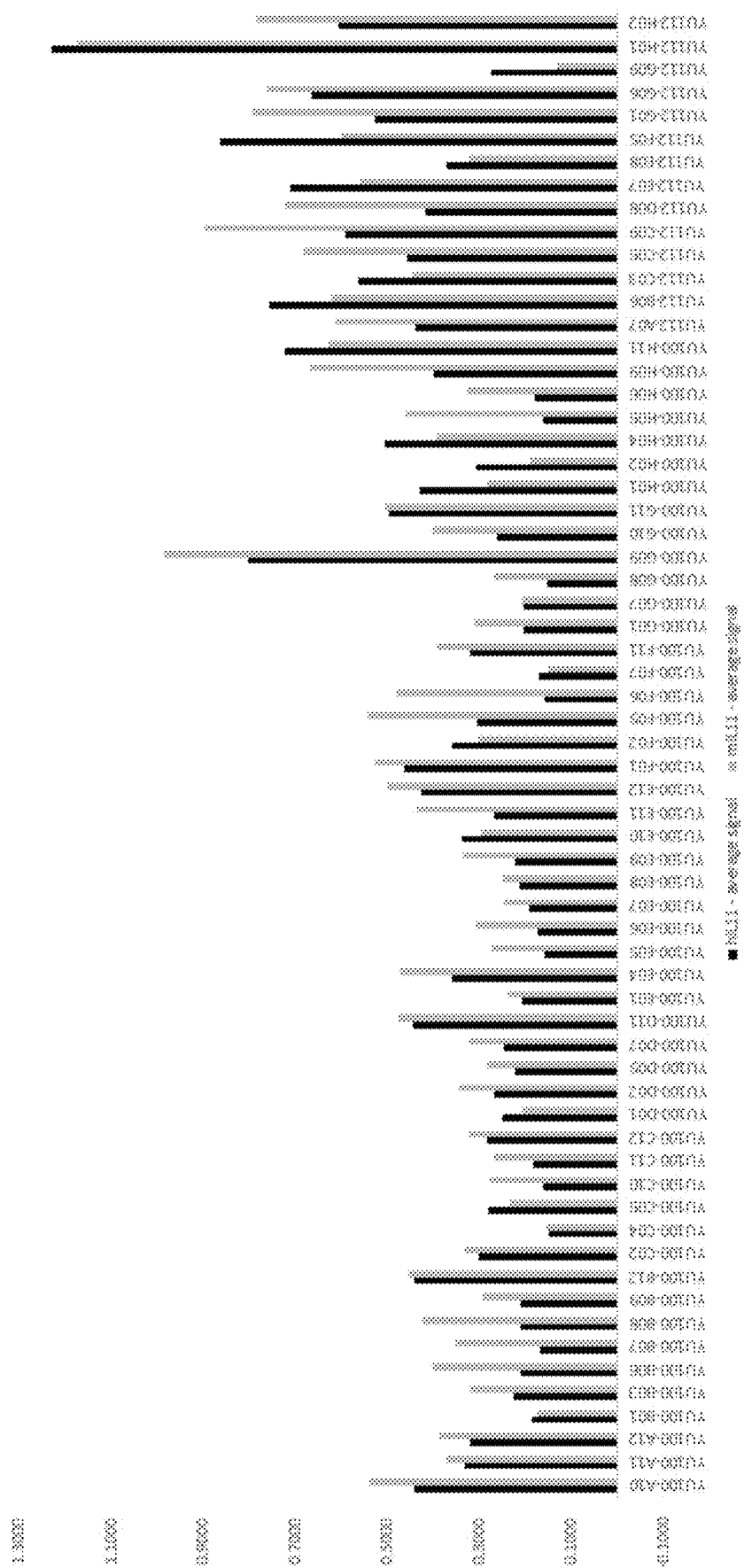

| Clone | hIL11 - average signal | mIL11 - average signal | Clone | hIL11 - average signal | mIL11 - average signal |
|---|---|---|---|---|---|
| YU100-A10 | 0.4430 | 0.5400 | YU100-F07 | 0.1730 | 0.1480 |
| YU100-A11 | 0.3328 | 0.3716 | YU100-F11 | 0.3190 | 0.3950 |
| YU100-A12 | 0.3200 | 0.3883 | YU100-G01 | 0.2050 | 0.3100 |
| YU100-B01 | 0.1870 | 0.1750 | YU100-G07 | 0.2030 | 0.2060 |
| YU100-B03 | 0.2270 | 0.3210 | YU100-G08 | 0.1530 | 0.3700 |
| YU100-B06 | 0.2090 | 0.4040 | YU100-G09 | 0.8023 | 0.3846 |
| YU100-B07 | 0.1670 | 0.3540 | YU100-G10 | 0.2620 | 0.4040 |
| YU100-B08 | 0.2090 | 0.4230 | YU100-G11 | 0.4980 | 0.5070 |
| YU100-B09 | 0.2100 | 0.2930 | YU100-H01 | 0.4300 | 0.2830 |
| YU100-B12 | 0.4430 | 0.4540 | YU100-H02 | 0.3090 | 0.1880 |
| YU100-C02 | 0.3010 | 0.3330 | YU100-H04 | 0.5080 | 0.3930 |
| YU100-C04 | 0.1480 | 0.1550 | YU100-H05 | 0.1630 | 0.4610 |
| YU100-C05 | 0.2810 | 0.2350 | YU100-H06 | 0.1810 | 0.3280 |
| YU100-C10 | 0.1610 | 0.2770 | YU100-H09 | 0.4000 | 0.6680 |
| YU100-C11 | 0.1830 | 0.2670 | YU100-H11 | 0.7240 | 0.6290 |
| YU100-C12 | 0.2829 | 0.3226 | YU112-A07 | 0.4380 | 0.6120 |
| YU100-D01 | 0.2510 | 0.2060 | YU112-B06 | 0.7563 | 0.6217 |
| YU100-D02 | 0.2680 | 0.3460 | YU112-C03 | 0.5660 | 0.4450 |
| YU100-D05 | 0.2230 | 0.2840 | YU112-C05 | 0.4576 | 0.6850 |
| YU100-D07 | 0.2460 | 0.3220 | YU112-C09 | 0.5930 | 0.8980 |
| YU100-D11 | 0.4470 | 0.4750 | YU112-D08 | 0.4180 | 0.7230 |
| YU100-E01 | 0.2070 | 0.2380 | YU112-E07 | 0.7100 | 0.5610 |
| YU100-E04 | 0.3600 | 0.4720 | YU112-E08 | 0.3733 | 0.3233 |
| YU100-E05 | 0.1600 | 0.2750 | YU112-F05 | 0.8630 | 0.6010 |
| YU100-E06 | 0.1730 | 0.3090 | YU112-G01 | 0.5280 | 0.7937 |
| YU100-E07 | 0.1930 | 0.2470 | YU112-G06 | 0.6640 | 0.7620 |
| YU100-E08 | 0.2140 | 0.2510 | YU112-G09 | 0.2760 | 0.1310 |
| YU100-E09 | 0.2240 | 0.3350 | YU112-H01 | 1.2290 | 1.1750 |
| YU100-E10 | 0.3380 | 0.2970 | YU112-H02 | 0.6060 | 0.7850 |
| YU100-E11 | 0.2675 | 0.4350 | | | |
| YU100-E12 | 0.4260 | 0.5000 | | | |
| YU100-F01 | 0.4640 | 0.5280 | | | |
| YU100-F02 | 0.3610 | 0.3030 | | | |
| YU100-F05 | 0.3040 | 0.5420 | | | |
| YU100-F06 | 0.1600 | 0.4810 | | | |

Figure 21B

|  | Affinity EC50 (ng/ml) | MMP2 production (ng/ml) (Experiment 1) | MMP2 production (ng/ml) (Experiment 2) |
|---|---|---|---|
| No TGFB1, IgG1 control (NEG) | - | 42.7 | 36.2 |
| + TGFB1, IgG1 control (POS) | - | 70.2 | 62.3 |
| YU100-C04* | 21 | 62.3 | 52.5 |
| YU100-C05* | 17 | 55.3 | 53.5 |
| YU100-C10* | 15 | 56.4 | 48.9 |
| YU100-C12* | 23 | 53.5 | 46.8 |
| YU100-E07* | 23 | 52.1 | 46.5 |
| YU100-E09* | 19 | 51.7 | 44.4 |
| YU100-E11* | 28 | 49.1 | 41.9 |
| YU100-E12* | 16 | 56.0 | 47.9 |
| YU100-F01* | 18 | 52.8 | 39.9 |
| YU100-F02* | 18 | 51.2 | 43.5 |
| YU100-G01* | 19 | 56.6 | 49.7 |
| YU100-G07* | 18 | 59.0 | 49.7 |
| YU100-G09* | 14 | 59.9 | 47.5 |
| YU100-H02* | 32 | 57.5 | 51.3 |
| YU100-H04* | 27 | 58.5 | 48.7 |
| YU100-H05* | 22 | 57.1 | 47.8 |
| YU100-H06* | 13 | 52.3 | 43.9 |
| YU100-H09* | 28 | 52.9 | 39.6 |
| YU100-H11* | 15 | 53.7 | 45.5 |
| YU112-A07 | 25 | 50.7 | 45.0 |
| YU112-B06 | 20 | 49.7 | 43.9 |
| YU112-C03 | 17 | 57.6 | 53.3 |
| YU112-C05 | 12 | 55.2 | 50.1 |
| YU112-D08 | 18 | 50.3 | 42.5 |
| YU112-F05 | 40 | 53.9 | 48.5 |
| YU112-G01 | N.D. | 47.6 | 43.8 |
| YU112-G06 | 17 | 55.0 | 47.8 |
| YU112-H01 | 20 | 51.9 | 47.7 |
| YU112-H02 | 20 | 65.3 | 58.0 |
| YU100-A10 | 23 | 52.1 | 50.1 |
| YU100-A11 | 20 | 51.6 | 45.7 |
| YU100-A12 | 23 | 59.5 | 50.4 |
| YU100-B01 | 23 | 52.5 | 40.0 |
| YU100-B03 | 25 | 47.3 | 46.6 |
| YU100-B06 | 33 | 47.6 | 49.6 |
| YU100-B07 | 23 | 55.9 | 47.4 |
| YU100-B08 | 21 | 55.3 | 40.6 |
| YU100-C02 | 14 | 54.6 | 49.4 |
| YU100-C11 | 33 | 53.8 | 44.2 |
| YU100-D02 | 22 | 49.6 | 42.2 |
| YU100-D05 | 42 | 53.3 | 48.8 |
| YU100-D11 | 38 | 51.2 | 47.2 |
| YU100-E01 | 30 | 59.3 | 51.8 |
| YU100-E04 | 36 | 50.0 | 43.5 |
| YU100-E05 | 27 | 56.3 | 50.2 |
| YU100-E06 | 24 | 54.1 | 48.2 |
| YU112-E07 | 58 | 53.5 | 49.1 |
| YU100-E08 | 32 | 48.2 | 59.7 |
| YU100-E10 | 33 | 56.1 | 47.0 |
| YU100-F07 | 41 | 53.1 | 46.6 |
| YU100-F11 | 27 | 44.5 | 37.6 |
| YU100-G08 | 28 | 42.3 | 38.0 |
| YU100-G10 | 34 | 54.0 | 45.4 |
| YU100-H01 | 53 | 48.3 | 42.2 |

Figure 24

| Ligand | $k_a$ (1/Ms) | $k_d$ (1/s) | $K_D$ (M) | Chi² (RU²) | Relative compared G03 |
|---|---|---|---|---|---|
| C89 | 3.69×10⁵ | 1.30×10⁻³ | 3.51×10⁻⁹ | 0.172 | 1.00 |
| C89A | 6.99E×10⁵ | 3.12×10⁻³ | 4.46×10⁻⁹ | 0.133 | 1.27 |
| C89G | 2.72×10⁴ | 5.37×10⁻² | 1.98×10⁻⁶ | 0.488 | 564 |
| C89I | 8.25×10⁵ | 2.38×10⁻³ | 2.89×10⁻⁹ | 0.145 | 0.82 |
| C89L | 4.63×10⁵ | 2.02×10⁻³ | 4.36×10⁻⁹ | 0.159 | 1.24 |
| C89Q | 4.26×10⁵ | 2.49×10⁻³ | 5.84×10⁻⁹ | 0.0681 | 1.66 |
| C89S | 1.28×10⁶ | 6.39×10⁻³ | 4.99×10⁻⁹ | 0.35 | 1.42 |
| C89T | 5.92×10⁴ | 2.07×10⁻³ | 3.50×10⁻⁸ | 0.327 | 9.97 |
| C89V | 2.07×10⁵ | 2.15×10⁻³ | 1.04×10⁻⁸ | 0.204 | 2.96 |

Figure 35J

| Ligand | $k_a$ (1/Ms) | $k_d$ (1/s) | $K_D$ (M) | $Chi^2$ (RU²) | Relative compared H01 |
|---|---|---|---|---|---|
| C89 | $1.48 \times 10^4$ | $6.58 \times 10^{-4}$ | $4.23 \times 10^{-8}$ | 0.0768 | 1.00 |
| C89A | $1.29 \times 10^4$ | $8.10 \times 10^{-4}$ | $6.26 \times 10^{-8}$ | 0.038 | 1.4 |
| C89G | $1.76 \times 10^3$ | $9.86 \times 10^{-4}$ | $5.60 \times 10^{-7}$ | 0.0125 | 13.2 |
| C89I | $9.21 \times 10^4$ | $2.69 \times 10^{-4}$ | $2.92 \times 10^{-8}$ | 0.0428 | 0.6 |
| C89L | $1.57 \times 10^4$ | $5.26 \times 10^{-4}$ | $3.35 \times 10^{-8}$ | 0.0532 | 0.7 |
| C89Q | $9.29 \times 10^3$ | $9.66 \times 10^{-4}$ | $1.04 \times 10^{-7}$ | 0.0171 | 2.4 |
| C89S | $8.47 \times 10^3$ | $9.05 \times 10^{-4}$ | $1.07 \times 10^{-7}$ | 0.0198 | 2.5 |
| C89T | $7.42 \times 10^4$ | $1.27 \times 10^{-4}$ | $1.71 \times 10^{-8}$ | 0.0136 | 0.4 |
| C89V | $9.19 \times 10^3$ | $7.78 \times 10^{-4}$ | $8.47 \times 10^{-8}$ | 0.0257 | 2.0 |

Figure 36J

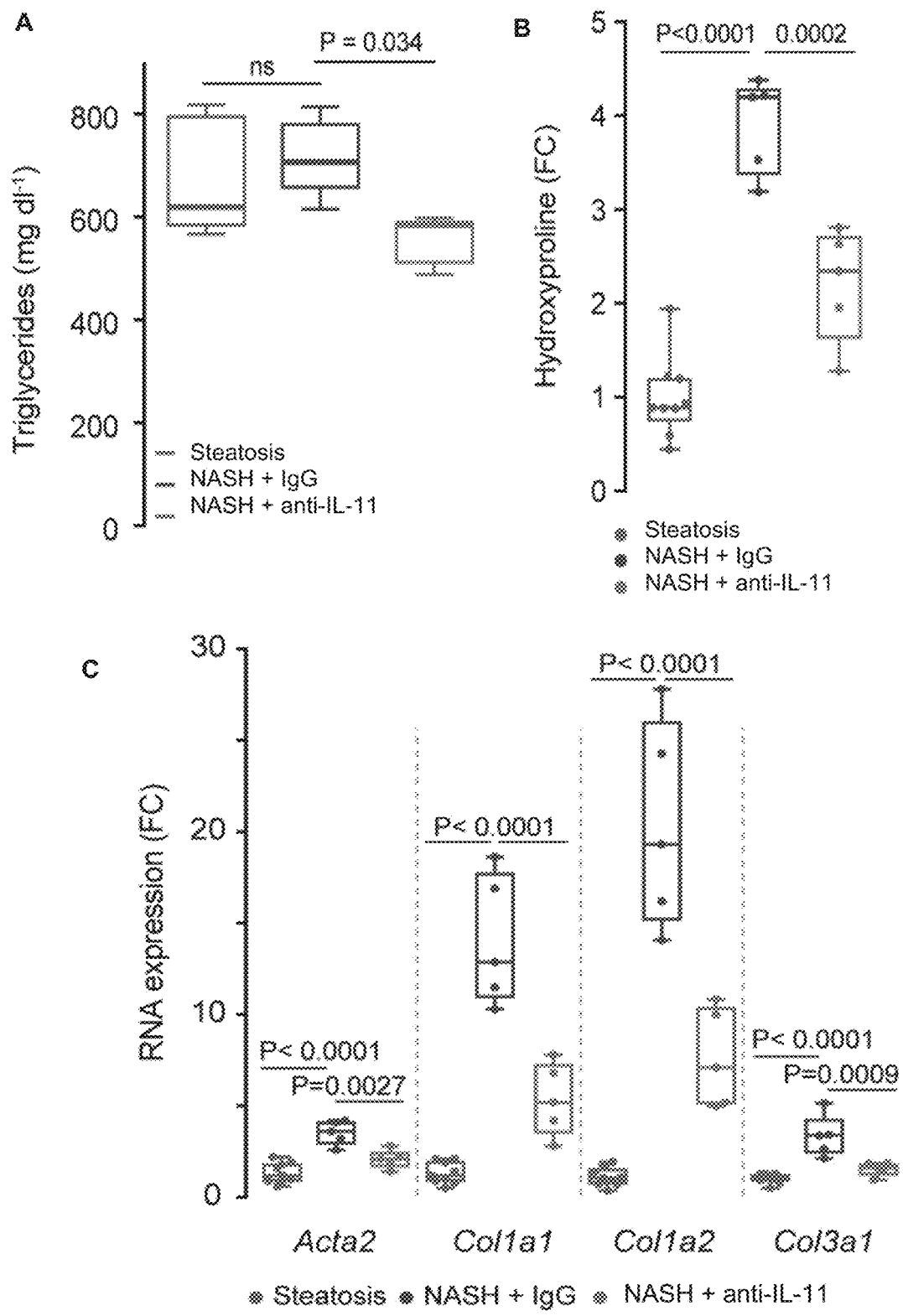
Figure 39A-C

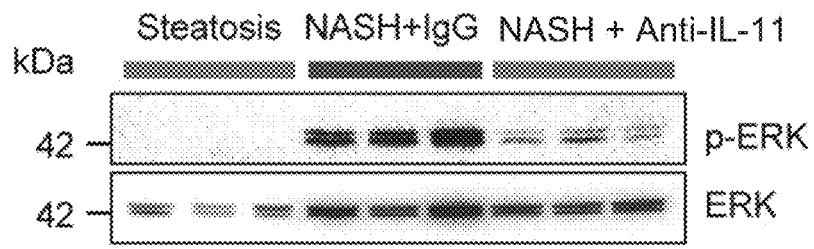
Figure 39F
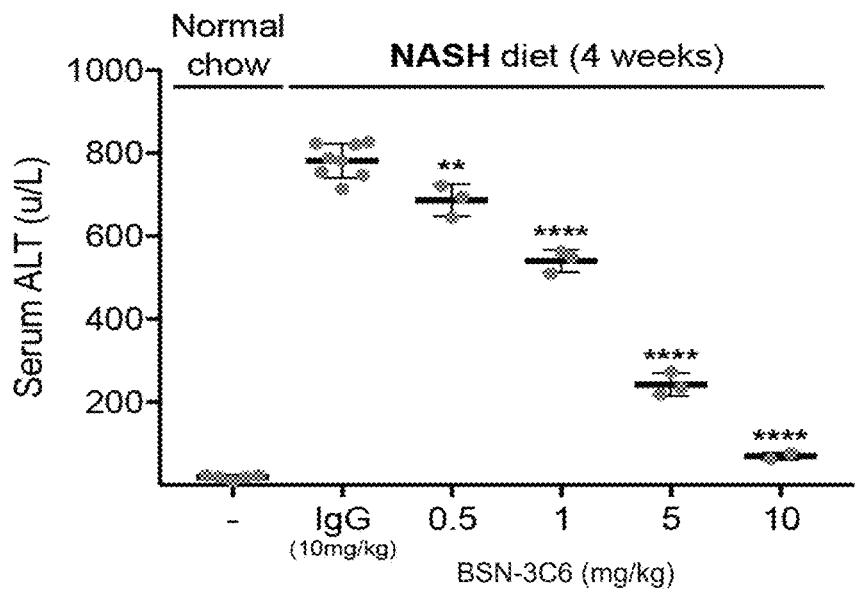
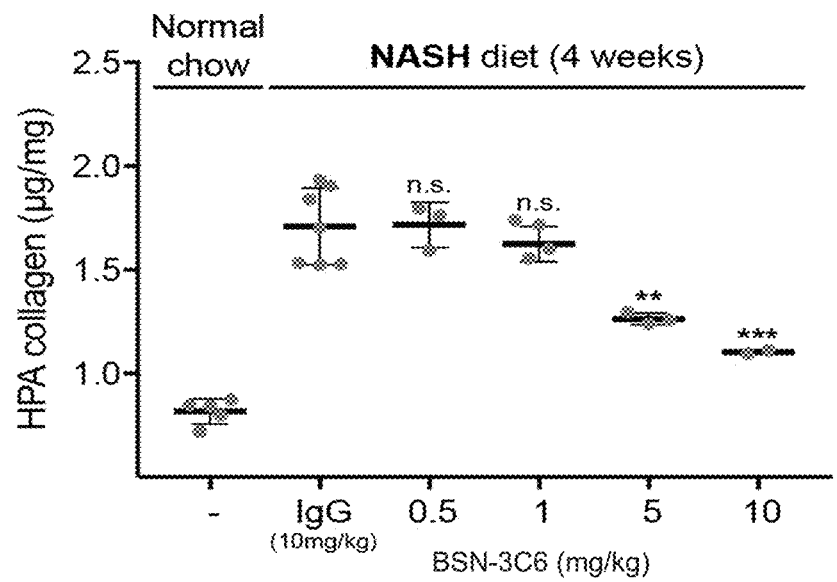
Figure 39G

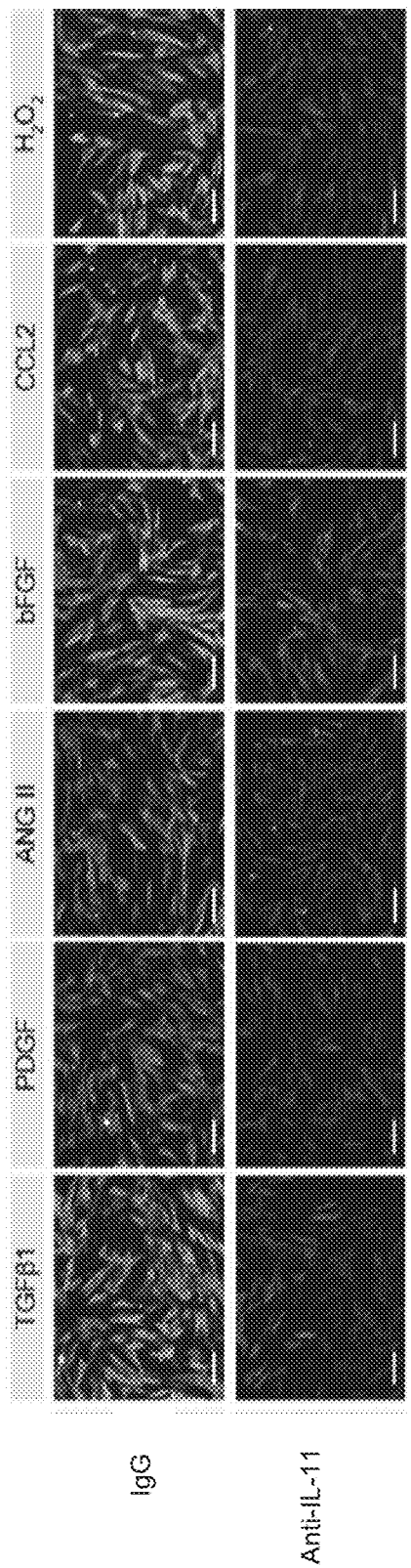
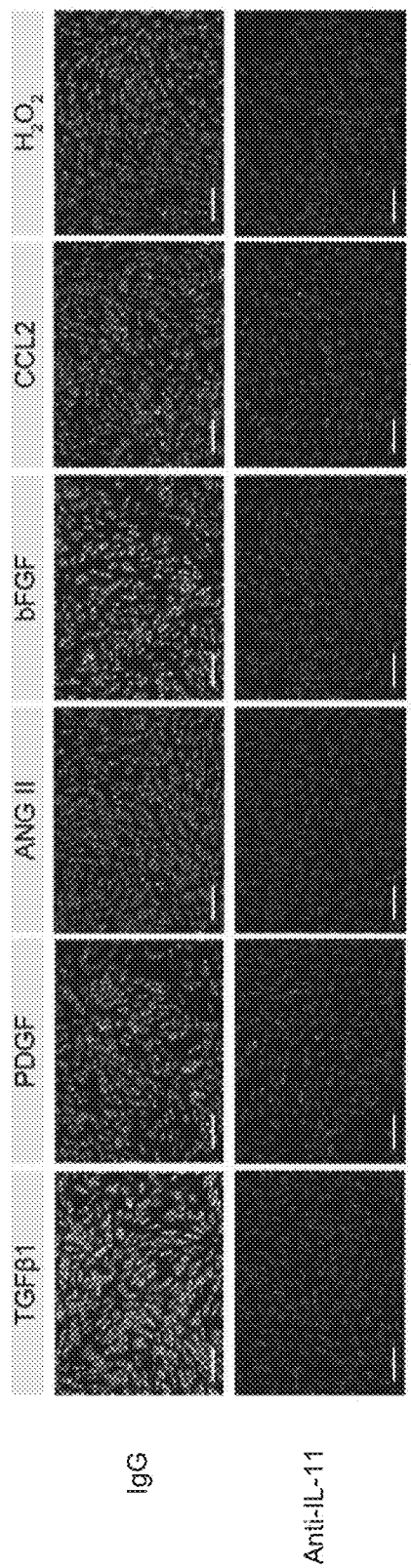
Figure 41A
Figure 41B

IL-11 ANTIBODIES

This application claims priority under 35 U.S.C. § 119 (a)-(d) to United Kingdom Patent Application Number GB1809699.0, filed Jun. 13, 2018, the contents of which are herein incorporated by reference in their entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Sep. 5, 2019, is named E060170005US00-SEQ-JOB, and is 192 kilobytes in size.

FIELD OF THE INVENTION

The present invention relates to the fields of molecular biology, more specifically antibody technology. The present invention also relates to methods of medical treatment and prophylaxis. In particular, antigen-binding molecules capable of binding to IL-11 are provided.

BACKGROUND TO THE INVENTION

IL-11-mediated signalling has been shown to stimulate haematopoiesis, stimulate osteoclast activity, stimulate neurogenesis, inhibit adipogenesis, reduce pro inflammatory cytokine expression, modulate extracellular matrix (ECM) metabolism, and mediate normal growth control of gastrointestinal epithelial cells. The physiological role of Interleukin 11 (IL-11) remains unclear. IL-11 has been most strongly linked with activation of haematopoietic cells and with platelet production, but has also been suggested to be pro-inflammatory as well as anti-inflammatory, pro-angiogenic and important for neoplasia.

SUMMARY OF THE INVENTION

In a first aspect the present invention provides an antigen-binding molecule, optionally isolated, which is capable of binding to IL-11, wherein the antigen-binding molecule comprises:
  (i) a heavy chain variable (VH) region incorporating the following CDRs:
  HC-CDR1 having the amino acid sequence of SEQ ID NO:36 or 37
  HC-CDR2 having the amino acid sequence of SEQ ID NO:38
  HC-CDR3 having the amino acid sequence of SEQ ID NO:39 or 40; and
  (ii) a light chain variable (VL) region incorporating the following CDRs:
  LC-CDR1 having the amino acid sequence of SEQ ID NO:41, 42 or 43
  LC-CDR2 having the amino acid sequence of SEQ ID NO:44, 45 or 46
  LC-CDR3 having the amino acid sequence of SEQ ID NO:80 or 81.

In some embodiments the antigen-binding molecule comprises:
  (i) a heavy chain variable (VH) region incorporating the following CDRs:
  HC-CDR1 having the amino acid sequence of SEQ ID NO:36
  HC-CDR2 having the amino acid sequence of SEQ ID NO:38
  HC-CDR3 having the amino acid sequence of SEQ ID NO:39; and
  (ii) a light chain variable (VL) region incorporating the following CDRs:
  LC-CDR1 having the amino acid sequence of SEQ ID NO:41
  LC-CDR2 having the amino acid sequence of SEQ ID NO:44
  LC-CDR3 having the amino acid sequence of SEQ ID NO:80.

In some embodiments the antigen-binding molecule comprises:
  (i) a heavy chain variable (VH) region incorporating the following CDRs:
  HC-CDR1 having the amino acid sequence of SEQ ID NO:37
  HC-CDR2 having the amino acid sequence of SEQ ID NO:38
  HC-CDR3 having the amino acid sequence of SEQ ID NO:40; and
  (ii) a light chain variable (VL) region incorporating the following CDRs:
  LC-CDR1 having the amino acid sequence of SEQ ID NO:42
  LC-CDR2 having the amino acid sequence of SEQ ID NO:45
  LC-CDR3 having the amino acid sequence of SEQ ID NO:81.

In some embodiments the antigen-binding molecule comprises:
  (i) a heavy chain variable (VH) region incorporating the following CDRs:
  HC-CDR1 having the amino acid sequence of SEQ ID NO:37
  HC-CDR2 having the amino acid sequence of SEQ ID NO:38
  HC-CDR3 having the amino acid sequence of SEQ ID NO:40; and
  (ii) a light chain variable (VL) region incorporating the following CDRs:
  LC-CDR1 having the amino acid sequence of SEQ ID NO:43
  LC-CDR2 having the amino acid sequence of SEQ ID NO:46
  LC-CDR3 having the amino acid sequence of SEQ ID NO:80.

In some embodiments the antigen-binding molecule comprises:
  (a)
  (i) a heavy chain variable (VH) region incorporating the following CDRs:
  HC-CDR1 having the amino acid sequence of SEQ ID NO:36
  HC-CDR2 having the amino acid sequence of SEQ ID NO:38
  HC-CDR3 having the amino acid sequence of SEQ ID NO:39; and
  (ii) a light chain variable (VL) region incorporating the following CDRs:
  LC-CDR1 having the amino acid sequence of SEQ ID NO:41
  LC-CDR2 having the amino acid sequence of SEQ ID NO:44
  LC-CDR3 having the amino acid sequence of SEQ ID NO:48;

(b)
(i) a heavy chain variable (VH) region incorporating the following CDRs:
HC-CDR1 having the amino acid sequence of SEQ ID NO:36
HC-CDR2 having the amino acid sequence of SEQ ID NO:38
HC-CDR3 having the amino acid sequence of SEQ ID NO:39; and
(ii) a light chain variable (VL) region incorporating the following CDRs:
LC-CDR1 having the amino acid sequence of SEQ ID NO:41
LC-CDR2 having the amino acid sequence of SEQ ID NO:44
LC-CDR3 having the amino acid sequence of SEQ ID NO:49;
(c)
(i) a heavy chain variable (VH) region incorporating the following CDRs:
HC-CDR1 having the amino acid sequence of SEQ ID NO:36
HC-CDR2 having the amino acid sequence of SEQ ID NO:38
HC-CDR3 having the amino acid sequence of SEQ ID NO:39; and
(ii) a light chain variable (VL) region incorporating the following CDRs:
LC-CDR1 having the amino acid sequence of SEQ ID NO:41
LC-CDR2 having the amino acid sequence of SEQ ID NO:44
LC-CDR3 having the amino acid sequence of SEQ ID NO:50;
(d)
(i) a heavy chain variable (VH) region incorporating the following CDRs:
HC-CDR1 having the amino acid sequence of SEQ ID NO:36
HC-CDR2 having the amino acid sequence of SEQ ID NO:38
HC-CDR3 having the amino acid sequence of SEQ ID NO:39; and
(ii) a light chain variable (VL) region incorporating the following CDRs:
LC-CDR1 having the amino acid sequence of SEQ ID NO:41
LC-CDR2 having the amino acid sequence of SEQ ID NO:44
LC-CDR3 having the amino acid sequence of SEQ ID NO:51;
(e)
(i) a heavy chain variable (VH) region incorporating the following CDRs:
HC-CDR1 having the amino acid sequence of SEQ ID NO:36
HC-CDR2 having the amino acid sequence of SEQ ID NO:38
HC-CDR3 having the amino acid sequence of SEQ ID NO:39; and
(ii) a light chain variable (VL) region incorporating the following CDRs:
LC-CDR1 having the amino acid sequence of SEQ ID NO:41
LC-CDR2 having the amino acid sequence of SEQ ID NO:44
LC-CDR3 having the amino acid sequence of SEQ ID NO:52;
(f)
(i) a heavy chain variable (VH) region incorporating the following CDRs:
HC-CDR1 having the amino acid sequence of SEQ ID NO:36
HC-CDR2 having the amino acid sequence of SEQ ID NO:38
HC-CDR3 having the amino acid sequence of SEQ ID NO:39; and
(ii) a light chain variable (VL) region incorporating the following CDRs:
LC-CDR1 having the amino acid sequence of SEQ ID NO:41
LC-CDR2 having the amino acid sequence of SEQ ID NO:44
LC-CDR3 having the amino acid sequence of SEQ ID NO:53;
(g)
(i) a heavy chain variable (VH) region incorporating the following CDRs:
HC-CDR1 having the amino acid sequence of SEQ ID NO:36
HC-CDR2 having the amino acid sequence of SEQ ID NO:38
HC-CDR3 having the amino acid sequence of SEQ ID NO:39; and
(ii) a light chain variable (VL) region incorporating the following CDRs:
LC-CDR1 having the amino acid sequence of SEQ ID NO:41
LC-CDR2 having the amino acid sequence of SEQ ID NO:44
LC-CDR3 having the amino acid sequence of SEQ ID NO:54; or
(h)
(i) a heavy chain variable (VH) region incorporating the following CDRs:
HC-CDR1 having the amino acid sequence of SEQ ID NO:36
HC-CDR2 having the amino acid sequence of SEQ ID NO:38
HC-CDR3 having the amino acid sequence of SEQ ID NO:39; and
(ii) a light chain variable (VL) region incorporating the following CDRs:
LC-CDR1 having the amino acid sequence of SEQ ID NO:41
LC-CDR2 having the amino acid sequence of SEQ ID NO:44
LC-CDR3 having the amino acid sequence of SEQ ID NO:55.
In some embodiments the antigen-binding molecule comprises:
(a)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:

LC-CDR1 having the amino acid sequence of SEQ ID NO:42
LC-CDR2 having the amino acid sequence of SEQ ID NO:45
LC-CDR3 having the amino acid sequence of SEQ ID NO:57;

(b)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:58;

(c)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:59;

(d)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:60;

(e)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:61;

(f)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:62;

(g)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:63; or (h)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:64.

In some embodiments the antigen-binding molecule comprises:
(a)
(i) a heavy chain variable (VH) region incorporating the following CDRs:
HC-CDR1 having the amino acid sequence of SEQ ID NO:37

HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:48;

(b)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:49;

(c)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:50;

(d)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:51;

(e)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:52;

(f)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:53;

(g)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:54; or (h)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:55.

In some embodiments the antigen-binding molecule comprises:

a VH region comprising an amino acid sequence having at least 70% sequence identity to the amino acid sequence of SEQ ID NO:6, 8 or 10; and a VL region comprising an amino acid sequence having at least 70% sequence identity to the amino acid sequence of SEQ ID NO:82, 83 or 84.

In some embodiments the antigen-binding molecule comprises:

a VH region comprising an amino acid sequence having at least 70% sequence identity to the amino acid sequence of SEQ ID NO:6; and a VL region comprising an amino acid sequence having at least 70% sequence identity to the amino acid sequence of SEQ ID NO:82.

In some embodiments the antigen-binding molecule comprises:

a VH region comprising an amino acid sequence having at least 70% sequence identity to the amino acid sequence of SEQ ID NO:8; and a VL region comprising an amino acid sequence having at least 70% sequence identity to the amino acid sequence of SEQ ID NO:83.

In some embodiments the antigen-binding molecule comprises:

a VH region comprising an amino acid sequence having at least 70% sequence identity to the amino acid sequence of SEQ ID NO:10; and a VL region comprising an amino acid sequence having at least 70% sequence identity to the amino acid sequence of SEQ ID NO:84.

In some embodiments the antigen-binding molecule comprises:

(a)
a VH region comprising an amino acid sequence having at least 70% sequence identity to the amino acid sequence of SEQ ID NO:6; and
a VL region comprising an amino acid sequence having at least 70% sequence identity to the amino acid sequence of SEQ ID NO:12;

(b)
a VH region comprising an amino acid sequence having at least 70% sequence identity to the amino acid sequence of SEQ ID NO:6; and
a VL region comprising an amino acid sequence having at least 70% sequence identity to the amino acid sequence of SEQ ID NO:13;

(c)
a VH region comprising an amino acid sequence having at least 70% sequence identity to the amino acid sequence of SEQ ID NO:6; and
a VL region comprising an amino acid sequence having at least 70% sequence identity to the amino acid sequence of SEQ ID NO:14;

(d)
a VH region comprising an amino acid sequence having at least 70% sequence identity to the amino acid sequence of SEQ ID NO:6; and
a VL region comprising an amino acid sequence having at least 70% sequence identity to the amino acid sequence of SEQ ID NO:15;

(e)
a VH region comprising an amino acid sequence having at least 70% sequence identity to the amino acid sequence of SEQ ID NO:6; and
a VL region comprising an amino acid sequence having at least 70% sequence identity to the amino acid sequence of SEQ ID NO:16;

(f)
a VH region comprising an amino acid sequence having at least 70% sequence identity to the amino acid sequence of SEQ ID NO:6; and
a VL region comprising an amino acid sequence having at least 70% sequence identity to the amino acid sequence of SEQ ID NO:17;

(g)
a VH region comprising an amino acid sequence having at least 70% sequence identity to the amino acid sequence of SEQ ID NO:6; and
a VL region comprising an amino acid sequence having at least 70% sequence identity to the amino acid sequence of SEQ ID NO:18; or (h)
a VH region comprising an amino acid sequence having at least 70% sequence identity to the amino acid sequence of SEQ ID NO:6; and
a VL region comprising an amino acid sequence having at least 70% sequence identity to the amino acid sequence of SEQ ID NO:19.

In some embodiments the antigen-binding molecule comprises:

(a)
a VH region comprising an amino acid sequence having at least 70% sequence identity to the amino acid sequence of SEQ ID NO:8; and
a VL region comprising an amino acid sequence having at least 70% sequence identity to the amino acid sequence of SEQ ID NO:20;

(b)
a VH region comprising an amino acid sequence having at least 70% sequence identity to the amino acid sequence of SEQ ID NO:8; and
a VL region comprising an amino acid sequence having at least 70% sequence identity to the amino acid sequence of SEQ ID NO:21;

(c)
a VH region comprising an amino acid sequence having at least 70% sequence identity to the amino acid sequence of SEQ ID NO:8; and
a VL region comprising an amino acid sequence having at least 70% sequence identity to the amino acid sequence of SEQ ID NO:22;

(d)
a VH region comprising an amino acid sequence having at least 70% sequence identity to the amino acid sequence of SEQ ID NO:8; and
a VL region comprising an amino acid sequence having at least 70% sequence identity to the amino acid sequence of SEQ ID NO:23;

(e)
a VH region comprising an amino acid sequence having at least 70% sequence identity to the amino acid sequence of SEQ ID NO:8; and
a VL region comprising an amino acid sequence having at least 70% sequence identity to the amino acid sequence of SEQ ID NO:24;

(f)
a VH region comprising an amino acid sequence having at least 70% sequence identity to the amino acid sequence of SEQ ID NO:8; and
a VL region comprising an amino acid sequence having at least 70% sequence identity to the amino acid sequence of SEQ ID NO:25;

(g)
a VH region comprising an amino acid sequence having at least 70% sequence identity to the amino acid sequence of SEQ ID NO:8; and
a VL region comprising an amino acid sequence having at least 70% sequence identity to the amino acid sequence of SEQ ID NO:26; or
(h)
a VH region comprising an amino acid sequence having at least 70% sequence identity to the amino acid sequence of SEQ ID NO:8; and
a VL region comprising an amino acid sequence having at least 70% sequence identity to the amino acid sequence of SEQ ID NO:27.

In some embodiments the antigen-binding molecule comprises:
(a)
a VH region comprising an amino acid sequence having at least 70% sequence identity to the amino acid sequence of SEQ ID NO:10; and
a VL region comprising an amino acid sequence having at least 70% sequence identity to the amino acid sequence of SEQ ID NO:28;
(b)
a VH region comprising an amino acid sequence having at least 70% sequence identity to the amino acid sequence of SEQ ID NO:10; and
a VL region comprising an amino acid sequence having at least 70% sequence identity to the amino acid sequence of SEQ ID NO:29;
(c)
a VH region comprising an amino acid sequence having at least 70% sequence identity to the amino acid sequence of SEQ ID NO:10; and
a VL region comprising an amino acid sequence having at least 70% sequence identity to the amino acid sequence of SEQ ID NO:30;
(d)
a VH region comprising an amino acid sequence having at least 70% sequence identity to the amino acid sequence of SEQ ID NO:10; and
a VL region comprising an amino acid sequence having at least 70% sequence identity to the amino acid sequence of SEQ ID NO:31;
(e)
a VH region comprising an amino acid sequence having at least 70% sequence identity to the amino acid sequence of SEQ ID NO:10; and
a VL region comprising an amino acid sequence having at least 70% sequence identity to the amino acid sequence of SEQ ID NO:32;
(f)
a VH region comprising an amino acid sequence having at least 70% sequence identity to the amino acid sequence of SEQ ID NO:10; and
a VL region comprising an amino acid sequence having at least 70% sequence identity to the amino acid sequence of SEQ ID NO:33;
(g)
a VH region comprising an amino acid sequence having at least 70% sequence identity to the amino acid sequence of SEQ ID NO:10; and
a VL region comprising an amino acid sequence having at least 70% sequence identity to the amino acid sequence of SEQ ID NO:34; or (h)
a VH region comprising an amino acid sequence having at least 70% sequence identity to the amino acid sequence of SEQ ID NO:10; and
a VL region comprising an amino acid sequence having at least 70% sequence identity to the amino acid sequence of SEQ ID NO:35.

The present invention also provides an antigen-binding molecule, optionally isolated, which is capable of binding to IL-11, wherein the antigen-binding molecule comprises:
(i) a heavy chain variable (VH) region incorporating the following CDRs:
HC-CDR1 having the amino acid sequence of SEQ ID NO:95
HC-CDR2 having the amino acid sequence of SEQ ID NO:96
HC-CDR3 having the amino acid sequence of SEQ ID NO:97; and
(ii) a light chain variable (VL) region incorporating the following CDRs:
LC-CDR1 having the amino acid sequence of SEQ ID NO:98 or 101
LC-CDR2 having the amino acid sequence of SEQ ID NO:99 or 102
LC-CDR3 having the amino acid sequence of SEQ ID NO:100 or 103.

In some embodiments the antigen-binding molecule comprises:
(a)
(i) a heavy chain variable (VH) region incorporating the following CDRs:
HC-CDR1 having the amino acid sequence of SEQ ID NO:95
HC-CDR2 having the amino acid sequence of SEQ ID NO:96
HC-CDR3 having the amino acid sequence of SEQ ID NO:97; and
(ii) a light chain variable (VL) region incorporating the following CDRs:
LC-CDR1 having the amino acid sequence of SEQ ID NO:98
LC-CDR2 having the amino acid sequence of SEQ ID NO:99
LC-CDR3 having the amino acid sequence of SEQ ID NO:100; or
(b)
(i) a heavy chain variable (VH) region incorporating the following CDRs:
HC-CDR1 having the amino acid sequence of SEQ ID NO:95
HC-CDR2 having the amino acid sequence of SEQ ID NO:96
HC-CDR3 having the amino acid sequence of SEQ ID NO:97; and
(ii) a light chain variable (VL) region incorporating the following CDRs:
LC-CDR1 having the amino acid sequence of SEQ ID NO:101
LC-CDR2 having the amino acid sequence of SEQ ID NO:102
LC-CDR3 having the amino acid sequence of SEQ ID NO:103.

In some embodiments the antigen-binding molecule comprises:
a VH region comprising an amino acid sequence having at least 70% sequence identity to the amino acid sequence of SEQ ID NO:91, 92, 116, 117, 118, 119 or 120; and a VL region comprising an amino acid sequence having at least 70% sequence identity to the amino acid sequence of SEQ ID NO:93, 94, 121, 122, 123, 124, 125, 126, 127 or 128.

In some embodiments the antigen-binding molecule comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:220. In some embodiments the antigen-binding molecule comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:223. In some embodiments the antigen-binding molecule comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:224. In some embodiments the antigen-binding molecule comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of one of SEQ ID NO:236 to 240. In some embodiments the antigen-binding molecule comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:220 or 223, and a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of one of SEQ ID NO:224, 236, 237, 238, 239, or 240.

In some embodiments the antigen-binding molecule comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:225. In some embodiments the antigen-binding molecule comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:228. In some embodiments the antigen-binding molecule comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:229. In some embodiments the antigen-binding molecule comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:230. In some embodiments the antigen-binding molecule comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:225 or 228, and a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:229 or 230.

In accordance with various aspects of the present invention, in some embodiments the antigen-binding molecule is capable of inhibiting IL-11 mediated signalling.

The present invention also provides an antigen-binding molecule, optionally isolated, comprising (i) an antigen-binding molecule described herein, and (ii) an antigen-binding molecule capable of binding to an antigen other than IL-11.

In accordance with various aspects of the present invention, in some embodiments the antigen-binding molecule is capable of inhibiting interaction between IL-11 or a complex comprising IL-11 and an IL-11 receptor.

The present invention also provides a chimeric antigen receptor (CAR) comprising an antigen-binding molecule described herein.

The present invention also provides a nucleic acid, or a plurality of nucleic acids, optionally isolated, encoding an antigen-binding molecule described herein or a CAR described herein.

The present invention also provides an expression vector, or a plurality of expression vectors, comprising a nucleic acid or a plurality of nucleic acids described herein.

The present invention also provides a cell comprising an antigen-binding molecule, a CAR, a nucleic acid or a plurality of nucleic acids, or an expression vector or a plurality of expression vectors described herein.

The present invention also provides a method comprising culturing a cell comprising a nucleic acid or a plurality of nucleic acids according or an expression vector or a plurality of expression vectors described herein, under conditions suitable for expression of the antigen-binding molecule or CAR from the nucleic acid(s) or expression vector(s).

The present invention also provides a composition comprising an antigen-binding molecule, a CAR, a nucleic acid or a plurality of nucleic acids, an expression vector or a plurality of expression vectors, and/or a cell as provided herein.

The present invention also provides an antigen-binding molecule, a CAR, a nucleic acid or a plurality of nucleic acids, an expression vector or a plurality of expression vectors, a cell, or a composition described herein for use in a method of medical treatment or prophylaxis.

The present invention also provides an antigen-binding molecule, a CAR, a nucleic acid or a plurality of nucleic acids, an expression vector or a plurality of expression vectors, a cell, or a composition described herein, for use in a method of treatment or prevention of fibrosis, a disease characterised by fibrosis, a cancer, inflammation, or a disease characterised by inflammation.

The present invention also provides the use of an antigen-binding molecule, a CAR, a nucleic acid or a plurality of nucleic acids, an expression vector or a plurality of expression vectors, a cell, or a composition described herein, in the manufacture of a medicament for use in a method of treatment or prevention of fibrosis, a disease characterised by fibrosis, a cancer, inflammation, or a disease characterised by inflammation.

The present invention also provides a method of treating or preventing fibrosis, a disease characterised by fibrosis, a cancer, inflammation, or a disease characterised by inflammation, comprising administering to a subject a therapeutically or prophylactically effective amount of an antigen-binding molecule, a CAR, a nucleic acid or a plurality of nucleic acids, an expression vector or a plurality of expression vectors, a cell, or a composition described herein.

The present invention also provides a method of inhibiting IL-11 mediated signalling, comprising contacting IL-11-expressing cells with an antigen-binding molecule described herein. The method may be performed in vitro, in vivo, in situ or ex vivo.

The present invention also provides an in vitro complex, optionally isolated, comprising an antigen-binding molecule described herein bound to IL-11 or a complex comprising IL-11.

The present invention also provides a method comprising contacting a sample containing, or suspected to contain, IL-11 or a complex comprising IL-11 with an antigen-binding molecule described herein, and detecting the formation of a complex of the antigen-binding molecule with IL-11 or a complex comprising IL-11.

The present invention also provides a method of selecting or stratifying a subject for treatment with an IL-11-targeted agent, the method comprising contacting, in vitro, a sample from the subject with an antigen-binding molecule described herein and detecting the formation of a complex of the antigen-binding molecule with IL-11 or a complex comprising IL-11.

The present invention also provides the use of an antigen-binding molecule described herein as an in vitro or in vivo diagnostic or prognostic agent.

The present invention also provides a kit of parts comprising a predetermined quantity of: an antigen-binding molecule, a CAR, a nucleic acid or a plurality of nucleic acids, an expression vector or a plurality of expression vectors, a cell, or a composition described herein.

Description

The present invention relates to novel IL-11-binding molecules having improved properties as compared to known anti-IL-11 antibodies. The IL-11-binding molecules of the present invention are provided with combinations of desirable biophysical and functional properties as compared to IL-11-binding antigen-binding molecules disclosed in the prior art.

Interleukin 11 and Receptors for IL-11

Interleukin 11 (IL-11), also known as adipogenesis inhibitory factor, is a pleiotropic cytokine and a member of the IL-6 family of cytokines that includes IL-6, IL-11, IL-27, IL-31, oncostatin, leukemia inhibitory factor (LIF), cardiotrophin-1 (CT-1), cardiotrophin-like cytokine (CLC), ciliary neurotrophic factor (CNTF) and neuropoetin (NP-1).

Interleukin 11 (IL-11) is expressed in a variety of mesenchymal cell types. IL-11 genomic sequences have been mapped onto chromosome 19 and the centromeric region of chromosome 71, and is transcribed with a canonical signal peptide that ensures efficient secretion from cells. The activator protein complex of IL-11, cJun/AP-1, located within its promoter sequence is critical for basal transcriptional regulation of IL-11 (Du and Williams, Blood 1997, Vol 89: 3897-3908). The immature form of human IL-11 is a 199 amino acid polypeptide whereas the mature form of IL-11 encodes a protein of 178 amino acid residues (Garbers and Scheller, Biol. Chem. 2013; 394(9):1145-1161). The human IL-11 amino acid sequence is available under UniProt accession no. P20809 (P20809.1 GI:124294; SEQ ID NO:1). Recombinant human IL-11 (oprelvekin) is also commercially available. IL-11 from other species, including mouse, rat, pig, cow, several species of bony fish and primates, have also been cloned and sequenced.

In this specification "IL-11" refers to an IL-11 from any species and includes isoforms, fragments, variants or homologues of an IL-11 from any species. As used herein, a "fragment", "variant" or "homologue" of a protein may optionally be characterised as having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of the reference protein. In some embodiments fragments, variants, isoforms and homologues of a reference protein may be characterised by ability to perform a function performed by the reference protein.

A "fragment" generally refers to a fraction of the reference protein. A "variant" generally refers to a protein having an amino acid sequence comprising one or more amino acid substitutions, insertions, deletions or other modifications relative to the amino acid sequence of the reference protein, but retaining a considerable degree of sequence identity (e.g. at least 60%) to the amino acid sequence of the reference protein. An "isoform" generally refers to a variant of the reference protein expressed by the same species as the species of the reference protein. A "homologue" generally refers to a variant of the reference protein produced by a different species as compared to the species of the reference protein. Homologues include orthologues. A "fragment" may be of any length (by number of amino acids), although may optionally be at least 20% of the length of the reference protein (that is, the protein from which the fragment is derived) and may have a maximum length of one of 50%, 75%, 80%, 85%, 90%, 91%, 92%, 93%, 94%, 95%, 96%, 97%, 98%, or 99% of the length of the reference protein. A fragment of IL-11 may have a minimum length of 10 amino acids, and a maximum length of one of 15, 20, 25, 30, 40, 50, 100, 110, 120, 130, 140, 150, 160, 170, 180, 190 or 195 amino acids.

In some embodiments, the IL-11 is IL-11 from a mammal (e.g. a primate (rhesus, cynomolgous, non-human primate or human) and/or a rodent (e.g. rat or murine) IL-11). Isoforms, fragments, variants or homologues of IL-11 may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of an immature or mature IL-11 isoform from a given species, e.g. human. In some embodiments, the IL-11 of the present disclosure comprises, or consists of, an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:1.

Isoforms, fragments, variants or homologues of an IL-11 may optionally be characterised by ability to bind an IL-11 receptor (e.g. IL-11Rα, gp130 and/or a complex comprising IL-11Rα and gp130, preferably from the same species) and stimulate signal transduction in cells expressing IL-11Rα and gp130 (e.g. as described in Curtis et al. Blood, 1997, 90(11); or Karpovich et al. Mol. Hum. Reprod. 2003 9(2): 75-80).

IL-11 signals through a homodimer of the ubiquitously expressed glycoprotein 130 (gp130; also known as glycoprotein 130, IL-6ST, IL-6-beta or CD130). Gp130 is a transmembrane protein that forms one subunit of the type I cytokine receptor with the IL-6 receptor family. Specificity is gained through an individual interleukin 11 receptor subunit alpha (IL-11Rα), which does not directly participate in signal transduction, although the initial cytokine binding event to the α-receptor leads to the final complex formation with gp130.

Human gp130 (including the 22 amino acid signal peptide) is a 918 amino acid protein, and the mature form is 866 amino acids, comprising a 597 amino acid extracellular domain, a 22 amino acid transmembrane domain, and a 277 amino acid intracellular domain. The extracellular domain of the protein comprises the cytokine-binding module (CBM) of gp130. The CBM of gp130 comprises the Ig-like domain D1, and the fibronectin-type III domains D2 and D3 of gp130. The amino acid sequence of human gp130 is available under UniProt accession no. P40189-1 (SEQ ID NO:2).

Human IL-11Rα is a 422 amino acid polypeptide (UniProt Q14626; SEQ ID NO:3) and shares ~85% nucleotide and amino acid sequence identity with the murine IL-11Rα (Du and Williams, Blood Vol, 89, No, 11, Jun. 1, 1997). Two isoforms of IL-11Rα have been reported, which differ in the cytoplasmic domain (Du and Williams, supra). The IL-11 receptor α-chain (IL-11Rα) shares many structural and functional similarities with the IL-6 receptor α-chain (IL-6Rα). The extracellular domain shows 24% amino acid identity including the characteristic conserved Trp-Ser-X-Trp-Ser (WSXWS) motif. The short cytoplasmic domain (34 amino acids) lacks the Box 1 and 2 regions that are required for activation of the JAK/STAT signalling pathway.

The receptor binding sites on murine IL-11 have been mapped and three sites—sites I, II and III—identified. Binding to gp130 is reduced by substitutions in the site II region and by substitutions in the site III region. Site III mutants show no detectable agonist activity and have IL-11Rα antagonist activity (Cytokine Inhibitors Chapter 8; edited by Gennaro Ciliberto and Rocco Savino, Marcel Dekker, Inc. 2001).

In this specification an IL-11 receptor/receptor for IL-11 (IL-11R) refers to a polypeptide or polypeptide complex capable of binding IL-11 and/or a complex comprising IL-11. In some embodiments an IL-11 receptor is capable of binding IL-11 and/or a complex comprising IL-11 and inducing signal transduction in cells expressing the IL-11 receptor. A "complex comprising IL-11" may be a non-covalent complex of IL-11 and a polypeptide capable of non-covalent association with IL-11.

An IL-11 receptor may be from any species and includes isoforms, fragments, variants or homologues of an IL-11 receptor from any species. In preferred embodiments the species is human (*Homo sapiens*).

In some embodiments the IL-11 receptor (IL-11R) may be IL-11Rα. In some embodiments a receptor for IL-11 may be a polypeptide complex comprising IL-11Rα. In some embodiments the IL-11 receptor may be a polypeptide complex comprising IL-11Rα and gp130. In some embodiments the IL-11 receptor may be gp130 or a complex comprising gp130 to which IL-11 binds.

Isoforms, fragments, variants or homologues of an IL-11Rα may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of IL-11Rα from a given species, e.g. human. Isoforms, fragments, variants or homologues of an IL-11Rα may optionally be characterised by ability to bind IL-11 (preferably from the same species) and stimulate signal transduction in cells expressing the IL-11Rα and gp130 (e.g. as described in Curtis et al. Blood, 1997, 90(11) or Karpovich et al. Mol. Hum. Reprod. 2003 9(2): 75-80). A fragment of an IL-11 receptor may be of any length (by number of amino acids), although may optionally be at least 25% of the length of the mature IL-11Rα and have a maximum length of one of 50%, 75%, 80%, 85%, 90%, 91%, 92%, 93%, 94%, 95%, 96%, 97%, 98%, or 99% of the length of the mature IL-11Rα. A fragment of an IL-11 receptor fragment may have a minimum length of 10 amino acids, and a maximum length of one of 15, 20, 25, 30, 40, 50, 100, 110, 120, 130, 140, 150, 160, 170, 180, 190, 200, 250, 300, 400, or 415 amino acids.

IL-11 Signalling

IL-11 binds to IL-11Rα with low affinity (Kd ~10 nmol/L), and interaction between these binding partners alone is insufficient to transduce a biological signal. The generation of a high affinity receptor (Kd ~400 to 800 pmol/L) capable of signal transduction requires co-expression of the IL-11Rα and gp130 (Curtis et al (Blood 1997 Dec. 1; 90 (11):4403-12; Hilton et al., EMBO J 13:4765, 1994; Nandurkar et al., Oncogene 12:585, 1996). Binding of IL-11 to cell-surface IL-11Rα induces heterodimerization, tyrosine phosphorylation, activation of gp130 and downstream signalling, predominantly through the mitogen-activated protein kinase (MAPK)-cascade and the Janus kinase/signal transducer and activator of transcription (Jak/STAT) pathway (Garbers and Scheller, supra).

In principle, a soluble IL-11Rα can also form biologically active soluble complexes with IL-11 (Pflanz et al., 1999 FEBS Lett, 450, 117-122) raising the possibility that, similar to IL-6, IL-11 may in some instances bind soluble IL-11Rα prior to binding cell-surface gp130 (Garbers and Scheller, supra). Curtis et al (Blood 1997 Dec. 1; 90 (11):4403-12) describe expression of a soluble murine IL-11 receptor alpha chain (sIL-11R) and examined signalling in cells expressing gp130. In the presence of gp130 but not transmembrane IL-11R the sIL-11R mediated IL-11 dependent differentiation of M1 leukemic cells and proliferation in Ba/F3 cells and early intracellular events including phosphorylation of gp130, STAT3 and SHP2 similar to signalling through transmembrane IL-11R. Activation of signalling through cell-membrane bound gp130 by IL-11 bound to soluble IL-11Rα has recently been demonstrated (Lokau et al., 2016 Cell Reports 14, 1761-1773). This so-called IL-11 trans signalling may be a very important component of IL-11-mediated signalling, and may even be the most common form of IL-11-mediated signalling, because whilst the expression of IL-11Rα is restricted to a relatively small subset of cell types, gp130 is expressed on a wide range of cell types.

As used herein, "IL-11 signalling" and "IL-11-mediated signalling" refers to signalling mediated by binding of IL-11, a fragment thereof having the function of the mature IL-11 molecule, or a complex comprising IL-11/a fragment thereof having the function of the mature IL-11 molecule to a receptor for IL-11.

As used herein, 'IL-11 trans signalling' is used to refer to signalling which is triggered by binding of IL-11 bound to IL-11Rα, to gp130. The IL-11 may be bound to IL-11Rα as a non-covalent complex. The gp130 is membrane-bound and expressed by the cell in which signalling occurs following binding of the IL-11:IL-11Rα complex to gp130. In some embodiments the IL-11Rα may be a soluble IL-11Rα. In some embodiments, the soluble IL-11Rα is a soluble (secreted) isoform of IL-11Rα (e.g. lacking a transmembrane domain). In some embodiments, the soluble IL-11Rα is the liberated product of proteolytic cleavage of the extracellular domain of cell membrane bound IL-11Rα. In some embodiments, the IL-11Rα may be cell membrane-bound, and signalling through gp130 may be triggered by binding of IL-11 bound to cell-membrane-bound IL-11Rα, termed "IL-11 cis signalling".

IL-11-mediated signalling has been shown to stimulate haematopoiesis and thrombopoiesis, stimulate osteoclast activity, stimulate neurogenesis, inhibit adipogenesis, reduce pro inflammatory cytokine expression, modulate extracellular matrix (ECM) metabolism, and mediate normal growth control of gastrointestinal epithelial cells (Du and Williams, supra).

The physiological role of Interleukin 11 (IL-11) remains unclear. IL-11 has been most strongly linked with activation of haematopoietic cells and with platelet production, but has also been suggested to be pro-inflammatory as well as anti-inflammatory, pro-angiogenic and important for neoplasia. It is known that TGFβ1 or tissue injury can induce IL-11 expression (Zhu, M. et al. PLOS ONE 10, (2015); Yashiro, R. et al. J. Clin. Periodontol. 33, 165-71 (2006); Obana, M. et al. Circulation 121, 684-91 (2010); Tang, W et al. J. Biol. Chem. 273, 5506-13 (1998)).

IL-11 is an important post-transcriptional modulator of TGFβ1-mediated signalling. TGFβ1 has been shown to stimulate the AP-1 promoter region of IL-11, and TGFβ1-induced secretion of IL-11 has been shown to induce activation of ERK p42/44 and p38 MAP kinases in intestinal myofibroblasts (Bamba et al. Am J Physiol Gastrointest Liver Physiol. (2003) (285(3):G529-38). MAP kinase inhibitors are able to significantly reduce TGFβ1-induced IL-11 secretion, and p38 MAP kinase-mediated stabilization of mRNA has been shown to be critical for TGFβ1-induced secretion of IL-11.

IL-11 mediated signalling has recently been demonstrated to play a key role in fibrotic processes in a wide variety of tissues; see for example WO 2017/103108 A1 and Schafer et al. (2017) Nature 552: 110-115, both of which are hereby incorporated by reference in their entirety.

WO 2017/103108 A1 (hereby incorporated by reference in its entirety) reports a pro-fibrotic role for IL-11, and establishes the therapeutic utility of antagonists of IL-11 mediated signalling in the treatment/prevention of fibrosis. Example 2 and FIGS. 7A and 7B of WO 2017/103108 A1 demonstrate that incubation of primary human atrial fibroblasts with recombinant human IL-11 increases deposition of collagen by fibroblasts, a well-established fibrotic process. Treatment with neutralising anti-IL-11 antibody (but not isotype control antibody) was shown to abrogate collagen production induced by stimulation of the fibroblasts with TGFβ1 (a known pro-fibrotic stimulus). Example 3 and FIG. 10 of WO 2017/103108 A1 further demonstrate the ability of neutralising anti-IL-11 antibody to abrogate increased collagen production by human atrial fibroblasts in response to various other pro-fibrotic stimuli (ANG2, PDGF, ET-1). Example 5.2 and FIGS. 20A-20E of WO 2017/103108 A1 provide further data supporting a pro-fibrotic role for IL-11 in heart tissue. Human atrial fibroblasts were shown to display significantly increased production of extracellular matrix components (collagen, periostin) and increased expression of pro-fibrotic markers (αSMA, IL-6, MMP2, TIMP1) in response to treatment with human IL-11 protein, in the same way as production of these factors is increased in response to treatment with the pro-fibrotic stimulus TGFβ1. Example 5.3.1 and FIGS. 38A to 38D of WO 2017/103108 A1 likewise show increased production of extracellular matrix components and increased expression of fibrotic markers by human primary liver fibroblasts in response to treatment with human IL-11, and also the ability of neutralising anti-IL-11 antibody to abrogate the profibrotic effects of stimulation with TGFβ1. FIGS. 22A to 22F and 23A and 23B of WO 2017/103108 A1 show that TGFβ1-mediated fibrosis can be inhibited by treatment with neutralising anti-IL-11 antibody, and FIG. 24 moreover shows that IL-11-binding decoy receptor molecules, neutralising anti-IL-11Rα antibodies and oligonucleotides encoding siRNA for antisense knockdown of IL-11 and IL-11RA gene expression are similarly able to inhibit TGFβ1-mediated transition of fibroblasts to myofibroblasts (fibrosis effector cells). Further data showing inhibition of the TGFβ1-mediated fibrotic response using decoy IL-11 receptors is provided at FIGS. 32A and 32B of WO 2017/103108 A1. Example 5.3.3 and FIGS. 21B and 21C of WO 2017/103108 A1 provide in vivo data demonstrating IL-11 to be pro-fibrotic in a variety of tissues. Injection of mice with recombinant mouse IL-11 caused an increase in the relative weight of heart, kidney, lung and liver (FIG. 21B), and that this was associated with increased collagen content in these tissues (FIG. 21C). Further in vivo data supporting a pro-fibrotic role for IL-11 is provided at Examples 7.2 and 7.3, and FIGS. 27A to 27D and FIG. 28 of WO 2017/103108 A1. These experiments show that IL-11 RA knockout mice are protected from fibrosis of the heart and kidney tissues induced by profibrotic stimuli, indicating signalling through the IL-11 receptor as an important mediator of fibrotic processes. Further still, FIGS. 31A and 31B, summarised at the legend to FIG. 31 of WO 2017/103108 A1 report that more fibrosis was detected in eye sections obtained from wildtype mice than IL-11RA knockout mice at 7 days following trabeculectomy. Thus WO 2017/103108 A1 provides abundant data from both in vitro and in vivo studies proving that IL-11/IL-11R signalling is a key mediator of fibrosis in a wide range of tissues, and demonstrates that inhibition of IL-11 mediated signalling reduces fibrosis, as determined by analysis of a variety of markers of the fibrotic response.

Antigen-Binding Molecules Capable of Binding to IL-11

The present invention provides antigen-binding molecules capable of binding to IL-11.

An "antigen-binding molecule" refers to a molecule which is capable of binding to a target antigen, and encompasses monoclonal antibodies, polyclonal antibodies, monospecific and multispecific antibodies (e.g., bispecific antibodies), and antibody fragments (e.g. Fv, scFv, Fab, scFab, F(ab')$_2$, Fab$_2$, diabodies, triabodies, scFv-Fc, minibodies, single domain antibodies (e.g. VhH), etc.), as long as they display binding to the relevant target molecule(s). By "antibody" we include fragments and derivatives thereof, including synthetic antibodies and fragments. As used herein, an antibody is a polypeptide capable of binding specifically to the relevant target molecule (i.e. the antigen for which the antibody is specific). Antibodies and antigen-binding molecules according to the present invention may be provided in isolated form.

In view of contemporary techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimeric antibodies are discussed by Neuberger et al (1988, 8th International Biotechnology Symposium Part 2, 792-799).

Monoclonal antibodies (mAbs) are useful in the methods of the invention and are a homogenous population of antibodies specifically targeting a single epitope on an antigen.

Antigen binding fragments of antibodies, such as Fab and Fab$_2$ fragments may also be used/provided as can genetically engineered antibodies and antibody fragments. The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parent antibody (Morrison et al (1984) Proc. Natl. Acad. Sd. USA 81, 6851-6855).

In some embodiments, the antigen-binding molecule of the invention is a fully human antibody/antibody fragment. A fully human antibody/antibody fragment is encoded by human nucleic acid sequence(s). Fully human antibodies/ antibody fragments are devoid of non-human amino acid sequences.

The two most commonly employed techniques to the production of fully human antibodies are (i) phage display, in which human antibody genes are expressed in phage display libraries, and (ii) production of antibodies in transgenic mice engineered to have human antibody genes (described in Park and Smolen Advances in Protein Chemistry (2001) 56: 369-421). Briefly, in the human antibody gene-phage display technique, genes encoding the VH and VL chains are generated by PCR amplification and cloning from "naive" human lymphocytes, and assembled into a library from which they can be expressed either as disulfide-linked Fab fragments or as single-chain Fv (scFv) fragments. The Fab- or scFv-encoding genes are fused to a surface coat protein of filamentous bacteriophage and Fab or scFv capable of binding to the target of interest can then be identified by screening the library with antigen. Molecular evolution or affinity maturation procedures can be employed to enhance the affinity of the Fab/scFv fragment. In the transgenic mouse technique, mice in which the endogenous murine Ig gene loci have been replaced by homologous recombination with their human homologues are immunized with antigen, and monoclonal antibody is prepared by conventional hybridoma technology, to yield fully human monoclonal antibody.

In some embodiments, the antigen-binding molecule of the invention is a murine antibody/antibody fragment. In some embodiments the antibody/antibody fragment may be prepared by phage display using a human naïve antibody gene library.

In some embodiments, the antigen-binding molecule of the invention is a mouse/human chimeric antibody/antibody fragment (e.g., an antigen-binding molecule comprising murine variable domains and human constant regions). In some embodiments, the antigen-binding molecule is a humanised antibody/antibody fragment (e.g., an antigen-binding molecule comprising murine CDRs and human framework and constant regions).

A mouse/human chimeric antigen-binding molecule can be prepared from a mouse monoclonal antibody by the process of chimerisation, e.g. as described in Human Monoclonal Antibodies: Methods and Protocols, Michael Steinitz (Editor), Methods in Molecular Biology 1060, Springer Protocols, Humana Press (2014), in Chapter 8 thereof, in particular section 3 of Chapter 8.

A humanised antigen-binding molecule can be prepared from a mouse antibody by the process of humanization, e.g. as described in Human Monoclonal Antibodies: Methods and Protocols, Michael Steinitz (Editor), Methods in Molecular Biology 1060, Springer Protocols, Humana Press (2014), in Chapter 7 thereof, in particular section 3.1 of Chapter 7 entitled 'Antibody Humanization'.

The antigen-binding molecule of the present invention comprises a moiety capable of binding to a target antigen(s). In some embodiments, the moiety capable of binding to a target antigen comprises an antibody heavy chain variable region (VH) and an antibody light chain variable region (VL) of an antibody capable of specific binding to the target antigen. In some embodiments, the moiety capable of binding to a target antigen comprises or consists of an aptamer capable of binding to the target antigen, e.g. a nucleic acid aptamer (reviewed, for example, in Zhou and Rossi Nat Rev Drug Discov. 2017 16(3):181-202). In some embodiments, the moiety capable of binding to a target antigen comprises or consists of a antigen-binding peptide/polypeptide, e.g. a peptide aptamer, thioredoxin, monobody, anticalin, Kunitz domain, avimer, knottin, fynomer, atrimer, DARPin, affibody, nanobody (i.e. a single-domain antibody (sdAb)) affilin, armadillo repeat protein (ArmRP), OBody or fibronectin—reviewed e.g. in Reverdatto et al., Curr Top Med Chem. 2015; 15(12): 1082-1101, which is hereby incorporated by reference in its entirety (see also e.g. Boersma et al., J Biol Chem (2011) 286:41273-85 and Emanuel et al., Mabs (2011) 3:38-48).

The antigen-binding molecules of the present invention generally comprise an antigen-binding domain comprising a VH and a VL of an antibody capable of specific binding to the target antigen. The antigen-binding domain formed by a VH and a VL may also be referred to herein as an Fv region.

An antigen-binding molecule may be, or may comprise, an antigen-binding polypeptide, or an antigen-binding polypeptide complex. An antigen-binding molecule may comprise more than one polypeptide which together form an antigen-binding domain. The polypeptides may associate covalently or non-covalently. In some embodiments the polypeptides form part of a larger polypeptide comprising the polypeptides (e.g. in the case of scFv comprising VH and VL, or in the case of scFab comprising VH-CH1 and VL-CL).

An antigen-binding molecule may refer to a non-covalent or covalent complex of more than one polypeptide (e.g. 2, 3, 4, 6, or 8 polypeptides), e.g. an IgG-like antigen-binding molecule comprising two heavy chain polypeptides and two light chain polypeptides.

The antigen-binding molecules of the present invention may be designed and prepared using the sequences of monoclonal antibodies (mAbs) capable of binding to IL-11. Antigen-binding regions of antibodies, such as single chain variable fragment (scFv), Fab and F(ab')$_2$ fragments may also be used/provided. An "antigen-binding region" is any fragment of an antibody which is capable of binding to the target for which the given antibody is specific.

Antibodies generally comprise six complementarity-determining regions CDRs; three in the heavy chain variable (VH) region: HC-CDR1, HC-CDR2 and HC-CDR3, and three in the light chain variable (VL) region: LC-CDR1, LC-CDR2, and LC-CDR3. The six CDRs together define the paratope of the antibody, which is the part of the antibody which binds to the target antigen.

The VH region and VL region comprise framework regions (FRs) either side of each CDR, which provide a scaffold for the CDRs. From N-terminus to C-terminus, VH regions comprise the following structure: N term-[HC-FR1]-[HC-CDR1]-[HC-FR2]-[HC-CDR2]-[HC-FR3]-[HC-CDR3]-[HC-FR4]-C term; and VL regions comprise the following structure: N term-[LC-FR1]-[LC-CDR1]-[LC-FR2]-[LC-CDR2]-[LC-FR3]-[LC-CDR3]-[LC-FR4]-C term.

There are several different conventions for defining antibody CDRs and FRs, such as those described in Kabat et al., Sequences of Proteins of Immunological Interest, 5th Ed. Public Health Service, National Institutes of Health, Bethesda, Md. (1991), Chothia et al., J. Mol. Biol. 196:901-917 (1987), and VBASE2, as described in Retter et al., Nucl. Acids Res. (2005) 33 (suppl 1): D671-D674. The CDRs and FRs of the VH regions and VL regions of the antibody clones described herein were defined according to the Kabat system.

In some embodiments, the antigen-binding molecule comprises the CDRs of an antigen-binding molecule which is capable of binding to IL-11. In some embodiments, the antigen-binding molecule comprises the FRs of an antigen-binding molecule which is capable of binding to IL-11. In some embodiments, the antigen-binding molecule comprises the CDRs and the FRs of an antigen-binding molecule which is capable of binding to IL-11. That is, in some embodiments the antigen-binding molecule comprises the VH region and the VL region of an antigen-binding molecule which is capable of binding to IL-11.

In some embodiments the antigen-binding molecule comprises a VH region and a VL region which is, or which is derived from, the VH/VL region of a IL-11-binding antibody clone described herein (e.g. anti-IL-11 antibody clone 01A, 01G, 01I, 01L, 01Q, 01S, 01T, 01V, 02A, 02G, 02I, 02L, 02Q, 02S, 02T, 02V, 03A, 03G, 03I, 03L, 03Q, 03S, 03T, 03V, BSN-3C6 (comprising 3C6 VH 1, 3C6 VH 2, 3C6 VH 2.1, 3C6 VH 2.2, 3C6 VH 2.3, 3C6 VH 2.4 or 3C6 VH 2.5 and 3C6 VL 1, 3C6 VL 2, 3C6 VL 1.1, 3C6 VL 1.2, 3C6 VL 1.3, 3C6 VL 1.4, 3C6 VL 2.1, 3C6 VL 2.2, 3C6 VL 2.3 or 3C6 VL 2.4), BSN-1H2, BSN-7D4, BSN-8H11).

In some embodiments the antigen-binding molecule comprises a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:7, wherein the VL region comprises a substitution of the cysteine residue at position 91 of SEQ ID NO:7 to an amino acid other than cysteine. In some embodiments the amino acid other than cysteine is selected from alanine, glycine, isoleucine, leucine, glutamine, serine, threonine or valine.

In some embodiments the antigen-binding molecule comprises a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:9, wherein the VL region comprises a substitution of the cysteine residue at position 91 of SEQ ID NO:9 to an amino acid other than cysteine. In some embodiments the amino acid other than cysteine is selected from alanine, glycine, isoleucine, leucine, glutamine, serine, threonine or valine.

In some embodiments the antigen-binding molecule comprises a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:11, wherein the VL region comprises a substitution of the cysteine residue at position 91 of SEQ ID NO:11 to an amino acid other than cysteine. In some embodiments the amino acid other than cysteine is selected from alanine, glycine, isoleucine, leucine, glutamine, serine, threonine or valine.

In some embodiments the antigen-binding molecule comprises a VH region having less than 100% sequence identity to the amino acid sequence of SEQ ID NO:91. In some embodiments the antigen-binding molecule does not comprise a VH region comprising or consisting of the amino acid sequence of SEQ ID NO:91. In some embodiments the antigen-binding molecule does not comprise a peptide/polypeptide comprising or consisting of the amino acid sequence of SEQ ID NO:91.

In some embodiments the antigen-binding molecule comprises a VL region having less than 100% sequence identity to the amino acid sequence of SEQ ID NO:93. In some embodiments the antigen-binding molecule does not comprise a VL region comprising or consisting of the amino acid sequence of SEQ ID NO:93. In some embodiments the antigen-binding molecule does not comprise a peptide/polypeptide comprising or consisting of the amino acid sequence of SEQ ID NO:93.

In some embodiments the antigen-binding molecule comprises a VH region according to one (1) or (2) below:
  (1) (01X) a VH region incorporating the following CDRs:
    HC-CDR1 having the amino acid sequence of SEQ ID NO:36
    HC-CDR2 having the amino acid sequence of SEQ ID NO:38
    HC-CDR3 having the amino acid sequence of SEQ ID NO:39,
    or a variant thereof in which one or two or three amino acids in one or more of HC-CDR1, HC-CDR2, or HC-CDR3 are substituted with another amino acid.
  (2) (02X, 03X) a VH region incorporating the following CDRs:
    HC-CDR1 having the amino acid sequence of SEQ ID NO:37
    HC-CDR2 having the amino acid sequence of SEQ ID NO:38
    HC-CDR3 having the amino acid sequence of SEQ ID NO:40,
    or a variant thereof in which one or two or three amino acids in one or more of HC-CDR1, HC-CDR2, or HC-CDR3 are substituted with another amino acid.

In some embodiments the antigen-binding molecule comprises a VH region according to one of (3) to (5) below:
  (3) (01X) a VH region incorporating the following FRs:
    HC-FR1 having the amino acid sequence of SEQ ID NO:65
    HC-FR2 having the amino acid sequence of SEQ ID NO:67
    HC-FR3 having the amino acid sequence of SEQ ID NO:68
    HC-FR4 having the amino acid sequence of SEQ ID NO:70,
    or a variant thereof in which one or two or three amino acids in one or more of HC-FR1, HC-FR2, HC-FR3, or HC-FR4 are substituted with another amino acid.
  (4) (02X) a VH region incorporating the following FRs:
    HC-FR1 having the amino acid sequence of SEQ ID NO:65
    HC-FR2 having the amino acid sequence of SEQ ID NO:67
    HC-FR3 having the amino acid sequence of SEQ ID NO:69

HC-FR4 having the amino acid sequence of SEQ ID NO:70,
or a variant thereof in which one or two or three amino acids in one or more of HC-FR1, HC-FR2, HC-FR3, or HC-FR4 are substituted with another amino acid.
(5) (03X) a VH region incorporating the following FRs:
HC-FR1 having the amino acid sequence of SEQ ID NO:66
HC-FR2 having the amino acid sequence of SEQ ID NO:67
HC-FR3 having the amino acid sequence of SEQ ID NO:69
HC-FR4 having the amino acid sequence of SEQ ID NO:70,
or a variant thereof in which one or two or three amino acids in one or more of HC-FR1, HC-FR2, HC-FR3, or HC-FR4 are substituted with another amino acid.

In some embodiments the antigen-binding molecule comprises a VH region comprising the CDRs according to (1) or (2) above, and the FRs according to one of (3) to (5) above.

In some embodiments the antigen-binding molecule comprises a VH region according to one of (6) to (8) below:
(6) (01X) a VH region comprising the CDRs according to (1) and the FRs according to (3).
(7) (02X) a VH region comprising the CDRs according to (2) and the FRs according to (4).
(8) (03X) a VH region comprising the CDRs according to (2) and the FRs according to (5).

In some embodiments the antigen-binding molecule comprises a VH region according to one of (9) to (1) below:
(9) (01X) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:6.
(10) (02X) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:8.
(11) (03X) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:10.

In some embodiments the antigen-binding molecule comprises a VL region according to one (12) to (38) below:
(12) (01X) a VL region incorporating the following CDRs:
LC-CDR1 having the amino acid sequence of SEQ ID NO:41
LC-CDR2 having the amino acid sequence of SEQ ID NO:44
LC-CDR3 having the amino acid sequence of SEQ ID NO:80,
or a variant thereof in which one or two or three amino acids in one or more of LC-CDR1, LC-CDR2, or LC-CDR3 are substituted with another amino acid.
(13) (01A) a VL region incorporating the following CDRs:
LC-CDR1 having the amino acid sequence of SEQ ID NO:41
LC-CDR2 having the amino acid sequence of SEQ ID NO:44
LC-CDR3 having the amino acid sequence of SEQ ID NO:48,
or a variant thereof in which one or two or three amino acids in one or more of LC-CDR1, LC-CDR2, or LC-CDR3 are substituted with another amino acid.
(14) (01G) a VL region incorporating the following CDRs:
LC-CDR1 having the amino acid sequence of SEQ ID NO:41
LC-CDR2 having the amino acid sequence of SEQ ID NO:44
LC-CDR3 having the amino acid sequence of SEQ ID NO:49,
or a variant thereof in which one or two or three amino acids in one or more of LC-CDR1, LC-CDR2, or LC-CDR3 are substituted with another amino acid.
(15) (01I) a VL region incorporating the following CDRs:
LC-CDR1 having the amino acid sequence of SEQ ID NO:41
LC-CDR2 having the amino acid sequence of SEQ ID NO:44
LC-CDR3 having the amino acid sequence of SEQ ID NO:50,
or a variant thereof in which one or two or three amino acids in one or more of LC-CDR1, LC-CDR2, or LC-CDR3 are substituted with another amino acid.
(16) (01L) a VL region incorporating the following CDRs:
LC-CDR1 having the amino acid sequence of SEQ ID NO:41
LC-CDR2 having the amino acid sequence of SEQ ID NO:44
LC-CDR3 having the amino acid sequence of SEQ ID NO:51,
or a variant thereof in which one or two or three amino acids in one or more of LC-CDR1, LC-CDR2, or LC-CDR3 are substituted with another amino acid.
(17) (01Q) a VL region incorporating the following CDRs:
LC-CDR1 having the amino acid sequence of SEQ ID NO:41
LC-CDR2 having the amino acid sequence of SEQ ID NO:44
LC-CDR3 having the amino acid sequence of SEQ ID NO:52,
or a variant thereof in which one or two or three amino acids in one or more of LC-CDR1, LC-CDR2, or LC-CDR3 are substituted with another amino acid.
(18) (01S) a VL region incorporating the following CDRs:
LC-CDR1 having the amino acid sequence of SEQ ID NO:41
LC-CDR2 having the amino acid sequence of SEQ ID NO:44
LC-CDR3 having the amino acid sequence of SEQ ID NO:53,
or a variant thereof in which one or two or three amino acids in one or more of LC-CDR1, LC-CDR2, or LC-CDR3 are substituted with another amino acid.
(19) (01T) a VL region incorporating the following CDRs:
LC-CDR1 having the amino acid sequence of SEQ ID NO:41
LC-CDR2 having the amino acid sequence of SEQ ID NO:44
LC-CDR3 having the amino acid sequence of SEQ ID NO:54, or a variant thereof in which one or two or three amino acids in one or more of LC-CDR1, LC-CDR2, or LC-CDR3 are substituted with another amino acid.

(20) (01V) a VL region incorporating the following CDRs:
LC-CDR1 having the amino acid sequence of SEQ ID NO:41
LC-CDR2 having the amino acid sequence of SEQ ID NO:44
LC-CDR3 having the amino acid sequence of SEQ ID NO:55,
or a variant thereof in which one or two or three amino acids in one or more of LC-CDR1, LC-CDR2, or LC-CDR3 are substituted with another amino acid.

(21) (02X) a VL region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:81,
or a variant thereof in which one or two or three amino acids in one or more of LC-CDR1, LC-CDR2, or LC-CDR3 are substituted with another amino acid.

(22) (02A) a VL region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:57,
or a variant thereof in which one or two or three amino acids in one or more of LC-CDR1, LC-CDR2, or LC-CDR3 are substituted with another amino acid.

(23) (02G) a VL region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:58,
or a variant thereof in which one or two or three amino acids in one or more of LC-CDR1, LC-CDR2, or LC-CDR3 are substituted with another amino acid.

(24) (02I) a VL region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:59,
or a variant thereof in which one or two or three amino acids in one or more of LC-CDR1, LC-CDR2, or LC-CDR3 are substituted with another amino acid.

(25) (02L) a VL region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:60,
or a variant thereof in which one or two or three amino acids in one or more of LC-CDR1, LC-CDR2, or LC-CDR3 are substituted with another amino acid.

(26) (02Q) a VL region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:61,
or a variant thereof in which one or two or three amino acids in one or more of LC-CDR1, LC-CDR2, or LC-CDR3 are substituted with another amino acid.

(27) (02S) a VL region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:62,
or a variant thereof in which one or two or three amino acids in one or more of LC-CDR1, LC-CDR2, or LC-CDR3 are substituted with another amino acid.

(28) (02T) a VL region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:63,
or a variant thereof in which one or two or three amino acids in one or more of LC-CDR1, LC-CDR2, or LC-CDR3 are substituted with another amino acid.

(29) (02V) a VL region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:64,
or a variant thereof in which one or two or three amino acids in one or more of LC-CDR1, LC-CDR2, or LC-CDR3 are substituted with another amino acid.

(30) (03X) a VL region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:80,
or a variant thereof in which one or two or three amino acids in one or more of LC-CDR1, LC-CDR2, or LC-CDR3 are substituted with another amino acid.

(31) (03A) a VL region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:48, or a variant thereof in which one or two or three amino acids in one or more of LC-CDR1, LC-CDR2, or LC-CDR3 are substituted with another amino acid.

(32) (03G) a VL region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:49,
or a variant thereof in which one or two or three amino acids in one or more of LC-CDR1, LC-CDR2, or LC-CDR3 are substituted with another amino acid.

(33) (03I) a VL region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:50,
or a variant thereof in which one or two or three amino acids in one or more of LC-CDR1, LC-CDR2, or LC-CDR3 are substituted with another amino acid.

(34) (03L) a VL region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:51,
or a variant thereof in which one or two or three amino acids in one or more of LC-CDR1, LC-CDR2, or LC-CDR3 are substituted with another amino acid.

(35) (03Q) a VL region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:52,
or a variant thereof in which one or two or three amino acids in one or more of LC-CDR1, LC-CDR2, or LC-CDR3 are substituted with another amino acid.

(36) (03S) a VL region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:53,
or a variant thereof in which one or two or three amino acids in one or more of LC-CDR1, LC-CDR2, or LC-CDR3 are substituted with another amino acid.

(37) (03T) a VL region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:54,
or a variant thereof in which one or two or three amino acids in one or more of LC-CDR1, LC-CDR2, or LC-CDR3 are substituted with another amino acid.

(38) (03V) a VL region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:55,
or a variant thereof in which one or two or three amino acids in one or more of LC-CDR1, LC-CDR2, or LC-CDR3 are substituted with another amino acid.

In some embodiments the antigen-binding molecule comprises a VH region incorporating the CDRs according to (2) and a VL region incorporating the CDRs according to (22).

In some embodiments the antigen-binding molecule comprises a VL region according to one of (39) to (41) below:
(39) (01X) a VL region incorporating the following FRs:
LC-FR1 having the amino acid sequence of SEQ ID NO:71
LC-FR2 having the amino acid sequence of SEQ ID NO:74
LC-FR3 having the amino acid sequence of SEQ ID NO:76
LC-FR4 having the amino acid sequence of SEQ ID NO:77,
or a variant thereof in which one or two or three amino acids in one or more of LC-FR1, LC-FR2, LC-FR3, or LC-FR4 are substituted with another amino acid.

(40) (02X) a VL region incorporating the following FRs:
LC-FR1 having the amino acid sequence of SEQ ID NO:72
LC-FR2 having the amino acid sequence of SEQ ID NO:75
LC-FR3 having the amino acid sequence of SEQ ID NO:76
LC-FR4 having the amino acid sequence of SEQ ID NO:78,
or a variant thereof in which one or two or three amino acids in one or more of LC-FR1, LC-FR2, LC-FR3, or LC-FR4 are substituted with another amino acid.

(41) (03X) a VL region incorporating the following FRs:
LC-FR1 having the amino acid sequence of SEQ ID NO:73
LC-FR2 having the amino acid sequence of SEQ ID NO:74
LC-FR3 having the amino acid sequence of SEQ ID NO:76
LC-FR4 having the amino acid sequence of SEQ ID NO:79,
or a variant thereof in which one or two or three amino acids in one or more of LC-FR1, LC-FR2, LC-FR3, or LC-FR4 are substituted with another amino acid.

In some embodiments the antigen-binding molecule comprises a VL region comprising the CDRs according to one of (12) to (38) above, and the FRs according to one of (39) to (41) above.

In some embodiments the antigen-binding molecule comprises a VL region according to one of (42) to (68) below:
(42) (01X) a VL region comprising the CDRs according to (12) and the FRs according to (39).
(43) (01A) a VL region comprising the CDRs according to (13) and the FRs according to (39).
(44) (01G) a VL region comprising the CDRs according to (14) and the FRs according to (39).
(45) (01I) a VL region comprising the CDRs according to (15) and the FRs according to (39).

(46) (01L) a VL region comprising the CDRs according to (16) and the FRs according to (39).

(47) (01Q) a VL region comprising the CDRs according to (17) and the FRs according to (39).

(48) (01S) a VL region comprising the CDRs according to (18) and the FRs according to (39).

(49) (01T) a VL region comprising the CDRs according to (19) and the FRs according to (39).

(50) (01V) a VL region comprising the CDRs according to (20) and the FRs according to (39).

(51) (02X) a VL region comprising the CDRs according to (21) and the FRs according to (40).

(52) (02A) a VL region comprising the CDRs according to (22) and the FRs according to (40).

(53) (02G) a VL region comprising the CDRs according to (23) and the FRs according to (40).

(54) (02I) a VL region comprising the CDRs according to (24) and the FRs according to (40).

(55) (02L) a VL region comprising the CDRs according to (25) and the FRs according to (40).

(56) (02Q) a VL region comprising the CDRs according to (26) and the FRs according to (40).

(57) (02S) a VL region comprising the CDRs according to (27) and the FRs according to (40).

(58) (02T) a VL region comprising the CDRs according to (28) and the FRs according to (40).

(59) (02V) a VL region comprising the CDRs according to (29) and the FRs according to (40).

(60) (03X) a VL region comprising the CDRs according to (30) and the FRs according to (41).

(61) (03A) a VL region comprising the CDRs according to (31) and the FRs according to (41).

(62) (03G) a VL region comprising the CDRs according to (32) and the FRs according to (41).

(63) (03I) a VL region comprising the CDRs according to (33) and the FRs according to (41).

(64) (03L) a VL region comprising the CDRs according to (34) and the FRs according to (41).

(65) (03Q) a VL region comprising the CDRs according to (35) and the FRs according to (41).

(66) (03S) a VL region comprising the CDRs according to (36) and the FRs according to (41).

(67) (03T) a VL region comprising the CDRs according to (37) and the FRs according to (41).

(68) (03V) a VL region comprising the CDRs according to (38) and the FRs according to (41).

In some embodiments the antigen-binding molecule comprises a VL region according to one of (69) to (95) below:

(69) (01X) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:82.

(70) (01A) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:12.

(71) (01G) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:13.

(72) (01I) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:14.

(73) (01L) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:15.

(74) (01Q) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:16.

(75) (01S) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:17.

(76) (01T) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:18.

(77) (01V) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:19.

(78) (02X) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:83.

(79) (02A) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:20.

(80) (02G) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:21.

(81) (02I) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:22.

(82) (02L) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:23.

(83) (02Q) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:24.

(84) (02S) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:25.

(85) (02T) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:26.

(86) (02V) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:27.

(87) (03X) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:84.

(88) (03A) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:28.

(89) (03G) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:29.

(90) (03I) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:30.

(91) (03L) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:31.

(92) (03Q) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:32.

(93) (03S) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:33.

(94) (03T) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:34.

(95) (03V) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:35.

In some embodiments the antigen-binding molecule comprises a VH region according to any one of (1) to (11) above, and a VL region according to any one of (12) to (95) above.

In some embodiments the antigen-binding molecule comprises a VH region according to (7) or (10) and a VH region according to (52) or (79). In some embodiments the antigen-binding molecule comprises a VH region according to (7) and a VH region according to (52). In some embodiments the antigen-binding molecule comprises a VH region according to (10) and a VL region according to (79). In some embodiments the antigen-binding molecule comprises an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:210. In some embodiments the antigen-binding molecule comprises a polypeptide comprising or consisting of an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:210.

In some embodiments the antigen-binding molecule comprises a VH region according to (96):

(96) (3C6 VH 1, 3C6 VH 2, 3C6 VH 2.1, 3C6 VH 2.2, 3C6 VH 2.3, 3C6 VH 2.4, 3C6 VH 2.5) a VH region incorporating the following CDRs:
  HC-CDR1 having the amino acid sequence of SEQ ID NO:95
  HC-CDR2 having the amino acid sequence of SEQ ID NO:96
  HC-CDR3 having the amino acid sequence of SEQ ID NO:97,
  or a variant thereof in which one or two or three amino acids in one or more of HC-CDR1, HC-CDR2, or HC-CDR3 are substituted with another amino acid.

In some embodiments the antigen-binding molecule comprises a VH region according to one of (97) to (103) below:

(97) (3C6 VH 1) a VH region incorporating the following FRs:
  HC-FR1 having the amino acid sequence of SEQ ID NO:104
  HC-FR2 having the amino acid sequence of SEQ ID NO:106
  HC-FR3 having the amino acid sequence of SEQ ID NO:107
  HC-FR4 having the amino acid sequence of SEQ ID NO:108,
  or a variant thereof in which one or two or three amino acids in one or more of HC-FR1, HC-FR2, HC-FR3, or HC-FR4 are substituted with another amino acid.

(98) (3C6 VH 2) a VH region incorporating the following FRs:
  HC-FR1 having the amino acid sequence of SEQ ID NO:105

HC-FR2 having the amino acid sequence of SEQ ID NO:106
HC-FR3 having the amino acid sequence of SEQ ID NO:107
HC-FR4 having the amino acid sequence of SEQ ID NO:108,
or a variant thereof in which one or two or three amino acids in one or more of HC-FR1, HC-FR2, HC-FR3, or HC-FR4 are substituted with another amino acid.
(99) (3C6 VH 2.1) a VH region incorporating the following FRs:
HC-FR1 having the amino acid sequence of SEQ ID NO:129
HC-FR2 having the amino acid sequence of SEQ ID NO:132
HC-FR3 having the amino acid sequence of SEQ ID NO:136
HC-FR4 having the amino acid sequence of SEQ ID NO:140,
or a variant thereof in which one or two or three amino acids in one or more of HC-FR1, HC-FR2, HC-FR3, or HC-FR4 are substituted with another amino acid.
(100) (3C6 VH 2.2) a VH region incorporating the following FRs:
HC-FR1 having the amino acid sequence of SEQ ID NO:130
HC-FR2 having the amino acid sequence of SEQ ID NO:133
HC-FR3 having the amino acid sequence of SEQ ID NO:137
HC-FR4 having the amino acid sequence of SEQ ID NO:140,
or a variant thereof in which one or two or three amino acids in one or more of HC-FR1, HC-FR2, HC-FR3, or HC-FR4 are substituted with another amino acid.
(101) (3C6 VH 2.3) a VH region incorporating the following FRs:
HC-FR1 having the amino acid sequence of SEQ ID NO:130
HC-FR2 having the amino acid sequence of SEQ ID NO:134
HC-FR3 having the amino acid sequence of SEQ ID NO:138
HC-FR4 having the amino acid sequence of SEQ ID NO:140,
or a variant thereof in which one or two or three amino acids in one or more of HC-FR1, HC-FR2, HC-FR3, or HC-FR4 are substituted with another amino acid.
(102) (3C6 VH 2.4) a VH region incorporating the following FRs:
HC-FR1 having the amino acid sequence of SEQ ID NO:131
HC-FR2 having the amino acid sequence of SEQ ID NO:134
HC-FR3 having the amino acid sequence of SEQ ID NO:139
HC-FR4 having the amino acid sequence of SEQ ID NO:140,
or a variant thereof in which one or two or three amino acids in one or more of HC-FR1, HC-FR2, HC-FR3, or HC-FR4 are substituted with another amino acid.
(103) (3C6 VH 2.5) a VH region incorporating the following FRs:
HC-FR1 having the amino acid sequence of SEQ ID NO:131
HC-FR2 having the amino acid sequence of SEQ ID NO:135
HC-FR3 having the amino acid sequence of SEQ ID NO:139
HC-FR4 having the amino acid sequence of SEQ ID NO:140,
or a variant thereof in which one or two or three amino acids in one or more of HC-FR1, HC-FR2, HC-FR3, or HC-FR4 are substituted with another amino acid.

In some embodiments the antigen-binding molecule comprises a VH region comprising the CDRs according to (96) above, and the FRs according to one of (97) to (103) above.

In some embodiments the antigen-binding molecule comprises a VH region according to one of (104) to (110) below:
(104) (3C6 VH 1) a VH region comprising the CDRs according to (96) and the FRs according to (97).
(105) (3C6 VH 2) a VH region comprising the CDRs according to (96) and the FRs according to (98).
(106) (3C6 VH 2.1) a VH region comprising the CDRs according to (96) and the FRs according to (99).
(107) (3C6 VH 2.2) a VH region comprising the CDRs according to (96) and the FRs according to (100).
(108) (3C6 VH 2.3) a VH region comprising the CDRs according to (96) and the FRs according to (101).
(109) (3C6 VH 2.4) a VH region comprising the CDRs according to (96) and the FRs according to (102).
(110) (3C6 VH 2.5) a VH region comprising the CDRs according to (96) and the FRs according to (103).

In some embodiments the antigen-binding molecule comprises a VH region according to one of (111) to (117) below:
(111) (3C6 VH 1) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:91.
(112) (3C6 VH 2) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:92.
(113) (3C6 VH 2.1) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:116.
(114) (3C6 VH 2.2) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:117.
(115) (3C6 VH 2.3) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:118.
(116) (3C6 VH 2.4) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:119.
(117) (3C6 VH 2.5) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:120.

In some embodiments the antigen-binding molecule comprises a VL region according to (118) or (119):

(118) (3C6 VL 1, 3C6 VL 1.1, 3C6 VL 1.2, 3C6 VL 1.3, 3C6 VL 1.4) a VL region incorporating the following CDRs:
LC-CDR1 having the amino acid sequence of SEQ ID NO:98
LC-CDR2 having the amino acid sequence of SEQ ID NO:99
LC-CDR3 having the amino acid sequence of SEQ ID NO:100,
or a variant thereof in which one or two or three amino acids in one or more of LC-CDR1, LC-CDR2, or LC-CDR3 are substituted with another amino acid.

(119) (3C6 VL 2, 3C6 VL 2.1, 3C6 VL 2.2, 3C6 VL 2.3, 3C6 VL 2.4) a VL region incorporating the following CDRs:
LC-CDR1 having the amino acid sequence of SEQ ID NO:101
LC-CDR2 having the amino acid sequence of SEQ ID NO:102
LC-CDR3 having the amino acid sequence of SEQ ID NO:103,
or a variant thereof in which one or two or three amino acids in one or more of LC-CDR1, LC-CDR2, or LC-CDR3 are substituted with another amino acid.

In some embodiments the antigen-binding molecule comprises a VL region according to one of (120) to (129) below:

(120) (3C6 VL 1) a VL region incorporating the following FRs:
LC-FR1 having the amino acid sequence of SEQ ID NO:109
LC-FR2 having the amino acid sequence of SEQ ID NO:111
LC-FR3 having the amino acid sequence of SEQ ID NO:113
LC-FR4 having the amino acid sequence of SEQ ID NO:115,
or a variant thereof in which one or two or three amino acids in one or more of LC-FR1, LC-FR2, LC-FR3, or LC-FR4 are substituted with another amino acid.

(121) (3C6 VL 2) a VL region incorporating the following FRs:
LC-FR1 having the amino acid sequence of SEQ ID NO:110
LC-FR2 having the amino acid sequence of SEQ ID NO:112
LC-FR3 having the amino acid sequence of SEQ ID NO:114
LC-FR4 having the amino acid sequence of SEQ ID NO:115,
or a variant thereof in which one or two or three amino acids in one or more of LC-FR1, LC-FR2, LC-FR3, or LC-FR4 are substituted with another amino acid.

(122) (3C6 VL 1.1) a VL region incorporating the following FRs:
LC-FR1 having the amino acid sequence of SEQ ID NO:150
LC-FR2 having the amino acid sequence of SEQ ID NO:112
LC-FR3 having the amino acid sequence of SEQ ID NO:153
LC-FR4 having the amino acid sequence of SEQ ID NO:149,
or a variant thereof in which one or two or three amino acids in one or more of LC-FR1, LC-FR2, LC-FR3, or LC-FR4 are substituted with another amino acid.

(123) (3C6 VL 1.2) a VL region incorporating the following FRs:
LC-FR1 having the amino acid sequence of SEQ ID NO:151
LC-FR2 having the amino acid sequence of SEQ ID NO:112
LC-FR3 having the amino acid sequence of SEQ ID NO:153
LC-FR4 having the amino acid sequence of SEQ ID NO:149,
or a variant thereof in which one or two or three amino acids in one or more of LC-FR1, LC-FR2, LC-FR3, or LC-FR4 are substituted with another amino acid.

(124) (3C6 VL 1.3) a VL region incorporating the following FRs:
LC-FR1 having the amino acid sequence of SEQ ID NO:152
LC-FR2 having the amino acid sequence of SEQ ID NO:112
LC-FR3 having the amino acid sequence of SEQ ID NO:154
LC-FR4 having the amino acid sequence of SEQ ID NO:149,
or a variant thereof in which one or two or three amino acids in one or more of LC-FR1, LC-FR2, LC-FR3, or LC-FR4 are substituted with another amino acid.

(125) (3C6 VL 1.4) a VL region incorporating the following FRs:
LC-FR1 having the amino acid sequence of SEQ ID NO:152
LC-FR2 having the amino acid sequence of SEQ ID NO:112
LC-FR3 having the amino acid sequence of SEQ ID NO:155
LC-FR4 having the amino acid sequence of SEQ ID NO:149,
or a variant thereof in which one or two or three amino acids in one or more of LC-FR1, LC-FR2, LC-FR3, or LC-FR4 are substituted with another amino acid.

(126) (3C6 VL 2.1) a VL region incorporating the following FRs:
LC-FR1 having the amino acid sequence of SEQ ID NO:141
LC-FR2 having the amino acid sequence of SEQ ID NO:144
LC-FR3 having the amino acid sequence of SEQ ID NO:146
LC-FR4 having the amino acid sequence of SEQ ID NO:149,
or a variant thereof in which one or two or three amino acids in one or more of LC-FR1, LC-FR2, LC-FR3, or LC-FR4 are substituted with another amino acid.

(127) (3C6 VL 2.2) a VL region incorporating the following FRs:
LC-FR1 having the amino acid sequence of SEQ ID NO:141
LC-FR2 having the amino acid sequence of SEQ ID NO:145
LC-FR3 having the amino acid sequence of SEQ ID NO:147
LC-FR4 having the amino acid sequence of SEQ ID NO:149, or a variant thereof in which one or two or three amino acids in one or more of LC-FR1, LC-FR2, LC-FR3, or LC-FR4 are substituted with another amino acid.

(128) (3C6 VL 2.3) a VL region incorporating the following FRs:
LC-FR1 having the amino acid sequence of SEQ ID NO:142
LC-FR2 having the amino acid sequence of SEQ ID NO:145
LC-FR3 having the amino acid sequence of SEQ ID NO:148
LC-FR4 having the amino acid sequence of SEQ ID NO:149,
or a variant thereof in which one or two or three amino acids in one or more of LC-FR1, LC-FR2, LC-FR3, or LC-FR4 are substituted with another amino acid.

(129) (3C6 VL 2.4) a VL region incorporating the following FRs:
LC-FR1 having the amino acid sequence of SEQ ID NO:143
LC-FR2 having the amino acid sequence of SEQ ID NO:145
LC-FR3 having the amino acid sequence of SEQ ID NO:148
LC-FR4 having the amino acid sequence of SEQ ID NO:149,
or a variant thereof in which one or two or three amino acids in one or more of LC-FR1, LC-FR2, LC-FR3, or LC-FR4 are substituted with another amino acid.

In some embodiments the antigen-binding molecule comprises a VL region comprising the CDRs according to (118) or (119) above, and the FRs according to one of (120) to (129) above.

In some embodiments the antigen-binding molecule comprises a VL region according to one of (130) to (139) below:
(130) (3C6 VL 1) a VL region comprising the CDRs according to (118) and the FRs according to (120).
(131) (3C6 VL 2) a VL region comprising the CDRs according to (119) and the FRs according to (121).
(132) (3C6 VL 1.1) a VL region comprising the CDRs according to (118) and the FRs according to (122).
(133) (3C6 VL 1.2) a VL region comprising the CDRs according to (118) and the FRs according to (123).
(134) (3C6 VL 1.3) a VL region comprising the CDRs according to (118) and the FRs according to (124).
(135) (3C6 VL 1.4) a VL region comprising the CDRs according to (118) and the FRs according to (125).
(136) (3C6 VL 2.1) a VL region comprising the CDRs according to (119) and the FRs according to (126).
(137) (3C6 VL 2.2) a VL region comprising the CDRs according to (119) and the FRs according to (127).
(138) (3C6 VL 2.3) a VL region comprising the CDRs according to (119) and the FRs according to (128).
(139) (3C6 VL 2.4) a VL region comprising the CDRs according to (119) and the FRs according to (129).

In some embodiments the antigen-binding molecule comprises a VL region according to one of (140) to (141) below:
(140) (3C6 VL 1) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:93.
(141) (3C6 VL 2) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:94.
(142) (3C6 VL 1.1) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:125.
(143) (3C6 VL 1.2) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:126.
(144) (3C6 VL 1.3) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:127.
(145) (3C6 VL 1.4) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:128.
(146) (3C6 VL 2.1) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:121.
(147) (3C6 VL 2.2) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:122.
(148) (3C6 VL 2.3) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:123.
(149) (3C6 VL 2.4) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:124.

In some embodiments the antigen-binding molecule comprises a VH region according to any one of (96) to (117) above, and a VL region according to any one of (118) to (149) above.

In some embodiments the antigen-binding molecule comprises a VH region according to (105) and a VL region according to (131). In some embodiments the antigen-binding molecule comprises a VH region according to (112) and a VL region according to (141).

In some embodiments the antigen-binding molecule comprises a VH region according to (107) and a VL region according to (137). In some embodiments the antigen-binding molecule comprises a VH region according to (107) and a VL region according to (136).

In some embodiments the antigen-binding molecule comprises a VH region according to (114) and a VL region according to (147). In some embodiments the antigen-binding molecule comprises a VH region according to (114) and a VL region according to (146).

In some embodiments the antigen-binding molecule comprises a VH region according to (107) and a VL region according to (138). In some embodiments the antigen-binding molecule comprises a VH region according to (114) and a VL region according to (148). In some embodiments the antigen-binding molecule comprises a VH region according to (107) and a VL region according to (139). In some embodiments the antigen-binding molecule comprises a VH region according to (114) and a VL region according to (149). In some embodiments the antigen-binding molecule comprises a VH region according to (108) and a VL region according to (137). In some embodiments the antigen-binding molecule comprises a VH region according to (115) and a VL region according to (147). In some embodiments the antigen-binding molecule comprises a VH region according to (108) and a VL region according to (138). In some embodiments the antigen-binding molecule comprises a VH region according to (115) and a VL region according to (148).

In some embodiments the antigen-binding molecule comprises a VH region according to one of (150) to (152) below:

(150) (1H2 VH) a VH region incorporating the following CDRs:
  HC-CDR1 having the amino acid sequence of SEQ ID NO:158
  HC-CDR2 having the amino acid sequence of SEQ ID NO:159
  HC-CDR3 having the amino acid sequence of SEQ ID NO:160,
  or a variant thereof in which one or two or three amino acids in one or more of HC-CDR1, HC-CDR2, or HC-CDR3 are substituted with another amino acid.

(151) (7D4 VH) a VH region incorporating the following CDRs:
  HC-CDR1 having the amino acid sequence of SEQ ID NO:176
  HC-CDR2 having the amino acid sequence of SEQ ID NO:177
  HC-CDR3 having the amino acid sequence of SEQ ID NO:178,
  or a variant thereof in which one or two or three amino acids in one or more of HC-CDR1, HC-CDR2, or HC-CDR3 are substituted with another amino acid.

(152) (8H11 VH) a VH region incorporating the following CDRs:
  HC-CDR1 having the amino acid sequence of SEQ ID NO:194
  HC-CDR2 having the amino acid sequence of SEQ ID NO:195
  HC-CDR3 having the amino acid sequence of SEQ ID NO:196,
  or a variant thereof in which one or two or three amino acids in one or more of HC-CDR1, HC-CDR2, or HC-CDR3 are substituted with another amino acid.

In some embodiments the antigen-binding molecule comprises a VH region according to one of (153) to (155) below:

(153) (1H2 VH) a VH region incorporating the following FRs:
  HC-FR1 having the amino acid sequence of SEQ ID NO:164
  HC-FR2 having the amino acid sequence of SEQ ID NO:165
  HC-FR3 having the amino acid sequence of SEQ ID NO:166
  HC-FR4 having the amino acid sequence of SEQ ID NO:167,
  or a variant thereof in which one or two or three amino acids in one or more of HC-FR1, HC-FR2, HC-FR3, or HC-FR4 are substituted with another amino acid.

(154) (7D4 VH) a VH region incorporating the following FRs:
  HC-FR1 having the amino acid sequence of SEQ ID NO:182
  HC-FR2 having the amino acid sequence of SEQ ID NO:183
  HC-FR3 having the amino acid sequence of SEQ ID NO:184
  HC-FR4 having the amino acid sequence of SEQ ID NO:185,
  or a variant thereof in which one or two or three amino acids in one or more of HC-FR1, HC-FR2, HC-FR3, or HC-FR4 are substituted with another amino acid.

(155) (8H11 VH) a VH region incorporating the following FRs:
  HC-FR1 having the amino acid sequence of SEQ ID NO:200
  HC-FR2 having the amino acid sequence of SEQ ID NO:201
  HC-FR3 having the amino acid sequence of SEQ ID NO:202
  HC-FR4 having the amino acid sequence of SEQ ID NO:203,
  or a variant thereof in which one or two or three amino acids in one or more of HC-FR1, HC-FR2, HC-FR3, or HC-FR4 are substituted with another amino acid.

In some embodiments the antigen-binding molecule comprises a VH region comprising the CDRs according to any one of (96) or (150) to (152) above, and the FRs according to any one of (97) to (103) or (153) to (155) above.

In some embodiments the antigen-binding molecule comprises a VH region according to one of (156) to (158) below:
  (156) (1H2 VH) a VH region comprising the CDRs according to (150) and the FRs according to (153).
  (157) (7D4 VH) a VH region comprising the CDRs according to (151) and the FRs according to (154).
  (158) (8H11 VH) a VH region comprising the CDRs according to (152) and the FRs according to (155).

In some embodiments the antigen-binding molecule comprises a VH region according to one of (159) to (161) below:
  (159) (1H2 VH) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:156.
  (160) (7D4 VH) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:174.
  (161) (8H11 VH) a VH region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:192.

In some embodiments the antigen-binding molecule comprises a VL region according to one of (162) to (164) below:
  (162) (1H2 VL) a VL region incorporating the following CDRs:

LC-CDR1 having the amino acid sequence of SEQ ID NO:161
LC-CDR2 having the amino acid sequence of SEQ ID NO:162
LC-CDR3 having the amino acid sequence of SEQ ID NO:163,
or a variant thereof in which one or two or three amino acids in one or more of LC-CDR1, LC-CDR2, or LC-CDR3 are substituted with another amino acid.
(163) (7D4 VL) a VL region incorporating the following CDRs:
LC-CDR1 having the amino acid sequence of SEQ ID NO:179
LC-CDR2 having the amino acid sequence of SEQ ID NO:180
LC-CDR3 having the amino acid sequence of SEQ ID NO:181,
or a variant thereof in which one or two or three amino acids in one or more of LC-CDR1, LC-CDR2, or LC-CDR3 are substituted with another amino acid.
(164) (8H11 VL) a VL region incorporating the following CDRs:
LC-CDR1 having the amino acid sequence of SEQ ID NO:197
LC-CDR2 having the amino acid sequence of SEQ ID NO:198
LC-CDR3 having the amino acid sequence of SEQ ID NO:199,
or a variant thereof in which one or two or three amino acids in one or more of LC-CDR1, LC-CDR2, or LC-CDR3 are substituted with another amino acid.

In some embodiments the antigen-binding molecule comprises a VL region according to one of (165) to (167) below:
(165) (1H2 VL) a VL region incorporating the following FRs:
LC-FR1 having the amino acid sequence of SEQ ID NO:168
LC-FR2 having the amino acid sequence of SEQ ID NO:169
LC-FR3 having the amino acid sequence of SEQ ID NO:170
LC-FR4 having the amino acid sequence of SEQ ID NO:171,
or a variant thereof in which one or two or three amino acids in one or more of LC-FR1, LC-FR2, LC-FR3, or LC-FR4 are substituted with another amino acid.
(166) (7D4 VL) a VL region incorporating the following FRs:
LC-FR1 having the amino acid sequence of SEQ ID NO:186
LC-FR2 having the amino acid sequence of SEQ ID NO:187
LC-FR3 having the amino acid sequence of SEQ ID NO:188
LC-FR4 having the amino acid sequence of SEQ ID NO:189,
or a variant thereof in which one or two or three amino acids in one or more of LC-FR1, LC-FR2, LC-FR3, or LC-FR4 are substituted with another amino acid.
(167) (8H11 VL) a VL region incorporating the following FRs:
LC-FR1 having the amino acid sequence of SEQ ID NO:204
LC-FR2 having the amino acid sequence of SEQ ID NO:205
LC-FR3 having the amino acid sequence of SEQ ID NO:206
LC-FR4 having the amino acid sequence of SEQ ID NO:207,
or a variant thereof in which one or two or three amino acids in one or more of LC-FR1, LC-FR2, LC-FR3, or LC-FR4 are substituted with another amino acid.

In some embodiments the antigen-binding molecule comprises a VL region comprising the CDRs according to any one of (118), (119) or (162) to (164) above, and the FRs according to any one of (120) to (129) or (165) to (167) above.

In some embodiments the antigen-binding molecule comprises a VL region according to one of (168) to (170) below:
(168) (1H2 VL) a VL region comprising the CDRs according to (162) and the FRs according to (165).
(169) (7D4 VL) a VL region comprising the CDRs according to (163) and the FRs according to (166).
(170) (8H11 VL) a VL region comprising the CDRs according to (164) and the FRs according to (167).

In some embodiments the antigen-binding molecule comprises a VL region according to one of (171) to (173) below:
(171) (1H2 VL) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:157.
(172) (7D4 VL) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:175.
(173) (8H11 VL) a VL region comprising an amino acid sequence having at least 70% sequence identity more preferably one of at least 75%, 80%, 85%, 86%, 87%, 88%, 89%, 90%, 91%, 92%, 93%, 94%, 95%, 96%, 97%, 98%, 99%, or 100%, sequence identity to the amino acid sequence of SEQ ID NO:193.

In some embodiments the antigen-binding molecule comprises a VH region according to any one of (96) to (117) or (150) to (161), and a VL region according to any one of (118) to (149) or (162) to (173).

In some embodiments the antigen-binding molecule comprises a VH region according to (150) and a VL region according to (162).

In some embodiments the antigen-binding molecule comprises a VH region according to (159) and a VL region according to (171).

In some embodiments the antigen-binding molecule comprises a VH region according to (151) and a VL region according to (163).

In some embodiments the antigen-binding molecule comprises a VH region according to (160) and a VL region according to (172).

In some embodiments the antigen-binding molecule comprises a VH region according to (152) and a VL region according to (164).

In some embodiments the antigen-binding molecule comprises a VH region according to (161) and a VL region according to (173).

In some embodiments provided is an antigen-binding molecule, optionally isolated, which is capable of binding to IL-11, wherein the antigen-binding molecule comprises:
(i) a heavy chain variable (VH) region incorporating the following CDRs:
HC-CDR1 having the amino acid sequence of SEQ ID NO:158

HC-CDR2 having the amino acid sequence of SEQ ID NO:159
HC-CDR3 having the amino acid sequence of SEQ ID NO:160; and
(ii) a light chain variable (VL) region incorporating the following CDRs:
LC-CDR1 having the amino acid sequence of SEQ ID NO:161
LC-CDR2 having the amino acid sequence of SEQ ID NO:162
LC-CDR3 having the amino acid sequence of SEQ ID NO:163.

In some embodiments provided is an antigen-binding molecule, optionally isolated, which is capable of binding to IL-11, wherein the antigen-binding molecule comprises:
(i) a heavy chain variable (VH) region incorporating the following CDRs:
HC-CDR1 having the amino acid sequence of SEQ ID NO:176
HC-CDR2 having the amino acid sequence of SEQ ID NO:177
HC-CDR3 having the amino acid sequence of SEQ ID NO:178; and
(ii) a light chain variable (VL) region incorporating the following CDRs:
LC-CDR1 having the amino acid sequence of SEQ ID NO:179
LC-CDR2 having the amino acid sequence of SEQ ID NO:180
LC-CDR3 having the amino acid sequence of SEQ ID NO:181.

In some embodiments provided is an antigen-binding molecule, optionally isolated, which is capable of binding to IL-11, wherein the antigen-binding molecule comprises:
(i) a heavy chain variable (VH) region incorporating the following CDRs:
HC-CDR1 having the amino acid sequence of SEQ ID NO:194
HC-CDR2 having the amino acid sequence of SEQ ID NO:195
HC-CDR3 having the amino acid sequence of SEQ ID NO:196; and
(ii) a light chain variable (VL) region incorporating the following CDRs:
LC-CDR1 having the amino acid sequence of SEQ ID NO:197
LC-CDR2 having the amino acid sequence of SEQ ID NO:198
LC-CDR3 having the amino acid sequence of SEQ ID NO:199.

In embodiments in accordance with the present invention in which one or more amino acids are substituted with another amino acid, the substitutions may conservative substitutions, for example according to the following Table. In some embodiments, amino acids in the same block in the middle column are substituted. In some embodiments, amino acids in the same line in the rightmost column are substituted:

| ALIPHATIC | Non-polar | G A P |
| | | I L V |
| | Polar - uncharged | C S T M |
| | | N Q |
| | Polar-charged | D E |
| | | K R |
| AROMATIC | | H F W Y |

In some embodiments, substitution(s) may be functionally conservative. That is, in some embodiments the substitution may not affect (or may not substantially affect) one or more functional properties (e.g. target binding) of the antigen-binding molecule comprising the substitution as compared to the equivalent unsubstituted molecule.

In some embodiments substitution(s) relative to a reference VH or VL sequence may be focussed in a particular region or regions of the VH or VL sequence. For example, variation from a reference VH or VL sequence may be focussed in one or more of the framework regions (FR1, FR2, FR3 and/or FR4).

The VH and VL region of an antigen-binding region of an antibody together constitute the Fv region. In some embodiments, the antigen-binding molecule according to the present invention comprises, or consists of, an Fv region which binds to IL-11. In some embodiments the VH and VL regions of the Fv are provided as single polypeptide joined by a linker region, i.e. a single chain Fv (scFv).

In some embodiments the antigen-binding molecule of the present invention comprises one or more regions of an immunoglobulin heavy chain constant sequence. In some embodiments the immunoglobulin heavy chain constant sequence is, or is derived from, the heavy chain constant sequence of an IgG (e.g. IgG1, IgG2, IgG3, IgG4), IgA (e.g. IgA1, IgA2), IgD, IgE or IgM.

In some embodiments the immunoglobulin heavy chain constant sequence is human immunoglobulin G 1 constant (IGHG1; UniProt: P01857-1, v1; SEQ ID NO:85). Positions 1 to 98 of SEQ ID NO:85 form the CH1 region (SEQ ID NO:86). Positions 99 to 110 of SEQ ID NO:85 form a hinge region between CH1 and CH2 regions (SEQ ID NO:87). Positions 111 to 223 of SEQ ID NO:85 form the CH2 region (SEQ ID NO:88). Positions 224 to 330 of SEQ ID NO:85 form the CH3 region (SEQ ID NO:89).

In some embodiments a CH1 region comprises or consists of the sequence of SEQ ID NO:86, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:86. In some embodiments a CH1-CH2 hinge region comprises or consists of the sequence of SEQ ID NO:87, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:87. In some embodiments a CH2 region comprises or consists of the sequence of SEQ ID NO:88, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:88. In some embodiments a CH3 region comprises or consists of the sequence of SEQ ID NO:89 or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:89.

In some embodiments the immunoglobulin heavy chain constant sequence is human immunoglobulin G 4 constant (IGHG4; UniProt: P01861, v1; SEQ ID NO:211). Positions 1-98 of SEQ ID NO:211 form the CH1 region (SEQ ID NO:212). Positions 99-110 of SEQ ID NO:211 form a hinge region between CH1 and CH2 regions (SEQ ID NO:213). Positions 111-220 of SEQ ID NO:211 form the CH2 region (SEQ ID NO:214). Positions 221-327 of SEQ ID NO:211 form the CH3 region (SEQ ID NO:215).

In some embodiments a CH1 region comprises or consists of the sequence of SEQ ID NO:212, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:212. In some embodiments a CH1-CH2 hinge region comprises or consists of the sequence of SEQ ID NO:213, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:213. In some embodiments a CH2 region comprises or consists of the sequence of SEQ ID NO:214, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:214. In some embodiments a CH3 region comprises or consists of the sequence of SEQ ID NO:215 or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:215.

In some embodiments the immunoglobulin heavy chain constant sequence is human immunoglobulin G 4 constant (IGHG4; UniProt: P01861, v1) comprising amino acid substitutions which impart improved properties on the antigen-binding molecules of the invention. In some embodiments the immunoglobulin heavy chain constant sequence is human IgG4 comprising substitutions S241P and/or L248E. The S241P mutation is hinge stabilising while the L248E mutation further reduces the already low ADCC effector function of IgG4 (Davies and Sutton, Immunol Rev. 2015 November; 268(1):139-159; Angal et al Mol Immunol. 1993 January; 30(1):105-8). The lower ADCC activity is advantageous for potential subcutaneous administration of the antibody.

In some embodiments the immunoglobulin heavy chain constant sequence is human immunoglobulin G 4 constant (IGHG4; UniProt: P01861, v1) comprising substitution S241P (numbered according to the Kabat system), as described in SEQ ID NO:216. Positions 1-98 of SEQ ID NO:216 form the CH1 region (SEQ ID NO:212). Positions 99-110 of SEQ ID NO:216 form a hinge region between CH1 and CH2 regions (SEQ ID NO:217) comprising the S241P substitution. Positions 111-220 of SEQ ID NO:216 form the CH2 region (SEQ ID NO:214). Positions 221-327 of SEQ ID NO:216 form the CH3 region (SEQ ID NO:215).

In some embodiments a CH1 region comprises or consists of the sequence of SEQ ID NO:212, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:212. In some embodiments a CH1-CH2 hinge region comprises or consists of the sequence of SEQ ID NO:217, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:217. In some embodiments a CH2 region comprises or consists of the sequence of SEQ ID NO:214, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:214. In some embodiments a CH3 region comprises or consists of the sequence of SEQ ID NO:215 or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:215.

In some embodiments the immunoglobulin heavy chain constant sequence is human immunoglobulin G 4 constant (IGHG4; UniProt: P01861, v1) comprising substitutions S241P and L248E (numbered according to the Kabat system), as described in SEQ ID NO:218. Positions 1-98 of SEQ ID NO:218 form the CH1 region (SEQ ID NO:212). Positions 99-110 of SEQ ID NO:218 form a hinge region between CH1 and CH2 regions (SEQ ID NO:217) comprising the S241P substitution. Positions 111-220 of SEQ ID NO:218 form the CH2 region (SEQ ID NO:219), comprising the L248E substitution. Positions 221-327 of SEQ ID NO:218 form the CH3 region (SEQ ID NO:215).

In some embodiments a CH1 region comprises or consists of the sequence of SEQ ID NO:212, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:212. In some embodiments a CH1-CH2 hinge region comprises or consists of the sequence of SEQ ID NO:217, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:217. In some embodiments a CH2 region comprises or consists of the sequence of SEQ ID NO:219, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:219. In some embodiments a CH3 region comprises or consists of the sequence of SEQ ID NO:215 or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:215.

In some embodiments the antigen-binding molecule of the present invention comprises one or more regions of an immunoglobulin light chain constant sequence. In some embodiments the immunoglobulin light chain constant sequence is human immunoglobulin kappa constant (IGKC; Cκ; UniProt: P01834-1, v2; SEQ ID NO:90). In some embodiments the immunoglobulin light chain constant sequence is a human immunoglobulin lambda constant (IGLC; Cλ), e.g. IGLC1, IGLC2, IGLC3, IGLC6 or IGLC7 (SEQ ID NO:231, 232, 233, 234 or 235). In some embodiments a CL region comprises or consists of the sequence of SEQ ID NO:90, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:90. In some embodiments a CL region comprises or consists of the sequence of SEQ ID NO:231, 232, 233, 234 or 235, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:231, 232, 233, 234 or 235.

The VL and light chain constant (CL) region, and the VH region and heavy chain constant 1 (CH1) region of an antigen-binding region of an antibody together constitute the Fab region. In some embodiments the antigen-binding molecule comprises a Fab region comprising a VH, a CH1, a VL and a CL (e.g. Cκ or Cλ). In some embodiments the Fab region comprises a polypeptide comprising a VH and a CH1 (e.g. a VH-CH1 fusion polypeptide), and a polypeptide comprising a VL and a CL (e.g. a VL-CL fusion polypeptide). In some embodiments the Fab region comprises a polypeptide comprising a VH and a CL (e.g. a VH-CL fusion polypeptide) and a polypeptide comprising a VL and a CH (e.g. a VL-CH1 fusion polypeptide); that is, in some embodiments the Fab region is a CrossFab region. In some embodiments the VH, CH1, VL and CL regions of the Fab or CrossFab are provided as single polypeptide joined by linker regions, i.e. as a single chain Fab (scFab) or a single chain CrossFab (scCrossFab).

In some embodiments, the antigen-binding molecule of the present invention comprises, or consists of, a Fab region which binds to IL-11.

In some embodiments, the antigen-binding molecule described herein comprises, or consists of, a whole antibody which binds to IL-11. As used herein, "whole antibody" refers to an antibody having a structure which is substantially similar to the structure of an immunoglobulin (Ig). Different kinds of immunoglobulins and their structures are described e.g. in Schroeder and Cavacini J Allergy Clin Immunol. (2010) 125(202): S41-S52, which is hereby incorporated by reference in its entirety.

Immunoglobulins of type G (i.e. IgG) are ~150 kDa glycoproteins comprising two heavy chains and two light chains. From N- to C-terminus, the heavy chains comprise a VH followed by a heavy chain constant region comprising three constant domains (CH1, CH2, and CH3), and similarly the light chain comprise a VL followed by a CL. Depending on the heavy chain, immunoglobulins may be classed as IgG (e.g. IgG1, IgG2, IgG3, IgG4), IgA (e.g. IgA1, IgA2), IgD, IgE, or IgM. The light chain may be kappa (κ) or lambda (λ).

In some embodiments, the antigen-binding molecule described herein comprises, or consists of, an IgG (e.g. IgG1, IgG2, IgG3, IgG4), IgA (e.g. IgA1, IgA2), IgD, IgE, or IgM which binds to IL-11.

In some embodiments, the antigen-binding molecule of the present invention is at least monovalent binding for IL-11. Binding valency refers to the number of binding sites in an antigen-binding molecule for a given antigenic determinant. Accordingly, in some embodiments the antigen-binding molecule comprises at least one binding site for IL-11.

In some embodiments the antigen-binding molecule comprises more than one binding site for IL-11, e.g. 2, 3 or 4 binding sites. The binding sites may be the same or different. In some embodiments the antigen-binding molecule is e.g. bivalent, trivalent or tetravalent for IL-11.

Aspects of the present invention relate to multispecific antigen-binding molecules. By "multispecific" it is meant that the antigen-binding molecule displays specific binding to more than one target. In some embodiments the antigen-binding molecule is a bispecific antigen-binding molecule. In some embodiments the antigen-binding molecule comprises at least two different antigen-binding domains (i.e. at least two antigen-binding domains, e.g. comprising non-identical VHs and VLs).

In some embodiments the antigen-binding molecule binds to IL-11 and another target (e.g. an antigen other than IL-11), and so is at least bispecific. The term "bispecific" means that the antigen-binding molecule is able to bind specifically to at least two distinct antigenic determinants.

It will be appreciated that an antigen-binding molecule according to the present invention (e.g. a multispecific antigen-binding molecule) may comprise antigen-binding molecules capable of binding to the targets for which the antigen-binding molecule is specific. For example, an antigen-binding molecule which is capable of binding to IL-11 and an antigen other than IL-11 may comprise: (i) an antigen-binding molecule which is capable of binding to IL-11, and (ii) an antigen-binding molecule which is capable of binding to an antigen other than IL-11.

It will also be appreciated that an antigen-binding molecule according to the present invention (e.g. a multispecific antigen-binding molecule) may comprise antigen-binding polypeptides or antigen-binding polypeptide complexes capable of binding to the targets for which the antigen-binding molecule is specific. For example, an antigen-binding molecule according to the invention may comprise e.g. (i) an antigen-binding polypeptide complex capable of binding to IL-11, comprising a light chain polypeptide (comprising the structure VL-CL) and a heavy chain polypeptide (comprising the structure VH-CH1-CH2-CH3), and (ii) an antigen-binding polypeptide complex capable of binding to an antigen other than IL-11, comprising a light chain polypeptide (comprising the structure VL-CL) and a heavy chain polypeptide (comprising the structure VH-CH1-CH2-CH3).

In some embodiments, a component antigen-binding molecule of a larger antigen-binding molecule (e.g. a multispecific antigen-biding molecule) may be referred to e.g. as an "antigen-binding domain" or "antigen-binding region" of the larger antigen-binding molecule.

In some embodiments the antigen-binding molecule comprises an antigen-binding molecule capable of binding to IL-11, and an antigen-binding molecule capable of binding to an antigen other than IL-11. In some embodiments, the antigen other than IL-11 is an immune cell surface molecule. In some embodiments, the antigen other than IL-11 is a cancer cell antigen. In some embodiments the antigen other than IL-11 is a receptor molecule, e.g. a cell surface receptor. In some embodiments the antigen other than IL-11 is a cell signalling molecule, e.g. a cytokine, chemokine, interferon, interleukin or lymphokine. In some embodiments the antigen other than IL-11 is a growth factor or a hormone.

A cancer cell antigen is an antigen which is expressed or over-expressed by a cancer cell. A cancer cell antigen may be any peptide/polypeptide, glycoprotein, lipoprotein, glycan, glycolipid, lipid, or fragment thereof. A cancer cell antigen's expression may be associated with a cancer. A cancer cell antigen may be abnormally expressed by a cancer cell (e.g. the cancer cell antigen may be expressed with abnormal localisation), or may be expressed with an abnormal structure by a cancer cell. A cancer cell antigen may be capable of eliciting an immune response. In some embodiments, the antigen is expressed at the cell surface of the cancer cell (i.e. the cancer cell antigen is a cancer cell surface antigen). In some embodiments, the part of the antigen which is bound by the antigen-binding molecule described herein is displayed on the external surface of the cancer cell (i.e. is extracellular). The cancer cell antigen may be a cancer-associated antigen. In some embodiments the cancer cell antigen is an antigen whose expression is associated with the development, progression or severity of symptoms of a cancer. The cancer-associated antigen may be associated with the cause or pathology of the cancer, or may be expressed abnormally as a consequence of the cancer. In some embodiments, the cancer cell antigen is an antigen whose expression is upregulated (e.g. at the RNA and/or protein level) by cells of a cancer, e.g. as compared to the level of expression of by comparable non-cancerous cells (e.g. non-cancerous cells derived from the same tissue/cell type). In some embodiments, the cancer-associated antigen may be preferentially expressed by cancerous cells, and not expressed by comparable non-cancerous cells (e.g. non-cancerous cells derived from the same tissue/cell type). In some embodiments, the cancer-associated antigen may be the product of a mutated oncogene or mutated tumor suppressor gene. In some embodiments, the cancer-associated antigen may be the product of an overexpressed cellular protein, a cancer antigen produced by an oncogenic virus, an oncofetal antigen, or a cell surface glycolipid or glycoprotein.

An immune cell surface molecule may be any peptide/polypeptide, glycoprotein, lipoprotein, glycan, glycolipid, lipid, or fragment thereof expressed at or on the cell surface of an immune cell. In some embodiments, the part of the immune cell surface molecule which is bound by the antigen-binding molecule of the present invention is on the external surface of the immune cell (i.e. is extracellular). The immune cell surface molecule may be expressed at the cell surface of any immune cell. In some embodiments, the immune cell may be a cell of hematopoietic origin, e.g. a neutrophil, eosinophil, basophil, dendritic cell, lymphocyte, or monocyte. The lymphocyte may be e.g. a T cell, B cell, natural killer (NK) cell, NKT cell or innate lymphoid cell (ILC), or a precursor thereof (e.g. a thymocyte or pre-B cell). In some embodiments the immune cell surface molecule may be a costimulatory molecule (e.g. CD28, OX40, 4-1BB, ICOS or CD27) or a ligand thereof. In some embodiments the immune cell surface molecule may be a checkpoint inhibitor (e.g. PD-1, CTLA-4, LAG-3, TIM-3, TIGIT or BTLA) or a ligand thereof.

Multispecific antigen-binding molecules according to the invention may be provided in any suitable format, such as those formats described in described in Brinkmann and Kontermann MAbs (2017) 9(2): 182-212, which is hereby incorporated by reference in its entirety. Suitable formats include those shown in FIG. 2 of Brinkmann and Kontermann MAbs (2017) 9(2): 182-212: antibody conjugates, e.g. IgG2, F(ab')$_2$ or CovX-Body; IgG or IgG-like molecules, e.g. IgG, chimeric IgG, κλ-body common HC; CH1/CL fusion proteins, e.g. scFv2-CH1/CL, VHH2-CH1/CL; 'variable domain only' bispecific antigen-binding molecules, e.g. tandem scFv (taFV), triplebodies, diabodies (Db), dsDb, Db(kih), DART, scDB, dsFv-dsFv, tandAbs, triple heads, tandem dAb/VHH, tertravalent dAb.VHH; Non-Ig fusion proteins, e.g. scFv$_2$-albumin, scDb-albumin, taFv-albumin, taFv-toxin, miniantibody, DNL-Fab$_2$, DNL-Fab$_2$-scFv, DNL-Fab$_2$-IgG-cytokine$_2$, ImmTAC (TCR-scFv); modified Fc and CH3 fusion proteins, e.g. scFv-Fc(kih), scFv-Fc(CH3 charge pairs), scFv-Fc (EW-RVT), scFv-fc (HA-TF), scFv-Fc (SEEDbody), taFv-Fc(kih), scFv-Fc(kih)-Fv, Fab-Fc (kih)-scFv, Fab-scFv-Fc(kih), Fab-scFv-Fc (BEAT), Fab-scFv-Fc (SEEDbody), DART-Fc, scFv-CH3(kih), TriFabs; Fc fusions, e.g. Di-diabody, scDb-Fc, taFv-Fc, scFv-Fc-scFv, HCAb-VHH, Fab-scFv-Fc, scFv$_4$-Ig, scFv$_2$-Fcab; CH3 fusions, e.g. Dia-diabody, scDb-CH3; IgE/IgM CH2 fusions, e.g. scFv-EHD2-scFv, scFvMHD2-scFv; Fab fusion proteins, e.g. Fab-scFv (bibody), Fab-scFv$_2$ (tribody), Fab-Fv, Fab-dsFv, Fab-VHH, orthogonal Fab-Fab; non-Ig fusion proteins, e.g. DNL-Fab$_3$, DNL-Fab$_2$-scFv, DNL-Fab$_2$-IgG-cytokine$_2$; asymmetric IgG or IgG-like molecules, e.g. IgG (kih), IgG(kih) common LC, ZW1 IgG common LC, Biclonics common LC, CrossMab, CrossMab(kih), scFab-IgG (kih), Fab-scFab-IgG(kih), orthogonal Fab IgG(kih), DuetMab, CH3 charge pairs+CH1/CL charge pairs, hinge/CH3 charge pairs, SEED-body, Duobody, four-in-one-CrossMab(kih), LUZ-Y common LC; LUZ-Y scFab-IgG, FcFc*; appended and Fc-modified IgGs, e.g. IgG(kih)-Fv, IgG HA-TF-Fv, IgG(kih)scFab, scFab-Fc(kih)-scFv2, scFab-Fc(kih)-scFv, half DVD-Ig, DVI-Ig (four-in-one), CrossMab-Fab; modified Fc and CH3 fusion proteins, e.g. Fab-Fc(kih)-scFv, Fab-scFv-Fc(kih), Fab-scFv-Fc(BEAT), Fab-scFv-Fc-SEEDbody, TriFab; appended IgGs-HC fusions, e.g. IgG-HC, scFv, IgG-dAb, IgG-taFV, IgG-Cross-Fab, IgG-orthogonal Fab, IgG-(CαCβ) Fab, scFv-HC-IgG, tandem Fab-IgG (orthogonal Fab) Fab-IgG(CαCβ Fab), Fab-IgG(CR3), Fab-hinge-IgG(CR3); appended IgGs-LC fusions, e.g. IgG-scFv(LC), scFv(LC)-IgG, dAb-IgG; appended IgGs-HC and LC fusions, e.g. DVD-Ig, TVD-Ig, CODV-Ig, scFv$_4$-IgG, Zybody; Fc fusions, e.g. Fab-scFv-Fc, scFv$_4$-Ig; F(ab')2 fusions, e.g. F(ab')$_2$-scFv$_2$; CH1/CL fusion proteins e.g. scFv$_2$-CH1-hinge/CL; modified IgGs, e.g. DAF (two-in one-IgG), DutaMab, Mab$^2$; and non-Ig fusions, e.g. DNL-Fab$_4$-IgG.

The skilled person is able to design and prepare bispecific antigen-binding molecules. Methods for producing bispecific antigen-binding molecules include chemically crosslinking of antigen-binding molecules or antibody fragments, e.g. with reducible disulphide or non-reducible thioether bonds, for example as described in Segal and Bast, 2001. Production of Bispecific Antigen-binding molecules. Current Protocols in Immunology. 14:IV:2.13:2.13.1-2.13.16, which is hereby incorporated by reference in its entirety. For example, N-succinimidyl-3-(-2-pyridyldithio)-propionate (SPDP) can be used to chemically crosslink e.g. Fab fragments via hinge region SH— groups, to create disulfide-linked bispecific F(ab)$_2$ heterodimers.

Other methods for producing bispecific antigen-binding molecules include fusing antibody-producing hybridomas e.g. with polyethylene glycol, to produce a quadroma cell capable of secreting bispecific antibody, for example as described in D. M. and Bast, B. J. 2001. Production of Bispecific Antigen-binding molecules. Current Protocols in Immunology. 14:IV:2.13:2.13.1-2.13.16.

Bispecific antigen-binding molecules according to the present invention can also be produced recombinantly, by expression from e.g. a nucleic acid construct encoding polypeptides for the antigen-binding molecules, for example as described in Antibody Engineering: Methods and Protocols, Second Edition (Humana Press, 2012), at Chapter 40: Production of Bispecific Antigen-binding molecules: Diabodies and Tandem scFv (Hornig and Färber-Schwarz), or French, How to make bispecific antigen-binding molecules, Methods Mol. Med. 2000; 40:333-339, the entire contents of both of which are hereby incorporated by reference. For example, a DNA construct encoding the light and heavy chain variable domains for the two antigen-binding fragments (i.e. the light and heavy chain variable domains for the antigen-binding fragment capable of binding IL-11, and the light and heavy chain variable domains for the antigen-binding fragment capable of binding to another target protein), and including sequences encoding a suitable linker or dimerization domain between the antigen-binding fragments can be prepared by molecular cloning techniques. Recombinant bispecific antibody can thereafter be produced by expression (e.g. in vitro) of the construct in a suitable host cell (e.g. a mammalian host cell), and expressed recombinant bispecific antibody can then optionally be purified.

In some embodiments the antigen-binding molecules of the present invention comprise an Fc region. An Fc region is composed of CH2 and CH3 regions from one polypeptide, and CH2 and CH3 regions from another polypeptide. The CH2 and CH3 regions from the two polypeptides together form the Fc region.

In some embodiments, the antigen-binding molecule of the present invention comprises an Fc region comprising modification in one or more of the CH2 and CH3 regions promoting association of the Fc region. Recombinant co-expression of constituent polypeptides of an antigen-binding molecule and subsequent association leads to several possible combinations. To improve the yield of the desired combinations of polypeptides in antigen-binding molecules in recombinant production, it is advantageous to introduce in the Fc regions modification(s) promoting association of the desired combination of heavy chain polypeptides. Modifications may promote e.g. hydrophobic and/or electrostatic interaction between CH2 and/or CH3 regions of different polypeptide chains. Suitable modifications are described e.g. in Ha et al., Front. Immnol (2016) 7:394, which is hereby incorporated by reference in its entirety. In some embodiments the antigen antigen-binding molecule of the present invention comprises an Fc region comprising paired substitutions in the CH3 regions of the Fc region according to one of the following formats, as shown in Table 1 of Ha et al., Front. Immnol (2016) 7:394: KiH, KiH$_{s-s}$, HA-TF, ZW1, 7.8.60, DD-KK, EW-RVT, EW-RVT$_{s-s}$, SEED or A107.

Polypeptides

The present invention also provides polypeptide constituents of antigen-binding molecules. The polypeptides may be provided in isolated or substantially purified form.

The antigen-binding molecule of the present invention may be, or may comprise, a complex of polypeptides.

In the present specification where a polypeptide comprises more than one domain or region, it will be appreciated that the plural domains/regions are preferably present in the same polypeptide chain. That is, the polypeptide comprises more than one domain or region is a fusion polypeptide comprising the domains/regions.

In some embodiments a polypeptide according to the present invention comprises, or consists of, a VH as described herein. In some embodiments a polypeptide according to the present invention comprises, or consists of, a VL as described herein.

In some embodiments, the polypeptide additionally comprises one or more antibody heavy chain constant regions (CH). In some embodiments, the polypeptide additionally comprises one or more antibody light chain constant regions (CL). In some embodiments, the polypeptide comprises a CH1, CH2 region and/or a CH3 region of an immunoglobulin (Ig).

In some embodiments the polypeptide comprises one or more regions of an immunoglobulin heavy chain constant sequence. In some embodiments the polypeptide comprises a CH1 region as described herein. In some embodiments the polypeptide comprises a CH1-CH2 hinge region as described herein. In some embodiments the polypeptide comprises a CH2 region as described herein. In some embodiments the polypeptide comprises a CH3 region as described herein.

In some embodiments the polypeptide comprises a CH3 region comprising any one of the amino acid substitutions/combinations of amino acid substitutions shown in Table 1 of Ha et al., Front. Immnol (2016) 7:394, incorporated by reference hereinabove.

In some embodiments the CH2 and/or CH3 regions of the polypeptide comprise one or more amino acid substitutions for promoting association of the polypeptide with another polypeptide comprising a CH2 and/or CH3 region.

In some embodiments the polypeptide comprises one or more regions of an immunoglobulin light chain constant sequence. In some embodiments the polypeptide comprises a CL region as described herein.

In some embodiments, the polypeptide according to the present invention comprises a structure from N- to C-terminus according to one of the following:
(i) VH
(ii) VL
(iii) VH-CH1
(iv) VL-CL
(v) VL-CH1
(vi) VH-CL
(vii) VH-CH1-CH2-CH3
(viii) VL-CL-CH2-CH3
(ix) VL-CH1-CH2-CH3
(x) VH-CL-CH2-CH3

Also provided by the present invention are antigen-binding molecules composed of the polypeptides of the present invention. In some embodiments, the antigen-binding molecule of the present invention comprises one of the following combinations of polypeptides:
(A) VH+VL
(B) VH-CH1+VL-CL
(C) VL-CH1+VH-CL
(D) VH-CH1-CH2-CH3+VL-CL
(E) VH-CL-CH2-CH3+VL-CH1
(F) VL-CH1-CH2-CH3+VH-CL
(G) VL-CL-CH2-CH3+VH-CH1
(H) VH-CH1-CH2-CH3+VL-CL-CH2-CH3
(I) VH-CL-CH2-CH3+VL-CH1-CH2-CH3

In some embodiments the antigen-binding molecule comprises more than one of a polypeptide of the combinations shown in (A) to (I) above. By way of example, with reference to (D) above, in some embodiments the antigen-binding molecule comprises two polypeptides comprising the structure VH-CH1-CH2-CH3, and two polypeptides comprising the structure VL-CL.

In some embodiments, the antigen-binding molecule of the present invention comprises one of the following combinations of polypeptides:
(J) VH (anti-IL-11)+VL (anti-IL-11)
(K) VH (anti-IL-11)-CH1+VL (anti-IL-11)-CL
(L) VL (anti-IL-11)-CH1+VH (anti-IL-11)-CL
(M) VH (anti-IL-11)-CH1-CH2-CH3+VL (anti-IL-11)-CL
(N) VH (anti-IL-11)-CL-CH2-CH3+VL (anti-IL-11)-CH1
(O) VL (anti-IL-11)-CH1-CH2-CH3+VH (anti-IL-11)-CL
(P) VL (anti-IL-11)-CL-CH2-CH3+VH (anti-IL-11)-CH1
(Q) VH (anti-IL-11)-CH1-CH2-CH3+VL (anti-IL-11)-CL-CH2-CH3
(R) VH (anti-IL-11)-CL-CH2-CH3+VL (anti-IL-11)-CH1-CH2-CH3

Wherein: "VH (anti-IL-11)" refers to the VH of an antigen-binding molecule capable of binding to IL-11 as described herein, e.g. as defined in any one of (1) to (11), (96) to (117) or (150) to (161); "VL (anti-IL-11)" refers to the VL of an antigen-binding molecule capable of binding to IL-11 as described herein, e.g. as defined in any one of (12) to (95), (118) to (149) or (162) to (173).

In some embodiments the polypeptide comprises or consists of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of one of SEQ ID NOs:6 to 35, 82 to 84, 91 to 94, 116 to 128, 156, 157, 174, 175, 192, 193 or 210.

In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:220. In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:221. In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:222. In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:223. In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:224. In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:236. In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:237. In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:238. In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:239. In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:240. In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:225. In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:226. In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:227. In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:228. In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:229. In some embodiments the antigen-binding molecule of the present invention comprises a polypeptide comprising or consisting of an amino acid sequence having at least 70%, preferably one of 75%, 80%, 85%, 90%, 91%, 92%, 93%, 94%, 95%, 96%, 97%, 98%, 99% or 100% amino acid sequence identity to the amino acid sequence of SEQ ID NO:230.

Linkers and Additional Sequences

In some embodiments the antigen-binding molecules and polypeptides of the present invention comprise one or more linker sequences between amino acid sequences. A linker sequence may be provided at one or both ends of one or more of a VH, VL, CH1-CH2 hinge region, CH2 region and a CH3 region of the antigen-binding molecule/polypeptide.

Linker sequences are known to the skilled person, and are described, for example in Chen et al., Adv Drug Deliv Rev (2013) 65(10): 1357-1369, which is hereby incorporated by reference in its entirety. In some embodiments, a linker sequence may be a flexible linker sequence. Flexible linker sequences allow for relative movement of the amino acid sequences which are linked by the linker sequence. Flexible linkers are known to the skilled person, and several are identified in Chen et al., Adv Drug Deliv Rev (2013) 65(10): 1357-1369. Flexible linker sequences often comprise high proportions of glycine and/or serine residues.

In some embodiments, the linker sequence comprises at least one glycine residue and/or at least one serine residue. In some embodiments the linker sequence consists of glycine and serine residues. In some embodiments, the linker sequence has a length of 1-2, 1-3, 1-4, 1-5 or 1-10 amino acids.

The antigen-binding molecules and polypeptides of the present invention may additionally comprise further amino acids or sequences of amino acids. For example, the antigen-binding molecules and polypeptides may comprise amino acid sequence(s) to facilitate expression, folding, trafficking, processing, purification or detection of the antigen-binding molecule/polypeptide. For example, the antigen-binding molecule/polypeptide may comprise a sequence encoding a His, (e.g. 6XHis), Myc, GST, MBP, FLAG, HA, E, or Biotin tag, optionally at the N- or C-terminus of the antigen-binding molecule/polypeptide. In some embodiments the antigen-binding molecule/polypeptide comprises a detectable moiety, e.g. a fluorescent, luminescent, immuno-detectable, radio, chemical, nucleic acid or enzymatic label.

The antigen-binding molecules and polypeptides of the present invention may additionally comprise a signal peptide (also known as a leader sequence or signal sequence). Signal peptides normally consist of a sequence of 5-30 hydrophobic amino acids, which form a single alpha helix. Secreted proteins and proteins expressed at the cell surface often comprise signal peptides.

The signal peptide may be present at the N-terminus of the antigen-binding molecule/polypeptide, and may be present in the newly synthesised antigen-binding molecule/polypeptide. The signal peptide provides for efficient trafficking and secretion of the antigen-binding molecule/polypeptide. Signal peptides are often removed by cleavage, and thus are not comprised in the mature antigen-binding molecule/polypeptide secreted from the cell expressing the antigen-binding molecule/polypeptide.

Signal peptides are known for many proteins, and are recorded in databases such as GenBank, UniProt, Swiss-Prot, TrEMBL, Protein Information Resource, Protein Data Bank, Ensembl, and InterPro, and/or can be identified/predicted e.g. using amino acid sequence analysis tools such as SignalP (Petersen et al., 2011 Nature Methods 8: 785-786) or Signal-BLAST (Frank and Sippl, 2008 Bioinformatics 24: 2172-2176).

Labels and Conjugates

In some embodiments the antigen-binding molecules of the present invention additionally comprise a detectable moiety or a chemical moiety.

In some embodiments the antigen-binding molecule comprises a detectable moiety, e.g. a fluorescent label, phosphorescent label, luminescent label, immuno-detectable label (e.g. an epitope tag), radiolabel, chemical, nucleic acid or enzymatic label. The antigen-binding molecule may be covalently or non-covalently labelled with the detectable moiety.

Fluorescent labels include e.g. fluorescein, rhodamine, allophycocyanin, eosine and NDB, green fluorescent protein (GFP) chelates of rare earths such as europium (Eu), terbium (Tb) and samarium (Sm), tetramethyl rhodamine, Texas Red, 4-methyl umbelliferone, 7-amino-4-methyl coumarin, Cy3, and Cy5. Radiolabels include radioisotopes such as Iodine$^{123}$, Iodine$^{125}$, Iodine$^{126}$, Iodine$^{131}$, Iodine$^{133}$, Bromine$^{77}$, Technetium$^{99m}$, Indium$^{111}$, Indium$^{113m}$, Gallium$^{67}$, Gallium$^{68}$, Ruthenium$^{95}$, Ruthenium$^{97}$, Ruthenium$^{103}$, Ruthenium$^{105}$, Mercury$^{207}$, Mercury$^{203}$, Rhenium$^{99m}$, Rhenium$^{101}$, Rhenium$^{105}$, Scandium$^{47}$, Tellurium$^{121m}$, Tellurium$^{122m}$, Tellurium$^{125m}$, Thulium$^{165}$, Thulium$^{167}$, Thulium$^{168}$, Copper$^{67}$, Fluorine$^{18}$, Yttrium$^{90}$, Palladium$^{100}$, Bismuth$^{217}$ and Antimony$^{211}$. Luminescent labels include as radioluminescent, chemiluminescent (e.g. acridinium ester, luminol, isoluminol) and bioluminescent labels. Immuno-detectable labels include haptens, peptides/polypeptides, antibodies, receptors and ligands such as biotin, avidin, streptavidin or digoxigenin. Nucleic acid labels include aptamers. Enzymatic labels include e.g. peroxidase, alkaline phosphatase, glucose oxidase, beta-galactosidase and luciferase.

In some embodiments the antigen-binding molecules of the present invention are conjugated to a chemical moiety. The chemical moiety may be a moiety for providing a therapeutic effect. Antibody-drug conjugates are reviewed e.g. in Parslow et al., Biomedicines. 2016 September; 4(3): 14. In some embodiments, the chemical moiety may be a drug moiety (e.g. a cytotoxic agent). In some embodiments, the drug moiety may be a chemotherapeutic agent. In some embodiments, the drug moiety is selected from calicheamicin, DM1, DM4, monomethylauristatin E (MMAE), monomethylauristatin F (MMAF), SN-38, doxorubicin, duocarmycin, D6.5 and PBD.

Functional Properties of the Antigen-Binding Molecules

The antigen-binding molecules described herein may be characterised by reference to certain functional properties. In some embodiments, the antigen-binding molecule described herein may possess one or more of the following properties:

a) Specific binding to IL-11 (e.g. human IL-11 and/or mouse IL-11);
b) Binding to IL-11 (e.g. human IL-11) with an affinity of binding of EC50=less than 1000 ng/ml, e.g. as determined by ELISA;
c) Inhibition of interaction between IL-11 and IL-11Rα;
d) Inhibition of interaction between IL-11 and gp130;
e) Inhibition of interaction between IL-11 and IL-11Rα: gp130 receptor complex;
f) Inhibition of interaction between IL-11:IL-11Rα complex and gp130;
g) Inhibition of interaction between IL-11 and IL-11;
h) Inhibition of signalling mediated by IL-11;
i) Inhibition of signalling mediated by binding of IL-11 to IL-11Rα:gp130 receptor complex;
j) Inhibition of signalling mediated by binding of IL-11: IL-11Rα complex to gp130 (i.e. IL-11 trans signalling);
k) Inhibition of fibroblast proliferation;
l) Inhibition of myofibroblast generation from fibroblasts;
m) Reversal/regression of myofibroblast generation from fibroblasts;
n) Inhibition of myofibroblast generation from stellate cells, e.g. hepatic or pancreatic stellate cells;
o) Reversal/regression of myofibroblast generation from stellate cells, e.g. hepatic or pancreatic stellate cells;
p) Inhibition of migratory and/or invasive behaviour (i.e. inhibition of migration and/or invasion) of fibroblasts, stellate cells or myofibroblasts;
q) Inhibition of the presence of immune cells in an organ;
r) Inhibition of a pathological process mediated by IL-11;
s) Inhibition of fibrosis;
t) Reversal/regression of fibrosis;
u) Inhibition of gene or protein expression in fibroblasts or stellate cells of one or more of collagen, fibronectin, periostin, IL-6, IL-11, αSMA (ACTA2), TIMP1, MMP2, TNFα, CCL2 e.g. following stimulation with a profibrotic factor;
v) Inhibition of extracellular matrix production by fibroblasts or stellate cells;
w) Inhibition of proliferation and/or survival of cells of a cancer;
x) Inhibition of development and/or progression of cancer in vivo;
y) Inhibition of tumour growth;
z) Killing of cells expressing/comprising IL-11 or a complex comprising IL-11.

Herein, 'inhibition' refers to a reduction, decrease or lessening relative to a control condition. For example, inhibition of a process by an antigen-binding molecule refers to a reduction, decrease or lessening of the extent/degree of that process in the absence of the antigen-binding molecule, and/or in the presence of an appropriate control antigen-binding molecule.

Inhibition may herein also be referred to as neutralisation or antagonism. That is, an IL-11 binding antigen-binding molecule which is capable of inhibiting a function or process (e.g. interaction, signalling or other activity mediated by IL-11 or a complex comprising IL-11) may be said to be a 'neutralising' or 'antagonist' antigen-binding molecule with respect to the relevant function or process. For example, antigen-binding molecule which is capable of inhibiting IL-11 mediated signalling may be referred to as an antigen-binding molecule which is capable of neutralising IL-11 mediated signalling, or may be referred to as an antagonist of IL-11 mediated signalling.

The skilled person is able to identify an appropriate control condition for a given assay. For example, a control antigen-binding molecule may be an antigen-binding molecule directed against a target protein which is known not to have a role involved in the property being investigated in the assay. A control antigen-binding molecule may be of the same isotype as the anti-IL-11 antigen-binding molecule being analysed, and may e.g. have the same constant regions.

The antigen-binding molecules described herein preferably display specific binding to IL-11. As used herein, "specific binding" refers to binding which is selective for the antigen, and which can be discriminated from non-specific binding to non-target antigen. An antigen-binding molecule that specifically binds to a target molecule preferably binds the target with greater affinity, and/or with greater duration than it binds to other, non-target molecules. In some embodiments the present antigen-binding molecules may bind with greater affinity to IL-11 than to one or more members of the IL-6 cytokine family. In some embodiments the present antigen-binding molecules may bind with greater affinity to IL-11 than to one or more of IL-6, leukemia inhibitory factor (LIF), oncostatin M (OSM), cardiotrophin-1 (CT-1), ciliary neurotrophic factor (CNTF), and cardiotrophin-like cytokine (CLC).

In embodiments, inhibition of IL-11-mediated signalling is achieved by disrupting IL-11-mediated cis signalling but not disrupting IL-11-mediated trans signalling, e.g. inhibition of IL-11-mediated signalling is achieved by inhibiting gp130-mediated cis complexes involving membrane bound IL-11Rα. In embodiments, inhibition of IL-11-mediated signalling is achieved by disrupting IL-11-mediated trans signalling but not disrupting IL-11-mediated cis signalling, i.e. inhibition of IL-11-mediated signalling is achieved by inhibiting gp130-mediated trans signalling complexes such as IL-11 bound to soluble IL-11Rα or IL-6 bound to soluble IL-6R. In embodiments, inhibition of IL-11-mediated signalling is achieved by disrupting IL-11-mediated cis signalling and IL-11-mediated trans signalling.

The ability of a given polypeptide to bind specifically to a given molecule can be determined by analysis according to methods known in the art, such as by ELISA, Surface Plasmon Resonance (SPR; see e.g. Hearty et al., Methods Mol Biol (2012) 907:411-442), Bio-Layer Interferometry (see e.g. Lad et al., (2015) J Biomol Screen 20(4): 498-507), flow cytometry, or by a radiolabeled antigen-binding assay (RIA) enzyme-linked immunosorbent assay. Through such analysis binding to a given molecule can be measured and quantified. In some embodiments, the binding may be the response detected in a given assay.

In some embodiments, the extent of binding of the antigen-binding molecule to a non-target molecule is less than about 10% of the binding of the antibody to the target molecule as measured, e.g. by ELISA, SPR, Bio-Layer Interferometry or by RIA. Alternatively, binding specificity may be reflected in terms of binding affinity where the antigen-binding molecule binds to IL-11 with a dissociation constant ($K_D$) that is at least 0.1 order of magnitude (i.e. $0.1 \times 10^n$, where n is an integer representing the order of magnitude) greater than the $K_D$ of the antigen-binding molecule towards a non-target molecule. This may optionally be one of at least 0.2, 0.3, 0.4, 0.5, 0.6, 0.7, 0.8, 0.9, 1.0, 1.5, or 2.0.

In some embodiments, the antigen-binding molecule displays binding to human IL-11. In some embodiments, the antigen-binding molecule displays binding to mouse IL-11. In some embodiments, the antigen-binding molecule displays binding to human IL-11 and mouse IL-11. That is, in some embodiments the antigen-binding molecule is cross-reactive for human IL-11 and mouse IL-11. In some embodiments the antigen-binding molecule of the present invention displays cross-reactivity with IL-11 of a non-human primate.

In some embodiments, the antigen-binding molecule according to the present invention binds to IL-11 with a $K_D$ of 5 μM or less, preferably one of ≤1 μM, ≤500 nM, ≤100 nM, ≤75 nM, ≤50 nM, ≤40 nM, ≤30 nM, ≤20 nM, ≤15 nM, ≤12.5 nM, ≤10 nM, ≤9 nM, ≤8 nM, ≤7 nM, ≤6 nM, ≤5 nM, ≤4 nM ≤3 nM, ≤2 nM, ≤1 nM, ≤500 pM.

In some embodiments, the antigen-binding molecule according to the present invention binds to IL-11 with an affinity of binding (e.g. as determined by ELISA) of EC50=1000 ng/ml or less, preferably one of ≤900 ng/ml, ≤800 ng/ml, ≤700 ng/ml, ≤600 ng/ml, ≤500 ng/ml, ≤400 ng/ml, ≤300 ng/ml, ≤200 ng/ml, ≤100 ng/ml, ≤90 ng/ml, ≤80 ng/ml, ≤70 ng/ml, ≤60 ng/ml, ≤50 ng/ml, ≤40 ng/ml, ≤30 ng/ml, ≤20 ng/ml, ≤15 ng/ml, ≤10 ng/ml, ≤7.5 ng/ml, ≤5 ng/ml, ≤2.5 ng/ml, or ≤1 ng/ml.

Affinity of binding to IL-11 by an antigen-binding molecule may be analysed in vitro by ELISA assay. Suitable assays are well known in the art and can be performed by the skilled person, for example, as described in Antibody Engineering, vol. 1 ($2^{nd}$ Edn), Springer Protocols, Springer (2010), Part V, pp 657-665. For example, the affinity of binding to IL-11 by an antigen-binding molecule may be analysed according to the methodology described herein in the experimental examples.

The ability of an antigen-binding molecule to inhibit interaction between two proteins can be determined for example by analysis of interaction in the presence of, or following incubation of one or both of the interaction partners with, the antigen-binding molecule. An example of a suitable assay to determine whether a given antigen-binding molecule is capable of inhibiting interaction between two interaction partners is a competition ELISA assay.

An antigen-binding molecule which is capable of inhibiting a given interaction (e.g. between IL-11 and IL-11Rα, or between IL-11 and gp130, or between IL-11 and IL-11Rα:gp130, or between IL-11:IL-11Rα and gp130) is identified by the observation of a reduction/decrease in the level of interaction between the interaction partners in the presence of—or following incubation of one or both of the interaction partners with—the antigen-binding molecule, as compared to the level of interaction in the absence of the antigen-binding molecule (or in the presence of an appropriate control antigen-binding molecule). Suitable analysis can be performed in vitro, e.g. using recombinant interaction partners or using cells expressing the interaction partners. Cells expressing interaction partners may do so endogenously, or may do so from nucleic acid introduced into the cell. For the purposes of such assays, one or both of the interaction partners and/or the antigen-binding molecule may be labelled or used in conjunction with a detectable entity for the purposes of detecting and/or measuring the level of interaction.

Ability of an antigen-binding molecule to inhibit interaction between two binding partners can also be determined by analysis of the downstream functional consequences of such interaction, e.g. receptor signalling. For example, downstream functional consequences of interaction between IL-11 and IL-11Rα:gp130 or between IL-11:IL-11Rα and gp130 may include proliferation of fibroblasts, myofibroblast generation from fibroblasts, or gene or protein expression of one or more of collagen, fibronectin, periostin, IL-6, IL-11, αSMA, TIMP1, MMP2.

Fibroblasts according to the present disclosure may be derived from any tissue, including liver, lungs, kidney, heart, blood vessels, eye, skin, pancreas, spleen, bowel (e.g. large or small intestine), brain, and bone marrow. In particular embodiments, for the purposes of analysis of the antigen-binding molecule, the fibroblasts may be cardiac fibroblasts (e.g. atrial fibroblasts), skin fibroblasts, lung fibroblasts, kidney fibroblasts or liver fibroblasts. Fibroblasts may be characterised by gene or protein expression of one or more of COL1A, ACTA2, prolyl-4-hydroxylase, MAS516, and FSP1.

Gene expression can be measured by various means known to those skilled in the art, for example by measuring levels of mRNA by quantitative real-time PCR (qRT-PCR), or by reporter-based methods. Similarly, protein expression can be measured by various methods well known in the art, e.g. by antibody-based methods, for example by western blot, immunohistochemistry, immunocytochemistry, flow cytometry, ELISA, ELISPOT, or reporter-based methods.

In some embodiments, the antigen-binding molecule according to the present invention may inhibit protein expression of one or more markers of fibrosis, e.g. protein expression of one or more of collagen, fibronectin, periostin, IL-6, IL-11, αSMA, TIMP1, MMP2.

The ability of an antigen-binding molecule to inhibit interaction between IL-11 and IL-11Rα:gp130 can, for example, be analysed by stimulating fibroblasts with TGFβ1, incubating the cells in the presence of the antigen-binding molecule and analysing the proportion of cells having αSMA-positive phenotype after a defined period of time. In such example, inhibition of interaction between IL-11 and IL-11Rα:gp130 can be identified by observation of a lower proportion of cells having an αSMA-positive phenotype as compared to positive control condition in which cells are treated with TGFβ1 in the absence of the antigen-binding molecule (or in the presence of an appropriate control antigen-binding molecule), or in the presence of an appropriate control antigen-binding molecule.

Such assays are also suitable for analysing the ability of antigen-binding molecule to inhibit IL-11-mediated signalling.

In some embodiments, the antigen-binding molecule according to the present invention is capable of inhibiting interaction between IL-11 and IL-11Rα to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and IL-11Rα in the absence of the antigen-binding molecule (or in the presence of an appropriate control antigen-binding molecule). In some embodiments, the antigen-binding molecule according to the present invention is capable of inhibiting interaction between IL-11 and IL-11Rα to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and IL-11Rα in the absence of the antigen-binding molecule (or in the presence of an appropriate control antigen-binding molecule).

In some embodiments, the antigen-binding molecule according to the present invention is capable of inhibiting interaction between IL-11 and gp130 to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and gp130 in the absence of the antigen-binding molecule (or in the presence of an appropriate control antigen-binding molecule). In some embodiments, the antigen-binding molecule according to the present invention is capable of inhibiting interaction between IL-11 and gp130 to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and gp130 in the absence of the antigen-binding molecule (or in the presence of an appropriate control antigen-binding molecule).

In some embodiments, the antigen-binding molecule according to the present invention is capable of inhibiting interaction between IL-11 and IL-11Rα:gp130 to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and IL-11Rα:gp130 in the absence of the antigen-binding molecule (or in the presence of an appropriate control antigen-binding molecule). In some embodiments, the antigen-binding molecule according to the present invention is capable of inhibiting interaction between IL-11 and IL-11Rα:gp130 to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and IL-11Rα:gp130 in the absence of the antigen-binding molecule (or in the presence of an appropriate control antigen-binding molecule).

In some embodiments, the antigen-binding molecule according to the present invention is capable of inhibiting interaction between IL-11:IL-11Rα complex and gp130 to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11:IL-11Rα complex and gp130 in the absence of the antigen-binding molecule (or in the presence of an appropriate control antigen-binding molecule). In some embodiments, the antigen-binding molecule is capable of inhibiting interaction between IL-11:IL-11Rα complex and gp130 to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11:IL-11Rα complex and gp130 in the absence of the antigen-binding molecule.

Inhibition of IL-11 mediated signalling can also be analysed using $^3$H-thymidine incorporation and/or Ba/F3 cell proliferation assays such as those described in e.g. Curtis et al. Blood, 1997, 90(11) and Karpovich et al. Mol. Hum. Reprod. 2003 9(2): 75-80. Ba/F3 cells co-express IL-11Rα and gp130.

As used herein, IL-11 mediated signalling and/or processes mediated by IL-11 includes signalling mediated by fragments of IL-11 and polypeptide complexes comprising IL-11 or fragments thereof. IL-11 mediated signalling may be signalling mediated by human IL-11 and/or mouse IL-11. Signalling mediated by IL-11 may occur following binding of IL-11 or a complex comprising IL-11 to a receptor to which IL-11 or said complex binds.

In some embodiments, antibodies and fragments according to the present invention are capable of inhibiting the biological activity of IL-11 or a complex comprising IL-11. In some embodiments, the antigen-binding molecule binds to IL-11 or the complex comprising IL-11 in a region which is important for binding to a receptor for the IL-11 or complex comprising IL-11, e.g. gp130 or IL-11Rα, and thereby disrupts binding to and/or signalling through the receptor.

In some embodiments, the antigen-binding molecule according to the present invention is an antagonist of one or more signalling pathways which are activated by signal transduction through receptors comprising IL-11Rα and/or gp130, e.g. IL-11Rα:gp130. In some embodiments, the antigen-binding molecule is capable of inhibiting signalling through one or more immune receptor complexes comprising IL-11Rα and/or gp130, e.g. IL-11Rα:gp130.

In some embodiments, the antigen-binding molecule according to the present invention is capable of inhibiting IL-11-mediated signalling to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of signalling in the absence of the antigen-binding molecule (or in the presence of an appropriate control antigen-binding molecule). In some embodiments, the antigen-binding molecule is capable of reducing IL-11 mediated signalling to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of signalling in the absence of the antigen-binding molecule (or in the presence of an appropriate control antigen-binding molecule).

In some embodiments, the IL-11 mediated signalling may be signalling mediated by binding of IL-11 to IL-11Rα:gp130 receptor. Such signalling can be analysed e.g. by treating cells expressing IL-11Rα and gp130 with IL-11, or by stimulating IL-11 production in cells which express IL-11Rα and gp130.

The $IC_{50}$ for antigen-binding molecule for inhibition of IL-11 mediated signalling may be determined, e.g. by culturing Ba/F3 cells expressing IL-11Rα and gp130 in the presence of human IL-11 and the IL-11 binding agent, and measuring $^3$H-thymidine incorporation into DNA.

In some embodiments, the antigen-binding molecule of the present invention may exhibit an $IC_{50}$ of 10 μg/ml or less, preferably one of ≤5 μg/ml, ≤4 μg/ml, ≤3.5 μg/ml, ≤3 μg/ml, ≤2 μg/ml, ≤1 μg/ml, ≤0.9 μg/ml, ≤0.8 μg/ml, ≤0.7 μg/ml, ≤0.6 μg/ml, or ≤0.5 μg/ml in such an assay.

In some embodiments, the IL-11 mediated signalling may be signalling mediated by binding of IL-11:IL-11Rα complex to gp130. In some embodiments, the IL-11:IL-11Rα complex may be soluble, e.g. complex of extracellular domain of IL-11Rα and IL-11, or complex of soluble IL-11Rα isoform/fragment, and IL-11. In some embodiments, the soluble IL-11Rα is a soluble (secreted) isoform of IL-11Rα, or is the liberated product of proteolytic cleavage of the extracellular domain of cell membrane bound IL-11Rα. IL-11 mediated signalling which is mediated by binding of IL-11 bound to IL-11Rα, to gp130 is referred to herein as 'IL-11 trans signalling'.

In some embodiments, the IL-11:IL-11Rα complex may be cell-bound, e.g. complex of cell-membrane bound IL-11Rα and IL-11. Signalling mediated by binding of IL-11:IL-11Rα complex to gp130 can be analysed by treating cells expressing gp130 with IL-11:IL-11Rα complex, e.g. recombinant fusion protein comprising IL-11 joined by a peptide linker to the extracellular domain of IL-11Rα (e.g. hyper IL-11 as described herein).

In some embodiments, the antigen-binding molecule according to the present invention is capable of inhibiting signalling mediated by binding of IL-11:IL-11Rα complex to gp130, and is also capable of inhibiting signalling mediated by binding of IL-11 to IL-11Rα:gp130 receptor.

In some embodiments, the binding agent may be capable of inhibiting interaction between IL-11 and IL-11 to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of interaction between IL-11 and IL-11 in the absence of the binding agent (or in the presence of an appropriate control binding agent). In some embodiments, the binding agent is capable of inhibiting interaction between IL-11 and IL-11 to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of interaction between IL-11 and IL-11 in the absence of the binding agent.

In some embodiments, the antigen-binding molecule is capable of inhibiting fibroblast proliferation. Proliferation of fibroblasts can be determined by analysing cell division over a period of time. Cell division for a given population of fibroblasts can be analysed, for example, by in vitro analysis of incorporation of $^3$H-thymidine or by CFSE dilution assay, e.g. as described in Fulcher and Wong, Immunol Cell Biol (1999) 77(6): 559-564, hereby incorporated by reference in entirety. Proliferating cells (e.g. proliferating fibroblasts) may also be identified by analysis of incorporation of 5-ethynyl-2'-deoxyuridine (EdU) by an appropriate assay, as described e.g. in Buck et al., Biotechniques. 2008 June; 44(7):927-9, and Sali and Mitchison, PNAS USA 2008 Feb. 19; 105(7): 2415-2420, both hereby incorporated by reference in their entirety.

Fibroblasts according to the present disclosure may be derived from any tissue, including liver, lungs, kidney, heart, blood vessels, eye, skin, pancreas, spleen, bowel (e.g. large or small intestine), brain, and bone marrow. In particular embodiments, for the purposes of analysis of the antigen-binding molecule, the fibroblasts may be cardiac fibroblasts (e.g. atrial fibroblasts), skin fibroblasts, lung fibroblasts, kidney fibroblasts or liver fibroblasts.

In some embodiments, the antigen-binding molecule according to the present invention is capable of inhibiting fibroblast proliferation to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of fibroblast proliferation in the absence of the antigen-binding molecule (or in the presence of an appropriate control antigen-binding molecule). In some embodiments, the antigen-binding molecule is capable of reducing fibroblast proliferation to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of fibroblast proliferation in the absence of the antigen-binding molecule (or in the presence of an appropriate control antigen-binding molecule).

In some embodiments, the antigen-binding molecule according to the present invention is capable of inhibiting a pathological process mediated by IL-11, e.g. following stimulation with a profibrotic factor (e.g. TGFβ1). Pathological processes mediated by IL-11 include fibrosis, and can be evaluated either in vitro, ex vivo or in vivo.

In some embodiments, the antigen-binding molecule according to the present invention is capable of inhibiting fibrosis. In some embodiments, the antigen-binding molecule according to the present invention is capable of reversing or regressing fibrosis. In some embodiments the fibrosis is established or severe fibrosis. Inhibiting or the inhibition of fibrosis, as used herein, refers to the ability of an antigen-binding molecule to reduce, restrain or prevent the development of fibrosis. In some embodiments inhibition of fibrosis refers to e.g. a prophylactic effect whereby fibrosis is prevented from developing. In some embodiments inhibition of fibrosis refers to e.g. a treatment effect whereby existing early or late-stage fibrosis is prevented from developing or advancing to a more advanced stage. Reversing/reversal of or regressing/regression of fibrosis, as used herein, refers to the ability of an antigen-binding molecule to ameliorate the fibrotic state from a more developed state to a less developed state, or to lessen the severity of the fibrosis itself or its symptoms. Reversing/reversal of fibrosis may be associated with an improvement in the fibrotic state.

In the experimental examples herein, inhibition, reversal or regression of fibrosis is analysed for example by measuring the number or percentage of ACTA2$^{+ve}$ cells using Operetta high-content imaging system, measuring cell or organ collagen content by assessing hydroxyproline content, measuring ERK activation/phosphorylation by western blotting, and/or measuring the expression level of inflammation markers such as TNFα and CCL2 or fibrotic markers such as TGFβ1, αSMA (ACTA2), TIMP1, COL1A1, COL1A2 or COL3A1 by quantitative PCR. In tissues such as the liver, inhibition, reversal or regression of fibrosis is analysed for example by determining triglyceride content and serum ALT levels.

Fibrosis may be of a particular tissue or several tissues, e.g. liver, lung, kidney, heart, blood vessel, eye, skin, pancreas, spleen, bowel (e.g. large or small intestine), brain, or bone marrow. Fibrosis may be measured by means well known to the skilled person, for example by analysing gene or protein expression of one or more myofibroblast markers and/or gene or protein expression of one or more markers of fibrosis in a given tissue or tissues.

Myofibroblast markers may include one or more of increased αSMA, vimentin, palladin, cofilin or desmin. Markers of fibrosis include increased level of collagen, fibronectin, periostin, IL-6, IL-11, αSMA, TIMP1 and MMP2, extracellular matrix components, number/proportion of myofibroblasts, and organ weight.

Inhibition/reversal/regression of fibrosis can be measured in vitro or in vivo. For example, whether an antigen-binding molecule is capable of inhibiting/reversing/regressing fibrosis in a given tissue can be analysed in vitro by treating fibroblasts derived from that tissue with a profibrotic stimulus, and then analysing whether the antibody can reduce or reverse myofibroblast generation from the fibroblasts (or e.g. some other marker of fibrosis). Whether an antigen-binding molecule is capable of inhibiting/reversing/regressing fibrosis can be analysed in vivo, for example, by administering the antigen-binding molecule to a subject (e.g. a subject that has been exposed to a profibrotic stimulus), and analysing tissue(s) for one or more markers of fibrosis.

In some embodiments, the antigen-binding molecule according to the present invention is capable of inhibiting/reversing/regressing fibrosis to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of fibrosis in the absence of the antigen-binding molecule (or in the presence of an appropriate control antigen-binding molecule). In some embodiments, the antigen-binding molecule is capable of reducing/reversing/regressing fibrosis to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of fibrosis in the absence of the antigen-binding molecule (or in the presence of an appropriate control antigen-binding molecule).

In some embodiments, the antigen-binding molecule according to the present invention is capable of inhibiting myofibroblast generation from fibroblasts or stellate cells (e.g. hepatic or pancreatic stellate cells), e.g. following exposure of the fibroblasts or stellate cells to profibrotic factor. Myofibroblast generation from fibroblasts or stellate cells can be investigated by analysis for myofibroblast markers. A profibrotic factor according to the present disclosure may be e.g. TGFβ1, IL-11, IL-13, PDGF, ET-1, oncostatin M (OSM) or ANG2 (AngII). In some embodiments, the antigen-binding molecule according to the present invention is capable of inhibiting fibroblast or stellate cell activation by profibrotic factor.

In some embodiments the antigen-binding molecule according to the present invention is capable of promoting stellate cell senescence. Senescence may be measured by detecting expression of senescence markers such as P16, P21 and P53.

In some embodiments, the antigen-binding molecule is capable of inhibiting gene or protein expression in fibroblasts, stellate cells, or fibroblast/stellate cell-derived cells (e.g. myofibroblasts), of one or more of collagen, fibronectin, periostin, IL-6, IL-11, αSMA, TIMP1, MMP2, TNFα, CCL2 e.g. following stimulation with a profibrotic factor. In some embodiments, the antigen-binding molecule is capable of inhibiting gene or protein expression in fibroblasts, or fibroblast-derived cells (e.g. myofibroblasts), of one or more extracellular matrix components, e.g. following stimulation with a profibrotic factor.

In the experimental examples herein, myofibroblast generation from fibroblasts or stellate cells is analysed by measuring αSMA protein expression levels using Operetta High-Content Imaging System following stimulation of the fibroblasts with TGFβ1.

In some embodiments, the antigen-binding molecule according to the present invention is capable of inhibiting myofibroblast generation from fibroblasts or stellate cells to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of myofibroblast generation from fibroblasts or stellate cells in the absence of the antigen-binding molecule (or in the presence of an appropriate control antigen-binding molecule). In some embodiments, the antigen-binding molecule is capable of reducing myofibroblast generation from fibroblasts or stellate cells to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of myofibroblast generation from fibroblasts or stellate cells in the absence of the antigen-binding molecule (or in the presence of an appropriate control antigen-binding molecule).

In some embodiments, the antigen-binding molecule according to the present invention is capable of inhibiting gene or protein expression in fibroblasts, stellate cells or myofibroblasts of one or more of collagen, fibronectin, periostin, IL-6, IL-11, αSMA, TIMP1, MMP2, TNFα, CCL2 e.g. following stimulation with a profibrotic factor (e.g. TGFβ1). In some embodiments, the antigen-binding molecule according to the present invention is capable of inhibiting gene or protein expression to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of gene or protein expression in the absence of the antigen-binding molecule (or in the presence of an appropriate control antigen-binding molecule). In some embodiments, the antigen-binding molecule is capable of reducing gene or protein expression to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of gene or protein expression in the absence of the antigen-binding molecule (or in the presence of an appropriate control antigen-binding molecule).

In some embodiments, the antigen-binding molecule according to the present invention is capable of inhibiting extracellular matrix production by fibroblasts or stellate cells, e.g. following stimulation with a profibrotic factor (e.g. TGFβ1). Extracellular matrix production can be evaluated, for example, by measuring the level of an extracellular matrix component. Extracellular matrix components according to the present invention include e.g. proteoglycan, heparan sulphate, chondroitin sulphate, keratan sulphate, hyaluronic acid, collagen, periostin, fibronectin, vitronectin, elastin, fibronectin, laminin, nidogen, gelatin and aggrecan.

In some embodiments, the antigen-binding molecule according to the present invention is capable of inhibiting collagen secretion from fibroblasts, stellate cells and/or myofibroblasts.

In some embodiments, the antigen-binding molecule according to the present invention is capable of inhibiting extracellular matrix production by fibroblasts or stellate cells to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of extracellular matrix production by fibroblasts or stellate cells in the absence of the antigen-binding molecule (or in the presence of an appropriate control antigen-binding molecule). In some embodiments, the antigen-binding molecule is capable of reducing extracellular matrix production by fibroblasts or stellate cells to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of extracellular matrix production in the absence of the antigen-binding molecule (or in the presence of an appropriate control antigen-binding molecule).

In some embodiments the antigen-binding molecule according to the present invention is capable of upregulating gene or protein expression in hepatic cells of one or more genes/proteins involved in lipogenesis and/or β-oxidation. Such genes/proteins may be e.g. ACOX1 (acyl-CoA oxidase 1), SCD1 (stearoyl-CoA desaturase 1), FASN (fatty acid synthase), or SREBF1 (sterol regulatory element-binding protein 1). In some embodiments, the antigen-binding molecule according to the present invention is capable of upregulating gene or protein expression by more than 1 times, e.g. one of ≥1.01 times, ≥1.05 times, ≥1.1 times, ≥1.15 times, ≥1.2 times, ≥1.25 times, ≥1.3 times, ≥1.35 times, ≥1.4 times, ≥1.45 times, ≥1.5 times, ≥1.55 times, ≥1.6 times, ≥1.65 times, ≥1.7 times, ≥1.75 times, ≥1.8 times, ≥1.85 times, ≥1.9 times, ≥1.95 times, ≥2 times, ≥2.5 times, ≥3 times, ≥3.5 times, ≥4 times, ≥4.5 times, ≥5 times, ≥6 times, ≥7 times, ≥8 times, ≥9 times or ≥10 times the level of gene or protein expression in the absence of the antigen-binding molecule (or in the presence of an appropriate control antigen-binding molecule).

In some embodiments the antigen-binding molecule according to the present invention is capable of inhibiting migratory and/or invasive behaviour, i.e. inhibiting migration and/or invasion, of fibroblasts, stellate cells or myofibroblasts. Migration and invasion of such cells can be critical in the pathology of fibrosis. Migration of cells can be evaluated using e.g. polycarbonate membranes and invasive stimulants such as TGFβ1 or CCL2. Invasion of cells can be measured using e.g. Boyden chamber invasion assays or ECM-coated matrigel. In some embodiments, the antigen-binding molecule according to the present invention is capable of inhibiting migration and/or invasion of fibroblasts, stellate cells or myofibroblasts to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of migration and/or invasion in the absence of the antigen-binding molecule (or in the presence of an appropriate control antigen-binding molecule). In some embodiments, the antigen-binding molecule is capable of reducing migration and/or invasion to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of migration and/or invasion in the absence of the antigen-binding molecule (or in the presence of an appropriate control antigen-binding molecule).

In some embodiments the antigen-binding molecule according to the present invention is capable of inhibiting the presence of immune cells in an organ. In some embodiments the antigen-binding molecule according to the present invention is capable of reducing the number of immune cells in an organ. The organ may be an organ susceptible to, or suffering from, fibrosis, e.g. liver or kidney. The immune cells may be CD45$^+$ cells, e.g. CD3$^+$CD4$^+$ T cells, CD3$^+$CD8$^+$ T cells, B lymphocytes, granulocytes and monocytes. The immune cells may express murine monocyte marker LyC6. In some embodiments the antigen-binding molecule according to the present invention is capable of reducing the number of immune cells in an organ to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the number of immune cells in an organ in the absence of the antigen-binding molecule (or in the presence of an appropriate control antigen-binding molecule). In some embodiments, the antigen-binding molecule is capable of reducing the number of immune cells in an organ to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the number of immune cells in an organ in the absence of the antigen-binding molecule (or in the presence of an appropriate control antigen-binding molecule).

In some embodiments, the antigen-binding molecule according to the present invention is capable of inhibiting proliferation and/or survival of cells of a cancer. The skilled person is able to determine whether an antigen-binding molecule is capable of inhibiting proliferation and/or survival of cells of a cancer for example by analysing the effect of the antigen-binding molecule on cells of the cancer. For example, proliferation of cells can be measured as described herein, e.g. by $^3$H thymidine incorporation or CFSE dilution assays. Cell survival can be analysed by measuring cells for markers of cell viability/cell death following treatment with the antigen-binding molecule.

In some embodiments, the antigen-binding molecule according to the present invention is capable of inhibiting proliferation and/or survival of cells of a cancer to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of proliferation and/or survival of cells of a cancer in the absence of the antigen-binding molecule (or in the presence of an appropriate control antigen-binding molecule). In some embodiments, the antigen-binding molecule is capable of reducing proliferation and/or survival of cells of a cancer to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of proliferation and/or survival of cells of a cancer in the absence of the antigen-binding molecule (or in the presence of an appropriate control antigen-binding molecule).

In some embodiments, the antigen-binding molecule of the present invention inhibits the development and/or progression of cancer in vivo. In some embodiments the antigen-binding molecule causes killing of cancer cells, e.g. by effector immune cells. In some embodiments the antigen-binding molecule causes a reduction in the number of cancer cells in vivo, e.g. as compared to an appropriate control condition. In some embodiments the antigen-binding molecule inhibits tumor growth, e.g. as determined by measuring tumor size/volume over time.

The antigen-binding molecule of the present invention may be analysed for the ability to inhibit development and/or progression of cancer in an appropriate in vivo model. The cancer may be a cancer in which IL-11 mediated signalling and/or cells expressing/comprising IL-11 or a complex comprising IL-11 are pathologically implicated. Such cancers include those described in Xu et al., Cancer Lett. (2016) 373(2):156-63 and Johnstone et al., Cytokine & Growth Reviews (2015) 26(5): 489-498, both of which are hereby incorporated by reference in their entirety.

In some embodiments, administration of an antigen-binding molecule according to the present invention may cause one or more of: inhibition of the development/progression of the cancer, a delay to/prevention of onset of the cancer, a reduction in/delay to/prevention of tumor growth, a reduction in/delay to/prevention of metastasis, a reduction in the severity of the symptoms of the cancer, a reduction in the number of cancer cells, a reduction in tumour size/volume, and/or an increase in survival (e.g. progression free survival), e.g. as determined in an appropriate in vivo model of the cancer. In some embodiments an antigen-binding molecule according to the present invention provides an additive effect when administered in conjunction, e.g. separately, simultaneously or sequentially, with a chemotherapeutic agent, compared to the chemotherapeutic agent administered alone. The additive effect may be any effect described herein, such as reduction of IL-11 signalling, inhibition of the development/progression of a cancer and/or inhibition of tumour growth.

In some embodiments, the antigen-binding molecule according to the present invention is capable of inhibiting tumour growth to less than 100%, e.g. one of 99% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, or 1% or less of the level of tumour growth in the absence of the antigen-binding molecule (or in the presence of an appropriate control antigen-binding molecule). In some embodiments, the antigen-binding molecule is capable of reducing tumour growth to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times the level of tumour growth in the absence of the antigen-binding molecule (or in the presence of an appropriate control antigen-binding molecule).

In some embodiments, the antigen-binding molecule of the present invention is capable of causing killing of cells expressing/comprising IL-11 or a complex comprising IL-11. Killing of cells expressing/comprising IL-11 or a complex comprising IL-11 may be increased through an effector function of the antigen-binding molecule. In embodiments wherein antigen-binding molecule comprises an Fc region the antigen-binding molecule may cause killing of cells expressing/comprising IL-11 or a complex comprising IL-11 through one or more of complement dependent cytotoxicity (CDC), antibody-dependent cell-mediated cytotoxicity (ADCC) and antibody-dependent cellular phagocytosis (ADCP).

An antigen-binding molecule which is capable of causing killing of cells expressing/comprising IL-11 or a complex comprising IL-11 can be identified by observation of a level of killing of cells expressing/comprising IL-11 or a complex comprising IL-11 in the presence of—or following incubation of the cells expressing/comprising IL-11 or a complex comprising IL-11 with—the antigen-binding molecule, as compared to the level of cell killing detected in the absence of the antigen-binding molecule (or in the presence of an appropriate control antigen-binding molecule), in an appropriate assay. Assays of CDC, ADCC and ADCP are well known to the skilled person. The level of killing of cells expressing/comprising IL-11 or a complex comprising IL-11 can also be determined by measuring the number/proportion of viable and/or non-viable cells expressing/comprising IL-11 or a complex comprising IL-11 following exposure to different treatment conditions.

In some embodiments, the antigen-binding molecule of the present invention is capable of causing killing of cells expressing/comprising IL-11 or a complex comprising IL-11 to more than 1 times, e.g. ≥1.01 times, ≥1.02 times, ≥1.03 times, ≥1.04 times, ≥1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times or ≥10 times the level of killing observed in the absence of the antigen-binding molecule (or in the presence of an appropriate control antigen-binding molecule).

In some embodiments, the antigen-binding molecule of the present invention is capable of reducing the number of cells expressing/comprising IL-11 or a complex comprising IL-11 to less than less than 1 times, e.g. ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the number of cells expressing/comprising IL-11 or a complex comprising IL-11 detected following incubation in the absence of the antigen-binding molecule (or following incubation in the presence of an appropriate control antigen-binding molecule), in a comparable assay. Cell numbers and proportions can be determined e.g. by flow cytometry analysis using antibodies allowing detection of cell types.

In some embodiments, the antigen-binding molecule according to the present invention has one or more similar or improved properties as compared to a reference antibody/antigen-binding fragment thereof capable of binding to IL-11.

In some embodiments, the antigen-binding molecule of the present invention displays one or more of the following properties as compared to a reference antibody/antigen-binding fragment thereof capable of binding to IL-11:

(i) binds to IL-11 with similar or greater specificity (i.e. has similar or reduced cross-reactivity for proteins of the IL-6 cytokine family other than IL-11);

(ii) binds to IL-11 (e.g. human IL-11 and/or mouse IL-11) with similar or greater affinity (e.g. has similar or lower EC50 as determined by ELISA; e.g. has similar or lower $K_D$ as determined by SPR analysis);

(iii) similar or greater inhibition of interaction between IL-11 and IL-11Rα;

(iv) similar or greater inhibition of interaction between IL-11 and gp130;

(v) similar or greater inhibition of interaction between IL-11 and IL-11Rα:gp130 receptor complex;

(vi) similar or greater inhibition of interaction between IL-11:IL-11Rα complex and gp130;

(vii) similar or greater inhibition of interaction between IL-11 and IL-11;

(viii) similar or greater inhibition of signalling mediated by IL-11 (e.g. has similar or lower IC50 as determined by ELISA in a suitable assay);

(ix) similar or greater inhibition of signalling mediated by binding of IL-11 to IL-11Rα:gp130 receptor complex;

(x) similar or greater inhibition of signalling mediated by binding of IL-11:IL-11Rα complex to gp130 (i.e. IL-11 trans signalling);

(xi) similar or greater inhibition of fibroblast proliferation;

(xii) similar or greater inhibition of myofibroblast generation from fibroblasts;

(xiii) similar or greater inhibition reversal/regression of myofibroblast generation from fibroblasts;

(xiv) similar or greater inhibition of myofibroblast generation from stellate cells, e.g. hepatic or pancreatic stellate cells;

(xv) similar or greater reversal/regression of myofibroblast generation from stellate cells, e.g. hepatic or pancreatic stellate cells;

(xvi) similar or greater inhibition of migratory and/or invasive behaviour (i.e. inhibition of migration and/or invasion) of fibroblasts, stellate cells or myofibroblasts;

(xvii) similar or greater inhibition of the presence of immune cells in an organ;

(xviii) similar or greater inhibition of a pathological process mediated by IL-11;

(xix) similar or greater inhibition of fibrosis;

(xx) similar or greater reversal/regression of fibrosis;

(xxi) similar or greater inhibition of gene or protein expression in fibroblasts of one or more of collagen, fibronectin, periostin, IL-6, IL-11, αSMA (ACTA2), TIMP1, MMP2, TNFα, CCL2 e.g. following stimulation with a profibrotic factor;

(xxii) similar or greater inhibition of extracellular matrix production by fibroblasts or stellate cells;

(xxiii) similar or greater inhibition of proliferation and/or survival of cells of a cancer;

(xxiv) similar or greater inhibition of development and/or progression of cancer in vivo;

(xxv) similar or greater inhibition of tumour growth;

(xxvi) similar or greater killing of cells expressing/comprising IL-11 or a complex comprising IL-11.

In some embodiments, "greater specificity" or "greater affinity" or "a greater inhibition" or "greater killing" refers, respectively, to a level of specificity, affinity, inhibition or killing which is greater than 1 times, e.g. ≥1.01 times, ≥1.02 times, ≥1.03 times, ≥1.04 times, ≥1.05 times, ≥1.06 times, ≥1.07 times, ≥1.08 times, ≥1.09 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥2.1 times, ≥2.2 times, ≥2.3 times, ≥2.4 times, ≥2.5 times, ≥2.6 times, ≥2.7 times, ≥2.8 times, ≥2.9 times, ≥3 times, ≥3.5 times, ≥4 times, 4.5 times, ≥5 times, ≥6 times, ≥7 times, ≥8 times, ≥9 times, ≥10 times, ≥15 times, ≥20 times, ≥25 times, ≥30 times, ≥35 times, ≥40 times, ≥45 times, ≥50 times, ≥60 times, ≥70 times, ≥80 times, ≥90 times, ≥100 times, ≥200 times, ≥300 times, ≥400 times, ≥500 times, ≥600 times, ≥700 times, ≥800 times, ≥900 times, ≥1000 times the level displayed by the reference antibody/antigen-binding fragment thereof capable of binding to IL-11, as determined in an appropriate assay.

In some embodiments, "similar specificity" or "similar affinity" or "a similar inhibition" or "similar killing" refers, respectively, to a level of specificity, affinity, inhibition or killing which is ≥0.2 times and ≤5 times, e.g. ≥0.3 times and ≤4 times, ≥0.4 times and ≤3 times, ≥0.5 times and ≤2 times, ≥0.6 times and ≤1.75 times, ≥0.7 times and ≤1.5 times, ≥0.75 times and ≤1.25 times, ≥0.8 times and ≤1.2 times, ≥0.85 times and ≤1.15 times, ≥0.9 times and ≤1.1 times, ≥0.91 times and ≤1.09 times, ≥0.92 times and ≤1.08 times, ≥0.93 times and ≤1.07 times, ≥0.94 times and ≤1.06 times, ≥0.95 times and ≤1.05 times, ≥0.96 times and ≤1.04 times, ≥0.97 times and ≤1.03 times, ≥0.98 times and ≤1.02 times, or ≥0.99 times and ≤1.01 times the level displayed by the reference antibody/antigen-binding fragment thereof capable of binding to IL-11, as determined in an appropriate assay.

In some embodiments the reference antibody/antibody fragment capable of binding to IL-11 may comprise the CDRs of an anti-IL-11 antibody clone selected from YU100-H01, YU100-G08 or YU100-F11. In some embodiments the reference antibody/antibody fragment capable of binding to IL-11 may comprise or consist of the VH and VL sequences of an anti-IL-11 antibody clone selected from YU100-H01, YU100-G08 or YU100-F11.

In some embodiments the reference antibody/antibody fragment capable of binding to IL-11 may comprise the CDRs of monoclonal mouse anti-human IL-11 antibody clone #22626; Catalog No. MAB218 (R&D Systems, MN, USA). In some embodiments the reference antibody/antibody fragment capable of binding to IL-11 may comprise or consist of the VH and VL sequences of monoclonal mouse anti-human IL-11 antibody clone #22626; Catalog No. MAB218 (R&D Systems, MN, USA).

Chimeric Antigen Receptors (CARs)

The present invention also provides Chimeric Antigen Receptors (CARs) comprising the antigen-binding molecules or polypeptides of the present invention.

CARs are recombinant receptors that provide both antigen-binding and T cell activating functions. CAR structure and engineering is reviewed, for example, in Dotti et al., Immunol Rev (2014) 257(1), hereby incorporated by reference in its entirety. CARs comprise an antigen-binding region linked to a cell membrane anchor region and a signalling region. An optional hinge region may provide separation between the antigen-binding region and cell membrane anchor region, and may act as a flexible linker.

The CAR of the present invention comprises an antigen-binding region which comprises or consists of the antigen-binding molecule of the present invention, or which comprises or consists of a polypeptide according to the invention.

The cell membrane anchor region is provided between the antigen-binding region and the signalling region of the CAR and provides for anchoring the CAR to the cell membrane of a cell expressing a CAR, with the antigen-binding region in the extracellular space, and signalling region inside the cell. In some embodiments, the CAR comprises a cell membrane anchor region comprising or consisting of an amino acid sequence which comprises, consists of, or is derived from, the transmembrane region amino acid sequence for one of CD3-ζ, CD4, CD8 or CD28. As used herein, a region which is 'derived from' a reference amino acid sequence comprises an amino acid sequence having at least 60%, e.g. one of at least 65%, 70%, 75%, 80%, 85%, 90%, 91%, 92%, 93%, 94%, 95%, 96%, 97%, 98%, 99% or 100% sequence identity to the reference sequence.

The signalling region of a CAR allows for activation of the T cell. The CAR signalling regions may comprise the amino acid sequence of the intracellular domain of CD3-ζ, which provides immunoreceptor tyrosine-based activation motifs (ITAMs) for phosphorylation and activation of the CAR-expressing T cell. Signalling regions comprising sequences of other ITAM-containing proteins such as FcγRI have also been employed in CARs (Haynes et al., 2001 J Immunol 166(1):182-187). Signalling regions of CARs may also comprise co-stimulatory sequences derived from the signalling region of co-stimulatory molecules, to facilitate activation of CAR-expressing T cells upon binding to the target protein. Suitable co-stimulatory molecules include CD28, OX40, 4-1BB, ICOS and CD27. In some cases CARs are engineered to provide for co-stimulation of different intracellular signalling pathways. For example, signalling associated with CD28 costimulation preferentially activates the phosphatidylinositol 3-kinase (PI3K) pathway, whereas the 4-1BB-mediated signalling is through TNF receptor associated factor (TRAF) adaptor proteins. Signalling regions of CARs therefore sometimes contain co-stimulatory sequences derived from signalling regions of more than one co-stimulatory molecule. In some embodiments, the CAR of the present invention comprises one or more co-stimulatory sequences comprising or consisting of an amino acid sequence which comprises, consists of, or is derived from, the amino acid sequence of the intracellular domain of one or more of CD28, OX40, 4-1BB, ICOS and CD27.

An optional hinge region may provide separation between the antigen-binding domain and the transmembrane domain, and may act as a flexible linker. Hinge regions may be derived from IgG1. In some embodiments, the CAR of the present invention comprises a hinge region comprising or consisting of an amino acid sequence which comprises, consists of, or is derived from, the amino acid sequence of the hinge region of IgG1.

Also provided is a cell comprising a CAR according to the invention. The CAR according to the present invention may be used to generate CAR-expressing immune cells, e.g. CAR-T or CAR-NK cells. Engineering of CARs into immune cells may be performed during culture, in vitro.

The antigen-binding region of the CAR of the present invention may be provided with any suitable format, e.g. scFv, scFab, etc.

Nucleic Acids and Vectors

The present invention provides a nucleic acid, or a plurality of nucleic acids, encoding an antigen-binding molecule, polypeptide or CAR according to the present invention.

In some embodiments, the nucleic acid is purified or isolated, e.g. from other nucleic acid, or naturally-occurring biological material. In some embodiments the nucleic acid(s) comprise or consist of DNA and/or RNA.

The present invention also provides a vector, or plurality of vectors, comprising the nucleic acid or plurality of nucleic acids according to the present invention.

The nucleotide sequence may be contained in a vector, e.g. an expression vector. A "vector" as used herein is a nucleic acid molecule used as a vehicle to transfer exogenous nucleic acid into a cell. The vector may be a vector for expression of the nucleic acid in the cell. Such vectors may include a promoter sequence operably linked to the nucleotide sequence encoding the sequence to be expressed. A vector may also include a termination codon and expression enhancers. Any suitable vectors, promoters, enhancers and termination codons known in the art may be used to express a peptide or polypeptide from a vector according to the invention.

The term "operably linked" may include the situation where a selected nucleic acid sequence and regulatory nucleic acid sequence (e.g. promoter and/or enhancer) are covalently linked in such a way as to place the expression of nucleic acid sequence under the influence or control of the regulatory sequence (thereby forming an expression cassette). Thus a regulatory sequence is operably linked to the selected nucleic acid sequence if the regulatory sequence is capable of effecting transcription of the nucleic acid sequence. The resulting transcript(s) may then be translated into a desired peptide(s)/polypeptide(s).

Suitable vectors include plasmids, binary vectors, DNA vectors, mRNA vectors, viral vectors (e.g. gammaretroviral vectors (e.g. murine Leukemia virus (MLV)-derived vectors), lentiviral vectors, adenovirus vectors, adeno-associated virus vectors, vaccinia virus vectors and herpesvirus vectors), transposon-based vectors, and artificial chromosomes (e.g. yeast artificial chromosomes).

In some embodiments, the vector may be a eukaryotic vector, e.g. a vector comprising the elements necessary for expression of protein from the vector in a eukaryotic cell. In some embodiments, the vector may be a mammalian vector, e.g. comprising a cytomegalovirus (CMV) or SV40 promoter to drive protein expression.

Constituent polypeptides of an antigen-binding molecule according to the present invention may be encoded by different nucleic acids of the plurality of nucleic acids, or by different vectors of the plurality of vectors.

Cells Comprising/Expressing the Antigen-Binding Molecules and Polypeptides

The present invention also provides a cell comprising or expressing an antigen-binding molecule, polypeptide or CAR according to the present invention. Also provided is a cell comprising or expressing a nucleic acid, a plurality of nucleic acids, a vector or a plurality of vectors according to the invention.

The cell may be a eukaryotic cell, e.g. a mammalian cell. The mammal may be a primate (rhesus, cynomolgous, non-human primate or human) or a non-human mammal (e.g. rabbit, guinea pig, rat, mouse or other rodent (including any animal in the order Rodentia), cat, dog, pig, sheep, goat, cattle (including cows, e.g. dairy cows, or any animal in the order Bos), horse (including any animal in the order Equidae), donkey, and non-human primate).

The present invention also provides a method for producing a cell comprising a nucleic acid(s) or vector(s) according to the present invention, comprising introducing a nucleic acid, a plurality of nucleic acids, a vector or a plurality of vectors according to the present invention into a cell. In some embodiments, introducing an isolated nucleic acid(s) or vector(s) according to the invention into a cell comprises transformation, transfection, electroporation or transduction (e.g. retroviral transduction).

The present invention also provides a method for producing a cell expressing/comprising an antigen-binding molecule, polypeptide or CAR according to the present invention, comprising introducing a nucleic acid, a plurality of nucleic acids, a vector or a plurality of vectors according to the present invention in a cell. In some embodiments, the methods additionally comprise culturing the cell under conditions suitable for expression of the nucleic acid(s) or vector(s) by the cell. In some embodiments, the methods are performed in vitro.

The present invention also provides cells obtained or obtainable by the methods according to the present invention.

Producing the Antigen-Binding Molecules and Polypeptides

Antigen-binding molecules and polypeptides according to the invention may be prepared according to methods for the production of polypeptides known to the skilled person.

Polypeptides may be prepared by chemical synthesis, e.g. liquid or solid phase synthesis. For example, peptides/polypeptides can by synthesised using the methods described in, for example, Chandrudu et al., Molecules (2013), 18: 4373-4388, which is hereby incorporated by reference in its entirety.

Alternatively, antigen-binding molecules and polypeptides may be produced by recombinant expression. Molecular biology techniques suitable for recombinant production of polypeptides are well known in the art, such as those set out in Green and Sambrook, Molecular Cloning: A Laboratory Manual (4th Edition), Cold Spring Harbor Press, 2012, and in Nat Methods. (2008); 5(2): 135-146 both of which are hereby incorporated by reference in their entirety. Methods for the recombinant production of antigen-binding molecules are also described in Frenzel et al., Front Immunol. (2013); 4: 217 and Kunert and Reinhart, Appl Microbiol Biotechnol. (2016) 100: 3451-3461, both of which are hereby incorporated by reference in their entirety.

In some cases the antigen-binding molecule of the present invention are comprised of more than one polypeptide chain. In such cases, production of the antigen-binding molecules may comprise transcription and translation of more than one polypeptide, and subsequent association of the polypeptide chains to form the antigen-binding molecule.

For recombinant production according to the invention, any cell suitable for the expression of polypeptides may be used. The cell may be a prokaryote or eukaryote. In some embodiments the cell is a prokaryotic cell, such as a cell of archaea or bacteria. In some embodiments the bacteria may be Gram-negative bacteria such as bacteria of the family Enterobacteriaceae, for example *Escherichia coli*. In some embodiments, the cell is a eukaryotic cell such as a yeast cell, a plant cell, insect cell or a mammalian cell, e.g. CHO, HEK (e.g. HEK293), HeLa or COS cells. In some embodiments, the cell is a CHO cell that transiently or stably expresses the polypeptides.

In some cases the cell is not a prokaryotic cell because some prokaryotic cells do not allow for the same folding or post-translational modifications as eukaryotic cells. In addition, very high expression levels are possible in eukaryotes and proteins can be easier to purify from eukaryotes using appropriate tags. Specific plasmids may also be utilised which enhance secretion of the protein into the media.

In some embodiments polypeptides may be prepared by cell-free-protein synthesis (CFPS), e.g. according using a system described in Zemella et al. Chembiochem (2015) 16(17): 2420-2431, which is hereby incorporated by reference in its entirety.

Production may involve culture or fermentation of a eukaryotic cell modified to express the polypeptide(s) of interest. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted polypeptide(s). Culture, fermentation and separation techniques are well known to those of skill in the art, and are described, for example, in Green and Sambrook, Molecular Cloning: A Laboratory Manual (4th Edition; incorporated by reference herein above).

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culturing the cells that express the antigen-binding molecule/polypeptide(s), the polypeptide(s) of interest may be isolated. Any suitable method for separating proteins from cells known in the art may be used. In order to isolate the polypeptide it may be necessary to separate the cells from nutrient medium. If the polypeptide(s) are secreted from the cells, the cells may be separated by centrifugation from the culture media that contains the secreted polypeptide(s) of interest. If the polypeptide(s) of interest collect within the cell, protein isolation may comprise centrifugation to separate cells from cell culture medium, treatment of the cell pellet with a lysis buffer, and cell disruption e.g. by sonification, rapid freeze-thaw or osmotic lysis.

It may then be desirable to isolate the polypeptide(s) of interest from the supernatant or culture medium, which may contain other protein and non-protein components. A common approach to separating protein components from a supernatant or culture medium is by precipitation. Proteins of different solubilities are precipitated at different concentrations of precipitating agent such as ammonium sulfate. For example, at low concentrations of precipitating agent, water soluble proteins are extracted. Thus, by adding different increasing concentrations of precipitating agent, proteins of different solubilities may be distinguished. Dialysis may be subsequently used to remove ammonium sulfate from the separated proteins.

Other methods for distinguishing different proteins are known in the art, for example ion exchange chromatography and size chromatography. These may be used as an alternative to precipitation, or may be performed subsequently to precipitation.

Once the polypeptide(s) of interest have been isolated from culture it may be desired or necessary to concentrate the polypeptide(s). A number of methods for concentrating proteins are known in the art, such as ultrafiltration or lyophilisation.

Compositions

The present invention also provides compositions comprising the antigen-binding molecules, polypeptides, CARs, nucleic acids, expression vectors and cells described herein.

The antigen-binding molecules, polypeptides, CARs, nucleic acids, expression vectors and cells described herein may be formulated as pharmaceutical compositions or medicaments for clinical use and may comprise a pharmaceutically acceptable carrier, diluent, excipient or adjuvant. The composition may be formulated for topical, parenteral, systemic, intracavitary, intravenous, intra-arterial, intramuscular, intrathecal, intraocular, intraconjunctival, intratumoral, subcutaneous, intradermal, intrathecal, oral or transdermal routes of administration which may include injection or infusion.

Suitable formulations may comprise the antigen-binding molecule in a sterile or isotonic medium. Medicaments and pharmaceutical compositions may be formulated in fluid, including gel, form. Fluid formulations may be formulated for administration by injection or infusion (e.g. via catheter) to a selected region of the human or animal body.

In some embodiments the composition is formulated for injection or infusion, e.g. into a blood vessel or tumour.

In accordance with the invention described herein methods are also provided for the production of pharmaceutically useful compositions, such methods of production may comprise one or more steps selected from: producing an antigen-binding molecule, polypeptide, CAR, nucleic acid (or plurality thereof), expression vector (or plurality thereof) or cell described herein; isolating an antigen-binding molecule, polypeptide, CAR, nucleic acid (or plurality thereof), expression vector (or plurality thereof) or cell described herein; and/or mixing an antigen-binding molecule, polypeptide, CAR, nucleic acid (or plurality thereof), expression vector (or plurality thereof) or cell described herein with a pharmaceutically acceptable carrier, adjuvant, excipient or diluent.

For example, a further aspect the invention described herein relates to a method of formulating or producing a medicament or pharmaceutical composition for use in the treatment of a disease/condition (e.g. a cancer), the method comprising formulating a pharmaceutical composition or medicament by mixing an antigen-binding molecule, polypeptide, CAR, nucleic acid (or plurality thereof), expression vector (or plurality thereof) or cell described herein with a pharmaceutically acceptable carrier, adjuvant, excipient or diluent.

Therapeutic and Prophylactic Applications

The antigen-binding molecules, polypeptides, CARs, nucleic acids, expression vectors, cells and compositions described herein find use in therapeutic and prophylactic methods.

The present invention provides an antigen-binding molecule, polypeptide, CAR, nucleic acid (or plurality thereof), expression vector (or plurality thereof), cell or composition described herein for use in a method of medical treatment or prophylaxis. Also provided is the use of an antigen-binding molecule, polypeptide, CAR, nucleic acid (or plurality thereof), expression vector (or plurality thereof), cell or composition described herein in the manufacture of a medicament for treating or preventing a disease or condition. Also provided is a method of treating or preventing a disease or condition, comprising administering to a subject a therapeutically or prophylactically effective amount of an antigen-binding molecule, polypeptide, CAR, nucleic acid (or plurality thereof), expression vector (or plurality thereof), cell or composition described herein.

The methods may be effective to reduce the development or progression of a disease/condition, alleviation of the symptoms of a disease/condition or reduction in the pathology of a disease/condition. The methods may be effective to prevent progression of the disease/condition, e.g. to prevent worsening of, or to slow the rate of development of, the disease/condition. In some embodiments the methods may lead to an improvement in the disease/condition, e.g. a reduction in the symptoms of the disease/condition or reduction in some other correlate of the severity/activity of the disease/condition. In some embodiments the methods may prevent development of the disease/condition a later stage (e.g. a chronic stage or metastasis). In some embodiments the methods may be effective to reverse or regress the disease/condition, e.g. the pathology of a disease/condition may be reversed from a later developmental stage to an earlier developmental stage. In some embodiments the methods may be effective to reverse or regress the symptoms of the disease/condition or some other correlate of the severity/activity of the disease/condition. In some embodiments the methods may be effective to reverse/regress a disease/condition to a state similar to the state observed in a subject without the disease/condition.

It will be appreciated that the articles of the present invention may be used for the treatment/prevention of any disease/condition that would derive therapeutic or prophylactic benefit from a reduction in the level of (i.e. inhibition or antagonism of) IL-11 mediated signalling, or a reduction in the number and/or activity of cells expressing IL-11.

For example, the disease/condition may be a disease/condition in which IL-11 mediated signalling is pathologically implicated, e.g. a disease/condition in which an increased level of IL-11 mediated signalling is positively associated with the onset, development or progression of the disease/condition, and/or severity of one or more symptoms of the disease/condition, or for which an increased level of IL-11 mediated signalling is a risk factor for the onset, development or progression of the disease/condition.

For example, the disease/condition may be a disease/condition in which cells expressing IL-11 are pathologically implicated, e.g. a disease/condition in which an increased number/proportion of cells expressing IL-11 is positively associated with the onset, development or progression of the disease/condition, and/or severity of one or more symptoms of the disease/condition, or for which an increased number/proportion of cells expressing IL-11 is a risk factor for the onset, development or progression of the disease/condition.

In some embodiments, the disease/condition to be treated/prevented in accordance with the present invention is a disease/condition characterised by an increase in the level of IL-11 mediated signalling or a correlate thereof (e.g. in an organ/tissue in which the symptoms of the disease/condition manifest) as compared to the level of IL-11 mediated signalling/correlate thereof in the absence of the disease/condition.

In some embodiments, the disease/condition to be treated/prevented in accordance with the present invention is a disease/condition characterised by an increase in the number/proportion/activity of cells expressing IL-11, e.g. as compared to the number/proportion/activity of cells expressing IL-11 in the absence of the disease/condition.

In some embodiments, a subject may be selected for treatment/prophylaxis as described herein based on the detection of an increase in the level of IL-11 mediated signalling or a correlate thereof and/or an increase in the number/proportion/activity of cells expressing IL-11, e.g. in the periphery, or in an organ/tissue which is affected by the disease/condition (e.g. an organ/tissue in which the symptoms of the disease/condition manifest). The disease/condition may affect any tissue or organ or organ system. In some embodiments the disease/condition may affect several tissues/organs/organ systems.

In some embodiments a subject may be selected for therapy/prophylaxis in accordance with the present invention based on determination that the subject has an increase in the level of IL-11 mediated signalling or a correlate thereof and/or an increase in the number/proportion/activity of cells expressing IL-11, e.g. in the periphery, or in an organ/tissue relative to the level of L-11 mediated signalling/correlate thereof, or number/proportion/activity of cells expressing IL-11 in a healthy subject.

The antigen-binding molecules of the present invention are preferably able to bind to and inhibit the biological activity of IL-11 and IL-11-containing molecules/complexes (e.g. IL-11:IL-11Rα complex). Accordingly, the antigen-binding molecules of the present invention find use in the treatment or prevention of diseases and disorders in which IL-11 is implicated in the pathology of the disease/disorder. That is, the antigen-binding molecules of the present invention find use in the treatment or prevention of diseases and disorders associated with IL-11 mediated signalling.

In some embodiments, the disease/disorder may be associated with increased IL-11, IL-11Rα and/or gp130 gene or protein expression, e.g. as compared to the control (i.e. non-diseased) state. In some embodiments, the disease/disorder may be associated with an increased level of IL-11-mediated signalling as compared to the control state. In some embodiments, the disease/disorder may be associated with an increased level of signalling through ERK and/or STAT3 pathways as compared to the control state. In some embodiments, the increased expression/activity of IL-11, IL-11Rα and/or gp130, and/or the increased level of IL-11-mediated signalling, may be observed in effector cells of the disease/disorder. In some embodiments, the increased expression/activity of IL-11, IL-11Rα and/or gp130, and/or the increased level of IL-11-mediated signalling, may be observed in cells other than the effector cells.

Signalling through ERK can be measured e.g. using an assay for ERK phosphorylation such as an assay described in Assay Guidance Manual: Phospho-ERK Assays, Kim E. Garbison, Beverly A. Heinz, Mary E. Lajiness, Jeffrey R. Weidner, and G. Sitta Sittampalam, Eli Lilly & Company, Sittampalam G S, Coussens N P, Nelson H, et al., editors Bethesda (Md.): Eli Lilly & Company and the National Center for Advancing Translational Sciences; 2004. Signalling through STAT3 can be measured e.g. using an assay for phosphorylation of STAT3, such as the Phospho-STAT3 (Tyr705) Cellular Assay Kit (Cisbio Assays).

In some embodiments, the treatment is of a disease/disorder for which a reduction in IL-11 mediated signalling is therapeutic. In some embodiments, the treatment is of a disease/disorder associated with excess ERK and/or STAT3 signalling. In some embodiments, the treatment is of a disease/disorder associated with excess proliferation or hyperactivation of fibroblasts, or associated with an excess of myofibroblasts.

In some embodiments, the treatment may be aimed at preventing or treating a disease/disorder by decreasing the number or proportion of myofibroblasts or αSMA-positive fibroblasts.

In some embodiments, the disease/disorder may be fibrosis, a fibrotic condition, or a disease/disorder characterised by fibrosis. As used herein, "fibrosis" refers to the formation of excess fibrous connective tissue as a result of the excess deposition of extracellular matrix components, for example collagen. Fibrous connective tissue is characterised by having extracellular matrix (ECM) with a high collagen content. The collagen may be provided in strands or fibers, which may be arranged irregularly or aligned. The ECM of fibrous connective tissue may also include glycosaminoglycans.

As used herein, "excess fibrous connective tissue" refers to an amount of connective tissue at a given location (e.g. a given tissue or organ, or part of a given tissue or organ) which is greater than the amount of connective tissue present at that location in the absence of fibrosis, e.g. under normal, non-pathological conditions. As used herein, "excess deposition of extracellular matrix components" refers to a level of deposition of one or more extracellular matrix components which is greater than the level of deposition in the absence of fibrosis, e.g. under normal, non-pathological conditions.

The cellular and molecular mechanisms of fibrosis are described in Wynn, J. Pathol. (2008) 214(2): 199-210, and Wynn and Ramalingam, Nature Medicine (2012) 18:1028-1040, which are hereby incorporated by reference in their entirety. The main cellular effectors of fibrosis are myofibroblasts, which produce a collagen-rich extracellular matrix.

In response to tissue injury, damaged cells and leukocytes produce pro-fibrotic factors such as TGFβ, IL-13 and PDGF, which activate fibroblasts to αSMA-expressing myofibroblasts, and recruit myofibroblasts to the site of injury. Myofibroblasts produce a large amount of extracellular matrix, and are important mediators in aiding contracture and closure of the wound. However, under conditions of persistent infection or during chronic inflammation there can be overactivation and recruitment of myofibroblasts, and thus over-production of extracellular matrix components, resulting in the formation of excess fibrous connective tissue.

In some embodiments fibrosis may be triggered by pathological conditions, e.g. conditions, infections or disease states that lead to production of pro-fibrotic factors such as TGFβ1. In some embodiments, fibrosis may be caused by physical injury/stimuli, chemical injury/stimuli or environmental injury/stimuli. Physical injury/stimuli may occur during surgery, e.g. iatrogenic causes. Chemical injury/stimuli may include drug induced fibrosis, e.g. following chronic administration of drugs such as bleomycin, cyclophosphamide, amiodarone, procainamide, penicillamine, gold and nitrofurantoin (Daba et al., Saudi Med J 2004 June; 25(6): 700-6). Environmental injury/stimuli may include exposure to asbestos fibres or silica.

Fibrosis can occur in many tissues of the body. For example, fibrosis can occur in the lung, liver (e.g. cirrhosis), kidney, heart, blood vessels, eye, skin, pancreas, spleen, bowel (e.g. large or small intestine), brain, and bone marrow. Fibrosis may also occur in multiple organs at once.

In embodiments herein, fibrosis may involve an organ of the gastrointestinal system, e.g. of the liver, small intestine, large intestine, or pancreas. In some embodiments, fibrosis may involve an organ of the respiratory system, e.g. the lungs. In embodiments, fibrosis may involve an organ of the cardiovascular system, e.g. of the heart or blood vessels. In some embodiments, fibrosis may involve the skin. In some embodiments, fibrosis may involve an organ of the nervous system, e.g. the brain. In some embodiments, fibrosis may involve an organ of the urinary system, e.g. the kidneys. In some embodiments, fibrosis may involve an organ of the musculoskeletal system, e.g. muscle tissue.

In some preferred embodiments, the fibrosis is cardiac or myocardial fibrosis, hepatic fibrosis, or renal fibrosis. In some embodiments cardiac or myocardial fibrosis is associated with dysfunction of the musculature or electrical properties of the heart, or thickening of the walls or valves of the heart. In some embodiments fibrosis is of the atrium and/or ventricles of the heart. Treatment or prevention of atrial or ventricular fibrosis may help reduce risk or onset of atrial fibrillation, ventricular fibrillation, or myocardial infarction.

In some preferred embodiments hepatic fibrosis is associated with chronic liver disease or liver cirrhosis. In some preferred embodiments renal fibrosis is associated with chronic kidney disease.

Diseases/disorders characterised by fibrosis in accordance with the present invention include but are not limited to: respiratory conditions such as pulmonary fibrosis, cystic fibrosis, idiopathic pulmonary fibrosis (IPF), progressive massive fibrosis, scleroderma, obliterative bronchiolitis, Hermansky-Pudlak syndrome, asbestosis, silicosis, chronic pulmonary hypertension, AIDS associated pulmonary hypertension, sarcoidosis, tumor stroma in lung disease, and asthma; chronic liver disease, primary biliary cirrhosis (PBC), schistosomal liver disease, liver cirrhosis, steatohepatitis, non-alcoholic steatohepatitis (NASH), early-stage NASH, late-stage NASH, alcoholic steatohepatitis, steatosis; pancreatic conditions such as chronic pancreatitis and pancreatic fibrosis; cardiovascular conditions such as hypertrophic cardiomyopathy, dilated cardiomyopathy (DCM), fibrosis of the atrium, atrial fibrillation, fibrosis of the ventricle, ventricular fibrillation, myocardial fibrosis, Brugada syndrome, myocarditis, endomyocardial fibrosis, myocardial infarction, fibrotic vascular disease, hypertensive heart disease, arrhythmogenic right ventricular cardiomyopathy (ARVC), tubulointerstitial and glomerular fibrosis, atherosclerosis, varicose veins, cerebral infarcts; neurological conditions such as gliosis and Alzheimer's disease; muscular dystrophy such as Duchenne muscular dystrophy (DMD) or Becker's muscular dystrophy (BMD); gastrointestinal conditions such as Chron's disease, microscopic colitis and primary sclerosing cholangitis (PSC); skin conditions such as scleroderma, nephrogenic systemic fibrosis and cutis keloid; arthrofibrosis; Dupuytren's contracture; mediastinal fibrosis; retroperitoneal fibrosis; myelofibrosis; Peyronie's disease; adhesive capsulitis; kidney disease (e.g., renal fibrosis, nephritic syndrome, Alport's syndrome, HIV associated nephropathy, polycystic kidney disease, Fabry's disease, diabetic nephropathy, chronic glomerulonephritis, nephritis associated with systemic lupus, kidney interstitial fibrosis (IF)); kidney injury e.g. acute kidney injury/renal failure; nephrotoxicity; progressive systemic sclerosis (PSS); chronic graft versus host disease; diseases/disorders of the eye and associated processes, such as Grave's opthalmopathy, epiretinal fibrosis (e.g. diabetic retinopathy (DR)), glaucoma, subretinal fibrosis (e.g. associated with macular degeneration (e.g. wet or dry age-related macular degeneration (AMD))), macular edema, drusen formation, choroidal neovascularization (CNV), post-surgical fibrosis (e.g. of the posterior capsule following cataract surgery, or of the bleb following trabeculectomy for glaucoma), conjunctival fibrosis, subconjunctival fibrosis; arthritis; fibrotic pre-neoplastic and fibrotic neoplastic disease; and fibrosis induced by chemical or environmental insult (e.g., cancer chemotherapy, pesticides, radiation/cancer radiotherapy).

Early stage NASH refers herein to steatotic stages of fatty liver disease, e.g. NAFLD, which may bridge into a NASH state in which the liver has become inflamed. Late-stage NASH refers herein to states of persistent liver inflammation which may include fibrosis.

It will be appreciated that many of the diseases/conditions listed above are interrelated. For example, fibrosis of the ventricle may occur post myocardial infarction, and is associated with DCM, HCM and myocarditis.

In particular embodiments, the disease/disorder may be one of pulmonary fibrosis, atrial fibrillation, ventricular fibrillation, hypertrophic cardiomyopathy (HCM), dilated cardiomyopathy (DCM), non-alcoholic steatohepatitis (NASH), cirrhosis, chronic kidney disease, scleroderma, systemic sclerosis, keloid, cystic fibrosis, Crohn's disease, post-surgical fibrosis or retinal fibrosis, e.g. associated with wet age-related macular degeneration (AMD).

In some embodiments the methods may be effective to reverse or regress fibrosis. The fibrosis may be established or severe fibrosis and may be associated with any of the diseases/conditions described herein. In some embodiments the methods may be effective to reverse or regress any of the diseases/disorders provided herein.

Fibrosis can lead directly or indirectly to, and/or increase susceptibility to development of, diseases/disorders. For example, more than 80% of hepatocellular carcinomas (HCCs) develop in fibrotic or cirrhotic livers (Affo et al. 2016, Annu Rev Pathol.), suggesting an important role for liver fibrosis in the premalignant environment (PME) of the liver.

Accordingly, the antigen-binding molecules of the present invention find use in methods for the treatment and prevention of diseases/disorders associated with fibrosis, and/or for which fibrosis is a risk factor. In some embodiments, the disease/disorder associated with fibrosis, or for which fibrosis is a risk factor, is a cancer, e.g. cancer of the liver (e.g. hepatocellular carcinoma).

IL-11 is also implicated in the pathology of other diseases/disorders, and the antibodies and fragments of the present invention accordingly find use in methods to treat, prevent, alleviate and/or reverse or regress the symptoms of these diseases/disorders also.

In some embodiments, fibrosis may be associated with angiogenesis e.g. in the eye. In some embodiments, methods of treating or preventing fibrosis, methods of determining the suitability of a subject for such treatment/prevention and methods of diagnosing/prognosing fibrosis as described herein are also applicable to treating/preventing/diagnosing/prognosing angiogenesis, and vice versa. Fibrosis of the eye may be associated with choroidal neovascularization (CNV).

In some embodiments the antigen-binding molecules of the present invention are provided for use in methods to treat and/or prevent metabolic diseases. That is, the present invention provides for the treatment/prevention of metabolic diseases through inhibition of IL-11 mediated signalling, in e.g. a cell, tissue/organ/organ system/subject. As used herein, a "metabolic disease" refers to any disease or condition which is caused by, or which is characterised by, abnormal metabolism. "Metabolism" in this context refers to the bodily conversion/processing of sources of energy, e.g. substances consumed to provide nutrition, into energy and/or for storage. "Normal metabolism" may be the metabolism of a healthy subject not having a disease, e.g. not having a metabolic disease, or not possessing a symptom/correlate of a metabolic disease.

A subject having a metabolic disease may display abnormal metabolism. A subject having a metabolic disease may have a symptom/correlate of abnormal metabolism. A subject having a metabolic disease may have been diagnosed as having metabolic disease. A subject may satisfy the diagnostic criteria for the diagnosis of a metabolic disease. In some embodiments, the present invention provides for the treatment/prevention of diseases/conditions in a subject for which a metabolic disease provides a poor prognosis.

In some embodiments, the metabolic disease affects one or more of: the liver, pancreas, cardiovascular system, digestive system, the excretory system, the respiratory system, the renal system, the reproductive system, the circulatory system, the muscular system, the endocrine system, the exocrine system, the lymphatic system, the immune system, the nervous system, and/or the skeletal system.

In some embodiments the metabolic disease is, or comprises (e.g. is characterised by), obesity, type 2 diabetes (T2D), type 1 diabetes (T1D), pre-diabetes, being overweight, metabolic syndrome, pregnancy-associated hyperglycemia (i.e. gestational diabetes), cholestatic liver disease, hyperglycaemia, hyperlipidaemia, hypertriglyceridemia, hypercholesterolemia, wasting, cachexia, chemotherapy-associated weight loss, pancreatic insufficiency, pancreatitis, acute pancreatitis, chronic pancreatitis, steatosis, non-alcoholic fatty liver disease (NAFLD), non-alcoholic fatty liver (NAFL), non-alcoholic steatohepatitis (NASH), lipodystrophy, lipohypertrophy, lipoatrophy, insulin deficiency, insulin resistance and hyperglucagonemia. In some embodiments the metabolic disease is, or comprises, obesity. In some embodiments the metabolic disease is, or comprises, cholestasis, i.e. a reduced flow of bile from the liver to the duodenum. The disease may be cholestatic liver disease (Jansen et al., Hepatology (2017) 65(2):722-738 and Pollock and Minuk, J Gastroenterol Hepatol (2017) 32(7):1303-1309, both of which are hereby incorporated by reference in their entirety), including e.g. primary biliary cholangitis (PBC) and primary sclerosing cholangitis (PSC).

Aspects of the present invention are concerned with the treatment and/or prevention of aberrant and/or insufficient function of cells/tissue(s)/organ(s)/organ systems having a role in metabolism. In particular, treatment and/or prevention of aberrant function and/or insufficient function of cells of the pancreas/pancreatic tissue/the pancreas is contemplated herein, as is the treatment and/or prevention of aberrant function and/or insufficient function of cells of the liver/hepatic tissue/the liver.

In some embodiments the metabolic disease is, or comprises, wasting. As used herein, the term "wasting" refers to involuntary weight loss, which may be progressive and/or degenerative. Wasting can be defined as loss of muscle with or without loss of fat mass, and typically involves significant, usually involuntary, loss of body mass (including skeletal muscle), and may or may not include loss of adipose tissue. In some instances, adipose tissue wasting can occur in isolation, as seen in lipodystrophy diseases. Wasting may be characterised by a negative protein and energy balance driven by a variable combination of reduced food intake and abnormal metabolism (Fearon et al. Lancet Oncol. (2011) 12(5):489-95). Wasting can lead to progressive functional impairment, impaired quality of life, increased risk for morbidity and mortality. In some cases, wasting leads to asthenia (abnormal physical weakness or lack of energy) and/or anaemia (deficiency of red cells or haemoglobin in the blood). In some cases, wasting cannot be fully reversed by conventional nutritional support or by therapeutic interventions that have been trialled to date. Death usually occurs once weight loss has reached 30% of the patient's historic stable body weight (Tisdale, Nature Reviews Cancer, 2, 862-871 (2002)).

Diseases/conditions characterised by wasting include cachexia (non-age-related loss of muscle mass), sarcopenia (loss of muscle mass: e.g. age-related, disuse, space travel or denervation), anorexic disorders (protein-energy malnutrition), muscular dystrophies, lipodystrophies (e.g. abnormal or degenerative condition of adipose tissue), lipoatrophy (age-related loss of subcutaneous fat in the face and other tissues) and myopenia (muscle wasting in any chronic illness; proposed by Fearon et al. J Cachexia Sarcopenia Muscle. 2011; 2:1-3). Herein, diseases/conditions characterised by wasting are also referred to as "wasting disorders".

In some embodiments a wasting disorder according to the present disclosure is cachexia, pre-cachexia, refractory cachexia, sarcopenia, anorexia, lipodystrophy, lipoatrophy and/or myopenia. In some embodiments according to the various aspects described herein, the wasting disorder is cachexia, pre-cachexia and/or refractory cachexia.

Wasting disorders arising due to chronic illness may include "mild muscle wasting disease" (with or without frailty), "moderate muscle wasting disease" (with or without frailty; sometimes known as "pre-cachexia"), or "severe muscle wasting disease" (sometimes called "cachexia", often with frailty present). Cachexia can be defined as involuntary weight loss of >5% from historical stable weight, a body mass index (BMI) of <20 kg/m2 (person younger than 65) or <22 kg/m2 (person aged 65 or older) with any degree of weight loss >2%, or a skeletal muscle index consistent with sarcopenia with any degree of weight loss >2%. The subject may also display <10% body fat and/or a low blood albumin level of <35 g/l. These criteria may also help to identify populations 'at-risk' of developing a wasting disorder (Fearon et al. Lancet Oncol. 2011; 12(5):489-95).

A three-step classification of cachexia has been proposed, with severity classified according to degree of depletion of energy stores and body protein (BMI) in combination with degree of ongoing weight loss.

1. Pre-cachexia—when a patient has weight loss <5%, but has not yet developed serious complications.

2. Cachexia—where the syndrome is progressing, with weight loss exceeding the above-mentioned parameters, but still potentially able to be treated.

3. Refractory cachexia—the point at which the disease is no longer responsive to treatment or when treatment benefits are outweighed by burden and risk (Fearon et al, supra). Often, the refractory stage is dictated by the overall stage of an underlying illness, described below, and the condition of the patient.

Metabolic diseases may be present in acute or chronic disease settings. Aspects of the present invention provide for the treatment/prevention of diseases/conditions associated with metabolic diseases. Disease/conditions associated with metabolic diseases include diseases/conditions that are positively associated with the onset of a metabolic disease. In some embodiments, the disease/condition associated with a metabolic disease is one which can cause/causes/has caused (i.e. can lead to, leads to or has led to) a metabolic disease.

Disease/conditions associated with metabolic diseases also include diseases/conditions which are caused and/or exacerbated (made worse, progressed and/or complicated) by a metabolic disease. In some embodiments a disease/condition associated with a metabolic disease, may be positively associated with the onset of a metabolic disease and may also be exacerbated by a metabolic disease. An "associated" disease/condition may be one comprising a metabolic disease-related pathology.

In embodiments of the invention, a metabolic disease, or a disease/condition associated with a metabolic disease may be present in or affect any organ/tissue, such as the heart, liver, kidney, brain, skin, muscular system, stomach, small intestine, large intestine, pancreas, mouth, salivary glands, pharynx, oesophagus, gallbladder, trachea, larynx, bladder, ovary, uterus, testes, glands of the endocrine system e.g. pituitary or thyroid, the lymphatic system e.g. spleen.

In embodiments of the invention, a disease/condition associated with a metabolic disease may be one or more of cancer, cardiac disease, kidney disease, lung disease, liver disease, chronic infection, neurological degenerative diseases, acute injury, traumatic injury/trauma, post-operative conditions, or ageing/senescence.

In accordance with various aspects of the present invention, a method of treating and/or preventing a metabolic disease according to the present invention may comprise one or more of the following:

Reducing blood lipid level;
Reducing blood glucose level;
Increasing glucose tolerance (e.g. of a glucose intolerant subject);
Increasing insulin tolerance (e.g. of an insulin resistant subject);
Increasing pancreatic function
Reducing body weight (e.g. of an overweight/obese subject);
Reducing body fat mass;
Increasing lean mass;
Reducing fasting blood glucose level;
Reducing serum triglyceride level;
Reducing serum cholesterol level;
Increasing glucose tolerance;
Increasing pancreatic function (e.g. exocrine and/or endocrine function);
Increasing the growth of pancreatic tissue;
Regenerating pancreatic tissue;
Increasing pancreas weight;
Reducing pancreatic islet cell hyperplasia;
Reducing glucagon expression;
Increasing insulin expression;
Increasing body weight (e.g. of a subject having a wasting disease, e.g. cachexia);
Reducing expression of IL-11 protein in the liver;
Reducing Erk activation in the liver;
Reducing steatosis, e.g. of the liver;
Reducing liver triglyceride level;
Reducing serum ALT level;
Reducing expression of a pro-inflammatory factor (e.g. TNFa, CCL2, CCL5, IL-6, CXCL5, and/or CXCL1);
Reducing expression of a pro-fibrotic factor (e.g. IL-11, TIMP1, ACTA2, TGFβ1, MMP2, TIMP2, MMP9, COL1A2, COL1A1 and/or COL3A1);
Reducing serum TGFβ1 level;
Reducing expression/production by HSCs of IL-11, ACTA2, MMP2, TGFβ1, PDGF, ANG II, bFGF, CCL2 and/or H2O2;
Inhibiting HSC-to-myofibroblast transition by HSCs;
Reducing the number/proportion of myofibroblasts in the liver;
Reducing liver hydroxyproline level;
Increasing liver function;
Increasing the function of an organ/tissue affected by a metabolic disease;
Reducing liver damage; and
Reducing the number/proportion of CD45+ cells in the liver.

IL-11 has been implicated in the development and progression of various cancers. Studies suggest that IL-11 is important for promoting chronic gastric inflammation and associated gastric, colonic, hepatocellular and breast cancer tumorogenesis through excessive activation of STAT3 (Ernst M, et al. J Clin Invest. (2008); 118:1727-1738), that IL-11 may promote tumorigenesis by triggering the JAK-STAT intracellular signalling pathway, and may also promote metastasis via signalling through the PI3K-AKT-mTORC1 pathway (Xu et al., Cancer Letters (2016) 373(2): 156-163). Through STAT3, IL-11 promotes survival, proliferation, invasion angiogenesis and metastasis, the IL-11/GP130/

JAK/STAT3 signalling axis may be rate-limiting for the progression of gastrointestinal tumors, and elevated IL-11 expression is associated with poor prognosis of breast cancer patients (Johnstone et al., Cytokine & Growth Reviews (2015) 26(5): 489-498). IL-11 has also been shown to influence breast cancer stem cell dynamics and tumor heterogeneity (Johnstone et al., Cytokine & Growth Reviews (2015) 26(5): 489-498). Recently, IL-11 signalling has been implicated in chemoresistance of lung adenocarcinoma; cancer associated fibroblasts were found to upregulate IL-11, and confer chemoresistance to lung cancer cells through activation of the IL-11/IL-11R/STAT3 anti-apoptotic signalling pathway (Tao et al. 2016, Sci Rep. 6; 6:38408). IL-11 signalling may promote the fibroblast-to-myofibroblast transition and extracellular matrix production by fibroblasts in the premalignant environment (PME) and tumour micro-environment (TME).

In some embodiments, the antigen-binding molecules of the present invention are provided for use in methods to treat/prevent a cancer. In some embodiments, the cancer may be a cancer which leads directly or indirectly to inflammation and/or fibrosis.

A cancer may be any unwanted cell proliferation (or any disease manifesting itself by unwanted cell proliferation), neoplasm or tumor or increased risk of or predisposition to the unwanted cell proliferation, neoplasm or tumor. The cancer may be benign or malignant and may be primary or secondary (metastatic). A neoplasm or tumor may be any abnormal growth or proliferation of cells and may be located in any tissue.

In some embodiments, the antigen-binding molecules of the present invention are provided for use in methods to treat/prevent a cancer, e.g. an epithelial cell cancer, breast cancer, gastrointestinal cancer (e.g. esophageal cancer, stomach cancer, pancreatic cancer, liver cancer (e.g. HCC), gallbladder cancer, colorectal cancer, anal cancer, gastrointestinal carcinoid tumor, and lung cancer (e.g. non-small cell lung cancer (NSCLC) or small cell lung cancer (SCLC)). In some embodiments, the cancer is a cancer for which acute and/or chronic inflammation is a risk factor. In some embodiments, the cancer is a cancer for which a disease/disorder characterised by fibrosis (e.g. as described herein) is a risk factor.

In some embodiments, the cancer may be associated with increased IL-11, IL-11Rα and/or gp130 gene or protein expression. For example, cells of the cancer may have increased expression of IL-11, IL-11Rα and/or gp130 as compared to comparable, non-cancerous cells, or may be associated with increased expression of IL-11, IL-11Rα and/or gp130 by other cells (e.g. non-cancerous cells) as compared to the level of expression by comparable cells in the absence of a cancer (e.g. in a healthy control subject). In some embodiments, cells of the cancer may be determined to have an increased level of signalling through ERK and/or STAT3 pathways as compared to comparable non-cancerous cells.

In some embodiments, the cancer may be associated with a mutation in IL-11, IL-11Rα and/or gp130. In some embodiments, such mutation may be associated with increased level of gene or protein expression, or may be associated with an increased level of IL-11/IL-11R signalling relative to the level of expression/signalling observed in the absence of the mutation.

IL-11 has also been implicated in diseases/disorders characterised by inflammation. Intra-articular injection of IL-11 has been shown to cause joint inflammation (Wong et al., Cytokine (2005) 29:72-76), and IL-11 has been shown to be proinflammatory at sites of IL-13-mediated tissue inflammation (Chen et al., J Immunol (2005) 174:2305-2313). IL-11 expression has also been observed to be significantly increased in chronic skin lesions in atopic dermatitis, and is known to be involved in bronchial inflammation (Toda et al., J Allergy Clin Immunol (2003) 111:875-881). IL-11-mediated signalling is implicated in inflammatory bowel disease (IBD) and asthma (Putoczki and Ernst, J Leuko Biol (2010) 88(6)1109-1117). IL-11 has also been identified as a risk factor for multiple sclerosis; IL-11 is elevated in the cerebrospinal fluid of patients with clinically isolated syndrome (CIS) as compared to control subjects, and serum levels of IL-11 are higher during relapses for patients with relapsing-remitting multiple sclerosis, and IL-11 may promote differentiation of CD4+ T cells to a TH17 phenotype—TH17 cells are important cells in the pathogenesis of multiple sclerosis (Zhang et al., Oncotarget (2015) 6(32): 32297-32298).

In some embodiments, the antigen-binding molecules of the present invention are provided for use in methods to treat/prevent a disease/disorder characterised by inflammation. In some embodiments, a disease or disorder characterised by inflammation may be a disease/disorder which leads directly or indirectly to a cancer and/or fibrosis. Diseases characterised by inflammation include e.g. allergic inflammation such as allergic asthma and bronchial inflammation, atopic dermatitis, allergic rhinitis and ocular allergic diseases, and autoimmune diseases such as multiple sclerosis, systemic lupus erythematosus, rheumatoid arthritis, chronic active hepatitis, type 1 diabetes mellitus, celiac disease, Grave's disease, uveitis, pemphigus, psoriasis, Crohn's disease, ulcerative colitis, inflammatory bowel disease, anaemia and autoimmune thyroiditis.

In some embodiments, the antigen-binding molecules of the present invention are provided for use in methods to treat/prevent hepatotoxicity and diseases/disorders characterised by hepatotoxicity. As used herein, hepatotoxicity refers to damage to and/or death of liver cells/tissue. Hepatotoxicity can refer to a state of toxic damage to the liver, specifically with death of the hepatocyte cells within the liver. Hepatotoxicity may be determined/diagnosed by detection of one or more correlates of hepatotoxicity as described hereinbelow. Hepatotoxicity may arise as a consequence of hepatotoxic insult. As used herein "hepatotoxic insult" refers to any treatment, event or conditions giving rise to hepatotoxicity. For example, hepatotoxic insult may be caused by a chemical/physical treatment/experience, or gaseous conditions. In some embodiments hepatotoxic insult is chemical, e.g. in the case of drug-induced liver injury, e.g. APAP-induced hepatotoxicity. In some embodiments hepatotoxic insult is physical, e.g. in the case of hepatotoxicity arising as a result of surgical damage to liver tissue, which may occur e.g. surgery to treat a disease and/or for liver transplantation (e.g. the hepatotoxicity may have iatrogenic causes). In some embodiments hepatotoxic insult arises from hypoxia, e.g. as a consequence of ischaemia, or may result from reperfusion (e.g. the hepatotoxic insult may arise from IRI).

Hepatotoxicity may be chemical-driven liver damage, for example damage or injury caused by a medicine, chemical, ischaemia, reperfusion, sepsis or herbal or dietary supplements. In some embodiments hepatotoxicity refers to drug-induced liver injury (DILI). In some embodiments hepatotoxicity refers to liver injury caused by a hepatotoxin. A hepatotoxin may be alcohol. Hepatotoxicity may also be termed toxic hepatitis. Hepatotoxicity may refer to acute and/or chronic hepatotoxicity.

Hepatotoxicity may be caused, directly or indirectly, by alcohol ingestion e.g. chronic alcohol consumption. Hepatotoxicity as referred to herein may be caused, directly or indirectly, by fasting, malnutrition, infection by an infectious agent (e.g. a hepatitis virus (e.g. hepatitis A, B, C, D or E), HIV), cancer or drug interactions.

Hepatotoxicity may be present in association with other disorders, diseases and conditions. Disorders, diseases or conditions associated with hepatotoxicity include acute liver injury (ALI), acute liver failure, acute liver disease, chronic liver disease, liver damage, hepatitis e.g. viral hepatitis, alcoholic hepatitis, liver ischemia-reperfusion injury (IRI) e.g. 'warm' ischemia-reperfusion (WIR), radiation-induced liver disease (RILD), drug-induced liver injury (DILI), autoimmune liver injury, cholestatic liver disease, HIV and cancer.

Drug-induced liver injury (DILI) includes intrinsic and idiosyncratic hepatotoxicity, and idiosyncratic DILI further includes allergic and nonallergic reaction. The intrinsic mechanism is related to dose dependent hepatotoxicity, whereas idiosyncratic hepatotoxicity is not dose dependent and may happen in an unpredictable fashion. Allergic idiosyncratic hepatotoxicity is further characterized by the presence of symptoms and signs typical of an adaptive immune system reaction, including fever, skin reactions, eosinophilia, formation of autoantibodies, and a short latency time particularly after re-exposure (Khoury et al., J Clin Transl Hepatol. 2015 Jun. 28; 3(2): 99-108).

In some embodiments antigen-binding molecules of the present invention may be used for the diagnosis, treatment and prophylaxis of acetaminophen (APAP)-induced hepatotoxicity. Acetaminophen is also known as N-acetyl-p-aminophenol or paracetamol, or by the brand names Tylenol and Panadol. Acetaminophen intoxication results in hepatotoxicity associated with increased serum concentrations of hepatocellular leakage enzymes such as aspartate aminotransferase, lactate dehydrogenase, and alanine aminotransferase, centrilobular degeneration and necrosis, and activation of Kupffer cells (Trepicchio W L et al., Toxicol Pathol. 2001; 29(2):242-9).

In some embodiments the antigen-binding molecules of the present invention are provided for use in methods to treat/prevent kidney injury, e.g. acute kidney injury (AKI; acute renal failure), or a disease/disorder associated with kidney injury. Kidney injury may be characterised by damage to tubular epithelial cells (TECs) and/or the transition of TECs to an epithelial-to-mesenchymal cell-like phenotype (i.e. EMT). Transition of TECs to a mesenchymal cell-like phenotype may be characterised e.g. by reduced expression of E-cadherin, increased expression of SNAIL and/or increased expression of ACTA2. The kidney injury may have any cause, examples include kidney injury resulting from mechanical (i.e. physical) damage or injury, chemical damage or injury, ischemia or genetic predisposition. The cause or damage will normally result in impaired kidney function, which may lead to kidney failure. Mechanical damage or injury may include physical injury to the subject, to the kidney, to TECs or to podocytes. It may also include tubular obstruction/blockage, e.g. of the urinary tract. In some embodiments the kidney injury is drug-induced kidney injury or drug-induced acute kidney injury.

Ischemic damage may arise from a decrease in blood flow to the kidney which may be caused by a number of factors such as low blood pressure e.g. due to sepsis, blood loss or surgery, or the effect of a chemical agent, e.g. a medicine or drug, administered to the subject to treat another disease, disorder or condition. Kidney injury caused by ischemia may be ischemia-induced kidney injury, or ischemia-induced acute kidney injury. Kidney injury caused by crush injury may be ischemia-induced kidney injury with vasoconstriction or can be caused by tubular cast mechanical factors or toxic effects of circulating factors e.g. myoglobin.

In some embodiments the kidney injury, which may be AKI, is characterised by damage to, which may in some cases include or lead to death of, tubular epithelial cells (TECs) of the kidney, i.e. renal tubular epithelial cells. The TECs may be proximal or distal, both of which may be damaged in AKI, as may also the podocytes in the kidney glomerulus. Damage to TECs may also be any type of damage, injury or insult, e.g. as described above this may be mechanical, chemical or ischemic damage. Damage to TECs is a common causative factor of kidney injury, particularly AKI. Proliferation of TECs provides a mechanism for recovery and restoration of kidney function, whereas failure of TECs to proliferate can lead to disease development and progression, e.g. to chronic kidney disease and renal failure. Proliferation of podocyte precursors to restore glomerulus function may also occur, but is not as well described as TEC proliferation. Mechanical damage may include e.g. unilateral ureteric obstruction (UUO).

In some embodiments the kidney injury is nephrotoxicity, referring to toxicity of the kidneys. Nephrotoxicity can arise as a result of toxic effects of certain substances on renal function, and may therefore be viewed as a consequence of chemical damage or injury. As with chemical damage or injury, nephrotoxicity may be a side effect of the administration of an agent to treat a disease or condition not occurring in the kidney, or occurring both in the kidney and in one or more other tissues. In some embodiments nephrotoxicity may be a side effect of administration of a chemotherapeutic agent administered to the subject in order to prevent or treat cancer. As such, nephrotoxicity may be a form of drug-induced kidney injury or drug-induced acute kidney injury. In some embodiments kidney injury may be induced by folic acid, i.e. is folate-induced kidney injury.

In some embodiments, the antigen-binding molecules are provided for use in the diagnosis, treatment and/or prophylaxis of cisplatin-induced kidney injury. This may include cisplatin-induced acute kidney injury or cisplatin-induced nephrotoxicity. Cisplatin (dichlorodiamino platinum; SP-4-2)-diamminedichloroplatinum(II)) is a chemotherapeutic agent that is widely used to treat a range of cancers including head and neck, breast, lung, testis, ovarian, brain, and bladder cancers and is widely acknowledged to lead to kidney injury and dysfunction involving tubular damage and necrosis (e.g. Oh et al., Electrolyte Blood Press 2014 December; 12(2): 55-65; P A Arunkumar et al., Asian Pac J Trop Biomed 2012 Aug. 2(8): 640-644). Other platinum-based chemotherapeutics agents also cause kidney damage.

It is recognised that a subject having kidney injury may also present with fibrosis of the kidney, either as a disease condition having a separable etiology or as a secondary effect of the kidney injury. In some embodiments the kidney injury being diagnosed, treated or prevented is not fibrosis of the kidney, e.g. renal fibrosis. In some embodiments the subject does not have fibrosis. In some embodiments TEC damage occurs in the absence of fibrosis. In some embodiments fibrosis arises separately (e.g. secondarily to) AKI, e.g. due to incomplete regeneration of TECs. In some embodiments, the damaged TECs in the subject are not pro-fibrotic TECs. In some embodiments, fibrosis does not arise.

In some embodiments, the antigen-binding molecules of the present invention are provided for use in methods to treat/prevent a disease/disorder associated with infection, in particular where infection leads directly or indirectly to fibrosis, cancer or inflammation. A disease associated with infection may be a disease which is caused or exacerbated by infection with the relevant infectious agent, or may be a disease for which infection with the relevant infectious agent is a risk factor.

An infection may be any infection or infectious disease, e.g. bacterial, viral, fungal, or parasitic infection. In particular embodiments, the disease/disorder may be associated with a viral infection. In some embodiments it may be particularly desirable to treat chronic/persistent infections, e.g. where such infections are associated with inflammation, cancer and/or fibrosis.

The infection may be chronic, persistent, latent or slow, and may be the result of bacterial, viral, fungal or parasitic infection. As such, treatment may be provided to patients having a bacterial, viral or fungal infection. Examples of bacterial infections include infection with *Helicobacter pylori* and *Mycobacterium tuberculosis* infection of the lung. Examples of viral infections include infection with EBV, HPV, HIV, hepatitis B or hepatitis C.

The treatment may involve ameliorating, treating, or preventing any disease/disorder/condition associated with IL-11 signalling, and/or described herein, by inhibiting the biological activity of IL-11 or a complex comprising IL-11. The treatment may involve reversing or regressing the disease/disorder by inhibiting the biological activity of IL-11 or a complex comprising IL-11. Such methods may include the administration of the antibodies/fragments/compositions according to the present invention to bind to and inhibit the biological activity of IL-11 or a complex comprising IL-11. Herein, inhibiting the biological activity of IL-11 or a complex comprising IL-11 may be referred to as 'neutralising'.

Methods of treatment may optionally include the co-administration of biological adjuvants (e.g., interleukins, cytokines, *Bacillus* Cornette-Guerin, monophosphoryl lipid A, etc.) in combination with conventional therapies for treating cancer such as treatment with an agent for treating cancer (e.g. chemotherapy), radiation, or surgery. Methods of medical treatment may also involve in vivo, ex vivo, and adoptive immunotherapies, including those using autologous and/or heterologous cells or immortalized cell lines.

The treatment may be aimed at prevention of a disease/disorder associated with overactive/elevated IL-11 mediated signalling. As such, the antibodies, antigen binding fragments and polypeptides may be used to formulate pharmaceutical compositions or medicaments and subjects may be prophylactically treated against development of a disease state. This may take place before the onset of symptoms of the disease state, and/or may be given to subjects considered to be at greater risk of the disease or disorder.

Administration of the agents according to the present disclosure is preferably in a "therapeutically effective" or "prophylactically effective" amount, this being sufficient to show benefit to the subject. The actual amount administered, and rate and time-course of administration, will depend on the nature and severity of the disease/condition and the nature of the agent. Prescription of treatment, e.g. decisions on dosage etc., is within the responsibility of general practitioners and other medical doctors, and typically takes account of the disease/condition to be treated, the condition of the individual subject, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

The antigen-binding molecules, polypeptides, CARs, nucleic acids, expression vectors, cells and compositions described herein are preferably formulated as a medicament or pharmaceutical together with one or more other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilisers, solubilisers, surfactants (e.g., wetting agents), masking agents, colouring agents, flavouring agents, and sweetening agents. The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation. Suitable carriers, adjuvants, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 2nd edition, 1994.

The formulations may be prepared for administration as suitable for the disease/condition to be treated. For example, formulations may be formulated for topical, parenteral, systemic, intravenous, intra-arterial, intramuscular, intrathecal, intraocular, local ocular (e.g. subconjunctival, intravitreal, retrobulbar, intracameral), intra-conjunctival, subcutaneous, oral, or transdermal routes of administration which may include injection. The agents of the present disclosure may be formulated in fluid or solid form. Fluid formulations may be formulated for administration by injection or infusion to a selected region of the human or animal body. Injectable formulations may comprise the selected agent in a sterile or isotonic medium.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

In accordance with the present invention methods are also provided for the production of pharmaceutically useful compositions, such methods of production may comprise one or more steps selected from: isolating an antibody or antigen binding fragment as described herein; and/or mixing an isolated antibody or antigen binding fragment as described herein with a pharmaceutically acceptable carrier, adjuvant, excipient or diluent. For example, a further aspect of the present invention relates to a method of formulating or producing a medicament or pharmaceutical composition for use in a method of medical treatment, the method comprising formulating a pharmaceutical composition or medicament by mixing an antibody or antigen binding fragment as described herein with a pharmaceutically acceptable carrier, adjuvant, excipient or diluent.

Multiple doses of the antigen-binding molecule, polypeptide, CAR, nucleic acid (or plurality thereof), expression vector (or plurality thereof), cell or composition may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

The antigen-binding molecules, polypeptides, CARs, nucleic acids, expression vectors, cells and compositions described herein may be administered alone or in combination with other therapeutic or prophylactic intervention. Such other therapeutic or prophylactic intervention may occur before, during and/or after the therapies encompassed by the disclosure, and the deliveries of the other therapeutic or prophylactic interventions may occur via the same or different administration routes as the therapies of the disclosure.

In some embodiments, administration of the antigen-binding molecules, polypeptides, CARs, nucleic acids, expression vectors, cells and compositions described herein may be accompanied by an agent for treating or preventing infection (e.g. an antibiotic, anti-viral, anti-fungal or anti-parasitic agent). In some embodiments, treatment with an antibody, antigen binding fragment or composition of the present invention may be accompanied by an agent for treating or preventing inflammation (e.g. a non-steroidal anti-inflammatory drug (NSAID). In some embodiments, treatment with an antibody, antigen binding fragment or composition of the present invention may be accompanied by radiotherapy (i.e. treatment with ionising radiation, e.g. X-rays or γ-rays) and/or an agent for treating or preventing cancer (e.g. a chemotherapeutic agent). In some embodiments the chemotherapeutic agent is an alkylating agent, e.g. cisplatin. In some embodiments, the antibody, antigen binding fragment or composition of the present invention may be administered as part of a combination treatment with an immunotherapy.

Simultaneous administration refers to administration of the agents together, for example as a pharmaceutical composition containing the agents (i.e. a combined preparation), or immediately after each other and optionally via the same route of administration, e.g. to the same artery, vein or other blood vessel. In certain embodiments upon simultaneous administration the two or more of the agents may be administered via different routes of administration. In some embodiments simultaneous administration refers to administration at the same time, or within e.g. 1 hr, 2 hrs, 3 hrs, 4 hrs, 5 hrs, 6 hrs, 8 hrs, 12 hrs, 24 hrs, 36 hrs or 48 hrs.

Sequential administration refers to administration of one or more of the agents followed after a given time interval by separate administration of another of the agents. It is not required that the two agents are administered by the same route, although this is the case in some embodiments. The time interval may be any time interval, including hours, days, weeks, months, or years. In some embodiments sequential administration refers to administrations separated by a time interval of one of at least 10 min, 30 min, 1 hr, 6 hrs, 8 hrs, 12 hrs, 24 hrs, 36 hrs, 48 hrs, 3 days, 4 days, 5 days, 6 days, 1 week, 2 weeks, 3 weeks, 1 month, 6 weeks, 2 months, 3 months, 4 months, 5 months or 6 months.

Methods of Detection

The invention also provides the articles of the present invention for use in methods for detecting, localizing or imaging IL-11 or a complex comprising IL-11, or cells expressing/comprising IL-11 or a complex comprising IL-11. The antigen-binding molecules described herein may be used in methods that involve binding of the antigen-binding molecule to IL-11 or a complex comprising IL-11. Such methods may involve detection of the bound complex of the antigen-binding molecule and IL-11 or a complex comprising IL-11.

Detection of IL-11 or a complex comprising IL-11 may be useful in methods of diagnosing/prognosing a disease/condition in which IL-11 mediated signalling and/or cells expressing/comprising IL-11 or a complex comprising IL-11 are pathologically implicated, identifying subjects at risk of developing such diseases/conditions, and/or may be useful in methods of predicting a subject's response to a therapeutic intervention.

As such, a method is provided, comprising contacting a sample containing, or suspected to contain, IL-11 or a complex comprising IL-11 or cells expressing/comprising IL-11 or a complex comprising IL-11 with an antigen-binding molecule as described herein, and detecting the formation of a complex of the antigen-binding molecule and IL-11/a complex comprising IL-11. Also provided is a method comprising contacting a sample containing, or suspected to contain, a cell expressing/comprising IL-11 or a complex comprising IL-11 with an antigen-binding molecule as described herein and detecting the formation of a complex of the antigen-binding molecule and a cell expressing/comprising IL-11 or a complex comprising IL-11.

Suitable method formats are well known in the art, including immunoassays such as sandwich assays, e.g. ELISA. The methods may involve labelling the antigen-binding molecule, or target(s), or both, with a detectable moiety, e.g. a fluorescent label, phosphorescent label, luminescent label, immuno-detectable label, radiolabel, chemical, nucleic acid or enzymatic label. IL-11 expression may be measured by immunohistochemistry (IHC), for example of a tissue sample obtained by biopsy. In some embodiments, the label may be selected from: a radio-nucleotide, positron-emitting radionuclide (e.g. for positron emission tomography (PET)), MRI contrast agent or fluorescent label.

Detection techniques are well known to those of skill in the art and can be selected to correspond with the labelling agent. Analysis in vitro or in vivo of processes mediated by IL-11 may involve analysis by positron emission tomography (PET), magnetic resonance imaging (MRI), or fluorescence imaging, e.g. by detection of appropriately labelled species.

Methods of this kind may provide the basis of a method of diagnosis of a disease or condition requiring detection and or quantitation of IL-11 or a complex comprising IL-11. Such methods may be performed in vitro on a subject sample, or following processing of a subject sample. Once the sample is collected, the subject is not required to be present for the in vitro method of diagnosis to be performed and therefore the method may be one which is not practised on the human or animal body. In some embodiments the antigen-binding molecules, polypeptides, CARs, nucleic acids, expression vectors, cell or compositions according to the present disclosure are provided for use in any method of diagnosis, detection or quantification described herein.

Such methods may involve detecting or quantifying IL-11 or a complex comprising IL-11, or cells expressing IL-11 or a complex comprising IL-11, e.g. in a patient sample. Where the method comprises quantifying the relevant factor, the method may further comprise comparing the determined amount against a standard or reference value as part of the diagnostic or prognostic evaluation. Other diagnostic/prognostic tests may be used in conjunction with those described herein to enhance the accuracy of the diagnosis or prognosis or to confirm a result obtained by using the tests described herein.

Detection in a sample of IL-11 or a complex comprising IL-11 may be used for the purpose of diagnosis of an infectious disease, autoimmune disorder or a cancerous condition in the subject, diagnosis of a predisposition to an infectious disease, autoimmune disorder or a cancerous condition or for providing a prognosis (prognosticating) of an infectious disease, autoimmune disorder or a cancerous condition. The diagnosis or prognosis may relate to an existing (previously diagnosed) infectious, inflammatory or autoimmune disease/disorder or cancerous condition.

Where an increased level of IL-11 or a complex comprising IL-11 is detected, or where the presence of—or an increased number/proportion of—cells expressing/comprising IL-11 or a complex comprising IL-11 is detected in a sample obtained from a subject, the subject may be diagnosed as having a disease/condition a disease/condition according to the present disclosure, or being at risk of developing such a disease/condition. In such methods, an "increased" level of expression or number/proportion of cells refers to a level/number/proportion which is greater than the level/number/proportion determined for an appropriate control condition, such as the level/number/proportion detected in a comparable sample (e.g. a sample of the same kind, e.g. obtained from the same fluid, tissue, organ etc.), e.g. obtained from a healthy subject.

Where an increased level of IL-11 or a complex comprising IL-11 is detected, or where the presence of—or an increased number/proportion of—cells expressing/comprising IL-11 or a complex comprising IL-11 is detected in a sample obtained from a subject, the subject may be determined to have a poorer prognosis as compared to a subject determined to have a lower level of IL-11 or a complex comprising IL-11, or a reduced number/proportion of cells expressing/comprising IL-11 or a complex comprising IL-11 in a comparable sample (e.g. a sample of the same kind, e.g. obtained from the same fluid, tissue, organ etc.).

Thus the present invention provides methods for selecting/stratifying a subject for treatment with the antigen-binding molecules, polypeptides, CARs, nucleic acids, expression vectors, cell or compositions according to the present invention. In some embodiments a subject is selected for treatment/prevention in accordance with the invention, or is identified as a subject which would benefit from such treatment/prevention, based on detection/quantification of IL-11 or a complex comprising IL-11, or cells expressing IL-11 or a complex comprising IL-11, e.g. in a sample obtained from the subject. The level of IL-11 or a complex comprising IL-11 present in a subject sample may be indicative that a subject may respond to treatment with an antigen-binding molecule or composition according to the present invention. The presence of a high level of IL-11 or a complex comprising IL-11 in a sample may be used to select a subject for treatment as described herein. The antigen-binding molecules of the present invention may therefore be used to select a subject for treatment with IL-11-targeted therapy.

A sample may be taken from any tissue or bodily fluid. The sample may comprise or may be derived from: a quantity of blood; a quantity of serum derived from the individual's blood which may comprise the fluid portion of the blood obtained after removal of the fibrin clot and blood cells; a tissue sample or biopsy; pleural fluid; cerebrospinal fluid (CSF); or cells isolated from said individual. In some embodiments, the sample may be obtained or derived from a tissue or tissues which are affected by the disease/disorder (e.g. tissue or tissues in which symptoms of the disease manifest, or which are involved in the pathogenesis of the disease/disorder).

Methods of diagnosis or prognosis according to the present invention may be performed in vitro on a sample obtained from a subject, or following processing of a sample obtained from a subject. Once the sample is collected, the patient is not required to be present for the in vitro method of diagnosis or prognosis to be performed and therefore the method may be one which is not practised on the human or animal body. The term "in vitro" is intended to encompass experiments with cells in culture whereas the term "in vivo" is intended to encompass experiments with and/or treatment of intact multi-cellular organisms.

The diagnostic and prognostic methods of the present invention may be performed on samples obtained from a subject at multiple time points throughout the course of the disease and/or treatment, and may be used monitor development of the disease/condition over time, e.g. in response to treatment administered to the subject. The results of characterisation in accordance with the methods may be used to inform clinical decisions as to when and what kind of therapy to administer to a subject.

Subjects

The subject in accordance with aspects the invention described herein may be any animal or human. The subject is preferably mammalian, more preferably human. The subject may be a non-human mammal, but is more preferably human. The subject may be male or female. The subject may be a patient. A subject may have been diagnosed with a disease or condition requiring treatment (e.g. a cancer), may be suspected of having such a disease/condition, or may be at risk of developing/contracting such a disease/condition.

The subject/patient may have a disease/disorder that would derive therapeutic or prophylactic benefit from a reduction in the level of (i.e. inhibition or antagonism of) IL-11 mediated signalling, or a reduction in the number and/or activity of cells expressing IL-11Rα or a complex comprising IL-11Rα. The subject/patient may have a disease/disorder as described herein. The subject/patient may have been diagnosed with a disease/disorder as described herein requiring treatment, may be suspected of having such a disease/disorder, or may be at risk of developing such a disease/disorder.

In embodiments according to the present invention the subject is preferably a human subject. In some embodiments, the subject to be treated according to a therapeutic or prophylactic method of the invention herein is a subject having, or at risk of developing, a cancer. In embodiments according to the present invention, a subject may be selected for treatment according to the methods based on characterisation for certain markers of such disease/condition.

Kits

In some aspects of the invention described herein a kit of parts is provided. In some embodiments the kit may have at least one container having a predetermined quantity of an antigen-binding molecule, polypeptide, CAR, nucleic acid (or plurality thereof), expression vector (or plurality thereof), cell or composition described herein.

In some embodiments, the kit may comprise materials for producing an antigen-binding molecule, polypeptide, CAR, nucleic acid (or plurality thereof), expression vector (or plurality thereof), cell or composition described herein.

The kit may provide the antigen-binding molecule, polypeptide, CAR, nucleic acid (or plurality thereof), expression vector (or plurality thereof), cell or composition together with instructions for administration to a patient in order to treat a specified disease/condition.

In some embodiments the kit may further comprise at least one container having a predetermined quantity of another therapeutic agent (e.g. anti-infective agent or chemotherapy agent). In such embodiments, the kit may also comprise a second medicament or pharmaceutical composition such that the two medicaments or pharmaceutical compositions may be administered simultaneously or separately such that they provide a combined treatment for the specific disease or condition. The therapeutic agent may also be formulated so as to be suitable for injection or infusion to a tumor or to the blood.

Sequence Identity

As used herein, "sequence identity" refers to the percent of nucleotides/amino acid residues in a subject sequence that are identical to nucleotides/amino acid residues in a reference sequence, after aligning the sequences and, if necessary, introducing gaps, to achieve the maximum percent sequence identity between the sequences. Pairwise and multiple sequence alignment for the purposes of determining percent sequence identity between two or more amino acid or nucleic acid sequences can be achieved in various ways known to a person of skill in the art, for instance, using publicly available computer software such as ClustalOmega (Söding, J. 2005, Bioinformatics 21, 951-960), T-coffee (Notredame et al. 2000, J. Mol. Biol. (2000) 302, 205-217), Kalign (Lassmann and Sonnhammer 2005, BMC Bioinformatics, 6(298)) and MAFFT (Katoh and Standley 2013, Molecular Biology and Evolution, 30(4) 772-780 software. When using such software, the default parameters, e.g. for gap penalty and extension penalty, are preferably used.

Sequences

| SEQ ID NO: | DESCRIPTION | SEQUENCE |
|---|---|---|
| 1 | Human IL-11 (UniProt: P20809) | MNCVCRLVLVVLSLWPDTAVAPGPPPGPPRVSPDPRAELDSTVLLTRSLLADTRQLAAQLRDKFP ADGDHNLDSLPTLAMSAGALGALQLPGVLTRLRADLLSYLRHVQWLRRAGGSSLKTLEPELGTLQ ARLDRLLRRLQLLMSRLALPQPPPDPPAPPLAPPSSAWGGIRAAHAILGGLHLTLDWAVRGLLLLK TRL |
| 2 | Human gp130 (UniProt P40189-1) | MLTLQTWLVQALFIFLTTESTGELLDPCGYISPESPVVQLHSNFTAVCVLKEKCMDYFHVNANYIV WKTNHFTIPKEQYTIINRTASSVTFTDIASLNIQLTCNILTFGQLEQNVYGITIISGLPPEKPKNLSCIV NEGKKMRCEWDGGRETHLETNFTLKSEWATHKFADCKAKRDTPTSCTVDYSTVYFVNIEVWVEA ENALGKVTSDHINFDPVYKVKPNPPHNLSVINSEELSSILKLTWTNPSIKSVIILKYNIQYRTKDAST WSQIPPEDTASTRSSFTVQDLKPFTEYVFRIRCMKEDGKGYWSDWSEEASGITYEDRPSKAPSF WYKIDPSHTQGYRTVQLVWKTLPPFEANGKILDYEVTLTRWKSHLQNYTVNATKLTVNLTNDRYL ATLTVRNLVGKSDAAVLTIPACDFQATHPVMDLKAFPKDNMLWVEWTTPRESVKKYILEWCVLSD KAPCITDWQQEDGTVHRTYLRGNLAESKCYLITVTPVYADGPGSPESIKAYLKQAPPSKGPTVRT KKVGKNEAVLEWDQLPVDVQNGFIRNYTIFYRTIIGNETAVNVDSSHTEYTLSSLTSDTLYMVRMA AYTDEGGKDGPEFTFTTPKFAQGEIEAIVVPVCLAFLLTTLLGVLFCFNKRDLIKKHIWPNVPDPSK SHIAQWSPHTPPRHNFNSKDQMYSDGNFTDVSVVEIEANDKKPFPEDLKSLDLFKKEKINTEGHS SGIGGSSCMSSSRPSISSSDENESSQNTSSTVQYSTVVHSGYRHQVPSVQVFSRSESTQPLLDS EERPEDLQLVDHVDGGDGILPRQQYFKQNCSQHESSPDISHFERSKQVSSVNEEDFVRLKQQIS DHISQSCGSGQMKMFQEVSAADAFGPGTEGQVERFETVGMEAATDEGMPKSYLPQTVRQGGY MPQ |
| 3 | Human MIRA (UniProt Q14626) | MSSSCSGLSRVLVAVATALVSASSPCPQAWGPPGVQYGQPGRSVKLCCPGVTAGDPVSWFRD GEPKLLQGPDSGLGHELVLAQADSTDEGTYICQTLDGALGGTVTLQLGYPPARPVVSCQAADYE NFSCTWSPSQISGLPTRYLTSYRKKTVLGADSQRRSPSTGPWPCPQDPLGAARCVVHGAEFWS QYRINVTEVNPLGASTRLLDVSLQSILRPDPPQGLRVESVPGYPRRLRASWTYPASWPCQPHFLL KFRLQYRPAQHPAWSTVEPAGLEEVITDAVAGLPHAVRVSARDFLDAGTWSTWSPEAWGTPST GTIPKEIPAWGQLHTQPEVEPQVDSPAPPRPSLQPHPRLLDHRDSVEQVAVLASLGILSFLGLVAG ALALGLWLRLRRGGKDGSPKPGFLASVIPVDRRPGAPNL |
| 4 | IL-11: IL-11Rα fusion protein | MGWSCIILFLVATATGVHSPQAWGPPGVQYGQPGRSVKLCCPGVTAGDPVSWFRDGEPKLLQG PDSGLGHELVLAQADSTDEGTYICQTLDGALGGTVTLQLGYPPARPVVSCQAADYENFSCTWSP SQISGLPTRYLTSYRKKTVLGADSQRRSPSTGPWPCPQDPLGAARCVVHGAEFWSQYRINVTEV NPLGASTRLLDVSLQSILRPDPPQGLRVESVPGYPRRLRASWTYPASWPCQPHFLLKFRLQYRPA QHPAWSTVEPAGLEEVITDAVAGLPHAVRVSARDFLDAGTWSTWSPEAWGTPSTGGPAGQSGG GGGSGGGSGGGSVPGPPPGPPRVSPDPRAELDSTVLLTRSLLADTRQLAAQLRDKFPADGDHN LDSLPTLAMSAGALGALQLPGVLTRLRADLLSYLRHVQWLRRAGGSSLKTLEPELGTLQARLDRL LRRLQLLMSRLALPQPPPDPPAPPLAPPSSAWGGIRAAHAILGGLHLTLDWAVRGLLLLKTRLHHH HHH |
| 5 | Nucleotide sequence encoding IL-11: IL-11Rα fusion protein | GAATTCCCGCCGCCACCATGGGCTGGTCCTGCATCATCCTGTTTCTGGTGGCCACAGCCACC GGCGTGCACTCTCCACAGGCTTGGGGACCTCCAGGCGTGCAGTATGGCCAGCCTGGCAGAT CCGTGAAGCTGTGCTGTCCTGGCGTGACAGCTGGCGACCCTGTGTCCTGGTTCAGAGATGG CGAGCCCAAGCTGCTGCAGGGCCCAGATTCTGGACTGGGCCACGAACTGGTGCTGGCCCAG GCCGATTCTACCGACGAGGGCACCTACATCTGCCAGACCCTGGATGGCGCCCTGGGCGGAA CAGTGACACTGCAGCTGGGCTACCCTCCCGCCAGACCTGTGGTGTCTTGTCAGGCCGCCGA CTACGAGAACTTCAGCTGCACATGGTCCCCCAGCCAGATCAGCGGCCTGCCCACCAGATACC TGACCAGCTACCGGAAGAAAACCGTGCTGGGCGCCGACAGCCAGAGGAAGAAGCCCTTCTAC AGGCCCCTGGCCCTGCCCTCAGGATCCTCTGGGAGCTGCCAGATGTGTGGTGCACGGCGCC GAGTTCTGGTCCCAGTACCGGATCAACGTGACCGAAGTGAACCCCCTGGGCGCCTCCACAA GACTGCTGGATGTGTCCCTGCAGAGCATCCTGCGGCCCGATCCTCCACAGGGCCTGAGAGT GGAAAGCGTGCCCGGCTACCCCAGAAGGCTGAGAGCCAGCTGGACATACCCCGCCTCTTGG CCTTGCCAGCCCCACTTCCTGCTGAAGTTTCGGCTGCAGTACCGGCCAGCCCAGCACCCTG CTTGGAGCACAGTGGAACCTGCCGGCCTGGAAGAAGTGATCACAGACGCCGTGGCCGGACT GCCTCATGCTGTGCGGGTGTCCGCCAGAGACTTTCTGGATGCCGGCACCTGGTCTACCTGG TCCCCAGAAGCCTGGGGCACACCTTCTACTGGCGGACCTGCTGGACAGTCTGGCGGAGGCG |

| SEQ ID NO: | DESCRIPTION | SEQUENCE |
|---|---|---|
| | | GAGGAAGTGGCGGAGGATCAGGGGGAGGATCTGTGCCTGGACCTCCTCCAGGACCCCCTA GAGTGTCCCCAGATCCTAGGGCCGAGCTGGACTCTACCGTGCTGCTGACCAGATCCCTGCT GGCCGACACAAGGCAGCTGGCTGCCCAGCTGAGAGACAAGTTCCCCGCCGACGGCGACCA CAACCTGGATAGCCTGCCTACCCTGGCCATGTCTGCTGGCGCACTGGGGGCTCTGCAGCTG CCTGGGGTGCTGACTAGACTGAGAGCCGACCTGCTGAGCTACCTGCGGCATGTGCAGTGGC TGAGAAGGGCTGGCGGCAGCAGCCTGAAAACCCTGGAACCTGAGCTGGGCACACTGCAGGC CAGACTGGACAGACTGCTGCGCAGACTGCTCAGCTGCTGATGAGCAGACTGGCTCTGCCCCAG CCTCCTCCTGACCCTCCTGCTCCTCCACTGGCTCCTCCAAGCTCTGCTTGGGGCGGAATTAG AGCCGCCCACGCCATTCTGGGAGGCCTGCACCTGACACTGGATTGGGCAGTGCGGGGCCTG CTGCTGCTGAAAACCAGACTGCACCACCACCATCACCACTGATAAGCTT |
| 6 | YU100-H01 VH | QVQLVQSGGGVVQPGRSLRLSCAASGFTFSSYAMHWVRQAPGKGLEWVAVISYDGSNKYYADS VKGRFTISRDNSKNTLYLQMNSLRAEDTAVYYCARIMGYDYGDYDVVDYWGQGTLVTVSS |
| 7 | YU100-H01 VL | QSALTQPRSVSGSPGQSVTISCTGTSSDVGAYNYVSWYQQHPGKAPKLMIYDVSERPSGVPDRF SGSKSGNTASLTISGLQAEDEADYYCCSYAGSYTWVFGGGTKLTVLG |
| 8 | YU100-G08 VH | QVQLVQSGGGVVQPGRSLRLSCAASGFTFSSYGMHWVRQAPGKGLEWVAVISYDGSNKYYAD SVKGRFTISRDNSKNTLYLQMNSLRAEDTAVYYCAKIGATDPLDYWGQGTLVTVSS |
| 9 | YU100-G08 VL | QSALTQPRSVSGSPGQSVTLSCTGTSSDVGGYNYVSWYQHPGKAPKLMIFDVNERSSGVPDR FSGSKSGNTASLTISGLQAEDEADYYCCSYAGRYTWMFGGGTKVTVLG |
| 10 | YU100-F11 VH | QVQLVESGGGVVQPGRSLRLSCAASGFTFSSYGMHWVRQAPGKGLEWVAVISYDGSNKYYADS VKGRFTISRDNSKNTLYLQMNSLRAEDTAVYYCAKIGATDPLDYWGQGTLVTVSS |
| 11 | YU100-F11 VL | QSALTQPASVSGSPGQSITISCTGSSSDVAGYNYVSWYQQHPGKAPKLMIYDVTKRPSGVPDRF SGSKSGNTASLTISGLQAEDEADYYCCSYAGSYTWVFGGGTQLTVLG |
| 12 | 01A VL | QSALTQPRSVSGSPGQSVTISCTGTSSDVGAYNYVSWYQQHPGKAPKLMIYDVSERPSGVPDRF SGSKSGNTASLTISGLQAEDEADYYCASYAGSYTWVFGGGTKLTVLG |
| 13 | 01G VL | QSALTQPRSVSGSPGQSVTISCTGTSSDVGAYNYVSWYQQHPGKAPKLMIYDVSERPSGVPDRF SGSKSGNTASLTISGLQAEDEADYYCGSYAGSYTWVFGGGTKLTVLG |
| 14 | 01I VL | QSALTQPRSVSGSPGQSVTISCTGTSSDVGAYNYVSWYQQHPGKAPKLMIYDVSERPSGVPDRF SGSKSGNTASLTISGLQAEDEADYYCISYAGSYTWVFGGGTKLTVLG |
| 15 | 01L VL | QSALTQPRSVSGSPGQSVTISCTGTSSDVGAYNYVSWYQQHPGKAPKLMIYDVSERPSGVPDRF SGSKSGNTASLTISGLQAEDEADYYCLSYAGSYTWVFGGGTKLTVLG |
| 16 | 01Q VL | QSALTQPRSVSGSPGQSVTISCTGTSSDVGAYNYVSWYQQHPGKAPKLMIYDVSERPSGVPDRF SGSKSGNTASLTISGLQAEDEADYYCQSYAGSYTWVFGGGTKLTVLG |
| 17 | 01S VL | QSALTQPRSVSGSPGQSVTISCTGTSSDVGAYNYVSWYQQHPGKAPKLMIYDVSERPSGVPDRF SGSKSGNTASLTISGLQAEDEADYYCSSYAGSYTWVFGGGTKLTVLG |
| 18 | 01T VL | QSALTQPRSVSGSPGQSVTISCTGTSSDVGAYNYVSWYQQHPGKAPKLMIYDVSERPSGVPDRF SGSKSGNTASLTISGLQAEDEADYYCTSYAGSYTWVFGGGTKLTVLG |
| 19 | 01V VL | QSALTQPRSVSGSPGQSVTISCTGTSSDVGAYNYVSWYQQHPGKAPKLMIYDVSERPSGVPDRF SGSKSGNTASLTISGLQAEDEADYYCVSYAGSYTWVFGGGTKLTVLG |
| 20 | 02A VL | QSALTQPRSVSGSPGQSVTLSCTGTSSDVGGYNYVSWYQHPGKAPKLMIFDVNERSSGVPDR FSGSKSGNTASLTISGLQAEDEADYYCASYAGRYTWMFGGGTKVTVLG |
| 21 | 02G VL | QSALTQPRSVSGSPGQSVTLSCTGTSSDVGGYNYVSWYQHPGKAPKLMIFDVNERSSGVPDR FSGSKSGNTASLTISGLQAEDEADYYCGSYAGRYTWMFGGGTKVTVLG |
| 22 | 02I VL | QSALTQPRSVSGSPGQSVTLSCTGTSSDVGGYNYVSWYQHPGKAPKLMIFDVNERSSGVPDR FSGSKSGNTASLTISGLQAEDEADYYCISYAGRYTWMFGGGTKVTVLG |
| 23 | 02L VL | QSALTQPRSVSGSPGQSVTLSCTGTSSDVGGYNYVSWYQHPGKAPKLMIFDVNERSSGVPDR FSGSKSGNTASLTISGLQAEDEADYYCLSYAGRYTWMFGGGTKVTVLG |
| 24 | 02Q VL | QSALTQPRSVSGSPGQSVTLSCTGTSSDVGGYNYVSWYQHPGKAPKLMIFDVNERSSGVPDR FSGSKSGNTASLTISGLQAEDEADYYCQSYAGRYTWMFGGGTKVTVLG |
| 25 | 02S VL | QSALTQPRSVSGSPGQSVTLSCTGTSSDVGGYNYVSWYQHPGKAPKLMIFDVNERSSGVPDR FSGSKSGNTASLTISGLQAEDEADYYCSSYAGRYTWMFGGGTKVTVLG |

-continued

| SEQ ID NO: | DESCRIPTION | SEQUENCE |
|---|---|---|
| 26 | 02T VL | QSALTQPRSVSGSPGQSVTLSCTGTSSDVGGYNYVSWYQHYPGKAPKLMIFDVNERSSGVPDRFSGSKSGNTASLTISGLQAEDEADYYCTSYAGRYTWMFGGGTKVTVLG |
| 27 | 02V VL | QSALTQPRSVSGSPGQSVTLSCTGTSSDVGGYNYVSWYQHYPGKAPKLMIFDVNERSSGVPDRFSGSKSGNTASLTISGLQAEDEADYYCVSYAGRYTWMFGGGTKVTVLG |
| 28 | 03A VL | QSALTQPASVSGSPGQSITISCTGSSSDVAGYNYVSWYQQHPGKAPKLMIYDVTKRPSGVPDRFSGSKSGNTASLTISGLQAEDEADYYCASYAGSYTWVFGGGTQLTVLG |
| 29 | 03G VL | QSALTQPASVSGSPGQSITISCTGSSSDVAGYNYVSWYQQHPGKAPKLMIYDVTKRPSGVPDRFSGSKSGNTASLTISGLQAEDEADYYCGSYAGSYTWVFGGGTQLTVLG |
| 30 | 03I VL | QSALTQPASVSGSPGQSITISCTGSSSDVAGYNYVSWYQQHPGKAPKLMIYDVTKRPSGVPDRFSGSKSGNTASLTISGLQAEDEADYYCISYAGSYTWVFGGGTQLTVLG |
| 31 | 03L VL | QSALTQPASVSGSPGQSITISCTGSSSDVAGYNYVSWYQQHPGKAPKLMIYDVTKRPSGVPDRFSGSKSGNTASLTISGLQAEDEADYYCLSYAGSYTWVFGGGTQLTVLG |
| 32 | 03Q VL | QSALTQPASVSGSPGQSITISCTGSSSDVAGYNYVSWYQQHPGKAPKLMIYDVTKRPSGVPDRFSGSKSGNTASLTISGLQAEDEADYYCQSYAGSYTWVFGGGTQLTVLG |
| 33 | 03S VL | QSALTQPASVSGSPGQSITISCTGSSSDVAGYNYVSWYQQHPGKAPKLMIYDVTKRPSGVPDRFSGSKSGNTASLTISGLQAEDEADYYCSSYAGSYTWVFGGGTQLTVLG |
| 34 | 03T VL | QSALTQPASVSGSPGQSITISCTGSSSDVAGYNYVSWYQQHPGKAPKLMIYDVTKRPSGVPDRFSGSKSGNTASLTISGLQAEDEADYYCTSYAGSYTWVFGGGTQLTVLG |
| 35 | 03V VL | QSALTQPASVSGSPGQSITISCTGSSSDVAGYNYVSWYQQHPGKAPKLMIYDVTKRPSGVPDRFSGSKSGNTASLTISGLQAEDEADYYCVSYAGSYTWVFGGGTQLTVLG |
| 36 | YU100-H01 HC-CDR1 | SYAMH |
| 37 | YU100-G08, YU100-F11 HC-CDR1 | SYGMH |
| 38 | YU100-H01 YU100-G08 YU100-F11 HC-CDR2 | VISYDGSNKYYADSVKG |
| 39 | YU100-H01 HC-CDR3 | IMGYDYGDYDVVDY |
| 40 | YU100-G08, YU100-F11 HC-CDR3 | IGATDPLDY |
| 41 | YU100-H01, 01A, 01G, 01I, 01L, 01Q, 01S, 01T, 01V LC-CDR1 | TGTSSDVGAYNYVS |
| 42 | YU100-G08, 02A, 02G, 02I, 02L, 02Q, 02S, 02T, 02V LC-CDR1 | TGTSSDVGGYNYVS |
| 43 | YU100-F11, 03A, 03G, 03I, 03L, 03Q, 03S, 03T, 03V LC-CDR1 | TGSSSDVAGYNYVS |
| 44 | YU100-H01, 01A, 01G, 01I, 01L, 01Q, 01S, 01T, 01V LC-CDR2 | DVSERPS |
| 45 | YU100-G08, 02A, 02G, 02I, 02L, 02Q, 02S, 02T, 02V LC-CDR2 | DVNERSS |

-continued

| SEQ ID NO: | DESCRIPTION | SEQUENCE |
|---|---|---|
| 46 | YU100-F11, 03A, 03G, 03I, 03L, 03Q, 03S, 03T, 03V LC-CDR2 | DVTKRPS |
| 47 | YU100-H01, YU100-F11 LC-CDR3 | CSYAGSYTWV |
| 48 | 01A, 03A, LC-CDR3 | ASYAGSYTWV |
| 49 | 01G, 03G LC-CDR3 | GSYAGSYTWV |
| 50 | 01I, 03I LC-CDR3 | ISYAGSYTWV |
| 51 | 01L, 03L LC-CDR3 | LSYAGSYTWV |
| 52 | 01Q, 03Q LC-CDR3 | QSYAGSYTWV |
| 53 | 01S, 03S LC-CDR3 | SSYAGSYTWV |
| 54 | 01T, 03T LC-CDR3 | TSYAGSYTWV |
| 55 | 01V, 03V LC-CDR3 | VSYAGSYTWV |
| 56 | YU100-G08 LC-CDR3 | CSYAGRYTWM |
| 57 | 02A LC-CDR3 | ASYAGRYTVVM |
| 58 | 02G LC-CDR3 | GSYAGRYTWM |
| 59 | 02I LC-CDR3 | ISYAGRYTWM |
| 60 | 02L LC-CDR3 | LSYAGRYTWM |
| 61 | 02Q LC-CDR3 | QSYAGRYTWM |
| 62 | 02S LC-CDR3 | SSYAGRYTWM |
| 63 | 02T LC-CDR3 | TSYAGRYTWM |
| 64 | 02V LC-CDR3 | VSYAGRYTWM |
| 65 | YU100-H01, YU100-G08 HC-FR1 | QVQLVQSGGGVVQPGRSLRLSCAASGFTFS |
| 66 | YU100-F11 HC-FR1 | QVQLVESGGGVVQPGRSLRLSCAASGFTFS |
| 67 | YU100-H01 YU100-G08 YU100-F11 HC-FR2 | WVRQAPGKGLEWVA |
| 68 | YU100-H01 HC-FR3 | RFTISRDNSKNTLYLQMNSLRAEDTAVYYCAR |

-continued

| SEQ ID NO: | DESCRIPTION | SEQUENCE |
|---|---|---|
| 69 | YU100-G08, YU100-F11 HC-FR3 | RFTISRDNSKNTLYLQMNSLRAEDTAVYYCAK |
| 70 | YU100-H01 YU100-G08 YU100-F11 HC-FR4 | WGQGTLVTVSS |
| 71 | YU100-H01, 01A, 01G, 01I, 01L, 01Q, 01S, 01T, 01V LC-FR1 | QSALTQPRSVSGSPGQSVTISC |
| 72 | YU100-G08, 02A, 02G, 02I, 02L, 02Q, 02S, 02T, 02V LC-FR1 | QSALTQPRSVSGSPGQSVTLSC |
| 73 | YU100-F11, 03A, 03G, 03I, 03L, 03Q, 03S, 03T, 03V LC-FR1 | QSALTQPASVSGSPGQSITISC |
| 74 | YU100-H01, 01A, 01G, 01I, 01L, 01Q, 01S, 01T, 01V, YU100-F11, 03A, 03G, 03I, 03L, 03Q, 03S, 03T, 03V LC-FR2 | WYQQHPGKAPKLMIY |
| 75 | YU100-G08, 02A, 02G, 02I, 02L, 02Q, 02S, 02T, 02V LC-FR2 | WYQHYPGKAPKLMIF |
| 76 | YU100-H01, 01A, 01G, 01I, 01L, 01Q, 01S, 01T, 01V, YU100-G08, 02A, 02G, 02I, 02L, 02Q, 02S, 02T, 02V, YU100-F11, 03A, 03G, 03I, 03L, 03Q, 03S, 03T, 03V LC-FR3 | GVPDRFSGSKSGNTASLTISGLQAEDEADYYC |
| 77 | YU100-H01, 01A, 01G, 01I, 01L, 01Q, 01S, 01T, 01V LC-FR4 | FGGGTKLTVLG |
| 78 | YU100-G08, 02A, 02G, 02I, 02L, 02Q, 02S, 02T, 02V LC-FR4 | FGGGTKVTVLG |
| 79 | YU100-F11, 03A, 03G, 03I, 03L, 03Q, 03S, 03T, 03V LC-FR4 | FGGGTQLTVLG |
| 80 | 01X 03X LC-CDR3 | $X_1$SYAGSYTWV<br>$X_1$ = A, G, I, L, Q, S, T or V |
| 81 | 02X LC-CDR3 | $X_1$SYAGRYTWM<br>$X_1$ = A, G, I, L, Q, S, T or V |
| 82 | 01X VL | QSALTQPRSVSGSPGQSVTISCTGTSSDVGAYNYVSWYQQHPGKAPKLMIYDVSERPSGVPDRF<br>SGSKSGNTASLTISGLQAEDEADYYC$X_1$SYAGSYTWVFGGGTKLTVLG<br>$X_1$ = A, G, I, L, Q, S, T or V |

| SEQ ID NO: | DESCRIPTION | SEQUENCE |
|---|---|---|
| 83 | 02X VL | QSALTQPRSVSGSPGQSVTLSCTGTSSDVGGYNYVSWYQHYPGKAPKLMIFDVNERSSGVPDR FSGSKSGNTASLTISGLQAEDEADYYCX₁SYAGRYTWMFGGGTKVTVLG<br>X₁ = A, G, I, L, Q, S, T or V |
| 84 | 03X VL | QSALTQPASVSGSPGQSITISCTGSSSDVAGYNYVSWYQQHPGKAPKLMIYDVTKRPSGVPDRF SGSKSGNTASLTISGLQAEDEADYYCX₁SYAGSYTWVFGGGTQLTVLG<br>X₁ = A, G, I, L, Q, S, T or V |
| 85 | Human IgG1 constant region (IGHG1; UniProt: P01857-1, v1) | ASTKGPSVFPLAPSSKSTSGGTAALGCLVKDYFPEPVTVSWNSGALTSGVHTFPAVLQSSGLYSL SSVVTVPSSSLGTQTYICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREEQYNSTYRVVSVLTVLHQ DWLNGKEYKCKVSNKALPAPIEKTISKAKGQPREPQVYTLPPSRDELTKNQVSLTCLVKGFYPSDI AVEWESNGQPENNYKTTPPVLDSDGSFFLYSKLTVDKSRWQQGNVFSCSVMHEALHNHYTQKS LSLSPGK |
| 86 | CH1 IgG1 (positions 1-98 of P01857-1, v1) | ASTKGPSVFPLAPSSKSTSGGTAALGCLVKDYFPEPVTVSWNSGALTSGVHTFPAVLQSSGLYSL SSVVTVPSSSLGTQTYICNVNHKPSNTKVDKKV |
| 87 | Hinge IgG1 (positions 99-110 of P01857-1, v1) | EPKSCDKTHTCP |
| 88 | CH2 IgG1 (positions 111-223 of P01857-1, v1) | PCPAPELLGGPSVFLFPPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAK |
| 89 | CH3 IgG1 (positions 224-330 of P01857-1, v1) | GQPREPQVYTLPPSRDELTKNQVSLTCLVKGFYPSDIAVEWESNGQPENNYKTTPPVLDSDGSF FLYSKLTVDKSRWQQGNVFSCSVMHEALHNHYTQKSLSLSPGK |
| 90 | Cκ CL (IGCK; UniProt: P01834-1, v2) | RTVAAPSVFIFPPSDEQLKSGTASVVCLLNNFYPREAKVQWKVDNALQSGNSQESVTEQDSKDS TYSLSSTLTLSKADYEKHKVYACEVTHQGLSSPVTKSFNRGEC |
| 91 | 3C6 VH 1 | QVQLQESGPELVKPGASVKIPCKASGYTFTDYNMDWVKQSHGKSLEWIGDINPHNGGPIYNQKF TGKATLTVDKSSSTAYMELRSLTSEDTAVYYCARGELGHWYFDVWGTGTTVTVSS |
| 92 | 3C6 VH 2 | EVQLQQSGPELVKPGASVKIPCKASGYTFTDYNMDWVKQSHGKSLEWIGDINPHNGGPIYNQKF TGKATLTVDKSSSTAYMELRSLTSEDTAVYYCARGELGHWYFDVWGTGTTVTVSS |
| 93 | 3C6 VL 1 | NIVMTQSPKSMSMSVGERVTLTCKASENVVTYVSWYQQKPEQSPKLLIYGASNRYTGVPDRFTG SGSATDFTLTISSVQAEDLADYHCGQGYSYPYTFGGGTKLEIK |
| 94 | 3C6 VL 2 | DIVLTQSPASLAVSLGQRATISCRASKSVSTSGYSYIHWYQQKPGQPPKLLIYLASNLDSGVPARF SGSGSGTDFTLNIHPVEEEDAATYYCQHSRDLPPTFGGGTKLEIK |
| 95 | 3C6 VH 1,<br>3C6 VH 2,<br>3C6 VH 2.1,<br>3C6 VH 2.2,<br>3C6 VH 2.3,<br>3C6 VH 2.4,<br>3C6 VH 2.5<br>HC-CDR1 | DYNMD |
| 96 | 3C6 VH 1,<br>3C6 VH 2,<br>3C6 VH 2.1,<br>3C6 VH 2.2,<br>3C6 VH 2.3,<br>3C6 VH 2.4,<br>3C6 VH 2.5<br>HC-CDR2 | DINPHNGGPIYNQKFTG |
| 97 | 3C6 VH 1,<br>3C6 VH 2,<br>3C6 VH 2.1,<br>3C6 VH 2.2,<br>3C6 VH 2.3,<br>3C6 VH 2.4,<br>3C6 VH 2.5<br>HC-CDR3 | GELGHWYFDV |

| SEQ ID NO: | DESCRIPTION | SEQUENCE |
|---|---|---|
| 98 | 3C6 VL 1<br>3C6 VL 1.1,<br>3C6 VL 1.2,<br>3C6 VL 1.3,<br>3C6 VL 1.4<br>LC-CDR1 | KASENVVTYVS |
| 99 | 3C6 VL 1<br>3C6 VL 1.1,<br>3C6 VL 1.2,<br>3C6 VL 1.3,<br>3C6 VL 1.4<br>LC-CDR2 | GASNRYT |
| 100 | 3C6 VL 1,<br>3C6 VL 1.1,<br>3C6 VL 1.2,<br>3C6 VL 1.3,<br>3C6 VL 1.4<br>LC-CDR3 | GQGYSYPYT |
| 101 | 3C6 VL 2,<br>3C6 VL 2.1,<br>3C6 VL 2.2,<br>3C6 VL 2.3,<br>3C6 VL 2.4<br>LC-CDR1 | RASKSVSTSGYSYIH |
| 102 | 3C6 VL 2,<br>3C6 VL 2.1,<br>3C6 VL 2.2,<br>3C6 VL 2.3,<br>3C6 VL 2.4<br>LC-CDR2 | LASNLDS |
| 103 | 3C6 VL 2,<br>3C6 VL 2.1,<br>3C6 VL 2.2,<br>3C6 VL 2.3,<br>3C6 VL 2.4<br>LC-CDR3 | QHSRDLPPT |
| 104 | 3C6 VH 1<br>HC-FR1 | QVQLQESGPELVKPGASVKIPCKASGYTFT |
| 105 | 3C6 VH 2<br>HC-FR1 | EVQLQQSGPELVKPGASVKIPCKASGYTFT |
| 106 | 3C6 VH 1,<br>3C6 VH 2<br>HC-FR2 | WVKQSHGKSLEWIG |
| 107 | 3C6 VH 1,<br>3C6 VH 2<br>HC-FR3 | KATLTVDKSSSTAYMELRSLTSEDTAVYYCAR |
| 108 | 3C6 VH 1,<br>3C6 VH 2<br>HC-FR4 | WGTGTTVTVSS |
| 109 | 3C6 VL 1<br>LC-FR1 | NIVMTQSPKSMSMSVGERVTLTC |
| 110 | 3C6 VL 2<br>LC-FR1 | DIVLTQSPASLAVSLGQRATISC |
| 111 | 3C6 VL 1<br>LC-FR2 | WYQQKPEQSPKLLIY |
| 112 | 3C6 VL 2,<br>3C6 VL 1.1,<br>3C6 VL 1.2,<br>3C6 VL 1.3,<br>3C6 VL 1.4LC-FR2 | WYQQKPGQPPKLLIY |

-continued

| SEQ ID NO: | DESCRIPTION | SEQUENCE |
|---|---|---|
| 113 | 3C6 VL 1 LC-FR3 | GVPDRFTGSGSATDFTLTISSVQAEDLADYHC |
| 114 | 3C6 VL 2 LC-FR3 | GVPARFSGSGSGTDFTLNIHPVEEEDAATYYC |
| 115 | 3C6 VL 1, 3C6 VL 2 LC-FR4 | FGGGTKLEIK |
| 116 | 3C6 VH 2.1 | EVQLVQSGPELKKPGASVKISCKASGYTFTDYNMDWVKQAHGQRLEWIGDINPHNGGPIYNQKF TGRATLTVDKSASTAYMELRSLTSEDTAVYYCARGELGHWYFDVWGQGTTVTVSS |
| 117 | 3C6 VH 2.2 | EVQLVQSGAEVKKPGASVKISCKASGYTFTDYNMDWVKQAPGQRLEWIGDINPHNGGPIYNQKF TGRATLTVDKSASTAYMELSSLRSEDTAVYYCARGELGHWYFDVWGQGTTVTVSS |
| 118 | 3C6 VH 2.3 | EVQLVQSGAEVKKPGASVKISCKASGYTFTDYNMDWVRQAPGQRLEWIGDINPHNGGPIYNQKF TGRVTLTVDKSASTAYMELSSLRSEDTAVYYCARGELGHWYFDVWGQGTTVTVSS |
| 119 | 3C6 VH 2.4 | QVQLVQSGAEVKKPGASVKVSCKASGYTFTDYNMDWVRQAPGQRLEWIGDINPHNGGPIYNQK FTGRVTITVDKSASTAYMELSSLRSEDTAVYYCARGELGHWYFDVWGQGTTVTVSS |
| 120 | 3C6 VH 2.5 | QVQLVQSGAEVKKPGASVKVSCKASGYTFTDYNMDWVRQAPGQRLEWMGDINPHNGGPIYNQ KFTGRVTITVDKSASTAYMELSSLRSEDTAVYYCARGELGHWYFDVWGQGTTVTVSS |
| 121 | 3C6 VL 2.1 | DIVLTQSPASLALSPGERATLSCRASKSVSTSGYSYIHWYQQKPGQPPRLLIYLASNLDSGVPARF SGSGSGTDFTLNIHPLEEEDFATYYCQHSRDLPPTFGQGTKLEIK |
| 122 | 3C6 VL 2.2 | DIVLTQSPASLALSPGERATLSCRASKSVSTSGYSYIHWYQQKPGQAPRLLIYLASNLDSGVPARF SGSGSGTDFTLTISSLEEEDFATYYCQHSRDLPPTFGQGTKLEIK |
| 123 | 3C6 VL 2.3 | DIVLTQSPATLSLSPGERATLSCRASKSVSTSGYSYIHWYQQKPGQAPRLLIYLASNLDSGVPARF SGSGSGTDFTLTISSLEPEDFATYYCQHSRDLPPTFGQGTKLEIK |
| 124 | 3C6 VL 2.4 | EIVLTQSPATLSLSPGERATLSCRASKSVSTSGYSYIHWYQQKPGQAPRLLIYLASNLDSGVPARF SGSGSGTDFTLTISSLEPEDFATYYCQHSRDLPPTFGQGTKLEIK |
| 125 | 3C6 VL 1.1 | NIVMTQSPDSLSVSVGERATLNCKASENVVTYVSWYQQKPGQPPKLLIYGASNRYTGVPDRFTG SGSATDFTLTISSLQAEDLADYHCGQGYSYPYTFGQGTKLEIK |
| 126 | 3C6 VL 1.2 | NIVMTQSPDSLAVSVGERATLNCKASENVVTYVSWYQQKPGQPPKLLIYGASNRYTGVPDRFTG SGSATDFTLTISSLQAEDLADYHCGQGYSYPYTFGQGTKLEIK |
| 127 | 3C6 VL 1.3 | DIVMTQSPDSLAVSLGERATINCKASENVVTYVSWYQQKPGQPPKLLIYGASNRYTGVPDRFSGS GSATDFTLTISSLQAEDLADYHCGQGYSYPYTFGQGTKLEIK |
| 128 | 3C6 VL 1.4 | DIVMTQSPDSLAVSLGERATINCKASENVVTYVSWYQQKPGQPPKLLIYGASNRYTGVPDRFSGS GSATDFTLTISSLQAEDVAVYHCGQGYSYPYTFGQGTKLEIK |
| 129 | 3C6 VH 2.1 HC-FR1 | EVQLVQSGPELKKPGASVKISCKASGYTFT |
| 130 | 3C6 VH 2.2, 3C6 VH 2.3 HC-FR1 | EVQLVQSGAEVKKPGASVKISCKASGYTFT |
| 131 | 3C6 VH 2.4, 3C6 VH 2.5 HC-FR1 | QVQLVQSGAEVKKPGASVKVSCKASGYTFT |
| 132 | 3C6 VH 2.1 HC-FR2 | WVKQAHGQRLEWIG |
| 133 | 3C6 VH 2.2 HC-FR2 | WVKQAPGQRLEWIG |
| 134 | 3C6 VH 2.3, 3C6 VH 2.4 HC-FR2 | WVRQAPGQRLEWIG |
| 135 | 3C6 VH 2.5 HC-FR2 | WVRQAPGQRLEWMG |
| 136 | 3C6 VH 2.1 HC-FR3 | RATLTVDKSASTAYMELRSLTSEDTAVYYCAR |

-continued

| SEQ ID NO: | DESCRIPTION | SEQUENCE |
|---|---|---|
| 137 | 3C6 VH 2.2 HC-FR3 | RATLTVDKSASTAYMELSSLRSEDTAVYYCAR |
| 138 | 3C6 VH 2.3 HC-FR3 | RVTLTVDKSASTAYMELSSLRSEDTAVYYCAR |
| 139 | 3C6 VH 2.4, 3C6 VH 2.5 HC-FR3 | RVTITVDKSASTAYMELSSLRSEDTAVYYCAR |
| 140 | 3C6 VH 2.1, 3C6 VH 2.2, 3C6 VH 2.3, 3C6 VH 2.4, 3C6 VH 2.5 HC-FR4 | WGQGTTVTVSS |
| 141 | 3C6 VL 2.1, 3C6 VL 2.2 LC-FR1 | DIVLTQSPASLALSPGERATLSC |
| 142 | 3C6 VL 2.3 LC-FR1 | DIVLTQSPATLSLSPGERATLSC |
| 143 | 3C6 VL 2.4 LC-FR1 | EIVLTQSPATLSLSPGERATLSC |
| 144 | 3C6 VL 2.1 LC-FR2 | WYQQKPGQPPRLLIY |
| 145 | 3C6 VL 2.2, 3C6 VL 2.3, 3C6 VL 2.4 LC-FR2 | WYQQKPGQAPRLLIY |
| 146 | 3C6 VL 2.1 LC-FR3 | GVPARFSGSGSGTDFTLNIHPLEEEDFATYYC |
| 147 | 3C6 VL 2.2 LC-FR3 | GVPARFSGSGSGTDFTLTISSLEEEDFATYYC |
| 148 | 3C6 VL 2.3, 3C6 VL 2.4 LC-FR3 | GVPARFSGSGSGTDFTLTISSLEPEDFATYYC |
| 149 | 3C6 VL 2.1 3C6 VL 2.2 3C6 VL 2.3 3C6 VL 2.4 3C6 VL 1.1 3C6 VL 1.2 3C6 VL 1.3 3C6 VL 1.4 LC-FR4 | FGQGTKLEIK |
| 150 | 3C6 VL 1.1 LC-FR1 | NIVMTQSPDSLSVSVGERATLNC |
| 151 | 3C6 VL 1.2 LC-FR1 | NIVMTQSPDSLAVSVGERATLNC |
| 152 | 3C6 VL 1.3, 3C6 VL 1.4 LC-FR1 | DIVMTQSPDSLAVSLGERATINC |
| 153 | 3C6 VL 1.1 3C6 VL 1.2 LC-FR3 | GVPDRFTGSGSATDFTLTISSLQAEDLADYHC |
| 154 | 3C6 VL 1.3 LC-FR3 | GVPDRFSGSGSATDFTLTISSLQAEDLADYHC |
| 155 | 3C6 VL 1.4 LC-FR3 | GVPDRFSGSGSATDFTLTISSLQAEDVAVYHC |

| SEQ ID NO: | DESCRIPTION | SEQUENCE |
|---|---|---|
| 156 | 1H2 VH | QAQLQQSGAELARPGASVKLSCKASGYTFTSYGITWVKQRTGQGLEWIGDIYPRSGNIYYNENFK GEATLTADKSSSTAYMQLSRLTSEDSAVYFCARSGWEGWFAYWGQGTLVTVSV |
| 157 | 1H2 VL | DIVMTQSHKFMSTSVGDRVNITCKASQDVGSAVVWYQQKPGQSPKVLIYWASTRHTGVPDRFTG SGSGTDFTLTISNVQSEDLADYFCQQYSSYRTFGGGTKLEIK |
| 158 | 1H2 HC-CDR1 | SYGIT |
| 159 | 1H2 HC-CDR2 | DIYPRSGNIYYNENFKG |
| 160 | 1H2 HC-CDR3 | SGWEGWFAY |
| 161 | 1H2 LC-CDR1 | KASQDVGSAVV |
| 162 | 1H2 LC-CDR2 | WASTRHT |
| 163 | 1H2 LC-CDR3 | QQYSSYRT |
| 164 | 1H2 HC-FR1 | QAQLQQSGAELARPGASVKLSCKASGYTFT |
| 165 | 1H2 HC-FR2 | WVKQRTGQGLEWIG |
| 166 | 1H2 HC-FR3 | EATLTADKSSSTAYMQLSRLTSEDSAVYFCAR |
| 167 | 1H2 HC-FR4 | WGQGTLVTVSV |
| 168 | 1H2 LC-FR1 | DIVMTQSHKFMSTSVGDRVNITC |
| 169 | 1H2 LC-FR2 | WYQQKPGQSPKVLIY |
| 170 | 1H2 LC-FR3 | GVPDRFTGSGSGTDFTLTISNVQSEDLADYFC |
| 171 | 1H2 LC-FR4 | FGGGTKLEIK |
| 172 | 1H2 VH | CAGGCTCAGCTGCAGCAGTCTGGAGCTGAGCTGGCGAGGCCTGGGGCTTCAGTGAAGCTGT CCTGCAAGGCTTCTGGCTACACCTTCACAAGCTATGGTATAACCTGGGTGAAGCAGAGAACT GGACAGGGCCTTGAGTGGATTGGAGATATTTATCCTAGAAGTGGTAATATTTATTACAATGAG AACTTCAAGGGCGAGGCACATTGACTGCAGACAAATCCTCCAGCACAGCCTATATGCAGCT CAGCAGACTGACATCTGAGGACTCTGCAGTCTATTTCTGTGCAAGATCCGGGTGGGAAGGCT GGTTTGCTTATTGGGGCCAAGGGACTCTGGTCACTGTCTCTGTA |
| 173 | 1H2 VL | GACATTGTGATGACCCAGTCTCACAAATTCATGTCCACATCAGTAGGAGACAGGGTCAACATC ACCTGCAAGGCCAGTCAGGATGTGGGTAGTGCTGTAGTCTGGTATCAACAGAAACCAGGGCA ATCTCCTAAAGTACTGATTTACTGGGCATCCACCCGGCACACTGGAGTCCCTGATCGCTTCAC AGGCAGTGGCTCTGGGACAGATTTCACTCTCACCATTAGCAATGTGCAGTCTGAAGACTTGG CAGATTATTTCTGTCAGCAATATAGCAGTTATCGGACGTTCGGTGGAGGCACCAAGCTGGAAA TCAAA |
| 174 | 7D4 VH | EVQLQQSGPELVKPGASVKISCKASGYTFTDYNMDWVKQSQGKRLEWIGDINPNYGGTIYNQKF KGKATLTVDKSSSTAYMELRSLTSEDTTVYYCTRGELGHWYFDVWGTGTTVTVSS |
| 175 | 7D4 VL | DIVLTQSPPSLTVSLGQRATISCRASKSVSASGYSYMHWYQQKPGQPPKLLIYLTSNLESGVPARF SGSGSGTDFTLNIHPVEEEDAATYYCQHSWDLPPTFGGGTKLEIK |
| 176 | 7D4 HC-CDR1 | DYNMD |
| 177 | 7D4 HC-CDR2 | DINPNYGGTIYNQKFKG |

| SEQ ID NO: | DESCRIPTION | SEQUENCE |
|---|---|---|
| 178 | 7D4 HC-CDR3 | GELGHWYFDV |
| 179 | 7D4 LC-CDR1 | RASKSVSASGYSYMH |
| 180 | 7D4 LC-CDR2 | LTSNLES |
| 181 | 7D4 LC-CDR3 | QHSWDLPPT |
| 182 | 7D4 HC-FR1 | EVQLQQSGPELVKPGASVKISCKASGYTFT |
| 183 | 7D4 HC-FR2 | WVKQSQGKRLEWIG |
| 184 | 7D4 HC-FR3 | KATLTVDKSSTAYMELRSLTSEDTTVYYCTR |
| 185 | 7D4 HC-FR4 | WGTGTTVTVSS |
| 186 | 7D4 LC-FR1 | DIVLTQSPPSLTVSLGQRATISC |
| 187 | 7D4 LC-FR2 | WYQQKPGQPPKLLIY |
| 188 | 7D4 LC-FR3 | GVPARFSGSGSGTDFTLNIHPVEEEDAATYYC |
| 189 | 7D4 LC-FR4 | FGGGTKLEIK |
| 190 | 7D4 VH | GAGGTCCAGCTGCAACAGTCTGGACCTGAGCTGGTGAAGCCTGGGGCTTCAGTGAAGATAT CCTGCAAGGCTTCTGGATACACATTCACTGACTACAACATGGACTGGGTGAAGCAGAGTCAA GGAAAGAGACTTGAGTGGATTGGAGATATTAATCCTAACTATGGTGGTACTATCTACAACCAG AAGTTCAAGGGCAAGGCCACATTGACTGTTGACAAGTCCTCCAGCACAGCCTACATGGAGCT CCGCAGCCTGACATCTGAGGACACTACAGTCTATTACTGTACAAGAGGGGAACTGGGTCACT GGTACTTCGATGTCTGGGGCACAGGGACCACGGTCACCGTCTCCTCA |
| 191 | 7D4 VL | GACATTGTGCTGACACAGTCTCCTCCTTCCTTAACTGTGTCTCTGGGGCAGAGGGCCACCAT CTCATGCAGGGCCAGTAAAAGTGTCAGTGCGTCTGGCTATAGTTATATGCACTGGTACCAACA GAAACCAGGACAGCCACCCAAACTCCTCATCTATCTTACATCCAACCTAGAATCTGGGGTCCC TGCCAGGTTCAGTGGCAGTGGGTCTGGGACAGACTTCACCCTCAACATCCATCCTGTGGAGG AGGAGGATGCTGCAACCTATTACTGTCAGCACAGTTGGGACCTTCCTCCGACGTTCGGTGGA GGCACCAAGCTGGAAATCAAA |
| 192 | 8H11 VH | EVQLQQSGPELVKPGASVKIPCKASGYTFTDYNIDWVKQSHGKSLEWIGDINPNYGGTLYNQKFK GKATLTVDKSSTAYMELRSLTSEDTAVYYCARGELGHWYFDVWGTGTTVTVSS |
| 193 | 8H11 VL | DIVLTQSPASLAVSLGQRATISCRASKSVSTSDYSYMHWYQQKPGHPPKLLIYLASNLESGVPARF SGSGSGTDFTLNIHPVEEEDAATYFCQHSRDLPPTFGGGTKLEIK |
| 194 | 8H11 HC-CDR1 | DYNID |
| 195 | 8H11 HC-CDR2 | DINPNYGGTLYNQKFKG |
| 196 | 8H11 HC-CDR3 | GELGHWYFDV |
| 197 | 8H11 LC-C DR1 | RASKSVSTSDYSYMH |
| 198 | 8H11 LC-CDR2 | LASNLES |
| 199 | 8H11 LC-CDR3 | QHSRDLPPT |

| SEQ ID NO: | DESCRIPTION | SEQUENCE |
|---|---|---|
| 200 | 8H11 HC-FR1 | EVQLQQSGPELVKPGASVKIPCKASGYTFT |
| 201 | 8H11 HC-FR2 | WVKQSHGKSLEWIG |
| 202 | 8H11 HC-FR3 | KATLTVDKSSSTAYMELRSLTSEDTAVYYCAR |
| 203 | 8H11 HC-FR4 | WGTGTTVTVSS |
| 204 | 8H11 LC-FR1 | DIVLTQSPASLAVSLGQRATISC |
| 205 | 8H11 LC-FR2 | WYQQKPGHPPKLLIY |
| 206 | 8H11 LC-FR3 | GVPARFSGSGSGTDFTLNIHPVEEEDAATYFC |
| 207 | 8H11 LC-FR4 | FGGGTKLEIK |
| 208 | 8H11 VH | GAGGTCCAGCTGCAACAGTCTGGACCTGAGCTGGTGAAGCCTGGGGCTTCAGTGAAGATAC CCTGCAAGGCTTCTGGATACACATTCACTGACTACAACATAGACTGGGTGAAGCAGAGCCAT GGAAAGAGCCTTGAGTGGATTGGAGATATTAATCCTAATTATGGTGGTACTCTCTACAACCAG AAGTTCAAGGGCAAGGCAACATTGACTGTAGACAAGTCCTCCAGCACAGCCTACATGGAACT CCGCAGCCTGACATCTGAGGACACTGCAGTCTATTACTGTGCAAGAGGGGAACTGGGTCACT GGTACTTCGATGTCTGGGGCACAGGGACCACGGTCACCGTCTCCTCA |
| 209 | 8H11 VL | GACATTGTGCTGACACAGTCTCCTGCTTCCTTAGCTGTATCTCTGGGGCAGAGGGCCACCAT CTCATGCAGGGCCAGCAAAAGTGTCAGTACATCTGACTATAGTTATATGCACTGGTACCAACA GAAACCAGGACACCCACCCAAACTCCTCATCTATCTTGCATCCAACCTAGAATCTGGGGTCCC TGCCAGGTTCAGTGGCAGTGGGTCTGGGACAGACTTCACCCTCAACATCCATCCTGTGGAGG AGGAGGATGCTGCAACCTATTTCTGTCAGCACAGTAGGGACCTTCCTCCGACGTTCGGTGGA GGCACCAAGCTGGAAATCAAA |
| 210 | YU100-G08 VH-02A VL | QVQLVQSGGGVVQPGRSLRLSCAASGFTFSSYGMHWVRQAPGKGLEWVAVISYDGSNKYYAD SVKGRFTISRDNSKNTLYLQMNSLRAEDTAVYYCAKIGATDPLDYWGQGTLVTVSSGSASAPKLE EGEFSEARVQSALTQPRSVSGSPGQSVTLSCTGTSSDVGGYNYVSWYQHYPGKAPKLMIFDVN ERSSGVPDRFSGSKSGNTASLTISGLQAEDEADYYCASYAGRYTWMFGGGTKVTVLGQPKAAPS VTLFPPS |
| 211 | Human IgG4 constant region (IGHG4; UniProt: P01861, v1) | ASTKGPSVFPLAPCSRSTSESTAALGCLVKDYFPEPVTVSWNSGALTSGVHTFPAVLQSSGLYSL SSVVTVPSSSLGTKTYTCNVDHKPSNTKVDKRVESKYGPPCPSCPAPEFLGGPSVFLFPPKPKDT LMISRTPEVTCVVVDVSQEDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQVSLTCLVKGFYPSDIAVE WESNGQPENNYKTTPPVLDSDGSFFLYSRLTVDKSRWQEGNVFSCSVMHEALHNHYTQKSLSL SLGK |
| 212 | CH1 IgG4 (positions 1-98 of P01861, v1) | ASTKGPSVFPLAPCSRSTSESTAALGCLVKDYFPEPVTVSWNSGALTSGVHTFPAVLQSSGLYSL SSVVTVPSSSLGTKTYTCNVDHKPSNTKVDKRV |
| 213 | Hinge IgG4 (positions 99-110 of P01861, v1) | ESKYGPPCPSCP |
| 214 | CH2 IgG4 (positions 111-220 of P01861 v1) | APEFLGGPSVFLFPPKPKDTLMISRTPEVTCVVVDVSQEDPEVQFNWYVDGVEVHNAKTKPREE QFNSTYRVVSVLTVLHQDWLNGKEYKCKVSNKGLPSSIEKTISKAK |
| 215 | CH3 IgG4 (positions 221-327 of P01861 v1) | GQPREPQVYTLPPSQEEMTKNQVSLTCLVKGFYPSDIAVEWESNGQPENNYKTTPPVLDS DGSFFLYSRLTVDKSRWQEGNVFSCSVMHEALHNHYTQKSLSLSLGK |
| 216 | Human IgG4 constant region (IGHG4; UniProt: P01861, v1; S241P) | ASTKGPSVFPLAPCSRSTSESTAALGCLVKDYFPEPVTVSWNSGALTSGVHTFPAVLQSSGLYSL SSVVTVPSSSLGTKTYTCNVDHKPSNTKVDKRVESKYGPPCPPCPAPEFLGGPSVFLFPPKPKDT LMISRTPEVTCVVVDVSQEDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQVSLTCLVKGFYPSDIAVE WESNGQPENNYKTTPPVLDSDGSFFLYSRLTVDKSRWQEGNVFSCSVMHEALHNHYTQKSLSL SLGK |

| SEQ ID NO: | DESCRIPTION | SEQUENCE |
|---|---|---|
| 217 | Hinge IgG4 (positions 99-110 of P01861, v1; S241P) | ESKYGPPCPPCP |
| 218 | Human IgG4 constant region (IGHG4; UniProt: P01861, v1; S241P and L248E) | ASTKGPSVFPLAPCSRSTSESTAALGCLVKDYFPEPVTVSWNSGALTSGVHTFPAVLQSSGLYSL SSVVTVPSSSLGTKTYTCNVDHKPSNTKVDKRVESKYGPPCPPCPAPEFEGGPSVFLFPPKPKDT LMISRTPEVTCVVVDVSQEDPEVQFNWYVDGVEVHNAKTKPREEQFNSTYRVVSVLTVLHQDWL NGKEYKCKVSNKGLPSSIEKTISKAKGQPREPQVYTLPPSQEEMTKNQVSLTCLVKGFYPSDIAVE WESNGQPENNYKTTPPVLDSDGSFFLYSRLTVDKSRWQEGNVFSCSVMHEALHNHYTQKSLSL SLGK |
| 219 | CH2 IgG4 (positions 111-220 of P01861 v1; L248E) | APEFEGGPSVFLFPPKPKDTLMISRTPEVTCVVVDVSQEDPEVQFNWYVDGVEVHNAKTKPREE QFNSTYRVVSVLTVLHQDWLNGKEYKCKVSNKGLPSSIEKTISKAK |
| 220 | YU100-G08 VH - Human IgG1 constant region (IGHG1; UniProt: P01857-1, v1) | QVQLVQSGGGVVQPGRSLRLSCAASGFTFSSYGMHWVRQAPGKGLEWVAVISYDGSNKYYAD SVKGRFTISRDNSKNTLYLQMNSLRAEDTAVYYCAKIGATDPLDYWGQGTLVTVSSASTKGPSVF PLAPSSKSTSGGTAALGCLVKDYFPEPVTVSWNSGALTSGVHTFPAVLQSSGLYSLSSVVTVPSS SLGTQTYICNVNHKPSNTKVDKKVEPKSCDKTHTCPPCPAPELLGGPSVFLFPPKPKDTLMISRTP EVTCVVVDVSHEDPEVKFNWYVDGVEVHNAKTKPREEQYNSTYRVVSVLTVLHQDWLNGKEYK CKVSNKALPAPIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSLSLSPGK |
| 221 | YU100-G08 VH - Human IgG4 constant region (IGHG4; UniProt: P01861, v1) | QVQLVQSGGGVVQPGRSLRLSCAASGFTFSSYGMHWVRQAPGKGLEWVAVISYDGSNKYYAD SVKGRFTISRDNSKNTLYLQMNSLRAEDTAVYYCAKIGATDPLDYWGQGTLVTVSSASTKGPSVF PLAPCSRSTSESTAALGCLVKDYFPEPVTVSWNSGALTSGVHTFPAVLQSSGLYSLSSVVTVPSS SLGTKTYTCNVDHKPSNTKVDKRVESKYGPPCPSCPAPEFLGGPSVFLFPPKPKDTLMISRTPEV TCVVVDVSQEDPEVQFNWYVDGVEVHNAKTKPREEQFNSTYRVVSVLTVLHQDWLNGKEYKCK VSNKGLPSSIEKTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKSLSLSLGK |
| 222 | YU100-G08 VH - Human IgG4 constant region (IGHG4; UniProt: P01861, v1; S241P) | QVQLVQSGGGVVQPGRSLRLSCAASGFTFSSYGMHWVRQAPGKGLEWVAVISYDGSNKYYAD SVKGRFTISRDNSKNTLYLQMNSLRAEDTAVYYCAKIGATDPLDYWGQGTLVTVSSASTKGPSVF PLAPCSRSTSESTAALGCLVKDYFPEPVTVSWNSGALTSGVHTFPAVLQSSGLYSLSSVVTVPSS SLGTKTYTCNVDHKPSNTKVDKRVESKYGPPCPPCPAPEFLGGPSVFLFPPKPKDTLMISRTPEV TCVVVDVSQEDPEVQFNWYVDGVEVHNAKTKPREEQFNSTYRVVSVLTVLHQDWLNGKEYKCK VSNKGLPSSIEKTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKSLSLSLGK |
| 223 | YU100-G08 VH - Human IgG4 constant region (IGHG4; UniProt: P01861, v1; S241P and L248E) | QVQLVQSGGGVVQPGRSLRLSCAASGFTFSSYGMHWVRQAPGKGLEWVAVISYDGSNKYYAD SVKGRFTISRDNSKNTLYLQMNSLRAEDTAVYYCAKIGATDPLDYWGQGTLVTVSSASTKGPSVF PLAPCSRSTSESTAALGCLVKDYFPEPVTVSWNSGALTSGVHTFPAVLQSSGLYSLSSVVTVPSS SLGTKTYTCNVDHKPSNTKVDKRVESKYGPPCPPCPAPEFEGGPSVFLFPPKPKDTLMISRTPEV TCVVVDVSQEDPEVQFNWYVDGVEVHNAKTKPREEQFNSTYRVVSVLTVLHQDWLNGKEYKCK VSNKGLPSSIEKTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKSLSLSLGK |
| 224 | 02A VL-Cκ CL (IGCK; UniProt: P01834-1, v2) | QSALTQPRSVSGSPGQSVTLSCTGTSSDVGGYNYVSWYQHYPGKAPKLMIFDVNERSSGVPDR FSGSKSGNTASLTISGLQAEDEADYYCASYAGRYTWMFGGGTKVTVLRTVAAPSVFIFPPSDEQL KSGTASVVCLLNNFYPREAKVQWKVDNALQSGNSQESVTEQDSKDSTYSLSSTLTLSKADYEKH KVYACEVTHQGLSSPVTKSFNRGEC |
| 225 | 3C6 VH 2.2 - Human IgG1 constant region (IGHG1; UniProt: P01857-1, v1) | EVQLVQSGAEVKKPGASVKISCKASGYTFTDYNMDWVKQAPGQRLEWIGDINPHNGGPIYNQKF TGRATLTVDKSASTAYMELSSLRSEDTAVYYCARGELGHWYFDVWGQGTTVTVSSASTKGPSVF PLAPSSKSTSGGTAALGCLVKDYFPEPVTVSWNSGALTSGVHTFPAVLQSSGLYSLSSVVTVPSS SLGTQTYICNVNHKPSNTKVDKKVEPKSCDKTHTCPPCPAPELLGGPSVFLFPPKPKDTLMISRTP EVTCVVVDVSHEDPEVKFNWYVDGVEVHNAKTKPREEQYNSTYRVVSVLTVLHQDWLNGKEYK CKVSNKALPAPIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSLSLSPGK |
| 226 | 3C6 VH 2.2- Human IgG4 constant region (IGHG4; UniProt: P01861, v1) | EVQLVQSGAEVKKPGASVKISCKASGYTFTDYNMDWVKQAPGQRLEWIGDINPHNGGPIYNQKF TGRATLTVDKSASTAYMELSSLRSEDTAVYYCARGELGHWYFDVWGQGTTVTVSSASTKGPSVF PLAPCSRSTSESTAALGCLVKDYFPEPVTVSWNSGALTSGVHTFPAVLQSSGLYSLSSVVTVPSS SLGTKTYTCNVDHKPSNTKVDKRVESKYGPPCPSCPAPEFLGGPSVFLFPPKPKDTLMISRTPEV TCVVVDVSQEDPEVQFNWYVDGVEVHNAKTKPREEQFNSTYRVVSVLTVLHQDWLNGKEYKCK VSNKGLPSSIEKTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKSLSLSLGK |
| 227 | 3C6 VH 2.2 - Human IgG4 constant region (IGHG4; UniProt: P01861, v1; S241P) | EVQLVQSGAEVKKPGASVKISCKASGYTFTDYNMDWVKQAPGQRLEWIGDINPHNGGPIYNQKF TGRATLTVDKSASTAYMELSSLRSEDTAVYYCARGELGHWYFDVWGQGTTVTVSSASTKGPSVF PLAPCSRSTSESTAALGCLVKDYFPEPVTVSWNSGALTSGVHTFPAVLQSSGLYSLSSVVTVPSS SLGTKTYTCNVDHKPSNTKVDKRVESKYGPPCPPCPAPEFLGGPSVFLFPPKPKDTLMISRTPEV TCVVVDVSQEDPEVQFNWYVDGVEVHNAKTKPREEQFNSTYRVVSVLTVLHQDWLNGKEYKCK VSNKGLPSSIEKTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKSLSLSLGK |

| SEQ ID NO: | DESCRIPTION | SEQUENCE |
|---|---|---|
| 228 | 3C6 VH 2.2 - Human IgG4 constant region (IGHG4; UniProt: P01861, v1; S241P and L248E) | EVQLVQSGAEVKKPGASVKISCKASGYTFTDYNMDWVKQAPGQRLEWIGDINPHNGGPIYNQKF TGRATLTVDKSASTAYMELSSLRSEDTAVYYCARGELGHWYFDVWGQGTTVTVSSASTKGPSVF PLAPCSRSTSESTAALGCLVKDYFPEPVTVSWNSGALTSGVHTFPAVLQSSGLYSLSSVVTVPSS SLGTKTYTCNVDHKPSNTKVDKRVESKYGPPCPPCPAPEFEGGPSVFLFPPKPKDTLMISRTPEV TCVVVDVSQEDPEVQFNWYVDGVEVHNAKTKPREEQFNSTYRVVSVLTVLHQDWLNGKEYKCK VSNKGLPSSIEKTISKAKGQPREPQVYTLPPSQEEMTKNQVSLTCLVKGFYPSDIAVEWESNGQP ENNYKTTPPVLDSDGSFFLYSRLTVDKSRWQEGNVFSCSVMHEALHNHYTQKSLSLSLGK |
| 229 | 3C6 VL 2.2 - CK CL (IGCK; UniProt: P01834-1, v2) | DIVLTQSPASLALSPGERATLSCRASKSVSTSGYSYIHWYQQKPGQAPRLLIYLASNLDSGVPARF SGSGSGTDFTLTISSLEEEDFATYYCQHSRDLPPTFGQGTKLEIKRTVAAPSVFIFPPSDEQLKSGT ASVVCLLNNFYPREAKVQWKVDNALQSGNSQESVTEQDSKDSTYSLSSTLTLSKADYEKHKVYA CEVTHQGLSSPVTKSFNRGEC |
| 230 | 3C6 VL 2.1 - CK CL (IGCK; UniProt: P01834-1, v2) | DIVLTQSPASLALSPGERATLSCRASKSVSTSGYSYIHWYQQKPGQPPRLLIYLASNLDSGVPARF SGSGSGTDFTLNIHPLEEEDFATYYCQHSRDLPPTFGQGTKLEIKRTVAAPSVFIFPPSDEQLKSG TASVVCLLNNFYPREAKVQWKVDNALQSGNSQESVTEQDSKDSTYSLSSTLTLSKADYEKHKVY ACEVTHQGLSSPVTKSFNRGEC |
| 231 | C$_L$ CL (IGLC1; UniProt: P0CG04, v1) | GQPKANPTVTLFPPSSEELQANKATLVCLISDFYPGAVTVAWKADGSPVKAGVETTKPSKQSNNK YAASSYLSLTPEQWKSHRSYSCQVTHEGSTVEKTVAPTECS |
| 232 | C$_L$ CL (IGLC2; UniProt: P0DOY2, v1) | GQPKAAPSVTLFPPSSEELQANKATLVCLISDFYPGAVTVAWKADSSPVKAGVETTTPSKQSNNK YAASSYLSLTPEQWKSHRSYSCQVTHEGSTVEKTVAPTECS |
| 233 | C$_L$ CL (IGLC3; UniProt: P0DOY3, v1) | GQPKAAPSVTLFPPSSEELQANKATLVCLISDFYPGAVTVAWKADSSPVKAGVETTTPSKQSNNK YAASSYLSLTPEQWKSHKSYSCQVTHEGSTVEKTVAPTECS |
| 234 | C$_L$ CL (IGLC6; UniProt: P0CF74, v1) | GQPKAAPSVTLFPPSSEELQANKATLVCLISDFYPGAVKVAWKADGSPVNTGVETTTPSKQSNNK YAASSYLSLTPEQWKSHRSYSCQVTHEGSTVEKTVAPAECS |
| 235 | C$_L$ CL (IGLC7; UniProt: A0M8Q6, v3) | GQPKAAPSVTLFPPSSEELQANKATLVCLVSDFNPGAVTVAWKADGSPVKVGVETTKPSKQSNN KYAASSYLSLTPEQWKSHRSYSCRVTHEGSTVEKTVAPAECS |
| 236 | 02A VL-C$_L$ CL (IGLC1; UniProt: P0CG04, v1) | QSALTQPRSVSGSPGQSVTLSCTGTSSDVGGYNYVSWYQHYPGKAPKLMIFDVNERSSGVPDR FSGSKSGNTASLTISGLQAEDEADYYCASYAGRYTWMFGGGTKVTVLGQPKANPTVTLFPPSSE ELQANKATLVCLISDFYPGAVTVAWKADGSPVKAGVETTKPSKQSNNKYAASSYLSLTPEQWKSH RSYSCQVTHEGSTVEKTVAPTECS |
| 237 | 02A VL-C$_L$ CL (IGLC2; UniProt: P0DOY2, v1)) | QSALTQPRSVSGSPGQSVTLSCTGTSSDVGGYNYVSWYQHYPGKAPKLMIFDVNERSSGVPDR FSGSKSGNTASLTISGLQAEDEADYYCASYAGRYTWMFGGGTKVTVLGQPKAAPSVTLFPPSSE ELQANKATLVCLISDFYPGAVTVAWKADSSPVKAGVETTTPSKQSNNKYAASSYLSLTPEQWKSH RSYSCQVTHEGSTVEKTVAPTECS |
| 238 | 02A VL-C$_L$ CL (IGLC3; UniProt: P0DOY3, v1) | QSALTQPRSVSGSPGQSVTLSCTGTSSDVGGYNYVSWYQHYPGKAPKLMIFDVNERSSGVPDR FSGSKSGNTASLTISGLQAEDEADYYCASYAGRYTWMFGGGTKVTVLGQPKAAPSVTLFPPSSE ELQANKATLVCLISDFYPGAVTVAWKADSSPVKAGVETTTPSKQSNNKYAASSYLSLTPEQWKSH KSYSCQVTHEGSTVEKTVAPTECS |
| 239 | 02A VL-C$_L$ CL (IGLC6; UniProt: P0CF74, v1) | QSALTQPRSVSGSPGQSVTLSCTGTSSDVGGYNYVSWYQHYPGKAPKLMIFDVNERSSGVPDR FSGSKSGNTASLTISGLQAEDEADYYCASYAGRYTWMFGGGTKVTVLGQPKAAPSVTLFPPSSE ELQANKATLVCLISDFYPGAVKVAWKADGSPVNTGVETTTPSKQSNNKYAASSYLSLTPEQWKSH RSYSCQVTHEGSTVEKTVAPAECS |
| 240 | 02A VL-C$_L$ CL (IGLC7; UniProt: A0M8Q6, v3) | QSALTQPRSVSGSPGQSVTLSCTGTSSDVGGYNYVSWYQHYPGKAPKLMIFDVNERSSGVPDR FSGSKSGNTASLTISGLQAEDEADYYCASYAGRYTWMFGGGTKVTVLGQPKAAPSVTLFPPSSE ELQANKATLVCLVSDFNPGAVTVAWKADGSPVKVGVETTKPSKQSNNKYAASSYLSLTPEQWKS HRSYSCRVTHEGSTVEKTVAPAECS |

Numbered Paragraphs (Paras) Relating to Aspects and Embodiments of the Invention:

1. An antigen-binding molecule, optionally isolated, which is capable of binding to IL-11, wherein the antigen-binding molecule comprises:
  (i) a heavy chain variable (VH) region incorporating the following CDRs:
    HC-CDR1 having the amino acid sequence of SEQ ID NO:36 or 37
    HC-CDR2 having the amino acid sequence of SEQ ID NO:38
    HC-CDR3 having the amino acid sequence of SEQ ID NO:39 or 40; and
  (ii) a light chain variable (VL) region incorporating the following CDRs:
    LC-CDR1 having the amino acid sequence of SEQ ID NO:41, 42 or 43

LC-CDR2 having the amino acid sequence of SEQ ID NO:44, 45 or 46
LC-CDR3 having the amino acid sequence of SEQ ID NO:80 or 81.

2. The antigen-binding molecule according to para 1, wherein the antigen-binding molecule comprises:
   (i) a heavy chain variable (VH) region incorporating the following CDRs:
   HC-CDR1 having the amino acid sequence of SEQ ID NO:36
   HC-CDR2 having the amino acid sequence of SEQ ID NO:38
   HC-CDR3 having the amino acid sequence of SEQ ID NO:39; and
   (ii) a light chain variable (VL) region incorporating the following CDRs:
   LC-CDR1 having the amino acid sequence of SEQ ID NO:41
   LC-CDR2 having the amino acid sequence of SEQ ID NO:44
   LC-CDR3 having the amino acid sequence of SEQ ID NO:80.

3. The antigen-binding molecule according to para 1, wherein the antigen-binding molecule comprises:
   (i) a heavy chain variable (VH) region incorporating the following CDRs:
   HC-CDR1 having the amino acid sequence of SEQ ID NO:37
   HC-CDR2 having the amino acid sequence of SEQ ID NO:38
   HC-CDR3 having the amino acid sequence of SEQ ID NO:40; and
   (ii) a light chain variable (VL) region incorporating the following CDRs:
   LC-CDR1 having the amino acid sequence of SEQ ID NO:42
   LC-CDR2 having the amino acid sequence of SEQ ID NO:45
   LC-CDR3 having the amino acid sequence of SEQ ID NO:81.

4. The antigen-binding molecule according to para 1, wherein the antigen-binding molecule comprises:
   (i) a heavy chain variable (VH) region incorporating the following CDRs:
   HC-CDR1 having the amino acid sequence of SEQ ID NO:37
   HC-CDR2 having the amino acid sequence of SEQ ID NO:38
   HC-CDR3 having the amino acid sequence of SEQ ID NO:40; and
   (ii) a light chain variable (VL) region incorporating the following CDRs:
   LC-CDR1 having the amino acid sequence of SEQ ID NO:43
   LC-CDR2 having the amino acid sequence of SEQ ID NO:46
   LC-CDR3 having the amino acid sequence of SEQ ID NO:80.

5. The antigen-binding molecule according to para 1 or para 2, wherein the antigen-binding molecule comprises:
   (a)
   (i) a heavy chain variable (VH) region incorporating the following CDRs:
   HC-CDR1 having the amino acid sequence of SEQ ID NO:36
   HC-CDR2 having the amino acid sequence of SEQ ID NO:38
   HC-CDR3 having the amino acid sequence of SEQ ID NO:39; and
   (ii) a light chain variable (VL) region incorporating the following CDRs:
   LC-CDR1 having the amino acid sequence of SEQ ID NO:41
   LC-CDR2 having the amino acid sequence of SEQ ID NO:44
   LC-CDR3 having the amino acid sequence of SEQ ID NO:48;
   (b)
   (i) a heavy chain variable (VH) region incorporating the following CDRs:
   HC-CDR1 having the amino acid sequence of SEQ ID NO:36
   HC-CDR2 having the amino acid sequence of SEQ ID NO:38
   HC-CDR3 having the amino acid sequence of SEQ ID NO:39; and
   (ii) a light chain variable (VL) region incorporating the following CDRs:
   LC-CDR1 having the amino acid sequence of SEQ ID NO:41
   LC-CDR2 having the amino acid sequence of SEQ ID NO:44
   LC-CDR3 having the amino acid sequence of SEQ ID NO:49;
   (c)
   (i) a heavy chain variable (VH) region incorporating the following CDRs:
   HC-CDR1 having the amino acid sequence of SEQ ID NO:36
   HC-CDR2 having the amino acid sequence of SEQ ID NO:38
   HC-CDR3 having the amino acid sequence of SEQ ID NO:39; and
   (ii) a light chain variable (VL) region incorporating the following CDRs:
   LC-CDR1 having the amino acid sequence of SEQ ID NO:41
   LC-CDR2 having the amino acid sequence of SEQ ID NO:44
   LC-CDR3 having the amino acid sequence of SEQ ID NO:50;
   (d)
   (i) a heavy chain variable (VH) region incorporating the following CDRs:
   HC-CDR1 having the amino acid sequence of SEQ ID NO:36
   HC-CDR2 having the amino acid sequence of SEQ ID NO:38
   HC-CDR3 having the amino acid sequence of SEQ ID NO:39; and
   (ii) a light chain variable (VL) region incorporating the following CDRs:
   LC-CDR1 having the amino acid sequence of SEQ ID NO:41
   LC-CDR2 having the amino acid sequence of SEQ ID NO:44
   LC-CDR3 having the amino acid sequence of SEQ ID NO:51;
   (e)
   (i) a heavy chain variable (VH) region incorporating the following CDRs:
   HC-CDR1 having the amino acid sequence of SEQ ID NO:36

HC-CDR2 having the amino acid sequence of SEQ ID NO:38
HC-CDR3 having the amino acid sequence of SEQ ID NO:39; and
(ii) a light chain variable (VL) region incorporating the following CDRs:
LC-CDR1 having the amino acid sequence of SEQ ID NO:41
LC-CDR2 having the amino acid sequence of SEQ ID NO:44
LC-CDR3 having the amino acid sequence of SEQ ID NO:52;
(f)
(i) a heavy chain variable (VH) region incorporating the following CDRs:
HC-CDR1 having the amino acid sequence of SEQ ID NO:36
HC-CDR2 having the amino acid sequence of SEQ ID NO:38
HC-CDR3 having the amino acid sequence of SEQ ID NO:39; and
(ii) a light chain variable (VL) region incorporating the following CDRs:
LC-CDR1 having the amino acid sequence of SEQ ID NO:41
LC-CDR2 having the amino acid sequence of SEQ ID NO:44
LC-CDR3 having the amino acid sequence of SEQ ID NO:53;
(g)
(i) a heavy chain variable (VH) region incorporating the following CDRs:
HC-CDR1 having the amino acid sequence of SEQ ID NO:36
HC-CDR2 having the amino acid sequence of SEQ ID NO:38
HC-CDR3 having the amino acid sequence of SEQ ID NO:39; and
(ii) a light chain variable (VL) region incorporating the following CDRs:
LC-CDR1 having the amino acid sequence of SEQ ID NO:41
LC-CDR2 having the amino acid sequence of SEQ ID NO:44
LC-CDR3 having the amino acid sequence of SEQ ID NO:54; or
(h)
(i) a heavy chain variable (VH) region incorporating the following CDRs:
HC-CDR1 having the amino acid sequence of SEQ ID NO:36
HC-CDR2 having the amino acid sequence of SEQ ID NO:38
HC-CDR3 having the amino acid sequence of SEQ ID NO:39; and
(ii) a light chain variable (VL) region incorporating the following CDRs:
LC-CDR1 having the amino acid sequence of SEQ ID NO:41
LC-CDR2 having the amino acid sequence of SEQ ID NO:44
LC-CDR3 having the amino acid sequence of SEQ ID NO:55.

6. The antigen-binding molecule according to para 1 or para 3, wherein the antigen-binding molecule comprises:
(a)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:57;
(b)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:58;
(c)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:59;
(d)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:42

LC-CDR2 having the amino acid sequence of SEQ ID NO:45
LC-CDR3 having the amino acid sequence of SEQ ID NO:60;
(e)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:61;
(f)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:62;
(g)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:63; or
(h)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:42
LC-CDR2 having the amino acid sequence of SEQ ID NO:45
LC-CDR3 having the amino acid sequence of SEQ ID NO:64.

7. The antigen-binding molecule according to para 1 or para 3, wherein the antigen-binding molecule comprises:
(a)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:48;
(b)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:49;
(c)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:50;
(d)
(i) a heavy chain variable (VH) region incorporating the following CDRs:
HC-CDR1 having the amino acid sequence of SEQ ID NO:37
HC-CDR2 having the amino acid sequence of SEQ ID NO:38

HC-CDR3 having the amino acid sequence of SEQ ID NO:40; and
(ii) a light chain variable (VL) region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:51;
(e)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:52;
(f)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:53;
(g)
(i) a heavy chain variable (VH) region incorporating the following CDRs:
HC-CDR1 having the amino acid sequence of SEQ ID NO:37
HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:54; or
(h)
(i) a heavy chain variable (VH) region incorporating the following CDRs:
HC-CDR1 having the amino acid sequence of SEQ ID NO:37

HC-CDR2 having the amino acid sequence of SEQ ID NO:38
HC-CDR3 having the amino acid sequence of SEQ ID NO:40; and
(ii) a light chain variable (VL) region incorporating the following CDRs:
LC-CDR1 having the amino acid sequence of SEQ ID NO:43
LC-CDR2 having the amino acid sequence of SEQ ID NO:46
LC-CDR3 having the amino acid sequence of SEQ ID NO:55.

8. The antigen-binding molecule according to any one of paras 1 to 7, wherein the antigen-binding molecule comprises:
  a VH region comprising an amino acid sequence having at least 70% sequence identity to the amino acid sequence of SEQ ID NO:6, 8 or 10; and
  a VL region comprising an amino acid sequence having at least 70% sequence identity to the amino acid sequence of SEQ ID NO:82, 83 or 84.

9. The antigen-binding molecule according to para 8, wherein the antigen-binding molecule comprises:
  a VH region comprising an amino acid sequence having at least 70% sequence identity to the amino acid sequence of SEQ ID NO:6; and
  a VL region comprising an amino acid sequence having at least 70% sequence identity to the amino acid sequence of SEQ ID NO:82.

10. The antigen-binding molecule according to para 8, wherein the antigen-binding molecule comprises:
  a VH region comprising an amino acid sequence having at least 70% sequence identity to the amino acid sequence of SEQ ID NO:8; and
  a VL region comprising an amino acid sequence having at least 70% sequence identity to the amino acid sequence of SEQ ID NO:83.

11. The antigen-binding molecule according to para 8, wherein the antigen-binding molecule comprises:
  a VH region comprising an amino acid sequence having at least 70% sequence identity to the amino acid sequence of SEQ ID NO:10; and
  a VL region comprising an amino acid sequence having at least 70% sequence identity to the amino acid sequence of SEQ ID NO:84.

12. The antigen-binding molecule according to para 8 or para 9, wherein the antigen-binding molecule comprises:
  (a)
  a VH region comprising an amino acid sequence having at least 70% sequence identity to the amino acid sequence of SEQ ID NO:6; and
  a VL region comprising an amino acid sequence having at least 70% sequence identity to the amino acid sequence of SEQ ID NO:12;
  (b)
  a VH region comprising an amino acid sequence having at least 70% sequence identity to the amino acid sequence of SEQ ID NO:6; and
  a VL region comprising an amino acid sequence having at least 70% sequence identity to the amino acid sequence of SEQ ID NO:13;
  (c)
  a VH region comprising an amino acid sequence having at least 70% sequence identity to the amino acid sequence of SEQ ID NO:6; and a VL region comprising an amino acid sequence having at least 70% sequence identity to the amino acid sequence of SEQ ID NO:14;

(d)

a VH region comprising an amino acid sequence having at least 70% sequence identity to the amino acid sequence of SEQ ID NO:6; and a VL region comprising an amino acid sequence having at least 70% sequence identity to the amino acid sequence of SEQ ID NO:15;

(e)

a VH region comprising an amino acid sequence having at least 70% sequence identity to the amino acid sequence of SEQ ID NO:6; and a VL region comprising an amino acid sequence having at least 70% sequence identity to the amino acid sequence of SEQ ID NO:16;

(f)

a VH region comprising an amino acid sequence having at least 70% sequence identity to the amino acid sequence of SEQ ID NO:6; and a VL region comprising an amino acid sequence having at least 70% sequence identity to the amino acid sequence of SEQ ID NO:17;

(g)

a VH region comprising an amino acid sequence having at least 70% sequence identity to the amino acid sequence of SEQ ID NO:6; and a VL region comprising an amino acid sequence having at least 70% sequence identity to the amino acid sequence of SEQ ID NO:18; or (h)

a VH region comprising an amino acid sequence having at least 70% sequence identity to the amino acid sequence of SEQ ID NO:6; and a VL region comprising an amino acid sequence having at least 70% sequence identity to the amino acid sequence of SEQ ID NO:19.

13. The antigen-binding molecule according to para 8 or para 10, wherein the antigen-binding molecule comprises:

(a)

a VH region comprising an amino acid sequence having at least 70% sequence identity to the amino acid sequence of SEQ ID NO:8; and a VL region comprising an amino acid sequence having at least 70% sequence identity to the amino acid sequence of SEQ ID NO:20;

(b)

a VH region comprising an amino acid sequence having at least 70% sequence identity to the amino acid sequence of SEQ ID NO:8; and a VL region comprising an amino acid sequence having at least 70% sequence identity to the amino acid sequence of SEQ ID NO:21;

(c)

a VH region comprising an amino acid sequence having at least 70% sequence identity to the amino acid sequence of SEQ ID NO:8; and a VL region comprising an amino acid sequence having at least 70% sequence identity to the amino acid sequence of SEQ ID NO:22;

(d)

a VH region comprising an amino acid sequence having at least 70% sequence identity to the amino acid sequence of SEQ ID NO:8; and a VL region comprising an amino acid sequence having at least 70% sequence identity to the amino acid sequence of SEQ ID NO:23;

(e)

a VH region comprising an amino acid sequence having at least 70% sequence identity to the amino acid sequence of SEQ ID NO:8; and a VL region comprising an amino acid sequence having at least 70% sequence identity to the amino acid sequence of SEQ ID NO:24;

(f)

a VH region comprising an amino acid sequence having at least 70% sequence identity to the amino acid sequence of SEQ ID NO:8; and a VL region comprising an amino acid sequence having at least 70% sequence identity to the amino acid sequence of SEQ ID NO:25;

(g)

a VH region comprising an amino acid sequence having at least 70% sequence identity to the amino acid sequence of SEQ ID NO:8; and a VL region comprising an amino acid sequence having at least 70% sequence identity to the amino acid sequence of SEQ ID NO:26; or (h)

a VH region comprising an amino acid sequence having at least 70% sequence identity to the amino acid sequence of SEQ ID NO:8; and a VL region comprising an amino acid sequence having at least 70% sequence identity to the amino acid sequence of SEQ ID NO:27.

14. The antigen-binding molecule according to para 8 or para 11, wherein the antigen-binding molecule comprises:

(a)

a VH region comprising an amino acid sequence having at least 70% sequence identity to the amino acid sequence of SEQ ID NO:10; and a VL region comprising an amino acid sequence having at least 70% sequence identity to the amino acid sequence of SEQ ID NO:28;

(b)

a VH region comprising an amino acid sequence having at least 70% sequence identity to the amino acid sequence of SEQ ID NO:10; and a VL region comprising an amino acid sequence having at least 70% sequence identity to the amino acid sequence of SEQ ID NO:29;

(c)

a VH region comprising an amino acid sequence having at least 70% sequence identity to the amino acid sequence of SEQ ID NO:10; and a VL region comprising an amino acid sequence having at least 70% sequence identity to the amino acid sequence of SEQ ID NO:30;

(d)

a VH region comprising an amino acid sequence having at least 70% sequence identity to the amino acid sequence of SEQ ID NO:10; and a VL region comprising an amino acid sequence having at least 70% sequence identity to the amino acid sequence of SEQ ID NO:31;

(e)

a VH region comprising an amino acid sequence having at least 70% sequence identity to the amino acid sequence of SEQ ID NO:10; and a VL region comprising an amino acid sequence having at least 70% sequence identity to the amino acid sequence of SEQ ID NO:32;
(f)
a VH region comprising an amino acid sequence having at least 70% sequence identity to the amino acid sequence of SEQ ID NO:10; and
a VL region comprising an amino acid sequence having at least 70% sequence identity to the amino acid sequence of SEQ ID NO:33;
(g)
a VH region comprising an amino acid sequence having at least 70% sequence identity to the amino acid sequence of SEQ ID NO:10; and
a VL region comprising an amino acid sequence having at least 70% sequence identity to the amino acid sequence of SEQ ID NO:34; or
(h)
a VH region comprising an amino acid sequence having at least 70% sequence identity to the amino acid sequence of SEQ ID NO:10; and
a VL region comprising an amino acid sequence having at least 70% sequence identity to the amino acid sequence of SEQ ID NO:35.

15. An antigen-binding molecule, optionally isolated, which is capable of binding to IL-11, wherein the antigen-binding molecule comprises:
(i) a heavy chain variable (VH) region incorporating the following CDRs:
HC-CDR1 having the amino acid sequence of SEQ ID NO:95
HC-CDR2 having the amino acid sequence of SEQ ID NO:96
HC-CDR3 having the amino acid sequence of SEQ ID NO:97; and
(ii) a light chain variable (VL) region incorporating the following CDRs:
LC-CDR1 having the amino acid sequence of SEQ ID NO:98 or 101
LC-CDR2 having the amino acid sequence of SEQ ID NO:99 or 102
LC-CDR3 having the amino acid sequence of SEQ ID NO:100 or 103.

16. The antigen-binding molecule according to para 15, wherein the antigen-binding molecule comprises:
(a)
(i) a heavy chain variable (VH) region incorporating the following CDRs:
HC-CDR1 having the amino acid sequence of SEQ ID NO:95
HC-CDR2 having the amino acid sequence of SEQ ID NO:96
HC-CDR3 having the amino acid sequence of SEQ ID NO:97; and
(ii) a light chain variable (VL) region incorporating the following CDRs:
LC-CDR1 having the amino acid sequence of SEQ ID NO:98
LC-CDR2 having the amino acid sequence of SEQ ID NO:99
LC-CDR3 having the amino acid sequence of SEQ ID NO:100; or
(b)
(i) a heavy chain variable (VH) region incorporating the following CDRs:
HC-CDR1 having the amino acid sequence of SEQ ID NO:95
HC-CDR2 having the amino acid sequence of SEQ ID NO:96
HC-CDR3 having the amino acid sequence of SEQ ID NO:97; and
(ii) a light chain variable (VL) region incorporating the following CDRs:
LC-CDR1 having the amino acid sequence of SEQ ID NO:101
LC-CDR2 having the amino acid sequence of SEQ ID NO:102
LC-CDR3 having the amino acid sequence of SEQ ID NO:103.

17. The antigen-binding molecule according to para 15 or 16, wherein the antigen-binding molecule comprises:
a VH region comprising an amino acid sequence having at least 70% sequence identity to the amino acid sequence of SEQ ID NO:91, 92, 116, 117, 118, 119 or 120; and
a VL region comprising an amino acid sequence having at least 70% sequence identity to the amino acid sequence of SEQ ID NO:93, 94, 121, 122, 123, 124, 125, 126, 127 or 128.

18. The antigen-binding molecule according to any one of paras 1 to 17, wherein the antigen-binding molecule is capable of inhibiting IL-11 mediated signalling.

19. An antigen-binding molecule, optionally isolated, comprising (i) an antigen-binding molecule according to any one of paras 1 to 18, and (ii) an antigen-binding molecule capable of binding to an antigen other than IL-11.

20. The antigen-binding molecule according to any one of paras 1 to 19, wherein the antigen-binding molecule is capable of inhibiting interaction between IL-11 or a complex comprising IL-11 and an IL-11 receptor.

21. A chimeric antigen receptor (CAR) comprising an antigen-binding molecule according to any one of paras 1 to 20.

22. A nucleic acid, or a plurality of nucleic acids, optionally isolated, encoding an antigen-binding molecule according to any one of paras 1 to 20 or a CAR according to para 21.

23. An expression vector, or a plurality of expression vectors, comprising a nucleic acid or a plurality of nucleic acids according to para 22.

24. A cell comprising an antigen-binding molecule according to any one of paras 1 to 20, a CAR according to para 21, a nucleic acid or a plurality of nucleic acids according to para 22, or an expression vector or a plurality of expression vectors according to para 23.

25. A method comprising culturing a cell comprising a nucleic acid or a plurality of nucleic acids according to para 22, or an expression vector or a plurality of expression vectors according to para 23, under conditions suitable for expression of the antigen-binding molecule or CAR from the nucleic acid(s) or expression vector(s).

26. A composition comprising an antigen-binding molecule according to any one of paras 1 to 20, a CAR according to para 21, a nucleic acid or a plurality of nucleic acids according to para 22, an expression vector or a plurality of expression vectors according to para 23, or a cell according to para 24.

27. An antigen-binding molecule according to any one of paras 1 to 20, a CAR according to para 21, a nucleic acid or a plurality of nucleic acids according to para 22, an expression vector or a plurality of expression vectors according to cl para aim 23, a cell according to para 24, or a composition according to para 26 for use in a method of medical treatment or prophylaxis.

28. An antigen-binding molecule according to any one of paras 1 to 20, a CAR according to para 21, a nucleic acid or a plurality of nucleic acids according to para 22, an expression vector or a plurality of expression vectors according to para 23, a cell according to para 24, or a composition according to para 26, for use in a method of treatment or prevention of fibrosis, a disease characterised by fibrosis, a cancer, inflammation, or a disease characterised by inflammation.

29. Use of an antigen-binding molecule according to any one of paras 1 to 20, a CAR according to para 21, a nucleic acid or a plurality of nucleic acids according to para 22, an expression vector or a plurality of expression vectors according to para 23, a cell according to para 24, or a composition according to para 26, in the manufacture of a medicament for use in a method of treatment or prevention of fibrosis, a disease characterised by fibrosis, a cancer, inflammation, or a disease characterised by inflammation.

30. A method of treating or preventing fibrosis, a disease characterised by fibrosis, a cancer, inflammation, or a disease characterised by inflammation, comprising administering to a subject a therapeutically or prophylactically effective amount of an antigen-binding molecule according to any one of paras 1 to 20, a CAR according to para 21, a nucleic acid or a plurality of nucleic acids according to para 22, an expression vector or a plurality of expression vectors according to para 23, a cell according to para 24, or a composition according to para 26.

31. A method of inhibiting IL-11 mediated signalling, comprising contacting IL-11-expressing cells with an antigen-binding molecule according to any one of paras 1 to 20.

32. An in vitro complex, optionally isolated, comprising an antigen-binding molecule according to any one of paras 1 to 20 bound to IL-11 or a complex comprising IL-11.

33. A method comprising contacting a sample containing, or suspected to contain, IL-11 or a complex comprising IL-11 with an antigen-binding molecule according to any one of paras 1 to 20, and detecting the formation of a complex of the antigen-binding molecule with IL-11 or a complex comprising IL-11.

34. A method of selecting or stratifying a subject for treatment with an IL-11-targeted agent, the method comprising contacting, in vitro, a sample from the subject with an antigen-binding molecule according to any one of paras 1 to 20 and detecting the formation of a complex of the antigen-binding molecule with IL-11 or a complex comprising IL-11.

35. Use of an antigen-binding molecule according to any one of paras 1 to 20 as an in vitro or in vivo diagnostic or prognostic agent.

36. A kit of parts comprising a predetermined quantity of: an antigen-binding molecule according to any one of paras 1 to 20, a CAR according to para 21, a nucleic acid or a plurality of nucleic acids according to para 22, an expression vector or a plurality of expression vectors according to para 23, a cell according to para 24, or a composition according to para 26.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Where a nucleic acid sequence is disclosed herein, the reverse complement thereof is also expressly contemplated.

Methods described herein may preferably performed in vitro. The term "in vitro" is intended to encompass procedures performed with cells in culture whereas the term "in vivo" is intended to encompass procedures with/on intact multi-cellular organisms.

BRIEF DESCRIPTION OF THE FIGURES

Embodiments and experiments illustrating the principles of the invention will now be discussed with reference to the accompanying figures.

FIG. 1. Table summarising panning strategies used to identify human anti-human IL-11 antibodies capable of binding to both human IL-11 and mouse IL-11.

FIG. 3. Table summarising the 56 human anti-human IL-11 antibody clones.

FIG. 7. Table summarising the fold-change data of FIGS. 4 to 6 for the 56 human anti-IL-11 antibodies. Antibody candidates numbered 1 to 56 correspond to clone designations as indicated in FIG. 3. "Industry Standard" is monoclonal mouse anti-IL-11 IgG2A; Clone #22626; Catalog No. MAB218; R&D Systems, MN, USA.

FIG. 11. Table summarising $EC_{50}$ values determined for binding of human anti-IL-11 antibodies to IL-11 as determined by ELISA analysis.

FIG. 19. Table summarising panning strategies used to identify human anti-human IL-11 antibodies capable of binding to both human IL-11 and mouse IL-11, after light chain shuffling.

FIGS. 21A and 21B. Bar chart (21A) and Table (21B) showing binding signal to human IL-11 and mouse IL-11 as determined by ELISA assay for the 64 unique light chain-shuffled human anti-IL-11 antibodies.

FIG. 24. Table summarising the results of FIGS. 22, 23A and 23B relating to functional characterisation of the indicated light-chain shuffled anti-IL-11 antibody clones. N.D.=not determined.

FIGS. 35A to 35J. Sensorgrams and Table showing the results by Single Cycle Kinetics analysis of affinity of binding of different antibody clones to IL-11. 35A to 35I show binding of YU100-G08 (35A), 02A (35B), 02G (35C), 02I (35D), 02L (35E), 02Q (35F), 02S (35G), 02T (35H) and 02V (35I). 35J summarises the kinetics determined for the binding of the different clones.

FIGS. 36A to 36J. Sensorgrams and Table showing the results by Single Cycle Kinetics analysis of affinity of binding of different antibody clones to IL-11. 36A to 36I show binding of YU100-H01 (36A), 01A (36B), 01G (36C), 01I (36D), 01L (36E), 01Q (36F), 01S (36G), 01T (36H) and 01V (36I). 36J summarises the kinetics determined for the binding of the different clones.

FIGS. 39A to 39H. Graphs showing effect of anti-IL-11 antibody in a mouse NASH model on (39A) hepatic triglyceride content, (39B) liver hydroxyproline content, (39C, 39D) expression of pro-inflammatory factors, (39E) serum ALT levels, and (39F) levels of phosphorylated ERK in livers. All measurements were compared to a steatosis control and IgG control. Dose-dependent effects of anti-IL-11 antibodies (39G) BSN-3C6 and (39H) YU100-G08_02A on serum ALT levels and liver hydroxyproline content in a NASH model.

FIGS. 41A to 41D. Representative fluorescent images and graphs showing effect of anti-IL-11 antibody on HSC transformation to myofibroblasts when stimulated with different NASH-promoting factors. Representative fluorescent images show (41A) the number of ACTA2$^{+ve}$ cells and (41B) cells producing collagen. Scale bars=200 μm. (41C) Percentage of ACTA2$^{+ve}$ cells following treatment. (41D) Collagen production in cells following treatment.

Western blot of phosphorylation status and total levels of Erk and Stat3 in lung homogenates.

FIGS. 50A to 50D. The effect of IL-11 therapy in a bleomycin (BLM)-induced mouse model of established pulmonary fibrosis. (50A) Representative Masson's trichrome staining of lung sections. Scale bars, 100 µm. (50B) Graphs showing indexed lung/body weight and lung hydroxyproline content. (50C) Western blots of Col3a1, fibronectin and IL-11 protein levels in lung homogenates. (50D) Western blot of phosphorylation status and total levels of Erk and Stat3 in lung homogenates.

Figure 51A:
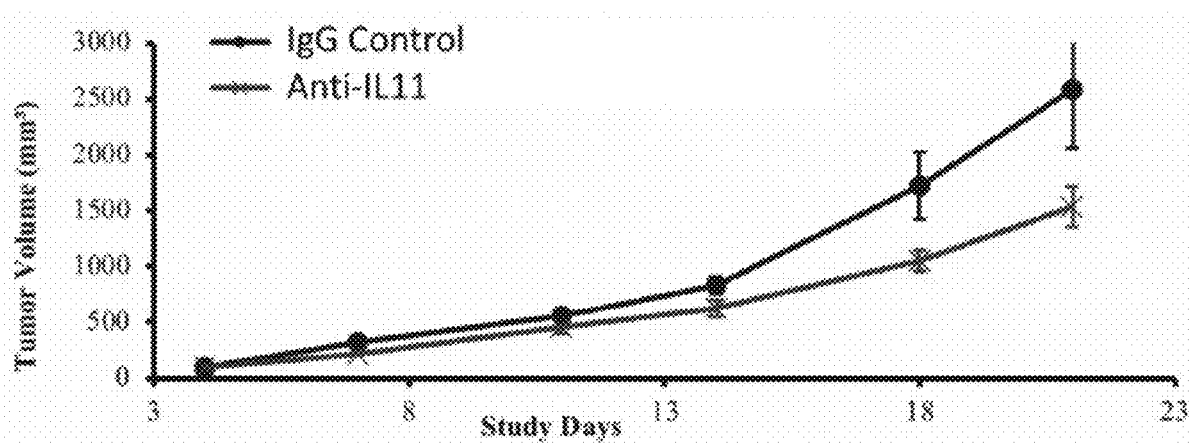
Figure 51B:
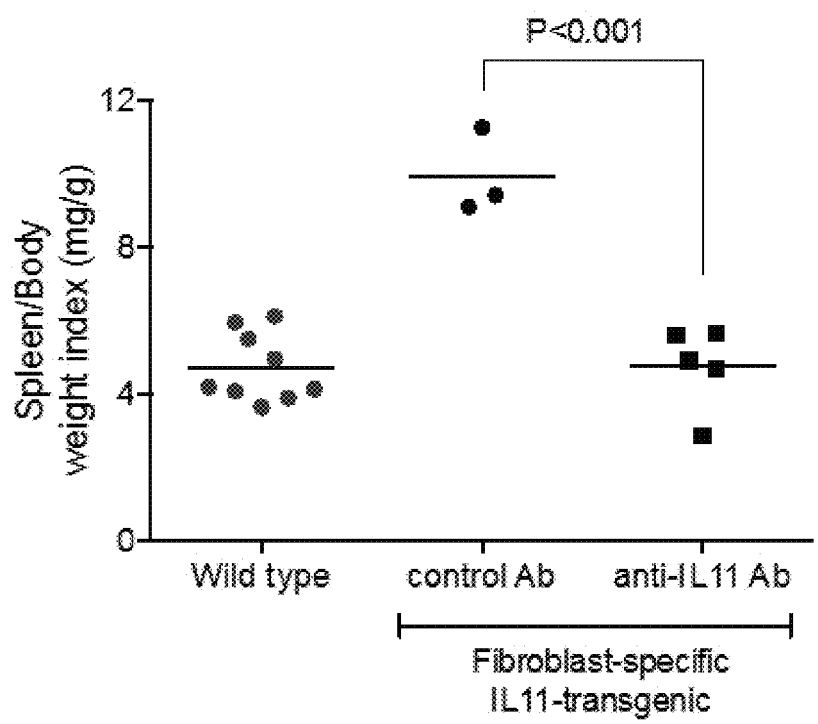
Figure 51C:
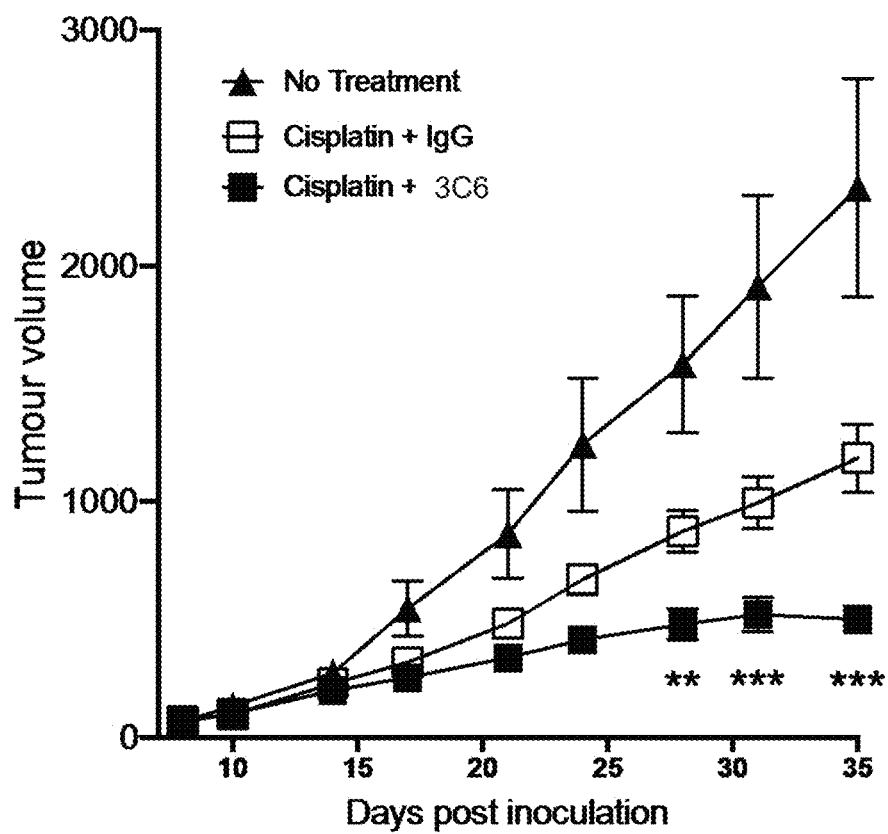

FIGS. 51A to 51C. Effect of anti-IL-11 antibody therapy on cancer. (51A) 3C6 prevents tumour growth in an HCC mouse flank model. (51B) 3C6 prevents IL-11 induced splenomegaly in a myelofibrosis mouse model expressing IL-11 in fibroblasts. (51C) 3C6 provides an additive effect on tumour volume inhibition in conjunction with cisplatin chemotherapy in a lung cancer (A549) mouse model. Anova with Tukey post hoc correction for multiple testing. Cisplatin+IgG vs cisplatin+3C6: , $P<0.01$; *, $P<0.001$. Group sizes: no treatment, n=5; Cisplatin+IgG, n=10; Cisplatin+3C6, n=10.

Figure 52:
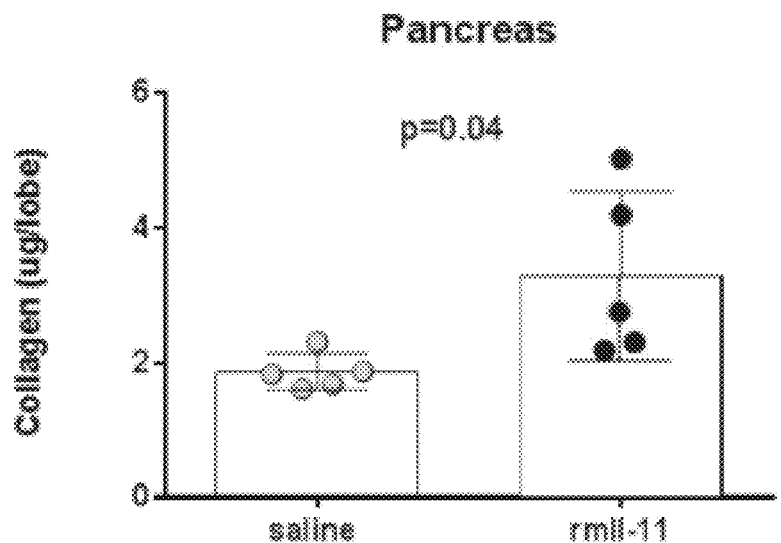

FIG. 52. Role of IL-11 in pancreatic fibrosis. Mice received daily injections of 100 µg/kg of recombinant mouse IL-11 or saline for 21 days. Collagen content of the pancreas was assessed using a calorimetric hydroxyproline assay.

Figure 53A:
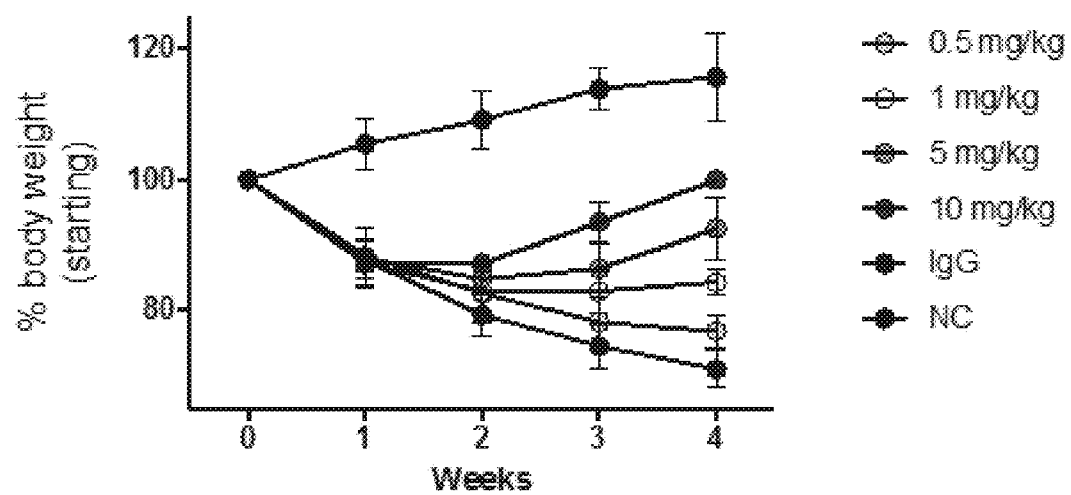
Figure 53A:
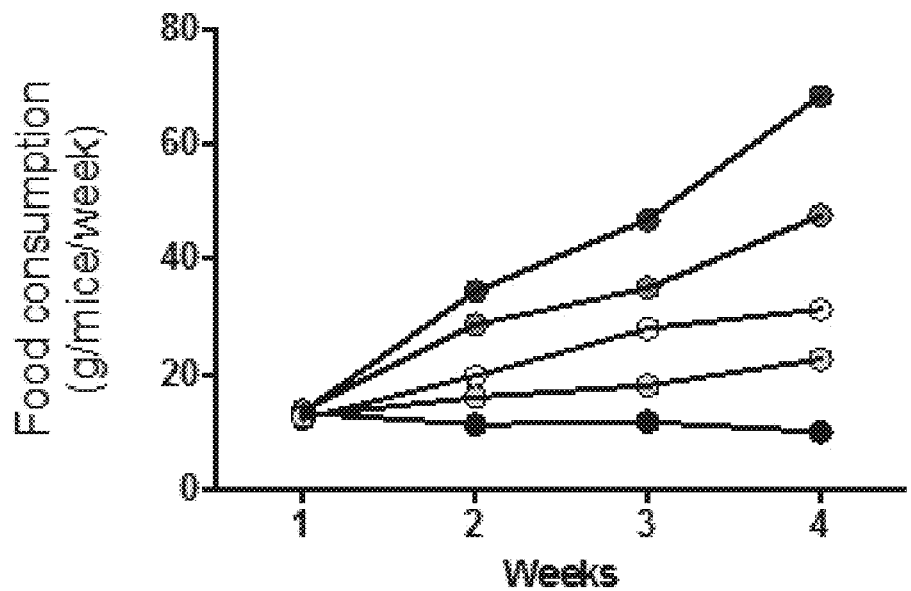
Figure 53B:
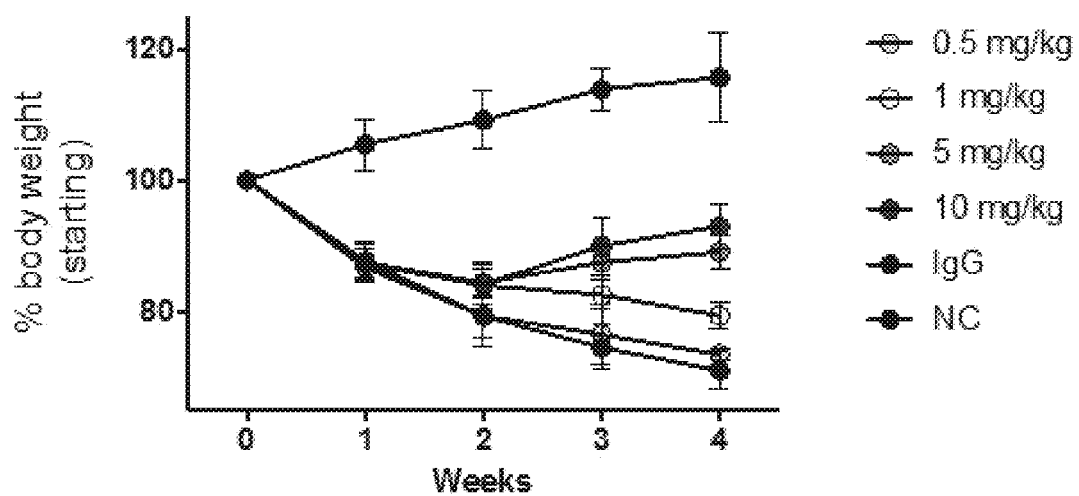
Figure 53B:
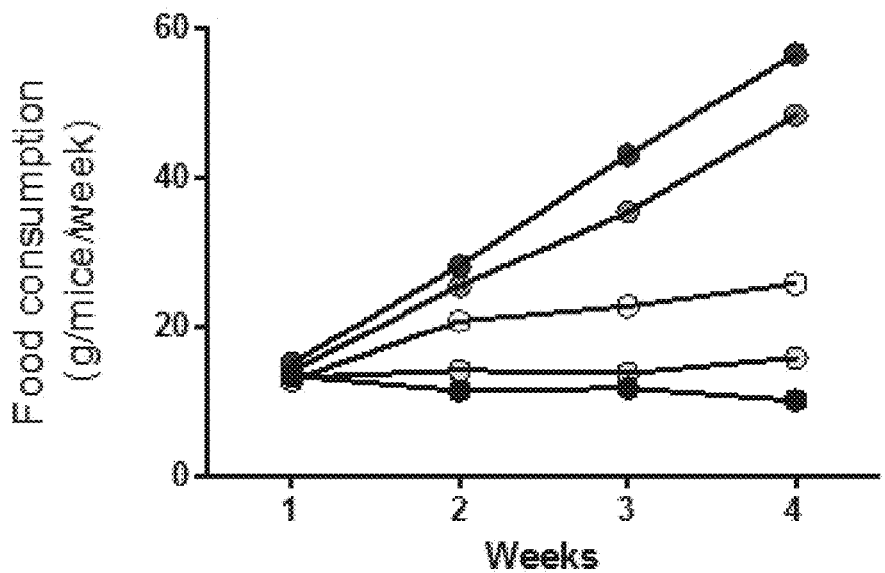
Figure 53C:
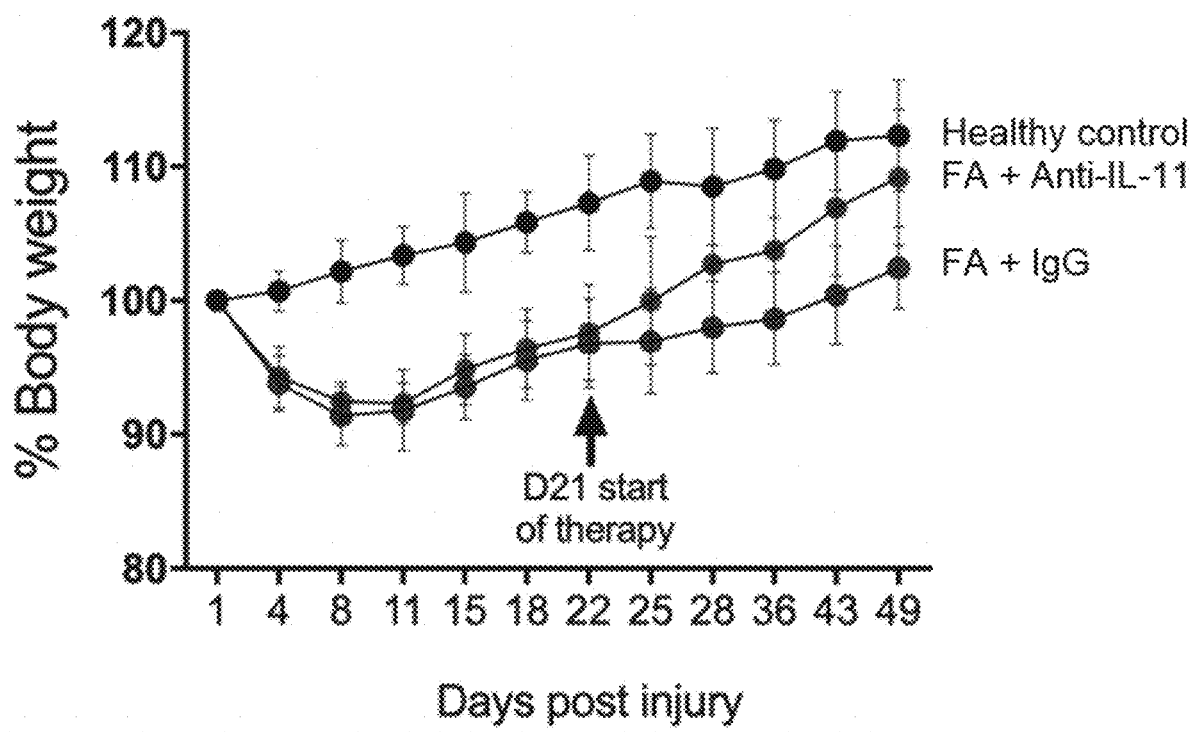

FIG. 53A to 53C. Graphs showing the effects of treatment with (53A) YU100-G08_02A or (53B) 3C6 on body weight and food consumption in a model of wasting-related weight loss. Mice fed a HFMCD diet were treated 2×/week with 0.5, 1, 5 or 10 mg/kg anti-IL-11 antibody. Control mice were either fed with normal chow (NC), or fed on a HFMCD diet and treated with IgG isotype control. (53C) Effect of anti-IL-11 antibody on mouse body weight after folate-induced kidney injury.

Figure 54A:
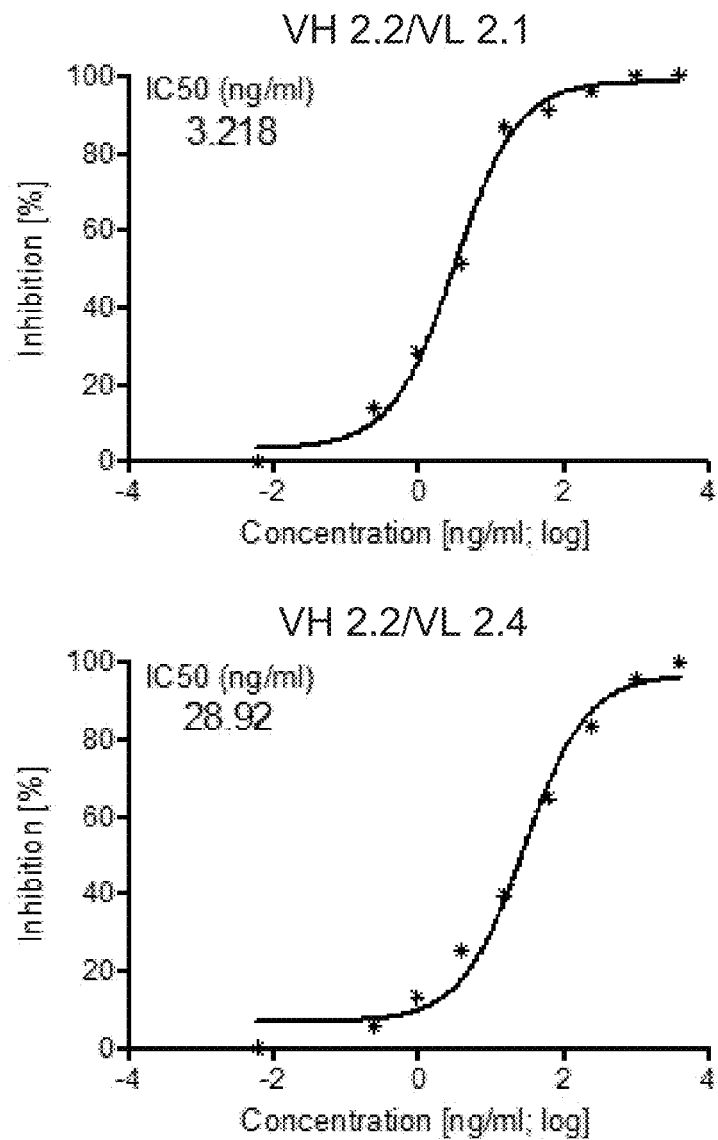
Figure 54A:
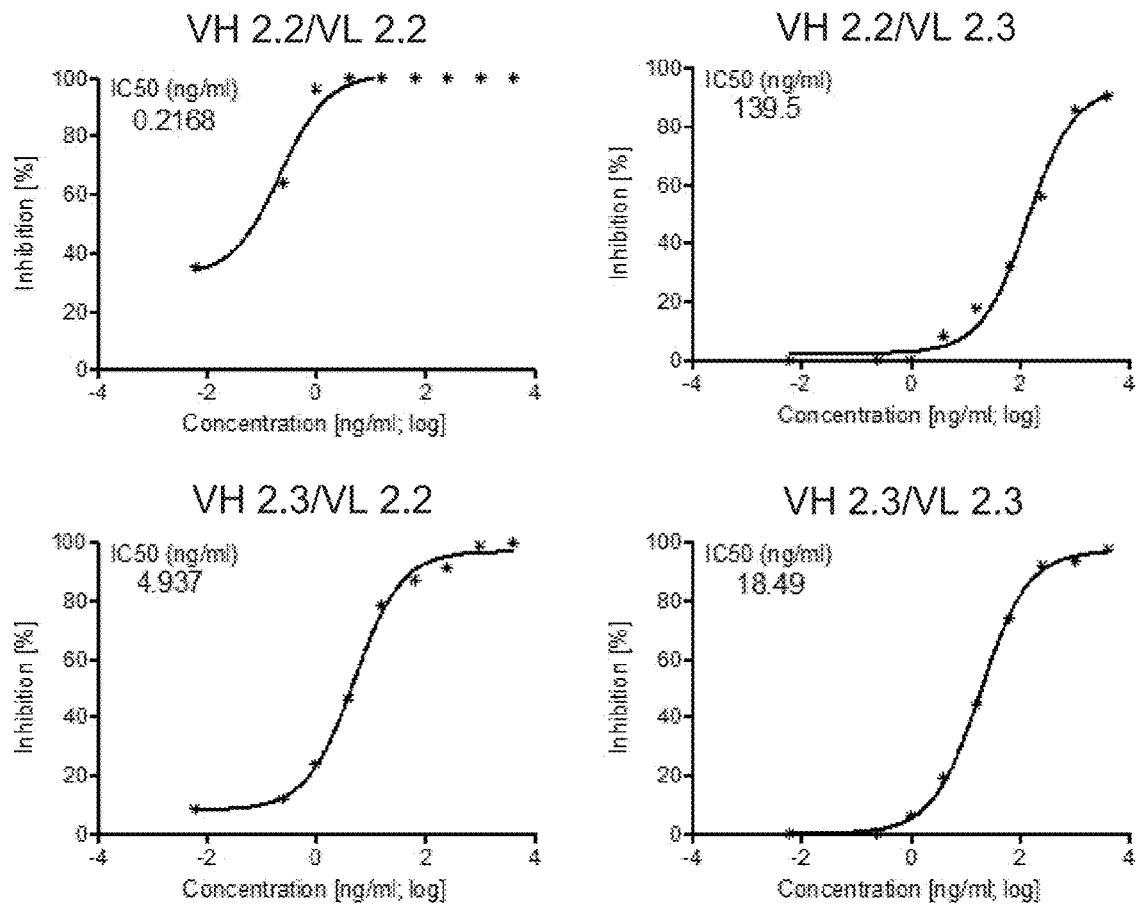
Figure 54B:
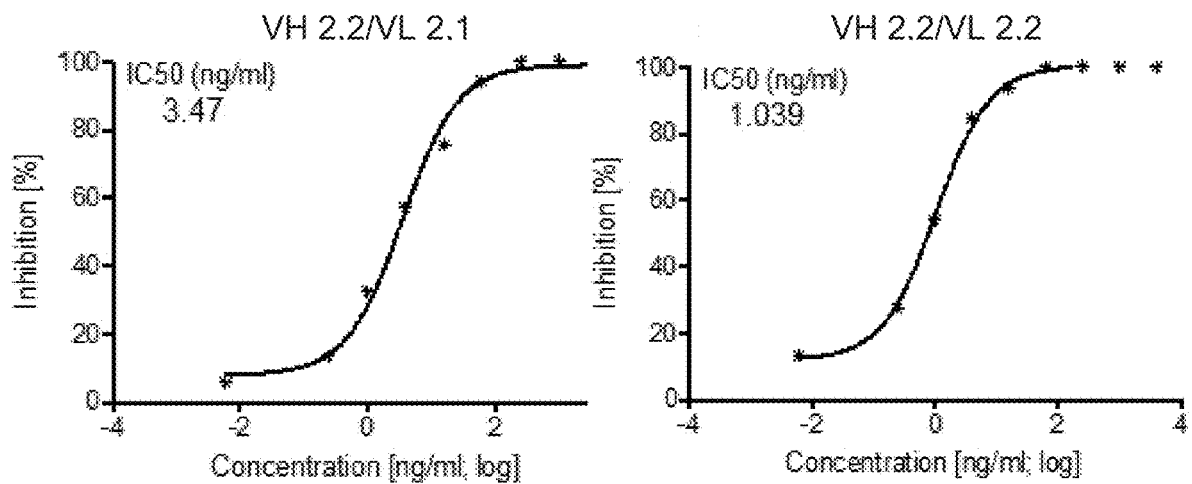
Figure 54B:
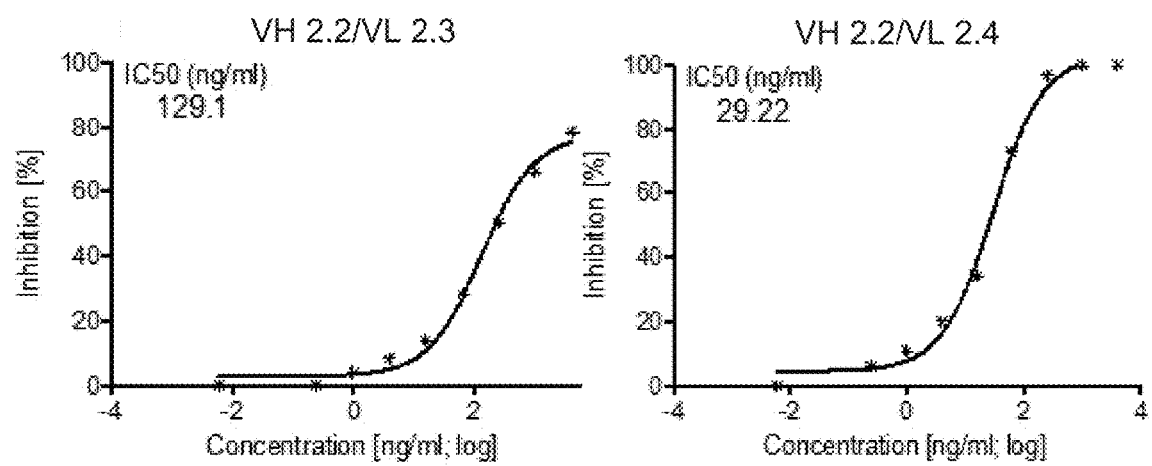

FIGS. 54A and 54B. Ability of humanised 3C6 clones VH 2.2/VL 2.1; VH 2.2/VL 2.2; VH 2.2/VL 2.3; VH 2.2/VL 2.4; VH 2.3/VL 2.2; and VH 2.3/VL 2.3 to block IL-11 signalling and inhibit MMP2 (fibrogenic protein) production in (A) primary human atrial fibroblasts and (B) human HSCs.

Figure 55A:
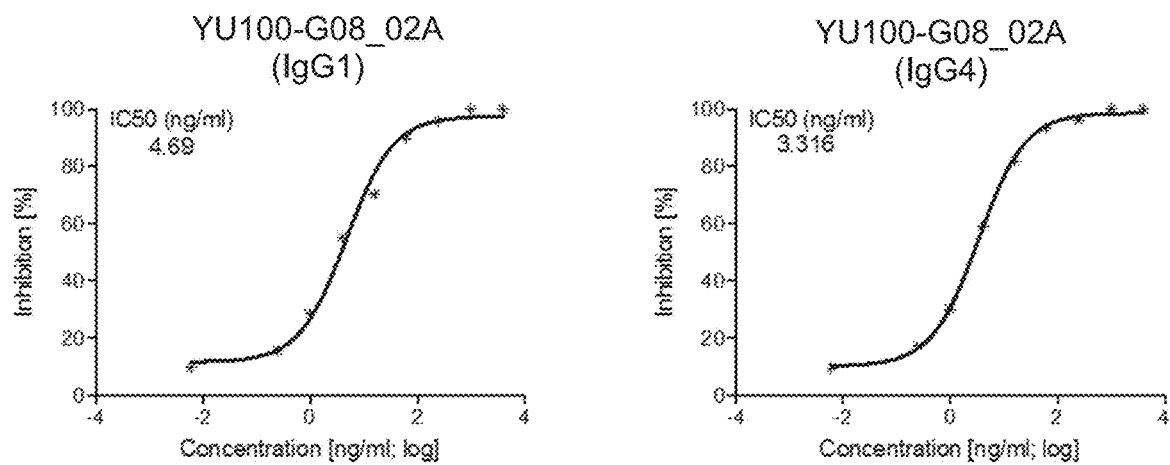
Figure 55B:
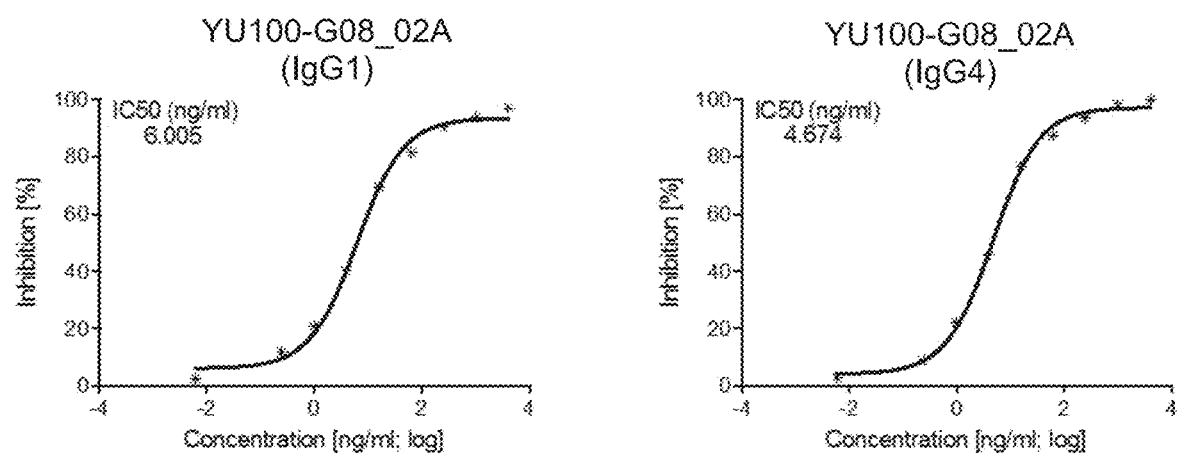
Figure 55C:
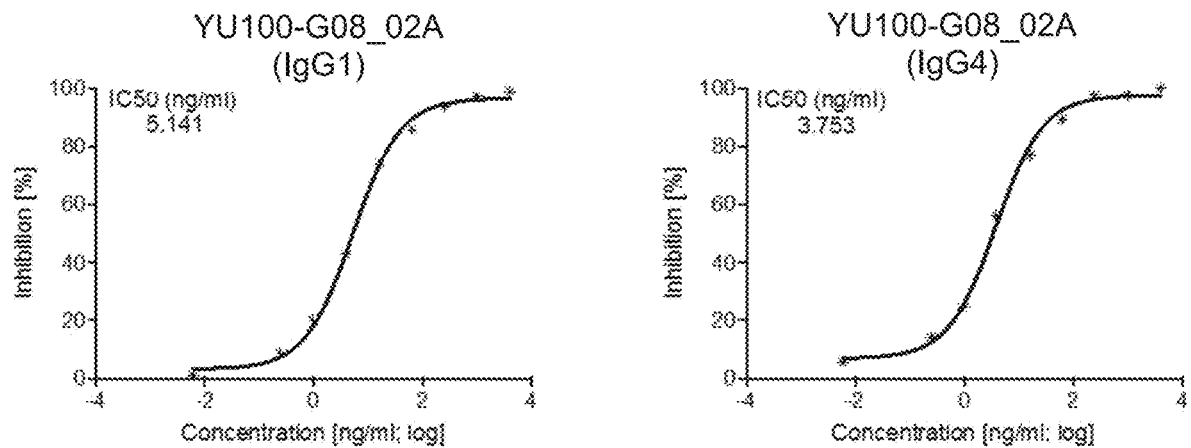

FIGS. 55A to 55C. Ability of YU100-G08_02A (IgG1) and YU100-G08_02A (lgG4) to block (55A) endogenous IL-11 signalling, (55B) exogenous IL-11 signalling and (55C) IL-11 trans signalling in vitro in human HSCs. MMP2 secretion into the supernatant by fibroblasts was assessed to estimate the % of inhibition.

Figure 56A:
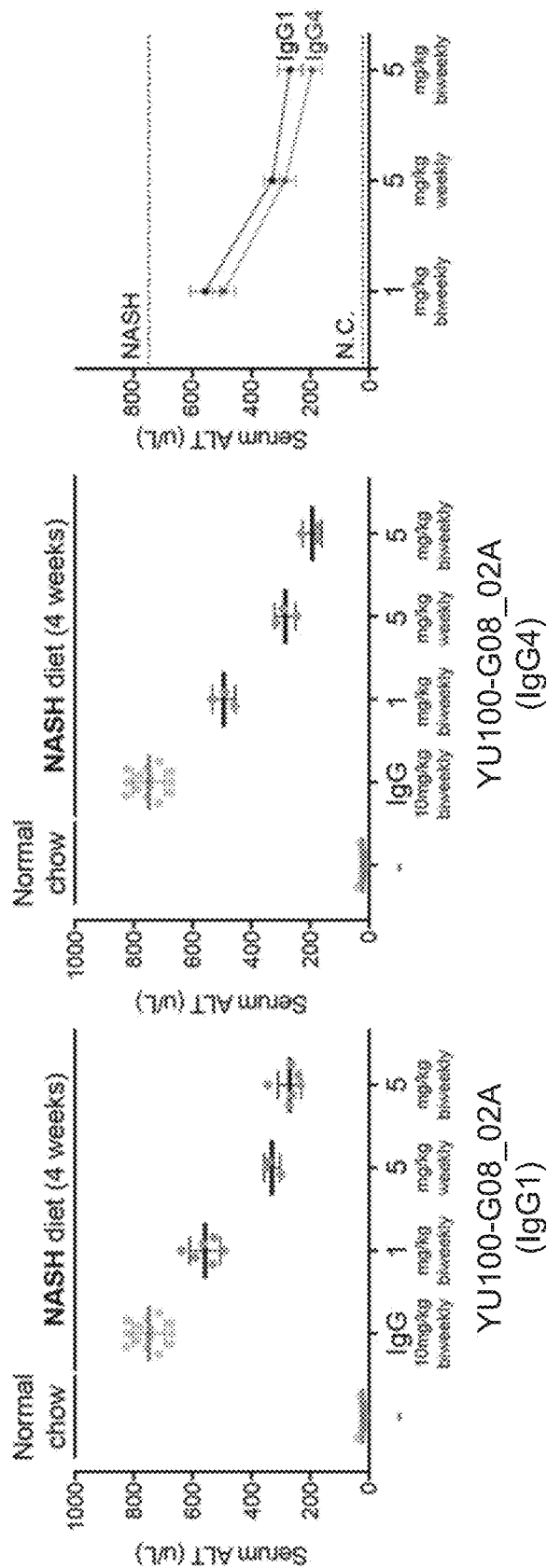
Figure 56B:
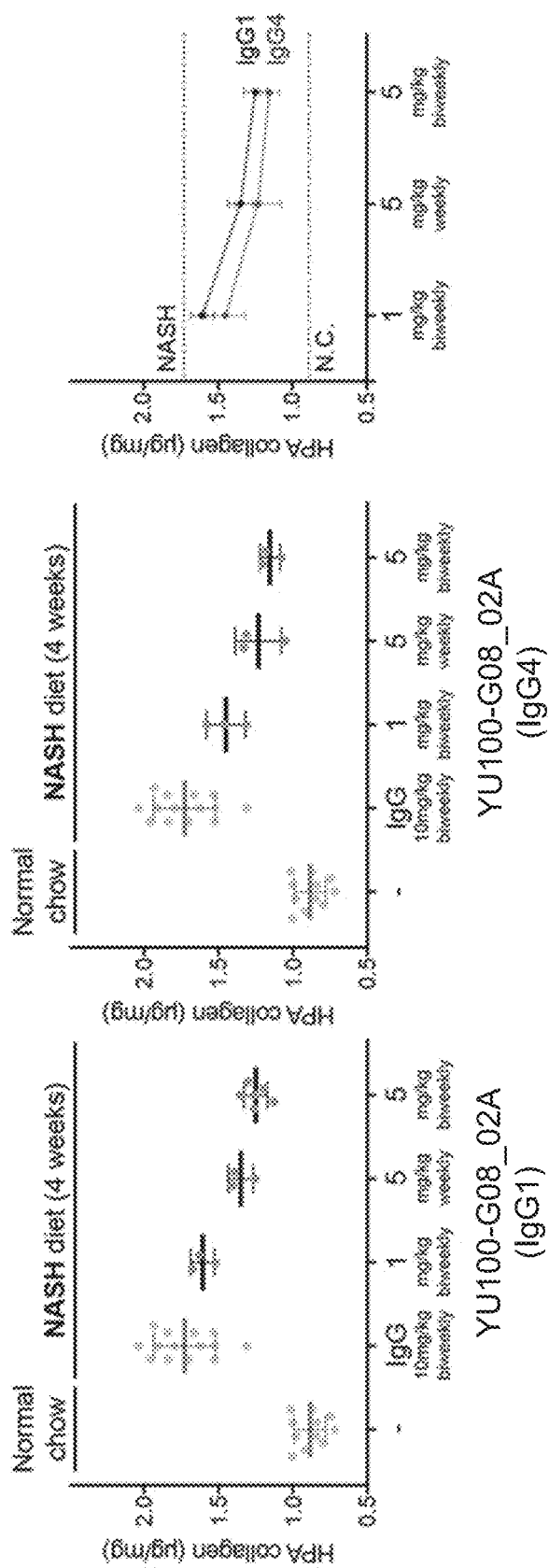

FIGS. 56A and 56B. Comparison of ability of YU100-G08_02A (IgG1) and YU100-G08_02A (IgG4) to reverse liver damage and fibrosis in an in vivo NASH model. Serum ALT levels (56A) and hepatic collagen content (HPA assay; 56B) were assessed after 4 weeks of diet and 3 weeks of antibody treatment.

EXAMPLES

In the following Examples, the inventors describe the generation of anti-IL-11 antibodies, and functional characterisation of the antibodies.

Example 1: Human Anti-Human IL-11 Antibodies

Fully human anti-human IL-11 antibodies were developed via phage display.

Recombinant human IL-11 (Cat. No. Z03108-1) and recombinant murine IL-11 (Cat. No. Z03052-1) were obtained from GenScript (NJ, USA). Recombinant human IL-11 was expressed in CHO cells, both as an Fc-tagged version and a tag-free version. Tag-free murine IL-11 was expressed in HEK293 cells.

IL-11 bioactivity of recombinant human IL-11 and mouse IL-11 was confirmed by in vitro analysis using primary fibroblast cell cultures.

Recombinant, biotinylated human IL-11 and murine IL-11 were also prepared by biotinylation of the recombinant human IL-11 and murine IL-11 molecules, according to standard methods.

Antibodies capable of binding to both human IL-11 and murine IL-11 (i.e. cross-reactive antibodies) were identified by phage display using a human naïve library by panning using biotinylated and non-biotinylated recombinant human and murine IL-11, based on 16 different panning strategies as summarised in FIG. 1.

The phage display identified 175 scFv binders, as 'first hits'. Sequence analysis of the CDR sequences from these 175 scFv identified 86 unique scFv.

The soluble scFv were produced by recombinant expression in *E. coli*, and analysed for their ability to bind to human IL-11 and murine IL-11 by ELISA. Briefly, the respective antigen was coated to wells of an ELISA plate, the cell culture supernatant containing the respective scFv was added at a 1:2 dilution, and binding was detected.

Figure 2:
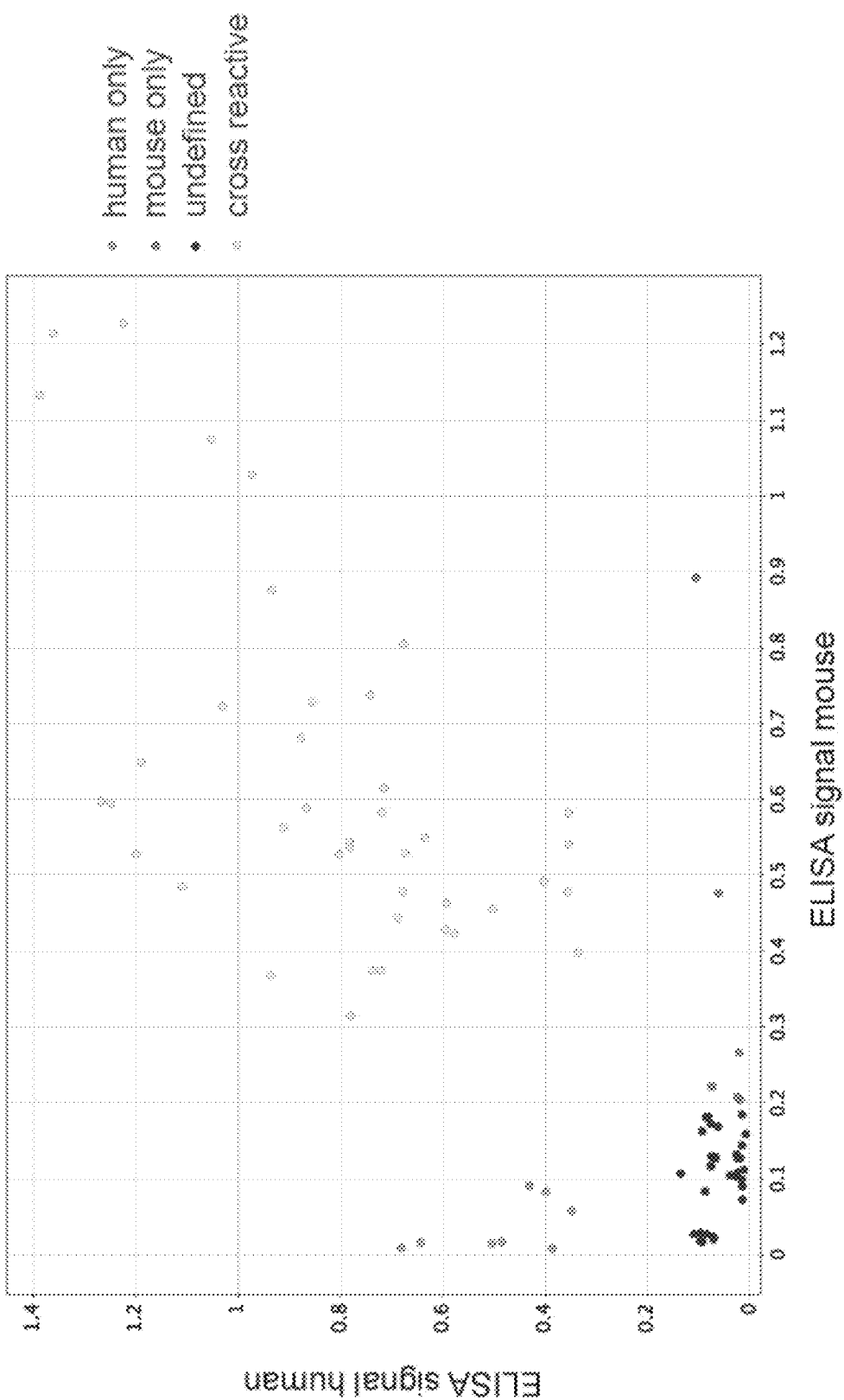
FIG. 2. Scatterplot showing strength of binding signal to human IL-11 and mouse IL-11 as determined by ELISA assay for 86 human anti-IL-11 antibody candidates.

The results of the ELISA analysis of binding to human IL-11 and murine IL-11 are shown in FIG. 2. The analysis revealed:

8 scFV capable of binding only to human IL-11;

6 scFv capable of binding to murine IL-11 only;

32 scFv displaying only weak binding to human/murine IL-11, with a high signal to noise ratio, and;

40 scFv having cross-reactivity for both human IL-11 and murine IL-11.

From these 86 scFV, 56 candidates were selected for further functional characterisation. For further analyses, the scFV were cloned into scFV-Fc format in *E. coli*.

The antibody clone designations are shown in FIG. 3.

The VH and VL sequences of the antibodies were cloned into expression vectors for the generation of scFv-Fc (human IgG1) antibodies. The vectors were transiently expressed in mammalian cells cultured in serum-free media, and isolated by protein A purification.

Example 2: Functional Characterisation of Human Anti-Human IL-11 Antibodies

The antibodies described in Example 1 were analysed in in vitro assays for their ability to (i) inhibit human IL-11-mediated signalling, (ii) inhibit mouse IL-11-mediated signalling, and (iii) inhibit IL-11 trans signalling, by IL-11 in complex with IL-11RA. The affinity of the antibodies for human IL-11 was also analysed by ELISA.

2.1 Ability to Inhibit Human IL-11 Mediated Signalling

To investigate ability to neutralise human IL-11-mediated signalling, cardiac atrial human fibroblasts were cultured in wells of 96-well plates in the presence of TGFβ1 (5 ng/ml) for 24 hours, in the presence or absence of the anti-IL-11 antibodies. TGFβ1 promotes the expression of IL-11, which in turn drives the transition of quiescent fibroblasts to activated, αSMA-positive fibroblasts. It has previously been shown that neutralising IL-11 prevents TGFβ1-induced transition to activated, αSMA-positive fibroblasts.

Expression of αSMA was analysed with the Operetta High-Content Imaging System in an automated high-throughput fashion.

In non-stimulated cultures, ~29.7% (=1) of the fibroblasts were αSMA-positive, activated fibroblasts at the end of the 24 hour culture period, whilst ~52% (=1.81) of fibroblasts were αSMA-positive in cultures that were stimulated with TGFβ1 in the absence of anti-IL-11 antibodies.

Anti-IL-11 antibodies (2 μg/ml) were added to fibroblast cultures that were stimulated with TGFβ1, and at the end of the 24 hour culture period, the percentage of αSMA-positive fibroblasts was determined. The percentages were normalised based on the percentage of αSMA-positive fibroblasts observed in cultures of fibroblasts which had not been stimulated with TGFβ1.

Figure 4A:
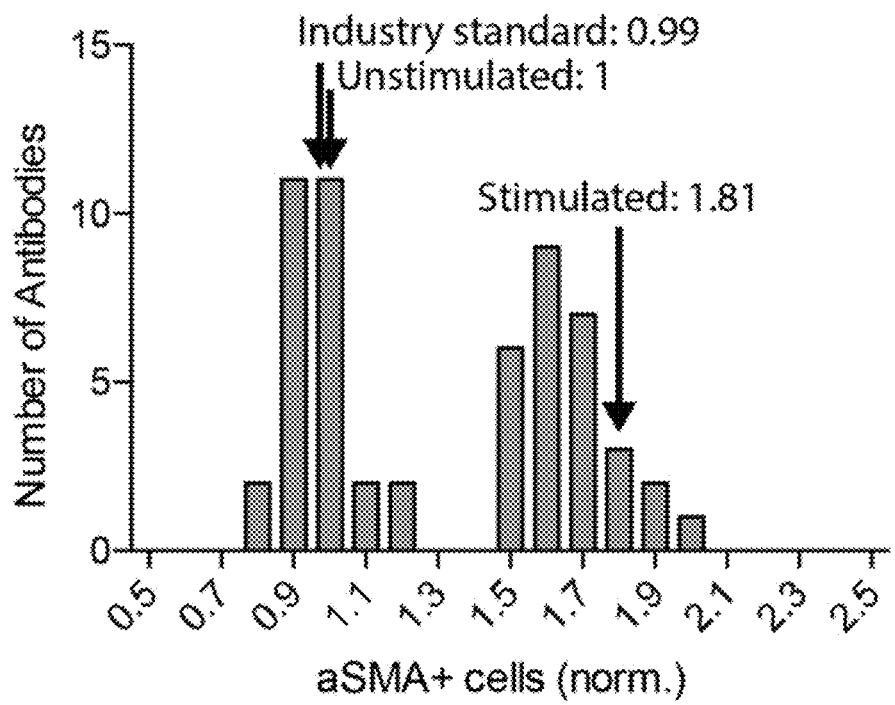
FIGS. 4A and 4B. Bar charts showing inhibition by the human anti-IL-11 antibodies of signalling mediated by IL-11 in vitro in human atrial fibroblasts, as determined by fold change in the percentage of αSMA positive cells as compared to control (unstimulated) fibroblasts, following stimulation with TGFβ1, in the presence of the human anti-IL-11 antibodies. (4A) Bar chart showing fold change in proportion of αSMA-positive cells relative to unstimulated cells (=1). (4B) Bar chart showing the percentage of αSMA-positive cells (activated fibroblasts).
Figure 4B:
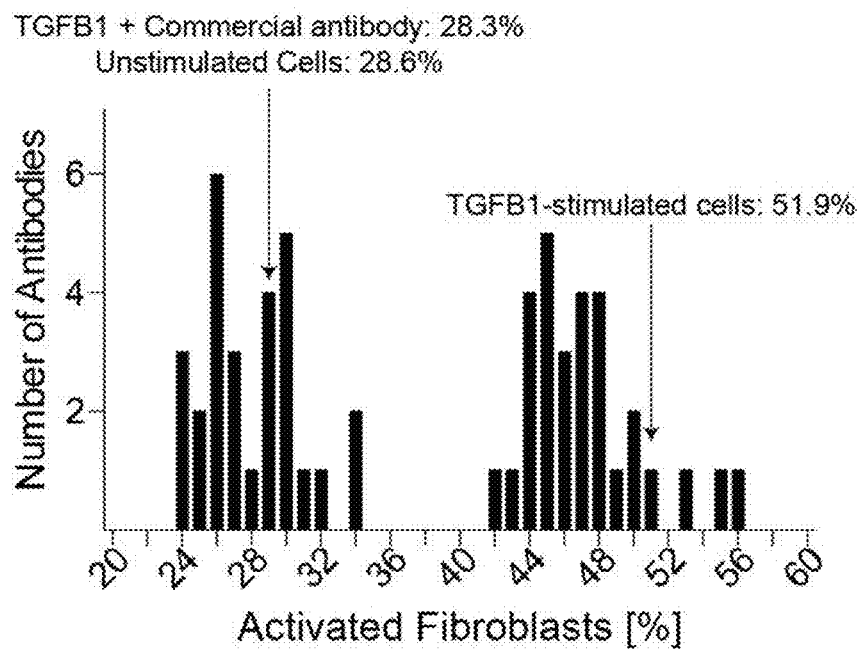

The results of the experiments are shown in FIGS. 4A, 4B and 7. 28 of the antibodies were demonstrated to be capable of neutralising signalling mediated by human IL-11.

A commercial monoclonal mouse anti-IL-11 antibody (Monoclonal Mouse IgG2A; Clone #22626; Catalog No. MAB218; R&D Systems, MN, USA) was also analysed for ability to inhibit signalling by human IL-11 in the experiments. This antibody was found to be able to reduce the percentage of activated fibroblasts to 28.3% (=0.99).

Several of the clones neutralised signalling by human IL-11 to a greater extent than the commercially available mouse anti-IL-11 antibody (industry standard): YU45-C11/A10 (#6), YU45-G1 (#11), YU45-E3 (#16), YU45-F8 (#18), YU45-F9 (#21), YU45-H10 (#22), YU45-F2 (#24), YU45-H3 (#25), YU45-G7 (#33), YU45-B6 (#36), YU45-C1 (#42), YU46-B6 (#47), YU46-E3 (#50), YU46-G8 (#54) and YU46-D3 (#56).

2.2 Ability to Inhibit Mouse IL-11 Mediated Signalling

The ability of the human antibodies to inhibit mouse IL-11-mediated signalling was also investigated, following the same procedure as described in section 2.1 above, but using mouse atrial fibroblasts instead of human atrial fibroblasts.

After 24 hours in culture, about 31.8% (=1) of non-stimulated cells in culture were activated fibroblasts. Stimulation with TGFβ1 resulted in a ~2-fold increase in the percentage of activated fibroblasts (68.8%=2.16) as compared to non-stimulated cultures.

Figure 5A:
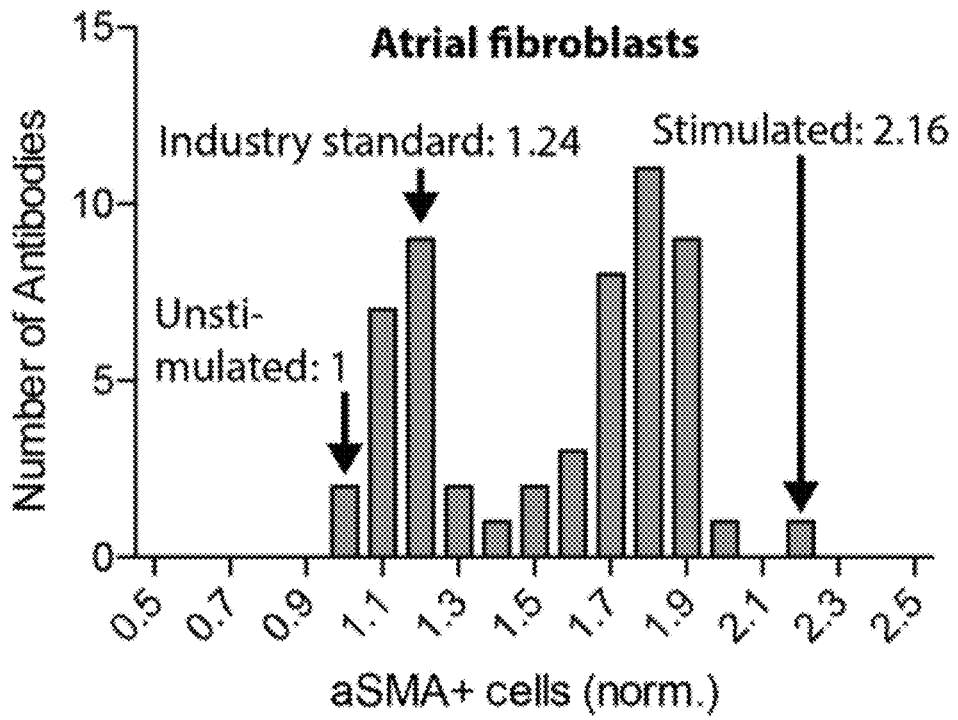
FIGS. 5A and 5B. Bar chart showing inhibition by the human anti-IL-11 antibodies of signalling mediated by IL-11 in vitro in (5A) mouse atrial fibroblasts and (5B) mouse dermal fibroblasts, as determined by fold change in the percentage of αSMA positive cells as compared to control (unstimulated) fibroblasts, following stimulation with TGFβ1, in the presence of the human anti-IL-11 antibodies.
Figure 5B:
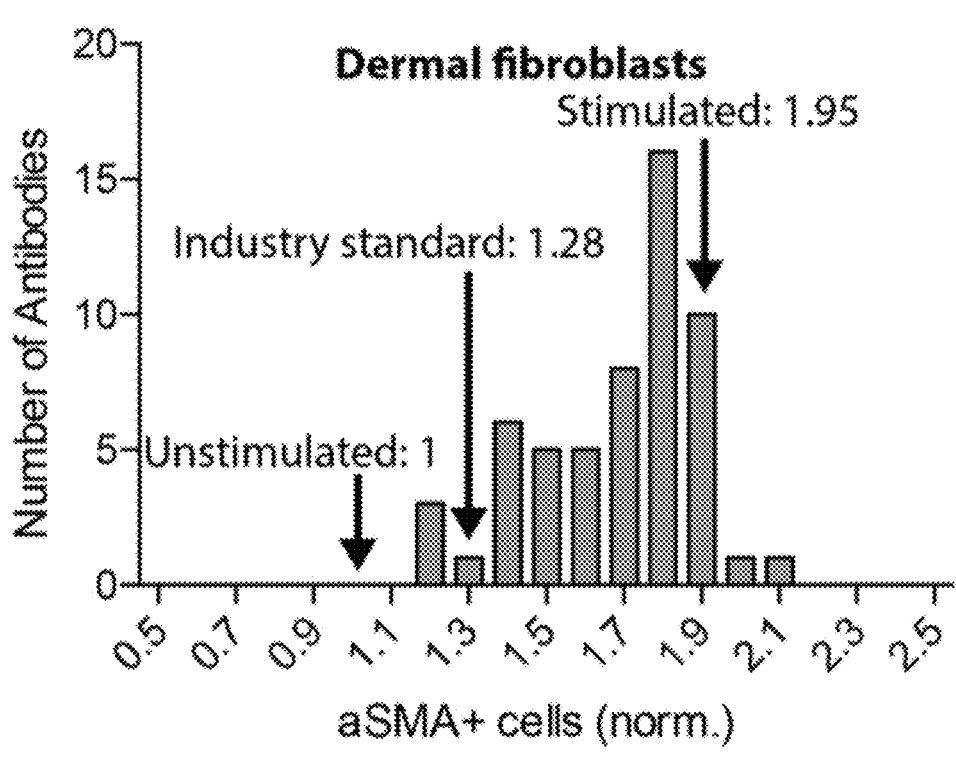

The results of the experiments are shown in FIGS. 5A, 5B and 7. The antibodies were demonstrated to be capable of neutralising signalling mediated by mouse IL-11. Monoclonal Mouse IgG2A clone #22626, catalog No. MAB218 anti-IL-11 antibody was also analysed for ability to inhibit signalling by mouse IL-11. This antibody was found to be able to reduce the percentage of activated fibroblasts to 39.4% (=1.24).

Several of the clones neutralised signalling by IL-11 in mouse atrial fibroblasts to a greater extent than the commercially available mouse anti-IL-11 antibody (industry standard): YU33-B4/YU45-G2/A3 (#3), YU45-H11/D12 (#9), YU45-G1 (#11), YU45-D2/H2/C7/F3/C9/E1/E9/C10/G3/H9/C5/A2/A5 (#14), YU45-B3 (#15), YU45-F8 (#18), YU45-H10 (#22), YU46-A10 (#23), YU45-A8/C6 (#27), YU45-D9/D3 (#31), YU45-B6 (#36), YU45-C1 (#42), YU46-A8 (#45), YU46-C1 (#48), YU46-H8 (#52), YU46-G8 (#54) and YU46-D3 (#56).

The ability of the human antibodies to inhibit mouse IL-11-mediated signalling was also investigated using mouse skin fibroblasts.

The results of the experiments are shown in FIG. 7. The antibodies were demonstrated to be capable of neutralising signalling mediated by mouse IL-11.

Several of the clones neutralised signalling by IL-11 in mouse skin fibroblasts to a greater extent than the commercially available mouse anti-IL-11 antibody (industry standard): YU45-B6 (#36), YU45-C1 (#42), and YU46-H8 (#52).

2.3 Ability to Inhibit IL-11 Trans Signalling, by IL-11 in Complex with IL-11RA

Trans signalling is recognised as a major aspect of IL-6 signalling, where a complex of IL-6 and soluble IL-6Rα can activate cells that express gp130, but lack the IL-6 receptor (Hunter and Jones, 2015 Nature Immunology 16, 448-457).

It has recently been suggested that trans signalling by a complex of IL-11 and soluble IL-11 RA is also important for IL-11 biology (Lokau et al., Cell Reports (2016) 14, 1761-1773). Using a recombinant fusion protein of IL-11 and IL-11Rα (as described in Pflanz et al., Febs Lett (1999) 450: 117-122), anti-IL-11 antibodies were screened for the ability to inhibit trans signalling mediated by IL-11:IL-11Rα complex.

Importantly, antibodies which are capable of inhibiting both classical IL-11 mediated signalling and IL-11 trans signalling by IL-11:IL-11Rα complex are able to inhibit all known modes of IL-11/IL-11R signalling.

The IL-11:IL-11Rα fusion protein (hereafter referred to as hyper IL-11) consists of the extracellular domain of the IL-11 receptor alpha (IL-11Rα) linked to IL-11. The IL-11:IL-11Rα fusion protein used in the present Example has the amino acid sequence of SEQ ID NO:4.

Figure 8A:
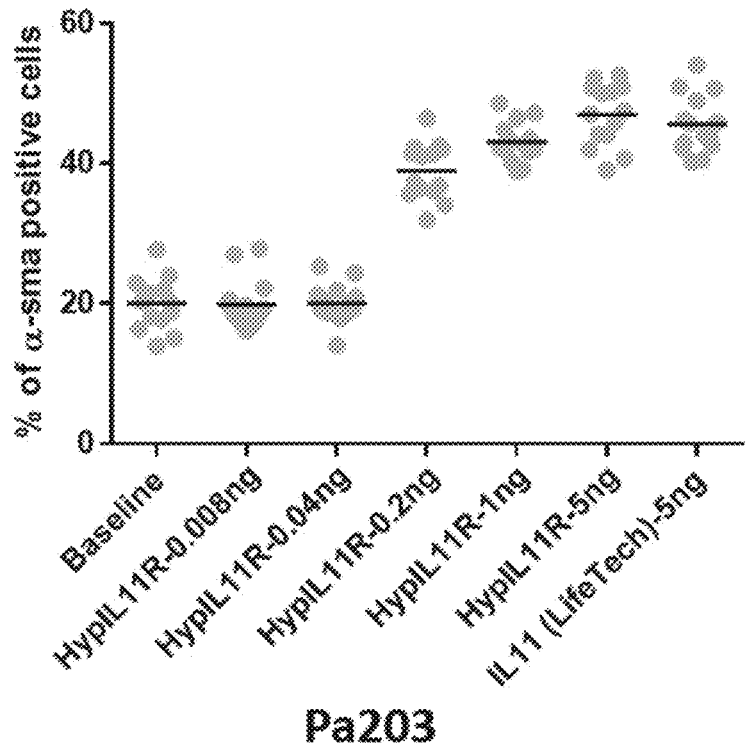
FIGS. 8A and 8B. Graphs showing fibroblast activation in response to hyper IL-11. Cells were stimulated with the indicated amount (in ng/ml) of hyper IL-11 or recombinant IL-11, and fibroblast activation was measured by analysis of the percentage of α-SMA positive cells. (8A) and (8B) present the results of two different experiments.
Figure 8B:
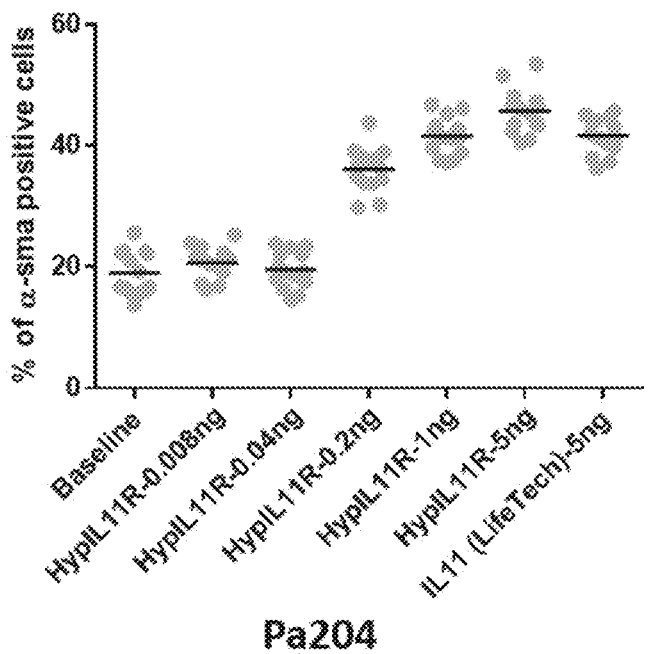

Hyper IL-11 was found to be a more potent activator of human fibroblasts than recombinant IL-11 protein. Briefly, in two separate experiments human fibroblasts were cultured without stimulation (Baseline), in the presence of different amounts of hyper IL-11 (0.008 ng/ml, 0.04 ng/ml, 0.2 ng/ml, 1 ng/ml and 5 ng/ml), or 5 ng/ml recombinant human IL-11 obtained from a commercial source, and fibroblast activation was analysed by determining the percentage of αSMA-positive cells as described herein. The results are shown in FIGS. 8A and 8B. Hyper-IL-11 activated fibroblasts in a dose-dependent fashion, and was a more potent activator than IL-11.

The IL-11:IL-11Rα fusion protein was prepared as follows:

DNA encoding IL-11:IL-11Rα fusion protein was cloned into pTT5 vector, and transfected into 293-6E cells in culture in serum-free FreeStyle™ 293 Expression Medium (Thermo Fisher Scientific).

Cells were maintained in Erlenmeyer Flasks (Corning Inc.) at 37° C. with 5% $CO_2$ on an orbital shaker (VWR Scientific).

Cell culture supernatants were collected on day 6 were used for purification.

Cell culture supernatant was loaded onto an affinity purification column.

After washing and elution with appropriate buffer, the eluted fractions were pooled and buffer exchanged to final formulation buffer.

The purified IL-11:IL-11Rα fusion protein was analyzed by SDS-PAGE, Western blot to confirm molecular weight and purity.

Figure 9:
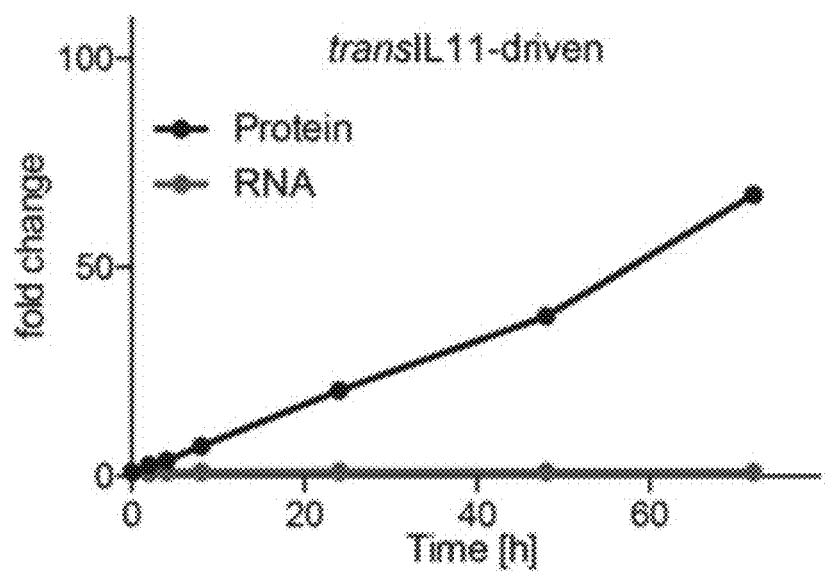
FIG. 9. Graph showing induction of IL-11 secretion in primary fibroblasts by hyper IL-11. Cells were stimulated with hyper IL-11, and IL-11 RNA and native IL-11 protein levels were measured in the cell culture supernatant by ELISA at the indicated time points.
Figure 10A:
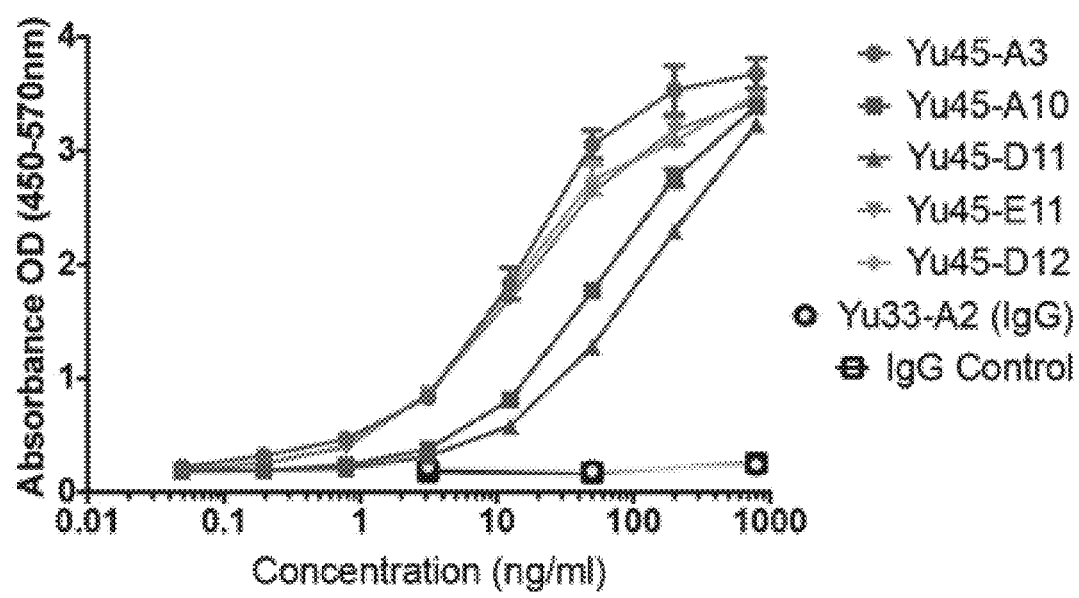
FIGS. 10A to 10F. Graphs showing binding of human anti-IL-11 antibodies to human IL-11 as determined by ELISA analysis. (10A) ELISA for clones YU45-A3, YU45-A10, YU45-D11, YU45-E11, YU45-D12 and YU33-A2 (IgG). (10B) ELISA for clones YU45-G1, YU45-B2, YU45-A5, YU45-E3, YU45-F8 and YU33-H3(IgG). (10C) ELISA for clones YU45-G8, YU45-F9, YU45-H10, YU45-F2, YU45-H3 and YU33-E3(IgG). (10D) ELISA for clones YU45-A8, YU45-B5, YU45-D9, YU45-G7, YU45-B6 and YU45-F9. (10E) ELISA for clones YU45-F5, YU46-B5, YU45-C1, YU46-A8, YU46-B6 and YU45-F9. (10F) ELISA for clones YU46-E3, YU46-G8, YU46-D3, YU45-B6, YU45-C1 and YU45-F9.
Figure 10B:
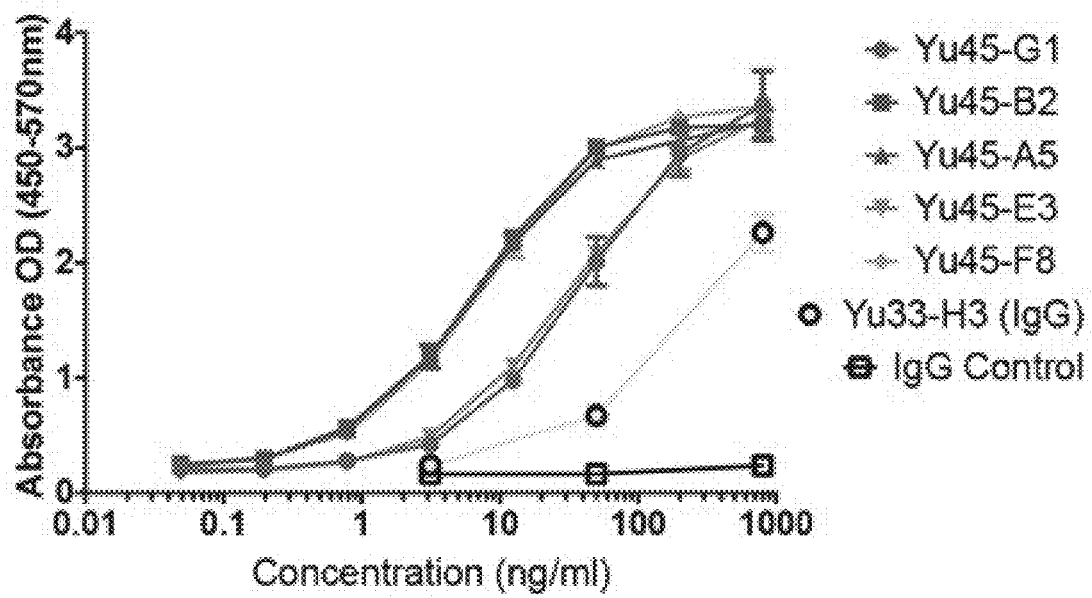
Figure 10C:
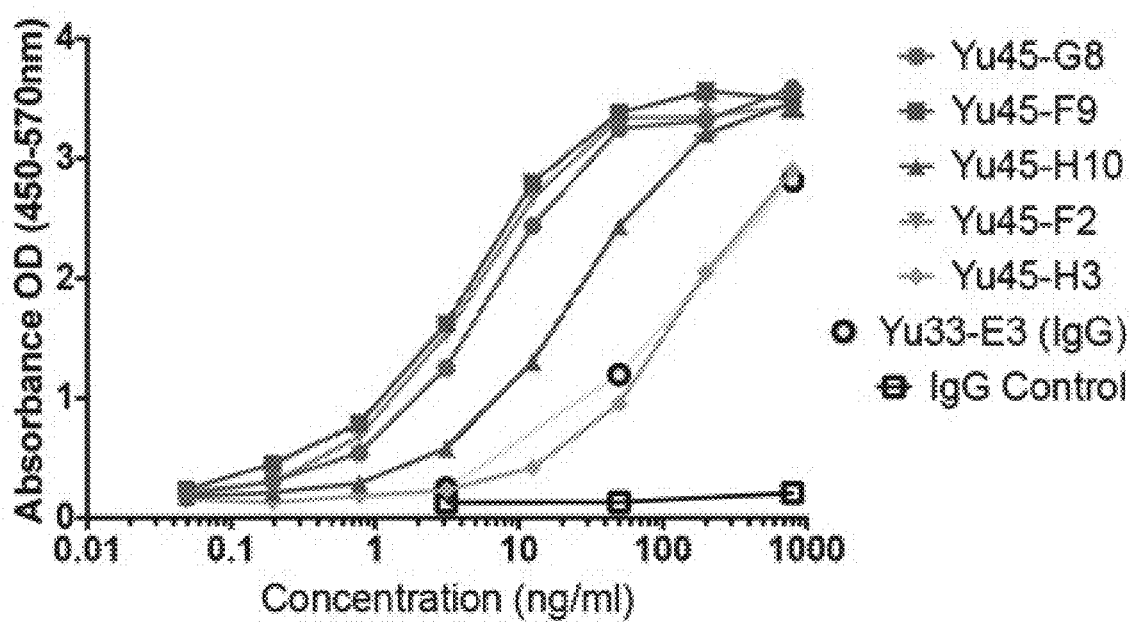
Figure 10D:
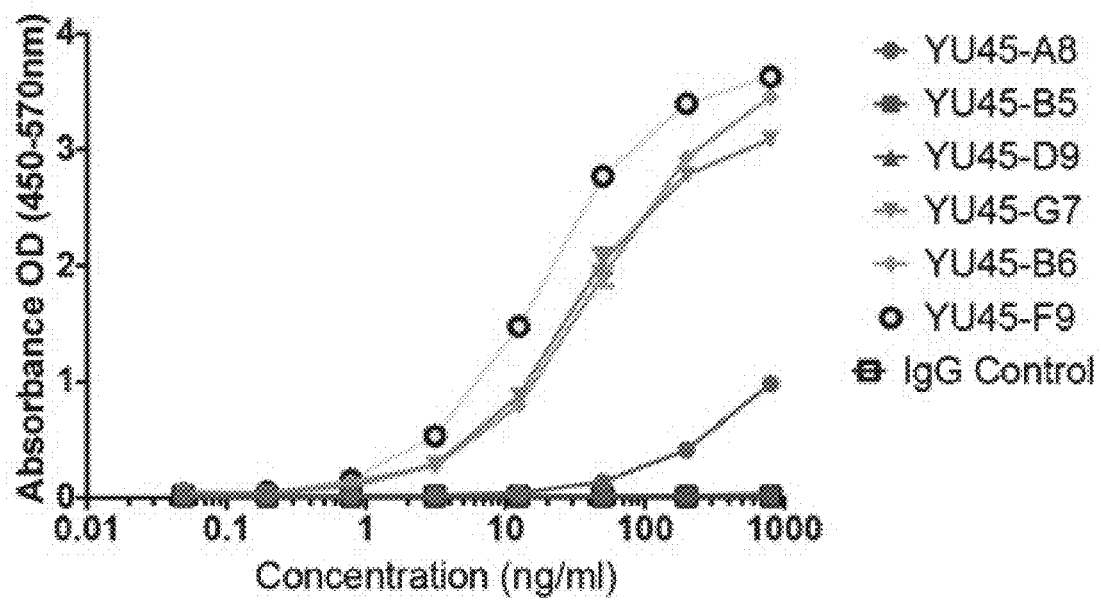
Figure 10E:
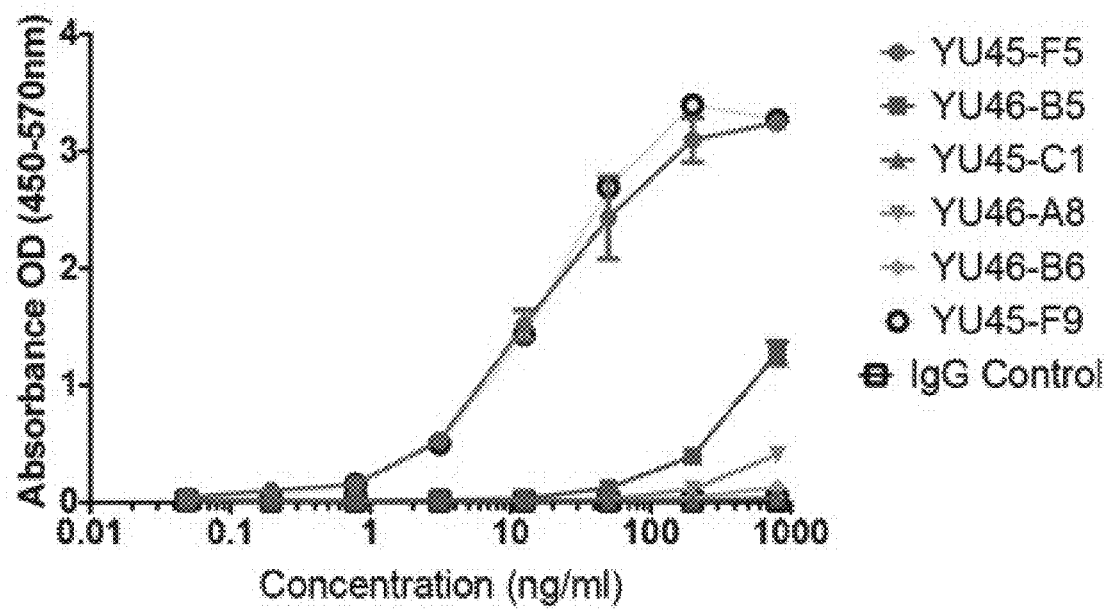
Figure 10F:
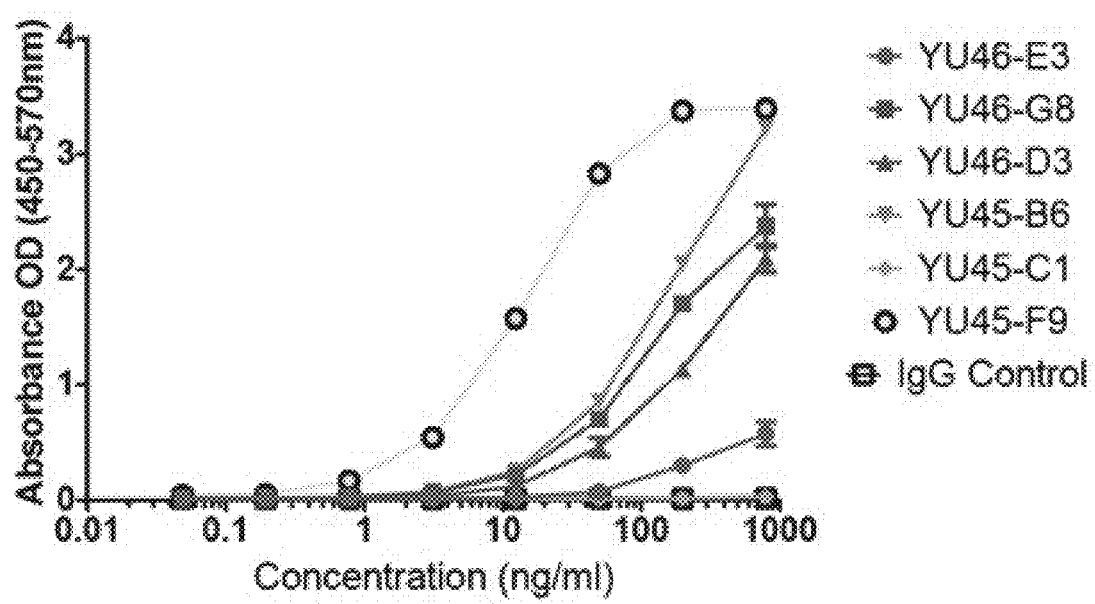

Fibroblasts cultured in vitro and stimulated with hyper IL-11 were shown to upregulate IL-11 protein expression, as determined by ELISA (FIG. 9). Interestingly, an increase in IL-11 RNA level was not detected in response to stimulation with hyper IL-11. Unlike TGFβ1, which increases IL-11 expression at both the RNA and the protein level, hyper IL-11 seems to upregulate IL-11 expression only post-transcriptionally, at the protein level.

The ability of the human antibodies to inhibit signalling mediated by hyper IL-11 was investigated.

Human atrial fibroblasts derived from 3 individuals were incubated for 24 h with hyper IL-11 (0.2 ng/ml) in the presence of neutralising anti-IL-11 antibody or isotype control antibody. Following incubation, cells were stained for αSMA to determine the fraction of myofibroblasts.

After 24 hours in culture, about 26.5.% (=1) of non-stimulated cells in culture were activated fibroblasts. Stimulation with hyper IL-11 resulted in a ~2-fold increase in the percentage of activated fibroblasts (56.4%=2.13) as compared to non-stimulated cultures.

Figure 6:
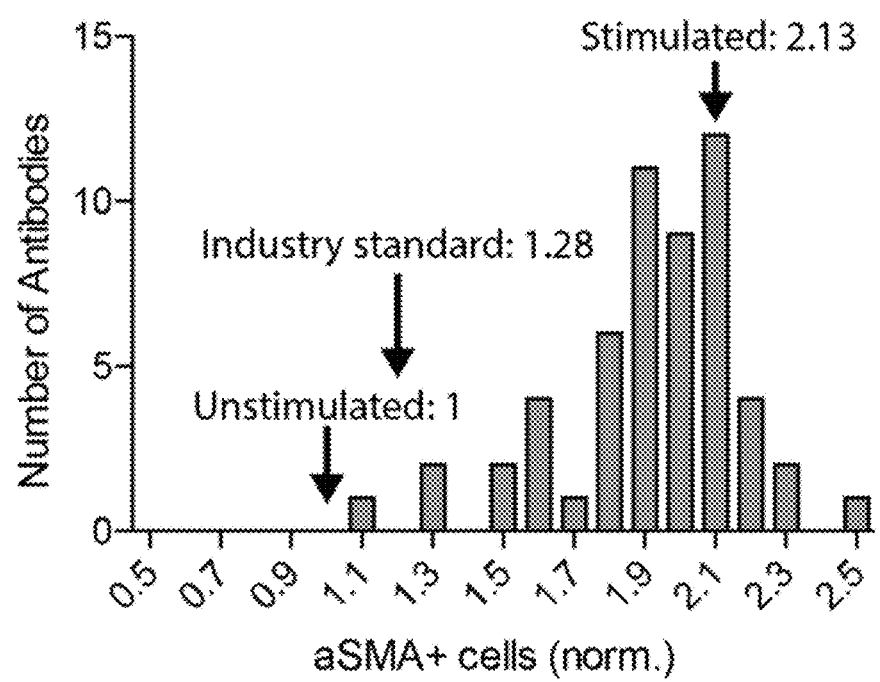
FIG. 6. Bar chart showing inhibition by the human anti-IL-11 antibodies of IL-11 trans signalling mediated by hyper IL-11 in vitro in human atrial fibroblasts, as determined by fold change in the percentage of αSMA positive cells as compared to control (unstimulated) fibroblasts, following stimulation with hyper IL-11, in the presence of the human anti-IL-11 antibodies.

The results of the experiments are shown in FIGS. 6 and 7. The antibodies were demonstrated to be capable of neutralising signalling mediated by hyper IL-11 (i.e. IL-11 trans signalling).

Monoclonal Mouse IgG2A clone #22626, catalog No. MAB218 anti-IL-11 antibody was also analysed for ability to inhibit signalling by hyper IL-11. This antibody was found to be able to reduce the percentage of activated fibroblasts to 33.8% (=1.28).

Clone YU33-64/YU45-G2/A3 (#3) neutralised IL-11 trans signalling by hyper IL-11 to a greater extent than the commercially available mouse anti-IL-11 antibody (industry standard).

The results of the experimental procedures described in hereinabove identified antibody clones which possess functional properties which are relevant for their pre-clinical and clinical development of antibodies capable of inhibiting IL-11/IL-11-R signalling.

Clones YU33-B4/YU45-G2/A3 (#3), YU45-E3 (#16), YU45-F2 (#24), YU45-F5 (#39), YU46-A8 (#45) and YU46-G8 (#54) were identified as particularly promising candidates, showing good ability to inhibit signalling by both human and mouse IL-11, and good inhibition of IL-11 trans signalling.

2.4 Analysis of Antibody Affinity for Human IL-11

The human anti-human IL-11 antibodies were analysed for their affinity of binding to human IL-11 by ELISA assay.

Recombinant human IL-11 was obtained from Genscript and Horseradish peroxidase (HRP)-conjugated anti-human IgG (Fc-specific) antibody was obtained from Sigma. Corning 96-well ELISA plates were obtained from Sigma. Pierce 3,3',5,5'-tetramethylbenzidine (TMB) ELISA substrate kit was obtained from Life Technologies (0.4 g/mL TMB solution, 0.02% hydrogen peroxide in citric acid buffer). Bovine serum albumin and sulphuric acid was obtained from Sigma. Wash buffer comprised 0.05% Tween-20 in phosphate buffered saline (PBS-T). ScFv-Fc antibodies were generated as described in Example 1. Purified mouse and human IgG controls were purchased from Life Technologies. Tecan Infinite 200 PRO NanoQuant was used to measure absorbance.

Criss-cross serial dilution analysis was performed as described by Hornbeck et al., (2015) Curr Protoc Immunol 110, 2.1.1-23) to determine the optimal concentration of coating antigen, primary and secondary antibodies.

An indirect ELISA was performed to assess the binding affinity of primary ScFv-Fc antibodies at 50% of effective concentration ($EC_{50}$) as previously described (Unverdorben et al., (2016) MAbs 8, 120-128). ELISA plates were coated with 1 µg/mL of recombinant human IL-11 overnight at 4° C. and remaining binding sites were blocked with 2% BSA in PBS. ScFv-Fc antibodies were diluted in 1% BSA in PBS, titrated to obtain working concentrations of 800, 200, 50, 12.5, 3.125, 0.78, 0.195, and 0.049 ng/mL, and incubated in duplicates for 2 hours at room temperature. Detection of antigen-antibody binding was performed with 15.625 ng/mL of HRP-conjugated anti-human IgG (Fc-specific) antibody. Following 2 hours of incubation with the detection antibody, 100 µl of TMB substrate was added for 15 mins and chromogenic reaction stopped with 100 µl of 2 M $H_2SO_4$. Absorbance reading was measured at 450 nm with reference wavelength correction at 570 nm. Data were fitted with GraphPad Prism software with log transformation of antibody concentrations followed by non-linear regression analysis with the asymmetrical (five-parameter) logistic dose-response curve to determine individual EC50 values.

The same materials and procedures as described above were performed to determine the affinity of binding for the murine monoclonal anti-IL-11 antibodies, with the exception that HRP-conjugated anti-mouse IgG (H&L) was used instead of HRP-conjugated anti-human IgG.

The same materials and procedures as described above were performed to determine the affinity of binding for the human monoclonal anti-IL-11 antibodies and murine monoclonal anti-IL-11 antibodies to recombinant murine IL-11 obtained from Genscript.

The results of the ELISA assays are shown in FIG. 10A to 10F, and were used to determine $EC_{50}$ values for the antibodies which are shown in FIG. 11.

2.5 Ability to Inhibit Human IL-11 Mediated Signalling in a Variety of Tissues

Ability of the antibodies to neutralise IL-11-mediated signalling and trans signalling in fibroblasts obtained from a variety of different tissues is investigated, essentially as described in sections 2.1 and 2.3 except that instead of cardiac atrial human fibroblasts, human fibroblasts derived from liver, lung, kidney, eye, skin, pancreas, spleen, bowel, brain, and bone marrow are used for the experiments.

Anti-IL-11 antibodies are demonstrated to be capable of neutralising signalling in fibroblasts derived from the various different tissues, as determined by observation of a relative decrease in the proportion of αSMA-positive fibroblasts at the end of the 24 h culture period in the presence of the anti-IL-11 antibodies as compared to culture in the absence of the antibodies.

Example 3: Light Chain Shuffling of Human Anti-Human IL-11 Antibodies

Human IL-11 antibodies are affinity-matured by light chain shuffling to obtain antibodies having improved affinity for IL-11.

Chain shuffling to improve antibody affinity is a well-known technique in the field of antibody technology, and is described in detail in Marks, Antibody Affinity Maturation by Chain Shuffling, Antibody Engineering Methods and Protocols, Humana Press (2004) Vol. 248, pp 327-343, incorporated by reference herein. In particular, Light chain shuffling is described in detail at sections 3.1 and 3.2 thereof.

The heavy chain variable regions of the human anti-human IL-11 antibodies are combined with a repertoire of light chain variable region partners to identify new VL/VH combinations having high affinity for IL-11.

Figures 12, 13:
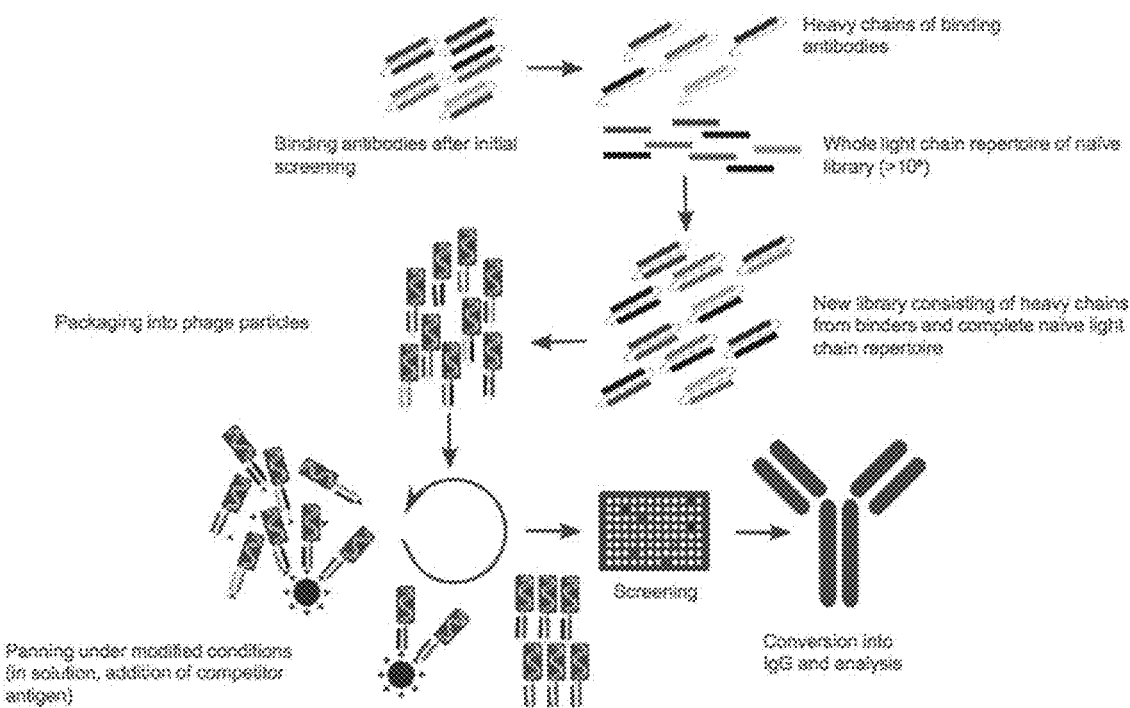
FIG. 12. Schematic representation of the process of antibody light chain shuffling.
FIG. 13. Table summarising the 16 mouse anti-human IL-11 antibody clones.

A schematic representation of light chain shuffling is shown in FIG. 12. Briefly, nucleic acid encoding the VH domain for an antibody is cloned into a phage display vector comprising a repertoire of VL chains, and scFv comprising new VH/VL combinations are analysed for binding to human IL-11 by ELISA.

The scFv having VH/VL combinations displaying the strongest binding affinity for IL-11 are then analysed for cross-reactivity against murine IL-11.

The VH/VL sequences of the scFv are then cloned into expression vectors for the generation of scFv-Fc (human IgG1) antibodies, the vectors are transiently expressed in mammalian cells cultured in serum-free media, and isolated by protein A purification.

Example 4: Mouse Monoclonal Anti-Human IL-11 Antibodies

Mouse monoclonal antibodies directed against human IL-11 protein were also generated, as follows.

cDNA encoding the amino acid for human IL-11 was cloned into expression plasmids (Aldevron GmbH, Freiburg, Germany).

Mice were immunised by intradermal application of DNA-coated gold-particles using a hand-held device for particle-bombardment ("gene gun"). Serum samples were collected from mice after a series of immunisations, and tested in flow cytometry on HEK cells which had been transiently transfected with human IL-11 expression plasmids (cell surface expression of human IL-11 by transiently transfected HEK cells was confirmed with anti-tag antibodies recognising a tag added to the N-terminus of the IL-11 protein).

Antibody-producing cells were isolated from the mice and fused with mouse myeloma cells (Ag8) according to standard procedures.

Hybridomas producing antibodies specific for IL-11 were identified by screening for ability to bind to IL-11 expressing HEK cells by flow cytometry.

Cell pellets of positive hybridomas cells were prepared using an RNA protection agent (RNAlater, cat. #AM7020 by ThermoFisher Scientific) and further processed for sequencing of the variable domains of the antibodies.

In total, 16 mouse monoclonal anti-human IL-11 antibodies were prepared (FIG. 13). The VH and VL sequences determined for clone BSN-3C6 are shown in SEQ ID NOs:91 to 94. The VH and VL sequences determined for clone BSN-1H2 are shown in SEQ ID NOs:156 and 157. The VH and VL sequences determined for clone BSN-7D4 are shown in SEQ ID NOs:174 and 175. The VH and VL sequences determined for clone BSN-8H11 are shown in SEQ ID NOs: 192 and 193.

Example 5: Functional Characterisation of Mouse Monoclonal Anti-Human IL-11 Antibodies 5.1 Ability to Inhibit Human IL-11 Mediated Signalling The ability of the murine monoclonal anti-human IL-11 antibodies to inhibit signalling mediated by human IL-11 was investigated using the same assay as described in Example 2.1 above.

Figure 14:
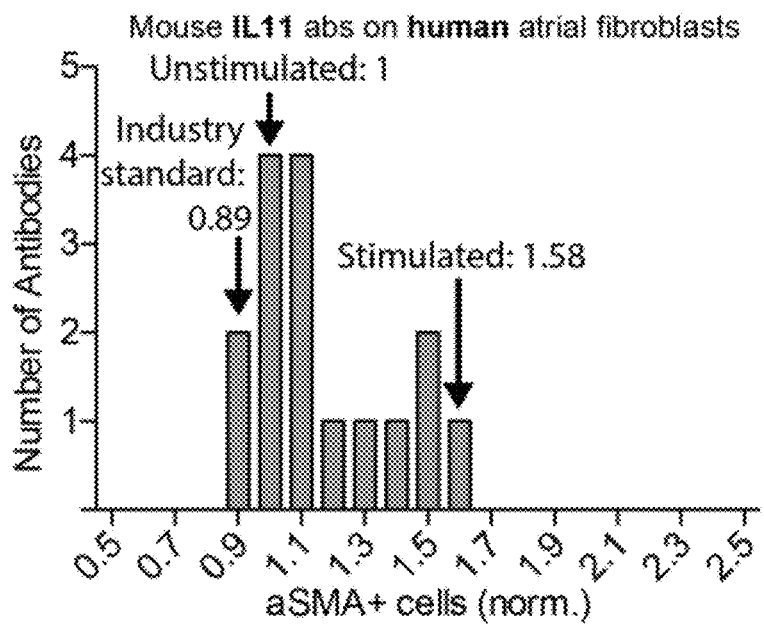
FIG. 14. Bar chart showing inhibition by the mouse anti-IL-11 antibodies of signalling mediated by IL-11 in vitro in human atrial fibroblasts, as determined by fold change in the percentage of αSMA positive cells as compared to control (unstimulated) fibroblasts, following stimulation with TGFβ1, in the presence of the mouse anti-IL-11 antibodies.
Figures 16, 17:
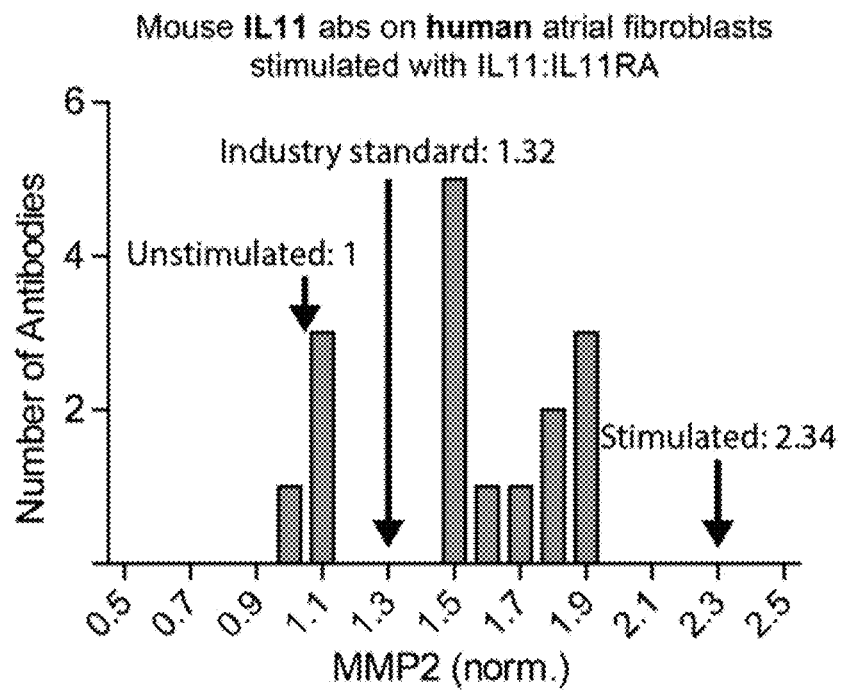
FIG. 16. Bar chart showing inhibition by the mouse anti-IL-11 antibodies of IL-11 trans signalling mediated by hyper IL-11 in vitro in human atrial fibroblasts, as determined by fold change in the amount of MMP2 in the cell culture supernatant as compared to control (unstimulated) fibroblasts, following stimulation with hyper IL-11, in the presence of the mouse anti-IL-11 antibodies.
FIG. 17. Table summarising the fold-change data of FIGS. 14 to 16 for the 16 mouse anti-IL-11 antibodies. Antibody candidates numbered 1 to 16 correspond to clone designations as indicated in FIG. 13. Industry standard is monoclonal mouse anti-IL-11 IgG2A; Clone #22626; Catalog No. MAB218; R&D Systems, MN, USA.

The results of the Experiments are shown in FIGS. 14 and 17. The antibodies were demonstrated to be capable of neutralising signalling mediated by human IL-11.

A commercial monoclonal mouse anti-IL-11 antibody (Monoclonal Mouse IgG2A; Clone #22626; Catalog No. MAB218; R&D Systems, MN, USA) was also analysed for ability to inhibit signalling by human IL-11 in the experiments. This antibody was found to be able to reduce the percentage of activated fibroblasts to 0.89 times.

Clone A7 (BSN-3C11) was found to neutralise signalling by human IL-11 to a greater extent than the commercially available mouse anti-IL-11 antibody (industry standard).

5.2 Ability to Inhibit Mouse IL-11 Mediated Signalling

The ability of the murine monoclonal anti-human IL-11 antibodies to inhibit signalling mediated by murine IL-11 was investigated using the same assay as described in Example 2.2 above, but using mouse atrial fibroblasts instead of mouse dermal fibroblasts.

Figure 15:
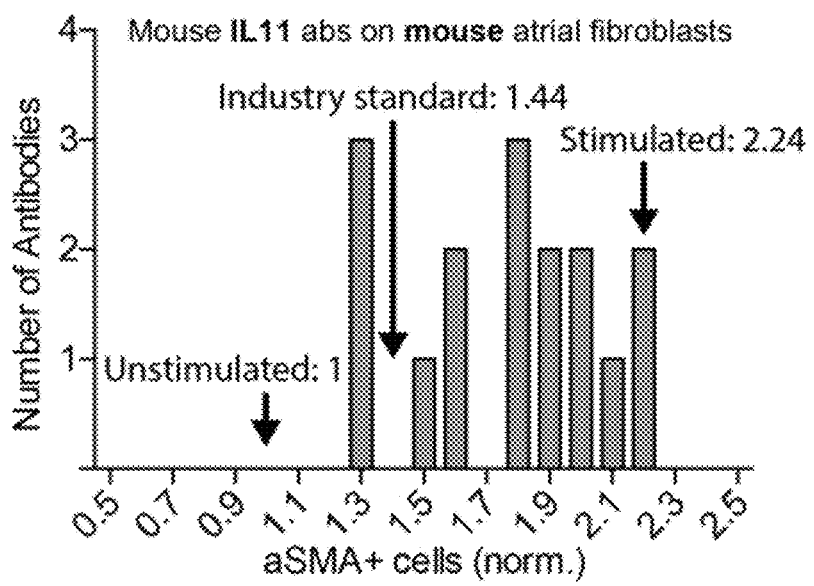
FIG. 15. Bar chart showing inhibition by the mouse anti-IL-11 antibodies of signalling mediated by IL-11 in vitro in mouse atrial fibroblasts, as determined by fold change in the percentage of αSMA positive cells as compared to control (unstimulated) fibroblasts, following stimulation with TGFβ1, in the presence of the mouse anti-IL-11 antibodies.

The results of the Experiments are shown in FIGS. 15 and 17. The antibodies were demonstrated to be capable of neutralising signalling mediated by murine IL-11.

A commercial monoclonal mouse anti-IL-11 antibody (Monoclonal Mouse IgG2A; Clone #22626; Catalog No. MAB218; R&D Systems, MN, USA) was also analysed for ability to inhibit signalling by human IL-11 in the experiments. This antibody was found to be able to reduce the percentage of activated fibroblasts to 43.0% (=1.44).

Several of the clones neutralised signalling by murine IL-11 to a greater extent than the commercially available mouse anti-IL-11 antibody (industry standard): A3 (BSN-2E1), A5 (BSN-2G6) and A6 (BSN-3C6).

9.3 Ability of Mouse Anti-IL-11 Antibodies to Inhibit IL-11 Trans Signalling, by IL-11 in Complex with IL-11RA The ability of the mouse anti-IL-11 antibodies to inhibit signalling mediated by hyper IL-11 was investigated.

Human atrial fibroblasts were incubated for 24 h with hyper IL-11 (0.2 ng/ml) in the presence of anti-IL-11 antibodies (2 µg/ml) or isotype control antibody. Following incubation, cell culture supernatant was analysed for MMP2. Stimulation with hyper IL-11 results in an increase in the secretion of MMP2 as compared to non-stimulated cultures.

The results of the experiments are shown in FIGS. 16 and 17. The mouse anti-IL-11 antibodies were found to be capable of neutralising signalling mediated by hyper IL-11 (i.e. IL-11 trans signalling), and several were found to be capable of inhibiting trans signalling to a greater extent than the commercial monoclonal mouse anti-IL-11 antibody (Monoclonal Mouse IgG2A; Clone #22626; Catalog No. MAB218; R&D Systems, MN, USA): BSN-2G6 (A5), BSN-3C6 (A6), BSN-5B8 (A9) and BSN-7D4 (A12).

Clone BSN-3C6 (A6) was identified as a particularly promising candidate for further development (highlighted in FIG. 17), showing good ability to inhibit both human IL-11 and mouse IL-11 mediated signalling, and good inhibition of IL-11 trans signalling.

5.4 Screening for Ability of Mouse Anti-IL-11 Antibodies to Bind IL-11

The mouse hybridomas producing anti-human IL-11 antibodies were sub-cloned, and cell culture supernatant from the subcloned hybridomas was analysed by "mix-and-measure" iQue assay for (i) ability to bind to human IL-11, and (ii) cross reactivity for antigen other than IL-11.

Briefly, labelled control cells (not expressing IL-11 at the cell surface) and unlabelled target cells expressing human IL-11 at their surface (following transient transfection with a plasmid encoding a FLAG-tagged human IL-11) were mixed together with the cell culture supernatant (containing mouse-anti-IL-11 antibodies) and secondary detection antibodies (fluorescently-labelled anti-mouse IgG antibody).

The cells were then analysed using the HTFC Screening System (iQue) for the two labels (i.e. the cell label and the label on the secondary antibody). Detection of the secondary antibody on the unlabelled, IL-11 expressing cells indicated ability of the mouse-anti-IL-11 antibodies to bind to IL-11. Detection of the secondary antibody on the labelled, control cells indicated cross-reactivity of the mouse-anti-IL-11 antibodies for target other than IL-11.

As a positive control condition, labelled and unlabelled cells were incubated with a mouse anti-FLAG tag antibody as the primary antibody.

Figures 18A, 18B:
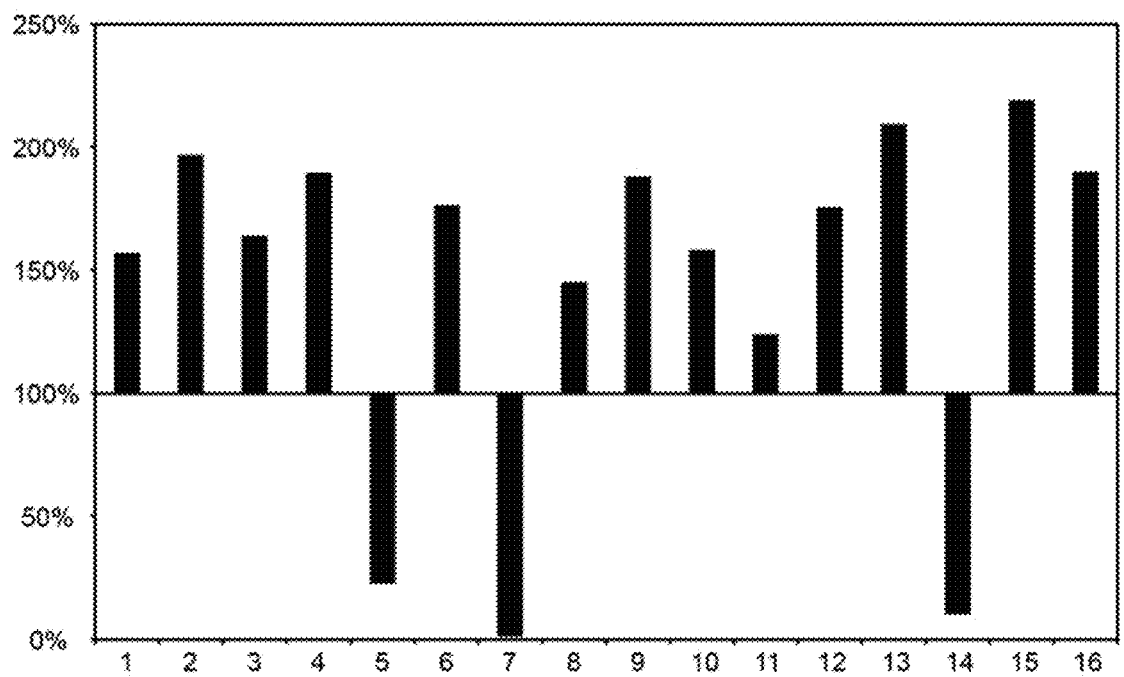
FIGS. 18A to 18H. (A-B) Table and bar chart showing binding of mouse-anti-IL-11 antibodies to human IL-11, as determined by iQue analysis (18A) Table summarising the results of the experiments. (18B) Bar chart showing strength of binding relative to the positive control anti-FLAG antibody (100%); numbers correspond to the clones as indicated in FIG. 17. (C-E) Antibodies that neutralise IL-11 signalling in (18C) human and (18D) mouse fibroblasts stimulated with TGFβ1, or (18E) in human fibroblasts stimulated with Hyper IL-11 (IL-11:IL11RA). (18F) Neutralisation of fibrotic response by 3C6 in human fibroblasts stimulated with recombinant IL-11. (18G) Neutralisation of fibrotic response by 3C6 in human fibroblasts stimulated with Hyper IL-11 (IL-11:IL11RA). (18H) Neutralisation of fibrotic response by 3C6 in human HSCs stimulated with TGFB1 (left) or IL-11 (right).

The results are shown in FIGS. 18A and 18B. The majority of the subcloned hybridomas expressed antibody which was able to bind to human IL-11, and which recognised this target with high specificity.

Clones BSN-2G6, BSN-5B8 and BSN-7F9 displayed some binding to cells not expressing IL-11, and so may have cross-reactivity for target(s) other than IL-11. Antibody produced by subclone BSN-3C11 was found not to bind to human IL-11.

13 of the 16 antibodies displayed stronger signal for binding to IL-11 than signal for the positive control anti-tag antibody for the tag, indicating that these antibodies bind to IL-11 with high affinity.

Human fibroblasts were stimulated with a maximum dose of TGFB1 (5 ng/ml), the strongest stimulator of IL-11 expression in atrial fibroblasts. This usually results in an IL-11 concentration of ~500 pg/ml-1 ng/ml in the supernatant after 24 h, depending also on the genotype of the primary atrial fibroblasts. The advantage of this approach is that it ensures the inhibition of correctly folded, endogenously produced IL-11 at physiologically relevant maximum levels of production. The fibrosis-relevant autocrine activity of IL-11 directly on fibroblasts is neutralised in this assay. TGFB1 stimulates the expression of IL-11, which subsequently drives the transition from quiescent fibroblasts to activated (ACTA2-positive) fibroblasts. Neutralising IL-11 antibodies inhibit this transition. Thus, antibodies lowering the percentage of activated fibroblasts after TGFB1 stimulation in our in vitro screening can be considered neutralisers and anti-fibrotic agents.

Figure 18C:
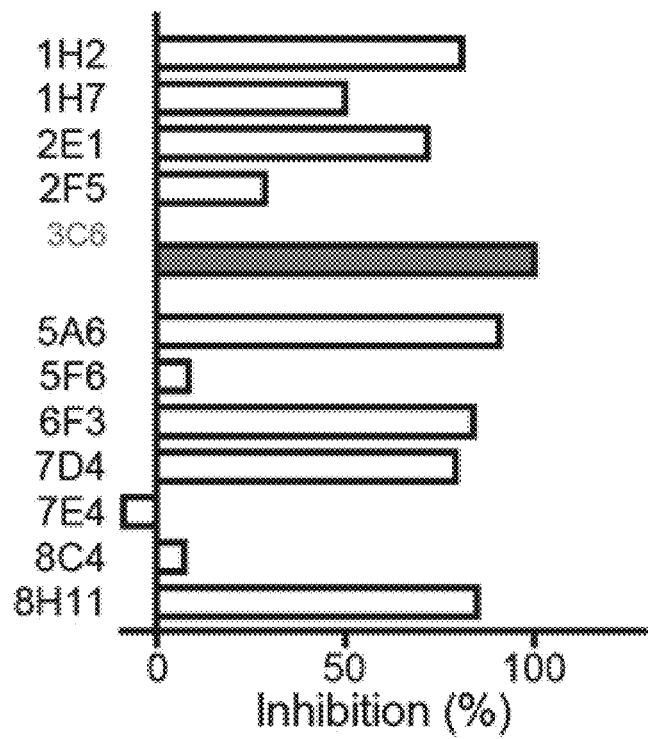

FIG. 18C shows the antibodies that neutralise IL-11 signalling. Human fibroblast activation was monitored to identify neutralising clones. 100% inhibition indicates myofibroblast (ACTA2+ve) levels of unstimulated fibroblasts and 0% corresponds to fully activated fibroblasts and the maximum amount of myofibroblasts.

Figure 18D:
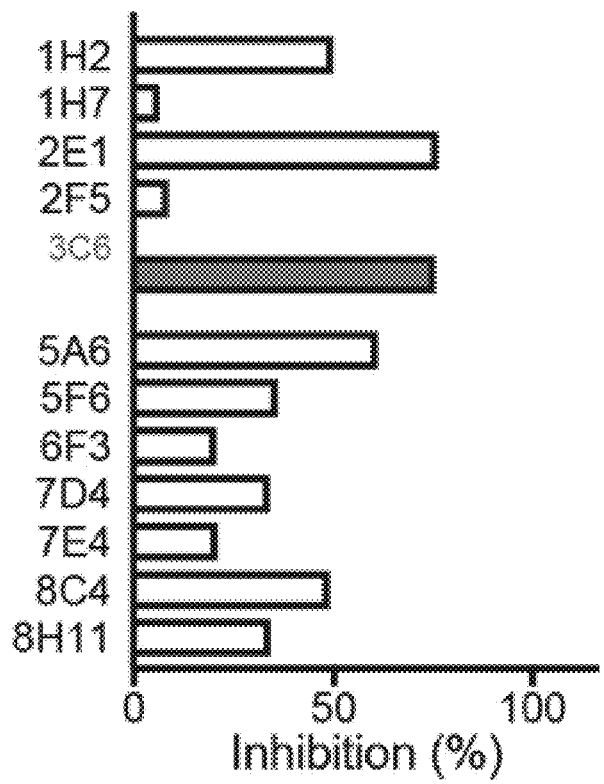

The experiment was repeated in mouse fibroblasts. The results are shown in FIG. 18D.

The antibodies were also tested for their ability to inhibit trans signalling using Hyper IL-11 (IL-11:IL11RA) activation of human fibroblasts. Antibodies that specifically bind IL-11 were incubated with IL-11:IL11RA-stimulated primary fibroblasts. Human fibroblast activation was monitored to identify neutralising clones. 100% inhibition indicates levels of unstimulated fibroblasts and 0% to fully activated fibroblasts.

Figure 18E:
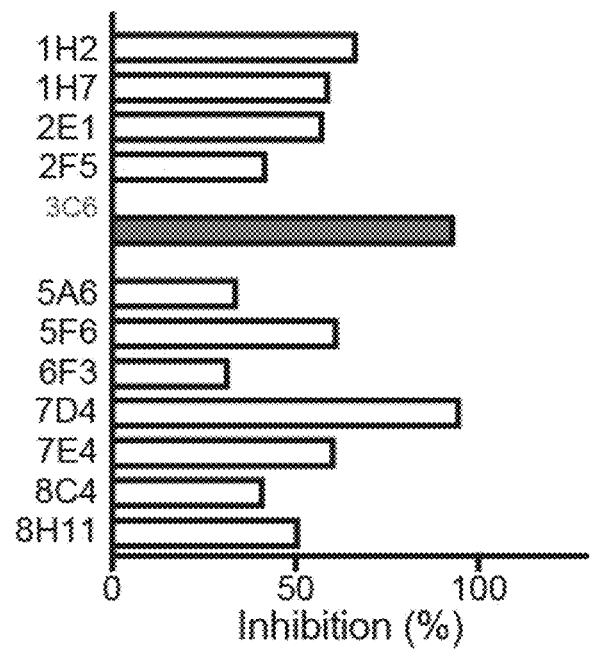

FIG. 18E shows the antibodies that neutralise IL-11 trans signalling.

IC50 values were determined for clone 3C6 in primary atrial human fibroblasts stimulated with human recombinant IL-11 (2 ng/ml, 24 h). The fibrotic response was determined by measuring MMP2 and TIMP1 concentrations in the supernatant. A similar experiment was performed using 200 pg/ml of hyper IL-11 for 24 h to assess blockage of trans signalling. Protein secretion into the supernatant by fibroblasts was assessed to estimate the % of inhibition.

Figure 18F:
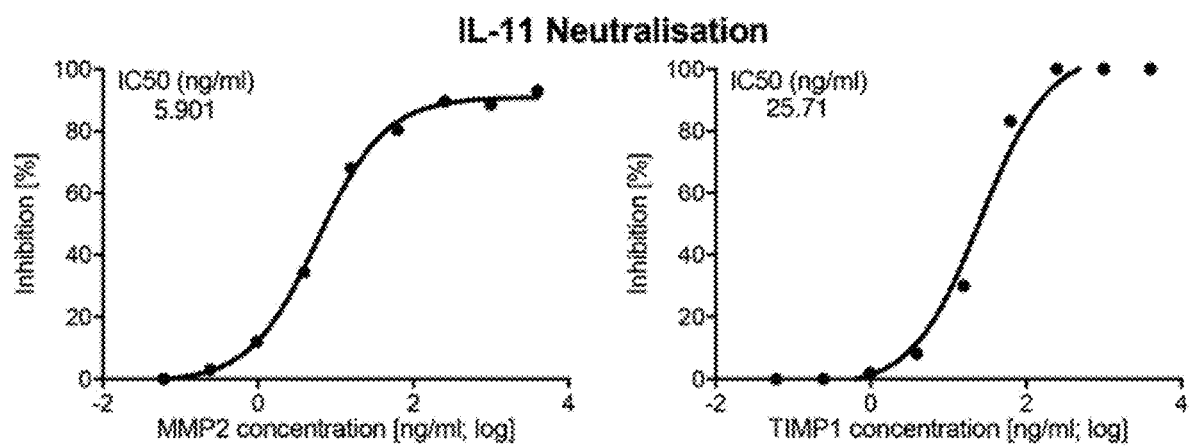
Figure 18G:
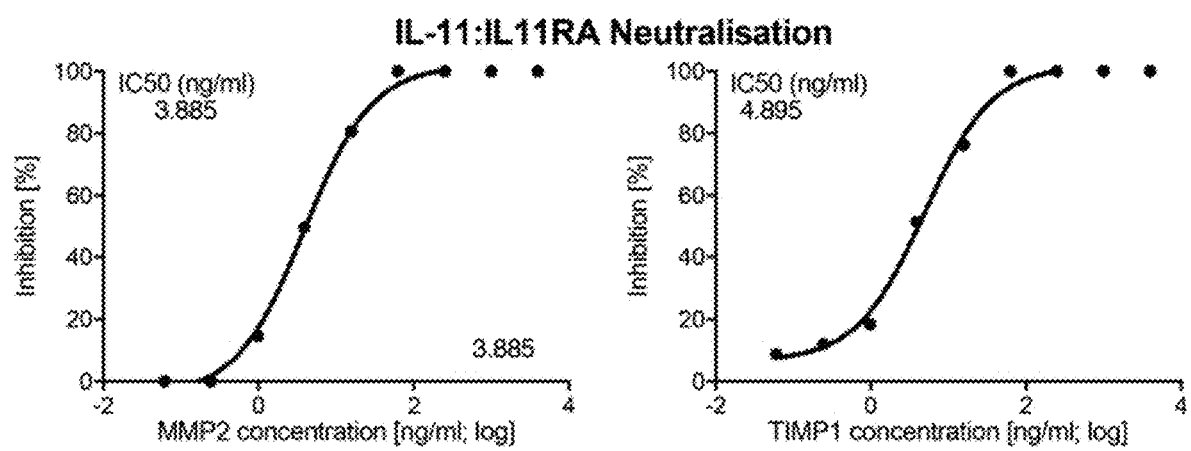

FIGS. 18F and 18G show neutralisation of the fibrotic response in both cases.

Figure 18H:
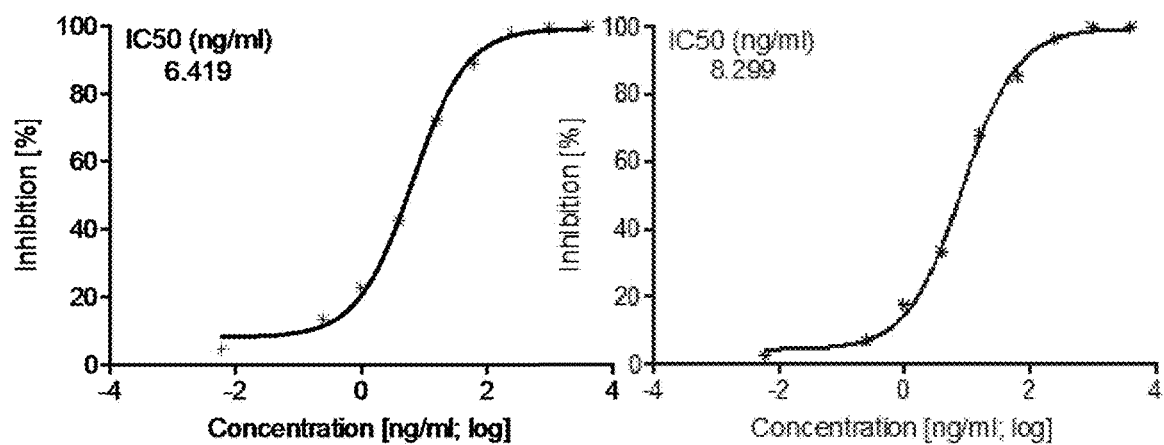

The experiment was repeated using human hepatic stellate cells (HSCs) incubated with TGFB1 (5 ng/ml) or IL-11 (2 ng/ml) and determining MMP2 secretion into the supernatant by fibroblasts to estimate the % of inhibition. FIG. 18H shows neutralisation of the fibrotic response by 3C6 in HSCs stimulated with TGFB1 (left) or IL-11 (right).

Example 6: Chimeric and Humanised Versions of the Mouse Anti-Human IL-11 Antibodies Mouse/human chimeric and humanised versions of the mouse monoclonal anti-human IL-11 antibodies of Example 4 are prepared according to standard methods.

6.1 Mouse/Human Chimeric Antibodies

Mouse/human chimeric antibodies are prepared from the mouse monoclonal anti-human IL-11 antibodies as described in Human Monoclonal Antibodies: Methods and Protocols, Michael Steinitz (Editor), Methods in Molecular Biology 1060, Springer Protocols, Humana Press (2014), in Chapter 8 thereof.

Briefly, the DNA sequences encoding the VH and VL of hybridomas producing the mouse anti-human IL-11 antibodies are determined, and combined with DNA sequence encoding human immunoglobulin constant regions to produce a mouse/human chimeric antibody sequence, from which a chimeric mouse/human antibody is expressed in mammalian cells.

6.2 Humanised Antibodies

Humanised antibodies are prepared from the mouse monoclonal anti-human IL-11 antibodies as described in Human Monoclonal Antibodies: Methods and Protocols, Michael Steinitz (Editor), Methods in Molecular Biology 1060, Springer Protocols, Humana Press (2014), in Chapter 7 thereof, in particular at section 3.1 of Chapter 7 entitled 'Antibody Humanization'.

Humanised versions of BSN-3C6 sequences were also designed, and these are shown in SEQ ID NOs:116 to 128.

Briefly, the DNA sequences encoding the VH and VL of hybridomas producing the mouse anti-human IL-11 antibodies are determined, and inserted into DNA sequence encoding human antibody variable region framework regions and immunoglobulin constant regions, to produce a humanised antibody sequence, from which a humanised antibody is expressed in mammalian cells.

Primary human atrial fibroblasts were incubated with TGFB1 (5 ng/ml) and varying concentrations of humanised 3C6 clones: VH 2.2/VL 2.1; VH 2.2/VL 2.2; VH 2.2/VL 2.3; VH 2.2/VL 2.4; VH 2.3/VL 2.2; and VH 2.3/VL 2.3.

| Name | Heavy chain | Light chain |
|---|---|---|
| VH 2.2/VL 2.1 | SEQ ID NO: 117 | SEQ ID NO: 121 |
| VH 2.2/VL 2.2 | SEQ ID NO: 117 | SEQ ID NO: 122 |
| VH 2.2/VL 2.3 | SEQ ID NO: 117 | SEQ ID NO: 123 |
| VH 2.2/VL 2.4 | SEQ ID NO: 117 | SEQ ID NO: 124 |
| VH 2.3/VL 2.2 | SEQ ID NO: 118 | SEQ ID NO: 122 |
| VH 2.3/VL 2.3 | SEQ ID NO: 118 | SEQ ID NO: 123 |

Primary human atrial fibroblasts were incubated with TGFB1 (5 ng/ml) and varying concentrations of humanised 3C6 clones. MMP2 secretion into the supernatant by human atrial fibroblasts was assessed to estimate the % of inhibition.

FIG. 54A shows that the antibodies bind to IL-11 and block endogenously produced IL-11 from interacting. IL-11 signalling is neutralised, which inhibits fibrogenic protein production.

The experiment was repeated using human HSCs and clones VH 2.2/VL 2.1, VH 2.2/VL 2.2, VH 2.2/VL 2.3 and VH 2.2/VL 2.4.

FIG. 54B shows that the antibodies bind to IL-11 and block endogenously produced IL-11 from interacting. IL-11 signalling is neutralised, which inhibits fibrogenic protein production.

Example 7: Further Biochemical Analysis of Anti-IL-11 Antibodies

The antibodies described herein are subjected to further biochemical analysis.

The antibodies are analysed by BIAcore, Biolayer interferometry (BLI) and MicroScale Thermophoresis (MST) analysis to determine the affinity of binding to human IL-11 and mouse IL-11.

BIAcore determination of antibody affinity by surface plasmon resonance (SPR) analysis is performed as described in Rich et al., Anal Biochem. 2008 Feb. 1; 373(1):112-20.

Biolayer interferometry analysis of antibody affinity is performed as described in Concepcion et al., Comb Chem High Throughput Screen. 2009 September; 12(8):791-800.

MicroScale Thermophoresis analysis of antibody affinity is performed as described in Jerabek-Willemsen et al., Assay Drug Dev Technol. 2011 August; 9(4): 342-353.

Aggregation of the antibodies is analysed by size exclusion chromatography (SEC), as described in Iacob et al., J Pharm Sci. 2013 December; 102(12): 4315-4329.

Hydophobicity of the antibodies is analysed by Hydrophobic interaction chromatography (HIC) as described in Haverick et al., MAbs. 2014 July-August; 6(4):852-8.

The melting temperature of the antibodies is analysed by Differential scanning fluorimetry (DSF) as described in Menzen and Friess, J Pharm Sci. 2013 February; 102(2): 415-28.

Example 8: Inhibition of Fibrosis In Vivo Using Anti-IL-11 Antibodies

The therapeutic utility of the anti-human IL-11 antibodies is demonstrated in in vivo mouse models of fibrosis for various different tissues. The mice used in the experiments are wildtype (i.e. IL-11RA+/+) mice.

8.1 Heart Fibrosis

A pump is implanted, and mice are treated with AngII (2 mg/kg/day) for 28 days.

Neutralising anti-IL-11 antibodies, or control antibodies, are administered to different groups of mice by intravenous injection. At the end of the experiment, collagen content is assessed in the atria of the mice using a calorimetric hydroxyproline-based assay kit, and the level of RNA expression of the markers or fibrosis Col1A2, αSMA (ACTA2) and fibronectin (Fn1) were analysed by qPCR.

Mice treated with neutralising anti-IL-11 antibodies have a reduced fibrotic response in heart tissue as compared to mice treated with control antibodies, as evidenced by reduced expression of markers of fibrosis.

8.2 Kidney Fibrosis

A mouse model for kidney fibrosis is established, in which fibrosis is induced by intraperitoneal injection of folic acid (180 mg/kg) in vehicle (0.3M $NaHCO_3$); control mice were administered vehicle alone.

Neutralising anti-IL-11 antibodies, or control antibodies, are administered to different groups of mice by intravenous injection. Kidneys are removed at day 28, weighed and either fixed in 10% neutral-buffered formalin for Masson's trichrome and Sirius staining or snap-frozen for collagen assay, RNA, and protein studies.

Total RNA is extracted from the snap-frozen kidney using Trizol reagent (Invitrogen) and Qiagen TissueLyzer method followed by RNeasy column (Qiagen) purification. The cDNA is prepared using iScript™ cDNA synthesis kit, in which each reaction contained 1 μg of total RNA, as per the manufacturer's instructions. Quantitative RT-PCR gene expression analysis is performed on triplicate samples with either TaqMan (Applied Biosystems) or fast SYBR green (Qiagen) technology using StepOnePlus™ (Applied Biosystem) over 40 cycles. Expression data are normalized to GAPDH mRNA expression level and the 2-ΔΔCt method is used to calculate the fold-change. The snap-frozen kidneys are subjected to acid hydrolysis by heating in 6M HCl at a concentration of 50 mg/ml (95° C., 20 hours). The amount of total collagen in the hydrolysate is quantified based on the colorimetric detection of hydroxyproline using Quickzyme Total Collagen assay kit (Quickzyme Biosciences) as per the manufacturer's instructions.

Mice treated with neutralising anti-IL-11 antibodies have a reduced fibrotic response in kidney tissue as compared to mice treated with control antibodies, as evidenced by reduced expression of markers of fibrosis.

8.3 Lung Fibrosis

Mice are treated by intratracheal administration of bleomycin on day 0 to establish a fibrotic response in the lung (pulmonary fibrosis).

Neutralising anti-IL-11 antibodies, or control antibodies, are administered to different groups of mice by intravenous injection. Mice are sacrificed at day 21, and analysed for differences in fibrosis markers.

Mice treated with neutralising anti-IL-11 antibodies have a reduced fibrotic response in lung tissue as compared to mice treated with control antibodies, as evidenced by reduced expression of markers of fibrosis.

8.4 Skin Fibrosis

Mice are treated by subcutaneous administration of bleomycin on day 0 to establish a fibrotic response in the skin.

Neutralising anti-IL-11 antibodies, or control antibodies, are administered to different groups of mice by intravenous injection. Mice are sacrificed at day 21, and analysed for differences in fibrosis markers.

Mice treated with neutralising anti-IL-11 antibodies have a reduced fibrotic response in skin tissue as compared to mice treated with control antibodies, as evidenced by reduced expression of markers of fibrosis.

8.5 Eye Fibrosis

To analyse fibrosis in the eye, IL-11RA−/− mice and IL-11RA+/+ mice undergo trabeculectomy (filtration surgery) on day 0 to initiate a wound healing response in the eye. This mouse model of glaucoma filtration surgery has been shown to be an efficient model to evaluate the wound healing response in the eye (Khaw et al. 2001, Curr Opin Ophthalmol 12, 143-148; Seet et al. 2011, Mol. Med. 17, 557-567) and has successfully shown the beneficial effect of fibrotic modulators in vivo (Mead et al. 2003, Invest. Ophthalmol. Vis. Sci. 44, 3394-3401; Wong et al. 2003 Invest. Ophthalmol. Vis. Sci. 44, 1097-1103; Wong et al. 2005, Invest. Ophthalmol. Vis. Sci. 46, 2018-2022).

Briefly, the conjunctiva are dissected to expose the underlying sclera, after which an incision is made through the sclera into the anterior chamber of the eye using a 30-gauge needle. The created fistula allows aqueous humor to exit into and underneath the conjunctiva. The dissected conjunctiva is then secured and closed at the limbus by a 10-0 (0.2 metric) Ethilon black monofilament nylon scleral suture. Fucithalmic ointment is instilled at the end of the procedure. The surgery is performed under anaesthesia by intraperitoneal injection of a 0.1 ml ketamine/xylazine mixture, as well as topical application of one drop per eye of 1% xylocaine. Fucithalmic ointment is instilled post-surgery to prevent infection. Surgery is performed with 70% propyl alcohol sterilized surgical scissors and forceps and sterile needles.

The accumulated fluid underneath the sutured conjunctiva is observed as a conjunctival bleb. Mice are euthanized on day 7 post-surgery for analyses. For qualitative immune-histological analyses, eyes from mice are harvested by enucleation and then sectioned. Maturation of collagen fibres is evaluated with using the picro-sirius red/polarization light technique (Szendroi et al. 1984, Acta Morphol Hung 32, 47-55); orange-red indicates mature collagen, and yellow/green indicates newly formed immature collagen.

Neutralising anti-IL-11 antibodies, or control antibodies, are administered to different groups of mice by intravenous injection, and fibrosis is monitored in the eye tissue.

Mice treated with neutralising anti-IL-11 antibodies have a reduced fibrotic response in eye tissue as compared to mice treated with control antibodies, as evidenced by reduced expression of markers of fibrosis.

8.6 Other Tissues

The effect of treatment with neutralising anti-IL-11 antibodies on fibrosis is also analysed in mouse models of fibrosis for other tissues, such as the liver, kidney, bowel, and is also analysed in a model relevant to multiorgan (i.e. systemic) fibrosis.

The fibrotic response is measured and compared between mice treated with neutralising anti-IL-11 antibodies and mice treated with control antibodies. Mice treated with neutralising anti-IL-11 antibodies have a reduced fibrotic response as compared to mice treated with control antibodies, as evidenced by reduced expression of markers of fibrosis.

Example 9: Treatment of Cancer In Vivo Using Anti-IL-11 Antibodies

The effect of treatment with neutralising anti-IL-11 antibodies on cancer is analysed in mouse models of cancer.

Models of breast, lung, and gastrointestinal cancers are established in mice, the mice are treated by administration of neutralising anti-IL-11 antibodies, or control antibodies, and the development/progression of cancer is monitored.

An anti-cancer effect is observed for the neutralising anti-IL-11 antibodies, as evidenced by reduced symptoms of cancer and/or increased survival as compared to mice treated with control antibodies.

Anti-IL-11 antibodies were assessed for their effect on tumour growth.

A number of different cancer models were investigated.

Liver cancer cells (HCC) were implanted into mice (flank model) and tumour volume was monitored for 3 weeks after implantation. Mice were treated either with 3C6 or IgG control antibodies. Tumour size was monitored.

FIG. 51A shows that tumour size was found to be significantly reduced during anti-IL-11 antibody treatment alone, indicating a therapeutic effect of inhibiting IL-11 signalling in liver cancer.

A murine model demonstrating IL-11 over-expression in fibroblasts was created which developed severe global organ fibrosis due to IL-11 secretion from fibroblasts. The spleen increases in size 2-fold over a period of 3 weeks and shows profound and easily measured IL-11 related changes, likely driven by myelofibrosis (a type of bone marrow cancer). 3C6 antibody prevents IL-11 induced splenomegaly in a transgenic mouse expressing IL-11 in fibroblasts in the myelofibrosis model, as shown in FIG. 51B.

The effect of anti-IL-11 antibody 3C6 was assessed in a lung cancer model in conjunction with cisplatin chemotherapy.

Mice were inoculated subcutaneously with A549 tumor cells ($5\times10^6$; day 0). Mice were either left untreated, or treated with cisplatin (6 mg/kg, twice weekly) supplemented by either IgG antibody (10 mg/kg×2/week, IP) or 3C6 (10 mg/kg×2/week, IP) for 5 weeks. Tumor volume was measured twice per week.

The results are shown in FIG. 51C. Anti-IL-11 therapy provides an additive effect for inhibition of tumour volume when administered in combination with cisplatin chemotherapy.

Example 10: Treatment of AMD Using Anti-IL-11 Antibodies

The effect of treatment with neutralising anti-IL-11 antibodies is investigated in wet age-related macular degeneration (AMD).

Neutralising anti-IL-11 antibody is administered to subjects having wet AMD. In some treatment conditions, subjects are administered with VEGF antagonist therapy (e.g. ranibizumab, bevacizumab, pegaptanib, brolucizumab or aflibercept), PDGF antagonist therapy (e.g. pegpleranib), or are treated by laser coagulation therapy in addition to treatment with anti-IL-11 antibody.

A reduction in wet AMD pathology and/or improvement in the symptoms of wet AMD is observed in subjects treated with anti-IL-11 antibody as compared to subjects not treated with anti-IL-11 antibody.

Example 11: Light Chain Shuffled Antibodies

Light chain shuffling was performed as represented schematically in FIG. 12.

The heavy chains of the following IL-11-binding antibody clones were used for light chain shuffling: YU45-E03, YU45-F02, YU45-F05, YU45-G02, YU46-A08, YU46-G08.

Variable regions of the heavy chains were amplified by PCR, and the resulting amplicons were pooled and cloned into phagemid vectors (phagemids) each containing a specific VL chain, and representing naïve lambda and kappa light chain library repertoires. The VH and VL containing phagemids were used to produce a new library of antibody-phages, which was used to select clones displaying binding to IL-11 under stringent conditions (i.e. antigen limitation, large number washing steps).

Antibodies capable of binding to both human IL-11 and murine IL-11 (i.e. cross-reactive antibodies) were identified by phage display by panning using biotinylated and non-biotinylated recombinant human and murine IL-11, based on the panning strategy shown in FIG. 19.

Figure 20:
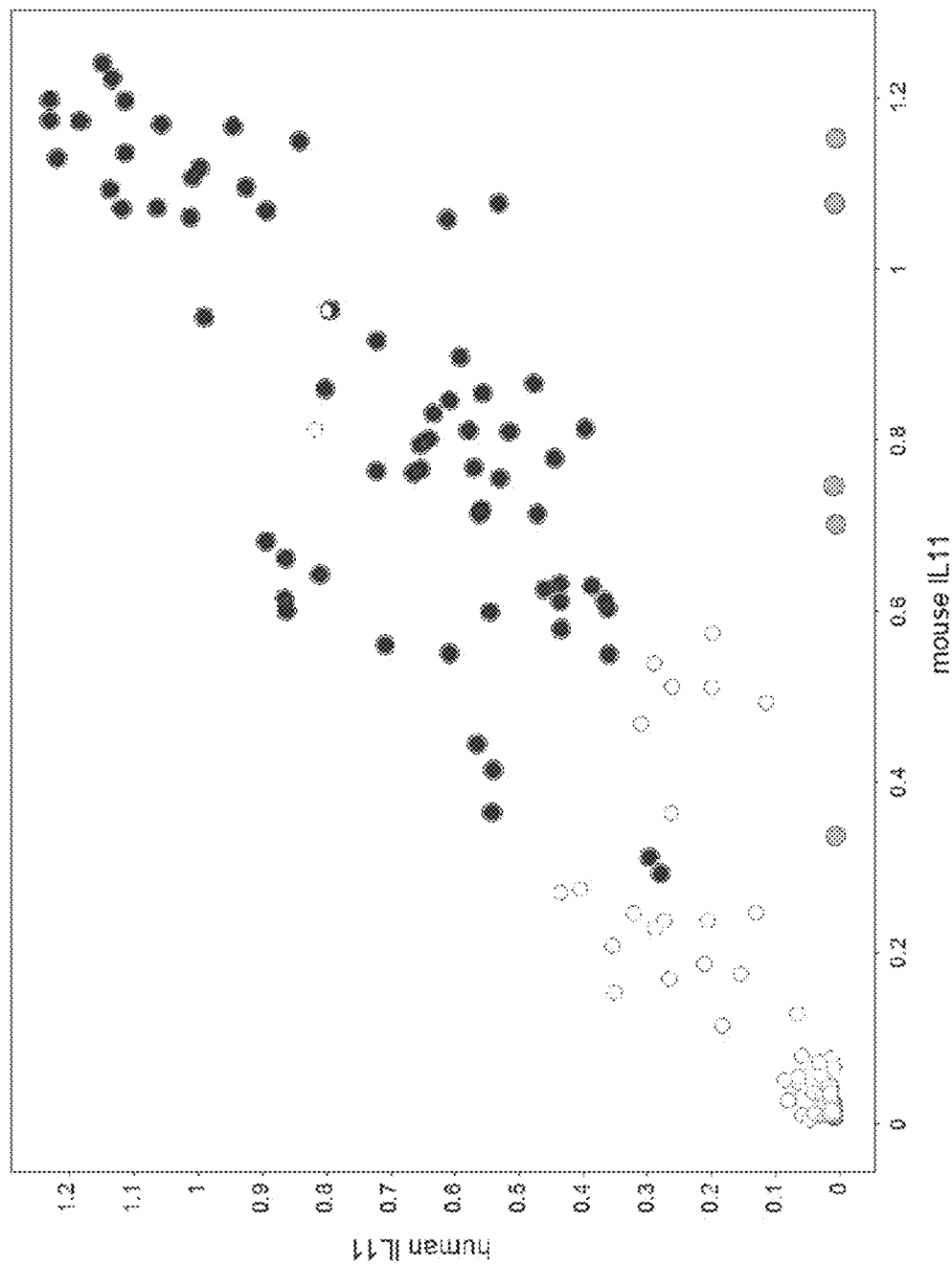
FIG. 20. Scatterplot showing binding signal to human IL-11 and mouse IL-11 as determined by ELISA assay for light chain-shuffled human anti-IL-11 antibodies. 66 antibodies displaying cross-reactive binding to human IL-11 and mouse IL-11 were identified (black circles). Antibodies displaying binding to mouse IL-11 only are indicated by grey circles.

The analysis identified 66 cross-reactive antibodies (FIG. 20). Sequence analysis identified 64 unique antibody clones.

The 64 antibody clones were analysed for binding signal to human IL-11 and murine IL-11 in an ELISA assay. The results are shown in FIGS. 21A and 21B.

Example 12: Functional Characterisation of the Light Chain Shuffled Antibodies 54 of the light chain shuffled antibodies were analysed for their ability to bind IL-11 and inhibit IL-11 mediated signalling.

12.1 Binding to Human IL-11

The light chain shuffled anti-IL-11 antibodies were analysed to determine the EC50 for binding to human IL-11 by ELISA according to standard methods. Briefly, wells of microtiter plates were coated with recombinant human IL-11 (100 ng/well), scFv-Fc comprising the VH and VL domains of the clones were added in a dilution series and antibody binding was detected using a polyclonal antibody detection system.

Figure 22:
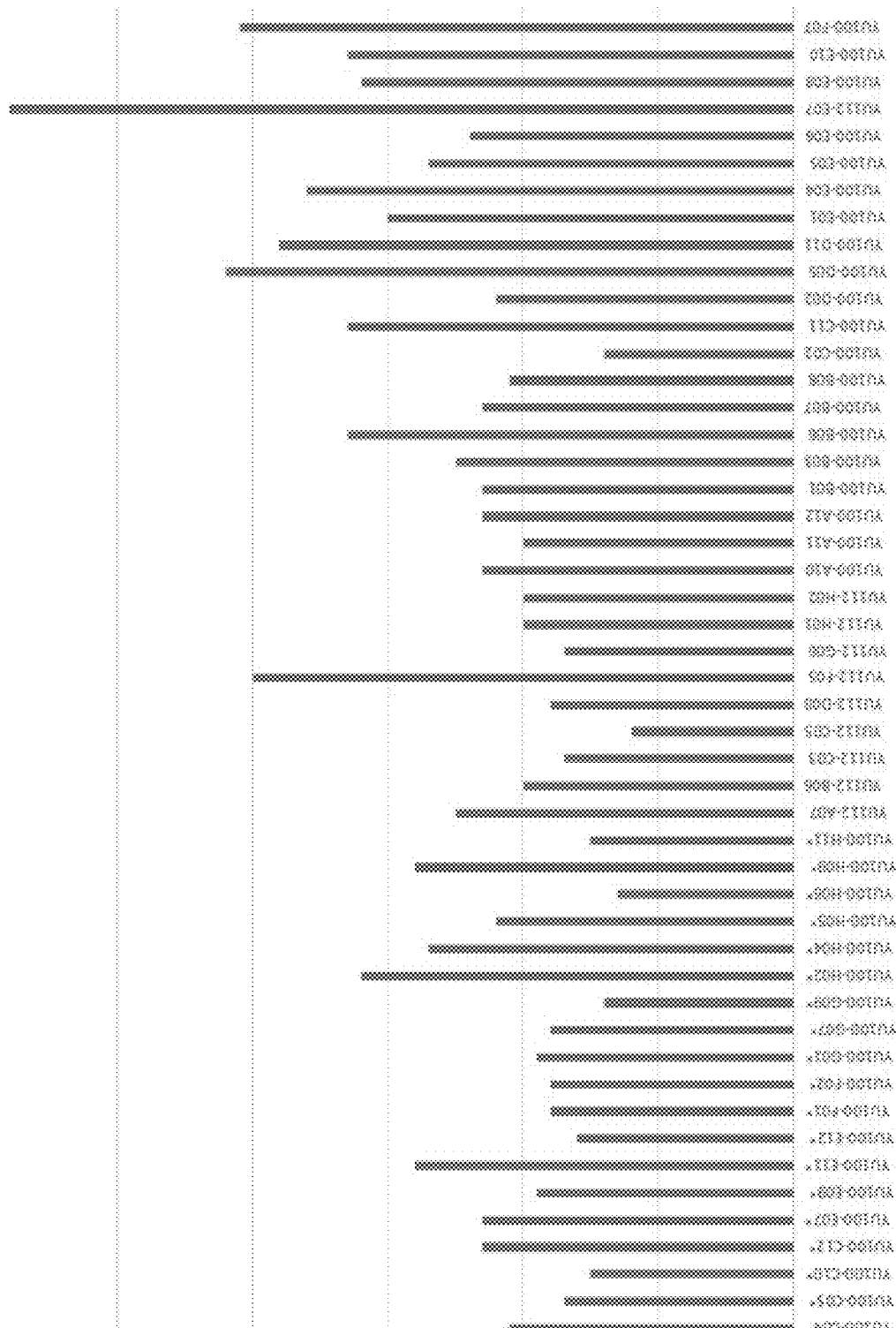
FIG. 22. Bar chart showing EC50 values in ng/ml for binding of the indicated light-chain shuffled anti-IL-11 antibodies to human IL-11, as determined by ELISA.

The results of the ELISA assays were used to calculate EC50 values (ng/ml) for the light chain shuffled antibody clones, and these are shown in FIG. 22.

12.2 Ability to Inhibit Human IL-11 Mediated Signalling

To investigate the ability of light chain shuffled antibody clones to neutralise human IL-11-mediated signalling, cardiac atrial human fibroblasts were cultured in wells of 96-well plates in the presence of TGFβ1 (5 ng/ml) for 24 hours, in the presence of anti-IL-11 antibodies in scFv-human IgG1-Fc format, or in the presence of human IgG1 isotype control antibody, at a final concentration of 2 mg/ml. Levels of the pro-fibrotic marker MMP2 in the cell culture supernatant were then measured by ELISA. Basal MMP2 secretion by the cells in culture was measured by culture in the absence of TGFβ1, in the presence of human IgG1 isotype control (2 mg/ml).

Figure 23A:
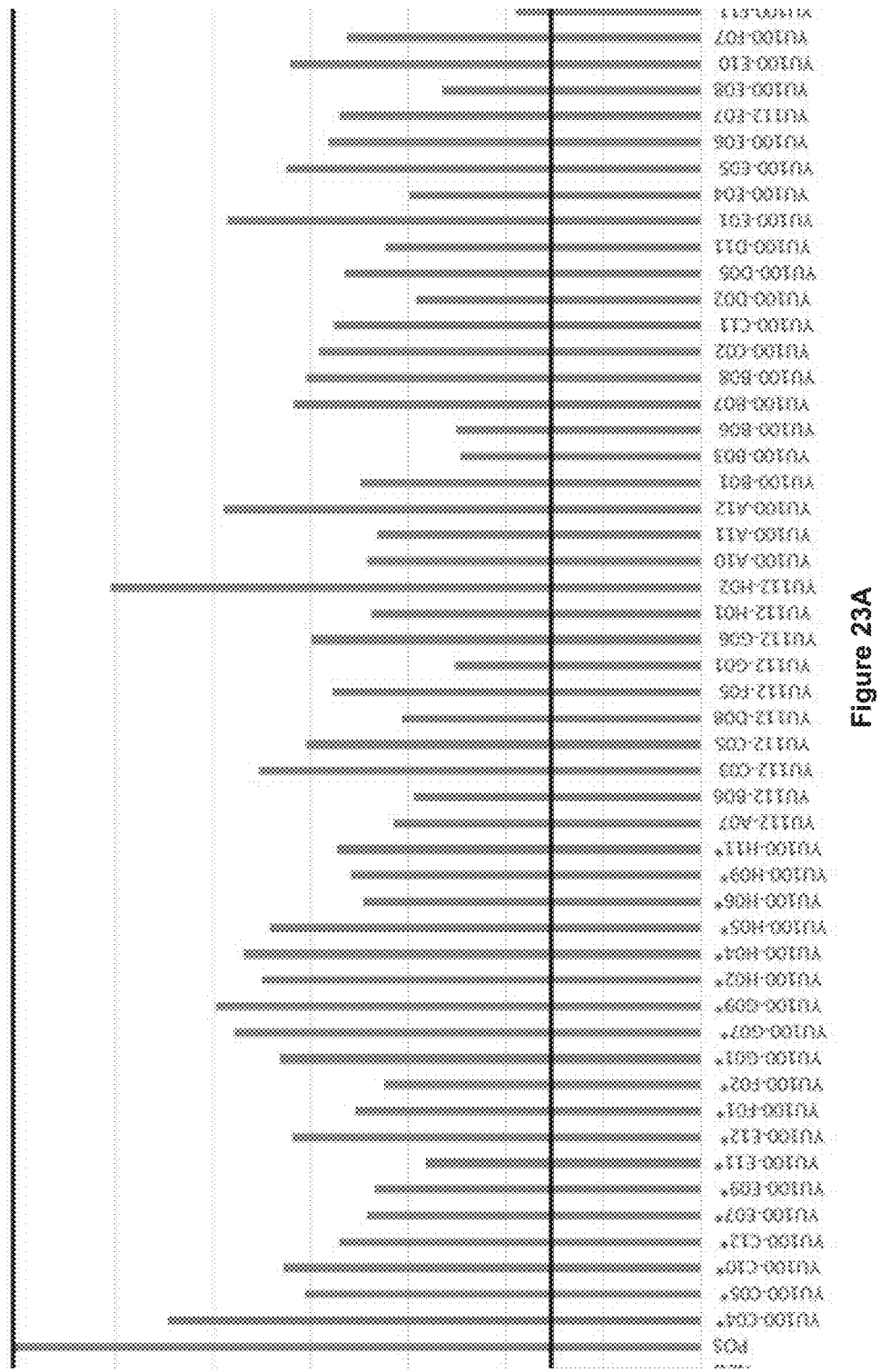
FIGS. 23A to 23E. Bar chart showing the effect of anti-IL-11 antibodies on MMP2 secretion by human cardiac atrial fibroblasts in response to TGFβ1. 23A and 23B show the results of two separate experiments. Cells were cultured in the presence of TGFβ1 (5 ng/ml) for 24 hours, in the presence of the indicated light chain shuffled anti-IL-11 antibodies, or in the presence of human IgG1 isotype control. Basal MMP2 secretion by the cells in culture was measured by culture in the absence of TGFβ1, in the presence of human IgG1 isotype control. Horizontal lines show basal MMP2 secretion by cardiac atrial human fibroblasts cultured for 24 hours in the presence of human IgG1 isotype control antibody in the absence of TGFβ1 (NEG); and MMP2 secretion by cardiac atrial human fibroblasts cultured for 24 hours in the presence of 5 ng/ml TGFβ and the human IgG1 isotype control antibody (POS). 23C shows neutralisation of the fibrotic response in vitro assessed by monitoring MMP2 levels. Primary human fibroblasts were incubated with TGFB1 (5 ng/ml) and varying concentrations of antibody candidates in IgG1 format. MMP2 secretion into the supernatant by fibroblasts was assessed to estimate the % of inhibition. 23D shows neutralisation of the fibrotic response in vitro for clones YU100-G08 and YU100-H01. 23E shows neutralisation of trans IL-11 signalling for clones YU100-G08 and YU100-H01.
Figure 23B:
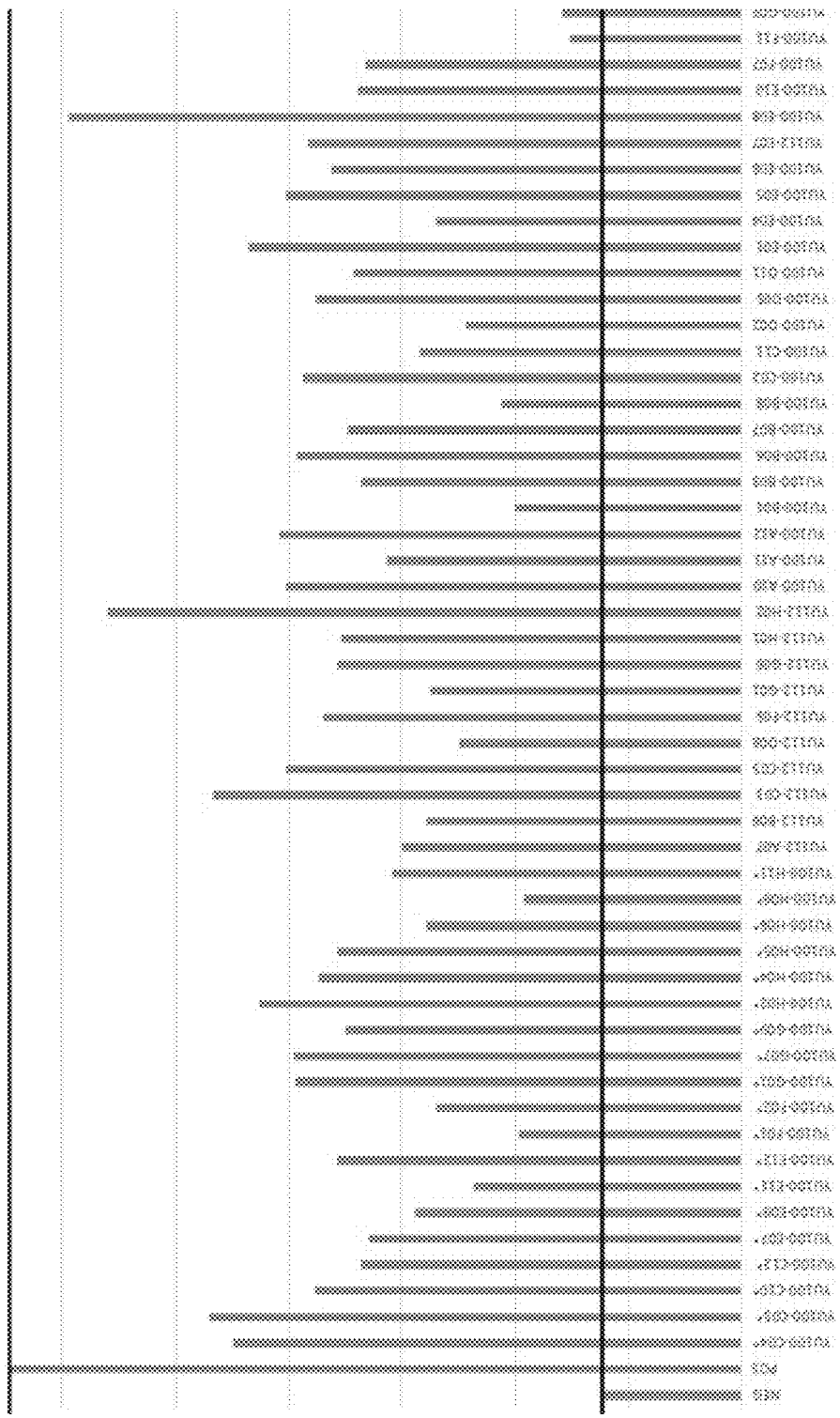

The results of two separate experiments are shown in FIGS. 23A and 23B. Horizontal lines in the bar charts represent the basal MMP2 secretion by cardiac atrial human fibroblasts cultured for 24 hours in the presence of human IgG1 isotype control antibody in the absence of TGFβ1 stimulation ('NEG' in FIGS. 23A and 23B), and MMP2 secretion by cardiac atrial human fibroblasts cultured for 24 hours in the presence of 5 ng/ml TGFβ and the human IgG1 isotype control antibody ('POS' in FIGS. 23A and 23B).

The light chain shuffled anti-IL-11 antibodies were shown to be able to bind to human IL-11, and to inhibit IL-11 mediated signalling. The results are summarised in FIG. 24.

Nine clones were assessed further based on their performance and were screened for neutralisation of endogenous IL-11, as above. MMP2 secretion into the supernatant by fibroblasts was assessed to estimate the % of inhibition.

Figure 23C:
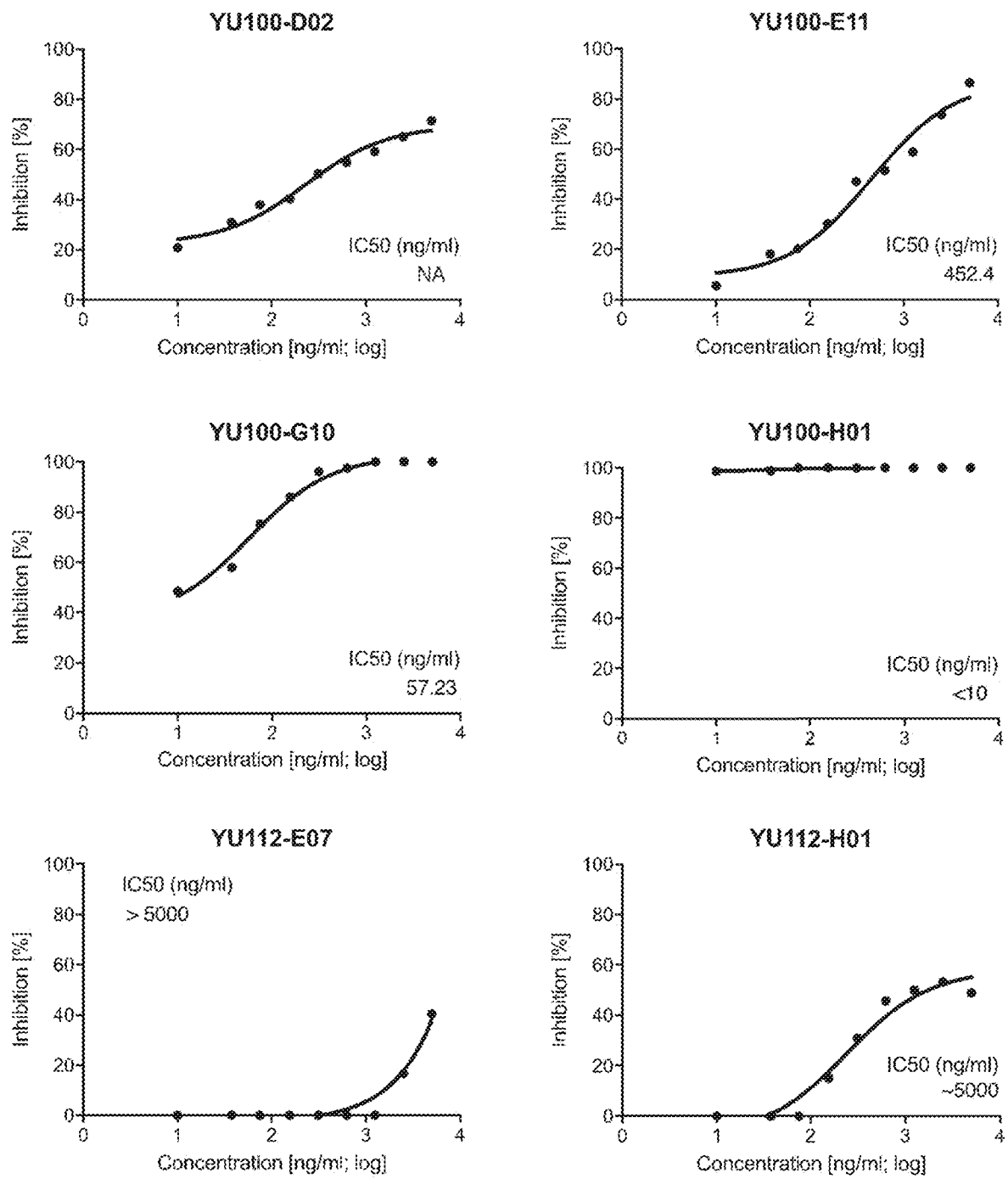
Figure 23C:
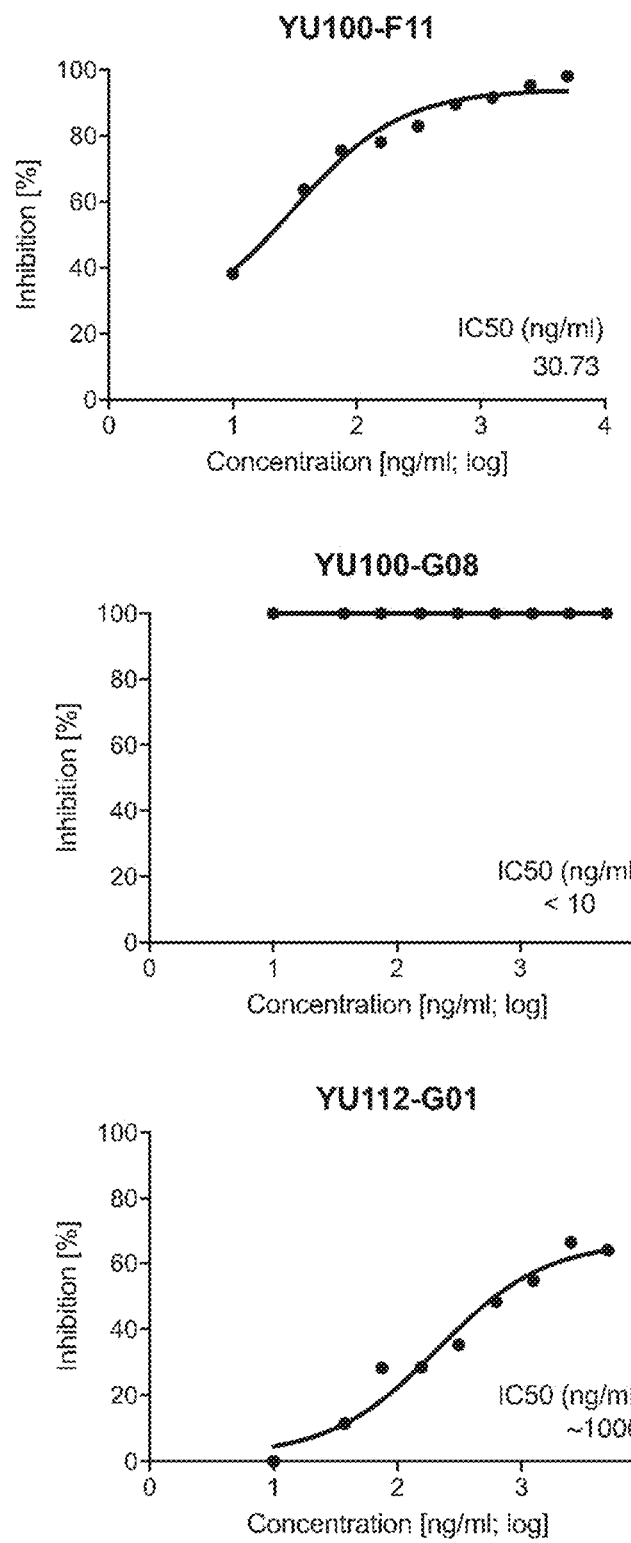

FIG. 23C shows that several of the antibodies bind to endogenously produced IL-11, neutralise IL-11 signalling in the fibroblasts and inhibit fibrogenic protein production.

To more accurately estimate the IC50 values of clones YU100-G08 and YU100-H01, the above experiment was repeated using lower antibody concentrations (range: 0.061, 0.244, 0.976, 3.9, 15.625, 62.5, 250, 1000 and 4000 ng/ml) and primary atrial fibroblasts. MMP2 secretion into the supernatant by fibroblasts was assessed to estimate the % of inhibition.

Figure 23D:
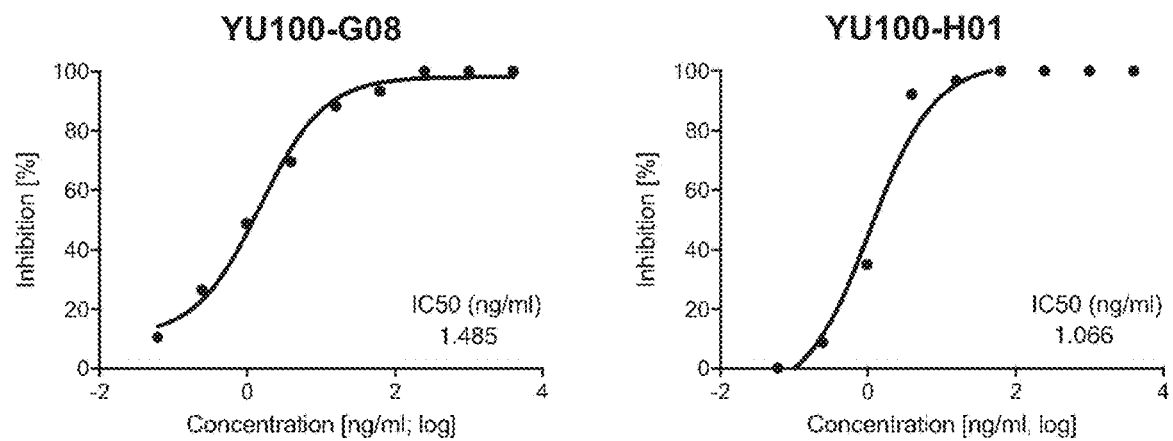

FIG. 23D shows that both antibodies bind to endogenously produced IL-11, neutralise IL-11 signalling in the fibroblasts and inhibit fibrogenic protein production. Stimulation of human fibroblasts with recombinant IL-11 (2 ng/ml, 24 h) also showed that both antibodies neutralise IL-11 signalling in the fibroblasts and inhibit fibrogenic protein production.

The ability of YU100-G08 and YU100-H01 to inhibit trans IL-11 signalling was assessed. Primary human fibroblasts were stimulated with IL-11:IL11RA (hyperIL-11; 0.2 ng/ml, 24 h). MMP2 secretion into the supernatant by fibroblasts was assessed to estimate the % of inhibition.

Figure 23E:
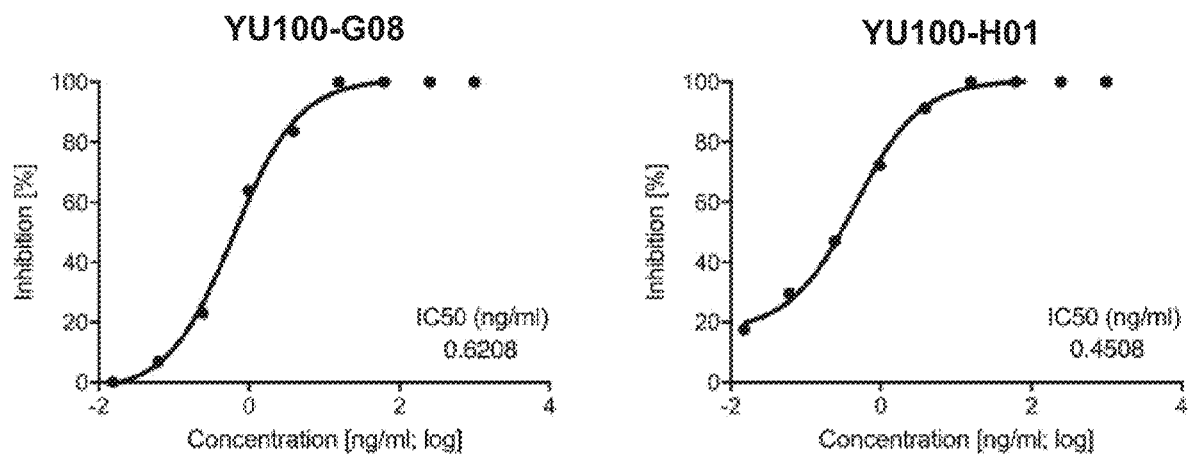

FIG. 23E shows that both antibodies neutralise trans IL-11 signalling and inhibit fibrogenic protein production.

Example 13: Inhibition of Kidney Fibrosis or Kidney Injury Using Anti-IL-11 Antibodies 10-12 week old littermate mice of similar weight had kidney fibrosis induced by intraperitoneal (i.p.) injection of folic acid (180 mg kg$^{-1}$) in vehicle (0.3 M NaHCO$_3$); control mice were administered vehicle alone.

Anti-IL11 antibody clone BSN-3C6 was administered one day after folic acid treatment and then 3 times per week at a dose of 20 mg/kg. Mice were euthanized 28 days post-injection.

The mouse plasma levels of urea and creatinine were quantified using urea assay kit (ab83362, Abcam) and creatinine assay kit (ab65340, Abcam), respectively according to the manufacturers instructions. The amount of total collagen in the kidney was quantified on the basis of colourimetric detection of hydroxyproline using a Quickzyme Total Collagen assay kit (Quickzyme Biosciences). All colourimetric assays were performed according to the manufacturer's instructions.

Tissues were paraffin-embedded, and kidneys were sectioned at 3 μm. For paraffin sections, tissues were fixed for 24 h, at room temperature in 10% neutral-buffered formalin (Sigma-Aldrich), dehydrated and embedded in paraffin. For cryosections, freshly dissected organs were embedded with Tissue-Tek Optimal Cutting Temperature compound (VWR International). Cryomoulds were then frozen in a metal beaker with isopentane cooled in liquid nitrogen and sections were stored in −80° C. Total collagen was stained with Masson's trichrome stain kit (HT15, Sigma-Aldrich) according to the manufacturer's instructions. Images of the sections were captured and blue-stained fibrotic areas were semi-quantitatively determined with ImageJ software (version 1.49). For immunohistochemistry, the tissue sections were incubated with anti-ACTA2 antibody (ab5694, Abcam). Primary antibody staining was visualized using an ImmPRESS HRP Anti-Rabbit IgG Polymer Detection kit (Vector Laboratories) with ImmPACT DAB Peroxidase Substrate (Vector Laboratories) as the chromogen. The sections were then counterstained with Mayer's haematoxylin (Merck).

Figure 25A:
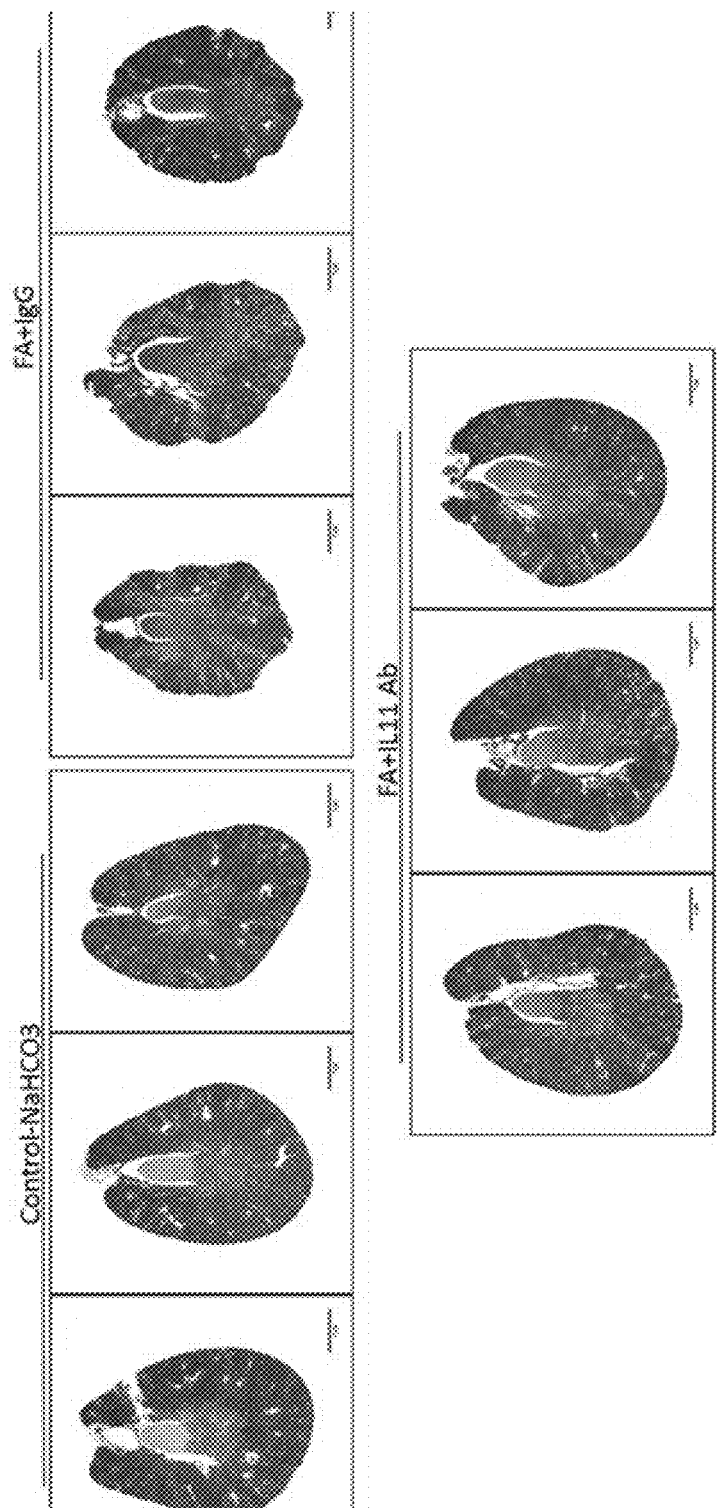
FIGS. 25A and 25B. Images and graph showing the results of histological analysis of kidney sections from mice subjected to different treatments in a mouse model of kidney fibrosis. Kidney fibrosis was induced by intraperitoneal (IP) injection of folic acid (FA, 180 mg/kg) in vehicle (0.3M $NaHCO_3$) mice; control mice were administered vehicle alone. Mice were administered isotype control IgG2 (20 mg/kg, 3× per week, intraperitoneal), anti-IL-11 antibody (20 mg/kg, 3× per week, intraperitoneally) from day 1 post folic acid injury and for the duration of the experiment. Animals were sacrificed 28 days after folic acid-induced kidney damage and analysed for fibrosis histologically using Masson's Trichrome stain. (25A) Images of Masson's Trichrome stained kidney sections. Fibrotic areas containing collagen appear darker as compared to healthy areas that appear lighter. (25B) Graphs showing semi-quantitative analysis of collagen area expressed as a percentage (%) of the total kidney area (graph). ***, P<0.001 compared to FA+IgG, ANOVA.
Figure 25B:
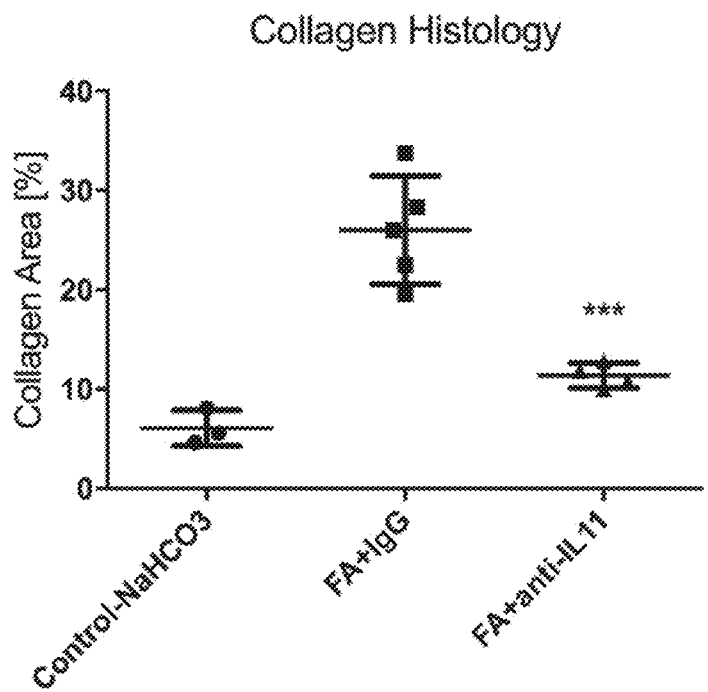

FIGS. 25A and 25B show that mice treated with anti-IL11 antibody were found to have significantly reduced staining for collagen, indicating that anti-IL-11 antibody treatment had inhibited kidney fibrosis.

Figure 26:
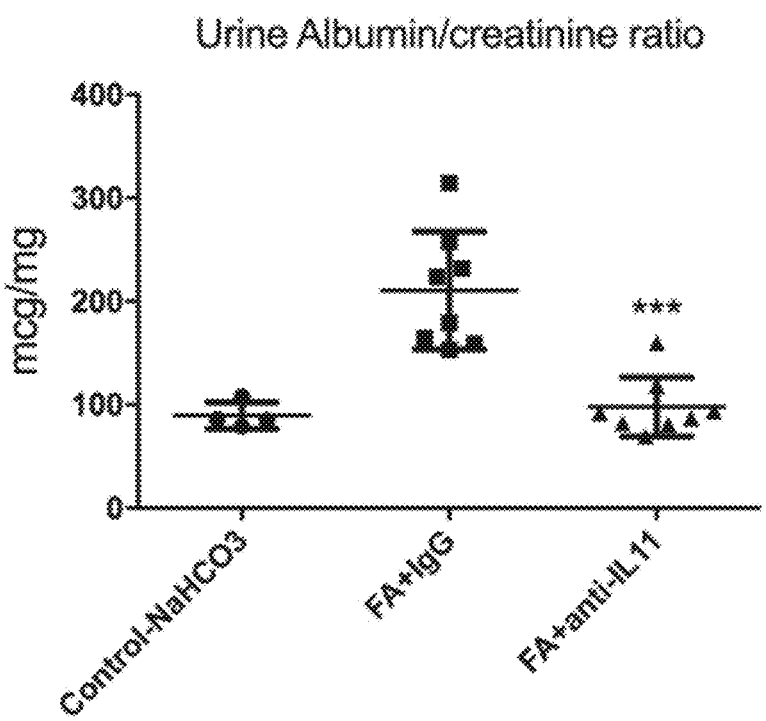
FIG. 26. Graph showing the urinary albumin/creatine ratio in mice subjected to different treatments in a mouse model of kidney fibrosis. Kidney fibrosis was induced by intraperitoneal (IP) injection of folic acid (FA, 180 mg/kg) in vehicle (0.3M NaHCO$_3$) mice; control mice were administered vehicle alone. FA treated mice were administered isotype control IgG2 (20 mg/kg, 3× per week, intraperitoneal) or anti-IL11 antibody (20 mg/kg, 3× per week, intraperitoneal) from day 1 post folic acid injury and for the duration of the experiment. Mice were placed in metabolic cages and urinary creatinine and albumin measured using commercial assays (Abcam) according to the manufacturers instructions. ***, P<0.001 compared to FA+IgG, ANOVA.

FIG. 26 shows that the urinary albumin/creatine ratio was significantly reduced by treatment with anti-IL11 antibody, indicating a reduced level of kidney damage in mice treated with anti-IL-11 antibody.

Figure 27A:
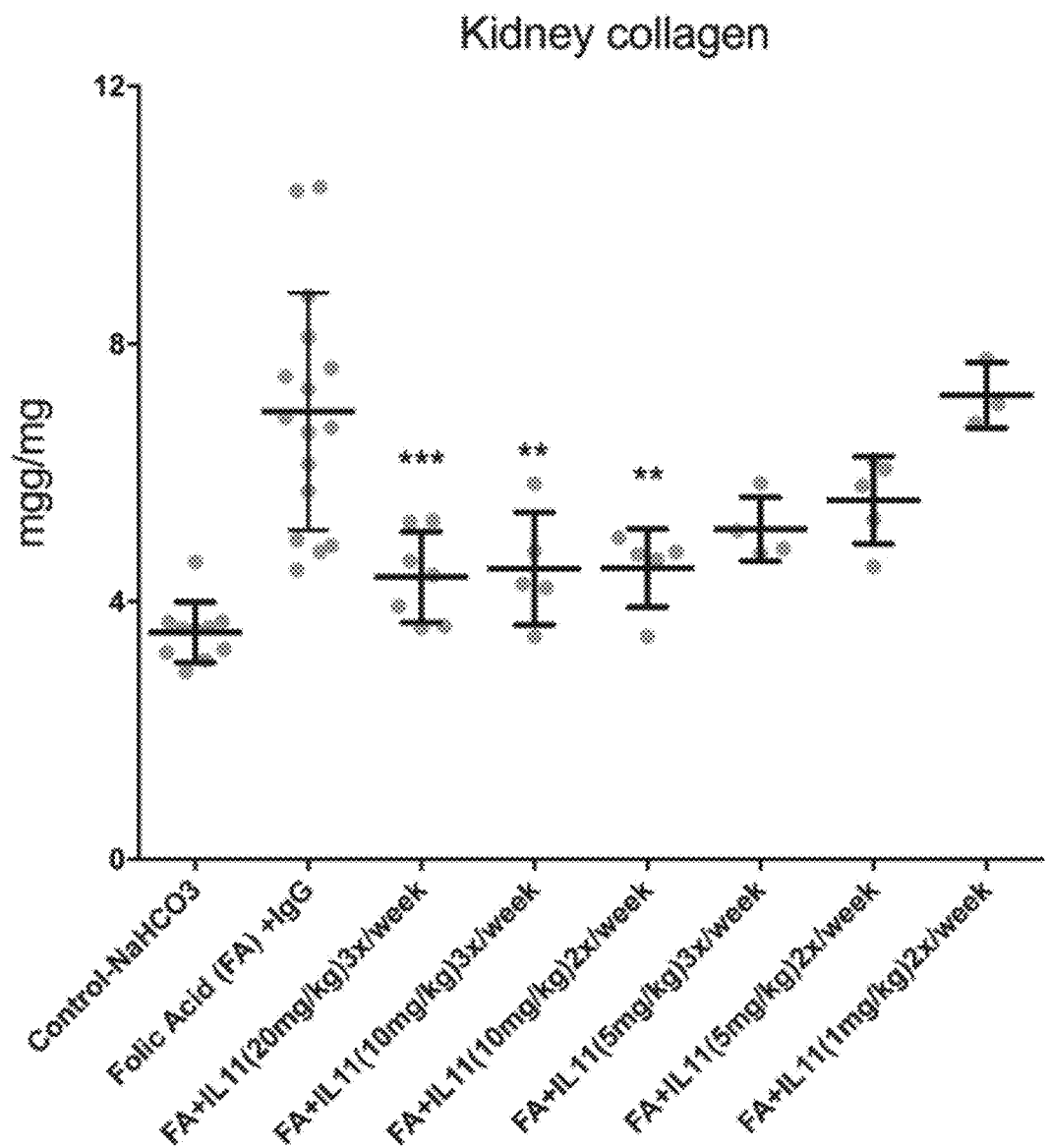
FIGS. 27A to 27C. Graph showing total collagen in kidney tissue in mice subjected to different treatments in a mouse model of kidney fibrosis. (27A) Kidney fibrosis was induced by intraperitoneal (IP) injection of folic acid (FA, 180 mg/kg) in vehicle (0.3M NaHCO$_3$) mice; control mice were administered vehicle alone. From day one of the experiment, mice in the treatment groups were given isotype control IgG2 (20 mg/kg, 3× per week) or neutralizing anti-IL11 antibody at varying doses: 20 mg/kg×3/week; 10 mg/kg×3/week; 10 mg/kg×2/week; 5 mg/kg×3/week; 5 mg/kg×2/week; 1 mg/kg×2/week), all intraperitoneal. Animals were sacrificed 28 days post-injection and kidney analysed for fibrosis (micrograms/g (μg/g)) by hydroxyproline assay using Quickzyme Total Collagen assay kit (Quickzyme Biosciences) according to the manufacturer's protocol. , P<0.01; *, P<0.001 compared to FA+IgG, ANOVA. Dose-dependent effects of anti-IL-11 antibodies (27B) BSN-3C6 and (27C) YU100-G08_02A on kidney collagen content in folic-acid induced kidney fibrosis.

FIG. 27A shows that treatment with the anti-IL-11 antibody inhibited folic acid-induced kidney fibrosis in a dose-dependent fashion.

Figure 27B:
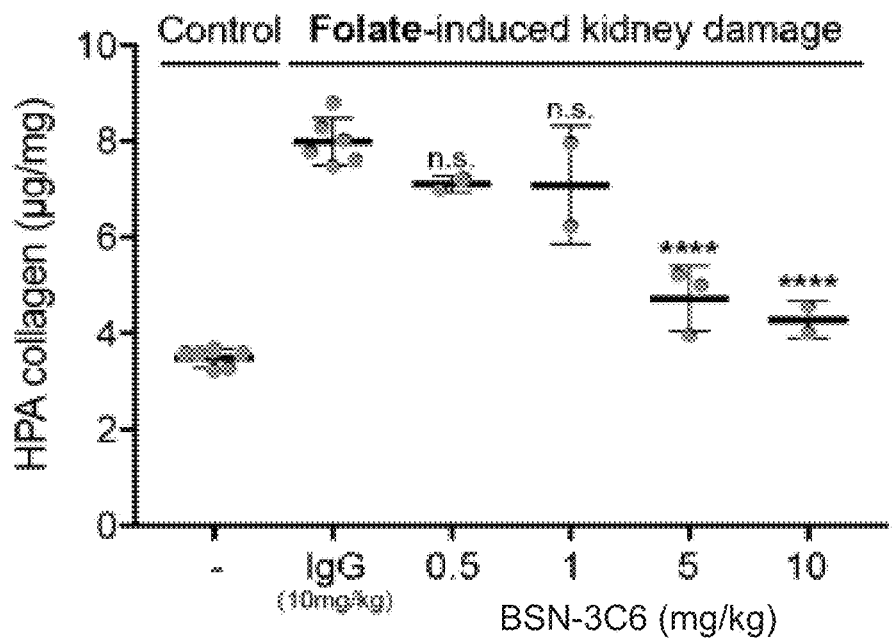
Figure 27C:
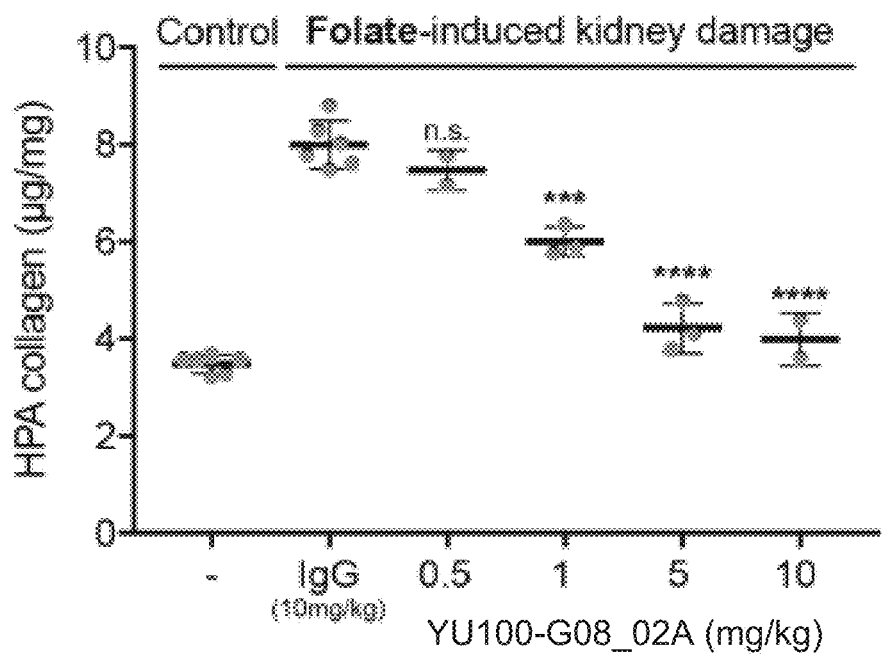

Anti-IL-11 antibodies BSN-3C6 and YU100-G08 02A were assessed for their ability to reduce folic acid-induced kidney fibrosis at different concentrations (0.5, 1, 5 and 10 mg/kg). IgG (10 mg/kg) was used as a control. Antibody injections were initiated one day before folate treatment and performed biweekly. Animals were sacrificed three weeks after folate induced injury to assess renal collagen content using the HPA assay FIGS. 27B and 27C show that anti-IL-11 therapy was found to reduce kidney collagen content in folic acid-induced kidney fibrosis in a dose-dependent fashion.

In another experiment a mouse model of acute renal injury was induced by unilateral ureteric obstruction (UUO). Briefly, mice were treated by sham operation or ureteric obstruction of one ureter. Mice received IgG, anti-IL-11 antibody clone BSN-3C6 (20 mg/kg; on surgical days −1, 1, 3, 5) and injured kidneys ('UUO') or contralateral uninjured kidneys (Con) were harvested on day 7 post surgery.

Semi-quantitative assessment of tubular injury was performed by histological analysis of casts, tubular atrophy or tubular expansion blinded to experimental conditions (Tubular injury score: 0, none; 1, minimal; 2, mild; 3, moderate; 4, severe).

Figure 28A:
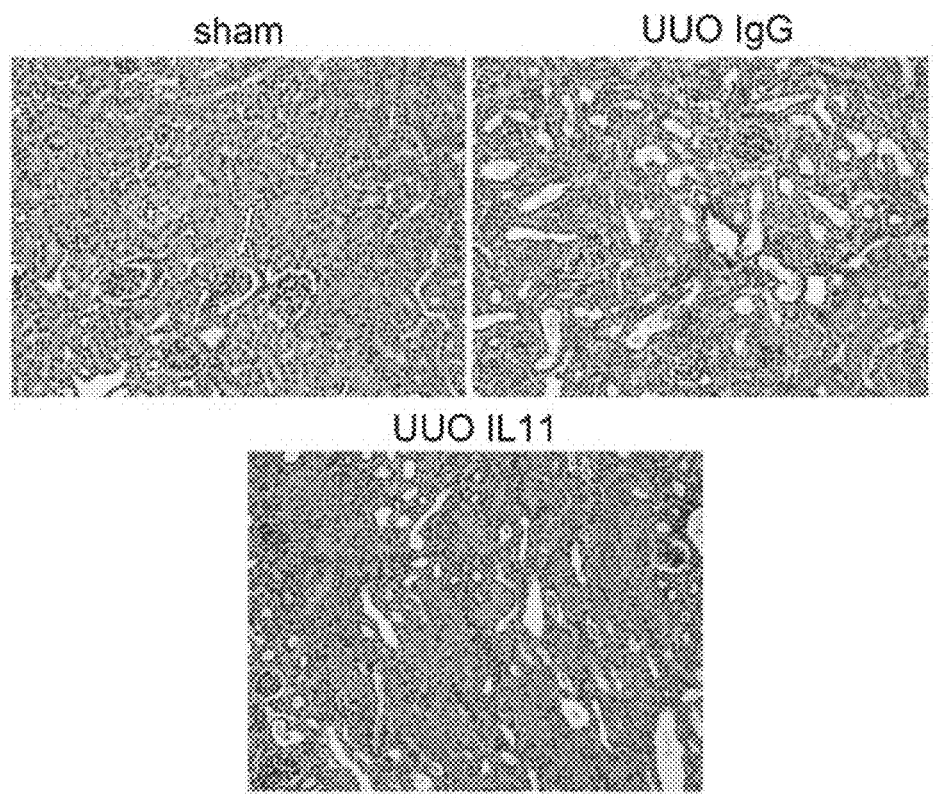
FIGS. 28A and 28B. Images and graph showing the results of histological analysis of kidney sections from mice subjected to different treatments in a mouse model of acute renal injury. (28A) Mice were treated by sham operation or ureteric obstruction of one ureter. Mice received IgG, anti-IL-11 antibody (20 mg/kg on surgical days −1, 1, 3, 5) and injured kidneys (UUO IgG, IL-11) or contralateral (Con) uninjured kidneys (Con IgG, IL-11) were harvested on day 7 post surgery. (28B) Semi-quantitative assessment of tubular injury was determined by histological analysis of casts, tubular atrophy or tubular expansion blinded to experimental conditions (Tubular injury score: 0, none; 1, minimal; 2, mild; 3, moderate; 4, severe). *, P<0.05 compared to UUO IgG, ANOVA.
Figure 28B:
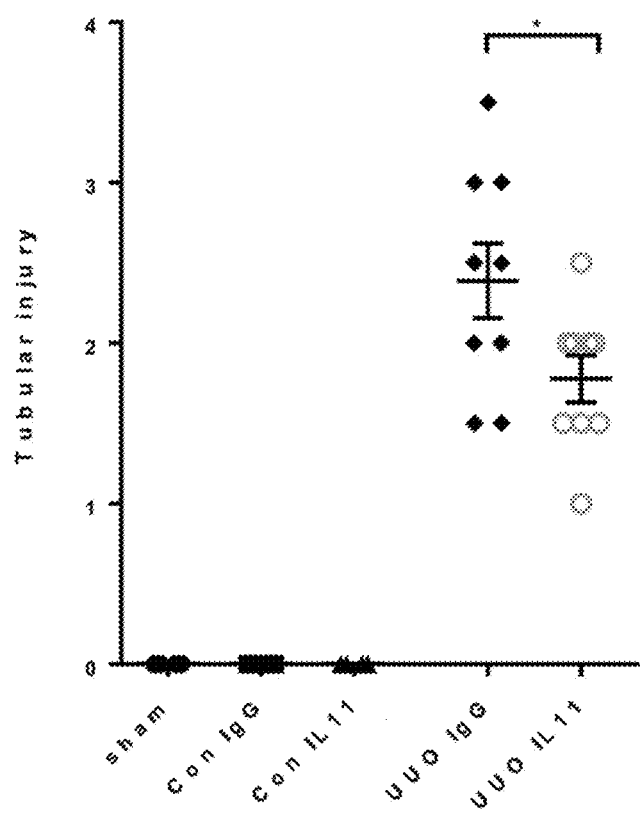

FIGS. 28A and 28B show that treatment with anti-IL-11 antibody reduced tubular damage in a mouse model of acute renal injury.

Example 14: IL-11 and Liver Fibrosis

Protein expression of IL-11 in healthy and diseased livers was confirmed by western blots in matched samples of human livers. Matched frozen liver samples were prepared for western blotting and levels of IL11 determined using Human IL-11 Antibody Monoclonal Mouse IgG2A Clone #22626, catalog number MAB218 from R&D Systems. Film images were generated.

Figure 29:
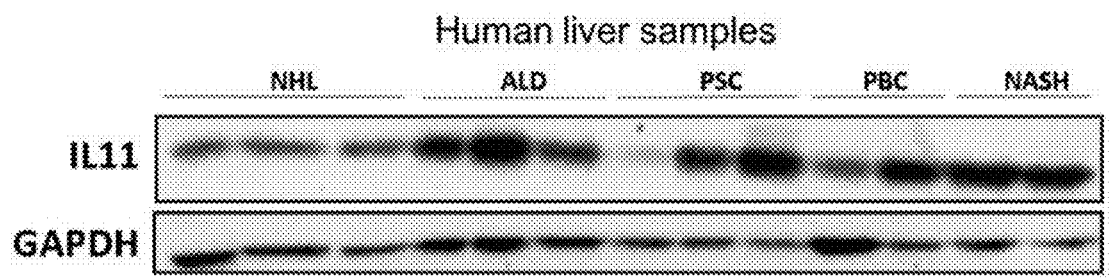
FIG. 29. Image showing the results of ELISA western blot for IL-11 of human liver samples. Liver samples obtained from patients undergoing liver surgery were used for western blot analysis. Blotting of GAPDH was used as a loading control. Samples from normal human liver (NHL) had low levels of IL-11 protein, whereas samples from patients with fibrotic liver diseases including alcoholic liver disease (ALD), primary sclerosing cholangitis (PSC), primary biliary cirrhosis (PBC) or non-alcoholic steatohepatitis (NASH) had higher levels of IL-11.

The results are shown in FIG. 29. Increased expression of IL-11 was detected in most diseased tissue as compared to normal healthy livers.

To determine whether IL-11 expression changed with disease, an ELISA was performed on media from Precision Cut Liver Slices (PCLS) using Human IL-11 DuoSet 15 plate kit, catalog number DY218 from R&D Systems.

Human PCLS were cut and incubated with media treatments after a 24 h rest period for acclimatisation to media plates. Samples were treated with media only (control), media with LPS, a combination of profibrogenic stimuli inducing TGFβ1, or a combination of profibrogenic stimuli inducing TGFβ1 and the TGFβ1 inhibitor ALK5.

Figure 30A:
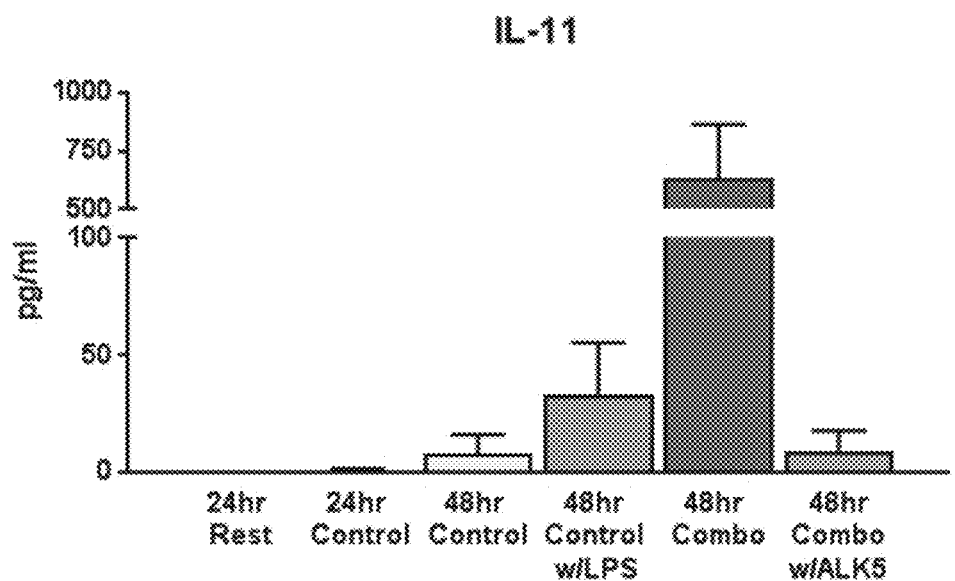
FIGS. 30A to 30C. IL-11 and liver fibrosis. (A) Bar chart showing the results of ELISA analysis of secretion of IL-11 by human PCLS subjected to different treatments. (B) Trans-differentiation of human hepatic stellate cells into myofibroblasts following IL-11 stimulation (24 h) in the presence of 2 ug/ml of IgG or anti-IL-11 antibody YU100-G08_02A. (C) YU100-G08_02A blocks fibrotic response in HSCs stimulate by endogenous and exogenous IL-11.

The results are shown in FIG. 30A. The profibrogenic stimuli induced upregulation of IL-11 protein expression, and ALK5 inhibitor was found to inhibit TGFβ1 receptor signalling, which reduced the expression of IL-11 protein down to control levels.

Hepatic stellate cells (HSCs) are the precursors of myofibroblasts in the liver. BSN-3C6 and YU100-G08_02A were assessed for their ability to block the HSC-to-myofibroblast transition, indicated by a reduction of ACTA2$^{+ve}$ cells when HSCs were incubated with TGFβ1 (24 h) and neutralising antibodies (2 ug/ml).

Figure 30B:
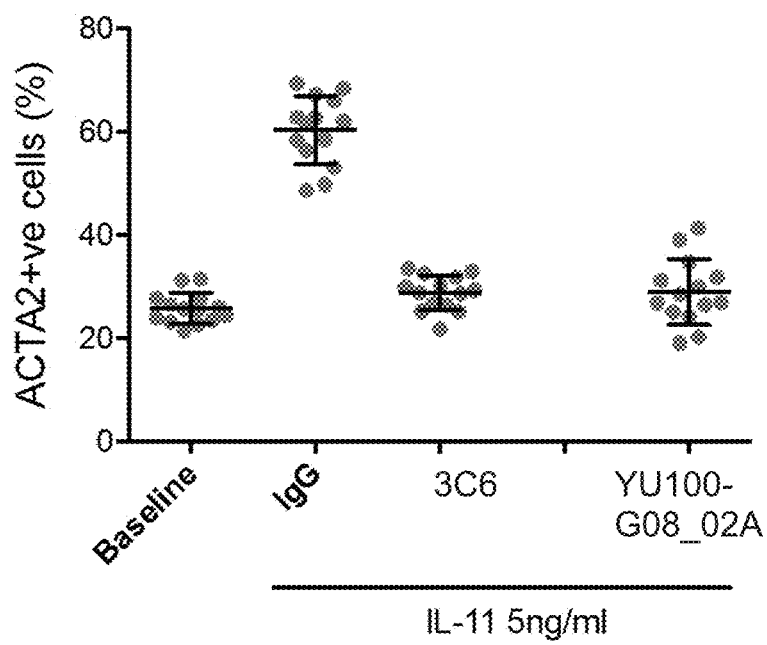

FIG. 30B shows that both anti-IL-11 antibodies inhibited the trans-differentiation of HSCs into myofibroblasts following IL-11 stimulation by TGFβ1.

The IC50 of YU100-G08_02A was determined by measuring MMP2 concentration from HSCs stimulated with IL-11. Primary human HSCs were incubated with TGFB1 (5 ng/ml) (left) or IL-11 (2 ng/ml) (right) and varying concentrations of antibody. MMP2 secretion into the supernatant by fibroblasts was assessed to estimate the % of inhibition.

Figure 30C:
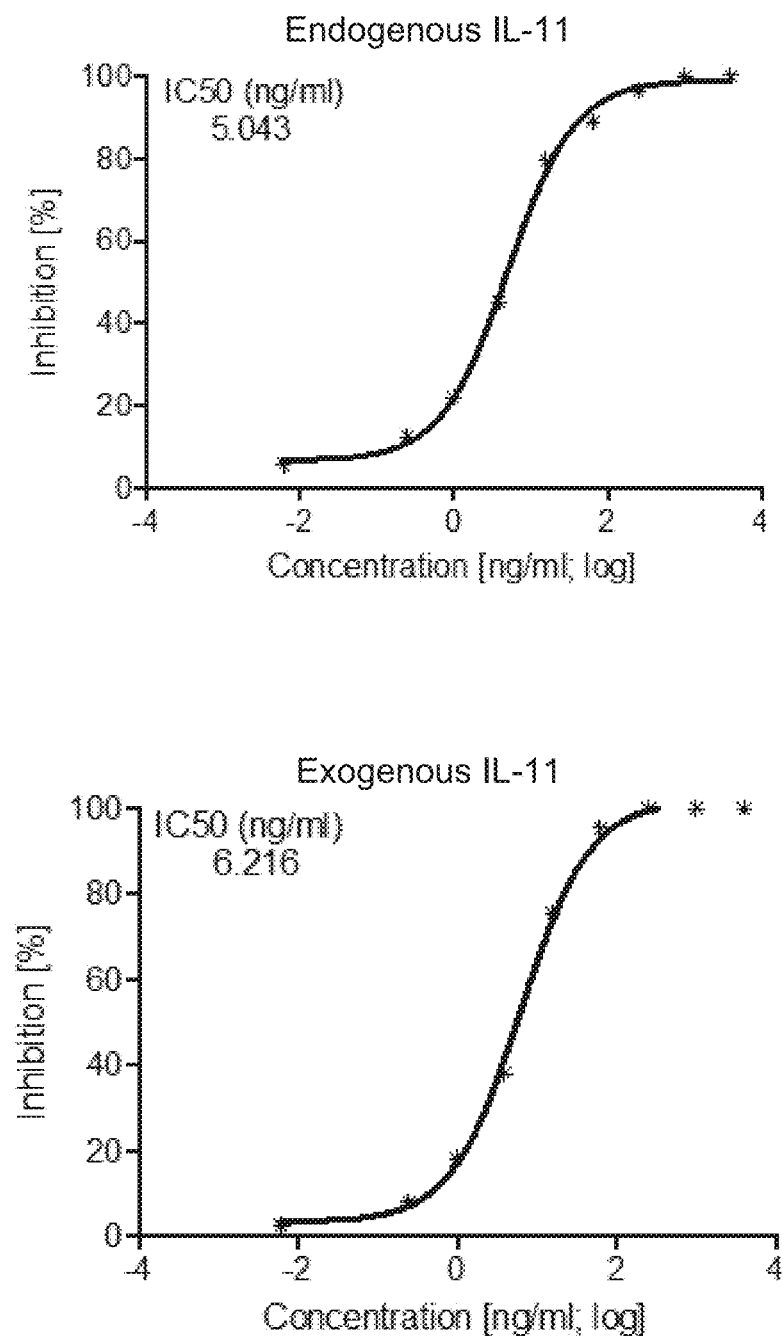

FIG. 30C shows that YU100-G08_02A neutralises the fibrotic response in HSCs.

14.1 Inhibition of Liver Fibrosis Using Anti-IL-11 Antibodies in a Preclinical Model of NASH Non-alcoholic steatohepatitis (NASH) is a common liver disease characterised by progression from inflammation to fibrosis and eventually liver failure.

Figure 31A:
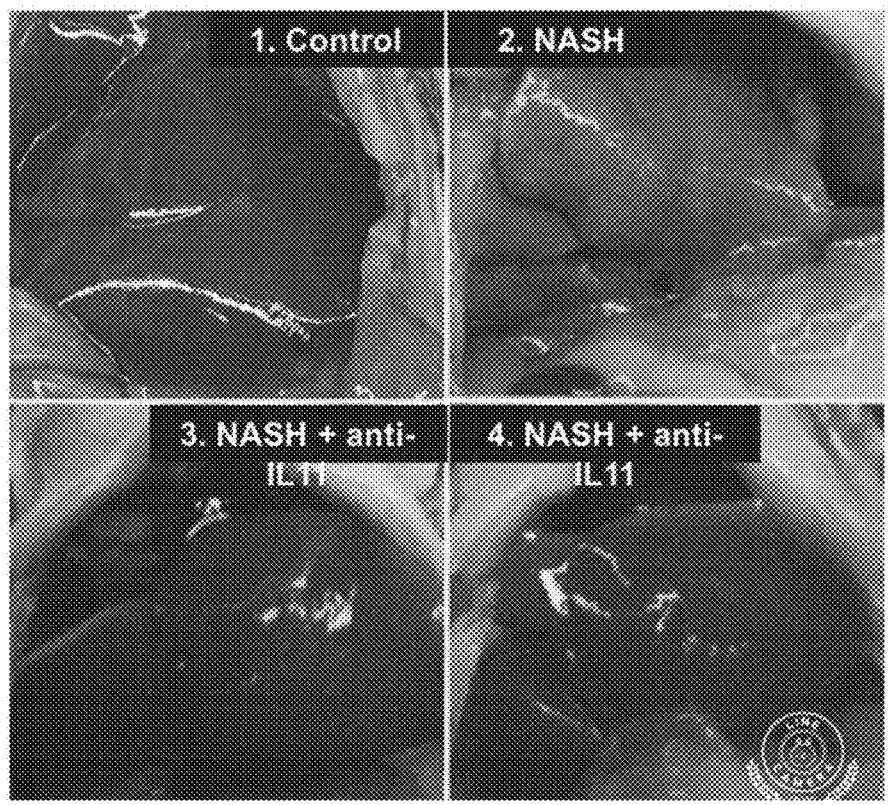
FIGS. 31A and 31B. Images and graph showing the results of analysis of liver tissue from mice subjected to different treatments in a mouse model of nonalcoholic steatohepatitis. Diabetic mice (db/db; deficient for the leptin receptor) were maintained for 8 weeks on a normal chow diet (left, round symbols) or on a NASH-inducing (methionine/choline deficient (MCD)) diet. In a subset of animals neutralizing anti-IL11 antibody was administered (20 mg/kg, 3×/week, intraperitoneal) for the final 3 weeks of the 8 week NASH diet. Liver samples were photographed (31A) and assessed for collagen content per mg of liver tissue (31B); each symbol represents an individual animal. P values shown on graph, ANOVA.

Diabetic mice (db/db; deficient for the leptin receptor) were maintained for 8 weeks on a normal chow diet or on a NASH-inducing (methionine/choline deficient (MCD)) diet. To test the efficacy of neutralizing anti-IL11 antibodies, anti-IL-11 antibody clone BSN-3C6 was administered (20 mg/kg, 3×/week, intraperitoneally) for the final 3 weeks of the 8 week NASH diet (FIG. 31A, bottom panels). Gross liver histology was assessed at time of euthanasia, and collagen content of the liver was analysed by hydroxyproline assay.

Figure 31B:
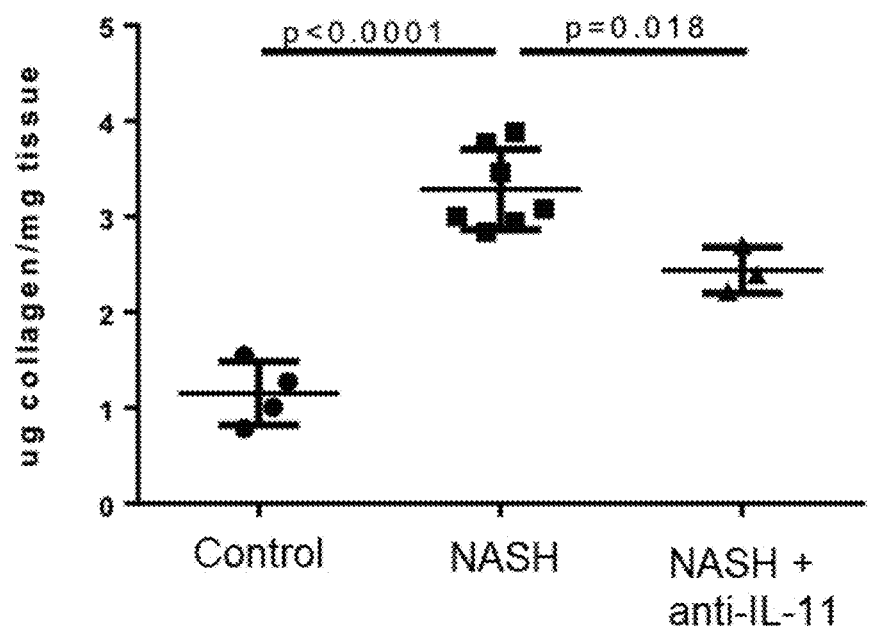

The results are shown in FIGS. 31A and 31B. Inhibition of IL-11 mediated signalling by anti-IL-11 antibody treatment improved liver histology in a mouse model of nonalcoholic steatohepatitis (FIG. 31A) as evidenced by partial restoration of liver morphology and texture in anti-IL-11 antibody-treated animals on NASH diet as compared to untreated animals on NASH diet. Livers from mice treated with anti-IL-11 antibody on NASH diet were also found to have reduced collagen content as compared to untreated animals on NASH diet (FIG. 31B).

In the same NASH model using diabetic mice, animals were fed on a normal chow (NC) diet for 12 weeks to reach the steatosis stage. Mice were then fed a MCD diet for 8 weeks to induce NASH. For those 8 weeks, mice were administered with 20 mg/kg anti-IL-11 antibody BSN-3C6 or IgG control twice per week.

Liver triglycerides (TG) measurements were performed using triglyceride colorimetric assay kit (Ser. No. 10/010, 303, Cayman). Total hydroxyproline content in the livers was measured using Quickzyme Total Collagen assay kit (Quickzyme Biosciences). Serum levels of alanine aminotransferase (ALT) was measured using Alanine Transaminase Activity Assay Kit (ab105134, abcam). To quantify expression of pro-inflammatory factors, total RNA was extracted from snap-frozen liver tissues using Trizol (Invitrogen) followed by RNeasy column (Qiagen) purification. The cDNAs were synthesized with iScript™ cDNA synthesis kit (Bio-Rad) according to manufacturer's instructions. Gene expression analysis was performed on duplicate samples with either TaqMan (Applied Biosystems) or fast SYBR green (Qiagen) technology using StepOnePlus™ (Applied Biosystem) over 40 cycles. Expression data were normalized to GAPDH mRNA expression and fold change was calculated using 2-ΔΔCt method. Total and phosphorylated ERK levels in livers were measured by Western blot. All measurements were compared to a steatosis control.

The results are shown in FIGS. 39A to 39F. Anti-IL-11 3C6 therapy was found to reduce hepatic triglyceride content (39A), liver hydroxyproline content (39B), expression of pro-inflammatory factors (39C, 39D), ALT serum levels (39E), and levels of phosphorylated ERK in livers (39F).

Thus, anti-IL-11 therapy was found to reduce hepatic steatosis, fibrosis, and inflammation in late-stage NASH compared to controls.

The effects of different concentrations of anti-IL-11 antibodies BSN-3C6 and YU100-G08_02A (0.5, 1, 5 and 10 mg/kg) were assessed in the NASH model after 4 weeks on the NASH (HFMCD) diet to induce liver damage and fibrosis. After one week of the NASH diet (at which time there is an established and robust steatohepatitis and ALT levels are ~800 u/L (~40-fold increase compared to normal chow)), animals were started on either IgG control antibody or ENx108A biweekly for a four-week period. Mice fed on the normal chow diet and IgG (10 mg/kg) were used as controls. Serum ALT levels and liver collagen content were measured as described above.

Figure 39D:
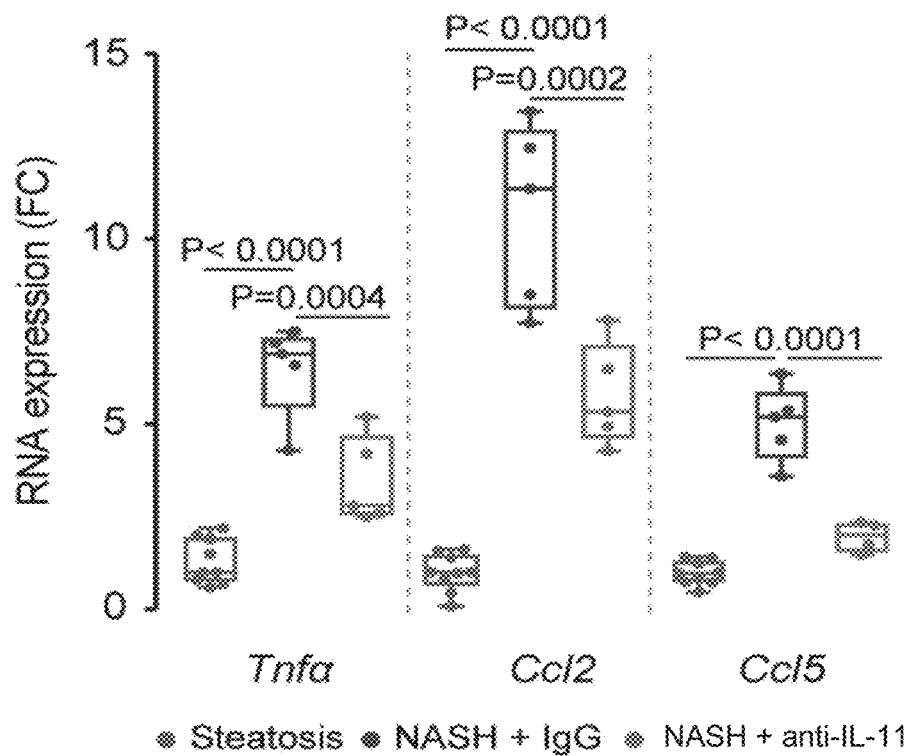
Figure 39E:
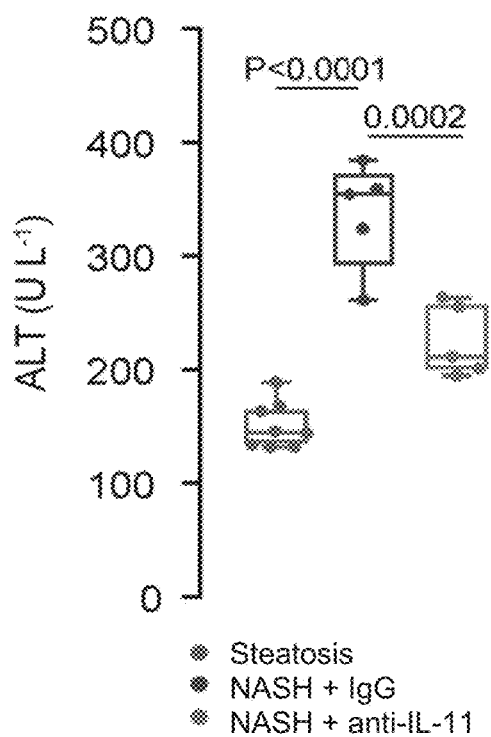
Figure 39H:
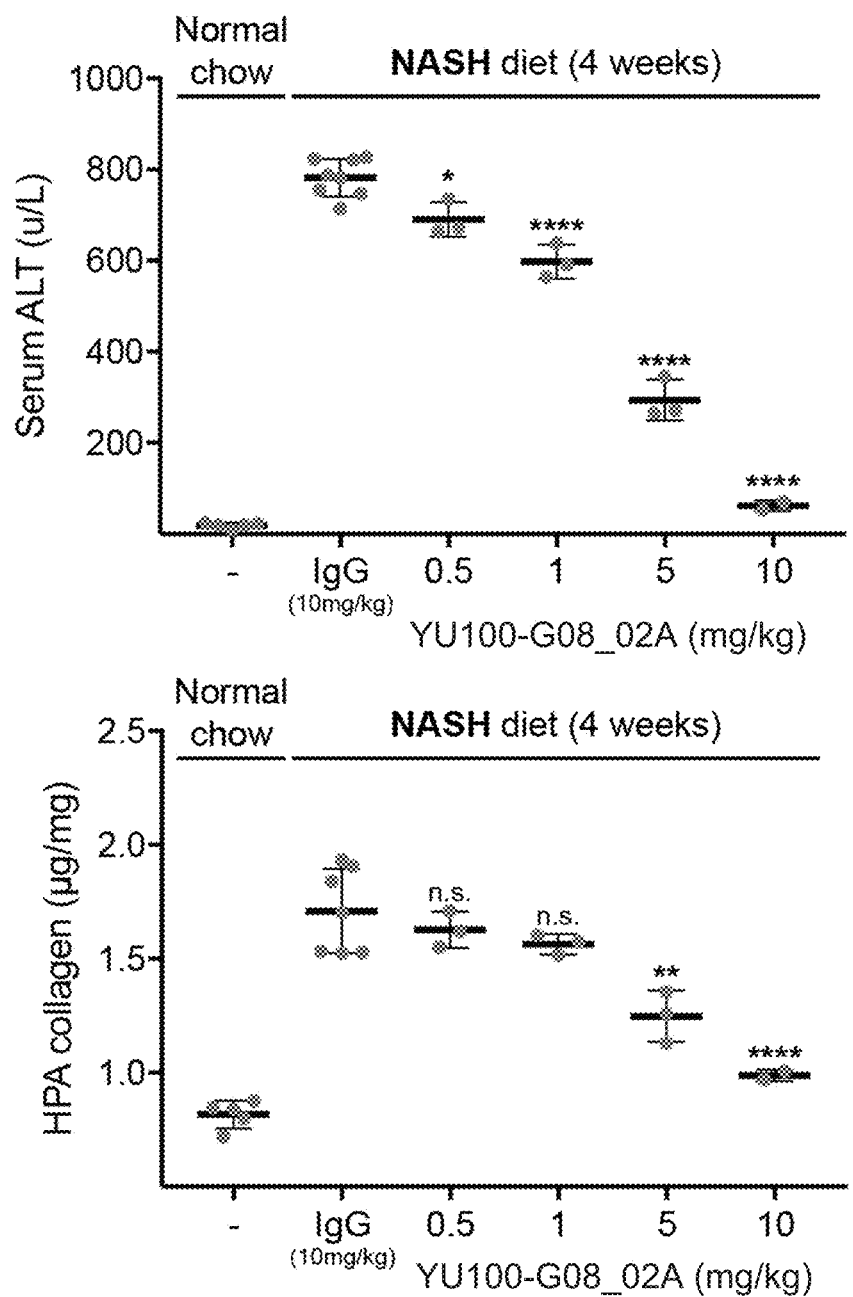

The results are shown in FIGS. 39G and 39H. Anti-IL-11 therapy was found to have a dose-dependent ameliorative effect on fibrosis indicators serum ALT levels and liver collagen content.

In a separate experiment, five-week old male C57BL/6N mice were fed MCD diet supplemented with 60 kcal % fat (A06071302, Research Diets) (HFMCD diet) to induce NASH. Control mice were fed with normal chow (NC, Specialty Feeds). After 6 weeks on the HFMCD diet, anti-IL-11 antibody BSN-3C6 (10 mg/kg) was administered biweekly for 4 weeks. Livers and serum were collected at week 10 and analysed for ERK activation, liver hydroxyproline content, and serum ALT levels, measured as previously described.

Figure 40A:
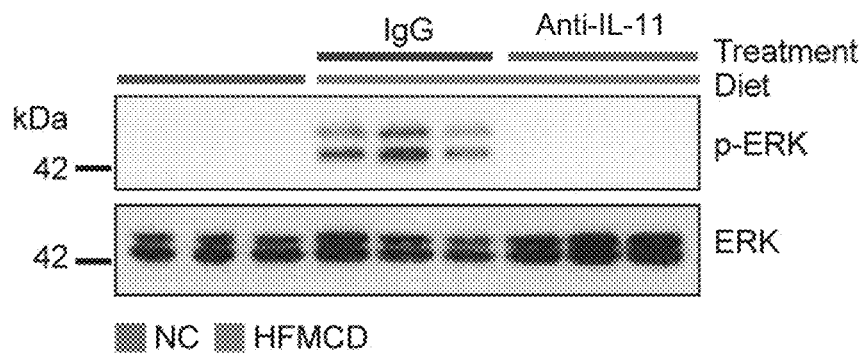
FIGS. 40A to 40D. Therapeutic effect of anti-IL-11 antibody in mouse models of advanced NASH. (A-C) Western blot and graphs showing the effect of anti-IL-11 antibody on ERK activation (40A), liver hydroxyproline content (40B) and serum ALT levels (40C) in a mouse NASH model after high fat methionine/choline-deficient (HFMCD) diet or normal chow (NC) diet. (40D) Another NASH model was stimulated by a single subcutaneous injection of streptozotocin and mice were fed on a normal chow diet for 4 weeks, then HFMCD diet for 7 weeks along with anti-IL-11 antibody or IgG control. Graph shows RNA expression of fibrosis and inflammation genes after 7 weeks.
Figures 40B, 40C:
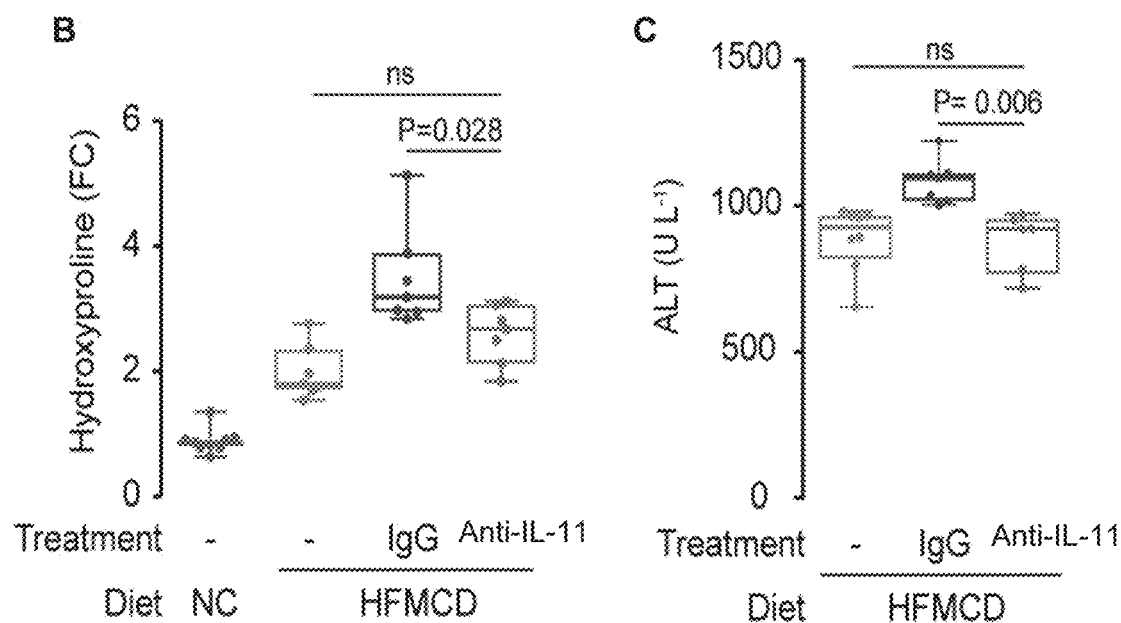

The results are shown in FIGS. 40A to 40C. Anti-IL-11 antibody was found to have abolished ERK activation (40A) and inhibited the progression of liver fibrosis (40B) and serum ALT levels (40C). FC: fold change.

Anti-IL-11 therapy was investigated in another model of advanced NASH. 2 day old C57BL/6 mice were administered a single subcutaneous injection of 200 μg streptozotocin and fed on a normal chow diet for 4 weeks. Mice were then switched onto a HFMCD diet for 7 weeks and then treated along with the HFMCD diet with 10 mg/kg anti-IL-11 antibody BSN-3C6 or IgG control 3× per week for a subsequent 7 weeks. RNA expression was measured for fibrosis and inflammation genes Col1a1, Col1a2, Col1a3, Timp1, Tgfβ1, Mmp2, Tnfα, Ccl2 and Ccl5.

Figure 40D:
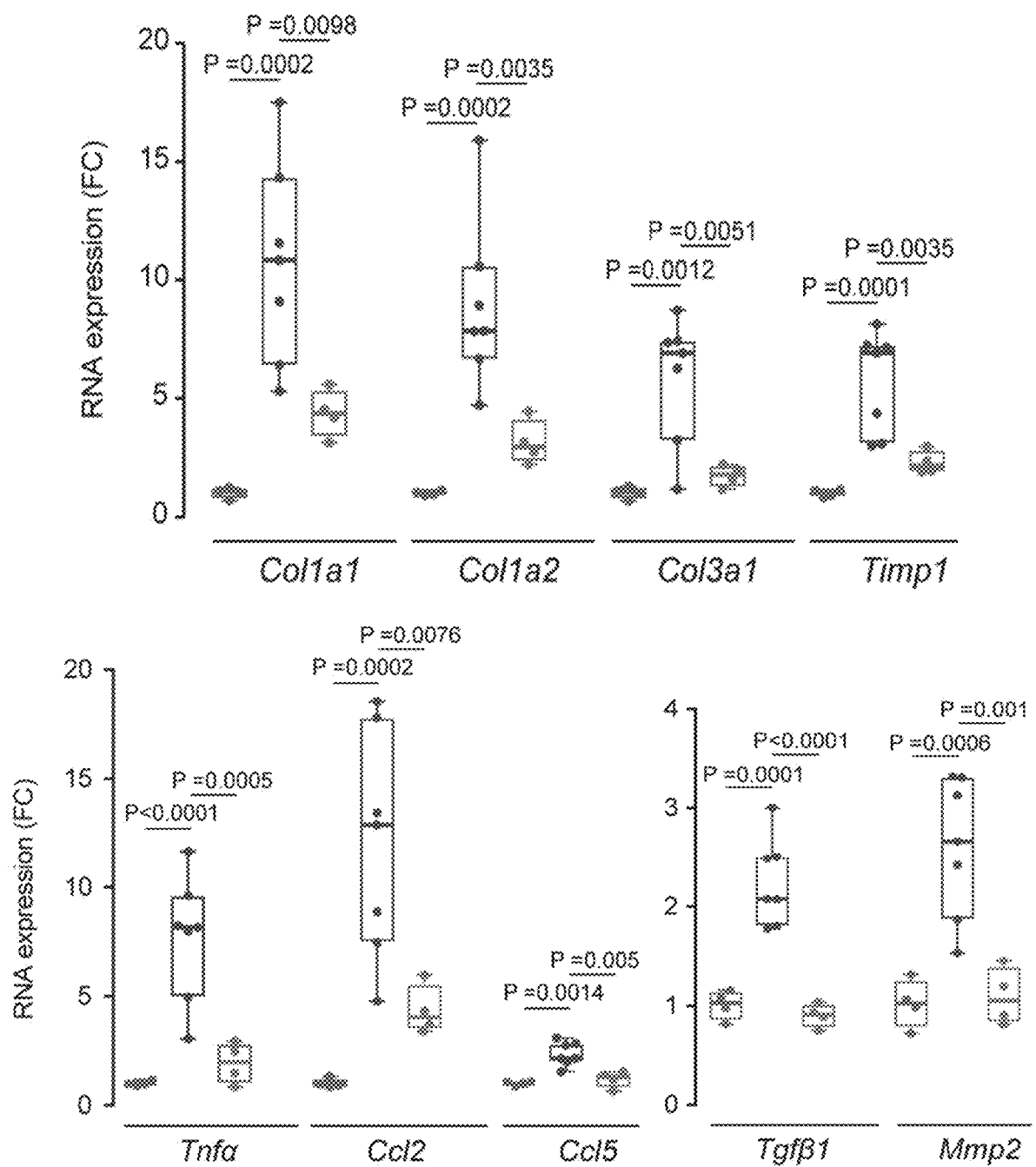
Figure 41C:
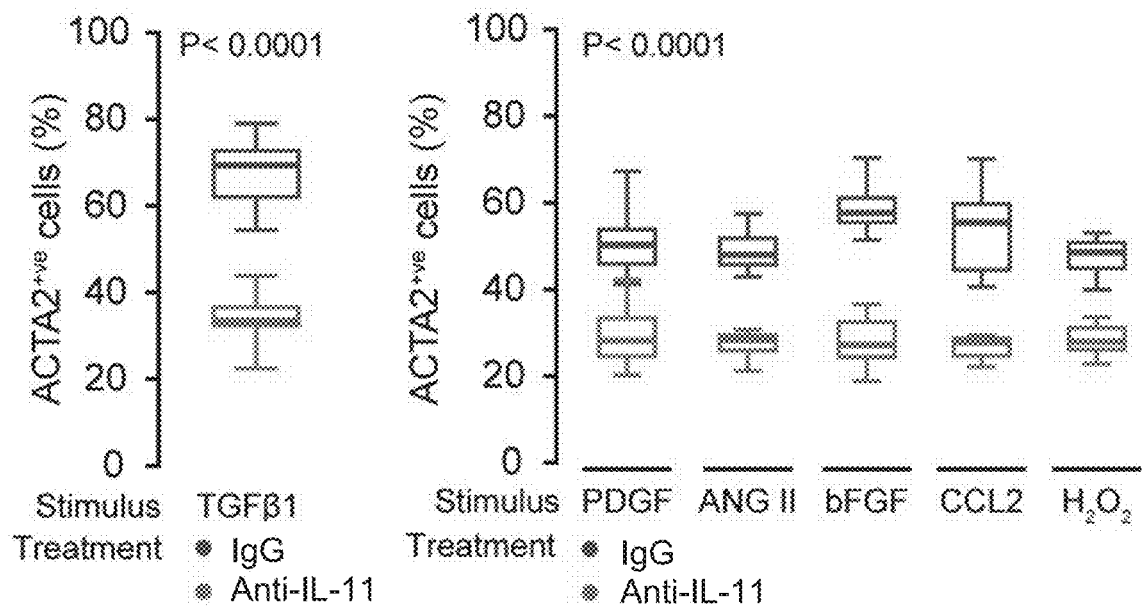
Figure 41D:
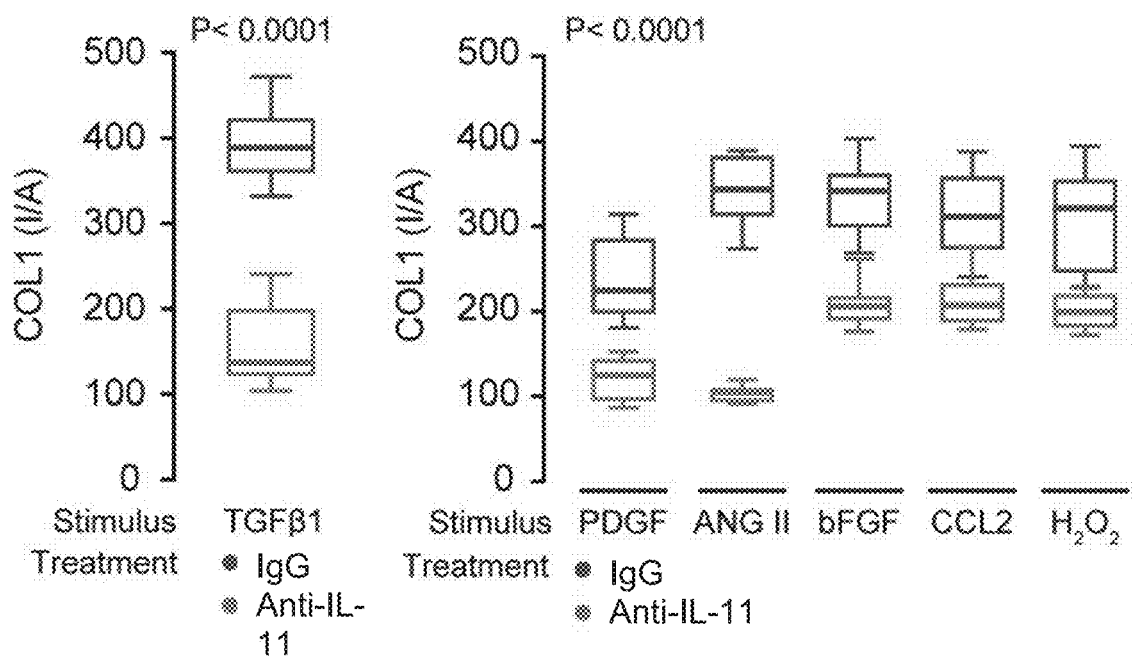

The results are shown in FIG. 40D. Anti-IL-11 therapy was found to robustly inhibit expression of genes indicative of fibrosis and inflammation.

Thus, anti-IL-11 therapy inhibits hepatic fibrosis and liver damage.

14.2 Inhibition of Myofibroblast Activation Using Anti-IL-11 Antibodies

Hepatic stellate cells (HSCs) play an important role in the pathogenesis of NASH. Pro-fibrotic stimuli e.g. TGFβ1, PDGF and pro-inflammatory factors can activate and transform HSCs into liver myofibroblasts which share features with fibroblast-derived myofibroblasts.

HSCs were treated with NASH-promoting factors in the presence or absence of anti-IL-11 antibody to investigate the transformation of HSCs to myofibroblasts.

HSCs were seeded in 96-well plates at a density of $5 \times 10^3$ cells per well and treated with TGFβ1 (5 ng ml$^{-1}$), PDGF (20 ng ml$^{-1}$), AngII (100 nM), bFGF (10 ng ml$^{-1}$), or CCL2 (5 ng ml$^{-1}$) in the presence of IgG control or anti-IL-11 antibody clone BSN-3C6 for 24 hours. Cells were then fixed in 4% paraformaldehyde (PFA, 28908, Thermo Fisher Scientific), permeabilized with 0.1% Triton X-100 (Sigma) and non-specific sites were blocked with 0.5% BSA and 0.1% Tween-20 in PBS. Cells were incubated overnight (4° C.) with primary antibodies (1:500), followed by incubation with the appropriate AlexaFluor 488 secondary antibodies (1:1000). EdU-Alexa Fluor 488 was incorporated using a Click-iT EdU Labelling kit (C10350, Thermo Fisher Scientific) according to manufacturer's protocol. Cells were counterstained with 1 μg ml-1 DAPI (D1306, Thermo Fisher Scientific) in blocking solution. Each condition was imaged from duplicated wells and a minimum of 7 fields per well using Operetta high-content imaging system 1483 (PerkinElmer). The quantification of ACTA2$^{+ve}$ cells was measured using Harmony v3.5.2 (PerkinElmer). The measurement of fluorescence intensity per area of Collagen I (normalized to the number of cells) was performed with Columbus 2.7.1 (PerkinElmer).

Anti-IL-11 antibody treatment was found to block transition of HSCs into myofibroblasts driven by NASH-promoting factors. The results are shown in FIGS. 41A to 41D. Representative fluorescent images show that anti-IL-11 antibody BSN-3C6 reduced the number of ACTA2$^{+ve}$ cells (41A) and the production of collagen I by HSCs (41B), scale bars=200 μm. The percentage of ACTA2$^{+ve}$ cells (41C) and collagen I production (41D) for each treatment was quantified, showing that fewer treated HSCs were ACTA2-positive or producing collagen, i.e. antibody treatment blocked the stimuli-driven transition of HSCs into myofibroblasts.

The effect of anti-IL-11 therapy on the invasive behaviour of human HSCs was assessed using 24-well Boyden chamber invasion assays (Cell Biolabs Inc.). HSCs were pre-treated with anti-IL-11 antibody clone BSN-3C6 or IgG control for 15 minutes prior to adding stimuli. Equal numbers of HSCs in serum-free HSC media were seeded in triplicates onto the ECM-coated matrigel and were allowed to invade towards HSC media containing 0.2% FBS. After 48 hours of incubation with invasive stimulants PDGF (20 ng ml$^{-1}$) or CCL2 (5 ng ml$^{-1}$), media was aspirated and non-invasive cells were removed using cotton swabs. The cells that invaded towards the bottom chamber were stained with cells staining solution (Cell Biolabs), imaged and counted under 40× magnification.

Figure 42:
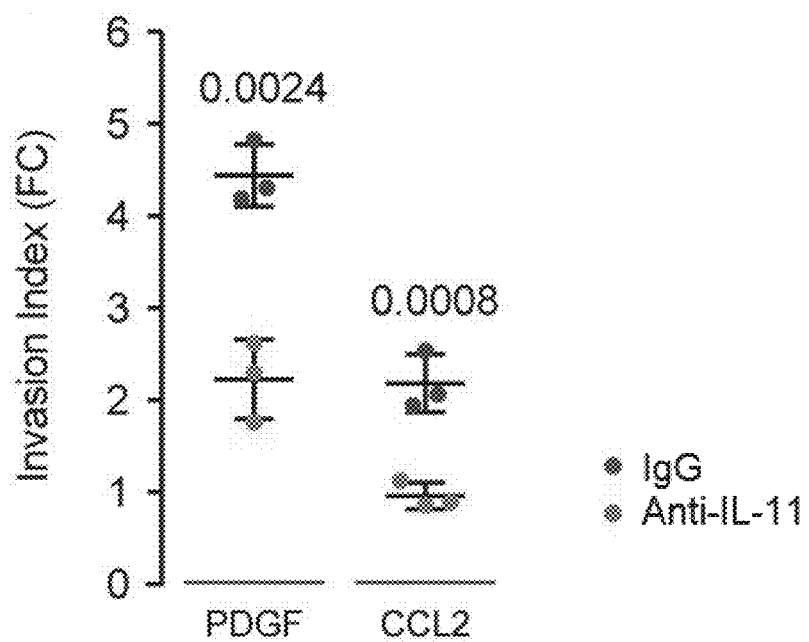
FIG. 42. Graph showing TGFβ1- and CCL2-induced matrigel invasion of HSCs pre-treated with anti-IL-11 antibody or IgG control.

The results are shown in FIG. 42. Anti-IL-11 antibody was found to prevent PDGF- and CCL2-induced matrigel invasion of HSCs.

14.3 Blocking IL-11 Signalling Inhibits Liver Inflammation in NASH

Beyond their role in liver fibrosis, HSCs have a central role in hepatic inflammation through the secretion and paracrine activity of pro-inflammatory cytokines and chemokines.

It was determined that IL-11 loss of function led to consistently lower levels of inflammation markers TNFα, CCL2 and CCL5. A study was performed to determine whether the effects on inflammation in vivo were related to the action of IL-11 on HSCs. CCL2 was measured by ELISA in the supernatants of HSCs (n=4/group) without stimulus (−), with IL-11, or with TGFβ1 in the presence of IgG control or anti-IL-11 antibody BSN-3C6; IL-11 (5 ng/ml), TGFβ1 (5 ng/ml), IgG, BSN-3C6 (2 μg/ml).

Figure 43:
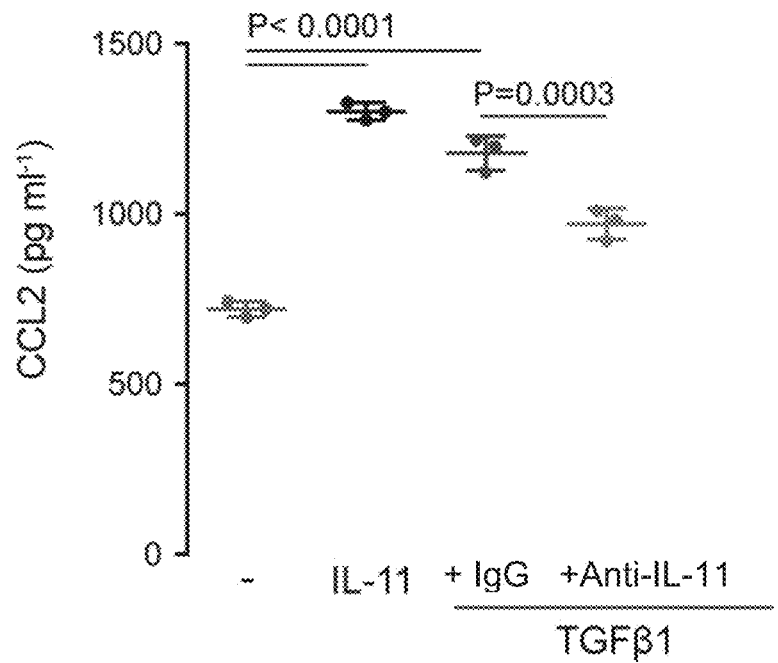
FIG. 43. Graph showing the effect of anti-IL-11 antibody on HSC CCL2 secretion without stimulus, stimulated with IL-11, or stimulated with TGFβ1 in the presence of IgG or anti-IL-11 antibody.

The results are shown in FIG. 43. It was found that IL-11 stimulated HSC secretion of CCL2 whereas IL-11 inhibition by anti-IL-11 antibody blocked CCL2 secretion. This reveals an unappreciated role for IL-11 in stromal immunity and shows that IL-11 neutralisation inhibits paracrine effects of pro-inflammatory factors secreted from HSCs on other cells in the hepatic niche.

14.4 Neutralisation of IL-11 Signalling Reverses Hepatic Fibrosis

Severe liver fibrosis was established by feeding mice the NASH MCD diet for 10 weeks. Feed was then switched to normal chow (NC) and mice were treated with anti-IL-11 antibody BSN-3C6 (20 mg/kg) twice per week for six weeks. Mice fed on NC diet for the duration of the experiment and IgG antibody were used as controls. Liver hydroxyproline content, i.e. total collagen content, was measured as previously described.

Figure 44A:
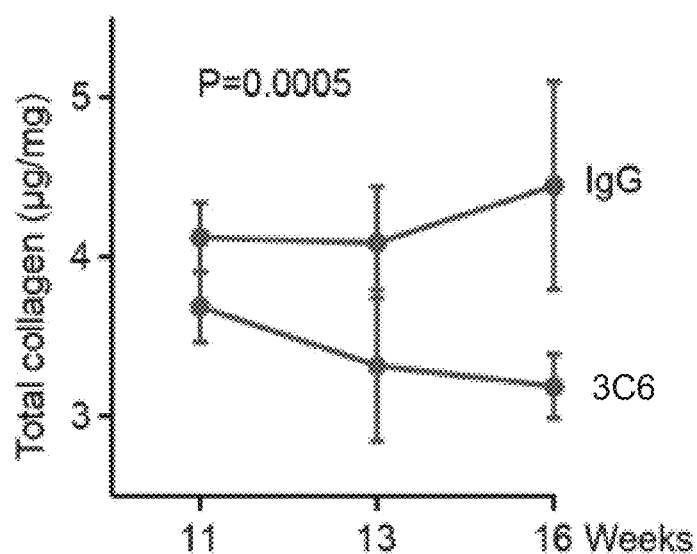
FIGS. 44A to 44D. The reversing effect of anti-IL-11 therapy on liver fibrosis. (44A) Liver hydroxyproline content indicating total hepatic collagen content (44B) Acta2 expression in HSCs. (44C) Percentage of ACTA2$^{+ve}$ HSCs stimulated by TGFβ1 or PDGF. (44D) MMP2 concentration after HSC stimulation by TGFβ1 or PDGF.

The results are shown in FIG. 44A. Hepatic collagen content was significantly reversed after three weeks of anti-IL-11 antibody treatment and even greater reversal was seen at six weeks. Notably, hepatic collagen content remained unchanged in IgG control-treated animals for the duration of the experiment.

Figure 44B:
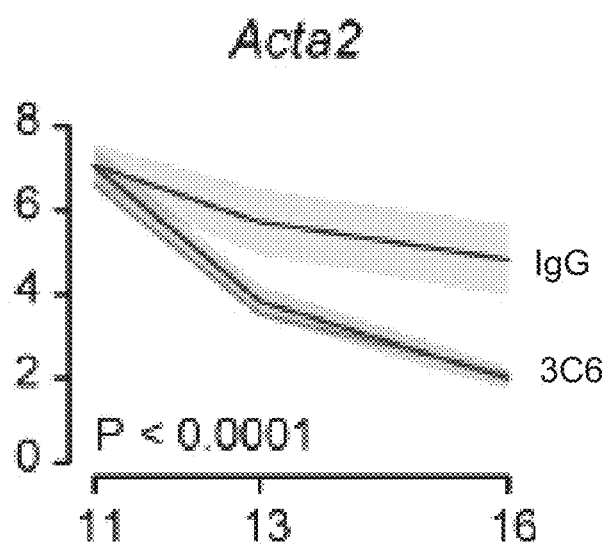

Reversal of hepatic fibrosis is favoured when transformed HSCs undergo senescence or reversion to an inactive, ACTA2$^{−ve}$ cellular state. FIG. 44B shows that anti-IL-11 therapy was found to decrease Acta2 expression.

To check directly if IL-11 signalling is required to maintain HSCs in a transformed state, HSCs were stimulated with TGFβ1 or PDGF for 72 hours and then treated with anti-IL-11 antibody BSN-3C6 for a further 24 or 48 hours in the presence of ongoing TGFβ1 or PDGF stimulation. Unstimulated HSCs were used as a non-fibrotic control.

Figure 44C:
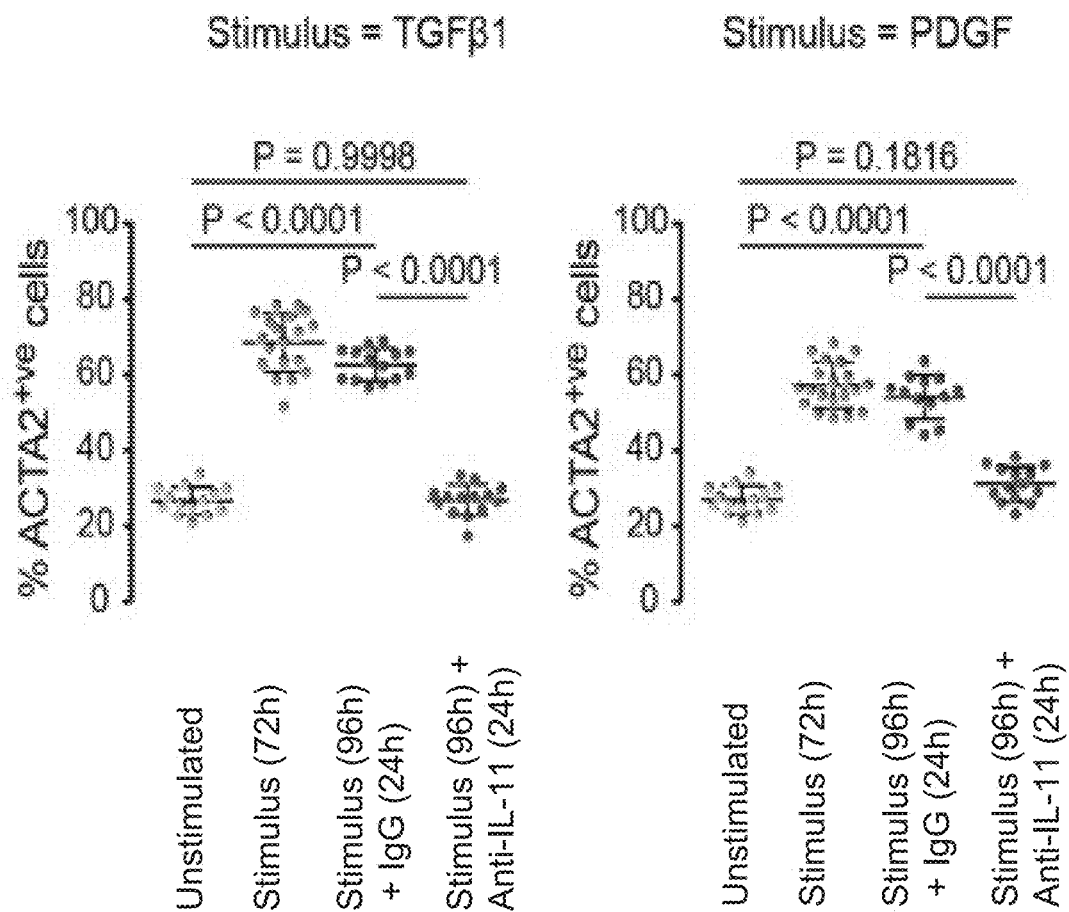

The results are shown in FIG. 44C. Within 24 h of IL-11 inhibition, the percentage of ACTA2$^{+ve}$ cells was reversed to near baseline levels, whether HSCs were stimulated with TGFβ1 or PDGF. The amount of secreted collagen was also reversed to near baseline levels.

Figure 44D:
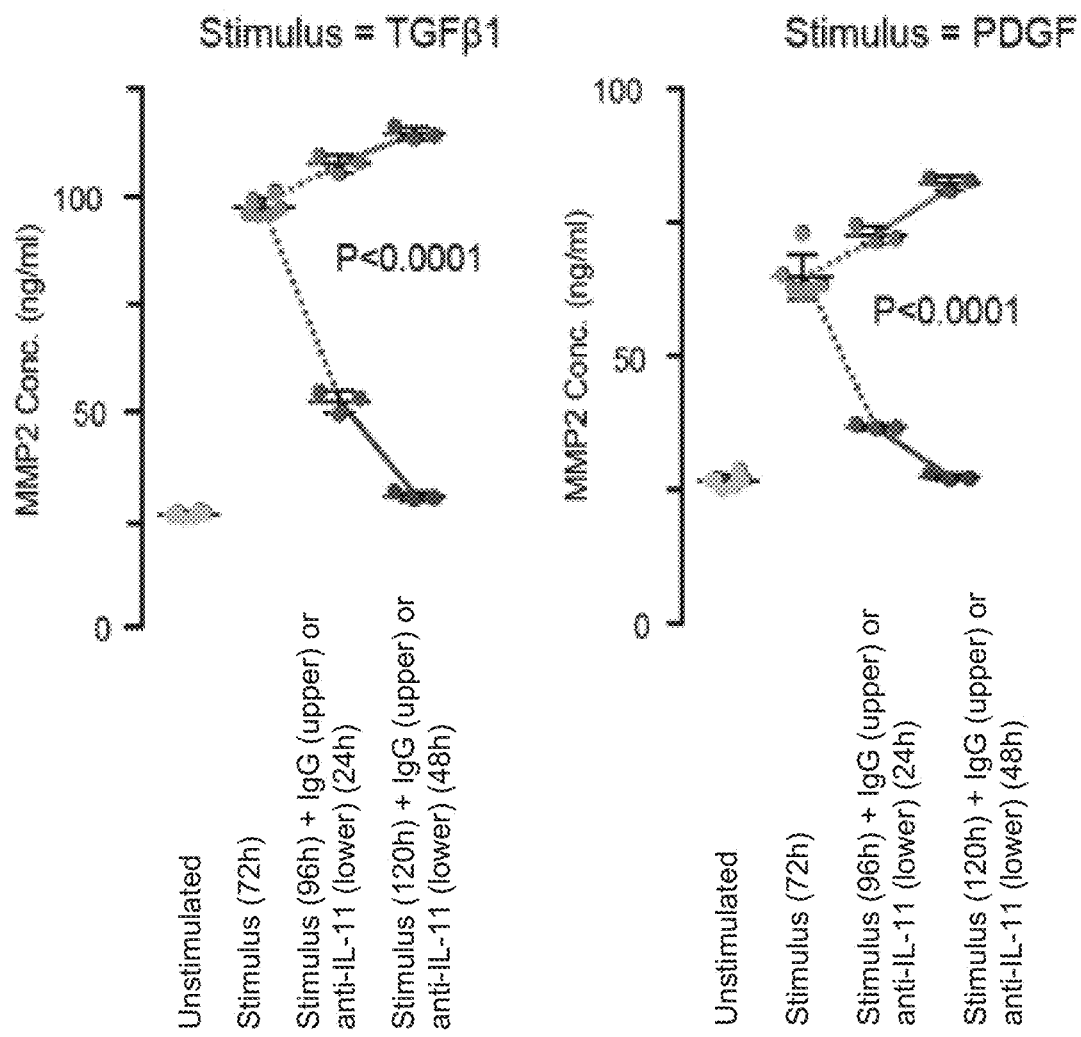

The MMP2 concentration was measured after 24 or 48 hours of treatment with anti-IL-11 therapy. The results are shown in FIG. 44D. Anti-IL-11 therapy reduced MMP2 concentration after 24 h and reversed MMP2 concentration to near baseline levels after 48 h.

Therefore, inhibition of IL-11-dependent HSC transformation causes HSC senescence/reversion and favourable matrix remodelling leading to fibrosis regression.

The effect of anti-IL-11 therapy in early stage NASH was investigated. In the HFMCD diet model of NASH, inflammation peaks at six weeks and is then followed by a phase of severe fibrosis. Mice were fed the HFMCD diet for one week and then treated twice a week for a further five weeks on the diet with 10 mg/kg anti-IL-11 antibody BSN-3C6 or IgG control. ERK phosphorylation, triglyceride content and serum ALT levels were assessed as before. Liver tissues were fixed for 48 hours at RT in 10% neutral-buffered formalin (NBF), dehydrated, embedded in paraffin blocks and sectioned at 7 μm. Sections stained with Masson's Trichrome were examined by light microscopy, scale bars 100 μm.

The results are shown in FIGS. 45A to 45E. Inhibition of IL-11 signalling during early steatohepatitis using anti-IL-11 therapy was found to result in mice having livers which were strikingly less steatotic (45A) and which had lesser ERK activation (45B). At the molecular level, there was a significant reduction in triglyceride content (45C) and livers of mice that received anti-IL-11 therapy did not show lipid droplets compared to IgG control (45D). HFMCD diet induces marked steatohepatitis and liver damage after one week (ALT>700 U L-1), which was reversed in a dose-dependent manner to near normal after three weeks of anti-IL-11 treatment (45E). The mice that received anti-IL-11 therapy did not develop fibrosis during the experiment, reaffirming the strong anti-fibrotic effects associated with inhibition of IL-11 signalling.

The effect of anti-IL-11 treatment on the expression of pro-fibrotic and pro-inflammatory genes in the NASH mouse model was assessed using RNA-seq and qPCR.

Figure 45A:
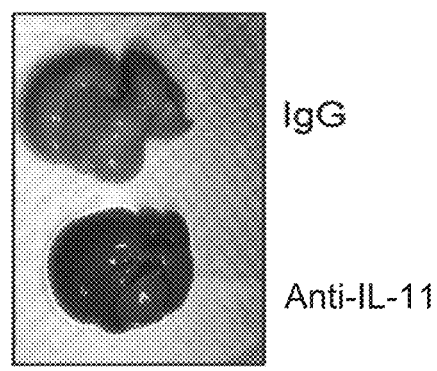
FIGS. 45A to 45H. The effect of anti-IL-11 therapy in early stage NASH. (45A) Representative gross liver images. (45B) Western blot showing ERK activation in mice on HFMCD diet after treatment with anti-IL-11 antibody or IgG control. (45C) Triglyceride content in mice on HFMCD diet after treatment with anti-IL-11 antibody or IgG control. (45D) Representative Masson's Trichrome stained images of livers of mice of mice that received anti-IL-11 therapy or IgG control. (45E) Serum ALT levels in mice on HFMCD diet after treatment with anti-IL-11 antibody or IgG control. (45F) Differential expression heatmap of pro-fibrotic and pro-inflammatory genes Z-scores in mice on normal chow diet and mice on HFMCD diet after treatment with anti-IL-11 antibody or IgG control. (45G) RNA expression of pro-inflammatory genes. (45H) RNA expression of pro-fibrotic genes.
Figure 45B:
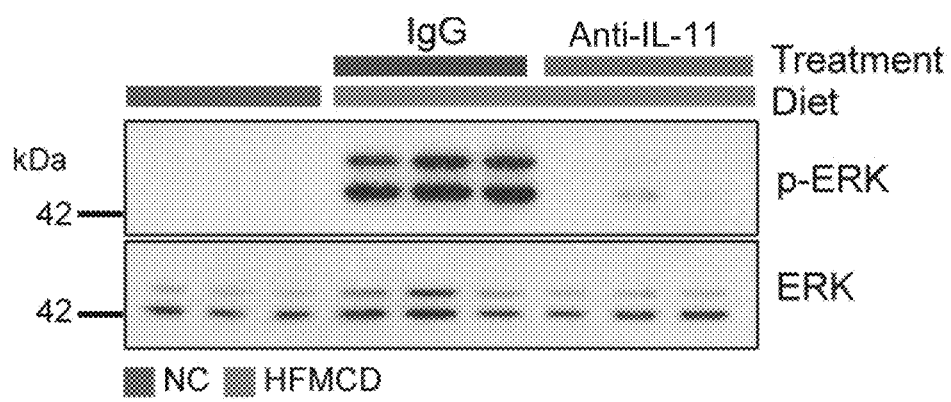
Figure 45C:
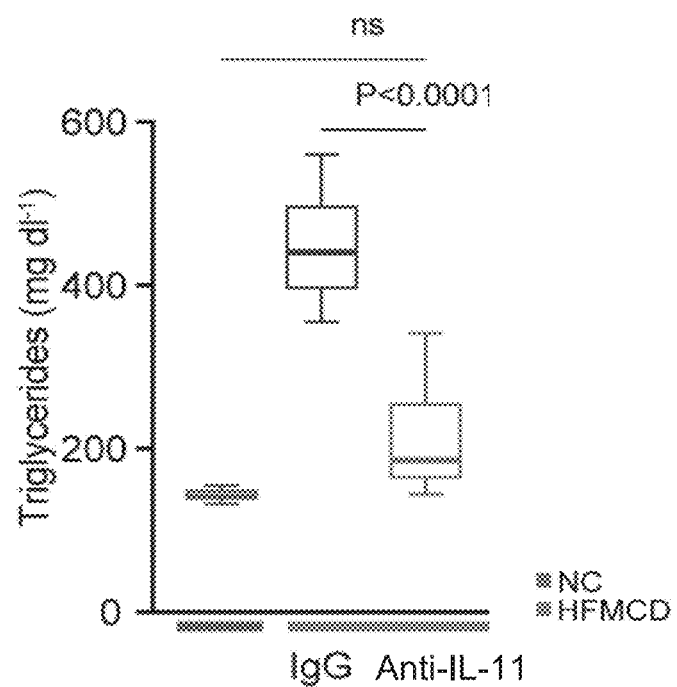
Figure 45D:
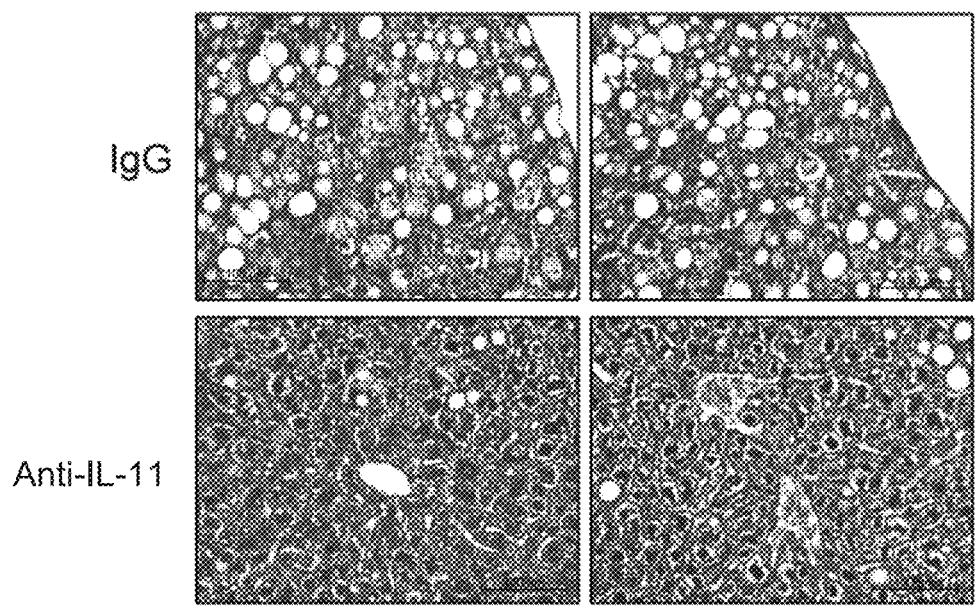
Figure 45E:
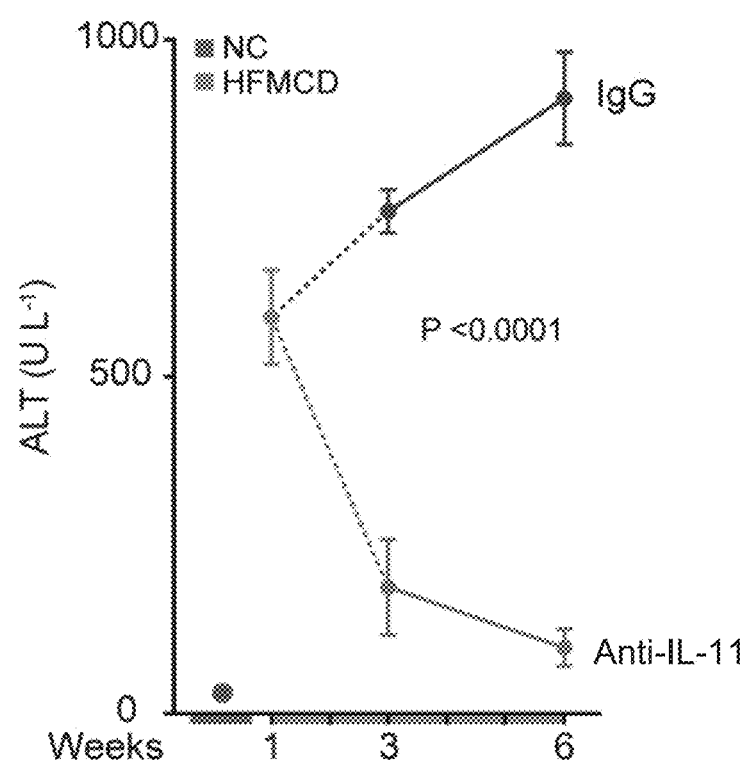
Figure 45F:
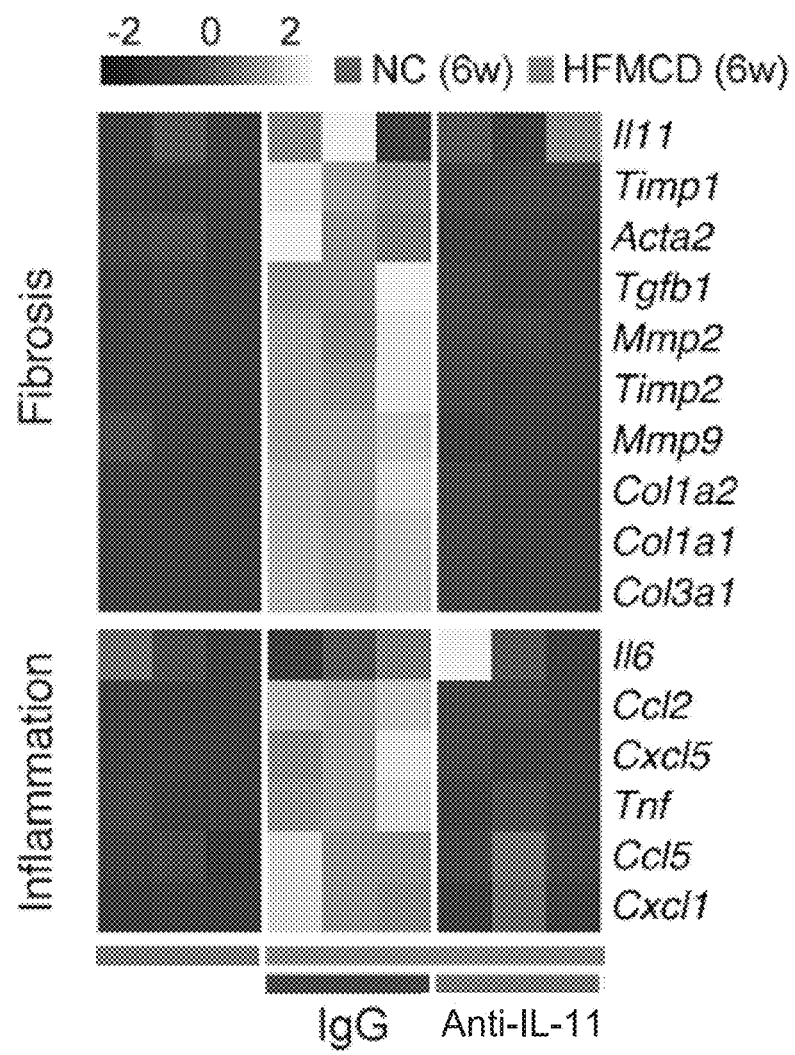
Figure 45G:
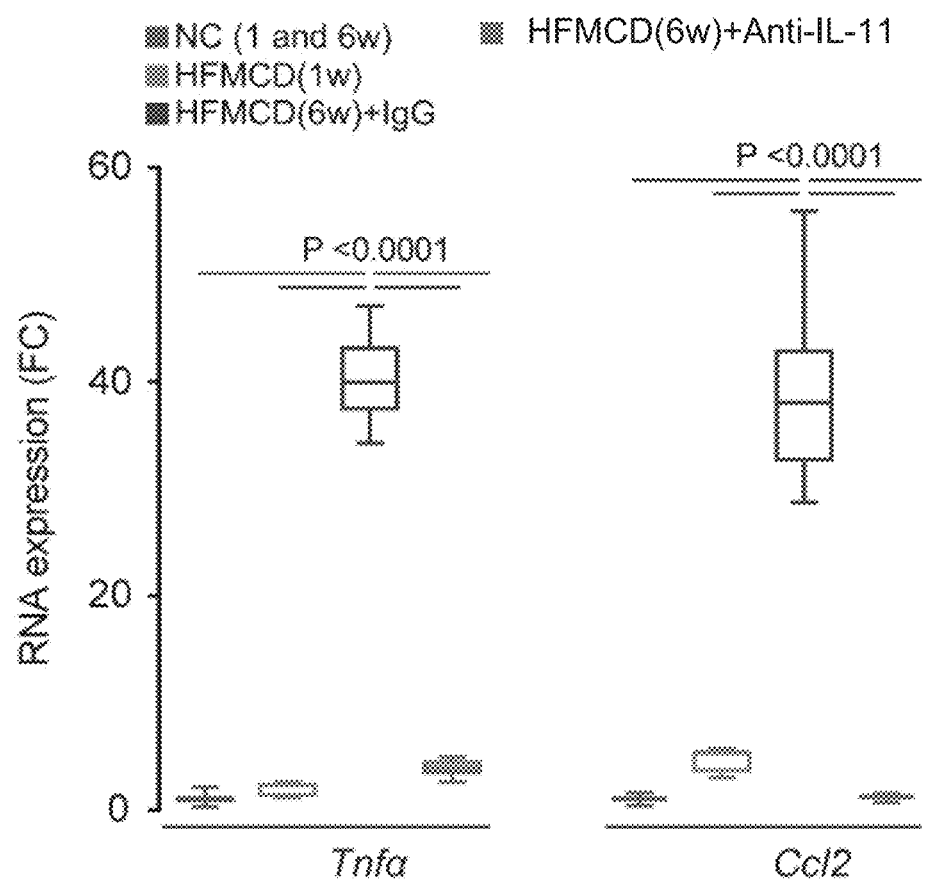
Figure 45H:
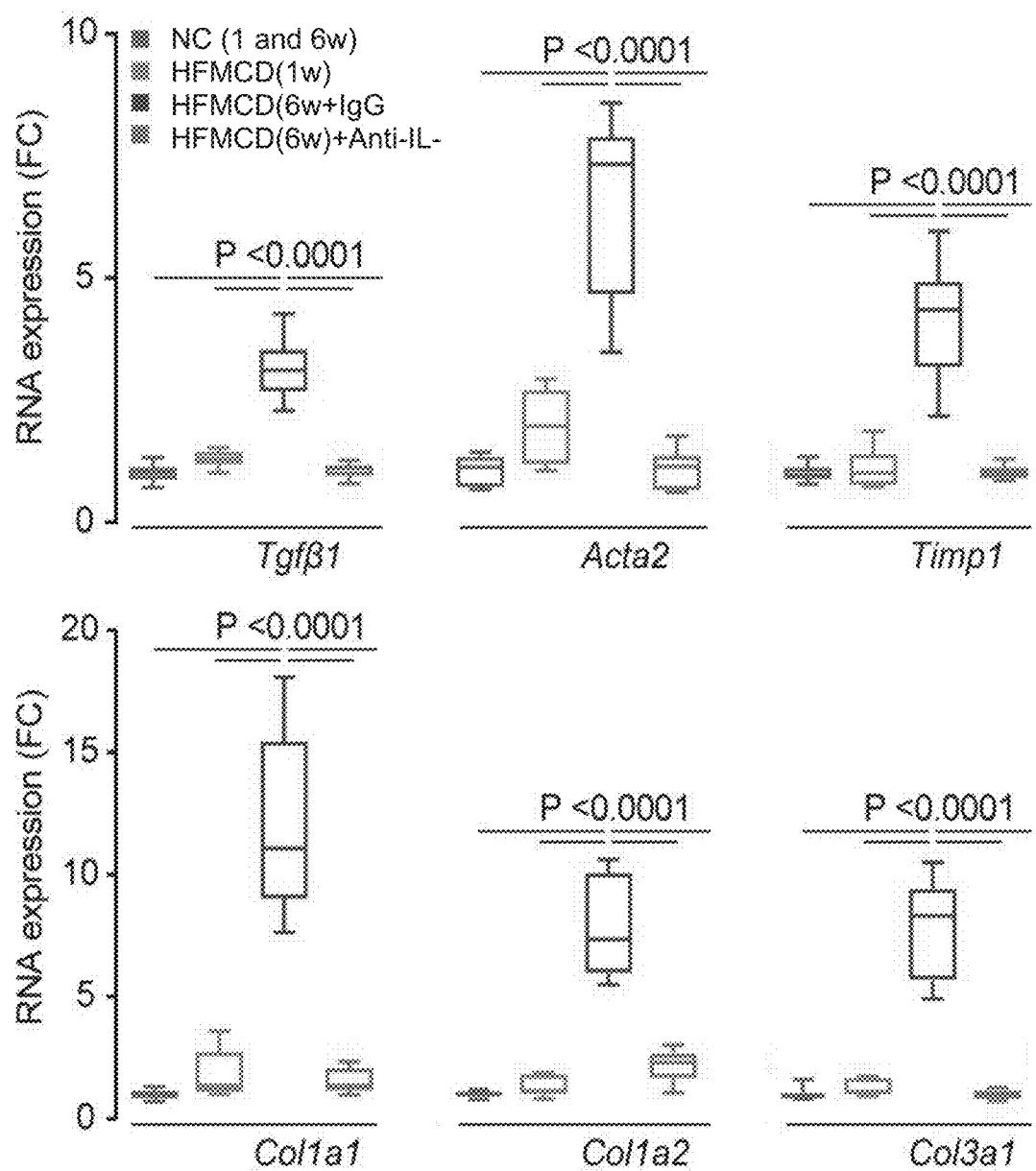

The results are shown in FIGS. 45F to 45H. Upregulation of pro-fibrotic and pro-inflammatory genes was abolished after treatment with anti-IL-11 antibody. Differential expression heatmap of pro-fibrotic and pro-inflammatory genes Z-scores (Transcripts Per Million mapped reads, TPM) shows that anti-IL-11 treatment produced similar expression of pro-fibrotic and pro-inflammatory genes as observed in mice on a NC control diet (non-NASH) (45F). Neither inflammation markers Tnfa and Cc/2 (45G) nor pro-fibrotic markers Tgfβ1, Acta2, Timp1, Col1a1, Col1a2 or Col3a1 (45H) were upregulated in mice treated with anti-IL-11 antibody.

Thus, neutralisation of IL-11 signalling reverses liver damage in early stage NASH.

In summary, IL-11 is required for HSC activation and transformation and has a central role in HSC pathobiology. IL-11 neutralising antibodies show disease-modifying therapeutic impact beyond anti-fibrotic effects alone. IL-11 antibodies could reverse hepatic stellate cell (HSC) activation downstream of TGFβ1 or PDGF. Inhibition of IL-11 signalling prevents inflammation and steatosis and can reverse liver fibrosis and hepatocyte damage during late stages of the disease. When given earlier, during steatohepatitis, anti-IL-11 therapy blocks inflammatory signals from HSCs and prevents hepatocyte damage.

Example 15: Inhibition of Eye Fibrosis Using Anti-IL-11 Antibodies

The anti-fibrotic effect of anti-IL-11 antibody treatment was assessed in a mouse model of retinal fibrosis in which Bruch's membrane is disrupted, as described in Caballero et al., Exp Eye Res. (2009) March; 88(3):367-77.

Briefly, mice were subjected to laser-induced retinal damage (4 burns per retina) and were then treated by intraocular administration of antibodies (0.5 μg of either IgG control or anti-IL11 antibody clone BSN-3C6) on days 1, 7, 14 and 21. Eyes were harvested for histological analyses on day 28. The area of fibrosis at burn sites was measured using Masson's Trichrome staining, blinded to treatment.

Figure 32A:
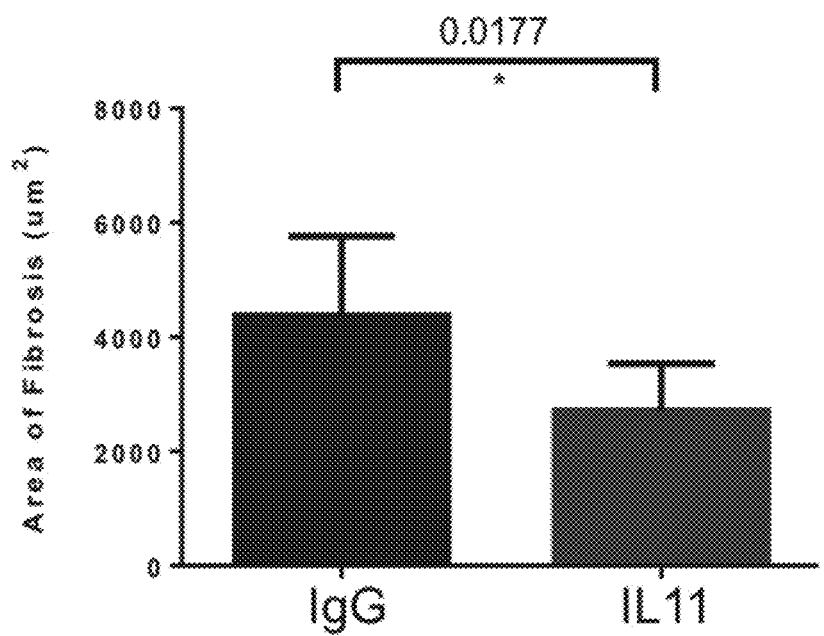
FIGS. 32A to 32D. Bar chart and images showing the results of analysis of eye fibrosis from mice subjected to different treatments in a mouse model of retinal fibrosis. Mice (10 per group) were subjected to laser-induced retinal damage (4 burns per retina) and administered intraocularly with 0.5 μg of anti-IL-11 antibody or IgG control antibody on days 1, 7, 14 and 21. Eyes were harvested for histological analyses on day 28. The area of fibrosis at burn sites were measured by Masson's Trichrome staining. (32A) Bar chart showing quantification of the fibrosis areas in control (IgG) or anti-IL11 (IL11) treated mice. (32B) representative images showing staining of fibrotic areas in control antibody treated eyes (IGG, top panel) or anti-IL11 treated eyes (IL11, bottom panel). (32C) Mice were treated with Eylea+IgG control or an Eylea+BSN-3C6 combination therapy. Bar chart showing quantification of the fibrosis area in control, low anti-IL-11, or high anti-IL-11 treatment. (32D) Bar chart showing area of leakage fold change in choroidal neovascularisation before and after intravitreal injections (IVT) of anti-IL-11 therapy (low and high concentration).
Figure 32B:
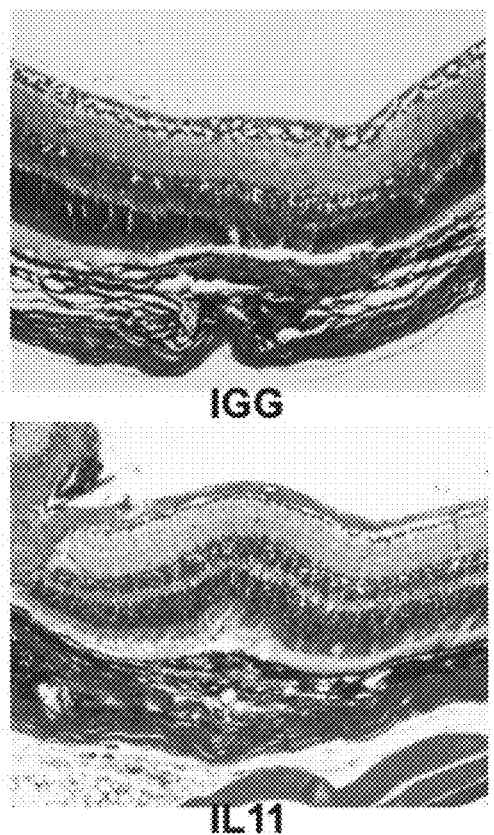

The results are shown in FIGS. 32A and 32B. The area of fibrosis was significantly greater in control IgG-treated mice as compared to anti-IL11 antibody treated mice.

In a separate experiment, mice (n=10) were subjected to retinal burns by laser (4 per eye) and treated with either Eylea (Aflibercept; Regeneron)+IgG control or an Eylea+BSN-3C6 combination therapy. Four weeks after injury, retina were stained/quantified for collagen (blinded).

Figure 32C:
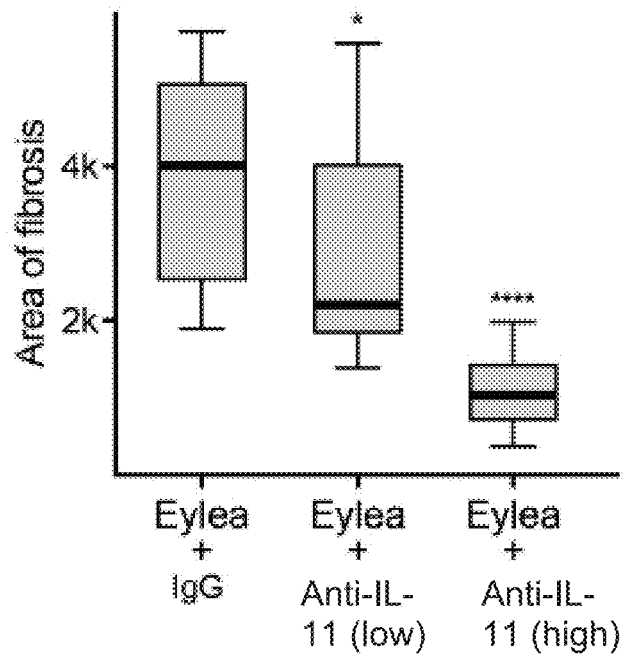

The results are shown in FIG. 32C. Anti-IL-11 therapy was found to reduce the area of fibrosis in the eye compared to IgG control. Thus, anti-IL-11 therapies reduce the fibrotic response in the context of anti-VEGF therapies.

Choroidal neovascularisation (CNV) was assessed using fluorescein fundus angiogram analysis. CNV lesions were monitored 7 and 28 days after laser-induced rupture of Bruch's membrane.

Figure 32D:
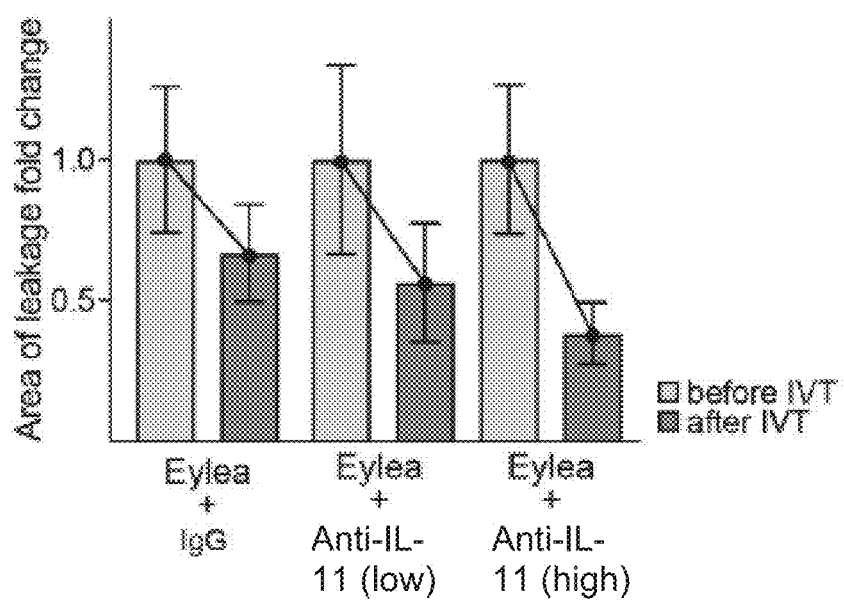

The results are shown in FIG. 32D. Measurements indicate the extent of CNV by area of leakage fold change before and after intravitreal injections (IVT) of antibodies. Anti-IL-11 therapy reduced the area of leakage fold change.

Example 16: Inhibition of Skin Fibrosis Using Anti-IL-11 Antibodies

The anti-fibrotic effect of anti-IL-11 antibody treatment was analysed in a mouse model of skin fibrosis stablished by subcutaneous injection of bleomycin (BLM, Sigma B2434, 50 μg/day).

Figure 33A:
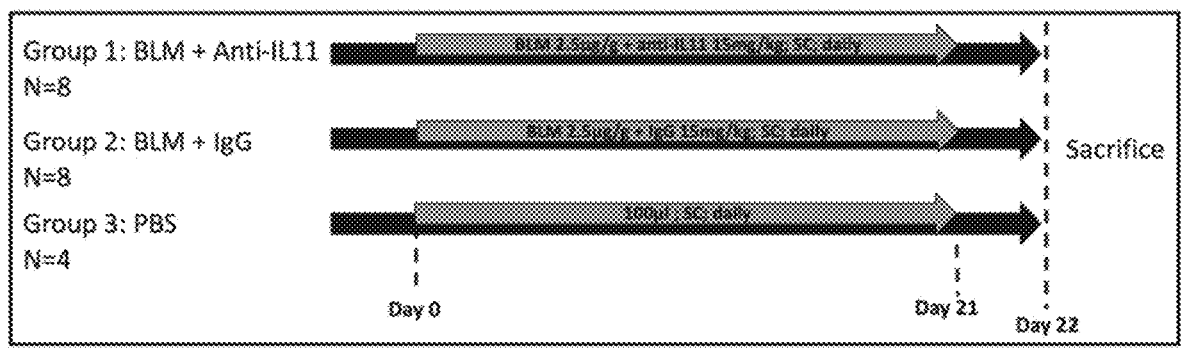
FIGS. 33A to 33C. Schematic, images and bar chart relating to analysis of skin fibrosis in mice subjected to different treatments in a mouse model of skin fibrosis. (33A) Schematic representation of experimental procedures for different treatment groups. Groups 1 and 2 were treated with bleomycin (BLM), and either anti-IL-11 antibody (Group 1) or IgG control antibody (Group 2). Group 3 were injected with vehicle (PBS) only and do not develop fibrosis. (33B) Images showing Masson's trichrome staining of skin section at equal distances from the injection site. Dermal thickness is indicated by the black bar. (33C) Bar chart showing the results of analysis of dermal thickness (blinded for treatment groups). Average dermal thickness was determined from the bottom of epithelial layer to top of dermal white adipose tissue layer across 40 fields of view per sample. Each point indicates an animal. P value was calculated using an unpaired two-tailed t-test.

Briefly, the fur on the middle of the back of the mice (~9 cm$^2$) was trimmed using scissors, and hair removal cream was applied to remove fur completely. Subcutaneous injections of 100 μL of bleomycin dissolved in PBS at a concentration of 0.5 mg/ml were performed on the top half of the injection site. Subcutaneous injections of 60 μL of anti-IL11 antibody clone BSN-3C6 or control IgG antibody were subsequently performed on the bottom half of the injection site (dosage=15 mg/kg/day). Injections were performed daily for 21 days and animals were sacrificed one day after the final injection and analysed histologically for dermal thickness and collagen content (by Masson's trichrome staining). FIG. 33A shows a schematic representation of experimental procedures for different treatment groups.

Figure 33B:
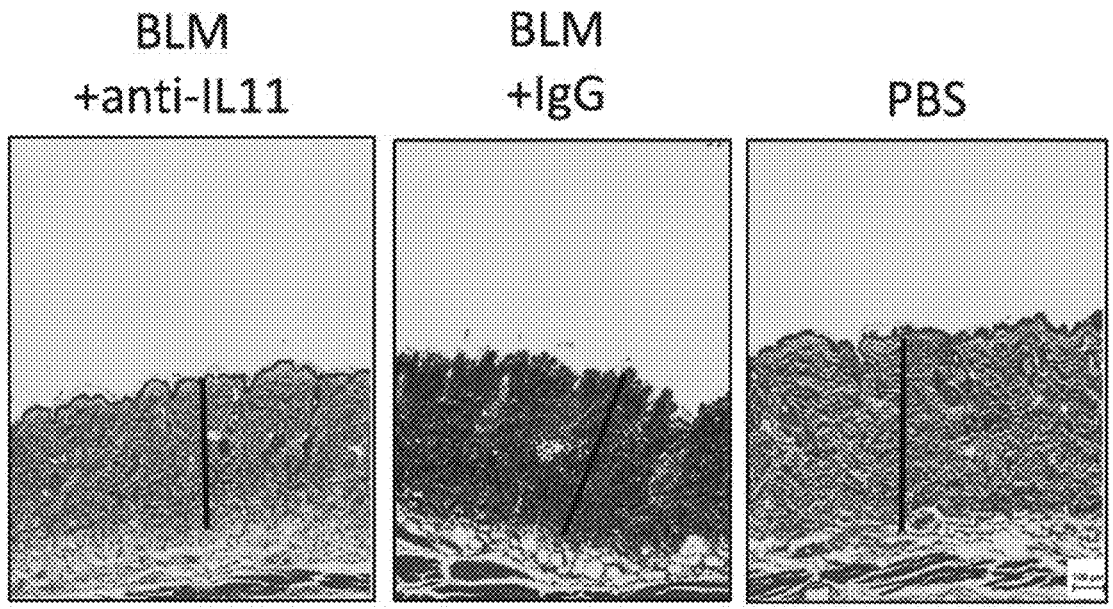
Figure 33C:
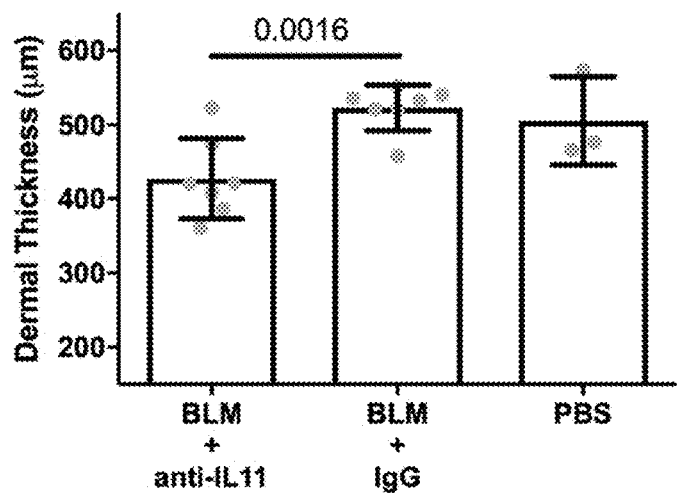

FIGS. 33B and 33C show that dermal thickness was significantly reduced in mice treated with neutralising anti-IL-11 antibody as compared to control IgG-treated mice. Increased collagen staining can also be seen for the control IgG-treated group (FIG. 33B, middle panel).

Example 17: Inhibition of Heart Fibrosis Using
Anti-IL-11 Antibodies

The anti-fibrotic effect of anti-IL-11 antibody treatment was analysed in a mouse model of cardiac fibrosis.

Briefly, transverse aortic constriction (TAC) was performed in male mice as described previously (Tarnayski, O. et al. Mouse cardiac surgery: comprehensive techniques for the generation of mouse models of human diseases and their application for genomic studies. Physiol. Genomics 16, 349-360 (2004)). Age-matched mice underwent a sham operative procedure without TAC. Trans-thoracic two-dimensional Doppler echocardiography was used to confirm increased pressure gradients (>40 mm Hg), indicative of successful TAC.

Mice were euthanized at 2 weeks post-TAC for histological and molecular assessment. Anti-IL-11 antibody clone BSN-3C6 or control IgG antibody were administered intraperitoneally 3 times per week at a dose of 20 mg/kg. After two weeks hearts were harvested and assessed for fibrosis extent using Masson's Trichrome stain kit (HT15, Sigma-Aldrich), in accordance with the manufacturer's instructions.

Figure 34:
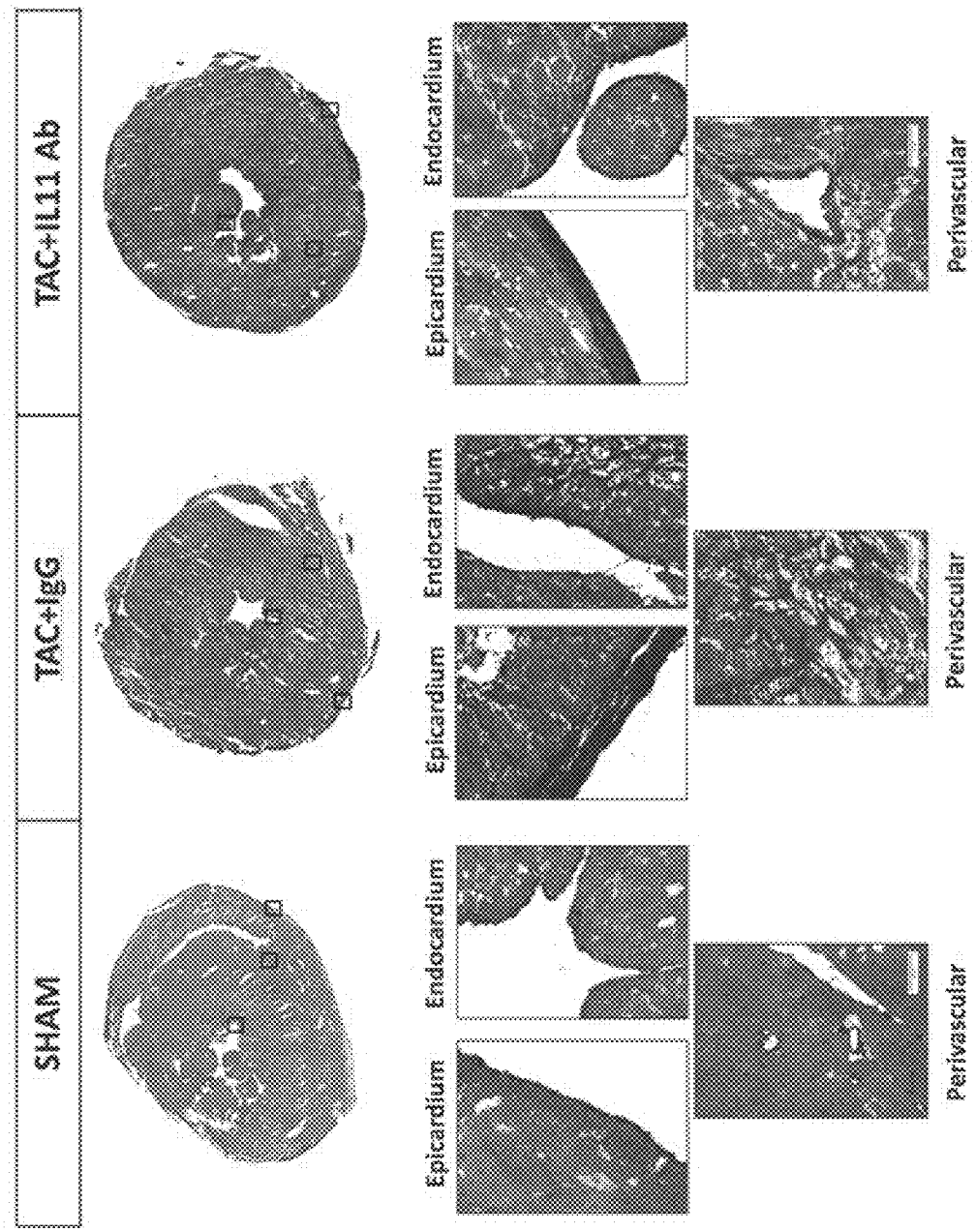
FIG. 34. Images showing the results of histological analysis of heart fibrosis in mice subjected to different treatments in a mouse model of cardiac fibrosis. Mice (C57Bl6, male, 8-12 weeks old) were subjected to fibrosis-inducing transverse aortic constriction (TAC) or sham operations. TAC-treated animals received either control antibody (20 mg/kg, 3×/week, intraperitoneal) or neutralizing anti-IL-11 antibody (20 mg/kg, 3×/week, intraperitoneal). After two weeks hearts were harvested and assessed for fibrosis extent using Masson's Trichrome stain.
Figure 35A:
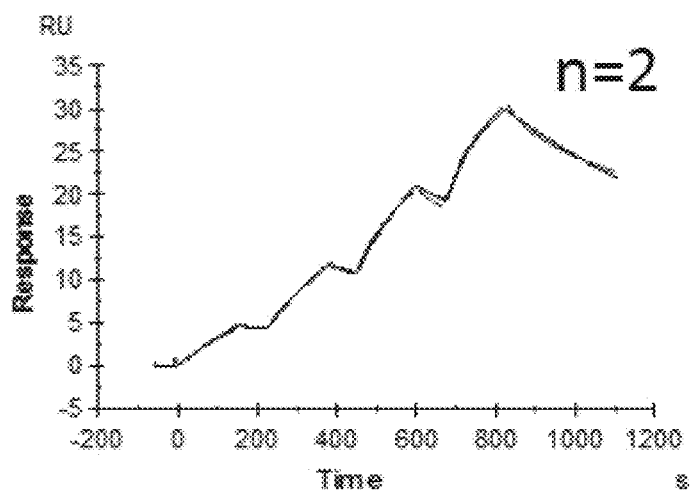
Figure 35B:
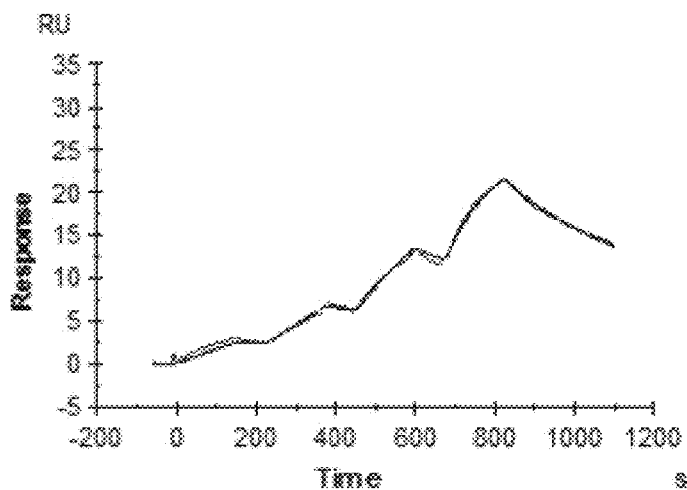
Figure 35C:
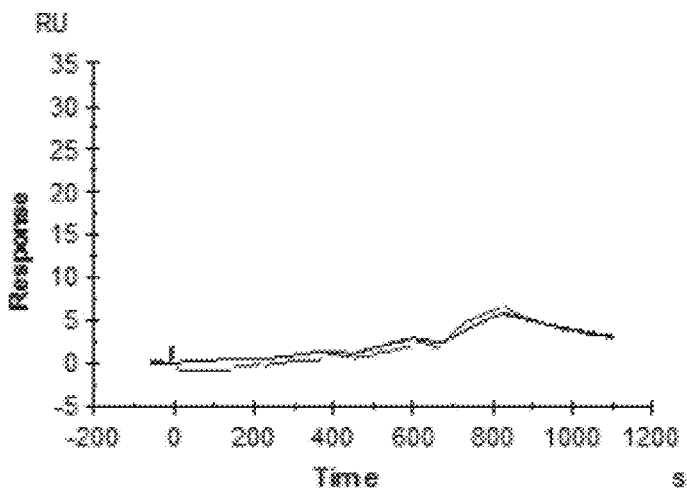
Figure 35D:
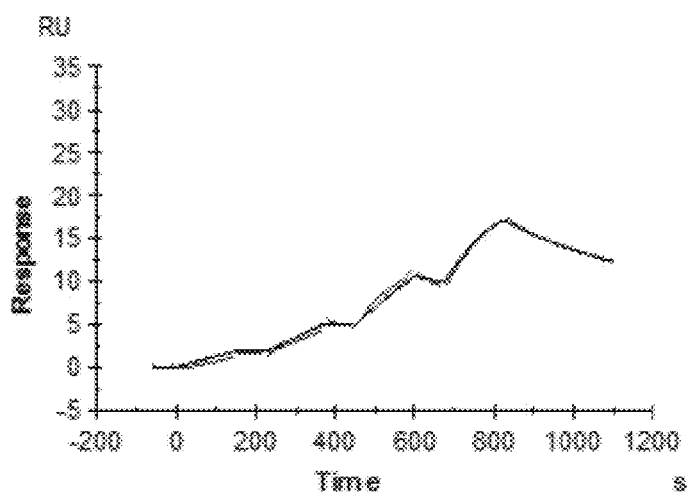
Figure 35E:
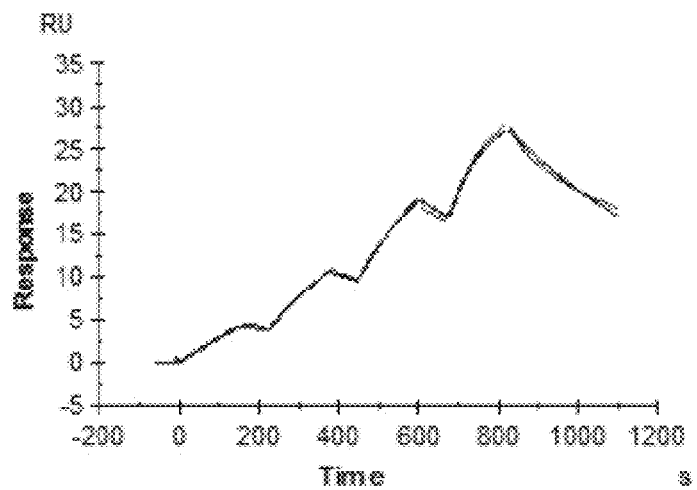
Figure 35F:
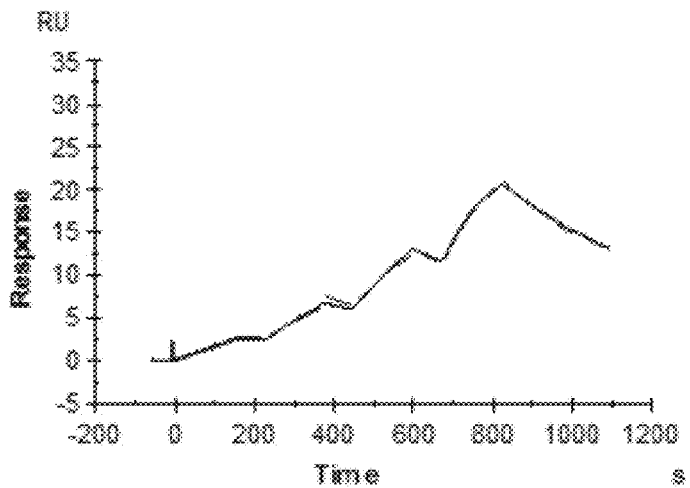
Figure 35G:
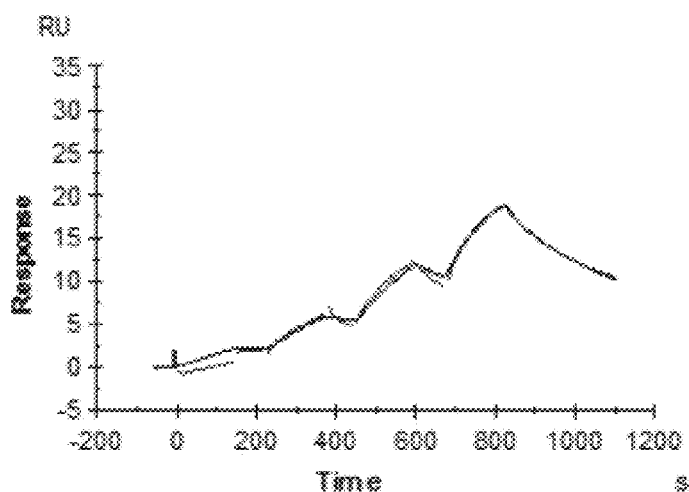
Figure 35H:
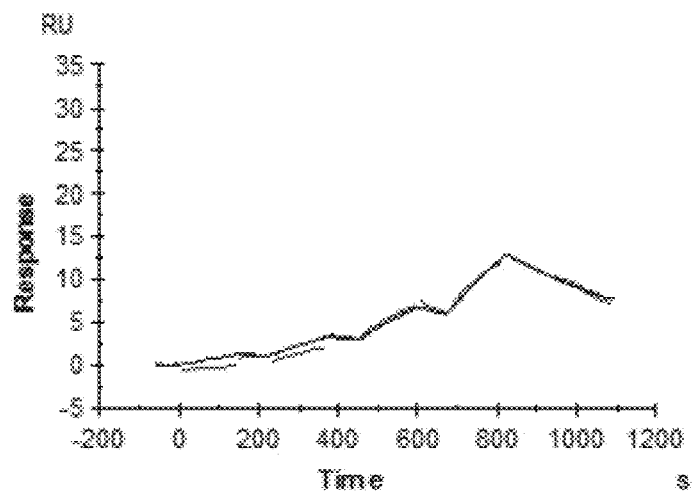
Figure 35I:
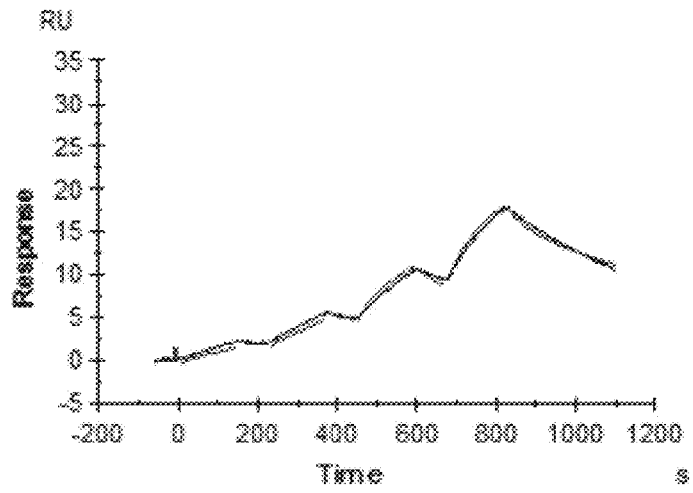
Figure 36A:
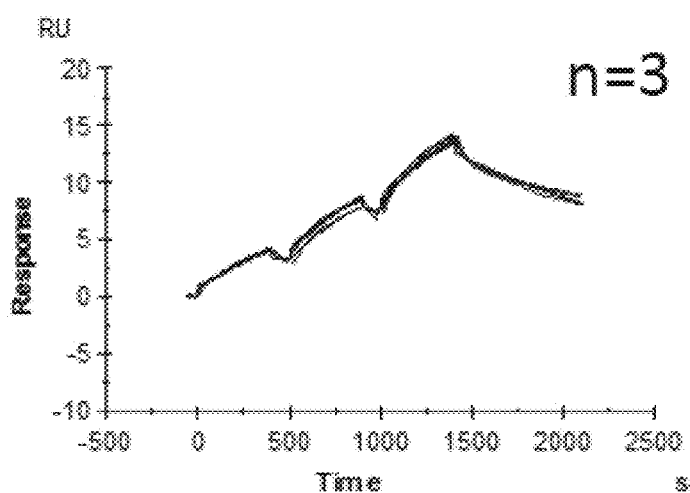
Figure 36B:
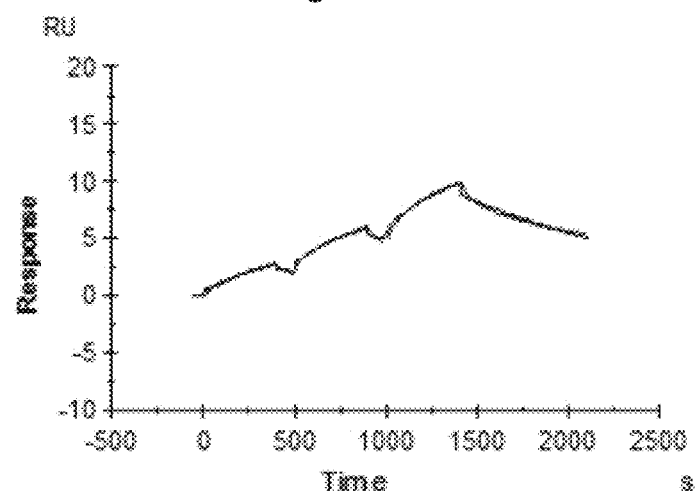
Figure 36C:
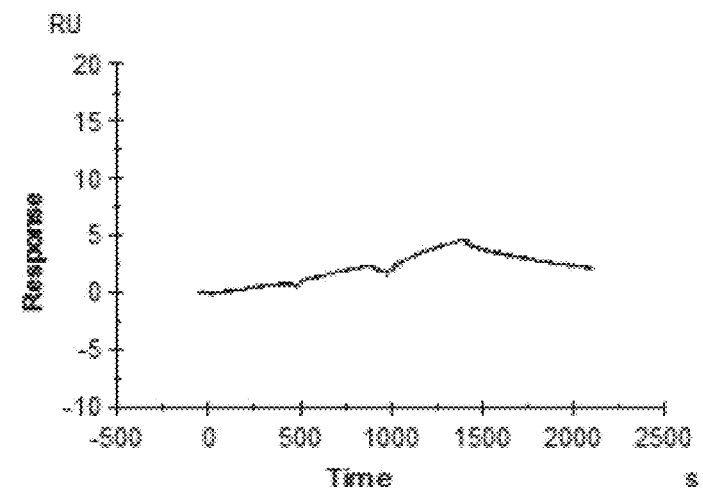
Figure 36D:
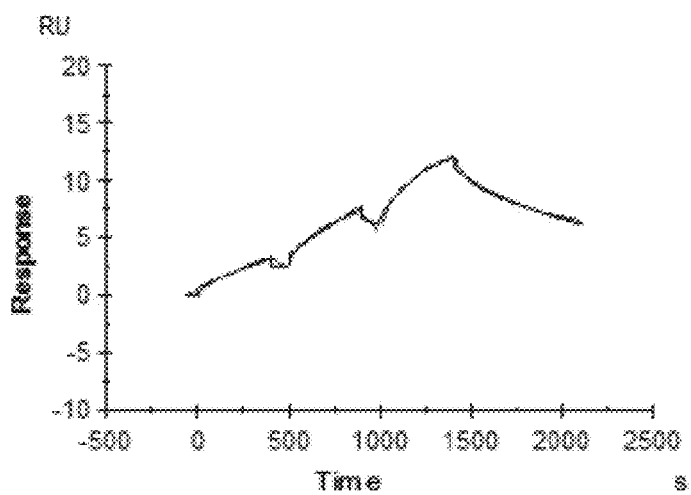
Figure 36E:
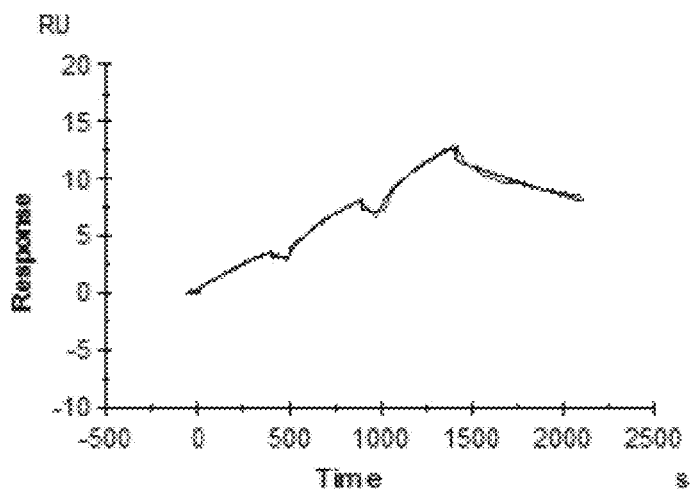
Figure 36F:
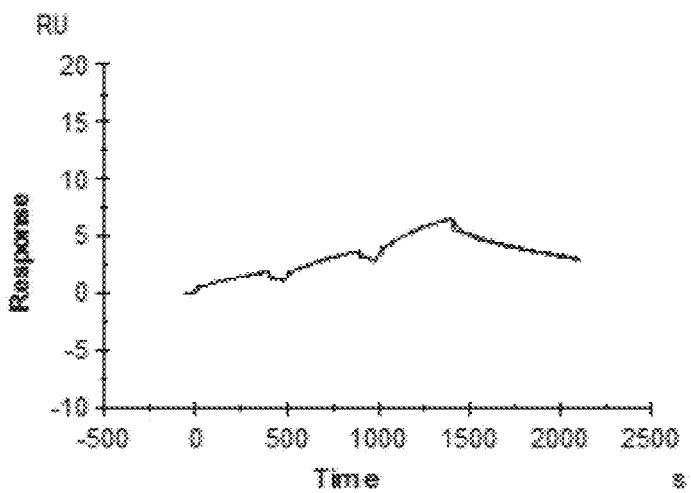
Figure 36G:
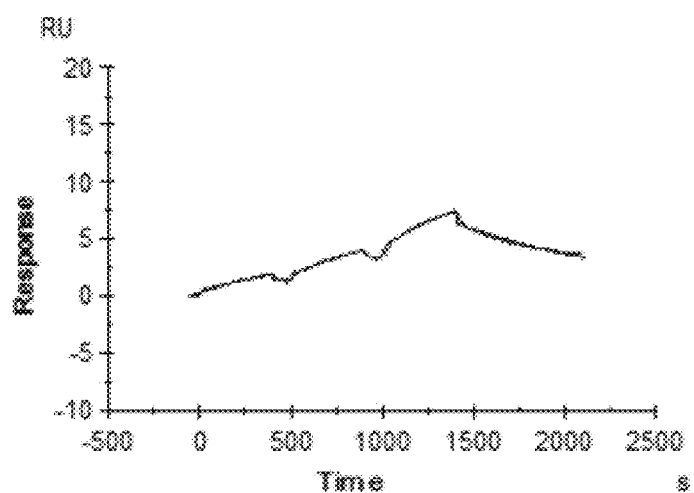
Figure 36H:
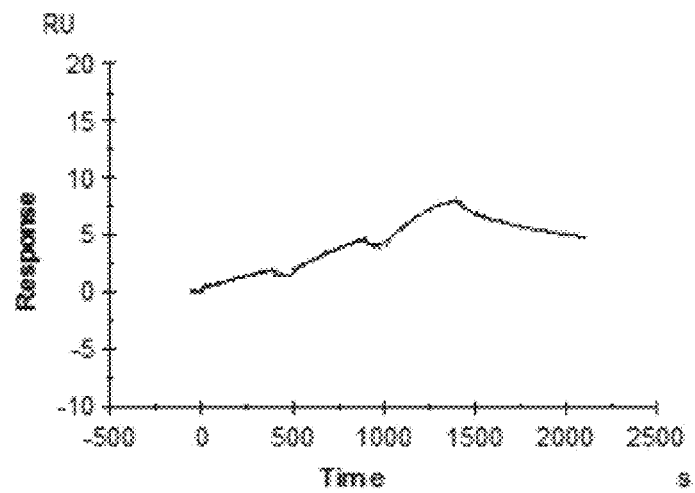
Figure 36I:
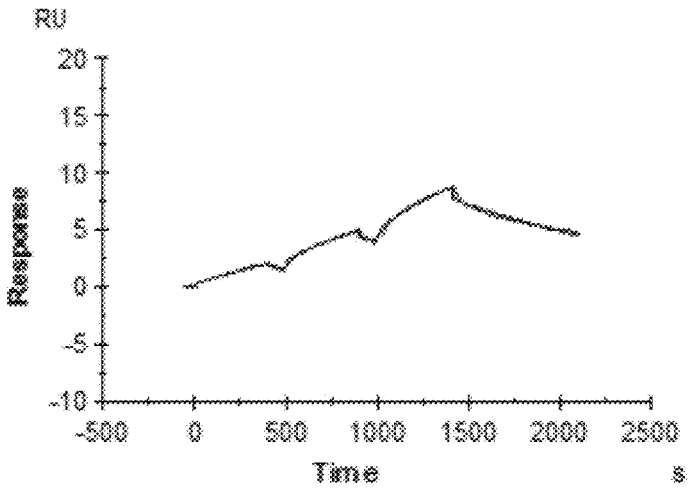
Figure 37A:
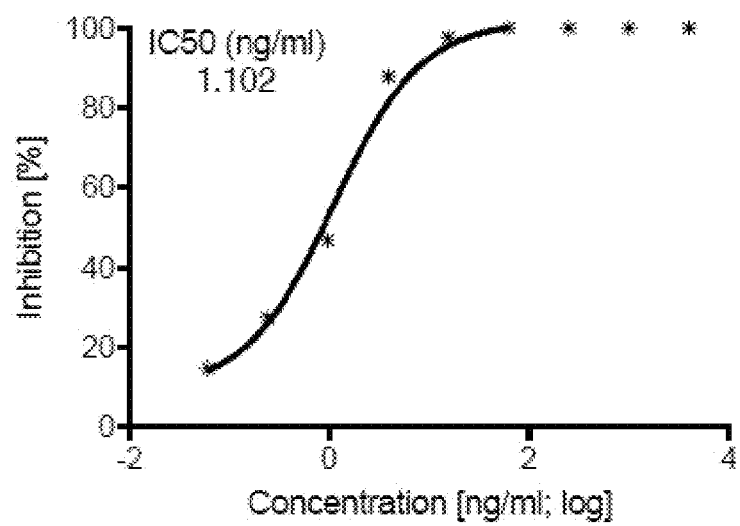
FIGS. 37A to 37I. Graphs showing inhibition of IL-11 mediated signalling by different antibody clones, as determined by analysis in vitro of inhibition of production of MMP2 by human cardiac atrial fibroblasts following stimulation with TGFβ1. 37A to 37I show the results obtained for clones YU100-H01 (37A), 01A (37B), 01G (37C), 01I (37D), 01L (37E), 01Q (37F), 01S (37G), 01T (37H) and 01V (37I).
Figure 37B:
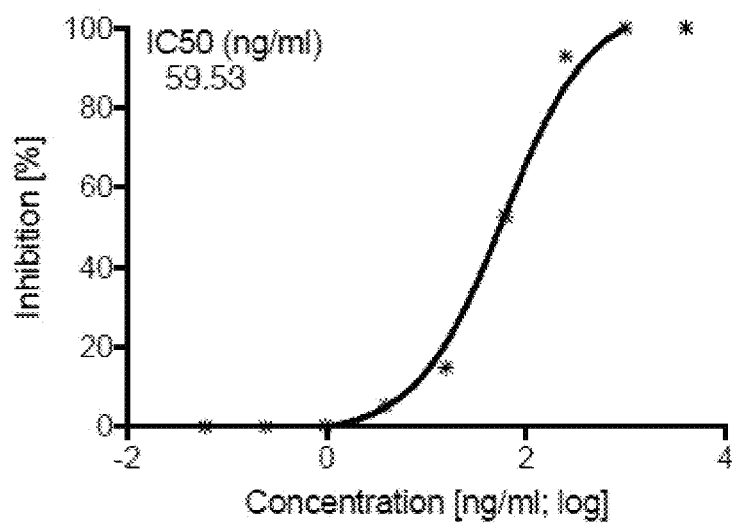
Figure 37C:
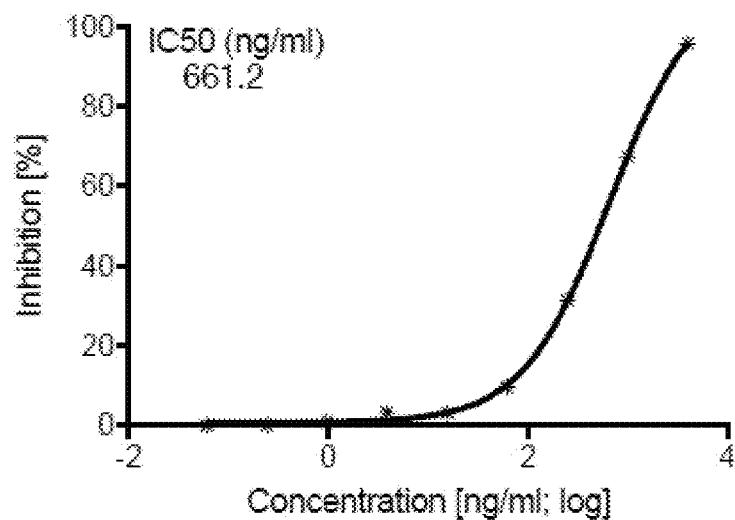
Figure 37D:
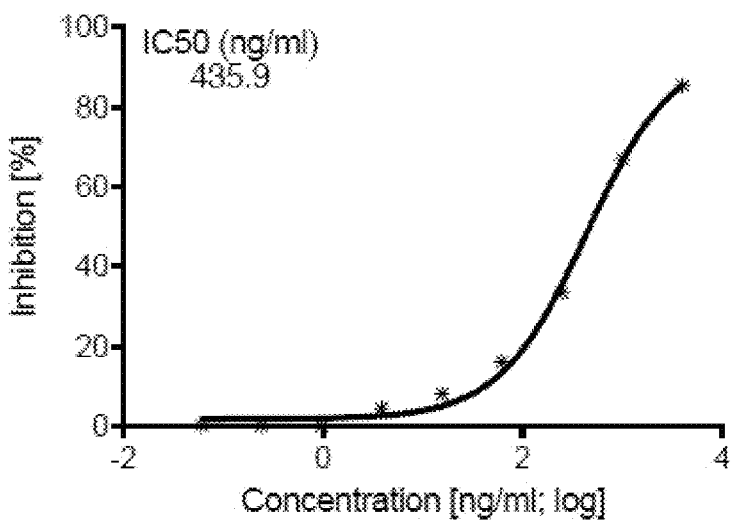
Figure 37E:
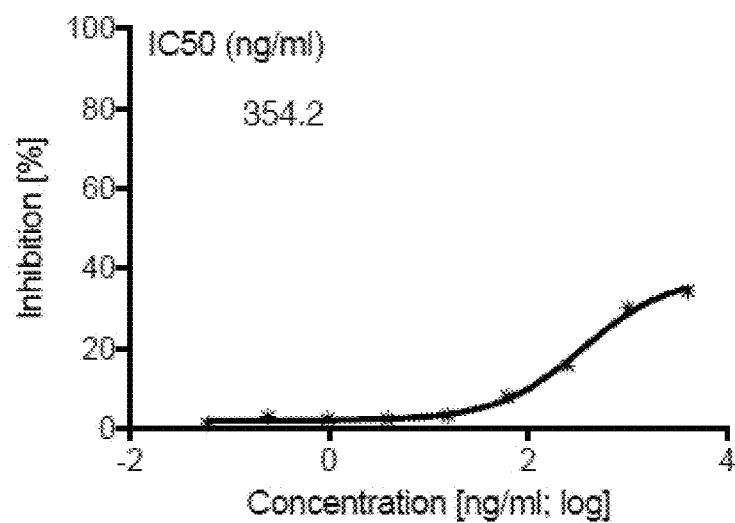
Figure 37F:
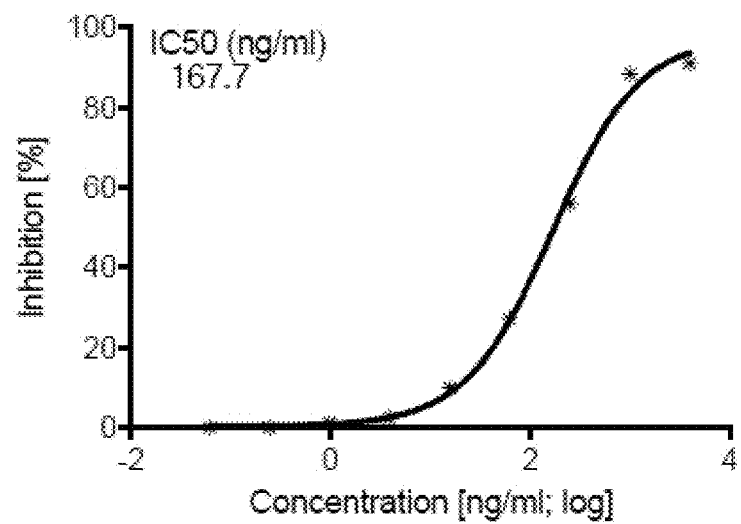
Figure 37G:
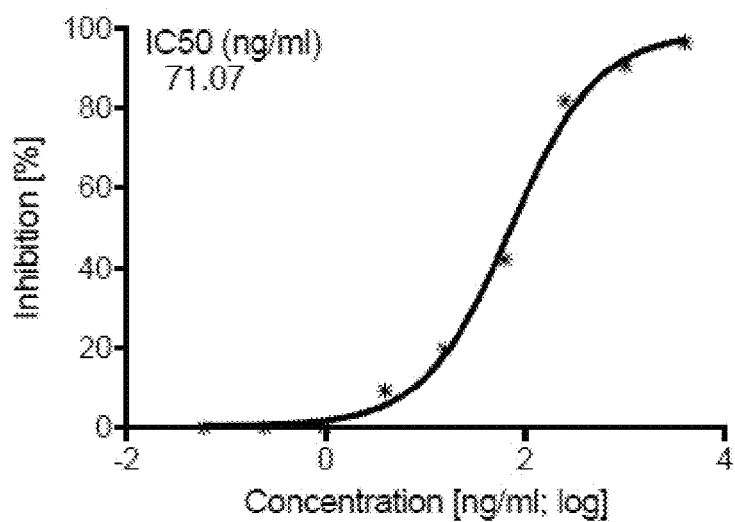
Figure 37H:
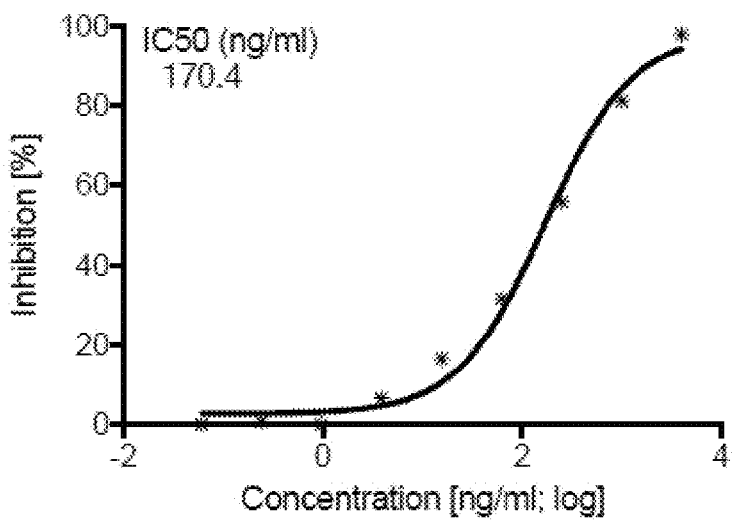
Figure 37I:
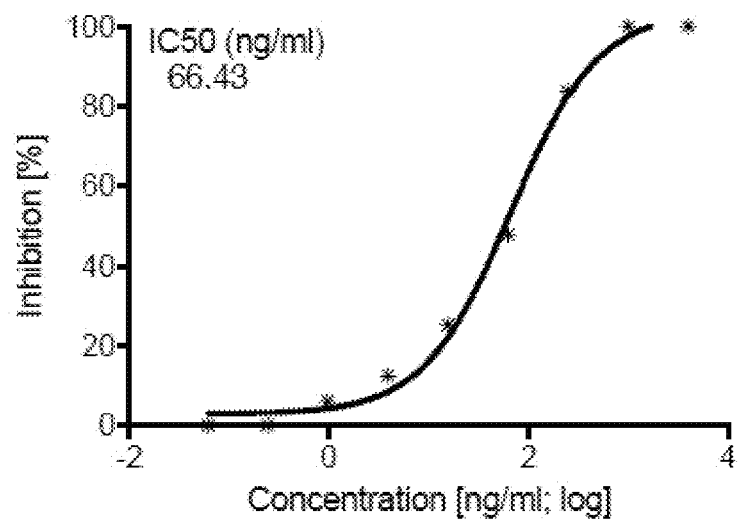
Figure 38A:
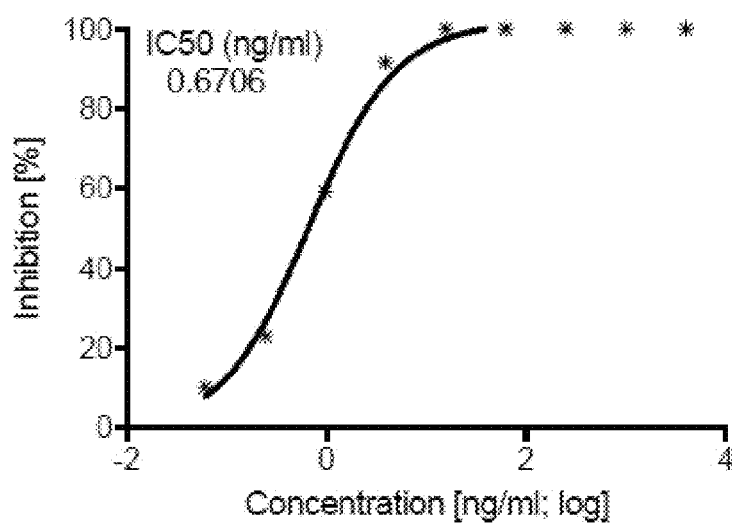
FIGS. 38A to 38M. Analysis of inhibition of IL-11 signalling. (A-I) Graphs showing inhibition of IL-11 mediated signalling by different antibody clones, as determined by analysis in vitro of inhibition of production of MMP2 by human cardiac atrial fibroblasts following stimulation with TGFβ1. 38A to 38I show the results obtained for clones YU100-G08 (38A), 02A (38B), 02G (38C), 02I (38D), 02L (38E), 02Q (38F), 02S (38G), 02T (38H) and 02V (38I). (J-M) Cross-species reactivity for IL-11 antibodies YU100-G08_02A (human) and 3C6 (mouse) using macaque dermal fibroblasts: (J) % of ACTA positive cells, (K) secreted collagen, (L) periostin, (M) collagen concentration.
Figure 38B:
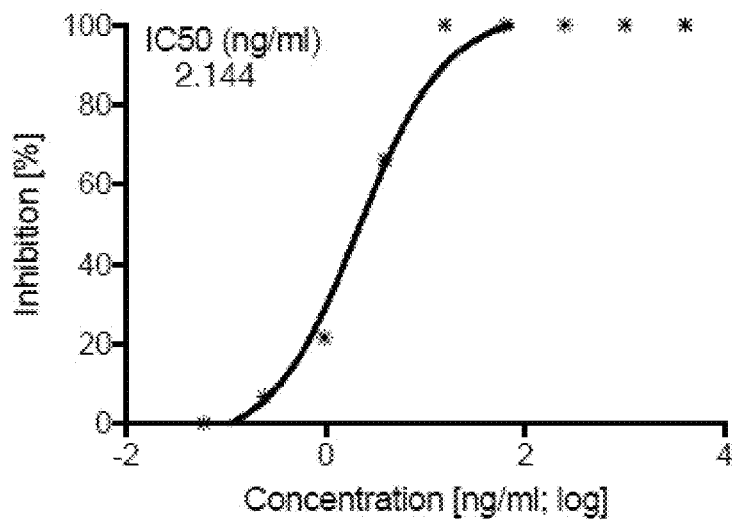
Figure 38C:
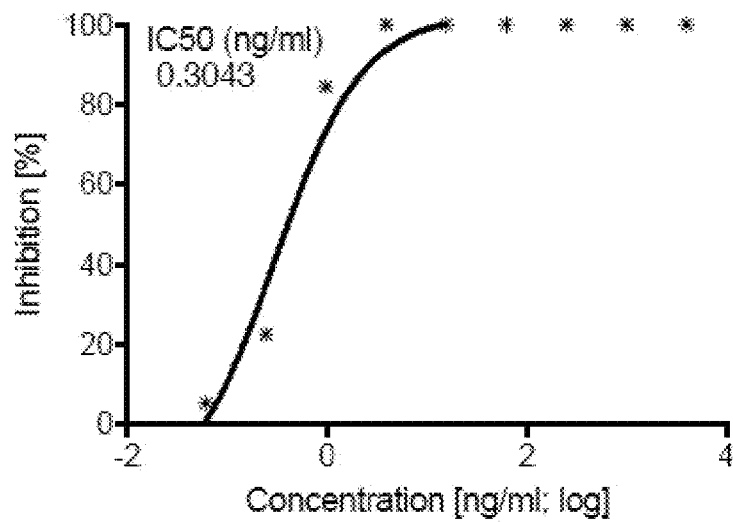
Figure 38D:
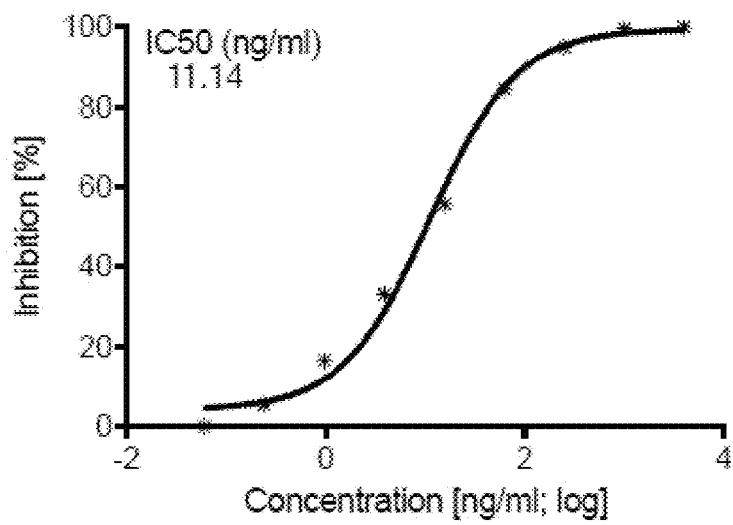
Figure 38E:
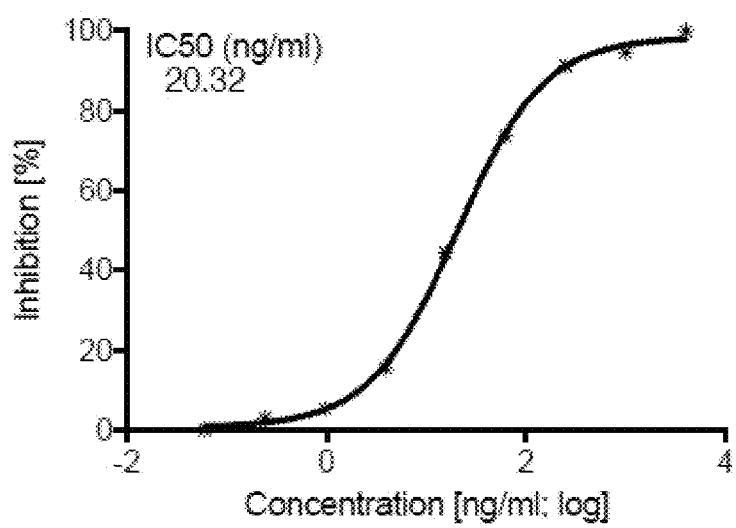
Figure 38F:
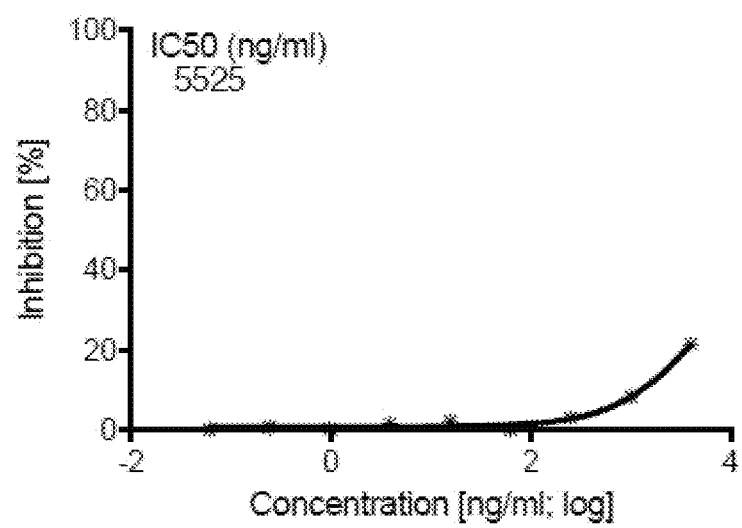
Figure 38G:
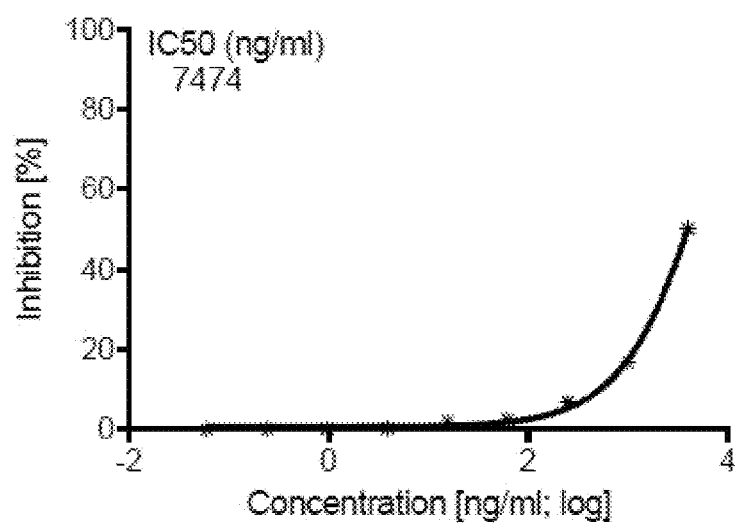
Figure 38H:
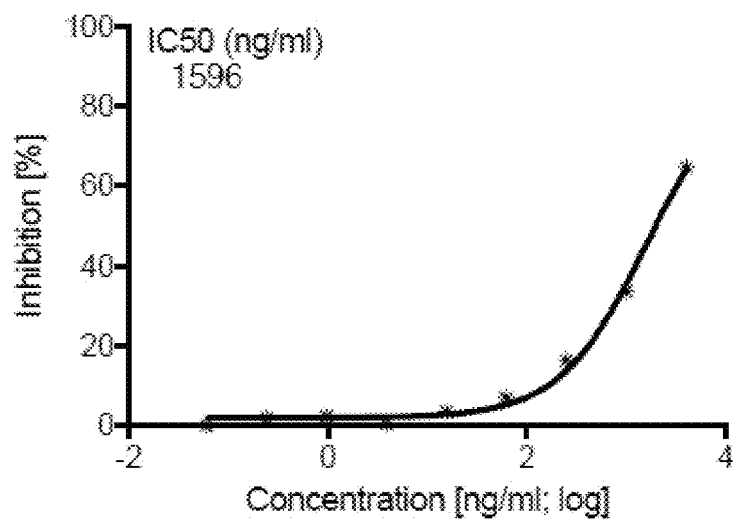
Figure 38I:
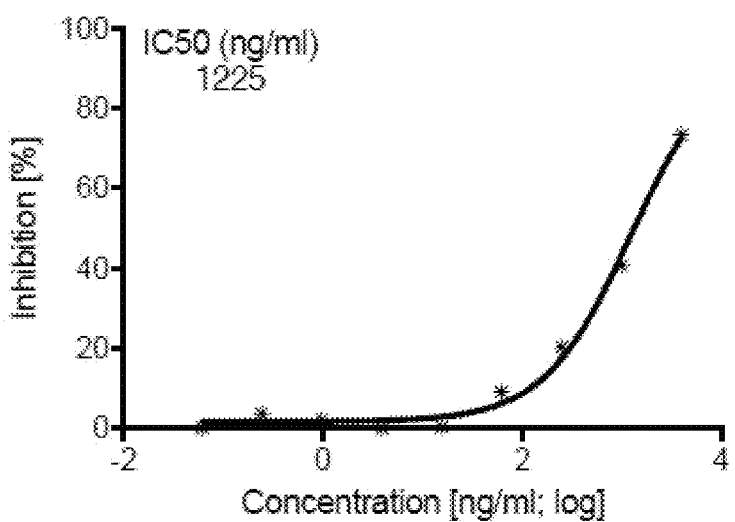
Figure 38J:
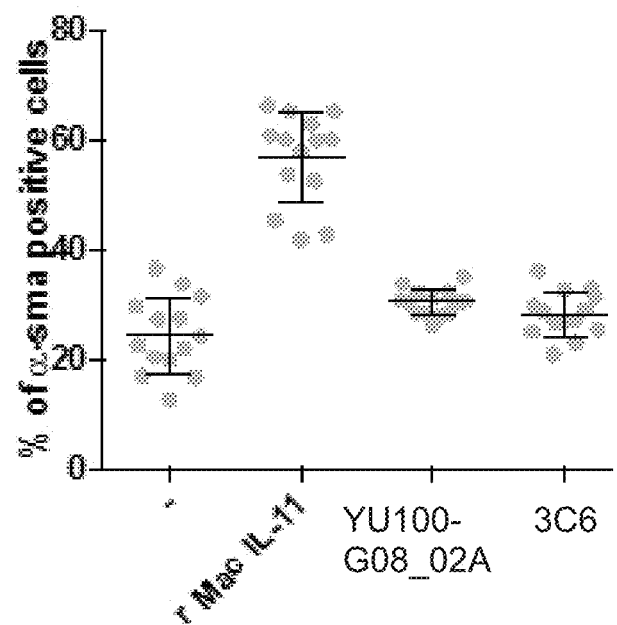
Figure 38K:
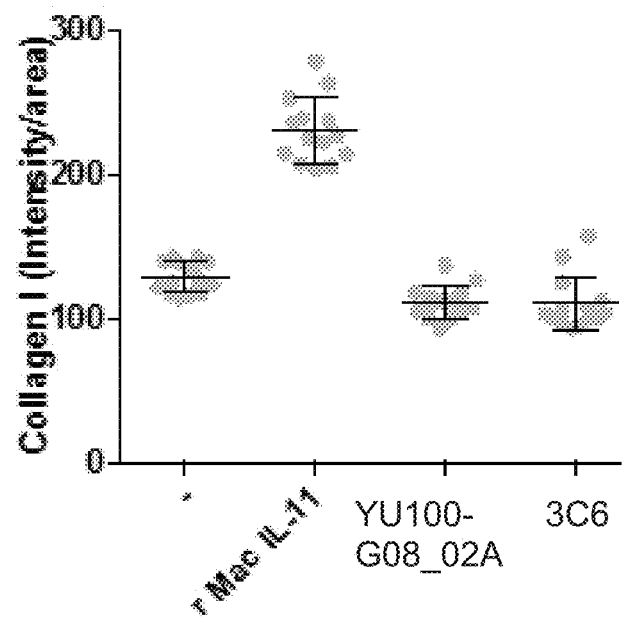
Figure 38L:
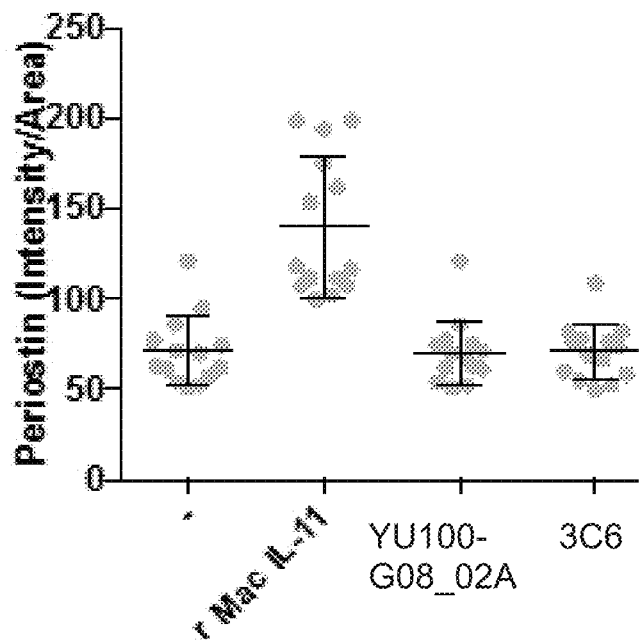
Figure 38M:
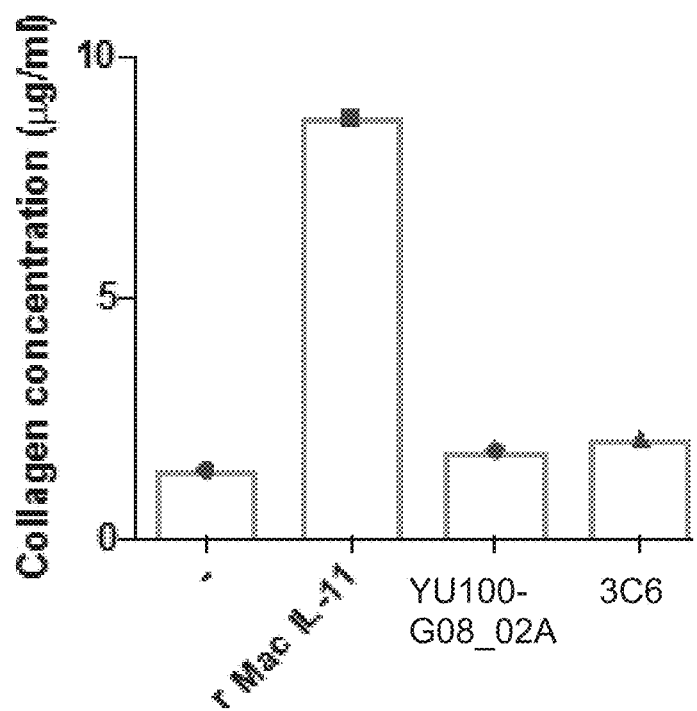

The results of the analysis is shown in FIG. 34. Mice treated with neutralising anti-IL-11 antibody were found to have reduced levels of fibrosis in the epicardium, endocardium and in perivascular regions as compared to mice treated with IgG control antibody.

Example 18: Variant Anti-IL-11 Antibody Clones

The cysteine residue at position 91 of the light chain variable region sequences shown in SEQ ID NOs:7, 9 and 11 was substituted with A, G, I, L, Q, S, T or V. The variant light chain variable region sequences are shown in SEQ ID NOs:12 to 35.

HEK293 EBNDA cells were transfected with vectors encoding scFv corresponding to YU100-H01, 01A, 01G, 01I, 01L, 01Q, 01S, 01T, 01V, YU100-G08, 02A, 02G, 02I, 02L, 02Q, 02S, 02T or 02V.

Example 19: Analysis of Affinity of Binding of
Variant Clones to IL-11

The 01 and 02 variant anti-IL-11 antibody clones described in Example 18 were analysed for affinity of binding to human IL-11 by Single Cycle Kinetics analysis using a BIAcore T200.

Briefly, recombinant human IL-11 was immobilised on a CM5 chip, and associations were performed by flowing increasing concentrations of purified anti-IL-11 antibodies corresponding to the different clones in IgG1 format over the chip at a flow rate of 30 μl/min, with no dissociation step between runs. A single dissociation step was used, and the surface was regenerated using 3.8 M $MgCl_2$.

For YU100-G08 and 02 variant clones, the following concentrations of antibody were used in the associations: 3.125 nM, 6.25 nM, 12.5 nM and 25 nM. For YU100-H01 and 01 variants the following concentrations of antibody were used: 37.5 nM, 75 nM, 150 nM For YU100-G08 and 02 variants the analyte injection time was 150 seconds, and for YU100-H01 and 01 variants the analyte injection time was 400 seconds.

For YU100-G08 and 02 variants the analyte dissociation time was 500 seconds, and for YU100-H01 and 01 variants the analyte dissociation time was 700 seconds.

The analysis of the raw data obtained was performed using BIAcore T200 evaluation software V3.0, fitting the background-subtracted data to a 1:1 interaction model.

The results obtained for YU100-G08 and the 02 variants are shown in FIGS. 35A to 35J. Variants 02A, 02I, 02L, 02Q and 02S displayed an affinity of binding to human IL-11 with greater affinity or within two-fold of the affinity of YU100-G08.

The results obtained for YU100-H01 and the 01 variants are shown in FIGS. 36A to 36J. Variants 01A, 01I, 01L, and 01T displayed an affinity of binding to human IL-11 with greater affinity or within two-fold of the affinity of YU100-H01.

Example 20: Analysis of Inhibition of IL-11
Mediated Signalling for Variant Clones The 01 and 02 variant anti-IL-11 antibody clones described in Example 18 were analysed for their ability to inhibit IL-11 mediated signalling in an in vitro assay.

Cardiac atrial human fibroblasts were cultured in wells of 96-well plates in the presence of TGFβ1 (5 ng/ml) for 24 hours, in the presence of different concentrations of the YU100-H01, 01A, 01G, 01I, 01L, 01Q, 01S, 01T, 01V, YU100-G08, 02A, 02G, 02I, 02L, 02Q, 02S, 02T or 02V anti-IL-11 antibodies in scFv-human IgG1-Fc format.

Levels of the pro-fibrotic marker MMP2 in the cell culture supernatant were then measured by ELISA. Basal MMP2 secretion by the cells in culture was measured by culture in the absence of TGFβ1.

MMP2 levels determined were used to derive IC50 values for inhibition of IL-11 mediated signalling by the different clones.

The results for YU100-H01, 01A, 01G, 01I, 01L, 01Q, 01S, 01T and 01V are shown in FIGS. 37A to 37I.

The results for YU100-G08, 02A, 02G, 02I, 02L, 02Q, 02S, 02T and 02V are shown in FIGS. 38A to 38I.

12.3 Cross-Species Reactivity

Macaque skin fibroblasts were stimulated with recombinant macaque IL-11 (5 ng/ml) for 24 h in the presence of IgG control, YU100-G08_02A, or 3C6 antibodies at 2 μg/ml. Collagen, ACTA2+ve and EdU+ve cells were quantified using the Operetta High content imaging platform. Secreted collagen was quantified using the calorimetric Sirius Red collagen assay.

The results are shown in FIGS. 38J to 38M. Both antibodies blocked IL-11 signalling in macaque fibroblasts. 3C6 was also tested in rat and pig cardiac fibroblasts and was found to inhibit the fibrotic response in these cells.

Example 21: IL-11 and Lung Fibrosis

Idiopathic pulmonary fibrosis (IPF) is a fibrotic lung disease characterised by invasive pulmonary myofibroblasts that deposit ECM components e.g. collagen and destroy lung integrity.

Lung sections from healthy individuals and IPF patients were immunostained for IL-11 and alpha smooth muscle actin (ACTA2), a marker for myofibroblasts. Human IPF tissues were obtained from lung transplant patients with IPF and normal control human lung tissues were obtained from IIAM (International Institute for the 197 Advancement of Medicine). Human lung tissue were fixed in 10% formalin overnight and embedded in paraffin. Tissue sections were incubated with primary antibodies (Anti-IL-11 (PA5-36544, ThermoFisher Scientific), Anti-ACTA2 (ab7817 and ab5694, abcam) overnight and visualized using an Imm- PRESS HRP anti-rabbit IgG polymer detection kit (Vector Laboratories) with ImmPACT DAB Peroxidase Substrate (Vector 209 Laboratories).

Figure 46A:
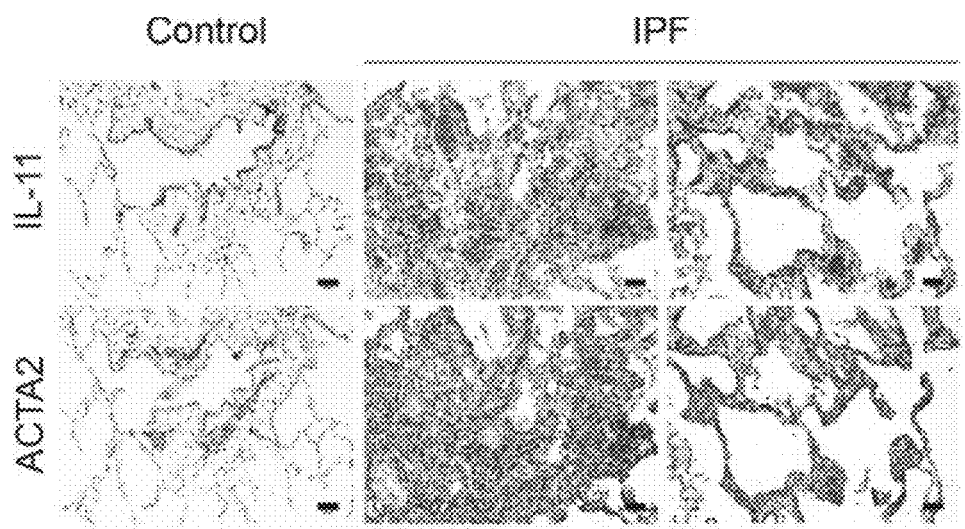
FIGS. 46A to 46D. The effect of IL-11 on lung fibroblast activation, migration and invasion. (46A) Representative immunostaining of IL-11 and ACTA2 in serial sections of lung tissue from an IPF patient and healthy donor (Control). Scale bars, 50 μm. (46B) Total secreted collagen in the supernatant of IL-11 treated fibroblasts. (46C) Transwell migration and (46D) matrigel invasion indices of wild-type mouse lung fibroblasts induced by IL-11. Scale bars, 150 μm.

The results are shown in FIG. 46A. IL-11 was found to be expressed at a low level in normal lung tissue, but markedly elevated in IPF lung samples along with ACTA2.

The role of IL-11 in lung fibroblast activation, migration and invasion was investigated. Murine pulmonary fibroblasts were incubated with recombinant mouse IL-11 (5 ng ml$^{-1}$, 24 h) and total secreted collagen in the supernatant of IL-11 treated fibroblasts was quantified by Sirius red collagen assay (n=5/group). Fibroblasts were cultured in serum-free DMEM for 24 h prior to cell migration or invasion assays. Equal numbers of fibroblast in serum-free DMEM were seeded in duplicates onto apical chambers containing polycarbonate membranes for migration assays or onto ECM-coated matrigel for invasion assays. Fibroblasts were allowed to migrate towards IL-11 or TGFβ1 as chemoattractants. For invasion assays, fibroblasts were allowed to invade towards DMEM containing 2% FBS. After 24 h of incubation at 37° C., media was removed and non-migratory or non-invasive cells were removed using cotton swabs. The cells that migrated or invaded towards the bottom chamber were stained with cell staining solution (Cell Biolabs Inc.). Cells that migrated were colourimetrically quantified at 540 nm. Invasive cells from 5 non-overlapping fields of each membrane were imaged and counted under 40× magnification.

Figure 46B:
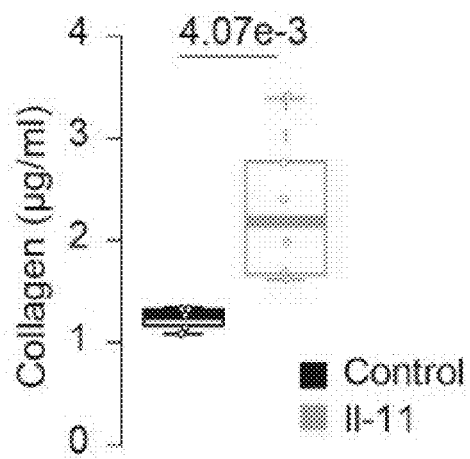
Figure 46C:
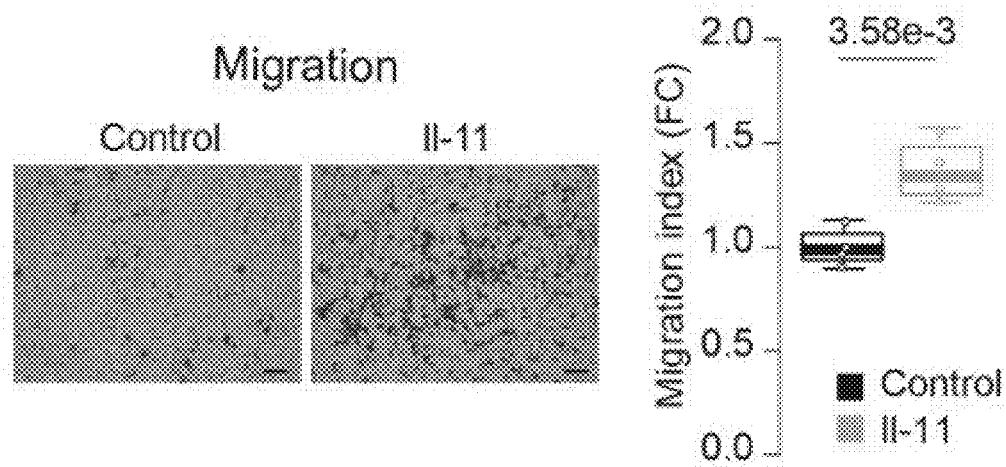
Figure 46D:
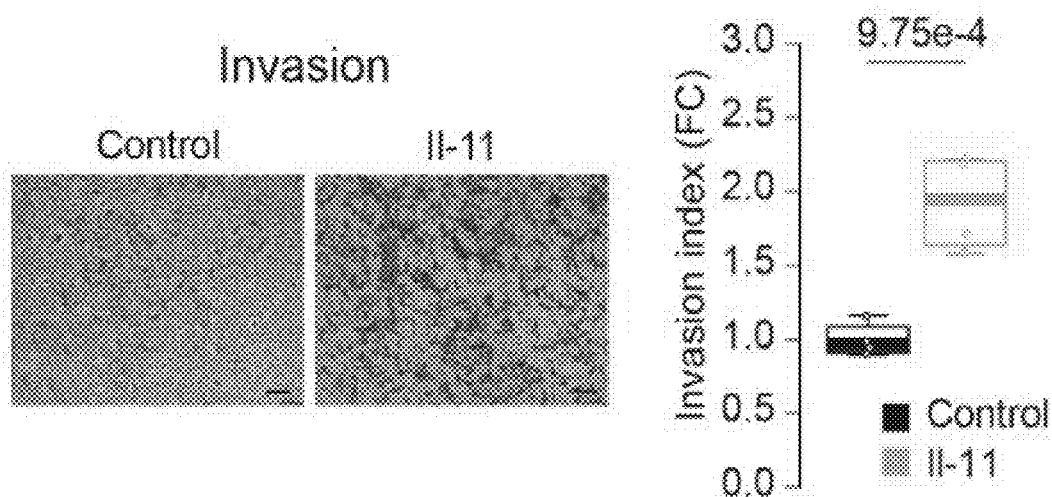

The results are shown in FIGS. 46B (secreted collagen), 46C (migration) and 46D (invasion). Il-11 induced marked fibroblast activation, proliferation, ECM production, migration and invasion.

Thus, IL-11 is upregulated in the lung in IPF which drives fibroblast-to-myofibroblast transformation and induces fibrosis.

21.1 Anti-IL-11 Therapy and Lung Fibrosis

Anti-IL-11 antibodies were generated as described herein.

Real-time binding kinetics of anti-IL-11 antibody BSN-3C6 to human and mouse IL-11 were measured by surface plasmon resonance (SPR) using a BIAcore T200 system (GE Healthcare, USA). The association and dissociation were measured for 250 s and 500 s respectively. The equilibrium binding constant $K_D$ was determined by the ratio of the binding rate constants kd/ka.

Figure 47A:
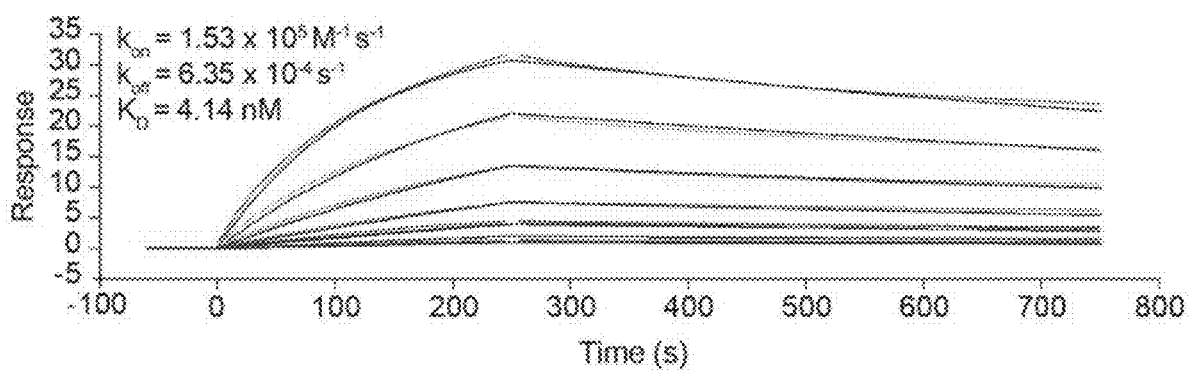
FIGS. 47A and 47B. Graphs showing binding kinetics of (47A) human and (47B) mouse IL-11 to anti-IL-11 antibody BSN-3C6. Equilibrium binding constants are shown.
Figure 47B:
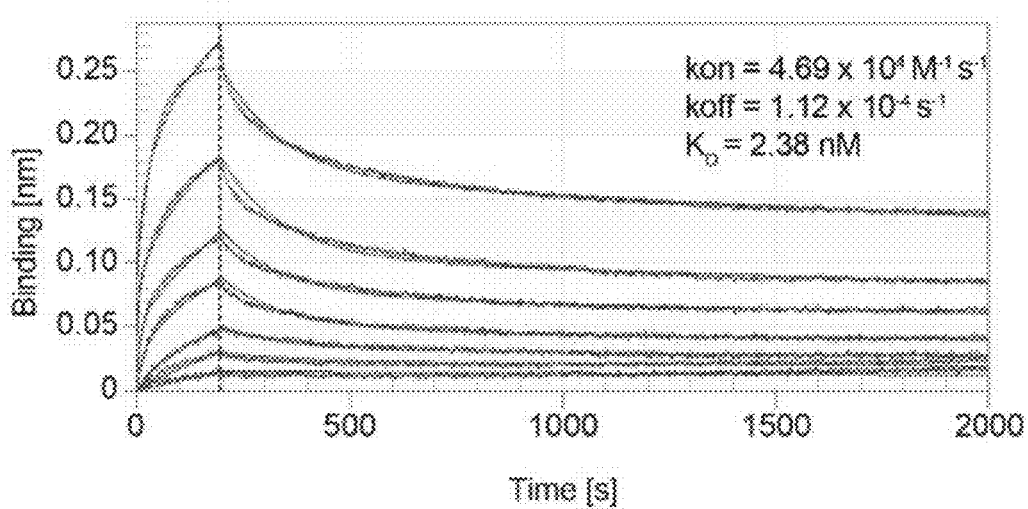

The results are shown in FIGS. 47A and 47B. Binding of BSN-3C6 to human IL-11 showed a $K_D$ of 4.14 nM (47A) and binding of BSN-3C6 to mouse IL-11 showed a $K_D$ of 2.38 nM (47B).

The effects of anti-IL-11 antibody BSN-3C6 on fibrotic characteristics were assessed.

Mouse lung fibroblasts were treated with multiple pro-fibrotic stimuli in the presence of BSN-3C6 or IgG control antibody. Cells were immunostained, as before, for Acta2 and Col1α1 (Anti-ACTA2 (ab7817 and ab5694, abcam), anti-COL1A1 (ab34710, abcam)) and the immunofluorescence was quantified. Secreted collagen in the cell culture supernatant was quantified using a Sirius red collagen detection kit.

Figure 48A:
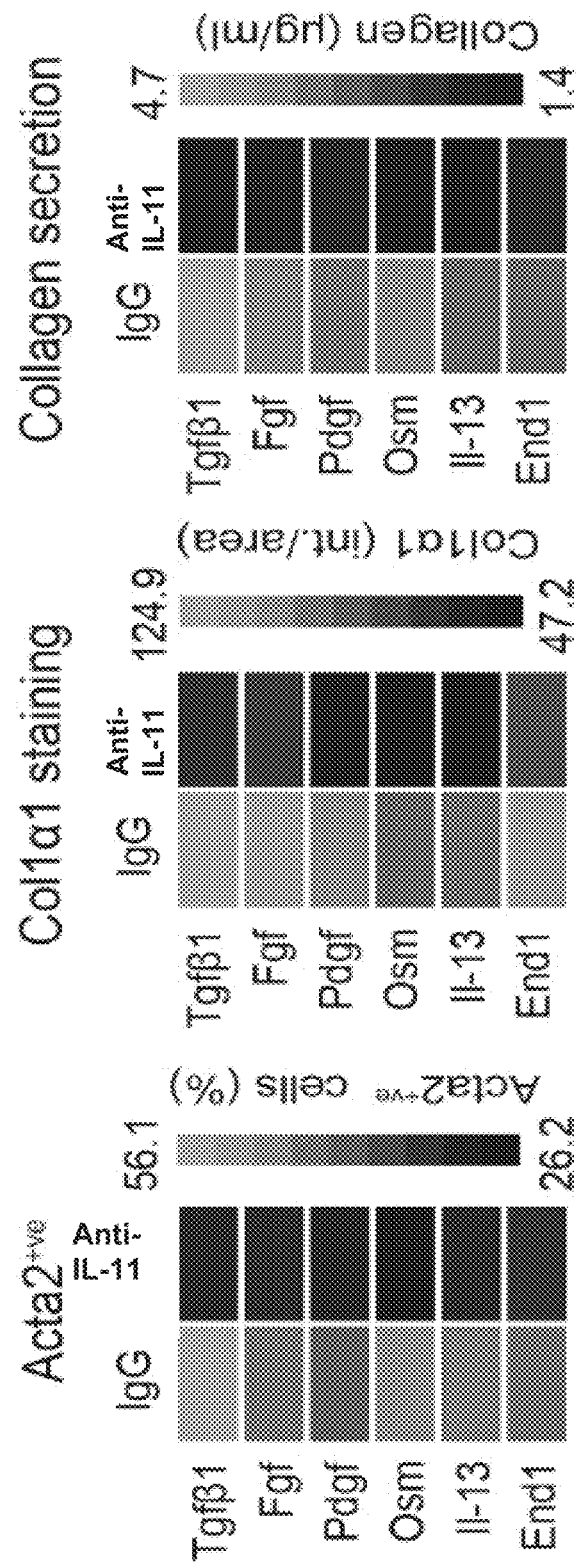
FIGS. 48A to 48E. The effect of anti-IL-11 therapy on lung fibrosis. (48A) Heatmaps showing the immunofluorescence quantification of Acta2+ve cells and Col1α1 immunostaining (intensity/area) in mouse lung fibroblasts treated with multiple pro-fibrotic stimuli in the presence of anti-IL-11 antibody or IgG control. (48B) Quantification of ACTA2+ve cells, COL1α1 immunostaining (intensity/area) and collagen secretion of TGFβ1-differentiated human lung fibroblasts treated with anti-IL-11 antibody or IgG control. (48C) Inhibition of MMP2 from TGFβ1-stimulated primary human lung fibroblasts in the presence of anti-IL-11 antibody. (48D) Inhibition of Mmp2 from TGFβ1-stimulated primary mouse lung fibroblasts in the presence of anti-IL-11 antibody. (48E) Effect of anti-IL-11 antibody on migration and invasion of mouse lung fibroblasts.

The results are shown in FIG. 48A. Heatmaps show the immunofluorescence quantification of Acta2$^{+ve}$ cells and Col1α1 immunostaining (intensity/area) in mouse lung fibroblasts treated with multiple pro-fibrotic stimuli was reduced in the presence of anti-IL-11 antibody when compared to IgG control. Collagen secretion in culture supernatant was reduced in the presence of anti-IL-11 antibody.

TGFβ1-differentiated human lung fibroblasts (5 ng ml$^{-1}$, 24 h pretreatment) were treated with BSN-3C6 or IgG control antibody (2 μg ml$^{-1}$, 24 h). The percentage of ACTA2$^{+ve}$ cells, COL1α1 immunostaining (intensity/area) and collagen secretion were determined.

Figure 48B:
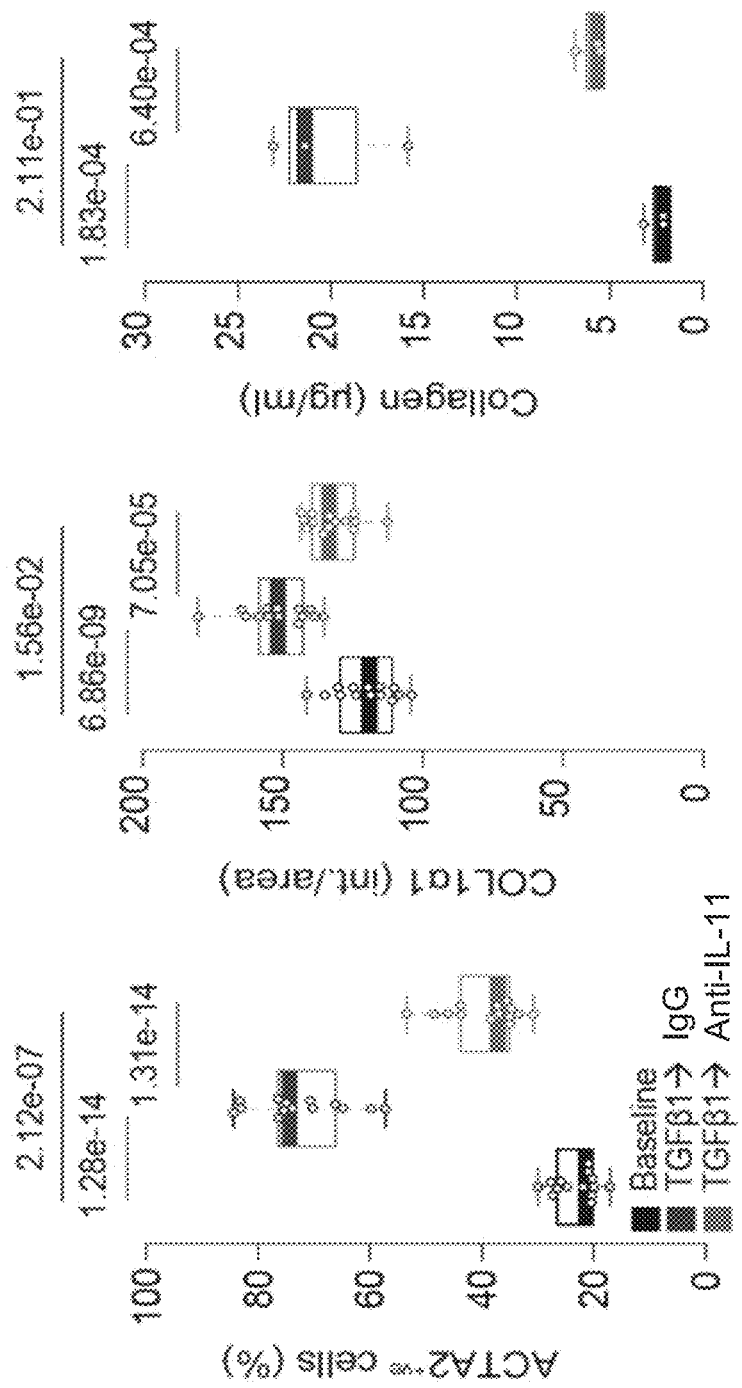

The results are shown in FIG. 48B. Anti-IL-11 antibody was found to reduce fibroblast activation, COL1α1 production and collagen secretion in pre-activated human lung fibroblasts, thus demonstrating that anti-IL-11 therapy can reverse fibrosis.

Primary mouse and human fibroblasts were stimulated with species-specific recombinant TGFβ1 (5 ng ml$^{-1}$, 24 h) and secreted MMP2 levels were monitored in the presence of purified anti-IL-11 BSN-3C6 antibody (6 μg ml$^{-1}$).

Figure 48C:
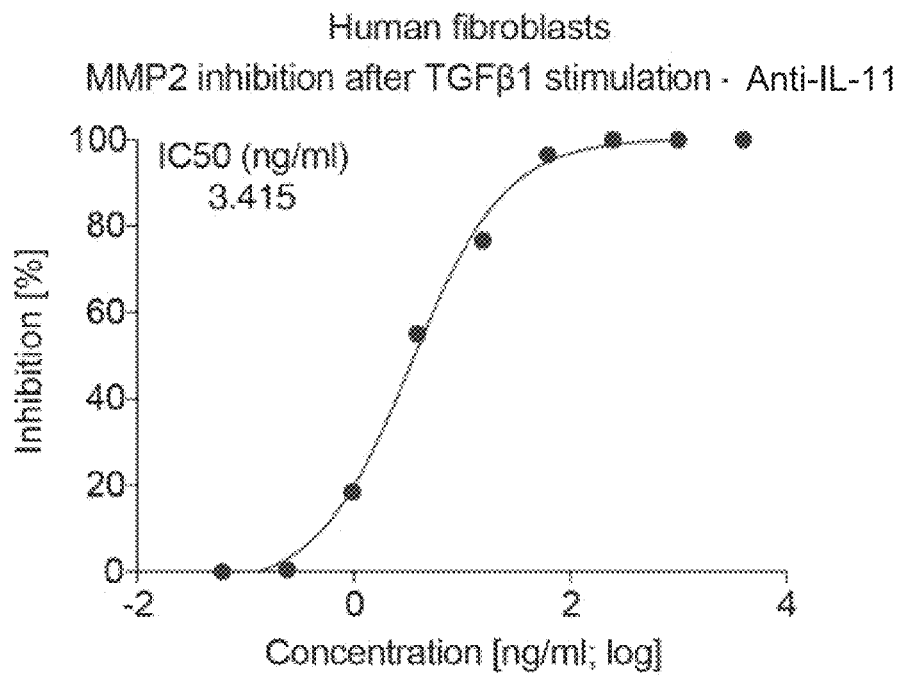
Figure 48D:
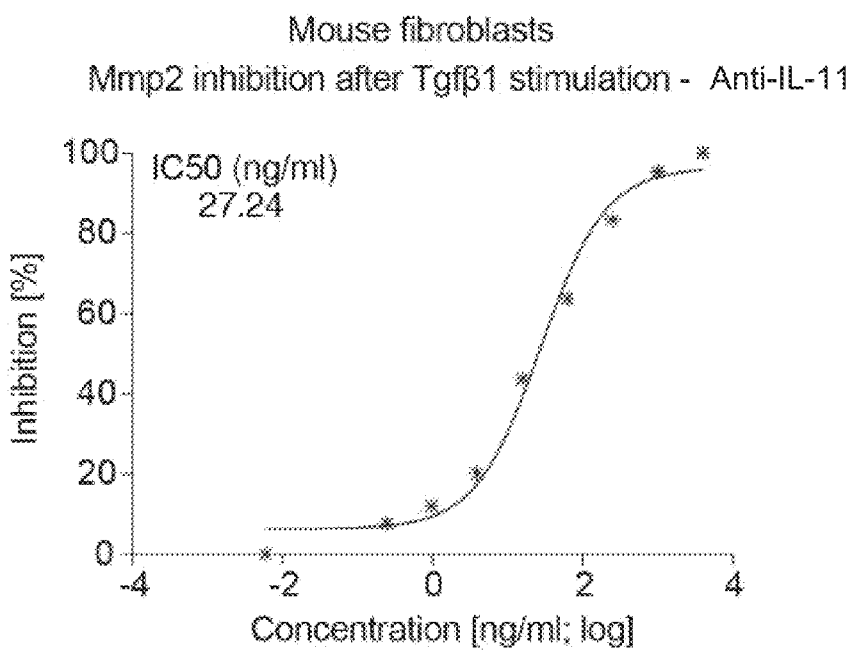

The results are shown in FIGS. 48C (human) and 48D (mouse). The anti-IL-11 antibody effectively inhibits TGFβ1-driven secretion of the pro-fibrotic marker MMP2 from both human and mouse fibroblasts by neutralizing the downstream IL-11 autocrine loop.

Figure 48E:
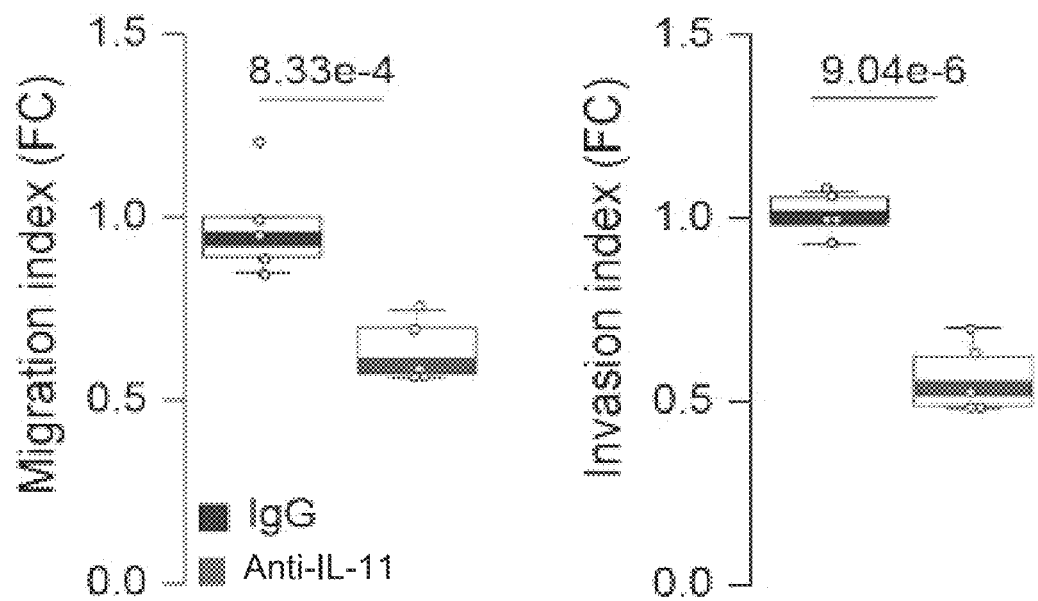
Figure 49A:
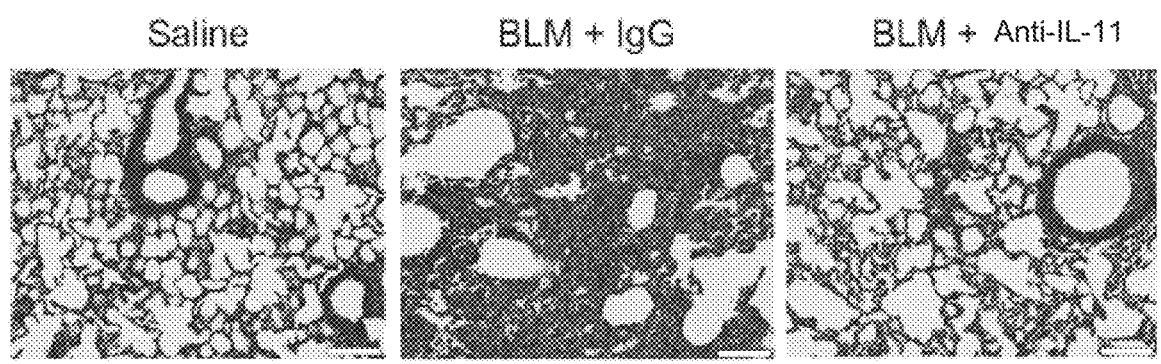
FIGS. 49A to 49E. The effect of IL-11 therapy in a bleomycin (BLM)-induced mouse model of early pulmonary fibrosis. Mice were treated with anti-IL-11 antibody or IgG control. (49A) Representative Masson's trichrome staining of lung sections. Scale bars, 100 μm. (49B) Graphs showing indexed lung/body weight and lung hydroxyproline content. (49C) Densitometry analysis of western blots of Col3a1, fibronectin and IL-11 protein levels in lung homogenates. (49D) mRNA expression of Col1a1, Col1a2, Col3a1, Fn1, Mmp2 and Timp1 in lung lysates. (49E)
Figure 49B:
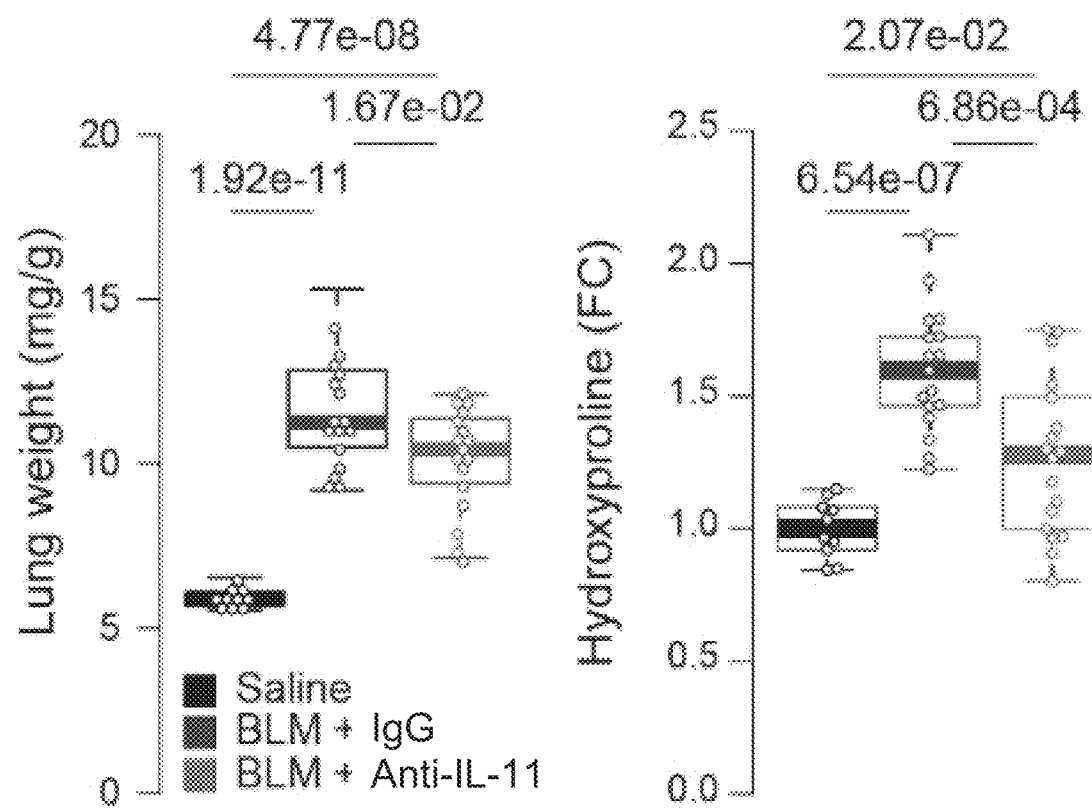
Figure 49C:
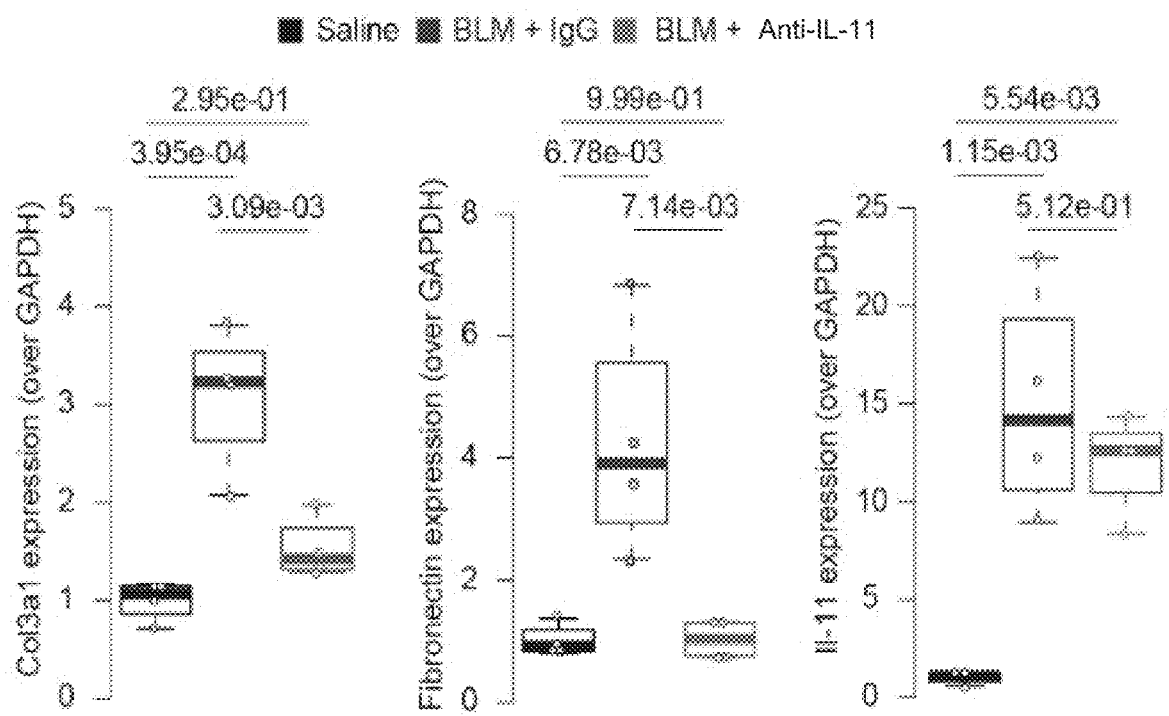
Figure 49D:
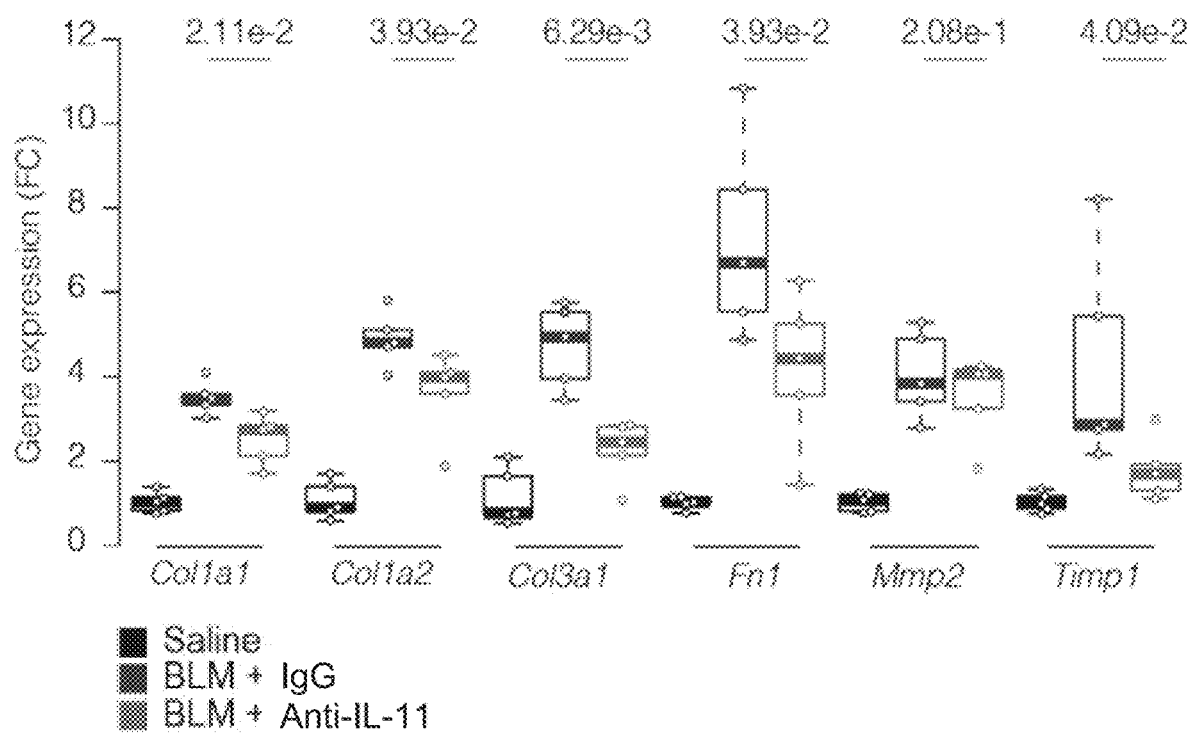
Figure 49E:
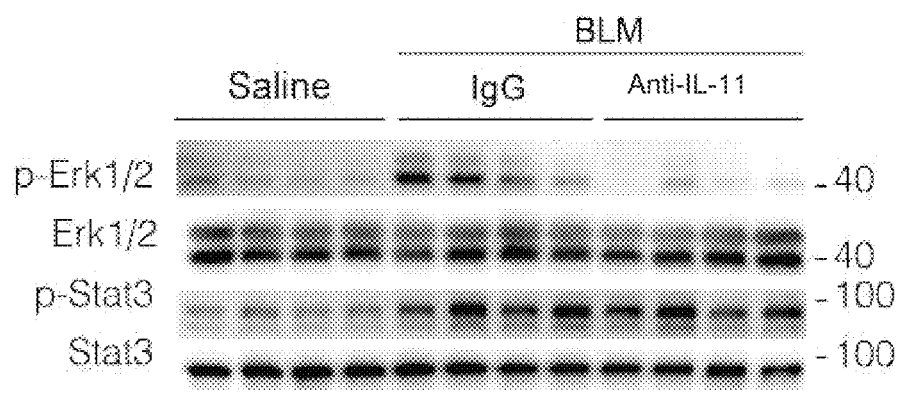
Figure 50A:
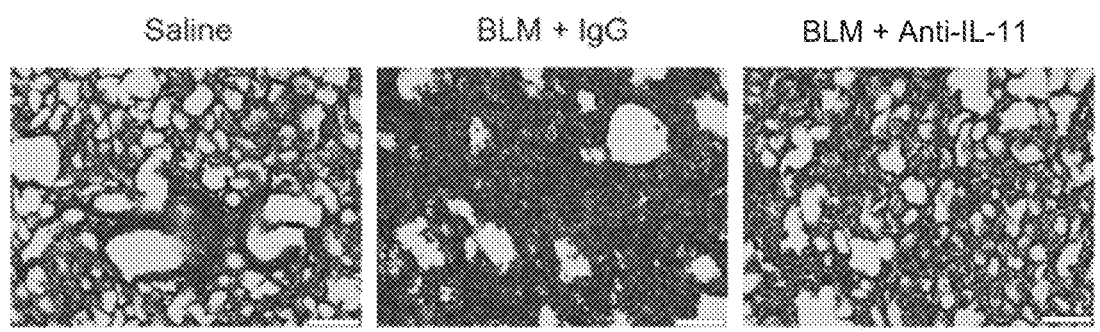
Figure 50B:
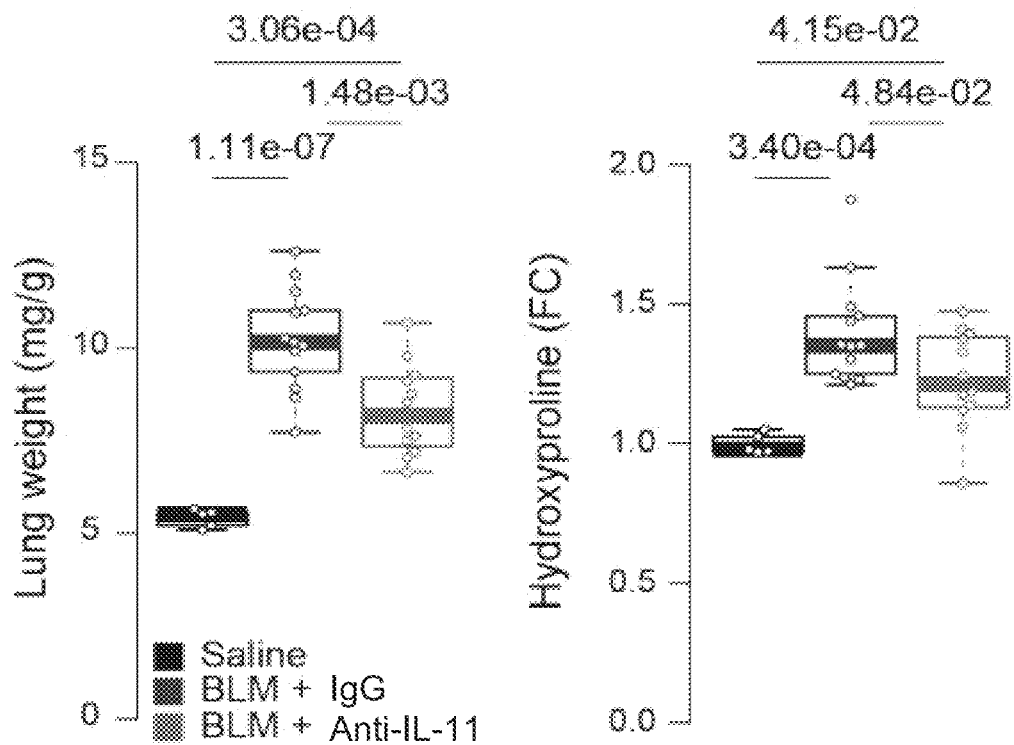
Figure 50C:
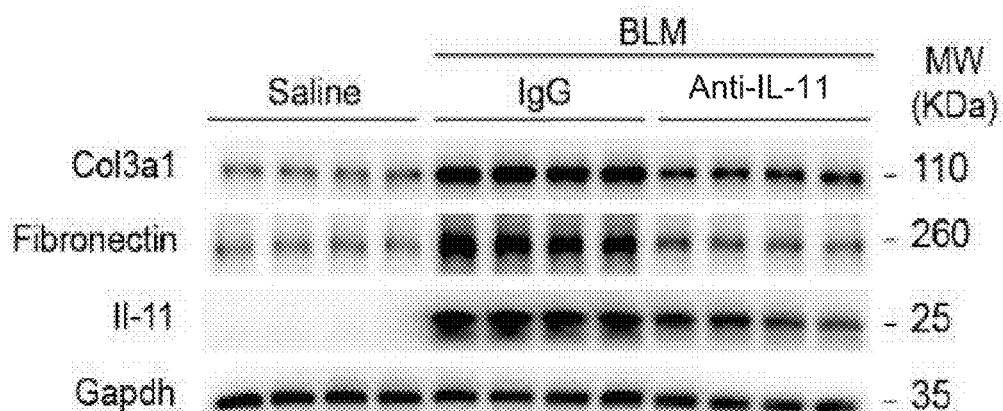
Figure 50D:
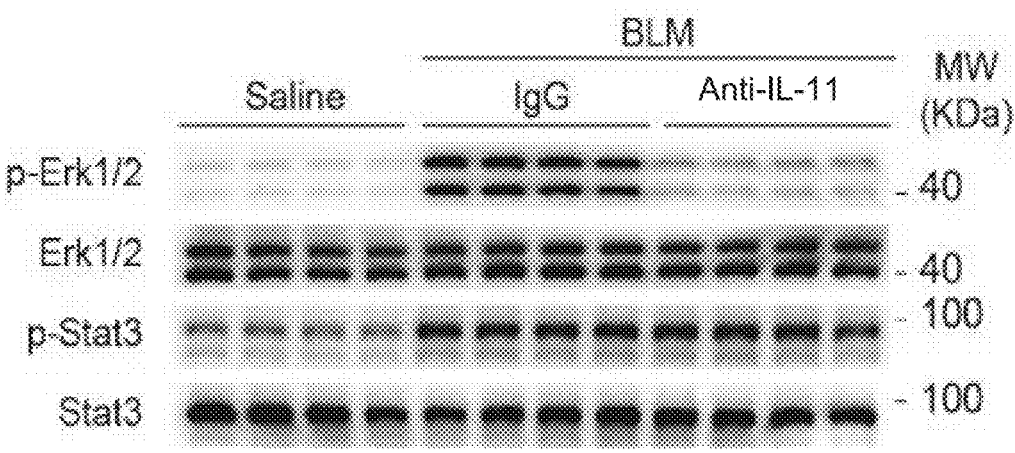

The effects of anti-IL-11 antibody BSN-3C6 on TGFβ1-induced migration or invasion of mouse lung fibroblasts was investigated. Fibroblasts were pretreated with anti-IL-11 antibody BSN-3C6 or IgG control antibodies for 15 min prior to addition of chemoattractants The results are shown in FIG. 48E. Anti-IL-11 antibody was found to reduce both migration and invasion.

Therefore, anti-IL-11 antibody BSN-3C6 was found to block fibroblast activation and ECM production, and inhibit fibroblast invasion and migration downstream of multiple stimuli. Anti-IL-11 antibody was also found to inhibit multiple fibrotic phenotypes of IPF patient-derived lung fibroblasts after TGFβ1 stimulation.

Importantly, anti-IL-11 therapy was not only able to prevent or inhibit fibrosis, but was also able to reverse the fibrotic phenotypes of established populations of TGFβ1-transformed pulmonary myofibroblasts (FIG. 48B).

21.2 Anti-IL-11 Therapy Prevents Pulmonary Fibrosis

The potential of anti-11-therapy to prevent pulmonary fibrosis was investigated in a mouse model of IPF.

The half-life of anti-IL-11 antibody BSN-3C6 in mouse blood was measured to be ~9 days using freshly labeled [$^{125I}$]BSN-3C6 (4.2 μCi/2.5 μg/100 μl) in PBS. Antibody was administered by retro orbital injections, mice were anesthetized with 2% isoflurane and blood collected at several time points: 2, 5, 10, 15, 30 min, 2 h, 6 h, 8 h and 2 d post injection via submandibular bleeding.

8-10 week old C57BL/6 female wild type mice were allowed to acclimatize for one week before bleomycin (BLM) administration. Mice were administered anti-IL-11 antibody BSN-3C6 (20 mg kg$^{-1}$, in PBS) via intraperitoneal injections on day 7, 9, 11, 14, 16, 18 and lungs were harvested on day 21 post-BLM challenge. Lung sections from anti-IL-11 antibody or IgG control were stained with Masson's trichrome: sections were subjected to Bouin's fixative, Beibrich Scarlet-Acid Fuchsin and differentiated in 5% Phosphomolybdic-phosphotungstic acid, counterstained in 2.5% Aniline blue and further differentiated in 1% Acetic acid. Total hydroxyproline content in the lungs (right superior lobe) of mice was measured using a Quickzyme Total Collagen assay kit (Quickzyme Biosciences). Protein expression of Col3a1, fibronectin, and IL-11 protein levels, and phosphorylation status and total levels of Erk and Stat3 in lung homogenates were detected by Western Blot analysis and visualised using the ECL detection system (Pierce). mRNA expression in lung lysates was quantified by RT-PCR over 40 cycles and normalised to GAPDH expression. TaqMan probes were obtained from Thermo Fisher Scientific (Col1a1, Mm00801666_g1; Col1a2, Mm00483888_m1; Col3a1, Mm01254476_m1; Fn1, Mm01256744_m1; Mmp2, Mm00439498_m1; Timp1, Mm01341361_m1; Gapdh, Mm99999915_g1).

The results are shown in FIGS. 49A to 49D. Lungs from mice treated with anti-IL-11 antibody were less fibrotic (49A). Mice treated with anti-IL-11 therapy were found to have reduced lung/body weight and lung hydroxyproline content (49B) and reduced expression of collagen proteins Col3a1 and fibronectin (49C) compared to those treated with IgG control. Anti-IL-11 treatment was found to reduce fibrosis marker RNA expression. Furthermore, anti-IL-11 antibody-treated mice were also found to have developed an RNA expression signature of preferential ECM remodelling which promotes fibrillar collagen degradation and fibrosis resolution (49D). Blocking IL-11 signalling was found to reduce non-canonical IL-11 signalling (Erk activation) whereas canonical (Stat3) signalling was unchanged (49E).

21.3 Anti-IL-11 Therapy Reverses Pulmonary Fibrosis

The potential of anti-11-therapy to treat and reverse pulmonary fibrosis was investigated in the BLM-induced IPF mouse model.

Mice were injected with anti-IL-11 antibody BSN-3C6 (20 mg kg$^{-1}$, alternate days) or IgG control starting at day 14 (late intervention) after BLM treatment, when collagen levels plateau. Lungs were assessed, as above, on day 28 post-BLM administration.

The results are shown in FIG. 50A to 50D. Fibrosis regression was observed in the lungs of mice treated with anti-IL-11 antibody compared to IgG control (50A). Mice treated with anti-IL-11 therapy were found to have reduced lung/body weight and lung hydroxyproline content (50B). Protein levels of Col3a1 and fibronectin were notably decreased by anti-IL-11 therapy, as was IL-11 (50C). Blocking IL-11 signalling was found to reduce non-canonical IL-11 signalling (Erk activation) whereas canonical (Stat3) signalling was unchanged (50D).

In summary, neutralising IL-11 signalling using an anti-IL-11 antibody blocks the fibrotic response of lung fibroblasts and reverses TGFβ1-transformed myofibroblast activation. In a mouse model of IPF, where IL-11 is strongly upregulated, administration of anti-IL-11 therapy either early or late after BML challenge resulted in prevention or reversal of lung fibrosis, respectively.

Example 22: Effect of IL-11 on Pancreatic Fibrosis

100 µg/kg of recombinant mouse IL-11 or saline were injected into mice daily subcutaneously for 21 days. Collagen content of the pancreas was then assessed using the calorimetric hydroxyproline assay.

The results are shown in FIG. 52. IL-11 induces collagen production in the pancreas. Pancreatic fibrosis will therefore benefit from therapy with anti-IL-11 antibodies.

Example 23: Effect of Anti-IL-11 Antibodies on Wasting Disorders

Animals on an HFMCD diet lose weight and become very unwell, see also Example 14. Inhibition of IL-11 signalling ameliorates HFMCD-induced loss of weight and 9A7 antibody showed a dose dependent effect on weight gain.

Five-week old male mice were fed on the HFMCD or normal chow (NC) diet as before for one week to induce wasting, resulting in a ~15% loss in body weight in MCD mice. After the initial week, mice were intraperitoneally injected twice per week with 0.5, 1, 5 or 10 mg/kg of anti-IL-11 antibody YU100-G08_02A or 3C6. 10 mg/kg of IgG isotype antibody was used as a control. Body weight and food consumption were measured weekly. For food consumption, average food intake was measured (g/mouse/week) in food hoppers from cages (n=3 mice per cage).

The results are shown in FIGS. 53A and 53B. Anti-IL-11 therapies (53A) YU100-G08_02A and (53B) 3C6 were found to provide a dose-dependent gain in body weight and food consumption, indicating reversal of wasting. The highest doses showed the greatest wasting-reversing effect. Mice fed with an NC diet steadily gained weight, whilst mice fed on the HFMCD diet and treated with IgG control lost ~30% of body weight over the course of the treatment. The highest doses had the greatest effect on food consumption, whereas mice treated with IgG control showed a slight reduction in food consumption.

Acute disease, e.g. trauma or sepsis, can also be associated with anorexia and cachexia, and so the inventors next investigated the effects of antagonism of IL-11-mediated signalling on anorexia and cachexia in mouse models of acute kidney injury.

Kidney injury was induced by IP injection of folic acid (180 mg/kg) in vehicle (0.3M NaHCO3) to 10-week old male mice; control mice were administered vehicle alone. Animals were sacrificed 28 days post-injection. Mice were intraperitoneally injected every 3 days with 20 mg/kg of anti-IL-11 antibody or identical concentration of IgG isotype control starting from 1 hour before folic acid administration until the mice were sacrificed.

It was found that folate-induced kidney injury resulted in rapid anorexia/cachexia-associated weight loss associated with the acute phase of severe and bilateral kidney injury. Mice (n=7/group) receiving anti-IL-11 therapy at the time of injury, and for the duration of the injury, regained weight more quickly compared to the IgG control and returned to normal, or near normal, weight by 3 weeks later.

Separately, kidney injury is induced as before by IP injection of folic acid. Mice are only treated with anti-IL-11 antibody or IgG control from 21 days after kidney injury. Animal weight is assessed before and after antibody treatment. Healthy mice that do not receive folic acid were used as a control.

FIG. 53C shows that mice treated with anti-IL-11 antibody start to regain weight upon initiation of treatment showing that wasting-associated weight loss can be improved in late-stage disease.

Example 24: Effect of Anti-IL-11 Antibodies on Metabolic Disorders

The effect of anti-IL-11 antibody is investigated in mice with metabolic diseases such as obesity and type II diabetes. Western diet along with fructose (WDF) is used to establish metabolic disorders that closely resemble those in humans during obesity, type II diabetes and non-alcoholic fatty liver disease (NAFLD) (Baena et al., Sci Rep (2016) 6: 26149, Machado et al., PLoS One (2015) 10:e0127991). Mice are fed Western diet (D12079B, Research Diets), supplemented with 15% weight/volume fructose in drinking water (WDF) for 16 weeks, from 12 weeks of age. Control subjects are fed normal chow (NC, Specialty Feeds) and drinking water. IgG antibody is used as a control.

Anti-IL-11 antibody-treated mice fed on WDF show significant reduction in body weight (A) and fat mass (B) when compared to control IgG anybody-treated mice fed on WDF. An increase in lean mass is also observed in mice treated with anti-IL-11 antibody compared to IgG control-treated mice, suggesting that inhibition of IL-11 signalling during WDF-induced metabolic pathogenesis recovered muscle mass. Furthermore, intraperitoneal glucose tolerance test (ipGTT) results show, along with fasting glucose, significant improvement in glucose tolerance in mice treated with anti-IL-11 antibody.

The analysis is extended to the effects on the pancreas. Anti-IL-11 antibody-treated mice fed on WDF are found to display remarkable protection against WDF-induced loss of pancreas whether treated from 8 to 16 weeks (for protecting against effects associated with metabolic disease) or treated from 16 to 24 week (for reversing effects associated with metabolic disease) when compared to IgG control-treated mice.

Anti-IL-11 antibody-treated mice fed on WDF show significantly lower serum cholesterol levels compared to control IgG anybody-treated mice fed on WDF, and show significantly lower serum triglyceride levels compared to control IgG anybody-treated mice fed on WDF. Anti-IL-11 antibody-treated mice fed on WDF show significantly lower fasting blood glucose levels compared to control IgG anybody-treated mice fed on WDF.

Immune-histology of pancreas reveals increase in glucagon and insulin staining in pancreatic islets along with islet hyperplasia in IgG treated WDF fed mice, which are classical features of type II diabetes (Bonner-Weir and O'Brien Diabetes (2008) 57:2899-2904). Anti-IL-11 antibody treatment in WDF fed mice from 16 to 24 weeks remarkably reduces islet hyperplasia and glucagon staining as well improved insulin expression in the islets of mice fed on WDF, suggesting that antagonism of IL-11 mediated signalling is useful to improve and reverse metabolic diseases caused by a Western-type diet.

The HFMCD model has early onset steatotic hepatitis followed by fibrosis. However, this model is not obese or insulin resistant. A model of WDF-induced NASH is used to test effects of anti-IL-11 therapy in the context of obesity, insulin resistance and diabetes. Mice are fed WDF for 16 weeks by which time they were obese and insulin resistant with liver steatosis, inflammation and fibrosis. Treatment with anti-IL11 antibody is then initiated. Hepatic Erk activation is inhibited in NASH livers when IL-11 signalling was targeted (e.g. FIG. 40A). Despite similar weight gain, reversal of liver fibrosis, steatosis, inflammation, and reduction in serum ALT levels in mice on anti-IL11 therapy is observed. This is accompanied by a reduction in serum glucose, triglycerides and cholesterol levels. Neutralizing anti-IL11 therapy reverses WDF-induced NASH pathologies.

Severe liver fibrosis is established using HFMCD for 10 weeks, then mice are converted to normal chow, mimicking a robust metabolic intervention, and anti-IL-11 antibody treatment is initiated in parallel.

Upon removal of the metabolic stimulus, Erk activation is found to slowly regress, which is accelerated by antibody treatment. Fibrosis is unchanged in IgG treated animals for the duration of the experiment, suggesting complete metabolic correction alone does not reverse fibrosis, or very slowly reverses fibrosis. In contrast, hepatic collagen content is significantly reversed in the early stages of antibody treatment with further reversal in later stages, showing a progressive and sustained effect.

Regression of fibrosis is associated with lower TIMP and higher MMP levels, which promotes favorable matrix remodelling. Consistent with this, anti-IL11 antibody treated mice with severe fibrosis are found to rapidly upregulate Mmp2 and downregulate Timp1. Reversal of hepatic fibrosis is favoured when transformed HSCs undergo apoptosis, senescence and/or revert to an inactive ACTA2−ve state. To check if IL-11 is required to maintain HSCs in a transformed state, HSCs are stimulated with TGFβ1 or PDGF followed by inhibition of IL-11 signalling. Within 24 h of IL-11 inhibition, the percentage of ACTA2+ve cells and the amount of secreted collagen are reversed to near baseline levels, and ERK activity is largely diminished despite ongoing TGFβ1/PDGF stimulation.

Example 25: Effect of Inhibiting IL-11 Signalling in Hepatotoxicity 25.1 Effect of Anti-IL-11 Therapy on Hepatotoxicity IL-11 directly causes hepatocyte cell death and drives hepatocyte to dysfunctional partial epithelial-mesenchymal cell transition (EMT) state that is known to limit the regenerative capacity of the liver (Grant Rowe et al. Molecular and Cellular Biology 2011; 31 (12): 2392-2403). Primary human hepatocytes were found to highly express the IL-11Rα receptor, IL-11 stimulation was found to induce dose-dependent hepatocyte cell death as evidenced by a progressive increase in alanine aminotransferase (ALT) over the physiologically relevant dose range, and stimulation of human hepatocytes with $H_2O_2$ results in IL-11 upregulation by 10-fold in the supernatant.

A mouse model of acetaminophen (APAP)-induced liver injury is employed to investigate the effect of anti-IL-11 therapy on hepatotoxicity. 12-14 weeks old male mice are starved and intraperitoneally (IP) injected with 10 mg/kg of anti-IL-11 antibody or IgG isotype control 16 hours prior to APAP injection (IP, 400 mg/kg). Mice were sacrificed 24 hours post-APAP administration. The levels of IL-11 in mouse serum and hepatocyte supernatant are quantified. Liver samples are excised and fixed for 48 hours at room temperature in 10% neutral-buffered formalin (NBF), dehydrated, embedded in paraffin blocks and sectioned at 7 μm. Sections are stained with Hematoxylin&Eosin (H&E) according to standard protocol and examined by light microscopy.

Mice receiving anti-IL-11 antibody are found to have lower ALT levels, i.e. less liver damage, and prevent APAP-induced loss of liver mass, which reflects destruction of liver cells. Antibody treated mice are also found to have normal mobility and activity, compared to control IgG-treated mice were found to be static/moribund with visible features of ill health (e.g. piloerection, hunched posture).

Inhibiting IL-11 signalling by blocking IL-11 is found to prevent hepatotoxicity in the accepted, translational model of APAP-induced liver injury (drug induced liver injury; DILI).

Severe APAP overdose (400 mg/kg) or an equivalent volume of saline is administered to 12-14 weeks old male mice by IP injection, and 10 hours later mice are administered IP with 20 mg/kg of antagonist anti-IL11Rα antibody, isotype-matched IgG control antibody, or untreated. Anti-IL-11 antibody administered 10 hours after severe APAP overdose is found to restore gross liver morphology to that mice which had not been treated with APAP. Liver function is also rescued in mice treated with anti-IL-11 antibody. Antagonist antibody inhibitor of IL-11 mediated signalling administered 10 hours after lethal APAP overdose is demonstrated to rescue mice from DILI-associated inhibition of liver function. 10 hours is thought to be equivalent to about 24 hours after overdose in humans.

Example 26: Isotype Selection

Clones YU100-G08_02A, 3C6 VH2.2A/L2.2 and 3C6 VH2.2A/L2.1 were generated in the human IgG1 and IgG4 formats. The IgG4 version contains the S241P L248E double mutation (Kabat numbering). The S241P mutation is hinge stabilising while the L248E mutation further reduces the already low ADCC effector function of IgG4 (Davies and Sutton, Immunol Rev. 2015 November; 268(1):139-159; Angal et al Mol Immunol. 1993 January; 30(1):105-8). The lower ADCC activity may be advantageous for subcutaneous administration of the antibody.

Forced degradation studies were performed to examine the effects of oxidation and deamidation on the integrity of the YU100-G08_02A antibodies. Forced oxidation using 0.5% v/v $H_2O_2$ showed that YU100-G08_02A (IgG4) was not susceptible to the effects of oxidation as assessed by micro-capillary zone electrophoresis (micro-CZE), whereas YU100-G08_02A in IgG1 format were slightly affected. SEC-HPLC analyses of both clones indicated a stable IgG4 clone after the oxidation treatment, whereas the IgG1 clone appeared to partially fragment into light and heavy chains. When antibodies were treated with 1% w/v ammonium bicarbonate, deamidation of YU100-G08_02A (IgG4) was observed, however this did not have an impact on antibody integrity. YU100-G08_02A in IgG1 format appeared less stable after deamidation in comparison.

Stability studies were performed, in which both clones were stored in either PBS—or—10 mM Histidine pH 6.5, 10% Trealose, 0.02% Polysorbate 80—or—25 mM Citrate pH 5.5, 150 mM Arginine, 0.02% Polysorbate 80. Antibodies were stored at −20, 25 or 45 degree Celsius. Stability was assessed using UV-Vis, SEC-HPLC, CE-SDS and CE-CZE at 0, 2, 4 and 12 weeks. Both antibodies appeared stable at similar levels with slight increase in degradation at 45 degrees Celsius.

YU100-G08_02A (IgG1) and YU100-G08_02A (IgG4) were tested in in vitro cellular assays. Primary hepatic stellate cells were activated with either TGFB1 (5 ng/ml), IL-11 (2 ng/ml) or hyperIL-11 (200 pg/ml) and incubated with varying concentrations of either antibody to determine IC50 values, as described previously. Neutralisation of the fibrotic response in vitro assessed by monitoring MMP2 secretion into the supernatant.

FIGS. 55A to 55C show that YU100-G08_02A in both formats block (A) endogenous IL-11 signalling, (B) exogenous IL-11 signalling and (C) IL-11 trans signalling. Fibrogenic protein production was inhibited in each case.

The performance of both antibodies in vivo was tested in the HFMCD preclinical model of NASH, as described in Example 14. Animals were fed with HFMCD or normal chow for 4 weeks. For the final 3 weeks of the diet, animals were also treated with varying amounts of YU100-G08_02A IgG1 or IgG4. Serum ALT levels and hepatic collagen content (HPA assay) were assessed after 4 weeks of diet and antibody treatment. Identical baseline and IgG control animals are plotted for each antibody to facilitate data interpretation.

The results are shown in FIGS. 56A and 56B. Both antibody formats were able to reduce serum ALT levels (A) and liver collagen (B), thus indicating reversal of liver damage and fibrosis. YU100-G08_02A IgG4 performed slightly better than the IgG1 version.

The invention claimed is:

1. An antigen-binding molecule that specifically binds to IL-11, comprising:
   (i) a heavy chain variable (VH) region incorporating the following CDRs:
      HC-CDR1 having the amino acid sequence of SEQ ID NO: 37;
      HC-CDR2 having the amino acid sequence of SEQ ID NO: 38; and
      HC-CDR3 having the amino acid sequence of SEQ ID NO: 40; and
   (ii) a light chain variable (VL) region incorporating the following CDRs:
      LC-CDR1 having the amino acid sequence of SEQ ID NO: 42;
      LC-CDR2 having the amino acid sequence of SEQ ID NO: 45; and
      LC-CDR3 having the amino acid sequence of SEQ ID NO: 81.

2. The antigen-binding molecule according to claim 1, wherein the antigen-binding molecule comprises:
   (i) a VH region incorporating the following CDRs:
      HC-CDR1 having the amino acid sequence of SEQ ID NO: 37;
      HC-CDR2 having the amino acid sequence of SEQ ID NO: 38; and
      HC-CDR3 having the amino acid sequence of SEQ ID NO: 40; and
   (ii) a VL region incorporating the following CDRs:
      LC-CDR1 having the amino acid sequence of SEQ ID NO: 42;
      LC-CDR2 having the amino acid sequence of SEQ ID NO: 45; and
      LC-CDR3 having the amino acid sequence of SEQ ID NO: 57.

3. The antigen-binding molecule according to claim 1, wherein the antigen-binding molecule comprises:
   (i) a VH region comprising an amino acid sequence having at least 70% sequence identity to the amino acid sequence of SEQ ID NO: 8; and
   (ii) a VL region comprising an amino acid sequence having at least 70% sequence identity to the amino acid sequence of SEQ ID NO: 83.

4. The antigen-binding molecule according to claim 1, wherein the antigen-binding molecule comprises:
   (i) a VH region comprising an amino acid sequence having at least 70% sequence identity to the amino acid sequence of SEQ ID NO: 8; and
   (ii) a VL region comprising an amino acid sequence having at least 70% sequence identity to the amino acid sequence of SEQ ID NO: 20.

5. The antigen-binding molecule according to claim 1, wherein the antigen-binding molecule comprises a heavy chain comprising the amino acid sequence of SEQ ID NO: 218.

6. The antigen-binding molecule according to claim 1, wherein the antigen-binding molecule comprises:
   (i) a heavy chain comprising the amino acid sequence of SEQ ID NO: 223; and
   (ii) a light chain comprising the amino acid sequence of SEQ ID NO: 237.

* * * * *

SEQUENCE LISTING

```
<160> NUMBER OF SEQ ID NOS: 240

<210> SEQ ID NO 1
<211> LENGTH: 199
<212> TYPE: PRT
<213> ORGANISM: Homo sapiens
<220> FEATURE:
<221> NAME/KEY: misc_feature
<222> LOCATION: (1)..(199)
<223> OTHER INFORMATION: IL-11 (UniProt: P20809)

<400> SEQUENCE: 1

Met Asn Cys Val Cys Arg Leu Val Leu Val Val Leu Ser Leu Trp Pro
1               5                   10                  15

Asp Thr Ala Val Ala Pro Gly Pro Pro Pro Gly Pro Pro Arg Val Ser
            20                  25                  30

Pro Asp Pro Arg Ala Glu Leu Asp Ser Thr Val Leu Leu Thr Arg Ser
        35                  40                  45

Leu Leu Ala Asp Thr Arg Gln Leu Ala Ala Gln Leu Arg Asp Lys Phe
    50                  55                  60

Pro Ala Asp Gly Asp His Asn Leu Asp Ser Leu Pro Thr Leu Ala Met
65                  70                  75                  80

Ser Ala Gly Ala Leu Gly Ala Leu Gln Leu Pro Gly Val Leu Thr Arg
                85                  90                  95

Leu Arg Ala Asp Leu Leu Ser Tyr Leu Arg His Val Gln Trp Leu Arg
            100                 105                 110

Arg Ala Gly Gly Ser Ser Leu Lys Thr Leu Glu Pro Glu Leu Gly Thr
        115                 120                 125

Leu Gln Ala Arg Leu Asp Arg Leu Leu Arg Arg Leu Gln Leu Leu Met
    130                 135                 140
```

```
Ser Arg Leu Ala Leu Pro Gln Pro Pro Asp Pro Pro Ala Pro Pro
145                 150                 155                 160

Leu Ala Pro Pro Ser Ser Ala Trp Gly Gly Ile Arg Ala Ala His Ala
            165                 170                 175

Ile Leu Gly Gly Leu His Leu Thr Leu Asp Trp Ala Val Arg Gly Leu
        180                 185                 190

Leu Leu Leu Lys Thr Arg Leu
        195

<210> SEQ ID NO 2
<211> LENGTH: 918
<212> TYPE: PRT
<213> ORGANISM: Homo sapiens
<220> FEATURE:
<221> NAME/KEY: misc_feature
<222> LOCATION: (1)..(918)
<223> OTHER INFORMATION: gp130 (UniProt P40189-1)

<400> SEQUENCE: 2

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
```

```
                290                 295                 300
Asp Gly Lys Gly Tyr Trp Ser Asp Trp Ser Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
                340                 345                 350

Thr Leu Pro Pro Phe Glu Ala Asn Gly Lys Ile Leu Asp Tyr Glu Val
                355                 360                 365

Thr Leu Thr Arg Trp Lys Ser His Leu Gln Asn Tyr Thr Val Asn Ala
370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
                420                 425                 430

Phe Pro Lys Asp Asn Met Leu Trp Val Glu Trp Thr Thr Pro Arg Glu
                435                 440                 445

Ser Val Lys Lys Tyr Ile Leu Glu Trp Cys Val Leu Ser Asp Lys Ala
                450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
                500                 505                 510

Tyr Leu Lys Gln Ala Pro Pro Ser Lys Gly Pro Thr Val Arg Thr Lys
                515                 520                 525

Lys Val Gly Lys Asn Glu Ala Val Leu Glu Trp Asp Gln Leu Pro Val
530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
                580                 585                 590

Ala Ala Tyr Thr Asp Glu Gly Gly Lys Asp Gly Pro Glu Phe Thr Phe
                595                 600                 605

Thr Thr Pro Lys Phe Ala Gln Gly Glu Ile Glu Ala Ile Val Val Pro
610                 615                 620

Val Cys Leu Ala Phe Leu Leu Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
                660                 665                 670

Arg His Asn Phe Asn Ser Lys Asp Gln Met Tyr Ser Asp Gly Asn Phe
                675                 680                 685

Thr Asp Val Ser Val Val Glu Ile Glu Ala Asn Asp Lys Lys Pro Phe
                690                 695                 700

Pro Glu Asp Leu Lys Ser Leu Asp Leu Phe Lys Lys Glu Lys Ile Asn
705                 710                 715                 720
```

```
Thr Glu Gly His Ser Ser Gly Ile Gly Gly Ser Ser Cys Met Ser Ser
                725                 730                 735

Ser Arg Pro Ser Ile Ser Ser Asp Glu Asn Glu Ser Ser Gln Asn
        740                 745                 750

Thr Ser Thr Val Gln Tyr Ser Thr Val Val His Ser Gly Tyr Arg
    755                 760                 765

His Gln Val Pro Ser Val Gln Val Phe Ser Arg Ser Glu Ser Thr Gln
770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Gln
850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
            900                 905                 910

Gly Gly Tyr Met Pro Gln
        915

<210> SEQ ID NO 3
<211> LENGTH: 422
<212> TYPE: PRT
<213> ORGANISM: Homo sapiens
<220> FEATURE:
<221> NAME/KEY: misc_feature
<222> LOCATION: (1)..(422)
<223> OTHER INFORMATION: IL11RA (UniProt Q14626)

<400> SEQUENCE: 3

Met Ser Ser Cys Ser Gly Leu Ser Arg Val Leu Val Ala Val Ala
1               5                   10                  15

Thr Ala Leu Val Ser Ala Ser Ser Pro Cys Pro Gln Ala Trp Gly Pro
            20                  25                  30

Pro Gly Val Gln Tyr Gly Gln Pro Gly Arg Ser Val Lys Leu Cys Cys
        35                  40                  45

Pro Gly Val Thr Ala Gly Asp Pro Val Ser Trp Phe Arg Asp Gly Glu
    50                  55                  60

Pro Lys Leu Leu Gln Gly Pro Asp Ser Gly Leu Gly His Glu Leu Val
65                  70                  75                  80

Leu Ala Gln Ala Asp Ser Thr Asp Glu Gly Thr Tyr Ile Cys Gln Thr
                85                  90                  95

Leu Asp Gly Ala Leu Gly Gly Thr Val Thr Leu Gln Leu Gly Tyr Pro
            100                 105                 110

Pro Ala Arg Pro Val Val Ser Cys Gln Ala Ala Asp Tyr Glu Asn Phe
        115                 120                 125

Ser Cys Thr Trp Ser Pro Ser Gln Ile Ser Gly Leu Pro Thr Arg Tyr
    130                 135                 140
```

```
Leu Thr Ser Tyr Arg Lys Lys Thr Val Leu Gly Ala Asp Ser Gln Arg
145                 150                 155                 160

Arg Ser Pro Ser Thr Gly Pro Trp Pro Cys Pro Gln Asp Pro Leu Gly
                165                 170                 175

Ala Ala Arg Cys Val Val His Gly Ala Glu Phe Trp Ser Gln Tyr Arg
            180                 185                 190

Ile Asn Val Thr Glu Val Asn Pro Leu Gly Ala Ser Thr Arg Leu Leu
        195                 200                 205

Asp Val Ser Leu Gln Ser Ile Leu Arg Pro Asp Pro Gln Gly Leu
    210                 215                 220

Arg Val Glu Ser Val Pro Gly Tyr Pro Arg Arg Leu Arg Ala Ser Trp
225                 230                 235                 240

Thr Tyr Pro Ala Ser Trp Pro Cys Gln Pro His Phe Leu Leu Lys Phe
                245                 250                 255

Arg Leu Gln Tyr Arg Pro Ala Gln His Pro Ala Trp Ser Thr Val Glu
            260                 265                 270

Pro Ala Gly Leu Glu Glu Val Ile Thr Asp Ala Val Ala Gly Leu Pro
        275                 280                 285

His Ala Val Arg Val Ser Ala Arg Asp Phe Leu Asp Ala Gly Thr Trp
    290                 295                 300

Ser Thr Trp Ser Pro Glu Ala Trp Gly Thr Pro Ser Thr Gly Thr Ile
305                 310                 315                 320

Pro Lys Glu Ile Pro Ala Trp Gly Gln Leu His Thr Gln Pro Glu Val
                325                 330                 335

Glu Pro Gln Val Asp Ser Pro Ala Pro Pro Arg Pro Ser Leu Gln Pro
            340                 345                 350

His Pro Arg Leu Leu Asp His Arg Asp Ser Val Glu Gln Val Ala Val
        355                 360                 365

Leu Ala Ser Leu Gly Ile Leu Ser Phe Leu Gly Leu Val Ala Gly Ala
    370                 375                 380

Leu Ala Leu Gly Leu Trp Leu Arg Leu Arg Arg Gly Gly Lys Asp Gly
385                 390                 395                 400

Ser Pro Lys Pro Gly Phe Leu Ala Ser Val Ile Pro Val Asp Arg Arg
                405                 410                 415

Pro Gly Ala Pro Asn Leu
            420

<210> SEQ ID NO 4
<211> LENGTH: 516
<212> TYPE: PRT
<213> ORGANISM: Artificial Sequence
<220> FEATURE:
<223> OTHER INFORMATION: IL-11:IL-11Ralpha fusion protein

<400> SEQUENCE: 4

Met Gly Trp Ser Cys Ile Ile Leu Phe Leu Val Ala Thr Ala Thr Gly
1               5                   10                  15

Val His Ser Pro Gln Ala Trp Gly Pro Gly Val Gln Tyr Gly Gln
                20                  25                  30

Pro Gly Arg Ser Val Lys Leu Cys Cys Pro Gly Val Thr Ala Gly Asp
            35                  40                  45

Pro Val Ser Trp Phe Arg Asp Gly Glu Pro Lys Leu Leu Gln Gly Pro
        50                  55                  60

Asp Ser Gly Leu Gly His Glu Leu Val Leu Ala Gln Ala Asp Ser Thr
65                  70                  75                  80
```

```
Asp Glu Gly Thr Tyr Ile Cys Gln Thr Leu Asp Gly Ala Leu Gly
                85                  90                  95

Thr Val Thr Leu Gln Leu Gly Tyr Pro Pro Ala Arg Pro Val Val Ser
            100                 105                 110

Cys Gln Ala Ala Asp Tyr Glu Asn Phe Ser Cys Thr Trp Ser Pro Ser
            115                 120                 125

Gln Ile Ser Gly Leu Pro Thr Arg Tyr Leu Thr Ser Tyr Arg Lys Lys
            130                 135                 140

Thr Val Leu Gly Ala Asp Ser Gln Arg Arg Ser Pro Ser Thr Gly Pro
145                 150                 155                 160

Trp Pro Cys Pro Gln Asp Pro Leu Gly Ala Ala Arg Cys Val Val His
                165                 170                 175

Gly Ala Glu Phe Trp Ser Gln Tyr Arg Ile Asn Val Thr Glu Val Asn
            180                 185                 190

Pro Leu Gly Ala Ser Thr Arg Leu Leu Asp Val Ser Leu Gln Ser Ile
            195                 200                 205

Leu Arg Pro Asp Pro Pro Gln Gly Leu Arg Val Glu Ser Val Pro Gly
210                 215                 220

Tyr Pro Arg Arg Leu Arg Ala Ser Trp Thr Tyr Pro Ala Ser Trp Pro
225                 230                 235                 240

Cys Gln Pro His Phe Leu Leu Lys Phe Arg Leu Gln Tyr Arg Pro Ala
                245                 250                 255

Gln His Pro Ala Trp Ser Thr Val Glu Pro Ala Gly Leu Glu Glu Val
            260                 265                 270

Ile Thr Asp Ala Val Ala Gly Leu Pro His Ala Val Arg Val Ser Ala
            275                 280                 285

Arg Asp Phe Leu Asp Ala Gly Thr Trp Ser Thr Trp Ser Pro Glu Ala
290                 295                 300

Trp Gly Thr Pro Ser Thr Gly Pro Ala Gly Gln Ser Gly Gly Gly
305                 310                 315                 320

Gly Gly Ser Gly Gly Gly Ser Gly Gly Gly Ser Val Pro Gly Pro Pro
            325                 330                 335

Pro Gly Pro Pro Arg Val Ser Pro Asp Pro Arg Ala Glu Leu Asp Ser
            340                 345                 350

Thr Val Leu Leu Thr Arg Ser Leu Leu Ala Asp Thr Arg Gln Leu Ala
            355                 360                 365

Ala Gln Leu Arg Asp Lys Phe Pro Ala Asp Gly Asp His Asn Leu Asp
            370                 375                 380

Ser Leu Pro Thr Leu Ala Met Ser Ala Gly Ala Leu Gly Ala Leu Gln
385                 390                 395                 400

Leu Pro Gly Val Leu Thr Arg Leu Arg Ala Asp Leu Leu Ser Tyr Leu
            405                 410                 415

Arg His Val Gln Trp Leu Arg Arg Ala Gly Gly Ser Ser Leu Lys Thr
            420                 425                 430

Leu Glu Pro Glu Leu Gly Thr Leu Gln Ala Arg Leu Asp Arg Leu Leu
            435                 440                 445

Arg Arg Leu Gln Leu Leu Met Ser Arg Leu Ala Leu Pro Gln Pro Pro
450                 455                 460

Pro Asp Pro Pro Ala Pro Leu Ala Pro Ser Ser Ala Trp Gly
465                 470                 475                 480

Gly Ile Arg Ala Ala His Ala Ile Leu Gly Gly Leu His Leu Thr Leu
            485                 490                 495

Asp Trp Ala Val Arg Gly Leu Leu Leu Leu Lys Thr Arg Leu His His
```

```
                500           505           510
His His His His
        515

<210> SEQ ID NO 5
<211> LENGTH: 1575
<212> TYPE: DNA
<213> ORGANISM: Artificial Sequence
<220> FEATURE:
<223> OTHER INFORMATION: Nucleotide sequence encoding IL-11:IL-11Ralpha
      fusion protein

<400> SEQUENCE: 5
gaattcccgc cgccaccatg ggctggtcct gcatcatcct gtttctggtg gccacagcca      60
ccggcgtgca ctctccacag gcttggggac ctccaggcgt gcagtatggc agcctggca     120 gatccgtgaa gctgtgctgt cctggcgtga cagctggcga ccctgtgtcc tggttcagag     180
atggcgagcc caagctgctg cagggccag attctggact gggccacgaa ctggtgctgg     240
cccaggccga ttctaccgac gagggcacct acatctgcca gaccctggat ggcgccctgg     300
gcggaacagt gacactgcag ctgggctacc ctcccgccag acctgtggtg tcttgtcagg     360
ccgccgacta cgagaacttc agctgcacat ggtcccccag ccagatcagc ggcctgccca     420
ccagatacct gaccagctac cggaagaaaa ccgtgctggg cgccgacagc cagagaagaa     480
gcccttctac aggcccctgg ccctgcctc aggatcctct gggagctgcc agatgtgtgg     540
tgcacggcgc cgagttctgg tcccagtacc ggatcaacgt gaccgaagtg aaccccctgg     600
gcgcctccac aagactgctg atgtgtccc tgcagagcat cctgcggccc gatcctccac     660
agggcctgag agtggaaagc gtgcccggct accccagaag gctgagagcc agctggacat     720
accccgcctc ttggccttgc cagccccact tcctgctgaa gtttcggctg cagtaccggc     780
cagcccagca ccctgcttgg agcacagtgg aacctgccgg cctggaagaa gtgatcacag     840
acgccgtggc cggactgcct catgctgtgc gggtgtccgc cagagacttt ctggatgccg     900
gcacctggtc tacctggtcc ccagaagcct ggggcacacc ttctactggc ggacctgctg     960
gacagtctgg cggaggcgga ggaagtggcg gaggatcagg ggaggatct gtgcctggac    1020 ctcctccagg accccctaga gtgtccccag atcctagggc cgagctggac tctaccgtgc    1080
tgctgaccag atccctgctg gccgacacaa ggcagctggc tgcccagctg agagacaagt    1140
tccccgccga cggcgaccac aacctggata gcctgcctac cctggccatg tctgctggcg    1200
cactgggggc tctgcagctg cctggggtgc tgactagact gagagccgac ctgctgagct    1260
acctgcggca tgtgcagtgg ctgagaaggg ctggcggcag cagcctgaaa accctggaac    1320
ctgagctggg cacactgcag gccagactgg acagactgct cgcagactg cagctgctga    1380 tgagcagact ggctctgccc cagcctcctc ctgaccctcc tgctcctcca ctggctcctc    1440
caagctctgc ttggggcgga attagagccg cccacgccat tctgggagggc ctgcacctga    1500 cactggattg ggcagtgcgg ggcctgctgc tgctgaaaac cagactgcac caccaccatc    1560
accactgata agctt                                                    1575

<210> SEQ ID NO 6
<211> LENGTH: 123
<212> TYPE: PRT
<213> ORGANISM: Artificial Sequence
<220> FEATURE:
<223> OTHER INFORMATION: YU100-H01 VH

<400> SEQUENCE: 6
```

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Met Gly Tyr Asp Tyr Gly Asp Tyr Asp Val Asp Tyr
            100                 105                 110

Trp Gly Gln Gly Thr Leu Val Thr Val Ser Ser
        115                 120
```

<210> SEQ ID NO 7
<211> LENGTH: 111
<212> TYPE: PRT
<213> ORGANISM: Artificial Sequence
<220> FEATURE:
<223> OTHER INFORMATION: YU100-H01 VL

<400> SEQUENCE: 7

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
            35                  40                  45

Met Ile Tyr Asp Val Ser Glu Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Trp Val Phe Gly Gly Gly Thr Lys Leu Thr Val Leu Gly
            100                 105                 110
```

<210> SEQ ID NO 8
<211> LENGTH: 118
<212> TYPE: PRT
<213> ORGANISM: Artificial Sequence
<220> FEATURE:
<223> OTHER INFORMATION: YU100-G08 VH

<400> SEQUENCE: 8

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
```

```
                 65                  70                  75                  80
Leu Gln Met Asn Ser Leu Arg Ala Glu Asp Thr Ala Val Tyr Tyr Cys
                        85                  90                  95

Ala Lys Ile Gly Ala Thr Asp Pro Leu Asp Tyr Trp Gly Gln Gly Thr
                100                 105                 110

Leu Val Thr Val Ser Ser
            115

<210> SEQ ID NO 9
<211> LENGTH: 111
<212> TYPE: PRT
<213> ORGANISM: Artificial Sequence
<220> FEATURE:
<223> OTHER INFORMATION: YU100-G08 VL

<400> SEQUENCE: 9

Gln Ser Ala Leu Thr Gln Pro Arg Ser Val Ser Gly Ser Pro Gly Gln
1               5                   10                  15

Ser Val Thr Leu Ser Cys Thr Gly Thr Ser Ser Asp Val Gly Gly Tyr
                20                  25                  30

Asn Tyr Val Ser Trp Tyr Gln His Tyr Pro Gly Lys Ala Pro Lys Leu
            35                  40                  45

Met Ile Phe Asp Val Asn Glu Arg Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Arg
                85                  90                  95

Tyr Thr Trp Met Phe Gly Gly Gly Thr Lys Val Thr Val Leu Gly
                100                 105                 110

<210> SEQ ID NO 10
<211> LENGTH: 118
<212> TYPE: PRT
<213> ORGANISM: Artificial Sequence
<220> FEATURE:
<223> OTHER INFORMATION: YU100-F11 VH

<400> SEQUENCE: 10

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
                100                 105                 110

Leu Val Thr Val Ser Ser
            115

<210> SEQ ID NO 11
<211> LENGTH: 111
```

```
<212> TYPE: PRT
<213> ORGANISM: Artificial Sequence
<220> FEATURE:
<223> OTHER INFORMATION: YU100-F11 VL

<400> SEQUENCE: 11
```

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Asp Val Ala Gly Tyr
            20                  25                  30

Asn Tyr Val Ser Trp Tyr Gln Gln His Pro Gly Lys Ala Pro Lys Leu
            35                  40                  45

Met Ile Tyr Asp Val Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Cys Ser Tyr Ala Gly Ser
                85                  90                  95

Tyr Thr Trp Val Phe Gly Gly Gly Thr Gln Leu Thr Val Leu Gly
                100                 105                 110

```
<210> SEQ ID NO 12
<211> LENGTH: 111
<212> TYPE: PRT
<213> ORGANISM: Artificial Sequence
<220> FEATURE:
<223> OTHER INFORMATION: 01A VL

<400> SEQUENCE: 12
```

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
            35                  40                  45

Met Ile Tyr Asp Val Ser Glu Arg Pro Ser Gly Val Pro Asp Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ala Ser Tyr Ala Gly Ser
                85                  90                  95

Tyr Thr Trp Val Phe Gly Gly Gly Thr Lys Leu Thr Val Leu Gly
                100                 105                 110

```
<210> SEQ ID NO 13
<211> LENGTH: 111
<212> TYPE: PRT
<213> ORGANISM: Artificial Sequence
<220> FEATURE:
<223> OTHER INFORMATION: 01G VL

<400> SEQUENCE: 13
```

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
            35                  40                  45

Met Ile Tyr Asp Val Ser Glu Arg Pro Ser Gly Val Pro Asp Arg Phe
    50                  55                  60

```
                    50                  55                  60
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gly Ser Tyr Ala Gly Ser
                     85                  90                  95

Tyr Thr Trp Val Phe Gly Gly Gly Thr Lys Leu Thr Val Leu Gly
                100                 105                 110

<210> SEQ ID NO 14
<211> LENGTH: 111
<212> TYPE: PRT
<213> ORGANISM: Artificial Sequence
<220> FEATURE:
<223> OTHER INFORMATION: 01I VL

<400> SEQUENCE: 14

Gln Ser Ala Leu Thr Gln Pro Arg Ser Val Ser Gly Ser Pro Gly Gln
 1               5                  10                  15

Ser Val Thr Ile Ser Cys Thr Gly Thr Ser Ser Asp Val Gly Ala Tyr
                20                  25                  30

Asn Tyr Val Ser Trp Tyr Gln Gln His Pro Gly Lys Ala Pro Lys Leu
             35                  40                  45

Met Ile Tyr Asp Val Ser Glu Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ile Ser Tyr Ala Gly Ser
                     85                  90                  95

Tyr Thr Trp Val Phe Gly Gly Gly Thr Lys Leu Thr Val Leu Gly
                100                 105                 110

<210> SEQ ID NO 15
<211> LENGTH: 111
<212> TYPE: PRT
<213> ORGANISM: Artificial Sequence
<220> FEATURE:
<223> OTHER INFORMATION: 01L VL

<400> SEQUENCE: 15

Gln Ser Ala Leu Thr Gln Pro Arg Ser Val Ser Gly Ser Pro Gly Gln
 1               5                  10                  15

Ser Val Thr Ile Ser Cys Thr Gly Thr Ser Ser Asp Val Gly Ala Tyr
                20                  25                  30

Asn Tyr Val Ser Trp Tyr Gln Gln His Pro Gly Lys Ala Pro Lys Leu
             35                  40                  45

Met Ile Tyr Asp Val Ser Glu Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Leu Ser Tyr Ala Gly Ser
                     85                  90                  95

Tyr Thr Trp Val Phe Gly Gly Gly Thr Lys Leu Thr Val Leu Gly
                100                 105                 110

<210> SEQ ID NO 16
<211> LENGTH: 111
<212> TYPE: PRT
<213> ORGANISM: Artificial Sequence
<220> FEATURE:
```

<223> OTHER INFORMATION: 01Q VL

<400> SEQUENCE: 16

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
        35                  40                  45

Met Ile Tyr Asp Val Ser Glu Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Ala Gly Ser
                85                  90                  95

Tyr Thr Trp Val Phe Gly Gly Gly Thr Lys Leu Thr Val Leu Gly
                100                 105                 110
```

<210> SEQ ID NO 17
<211> LENGTH: 111
<212> TYPE: PRT
<213> ORGANISM: Artificial Sequence
<220> FEATURE:
<223> OTHER INFORMATION: 01S VL

<400> SEQUENCE: 17

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
        35                  40                  45

Met Ile Tyr Asp Val Ser Glu Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Tyr Thr Trp Val Phe Gly Gly Gly Thr Lys Leu Thr Val Leu Gly
                100                 105                 110
```

<210> SEQ ID NO 18
<211> LENGTH: 111
<212> TYPE: PRT
<213> ORGANISM: Artificial Sequence
<220> FEATURE:
<223> OTHER INFORMATION: 01T VL

<400> SEQUENCE: 18

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
        35                  40                  45

Met Ile Tyr Asp Val Ser Glu Arg Pro Ser Gly Val Pro Asp Arg Phe
    50                  55                  60

Ser Gly Ser Lys Ser Gly Asn Thr Ala Ser Leu Thr Ile Ser Gly Leu
```

```
                65                  70                  75                  80
Gln Ala Glu Asp Glu Ala Asp Tyr Tyr Cys Thr Ser Tyr Ala Gly Ser
                    85                  90                  95

Tyr Thr Trp Val Phe Gly Gly Gly Thr Lys Leu Thr Val Leu Gly
            100                 105                 110
```

<210> SEQ ID NO 19
<211> LENGTH: 111
<212> TYPE: PRT
<213> ORGANISM: Artificial Sequence
<220> FEATURE:
<223> OTHER INFORMATION: 01V VL

<400> SEQUENCE: 19

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ala Tyr
                20                  25                  30

Asn Tyr Val Ser Trp Tyr Gln Gln His Pro Gly Lys Ala Pro Lys Leu
            35                  40                  45

Met Ile Tyr Asp Val Ser Glu Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Val Ser Tyr Ala Gly Ser
                85                  90                  95

Tyr Thr Trp Val Phe Gly Gly Gly Thr Lys Leu Thr Val Leu Gly
            100                 105                 110
```

<210> SEQ ID NO 20
<211> LENGTH: 111
<212> TYPE: PRT
<213> ORGANISM: Artificial Sequence
<220> FEATURE:
<223> OTHER INFORMATION: 02A VL

<400> SEQUENCE: 20

```
Gln Ser Ala Leu Thr Gln Pro Arg Ser Val Ser Gly Ser Pro Gly Gln
1               5                   10                  15

Ser Val Thr Leu Ser Cys Thr Gly Thr Ser Ser Asp Val Gly Gly Tyr
                20                  25                  30

Asn Tyr Val Ser Trp Tyr Gln His Tyr Pro Gly Lys Ala Pro Lys Leu
            35                  40                  45

Met Ile Phe Asp Val Asn Glu Arg Ser Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Ala Gly Arg
                85                  90                  95

Tyr Thr Trp Met Phe Gly Gly Gly Thr Lys Val Thr Val Leu Gly
            100                 105                 110
```

<210> SEQ ID NO 21
<211> LENGTH: 111
<212> TYPE: PRT
<213> ORGANISM: Artificial Sequence
<220> FEATURE:
<223> OTHER INFORMATION: 02G VL

<400> SEQUENCE: 21

Gln Ser Ala Leu Thr Gln Pro Arg Ser Val Ser Gly Ser Pro Gly Gln
1               5                   10                  15

Ser Val Thr Leu Ser Cys Thr Gly Thr Ser Ser Asp Val Gly Gly Tyr
                20                  25                  30

Asn Tyr Val Ser Trp Tyr Gln His Tyr Pro Gly Lys Ala Pro Lys Leu
            35                  40                  45

Met Ile Phe Asp Val Asn Glu Arg Ser Gly Val Pro Asp Arg Phe
        50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ser Tyr Ala Gly Arg
                85                  90                  95

Tyr Thr Trp Met Phe Gly Gly Gly Thr Lys Val Thr Val Leu Gly
                100                 105                 110

<210> SEQ ID NO 22
<211> LENGTH: 111
<212> TYPE: PRT
<213> ORGANISM: Artificial Sequence
<220> FEATURE:
<223> OTHER INFORMATION: 02I VL

<400> SEQUENCE: 22

Gln Ser Ala Leu Thr Gln Pro Arg Ser Val Ser Gly Ser Pro Gly Gln
1               5                   10                  15

Ser Val Thr Leu Ser Cys Thr Gly Thr Ser Ser Asp Val Gly Gly Tyr
                20                  25                  30

Asn Tyr Val Ser Trp Tyr Gln His Tyr Pro Gly Lys Ala Pro Lys Leu
            35                  40                  45

Met Ile Phe Asp Val Asn Glu Arg Ser Gly Val Pro Asp Arg Phe
        50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ile Ser Tyr Ala Gly Arg
                85                  90                  95

Tyr Thr Trp Met Phe Gly Gly Gly Thr Lys Val Thr Val Leu Gly
                100                 105                 110

<210> SEQ ID NO 23
<211> LENGTH: 111
<212> TYPE: PRT
<213> ORGANISM: Artificial Sequence
<220> FEATURE:
<223> OTHER INFORMATION: 02L VL

<400> SEQUENCE: 23

Gln Ser Ala Leu Thr Gln Pro Arg Ser Val Ser Gly Ser Pro Gly Gln
1               5                   10                  15

Ser Val Thr Leu Ser Cys Thr Gly Thr Ser Ser Asp Val Gly Gly Tyr
                20                  25                  30

Asn Tyr Val Ser Trp Tyr Gln His Tyr Pro Gly Lys Ala Pro Lys Leu
            35                  40                  45

Met Ile Phe Asp Val Asn Glu Arg Ser Gly Val Pro Asp Arg Phe
        50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Leu Ser Tyr Ala Gly Arg 85                  90                  95

Tyr Thr Trp Met Phe Gly Gly Gly Thr Lys Val Thr Val Leu Gly
                100                 105                 110

<210> SEQ ID NO 24
<211> LENGTH: 111
<212> TYPE: PRT
<213> ORGANISM: Artificial Sequence
<220> FEATURE:
<223> OTHER INFORMATION: 02Q VL

<400> SEQUENCE: 24

Gln Ser Ala Leu Thr Gln Pro Arg Ser Val Ser Gly Ser Pro Gly Gln
1               5                   10                  15

Ser Val Thr Leu Ser Cys Thr Gly Thr Ser Ser Asp Val Gly Gly Tyr
                20                  25                  30

Asn Tyr Val Ser Trp Tyr Gln His Tyr Pro Gly Lys Ala Pro Lys Leu
            35                  40                  45

Met Ile Phe Asp Val Asn Glu Arg Ser Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Ala Gly Arg
                85                  90                  95

Tyr Thr Trp Met Phe Gly Gly Gly Thr Lys Val Thr Val Leu Gly
                100                 105                 110

<210> SEQ ID NO 25
<211> LENGTH: 111
<212> TYPE: PRT
<213> ORGANISM: Artificial Sequence
<220> FEATURE:
<223> OTHER INFORMATION: 02S VL

<400> SEQUENCE: 25

Gln Ser Ala Leu Thr Gln Pro Arg Ser Val Ser Gly Ser Pro Gly Gln
1               5                   10                  15

Ser Val Thr Leu Ser Cys Thr Gly Thr Ser Ser Asp Val Gly Gly Tyr
                20                  25                  30

Asn Tyr Val Ser Trp Tyr Gln His Tyr Pro Gly Lys Ala Pro Lys Leu
            35                  40                  45

Met Ile Phe Asp Val Asn Glu Arg Ser Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Arg
                85                  90                  95

Tyr Thr Trp Met Phe Gly Gly Gly Thr Lys Val Thr Val Leu Gly
                100                 105                 110

<210> SEQ ID NO 26
<211> LENGTH: 111
<212> TYPE: PRT
<213> ORGANISM: Artificial Sequence
<220> FEATURE:
<223> OTHER INFORMATION: 02T VL

<400> SEQUENCE: 26

Gln Ser Ala Leu Thr Gln Pro Arg Ser Val Ser Gly Ser Pro Gly Gln
1               5                   10                  15

Ser Val Thr Leu Ser Cys Thr Gly Thr Ser Ser Asp Val Gly Gly Tyr
            20                  25                  30

Asn Tyr Val Ser Trp Tyr Gln His Tyr Pro Gly Lys Ala Pro Lys Leu
            35                  40                  45

Met Ile Phe Asp Val Asn Glu Arg Ser Ser Gly Val Pro Asp Arg Phe
 50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Thr Ser Tyr Ala Gly Arg
                85                  90                  95

Tyr Thr Trp Met Phe Gly Gly Gly Thr Lys Val Thr Val Leu Gly
            100                 105                 110

<210> SEQ ID NO 27
<211> LENGTH: 111
<212> TYPE: PRT
<213> ORGANISM: Artificial Sequence
<220> FEATURE:
<223> OTHER INFORMATION: 02V VL

<400> SEQUENCE: 27

Gln Ser Ala Leu Thr Gln Pro Arg Ser Val Ser Gly Ser Pro Gly Gln
1               5                   10                  15

Ser Val Thr Leu Ser Cys Thr Gly Thr Ser Ser Asp Val Gly Gly Tyr
            20                  25                  30

Asn Tyr Val Ser Trp Tyr Gln His Tyr Pro Gly Lys Ala Pro Lys Leu
            35                  40                  45

Met Ile Phe Asp Val Asn Glu Arg Ser Ser Gly Val Pro Asp Arg Phe
 50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Val Ser Tyr Ala Gly Arg
                85                  90                  95

Tyr Thr Trp Met Phe Gly Gly Gly Thr Lys Val Thr Val Leu Gly
            100                 105                 110

<210> SEQ ID NO 28
<211> LENGTH: 111
<212> TYPE: PRT
<213> ORGANISM: Artificial Sequence
<220> FEATURE:
<223> OTHER INFORMATION: 03A VL

<400> SEQUENCE: 28

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Asp Val Ala Gly Tyr
            20                  25                  30

Asn Tyr Val Ser Trp Tyr Gln Gln His Pro Gly Lys Ala Pro Lys Leu
            35                  40                  45

Met Ile Tyr Asp Val Thr Lys Arg Pro Ser Gly Val Pro Asp Arg Phe
 50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Ala Gly Ser
                85                  90                  95

Tyr Thr Trp Val Phe Gly Gly Gly Thr Gln Leu Thr Val Leu Gly

<210> SEQ ID NO 29
<211> LENGTH: 111
<212> TYPE: PRT
<213> ORGANISM: Artificial Sequence
<220> FEATURE:
<223> OTHER INFORMATION: 03G VL

<400> SEQUENCE: 29

```
Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Val Ala Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Ala Gly Ser
                85                  90                  95

Tyr Thr Trp Val Phe Gly Gly Gly Thr Gln Leu Thr Val Leu Gly
            100                 105                 110
```

<210> SEQ ID NO 30
<211> LENGTH: 111
<212> TYPE: PRT
<213> ORGANISM: Artificial Sequence
<220> FEATURE:
<223> OTHER INFORMATION: 03I VL

<400> SEQUENCE: 30

```
Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Val Ala Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ile Ser Tyr Ala Gly Ser
                85                  90                  95

Tyr Thr Trp Val Phe Gly Gly Gly Thr Gln Leu Thr Val Leu Gly
            100                 105                 110
```

<210> SEQ ID NO 31
<211> LENGTH: 111
<212> TYPE: PRT
<213> ORGANISM: Artificial Sequence
<220> FEATURE:
<223> OTHER INFORMATION: 03L VL

<400> SEQUENCE: 31

```
Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Val Ala Gly Tyr
            20                  25                  30
```

Asn Tyr Val Ser Trp Tyr Gln Gln His Pro Gly Lys Ala Pro Lys Leu
            35                  40                  45

Met Ile Tyr Asp Val Thr Lys Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Leu Ser Tyr Ala Gly Ser
                85                  90                  95

Tyr Thr Trp Val Phe Gly Gly Gly Thr Gln Leu Thr Val Leu Gly
            100                 105                 110

<210> SEQ ID NO 32
<211> LENGTH: 111
<212> TYPE: PRT
<213> ORGANISM: Artificial Sequence
<220> FEATURE:
<223> OTHER INFORMATION: 03Q VL

<400> SEQUENCE: 32

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Val Ala Gly Tyr
            20                  25                  30

Asn Tyr Val Ser Trp Tyr Gln Gln His Pro Gly Lys Ala Pro Lys Leu
            35                  40                  45

Met Ile Tyr Asp Val Thr Lys Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Tyr Ala Gly Ser
                85                  90                  95

Tyr Thr Trp Val Phe Gly Gly Gly Thr Gln Leu Thr Val Leu Gly
            100                 105                 110

<210> SEQ ID NO 33
<211> LENGTH: 111
<212> TYPE: PRT
<213> ORGANISM: Artificial Sequence
<220> FEATURE:
<223> OTHER INFORMATION: 03S VL

<400> SEQUENCE: 33

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Val Ala Gly Tyr
            20                  25                  30

Asn Tyr Val Ser Trp Tyr Gln Gln His Pro Gly Lys Ala Pro Lys Leu
            35                  40                  45

Met Ile Tyr Asp Val Thr Lys Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Tyr Thr Trp Val Phe Gly Gly Gly Thr Gln Leu Thr Val Leu Gly
            100                 105                 110

```
<210> SEQ ID NO 34
<211> LENGTH: 111
<212> TYPE: PRT
<213> ORGANISM: Artificial Sequence
<220> FEATURE:
<223> OTHER INFORMATION: 03T VL

<400> SEQUENCE: 34

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Asp Val Ala Gly Tyr
            20                  25                  30

Asn Tyr Val Ser Trp Tyr Gln Gln His Pro Gly Lys Ala Pro Lys Leu
            35                  40                  45

Met Ile Tyr Asp Val Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Thr Ser Tyr Ala Gly Ser
                85                  90                  95

Tyr Thr Trp Val Phe Gly Gly Gly Thr Gln Leu Thr Val Leu Gly
            100                 105                 110

<210> SEQ ID NO 35
<211> LENGTH: 111
<212> TYPE: PRT
<213> ORGANISM: Artificial Sequence
<220> FEATURE:
<223> OTHER INFORMATION: 03V VL

<400> SEQUENCE: 35

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Asp Val Ala Gly Tyr
            20                  25                  30

Asn Tyr Val Ser Trp Tyr Gln Gln His Pro Gly Lys Ala Pro Lys Leu
            35                  40                  45

Met Ile Tyr Asp Val Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Val Ser Tyr Ala Gly Ser
                85                  90                  95

Tyr Thr Trp Val Phe Gly Gly Gly Thr Gln Leu Thr Val Leu Gly
            100                 105                 110

<210> SEQ ID NO 36
<211> LENGTH: 5
<212> TYPE: PRT
<213> ORGANISM: Artificial Sequence
<220> FEATURE:
<223> OTHER INFORMATION: YU100-H01 HC-CDR1

<400> SEQUENCE: 36

Ser Tyr Ala Met His
1               5

<210> SEQ ID NO 37
<211> LENGTH: 5
<212> TYPE: PRT
<213> ORGANISM: Artificial Sequence
```

```
<220> FEATURE:
<223> OTHER INFORMATION: YU100-G08, YU100-F11 HC-CDR1

<400> SEQUENCE: 37

Ser Tyr Gly Met His
1               5

<210> SEQ ID NO 38
<211> LENGTH: 17
<212> TYPE: PRT
<213> ORGANISM: Artificial Sequence
<220> FEATURE:
<223> OTHER INFORMATION: YU100-H01 YU100-G08 YU100-F11 HC-CDR2

<400> SEQUENCE: 38

Val Ile Ser Tyr Asp Gly Ser Asn Lys Tyr Tyr Ala Asp Ser Val Lys
1               5                   10                  15

Gly

<210> SEQ ID NO 39
<211> LENGTH: 14
<212> TYPE: PRT
<213> ORGANISM: Artificial Sequence
<220> FEATURE:
<223> OTHER INFORMATION: YU100-H01 HC-CDR3

<400> SEQUENCE: 39

Ile Met Gly Tyr Asp Tyr Gly Asp Tyr Asp Val Val Asp Tyr
1               5                   10

<210> SEQ ID NO 40
<211> LENGTH: 9
<212> TYPE: PRT
<213> ORGANISM: Artificial Sequence
<220> FEATURE:
<223> OTHER INFORMATION: YU100-G08, YU100-F11 HC-CDR3

<400> SEQUENCE: 40

Ile Gly Ala Thr Asp Pro Leu Asp Tyr
1               5

<210> SEQ ID NO 41
<211> LENGTH: 14
<212> TYPE: PRT
<213> ORGANISM: Artificial Sequence
<220> FEATURE:
<223> OTHER INFORMATION: YU100-H01, 01A, 01G, 01I, 01L, 01Q, 01S, 01T,
      01V LC-CDR1

<400> SEQUENCE: 41

Thr Gly Thr Ser Ser Asp Val Gly Ala Tyr Asn Tyr Val Ser
1               5                   10

<210> SEQ ID NO 42
<211> LENGTH: 14
<212> TYPE: PRT
<213> ORGANISM: Artificial Sequence
<220> FEATURE:
<223> OTHER INFORMATION: YU100-G08, 02A, 02G, 02I, 02L, 02Q, 02S, 02T,
      02V LC-CDR1

<400> SEQUENCE: 42

Thr Gly Thr Ser Ser Asp Val Gly Gly Tyr Asn Tyr Val Ser
1               5                   10

<210> SEQ ID NO 43
```

```
<211> LENGTH: 14
<212> TYPE: PRT
<213> ORGANISM: Artificial Sequence
<220> FEATURE:
<223> OTHER INFORMATION: YU100-F11, 03A, 03G, 03I, 03L, 03Q, 03S, 03T,
      03V LC-CDR1

<400> SEQUENCE: 43

Thr Gly Ser Ser Ser Asp Val Ala Gly Tyr Asn Tyr Val Ser
1               5                   10

<210> SEQ ID NO 44
<211> LENGTH: 7
<212> TYPE: PRT
<213> ORGANISM: Artificial Sequence
<220> FEATURE:
<223> OTHER INFORMATION: YU100-H01, 01A, 01G, 01I, 01L, 01Q, 01S, 01T,
      01V LC-CDR2

<400> SEQUENCE: 44

Asp Val Ser Glu Arg Pro Ser
1               5

<210> SEQ ID NO 45
<211> LENGTH: 7
<212> TYPE: PRT
<213> ORGANISM: Artificial Sequence
<220> FEATURE:
<223> OTHER INFORMATION: YU100-G08, 02A, 02G, 02I, 02L, 02Q, 02S, 02T,
      02V LC-CDR2

<400> SEQUENCE: 45

Asp Val Asn Glu Arg Ser Ser
1               5

<210> SEQ ID NO 46
<211> LENGTH: 7
<212> TYPE: PRT
<213> ORGANISM: Artificial Sequence
<220> FEATURE:
<223> OTHER INFORMATION: YU100-F11, 03A, 03G, 03I, 03L, 03Q, 03S, 03T,
      03V LC-CDR2

<400> SEQUENCE: 46

Asp Val Thr Lys Arg Pro Ser
1               5

<210> SEQ ID NO 47
<211> LENGTH: 10
<212> TYPE: PRT
<213> ORGANISM: Artificial Sequence
<220> FEATURE:
<223> OTHER INFORMATION: YU100-H01, YU100-F11 LC-CDR3

<400> SEQUENCE: 47

Cys Ser Tyr Ala Gly Ser Tyr Thr Trp Val
1               5                   10

<210> SEQ ID NO 48
<211> LENGTH: 10
<212> TYPE: PRT
<213> ORGANISM: Artificial Sequence
<220> FEATURE:
<223> OTHER INFORMATION: 01A, 03A, LC-CDR3

<400> SEQUENCE: 48

Ala Ser Tyr Ala Gly Ser Tyr Thr Trp Val
1               5                   10
```

```
<210> SEQ ID NO 49
<211> LENGTH: 10
<212> TYPE: PRT
<213> ORGANISM: Artificial Sequence
<220> FEATURE:
<223> OTHER INFORMATION: 01G, 03G LC-CDR3

<400> SEQUENCE: 49

Gly Ser Tyr Ala Gly Ser Tyr Thr Trp Val
1               5                   10

<210> SEQ ID NO 50
<211> LENGTH: 10
<212> TYPE: PRT
<213> ORGANISM: Artificial Sequence
<220> FEATURE:
<223> OTHER INFORMATION: 01I, 03I LC-CDR3

<400> SEQUENCE: 50

Ile Ser Tyr Ala Gly Ser Tyr Thr Trp Val
1               5                   10

<210> SEQ ID NO 51
<211> LENGTH: 10
<212> TYPE: PRT
<213> ORGANISM: Artificial Sequence
<220> FEATURE:
<223> OTHER INFORMATION: 01L, 03L LC-CDR3

<400> SEQUENCE: 51

Leu Ser Tyr Ala Gly Ser Tyr Thr Trp Val
1               5                   10

<210> SEQ ID NO 52
<211> LENGTH: 10
<212> TYPE: PRT
<213> ORGANISM: Artificial Sequence
<220> FEATURE:
<223> OTHER INFORMATION: 01Q, 03Q LC-CDR3

<400> SEQUENCE: 52

Gln Ser Tyr Ala Gly Ser Tyr Thr Trp Val
1               5                   10

<210> SEQ ID NO 53
<211> LENGTH: 10
<212> TYPE: PRT
<213> ORGANISM: Artificial Sequence
<220> FEATURE:
<223> OTHER INFORMATION: 01S, 03S LC-CDR3

<400> SEQUENCE: 53

Ser Ser Tyr Ala Gly Ser Tyr Thr Trp Val
1               5                   10

<210> SEQ ID NO 54
<211> LENGTH: 10
<212> TYPE: PRT
<213> ORGANISM: Artificial Sequence
<220> FEATURE:
<223> OTHER INFORMATION: 01T, 03T LC-CDR3

<400> SEQUENCE: 54

Thr Ser Tyr Ala Gly Ser Tyr Thr Trp Val
1               5                   10
```

```
<210> SEQ ID NO 55
<211> LENGTH: 10
<212> TYPE: PRT
<213> ORGANISM: Artificial Sequence
<220> FEATURE:
<223> OTHER INFORMATION: 01V, 03V LC-CDR3

<400> SEQUENCE: 55

Val Ser Tyr Ala Gly Ser Tyr Thr Trp Val
1               5                   10

<210> SEQ ID NO 56
<211> LENGTH: 10
<212> TYPE: PRT
<213> ORGANISM: Artificial Sequence
<220> FEATURE:
<223> OTHER INFORMATION: YU100-G08 LC-CDR3

<400> SEQUENCE: 56

Cys Ser Tyr Ala Gly Arg Tyr Thr Trp Met
1               5                   10

<210> SEQ ID NO 57
<211> LENGTH: 10
<212> TYPE: PRT
<213> ORGANISM: Artificial Sequence
<220> FEATURE:
<223> OTHER INFORMATION: 02A LC-CDR3

<400> SEQUENCE: 57

Ala Ser Tyr Ala Gly Arg Tyr Thr Trp Met
1               5                   10

<210> SEQ ID NO 58
<211> LENGTH: 10
<212> TYPE: PRT
<213> ORGANISM: Artificial Sequence
<220> FEATURE:
<223> OTHER INFORMATION: 02G LC-CDR3

<400> SEQUENCE: 58

Gly Ser Tyr Ala Gly Arg Tyr Thr Trp Met
1               5                   10

<210> SEQ ID NO 59
<211> LENGTH: 10
<212> TYPE: PRT
<213> ORGANISM: Artificial Sequence
<220> FEATURE:
<223> OTHER INFORMATION: 02I LC-CDR3

<400> SEQUENCE: 59

Ile Ser Tyr Ala Gly Arg Tyr Thr Trp Met
1               5                   10

<210> SEQ ID NO 60
<211> LENGTH: 10
<212> TYPE: PRT
<213> ORGANISM: Artificial Sequence
<220> FEATURE:
<223> OTHER INFORMATION: 02L LC-CDR3

<400> SEQUENCE: 60

Leu Ser Tyr Ala Gly Arg Tyr Thr Trp Met
1               5                   10
```

```
<210> SEQ ID NO 61
<211> LENGTH: 10
<212> TYPE: PRT
<213> ORGANISM: Artificial Sequence
<220> FEATURE:
<223> OTHER INFORMATION: 02Q LC-CDR3

<400> SEQUENCE: 61

Gln Ser Tyr Ala Gly Arg Tyr Thr Trp Met
1               5                   10

<210> SEQ ID NO 62
<211> LENGTH: 10
<212> TYPE: PRT
<213> ORGANISM: Artificial Sequence
<220> FEATURE:
<223> OTHER INFORMATION: 02S LC-CDR3

<400> SEQUENCE: 62

Ser Ser Tyr Ala Gly Arg Tyr Thr Trp Met
1               5                   10

<210> SEQ ID NO 63
<211> LENGTH: 10
<212> TYPE: PRT
<213> ORGANISM: Artificial Sequence
<220> FEATURE:
<223> OTHER INFORMATION: 02T LC-CDR3

<400> SEQUENCE: 63

Thr Ser Tyr Ala Gly Arg Tyr Thr Trp Met
1               5                   10

<210> SEQ ID NO 64
<211> LENGTH: 10
<212> TYPE: PRT
<213> ORGANISM: Artificial Sequence
<220> FEATURE:
<223> OTHER INFORMATION: 02V LC-CDR3

<400> SEQUENCE: 64

Val Ser Tyr Ala Gly Arg Tyr Thr Trp Met
1               5                   10

<210> SEQ ID NO 65
<211> LENGTH: 30
<212> TYPE: PRT
<213> ORGANISM: Artificial Sequence
<220> FEATURE:
<223> OTHER INFORMATION: YU100-H01, YU100-G08 HC-FR1

<400> SEQUENCE: 65

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 66
<211> LENGTH: 30
<212> TYPE: PRT
<213> ORGANISM: Artificial Sequence
<220> FEATURE:
<223> OTHER INFORMATION: YU100-F11 HC-FR1

<400> SEQUENCE: 66

Gln Val Gln Leu Val Glu Ser Gly Gly Gly Val Val Gln Pro Gly Arg
1               5                   10                  15
```

Ser Leu Arg Leu Ser Cys Ala Ala Ser Gly Phe Thr Phe Ser
            20                  25                  30

<210> SEQ ID NO 67
<211> LENGTH: 14
<212> TYPE: PRT
<213> ORGANISM: Artificial Sequence
<220> FEATURE:
<223> OTHER INFORMATION: YU100-H01 YU100-G08 YU100-F11 HC-FR2

<400> SEQUENCE: 67

Trp Val Arg Gln Ala Pro Gly Lys Gly Leu Glu Trp Val Ala
1               5                  10

<210> SEQ ID NO 68
<211> LENGTH: 32
<212> TYPE: PRT
<213> ORGANISM: Artificial Sequence
<220> FEATURE:
<223> OTHER INFORMATION: YU100-H01 HC-FR3

<400> SEQUENCE: 68

Arg Phe Thr Ile Ser Arg Asp Asn Ser Lys Asn Thr Leu Tyr Leu Gln
1               5                  10                  15

Met Asn Ser Leu Arg Ala Glu Asp Thr Ala Val Tyr Tyr Cys Ala Arg
            20                  25                  30

<210> SEQ ID NO 69
<211> LENGTH: 32
<212> TYPE: PRT
<213> ORGANISM: Artificial Sequence
<220> FEATURE:
<223> OTHER INFORMATION: YU100-G08, YU100-F11 HC-FR3

<400> SEQUENCE: 69

Arg Phe Thr Ile Ser Arg Asp Asn Ser Lys Asn Thr Leu Tyr Leu Gln
1               5                  10                  15

Met Asn Ser Leu Arg Ala Glu Asp Thr Ala Val Tyr Tyr Cys Ala Lys
            20                  25                  30

<210> SEQ ID NO 70
<211> LENGTH: 11
<212> TYPE: PRT
<213> ORGANISM: Artificial Sequence
<220> FEATURE:
<223> OTHER INFORMATION: YU100-H01 YU100-G08 YU100-F11 HC-FR4

<400> SEQUENCE: 70

Trp Gly Gln Gly Thr Leu Val Thr Val Ser Ser
1               5                  10

<210> SEQ ID NO 71
<211> LENGTH: 22
<212> TYPE: PRT
<213> ORGANISM: Artificial Sequence
<220> FEATURE:
<223> OTHER INFORMATION: YU100-H01, 01A, 01G, 01I, 01L, 01Q, 01S, 01T,
      01V LC-FR1

<400> SEQUENCE: 71

Gln Ser Ala Leu Thr Gln Pro Arg Ser Val Ser Gly Ser Pro Gly Gln
1               5                  10                  15

Ser Val Thr Ile Ser Cys
            20

```
<210> SEQ ID NO 72
<211> LENGTH: 22
<212> TYPE: PRT
<213> ORGANISM: Artificial Sequence
<220> FEATURE:
<223> OTHER INFORMATION: YU100-G08, 02A, 02G, 02I, 02L, 02Q, 02S, 02T,
      02V LC-FR1

<400> SEQUENCE: 72

Gln Ser Ala Leu Thr Gln Pro Arg Ser Val Ser Gly Ser Pro Gly Gln
1               5                   10                  15

Ser Val Thr Leu Ser Cys
            20

<210> SEQ ID NO 73
<211> LENGTH: 22
<212> TYPE: PRT
<213> ORGANISM: Artificial Sequence
<220> FEATURE:
<223> OTHER INFORMATION: YU100-F11, 03A, 03G, 03I, 03L, 03Q, 03S, 03T,
      03V LC-FR1

<400> SEQUENCE: 73

Gln Ser Ala Leu Thr Gln Pro Ala Ser Val Ser Gly Ser Pro Gly Gln
1               5                   10                  15

Ser Ile Thr Ile Ser Cys
            20

<210> SEQ ID NO 74
<211> LENGTH: 15
<212> TYPE: PRT
<213> ORGANISM: Artificial Sequence
<220> FEATURE:
<223> OTHER INFORMATION: YU100-H01, 01A, 01G, 01I, 01L, 01Q, 01S, 01T,
      01V, YU100-F11, 03A, 03G, 03I, 03L, 03Q, 03S, 03T, 03V LC-FR2

<400> SEQUENCE: 74

Trp Tyr Gln Gln His Pro Gly Lys Ala Pro Lys Leu Met Ile Tyr
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: YU100-G08, 02A, 02G, 02I, 02L, 02Q, 02S, 02T,
      02V LC-FR2

<400> SEQUENCE: 75

Trp Tyr Gln His Tyr Pro Gly Lys Ala Pro Lys Leu Met Ile Phe
1               5                   10                  15

<210> SEQ ID NO 76
<211> LENGTH: 32
<212> TYPE: PRT
<213> ORGANISM: Artificial Sequence
<220> FEATURE:
<223> OTHER INFORMATION: YU100-H01, 01A, 01G, 01I, 01L, 01Q, 01S, 01T,
      01V, YU100-G08, 02A, 02G, 02I, 02L, 02Q, 02S, 02T, 02V, YU100-F11,
      03A, 03G, 03I, 03L, 03Q, 03S, 03T, 03V LC-FR3

<400> SEQUENCE: 76

Gly Val Pro Asp Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30
```

```
<210> SEQ ID NO 77
<211> LENGTH: 11
<212> TYPE: PRT
<213> ORGANISM: Artificial Sequence
<220> FEATURE:
<223> OTHER INFORMATION: YU100-H01, 01A, 01G, 01I, 01L, 01Q, 01S, 01T,
      01V LC-FR4

<400> SEQUENCE: 77

Phe Gly Gly Gly Thr Lys Leu Thr Val Leu Gly
1               5                   10

<210> SEQ ID NO 78
<211> LENGTH: 11
<212> TYPE: PRT
<213> ORGANISM: Artificial Sequence
<220> FEATURE:
<223> OTHER INFORMATION: YU100-G08, 02A, 02G, 02I, 02L, 02Q, 02S, 02T,
      02V LC-FR4

<400> SEQUENCE: 78

Phe Gly Gly Gly Thr Lys Val Thr Val Leu Gly
1               5                   10

<210> SEQ ID NO 79
<211> LENGTH: 11
<212> TYPE: PRT
<213> ORGANISM: Artificial Sequence
<220> FEATURE:
<223> OTHER INFORMATION: YU100-F11, 03A, 03G, 03I, 03L, 03Q, 03S, 03T,
      03V LC-FR4

<400> SEQUENCE: 79

Phe Gly Gly Gly Thr Gln Leu Thr Val Leu Gly
1               5                   10

<210> SEQ ID NO 80
<211> LENGTH: 10
<212> TYPE: PRT
<213> ORGANISM: Artificial Sequence
<220> FEATURE:
<223> OTHER INFORMATION: 01X 03X LC-CDR3
<220> FEATURE:
<221> NAME/KEY: MISC_FEATURE
<222> LOCATION: (1)..(1)
<223> OTHER INFORMATION: X = A, G, I, L, Q, S, T or V

<400> SEQUENCE: 80

Xaa Ser Tyr Ala Gly Ser Tyr Thr Trp Val
1               5                   10

<210> SEQ ID NO 81
<211> LENGTH: 10
<212> TYPE: PRT
<213> ORGANISM: Artificial Sequence
<220> FEATURE:
<223> OTHER INFORMATION: 02X LC-CDR3
<220> FEATURE:
<221> NAME/KEY: MISC_FEATURE
<222> LOCATION: (1)..(1)
<223> OTHER INFORMATION: X = A, G, I, L, Q, S, T or V

<400> SEQUENCE: 81

Xaa Ser Tyr Ala Gly Arg Tyr Thr Trp Met
1               5                   10

<210> SEQ ID NO 82
```

```
<211> LENGTH: 111
<212> TYPE: PRT
<213> ORGANISM: Artificial Sequence
<220> FEATURE:
<223> OTHER INFORMATION: 01X VL
<220> FEATURE:
<221> NAME/KEY: MISC_FEATURE
<222> LOCATION: (91)..(91)
<223> OTHER INFORMATION: X = A, G, I, L, Q, S, T or V

<400> SEQUENCE: 82

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ala Tyr
            20                  25                  30

Asn Tyr Val Ser Trp Tyr Gln Gln His Pro Gly Lys Ala Pro Lys Leu
        35                  40                  45

Met Ile Tyr Asp Val Ser Glu Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Xaa Ser Tyr Ala Gly Ser
                85                  90                  95

Tyr Thr Trp Val Phe Gly Gly Gly Thr Lys Leu Thr Val Leu Gly
            100                 105                 110

<210> SEQ ID NO 83
<211> LENGTH: 111
<212> TYPE: PRT
<213> ORGANISM: Artificial Sequence
<220> FEATURE:
<223> OTHER INFORMATION: 02X VL
<220> FEATURE:
<221> NAME/KEY: MISC_FEATURE
<222> LOCATION: (91)..(91)
<223> OTHER INFORMATION: X = A, G, I, L, Q, S, T or V

<400> SEQUENCE: 83

Gln Ser Ala Leu Thr Gln Pro Arg Ser Val Ser Gly Ser Pro Gly Gln
1               5                   10                  15

Ser Val Thr Leu Ser Cys Thr Gly Thr Ser Ser Asp Val Gly Gly Tyr
            20                  25                  30

Asn Tyr Val Ser Trp Tyr Gln His Tyr Pro Gly Lys Ala Pro Lys Leu
        35                  40                  45

Met Ile Phe Asp Val Asn Glu Arg Ser Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Xaa Ser Tyr Ala Gly Arg
                85                  90                  95

Tyr Thr Trp Met Phe Gly Gly Gly Thr Lys Val Thr Val Leu Gly
            100                 105                 110

<210> SEQ ID NO 84
<211> LENGTH: 111
<212> TYPE: PRT
<213> ORGANISM: Artificial Sequence
<220> FEATURE:
<223> OTHER INFORMATION: 03X VL
<220> FEATURE:
<221> NAME/KEY: MISC_FEATURE
<222> LOCATION: (91)..(91)
<223> OTHER INFORMATION: X = A, G, I, L, Q, S, T or V
```

<400> SEQUENCE: 84

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Val Ala Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Xaa Ser Tyr Ala Gly Ser
                85                  90                  95

Tyr Thr Trp Val Phe Gly Gly Thr Gln Leu Thr Val Leu Gly
            100                 105                 110

<210> SEQ ID NO 85
<211> LENGTH: 330
<212> TYPE: PRT
<213> ORGANISM: Homo sapiens
<220> FEATURE:
<221> NAME/KEY: misc_feature
<222> LOCATION: (1)..(330)
<223> OTHER INFORMATION: IgG1 constant region (IGHG1; UniProt:P01857-1,
      v1)

<400> SEQUENCE: 85

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 86
<211> LENGTH: 98
<212> TYPE: PRT
<213> ORGANISM: Artificial Sequence
<220> FEATURE:
<223> OTHER INFORMATION: CH1 IgG1 (positions 1-98 of P01857-1, v1)

<400> SEQUENCE: 86

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 87
<211> LENGTH: 12
<212> TYPE: PRT
<213> ORGANISM: Artificial Sequence
<220> FEATURE:
<223> OTHER INFORMATION: Hinge IgG1 (positions 99-110 of P01857-1, v1)

<400> SEQUENCE: 87

Glu Pro Lys Ser Cys Asp Lys Thr His Thr Cys Pro
1               5                   10

<210> SEQ ID NO 88
<211> LENGTH: 113
<212> TYPE: PRT
<213> ORGANISM: Artificial Sequence
<220> FEATURE:
<223> OTHER INFORMATION: CH2 IgG1 (positions 111-223 of P01857-1, v1)

<400> SEQUENCE: 88

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30
```

```
Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys
```

<210> SEQ ID NO 89
<211> LENGTH: 107
<212> TYPE: PRT
<213> ORGANISM: Artificial Sequence
<220> FEATURE:
<223> OTHER INFORMATION: CH3 IgG1 (positions 224-330 of P01857-1, v1)

<400> SEQUENCE: 89

```
Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
            85                  90                  95

Thr Gln Lys Ser Leu Ser Leu Ser Pro Gly Lys
            100                 105
```

<210> SEQ ID NO 90
<211> LENGTH: 107
<212> TYPE: PRT
<213> ORGANISM: Artificial Sequence
<220> FEATURE:
<223> OTHER INFORMATION: Ckappa CL (IGCK; UniProt: P01834-1, v2)

<400> SEQUENCE: 90

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105
```

```
<210> SEQ ID NO 91
<211> LENGTH: 119
<212> TYPE: PRT
<213> ORGANISM: Artificial Sequence
<220> FEATURE:
<223> OTHER INFORMATION: 3C6 VH 1

<400> SEQUENCE: 91
```

Gln Val Gln Leu Gln Glu Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asn Pro His Asn Gly Gly Pro Ile Tyr Asn Gln Lys Phe
    50                  55                  60

Thr Gly Lys Ala Thr Leu Thr Val Asp Lys Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Gly Glu Leu Gly His Trp Tyr Phe Asp Val Trp Gly Thr Gly
            100                 105                 110

Thr Thr Val Thr Val Ser Ser
        115

```
<210> SEQ ID NO 92
<211> LENGTH: 119
<212> TYPE: PRT
<213> ORGANISM: Artificial Sequence
<220> FEATURE:
<223> OTHER INFORMATION: 3C6 VH 2

<400> SEQUENCE: 92
```

Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asn Pro His Asn Gly Gly Pro Ile Tyr Asn Gln Lys Phe
    50                  55                  60

Thr Gly Lys Ala Thr Leu Thr Val Asp Lys Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Gly Glu Leu Gly His Trp Tyr Phe Asp Val Trp Gly Thr Gly
            100                 105                 110

Thr Thr Val Thr Val Ser Ser
        115

```
<210> SEQ ID NO 93
<211> LENGTH: 107
<212> TYPE: PRT
<213> ORGANISM: Artificial Sequence
<220> FEATURE:
<223> OTHER INFORMATION: 3C6 VL 1

<400> SEQUENCE: 93
```

Asn Ile Val Met Thr Gln Ser Pro Lys Ser Met Ser Met Ser Val Gly
1               5                  10                 15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
            35                  40                  45

Tyr Gly Ala Ser Asn Arg Tyr Thr Gly Val Pro Asp Arg Phe Thr Gly
50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
            85                  90                  95

Thr Phe Gly Gly Gly Thr Lys Leu Glu Ile Lys
            100                 105

<210> SEQ ID NO 94
<211> LENGTH: 111
<212> TYPE: PRT
<213> ORGANISM: Artificial Sequence
<220> FEATURE:
<223> OTHER INFORMATION: 3C6 VL 2

<400> SEQUENCE: 94

Asp Ile Val Leu Thr Gln Ser Pro Ala Ser Leu Ala Val Ser Leu Gly
1               5                  10                 15

Gln Arg Ala Thr Ile Ser Cys Arg Ala Ser Lys Ser Val Ser Thr Ser
            20                  25                  30

Gly Tyr Ser Tyr Ile His Trp Tyr Gln Gln Lys Pro Gly Gln Pro Pro
            35                  40                  45

Lys Leu Leu Ile Tyr Leu Ala Ser Asn Leu Asp Ser Gly Val Pro Ala
50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
            85                  90                  95

Asp Leu Pro Pro Thr Phe Gly Gly Gly Thr Lys Leu Glu Ile Lys
            100                 105                 110

<210> SEQ ID NO 95
<211> LENGTH: 5
<212> TYPE: PRT
<213> ORGANISM: Artificial Sequence
<220> FEATURE:
<223> OTHER INFORMATION: 3C6 VH 1, 3C6 VH 2, 3C6 VH 2.1, 3C6 VH 2.2, 3C6
    VH 2.3, 3C6 VH 2.4, 3C6 VH 2.5 HC-CDR1

<400> SEQUENCE: 95

Asp Tyr Asn Met Asp
1               5

<210> SEQ ID NO 96
<211> LENGTH: 17
<212> TYPE: PRT
<213> ORGANISM: Artificial Sequence
<220> FEATURE:
<223> OTHER INFORMATION: 3C6 VH 1, 3C6 VH 2, 3C6 VH 2.1, 3C6 VH 2.2, 3C6
    VH 2.3, 3C6 VH 2.4, 3C6 VH 2.5 HC-CDR2

<400> SEQUENCE: 96

Asp Ile Asn Pro His Asn Gly Gly Pro Ile Tyr Asn Gln Lys Phe Thr
1               5                  10                 15

Gly

<210> SEQ ID NO 97
<211> LENGTH: 10
<212> TYPE: PRT
<213> ORGANISM: Artificial Sequence
<220> FEATURE:
<223> OTHER INFORMATION: 3C6 VH 1, 3C6 VH 2, 3C6 VH 2.1, 3C6 VH 2.2, 3C6
      VH 2.3, 3C6 VH 2.4, 3C6 VH 2.5 HC-CDR3

<400> SEQUENCE: 97

Gly Glu Leu Gly His Trp Tyr Phe Asp Val
1               5                   10

<210> SEQ ID NO 98
<211> LENGTH: 11
<212> TYPE: PRT
<213> ORGANISM: Artificial Sequence
<220> FEATURE:
<223> OTHER INFORMATION: 3C6 VL 1 3C6 VL 1.1, 3C6 VL 1.2, 3C6 VL 1.3,
      3C6 VL 1.4 LC-CDR1

<400> SEQUENCE: 98

Lys Ala Ser Glu Asn Val Val Thr Tyr Val Ser
1               5                   10

<210> SEQ ID NO 99
<211> LENGTH: 7
<212> TYPE: PRT
<213> ORGANISM: Artificial Sequence
<220> FEATURE:
<223> OTHER INFORMATION: 3C6 VL 1 3C6 VL 1.1, 3C6 VL 1.2, 3C6 VL 1.3,
      3C6 VL 1.4 LC-CDR2

<400> SEQUENCE: 99

Gly Ala Ser Asn Arg Tyr Thr
1               5

<210> SEQ ID NO 100
<211> LENGTH: 9
<212> TYPE: PRT
<213> ORGANISM: Artificial Sequence
<220> FEATURE:
<223> OTHER INFORMATION: 3C6 VL 1, 3C6 VL 1.1, 3C6 VL 1.2, 3C6 VL 1.3,
      3C6 VL 1.4 LC-CDR3

<400> SEQUENCE: 100

Gly Gln Gly Tyr Ser Tyr Pro Tyr Thr
1               5

<210> SEQ ID NO 101
<211> LENGTH: 15
<212> TYPE: PRT
<213> ORGANISM: Artificial Sequence
<220> FEATURE:
<223> OTHER INFORMATION: 3C6 VL 2, 3C6 VL 2.1, 3C6 VL 2.2, 3C6 VL 2.3,
      3C6 VL 2.4 LC-CDR1

<400> SEQUENCE: 101

Arg Ala Ser Lys Ser Val Ser Thr Ser Gly Tyr Ser Tyr Ile His
1               5                   10                  15

<210> SEQ ID NO 102
<211> LENGTH: 7
<212> TYPE: PRT
<213> ORGANISM: Artificial Sequence
<220> FEATURE:

```
<223> OTHER INFORMATION: 3C6 VL 2, 3C6 VL 2.1, 3C6 VL 2.2, 3C6 VL 2.3,
      3C6 VL 2.4 LC-CDR2

<400> SEQUENCE: 102

Leu Ala Ser Asn Leu Asp Ser
1               5

<210> SEQ ID NO 103
<211> LENGTH: 9
<212> TYPE: PRT
<213> ORGANISM: Artificial Sequence
<220> FEATURE:
<223> OTHER INFORMATION: 3C6 VL 2, 3C6 VL 2.1, 3C6 VL 2.2, 3C6 VL 2.3,
      3C6 VL 2.4 LC-CDR3

<400> SEQUENCE: 103

Gln His Ser Arg Asp Leu Pro Pro Thr
1               5

<210> SEQ ID NO 104
<211> LENGTH: 30
<212> TYPE: PRT
<213> ORGANISM: Artificial Sequence
<220> FEATURE:
<223> OTHER INFORMATION: 3C6 VH 1 HC-FR1

<400> SEQUENCE: 104

Gln Val Gln Leu Gln Glu Ser Gly Pro Glu Leu Val Lys Pro Gly Ala
1               5                   10                  15

Ser Val Lys Ile Pro Cys Lys Ala Ser Gly Tyr Thr Phe Thr
            20                  25                  30

<210> SEQ ID NO 105
<211> LENGTH: 30
<212> TYPE: PRT
<213> ORGANISM: Artificial Sequence
<220> FEATURE:
<223> OTHER INFORMATION: 3C6 VH 2 HC-FR1

<400> SEQUENCE: 105

Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr
            20                  25                  30

<210> SEQ ID NO 106
<211> LENGTH: 14
<212> TYPE: PRT
<213> ORGANISM: Artificial Sequence
<220> FEATURE:
<223> OTHER INFORMATION: 3C6 VH 1, 3C6 VH 2  HC-FR2

<400> SEQUENCE: 106

Trp Val Lys Gln Ser His Gly Lys Ser Leu Glu Trp Ile Gly
1               5                   10

<210> SEQ ID NO 107
<211> LENGTH: 32
<212> TYPE: PRT
<213> ORGANISM: Artificial Sequence
<220> FEATURE:
<223> OTHER INFORMATION: 3C6 VH 1, 3C6 VH 2 HC-FR3

<400> SEQUENCE: 107

Lys Ala Thr Leu Thr Val Asp Lys Ser Ser Ser Thr Ala Tyr Met Glu
1               5                   10                  15
```

Leu Arg Ser Leu Thr Ser Glu Asp Thr Ala Val Tyr Tyr Cys Ala Arg
            20                  25                  30

<210> SEQ ID NO 108
<211> LENGTH: 11
<212> TYPE: PRT
<213> ORGANISM: Artificial Sequence
<220> FEATURE:
<223> OTHER INFORMATION: 3C6 VH 1, 3C6 VH 2 HC-FR4

<400> SEQUENCE: 108

Trp Gly Thr Gly Thr Thr Val Thr Val Ser Ser
1               5                   10

<210> SEQ ID NO 109
<211> LENGTH: 23
<212> TYPE: PRT
<213> ORGANISM: Artificial Sequence
<220> FEATURE:
<223> OTHER INFORMATION: 3C6 VL 1 LC-FR1

<400> SEQUENCE: 109

Asn Ile Val Met Thr Gln Ser Pro Lys Ser Met Ser Met Ser Val Gly
1               5                   10                  15

Glu Arg Val Thr Leu Thr Cys
            20

<210> SEQ ID NO 110
<211> LENGTH: 23
<212> TYPE: PRT
<213> ORGANISM: Artificial Sequence
<220> FEATURE:
<223> OTHER INFORMATION: 3C6 VL 2 LC-FR1

<400> SEQUENCE: 110

Asp Ile Val Leu Thr Gln Ser Pro Ala Ser Leu Ala Val Ser Leu Gly
1               5                   10                  15

Gln Arg Ala Thr Ile Ser Cys
            20

<210> SEQ ID NO 111
<211> LENGTH: 15
<212> TYPE: PRT
<213> ORGANISM: Artificial Sequence
<220> FEATURE:
<223> OTHER INFORMATION: 3C6 VL 1 LC-FR2

<400> SEQUENCE: 111

Trp Tyr Gln Gln Lys Pro Glu Gln Ser Pro Lys Leu Leu Ile Tyr
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: 3C6 VL 2, 3C6 VL 1.1, 3C6 VL 1.2, 3C6 VL 1.3,
      3C6 VL 1.4LC-FR2

<400> SEQUENCE: 112

Trp Tyr Gln Gln Lys Pro Gly Gln Pro Pro Lys Leu Leu Ile Tyr
1               5                   10                  15

<210> SEQ ID NO 113
<211> LENGTH: 32

<212> TYPE: PRT
<213> ORGANISM: Artificial Sequence
<220> FEATURE:
<223> OTHER INFORMATION: 3C6 VL 1 LC-FR3

<400> SEQUENCE: 113

Gly Val Pro Asp Arg Phe Thr Gly Ser Gly Ala Thr Asp Phe Thr
1               5                   10                  15

Leu Thr Ile Ser Ser Val Gln Ala Glu Asp Leu Ala Asp Tyr His Cys
                20                  25                  30

<210> SEQ ID NO 114
<211> LENGTH: 32
<212> TYPE: PRT
<213> ORGANISM: Artificial Sequence
<220> FEATURE:
<223> OTHER INFORMATION: 3C6 VL 2 LC-FR3

<400> SEQUENCE: 114

Gly Val Pro Ala Arg Phe Ser Gly Ser Gly Ser Gly Thr Asp Phe Thr
1               5                   10                  15

Leu Asn Ile His Pro Val Glu Glu Glu Asp Ala Ala Thr Tyr Tyr Cys
                20                  25                  30

<210> SEQ ID NO 115
<211> LENGTH: 10
<212> TYPE: PRT
<213> ORGANISM: Artificial Sequence
<220> FEATURE:
<223> OTHER INFORMATION: 3C6 VL 1, 3C6 VL 2 LC-FR4

<400> SEQUENCE: 115

Phe Gly Gly Gly Thr Lys Leu Glu Ile Lys
1               5                   10

<210> SEQ ID NO 116
<211> LENGTH: 119
<212> TYPE: PRT
<213> ORGANISM: Artificial Sequence
<220> FEATURE:
<223> OTHER INFORMATION: 3C6 VH 2.1

<400> SEQUENCE: 116

Glu Val Gln Leu Val Gln Ser Gly Pro Glu Leu Lys Lys Pro Gly Ala
1               5                   10                  15

Ser Val Lys Ile Ser Cys Lys Ala Ser Gly Tyr Thr Phe Thr Asp Tyr
                20                  25                  30

Asn Met Asp Trp Val Lys Gln Ala His Gly Gln Arg Leu Glu Trp Ile
            35                  40                  45

Gly Asp Ile Asn Pro His Asn Gly Gly Pro Ile Tyr Asn Gln Lys Phe
        50                  55                  60

Thr Gly Arg Ala Thr Leu Thr Val Asp Lys Ser Ala Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Gly Glu Leu Gly His Trp Tyr Phe Asp Val Trp Gly Gln Gly
            100                 105                 110

Thr Thr Val Thr Val Ser Ser
            115

<210> SEQ ID NO 117
<211> LENGTH: 119

```
<212> TYPE: PRT
<213> ORGANISM: Artificial Sequence
<220> FEATURE:
<223> OTHER INFORMATION: 3C6 VH 2.2

<400> SEQUENCE: 117

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ala Pro Gly Gln Arg Leu Glu Trp Ile
        35                  40                  45

Gly Asp Ile Asn Pro His Asn Gly Gly Pro Ile Tyr Asn Gln Lys Phe
50                  55                  60

Thr Gly Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Glu Leu Gly His Trp Tyr Phe Asp Val Trp Gly Gln Gly
            100                 105                 110

Thr Thr Val Thr Val Ser Ser
            115

<210> SEQ ID NO 118
<211> LENGTH: 119
<212> TYPE: PRT
<213> ORGANISM: Artificial Sequence
<220> FEATURE:
<223> OTHER INFORMATION: 3C6 VH 2.3

<400> SEQUENCE: 118

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Arg Gln Ala Pro Gly Gln Arg Leu Glu Trp Ile
        35                  40                  45

Gly Asp Ile Asn Pro His Asn Gly Gly Pro Ile Tyr Asn Gln Lys Phe
50                  55                  60

Thr Gly Arg Val Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Glu Leu Gly His Trp Tyr Phe Asp Val Trp Gly Gln Gly
            100                 105                 110

Thr Thr Val Thr Val Ser Ser
            115

<210> SEQ ID NO 119
<211> LENGTH: 119
<212> TYPE: PRT
<213> ORGANISM: Artificial Sequence
<220> FEATURE:
<223> OTHER INFORMATION: 3C6 VH 2.4

<400> SEQUENCE: 119

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
```

-continued

```
                    20                  25                  30
Asn Met Asp Trp Val Arg Gln Ala Pro Gly Gln Arg Leu Glu Trp Ile
            35                  40                  45
Gly Asp Ile Asn Pro His Asn Gly Gly Pro Ile Tyr Asn Gln Lys Phe
        50                  55                  60
Thr Gly Arg Val Thr Ile Thr Val Asp Lys Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Glu Leu Gly His Trp Tyr Phe Asp Val Trp Gly Gln Gly
            100                 105                 110
Thr Thr Val Thr Val Ser Ser
        115
```

<210> SEQ ID NO 120
<211> LENGTH: 119
<212> TYPE: PRT
<213> ORGANISM: Artificial Sequence
<220> FEATURE:
<223> OTHER INFORMATION: 3C6 VH 2.5

<400> SEQUENCE: 120

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Asn Met Asp Trp Val Arg Gln Ala Pro Gly Gln Arg Leu Glu Trp Met
        35                  40                  45
Gly Asp Ile Asn Pro His Asn Gly Gly Pro Ile Tyr Asn Gln Lys Phe
    50                  55                  60
Thr Gly Arg Val Thr Ile Thr Val Asp Lys Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Glu Leu Gly His Trp Tyr Phe Asp Val Trp Gly Gln Gly
            100                 105                 110
Thr Thr Val Thr Val Ser Ser
        115
```

<210> SEQ ID NO 121
<211> LENGTH: 111
<212> TYPE: PRT
<213> ORGANISM: Artificial Sequence
<220> FEATURE:
<223> OTHER INFORMATION: 3C6 VL 2.1

<400> SEQUENCE: 121

```
Asp Ile Val Leu Thr Gln Ser Pro Ala Ser Leu Ala Leu Ser Pro Gly
1               5                   10                  15
Glu Arg Ala Thr Leu Ser Cys Arg Ala Ser Lys Ser Val Ser Thr Ser
            20                  25                  30
Gly Tyr Ser Tyr Ile His Trp Tyr Gln Gln Lys Pro Gly Gln Pro Pro
        35                  40                  45
Arg Leu Leu Ile Tyr Leu Ala Ser Asn Leu Asp Ser Gly Val Pro Ala
    50                  55                  60
Arg Phe Ser Gly Ser Gly Ser Gly Thr Asp Phe Thr Leu Asn Ile His
65                  70                  75                  80
```

Pro Leu Glu Glu Glu Asp Phe Ala Thr Tyr Tyr Cys Gln His Ser Arg
            85                  90                  95

Asp Leu Pro Pro Thr Phe Gly Gln Gly Thr Lys Leu Glu Ile Lys
        100                 105                 110

<210> SEQ ID NO 122
<211> LENGTH: 111
<212> TYPE: PRT
<213> ORGANISM: Artificial Sequence
<220> FEATURE:
<223> OTHER INFORMATION: 3C6 VL 2.2

<400> SEQUENCE: 122

Asp Ile Val Leu Thr Gln Ser Pro Ala Ser Leu Ala Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Ile His Trp Tyr Gln Gln Lys Pro Gly Gln Ala Pro
        35                  40                  45

Arg Leu Leu Ile Tyr Leu Ala Ser Asn Leu Asp Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Glu Glu Asp Phe Ala Thr Tyr Tyr Cys Gln His Ser Arg
                85                  90                  95

Asp Leu Pro Pro Thr Phe Gly Gln Gly Thr Lys Leu Glu Ile Lys
            100                 105                 110

<210> SEQ ID NO 123
<211> LENGTH: 111
<212> TYPE: PRT
<213> ORGANISM: Artificial Sequence
<220> FEATURE:
<223> OTHER INFORMATION: 3C6 VL 2.3

<400> SEQUENCE: 123

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Ile His Trp Tyr Gln Gln Lys Pro Gly Gln Ala Pro
        35                  40                  45

Arg Leu Leu Ile Tyr Leu Ala Ser Asn Leu Asp Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Thr Tyr Tyr Cys Gln His Ser Arg
                85                  90                  95

Asp Leu Pro Pro Thr Phe Gly Gln Gly Thr Lys Leu Glu Ile Lys
            100                 105                 110

<210> SEQ ID NO 124
<211> LENGTH: 111
<212> TYPE: PRT
<213> ORGANISM: Artificial Sequence
<220> FEATURE:
<223> OTHER INFORMATION: 3C6 VL 2.4

<400> SEQUENCE: 124

Glu Ile Val Leu Thr Gln Ser Pro Ala Thr Leu Ser Leu Ser Pro Gly

```
                1               5                  10                 15
Glu Arg Ala Thr Leu Ser Cys Arg Ala Ser Lys Ser Val Ser Thr Ser
                20                  25                  30

Gly Tyr Ser Tyr Ile His Trp Tyr Gln Gln Lys Pro Gly Gln Ala Pro
        35                  40                  45

Arg Leu Leu Ile Tyr Leu Ala Ser Asn Leu Asp Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Thr Tyr Tyr Cys Gln His Ser Arg
                85                  90                  95

Asp Leu Pro Pro Thr Phe Gly Gln Gly Thr Lys Leu Glu Ile Lys
            100                 105                 110
```

<210> SEQ ID NO 125
<211> LENGTH: 107
<212> TYPE: PRT
<213> ORGANISM: Artificial Sequence
<220> FEATURE:
<223> OTHER INFORMATION: 3C6 VL 1.1

<400> SEQUENCE: 125

```
Asn Ile Val Met Thr Gln Ser Pro Asp Ser Leu Ser Val Ser Val Gly
1               5                   10                  15

Glu Arg Ala Thr Leu Asn Cys Lys Ala Ser Glu Asn Val Val Thr Tyr
                20                  25                  30

Val Ser Trp Tyr Gln Gln Lys Pro Gly Gln Pro Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Leu Gln Ala
65                  70                  75                  80

Glu Asp Leu Ala Asp Tyr His Cys Gly Gln Gly Tyr Ser Tyr Pro Tyr
                85                  90                  95

Thr Phe Gly Gln Gly Thr Lys Leu Glu Ile Lys
            100                 105
```

<210> SEQ ID NO 126
<211> LENGTH: 107
<212> TYPE: PRT
<213> ORGANISM: Artificial Sequence
<220> FEATURE:
<223> OTHER INFORMATION: 3C6 VL 1.2

<400> SEQUENCE: 126

```
Asn Ile Val Met Thr Gln Ser Pro Asp Ser Leu Ala Val Ser Val Gly
1               5                   10                  15

Glu Arg Ala Thr Leu Asn Cys Lys Ala Ser Glu Asn Val Val Thr Tyr
                20                  25                  30

Val Ser Trp Tyr Gln Gln Lys Pro Gly Gln Pro Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Leu Gln Ala
65                  70                  75                  80

Glu Asp Leu Ala Asp Tyr His Cys Gly Gln Gly Tyr Ser Tyr Pro Tyr
                85                  90                  95
```

```
Thr Phe Gly Gln Gly Thr Lys Leu Glu Ile Lys
            100                 105

<210> SEQ ID NO 127
<211> LENGTH: 107
<212> TYPE: PRT
<213> ORGANISM: Artificial Sequence
<220> FEATURE:
<223> OTHER INFORMATION: 3C6 VL 1.3

<400> SEQUENCE: 127

Asp Ile Val Met Thr Gln Ser Pro Asp Ser Leu Ala Val Ser Leu Gly
1               5                   10                  15

Glu Arg Ala Thr Ile Asn Cys Lys Ala Ser Glu Asn Val Val Thr Tyr
            20                  25                  30

Val Ser Trp Tyr Gln Gln Lys Pro Gly Gln Pro Pro Lys Leu Leu Ile
        35                  40                  45

Tyr Gly Ala Ser Asn Arg Tyr Thr Gly Val Pro Asp Arg Phe Ser Gly
    50                  55                  60

Ser Gly Ser Ala Thr Asp Phe Thr Leu Thr Ile Ser Ser Leu Gln Ala
65                  70                  75                  80

Glu Asp Leu Ala Asp Tyr His Cys Gly Gln Gly Tyr Ser Tyr Pro Tyr
                85                  90                  95

Thr Phe Gly Gln Gly Thr Lys Leu Glu Ile Lys
            100                 105

<210> SEQ ID NO 128
<211> LENGTH: 107
<212> TYPE: PRT
<213> ORGANISM: Artificial Sequence
<220> FEATURE:
<223> OTHER INFORMATION: 3C6 VL 1.4

<400> SEQUENCE: 128

Asp Ile Val Met Thr Gln Ser Pro Asp Ser Leu Ala Val Ser Leu Gly
1               5                   10                  15

Glu Arg Ala Thr Ile Asn Cys Lys Ala Ser Glu Asn Val Val Thr Tyr
            20                  25                  30

Val Ser Trp Tyr Gln Gln Lys Pro Gly Gln Pro Pro Lys Leu Leu Ile
        35                  40                  45

Tyr Gly Ala Ser Asn Arg Tyr Thr Gly Val Pro Asp Arg Phe Ser Gly
    50                  55                  60

Ser Gly Ser Ala Thr Asp Phe Thr Leu Thr Ile Ser Ser Leu Gln Ala
65                  70                  75                  80

Glu Asp Val Ala Val Tyr His Cys Gly Gln Gly Tyr Ser Tyr Pro Tyr
                85                  90                  95

Thr Phe Gly Gln Gly Thr Lys Leu Glu Ile Lys
            100                 105

<210> SEQ ID NO 129
<211> LENGTH: 30
<212> TYPE: PRT
<213> ORGANISM: Artificial Sequence
<220> FEATURE:
<223> OTHER INFORMATION: 3C6 VH 2.1 HC-FR1

<400> SEQUENCE: 129

Glu Val Gln Leu Val Gln Ser Gly Pro Glu Leu Lys Lys Pro Gly Ala
1               5                   10                  15

Ser Val Lys Ile Ser Cys Lys Ala Ser Gly Tyr Thr Phe Thr
```

-continued

```
                 20                  25                  30
```

<210> SEQ ID NO 130
<211> LENGTH: 30
<212> TYPE: PRT
<213> ORGANISM: Artificial Sequence
<220> FEATURE:
<223> OTHER INFORMATION: 3C6 VH 2.2, 3C6 VH 2.3 HC-FR1

<400> SEQUENCE: 130

```
Glu Val Gln Leu Val Gln Ser Gly Ala Glu Val Lys Lys Pro Gly Ala
1               5                   10                  15
Ser Val Lys Ile Ser Cys Lys Ala Ser Gly Tyr Thr Phe Thr
            20                  25                  30
```

<210> SEQ ID NO 131
<211> LENGTH: 30
<212> TYPE: PRT
<213> ORGANISM: Artificial Sequence
<220> FEATURE:
<223> OTHER INFORMATION: 3C6 VH 2.4, 3C6 VH 2.5 HC-FR1

<400> SEQUENCE: 131

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr
            20                  25                  30
```

<210> SEQ ID NO 132
<211> LENGTH: 14
<212> TYPE: PRT
<213> ORGANISM: Artificial Sequence
<220> FEATURE:
<223> OTHER INFORMATION: 3C6 VH 2.1 HC-FR2

<400> SEQUENCE: 132

```
Trp Val Lys Gln Ala His Gly Gln Arg Leu Glu Trp Ile Gly
1               5                   10
```

<210> SEQ ID NO 133
<211> LENGTH: 14
<212> TYPE: PRT
<213> ORGANISM: Artificial Sequence
<220> FEATURE:
<223> OTHER INFORMATION: 3C6 VH 2.2 HC-FR2

<400> SEQUENCE: 133

```
Trp Val Lys Gln Ala Pro Gly Gln Arg Leu Glu Trp Ile Gly
1               5                   10
```

<210> SEQ ID NO 134
<211> LENGTH: 14
<212> TYPE: PRT
<213> ORGANISM: Artificial Sequence
<220> FEATURE:
<223> OTHER INFORMATION: 3C6 VH 2.3, 3C6 VH 2.4 HC-FR2

<400> SEQUENCE: 134

```
Trp Val Arg Gln Ala Pro Gly Gln Arg Leu Glu Trp Ile Gly
1               5                   10
```

<210> SEQ ID NO 135
<211> LENGTH: 14
<212> TYPE: PRT
<213> ORGANISM: Artificial Sequence
<220> FEATURE:

```
<223> OTHER INFORMATION: 3C6 VH 2.5 HC-FR2

<400> SEQUENCE: 135

Trp Val Arg Gln Ala Pro Gly Gln Arg Leu Glu Trp Met Gly
1               5                   10

<210> SEQ ID NO 136
<211> LENGTH: 32
<212> TYPE: PRT
<213> ORGANISM: Artificial Sequence
<220> FEATURE:
<223> OTHER INFORMATION: 3C6 VH 2.1 HC-FR3

<400> SEQUENCE: 136

Arg Ala Thr Leu Thr Val Asp Lys Ser Ala Ser Thr Ala Tyr Met Glu
1               5                   10                  15

Leu Arg Ser Leu Thr Ser Glu Asp Thr Ala Val Tyr Tyr Cys Ala Arg
            20                  25                  30

<210> SEQ ID NO 137
<211> LENGTH: 32
<212> TYPE: PRT
<213> ORGANISM: Artificial Sequence
<220> FEATURE:
<223> OTHER INFORMATION: 3C6 VH 2.2 HC-FR3

<400> SEQUENCE: 137

Arg Ala Thr Leu Thr Val Asp Lys Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 138
<211> LENGTH: 32
<212> TYPE: PRT
<213> ORGANISM: Artificial Sequence
<220> FEATURE:
<223> OTHER INFORMATION: 3C6 VH 2.3 HC-FR3

<400> SEQUENCE: 138

Arg Val Thr Leu Thr Val Asp Lys Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 139
<211> LENGTH: 32
<212> TYPE: PRT
<213> ORGANISM: Artificial Sequence
<220> FEATURE:
<223> OTHER INFORMATION: 3C6 VH 2.4, 3C6 VH 2.5 HC-FR3

<400> SEQUENCE: 139

Arg Val Thr Ile Thr Val Asp Lys Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 140
<211> LENGTH: 11
<212> TYPE: PRT
<213> ORGANISM: Artificial Sequence
<220> FEATURE:
<223> OTHER INFORMATION: 3C6 VH 2.1, 3C6 VH 2.2, 3C6 VH 2.3, 3C6 VH 2.4,
      3C6 VH 2.5 HC-FR4
```

```
<400> SEQUENCE: 140

Trp Gly Gln Gly Thr Thr Val Thr Val Ser Ser
1               5                   10

<210> SEQ ID NO 141
<211> LENGTH: 23
<212> TYPE: PRT
<213> ORGANISM: Artificial Sequence
<220> FEATURE:
<223> OTHER INFORMATION: 3C6 VL 2.1, 3C6 VL 2.2 LC-FR1

<400> SEQUENCE: 141

Asp Ile Val Leu Thr Gln Ser Pro Ala Ser Leu Ala Leu Ser Pro Gly
1               5                   10                  15

Glu Arg Ala Thr Leu Ser Cys
            20

<210> SEQ ID NO 142
<211> LENGTH: 23
<212> TYPE: PRT
<213> ORGANISM: Artificial Sequence
<220> FEATURE:
<223> OTHER INFORMATION: 3C6 VL 2.3 LC-FR1

<400> SEQUENCE: 142

Asp Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 143
<211> LENGTH: 23
<212> TYPE: PRT
<213> ORGANISM: Artificial Sequence
<220> FEATURE:
<223> OTHER INFORMATION: 3C6 VL 2.4 LC-FR1

<400> SEQUENCE: 143

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 144
<211> LENGTH: 15
<212> TYPE: PRT
<213> ORGANISM: Artificial Sequence
<220> FEATURE:
<223> OTHER INFORMATION: 3C6 VL 2.1 LC-FR2

<400> SEQUENCE: 144

Trp Tyr Gln Gln Lys Pro Gly Gln Pro Pro Arg Leu Leu Ile Tyr
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: 3C6 VL 2.2, 3C6 VL 2.3, 3C6 VL 2.4 LC-FR2

<400> SEQUENCE: 145

Trp Tyr Gln Gln Lys Pro Gly Gln Ala Pro Arg Leu Leu Ile Tyr
1               5                   10                  15
```

<210> SEQ ID NO 146
<211> LENGTH: 32
<212> TYPE: PRT
<213> ORGANISM: Artificial Sequence
<220> FEATURE:
<223> OTHER INFORMATION: 3C6 VL 2.1 LC-FR3

<400> SEQUENCE: 146

Gly Val Pro Ala Arg Phe Ser Gly Ser Gly Ser Gly Thr Asp Phe Thr
1               5                   10                  15

Leu Asn Ile His Pro Leu Glu Glu Glu Asp Phe Ala Thr Tyr Tyr Cys
            20                  25                  30

<210> SEQ ID NO 147
<211> LENGTH: 32
<212> TYPE: PRT
<213> ORGANISM: Artificial Sequence
<220> FEATURE:
<223> OTHER INFORMATION: 3C6 VL 2.2 LC-FR3

<400> SEQUENCE: 147

Gly Val Pro Ala Arg Phe Ser Gly Ser Gly Ser Gly Thr Asp Phe Thr
1               5                   10                  15

Leu Thr Ile Ser Ser Leu Glu Glu Glu Asp Phe Ala Thr Tyr Tyr Cys
            20                  25                  30

<210> SEQ ID NO 148
<211> LENGTH: 32
<212> TYPE: PRT
<213> ORGANISM: Artificial Sequence
<220> FEATURE:
<223> OTHER INFORMATION: 3C6 VL 2.3, 3C6 VL 2.4 LC-FR3

<400> SEQUENCE: 148

Gly Val Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Thr Tyr Tyr Cys
            20                  25                  30

<210> SEQ ID NO 149
<211> LENGTH: 10
<212> TYPE: PRT
<213> ORGANISM: Artificial Sequence
<220> FEATURE:
<223> OTHER INFORMATION: 3C6 VL 2.1 3C6 VL 2.2 3C6 VL 2.3 3C6 VL 2.4 3C6
      VL 1.1 3C6 VL 1.2 3C6 VL 1.3 3C6 VL 1.4 LC-FR4

<400> SEQUENCE: 149

Phe Gly Gln Gly Thr Lys Leu Glu Ile Lys
1               5                   10

<210> SEQ ID NO 150
<211> LENGTH: 23
<212> TYPE: PRT
<213> ORGANISM: Artificial Sequence
<220> FEATURE:
<223> OTHER INFORMATION: 3C6 VL 1.1 LC-FR1

<400> SEQUENCE: 150

Asn Ile Val Met Thr Gln Ser Pro Asp Ser Leu Ser Val Ser Val Gly
1               5                   10                  15

Glu Arg Ala Thr Leu Asn Cys
            20

<210> SEQ ID NO 151
<211> LENGTH: 23
<212> TYPE: PRT
<213> ORGANISM: Artificial Sequence
<220> FEATURE:
<223> OTHER INFORMATION: 3C6 VL 1.2 LC-FR1

<400> SEQUENCE: 151

Asn Ile Val Met Thr Gln Ser Pro Asp Ser Leu Ala Val Ser Val Gly
1               5                   10                  15

Glu Arg Ala Thr Leu Asn Cys
            20

<210> SEQ ID NO 152
<211> LENGTH: 23
<212> TYPE: PRT
<213> ORGANISM: Artificial Sequence
<220> FEATURE:
<223> OTHER INFORMATION: 3C6 VL 1.3, 3C6 VL 1.4 LC-FR1

<400> SEQUENCE: 152

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 153
<211> LENGTH: 32
<212> TYPE: PRT
<213> ORGANISM: Artificial Sequence
<220> FEATURE:
<223> OTHER INFORMATION: 3C6 VL 1.1 3C6 VL 1.2 LC-FR3

<400> SEQUENCE: 153

Gly Val Pro Asp Arg Phe Thr Gly Ser Gly Ser Ala Thr Asp Phe Thr
1               5                   10                  15

Leu Thr Ile Ser Ser Leu Gln Ala Glu Asp Leu Ala Asp Tyr His Cys
            20                  25                  30

<210> SEQ ID NO 154
<211> LENGTH: 32
<212> TYPE: PRT
<213> ORGANISM: Artificial Sequence
<220> FEATURE:
<223> OTHER INFORMATION: 3C6 VL 1.3 LC-FR3

<400> SEQUENCE: 154

Gly Val Pro Asp Arg Phe Ser Gly Ser Gly Ser Ala Thr Asp Phe Thr
1               5                   10                  15

Leu Thr Ile Ser Ser Leu Gln Ala Glu Asp Leu Ala Asp Tyr His Cys
            20                  25                  30

<210> SEQ ID NO 155
<211> LENGTH: 32
<212> TYPE: PRT
<213> ORGANISM: Artificial Sequence
<220> FEATURE:
<223> OTHER INFORMATION: 3C6 VL 1.4 LC-FR3

<400> SEQUENCE: 155

Gly Val Pro Asp Arg Phe Ser Gly Ser Gly Ser Ala Thr Asp Phe Thr
1               5                   10                  15

Leu Thr Ile Ser Ser Leu Gln Ala Glu Asp Val Ala Val Tyr His Cys
            20                  25                  30

<210> SEQ ID NO 156
<211> LENGTH: 118
<212> TYPE: PRT
<213> ORGANISM: Artificial Sequence
<220> FEATURE:
<223> OTHER INFORMATION: 1H2 VH

<400> SEQUENCE: 156

Gln Ala Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Thr Trp Val Lys Gln Arg Thr Gly Gln Gly Leu Glu Trp Ile
        35                  40                  45

Gly Asp Ile Tyr Pro Arg Ser Gly Asn Ile Tyr Tyr Asn Glu Asn Phe
    50                  55                  60

Lys Gly Glu Ala Thr Leu Thr Ala Asp Lys Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Ser Gly Trp Glu Gly Trp Phe Ala Tyr Trp Gly Gln Gly Thr
            100                 105                 110

Leu Val Thr Val Ser Val
        115

<210> SEQ ID NO 157
<211> LENGTH: 106
<212> TYPE: PRT
<213> ORGANISM: Artificial Sequence
<220> FEATURE:
<223> OTHER INFORMATION: 1H2 VL

<400> SEQUENCE: 157

Asp Ile Val Met Thr Gln Ser His Lys Phe Met Ser Thr Ser Val Gly
1               5                   10                  15

Asp Arg Val Asn Ile Thr Cys Lys Ala Ser Gln Asp Val Gly Ser Ala
            20                  25                  30

Val Val Trp Tyr Gln Gln Lys Pro Gly Gln Ser Pro Lys Val Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Arg Thr
                85                  90                  95

Phe Gly Gly Gly Thr Lys Leu Glu Ile Lys
            100                 105

<210> SEQ ID NO 158
<211> LENGTH: 5
<212> TYPE: PRT
<213> ORGANISM: Artificial Sequence
<220> FEATURE:
<223> OTHER INFORMATION: 1H2 HC-CDR1

<400> SEQUENCE: 158

Ser Tyr Gly Ile Thr
1               5

<210> SEQ ID NO 159
<211> LENGTH: 17
<212> TYPE: PRT
<213> ORGANISM: Artificial Sequence
<220> FEATURE:
<223> OTHER INFORMATION: 1H2 HC-CDR2

<400> SEQUENCE: 159

```
Asp Ile Tyr Pro Arg Ser Gly Asn Ile Tyr Tyr Asn Glu Asn Phe Lys
1               5                   10                  15

Gly
```

<210> SEQ ID NO 160
<211> LENGTH: 9
<212> TYPE: PRT
<213> ORGANISM: Artificial Sequence
<220> FEATURE:
<223> OTHER INFORMATION: 1H2 HC-CDR3

<400> SEQUENCE: 160

```
Ser Gly Trp Glu Gly Trp Phe Ala Tyr
1               5
```

<210> SEQ ID NO 161
<211> LENGTH: 11
<212> TYPE: PRT
<213> ORGANISM: Artificial Sequence
<220> FEATURE:
<223> OTHER INFORMATION: 1H2 LC-CDR1

<400> SEQUENCE: 161

```
Lys Ala Ser Gln Asp Val Gly Ser Ala Val Val
1               5                   10
```

<210> SEQ ID NO 162
<211> LENGTH: 7
<212> TYPE: PRT
<213> ORGANISM: Artificial Sequence
<220> FEATURE:
<223> OTHER INFORMATION: 1H2 LC-CDR2

<400> SEQUENCE: 162

```
Trp Ala Ser Thr Arg His Thr
1               5
```

<210> SEQ ID NO 163
<211> LENGTH: 8
<212> TYPE: PRT
<213> ORGANISM: Artificial Sequence
<220> FEATURE:
<223> OTHER INFORMATION: 1H2 LC-CDR3

<400> SEQUENCE: 163

```
Gln Gln Tyr Ser Ser Tyr Arg Thr
1               5
```

<210> SEQ ID NO 164
<211> LENGTH: 30
<212> TYPE: PRT
<213> ORGANISM: Artificial Sequence
<220> FEATURE:
<223> OTHER INFORMATION: 1H2 HC-FR1

<400> SEQUENCE: 164

```
Gln Ala Gln Leu Gln Gln Ser Gly Ala Glu Leu Ala Arg Pro Gly Ala
1               5                   10                  15
```

Ser Val Lys Leu Ser Cys Lys Ala Ser Gly Tyr Thr Phe Thr
            20                  25                  30

<210> SEQ ID NO 165
<211> LENGTH: 14
<212> TYPE: PRT
<213> ORGANISM: Artificial Sequence
<220> FEATURE:
<223> OTHER INFORMATION: 1H2 HC-FR2

<400> SEQUENCE: 165

Trp Val Lys Gln Arg Thr Gly Gln Gly Leu Glu Trp Ile Gly
1               5                   10

<210> SEQ ID NO 166
<211> LENGTH: 32
<212> TYPE: PRT
<213> ORGANISM: Artificial Sequence
<220> FEATURE:
<223> OTHER INFORMATION: 1H2 HC-FR3

<400> SEQUENCE: 166

Glu Ala Thr Leu Thr Ala Asp Lys Ser Ser Thr Ala Tyr Met Gln
1               5                   10                  15

Leu Ser Arg Leu Thr Ser Glu Asp Ser Ala Val Tyr Phe Cys Ala Arg
            20                  25                  30

<210> SEQ ID NO 167
<211> LENGTH: 11
<212> TYPE: PRT
<213> ORGANISM: Artificial Sequence
<220> FEATURE:
<223> OTHER INFORMATION: 1H2 HC-FR4

<400> SEQUENCE: 167

Trp Gly Gln Gly Thr Leu Val Thr Val Ser Val
1               5                   10

<210> SEQ ID NO 168
<211> LENGTH: 23
<212> TYPE: PRT
<213> ORGANISM: Artificial Sequence
<220> FEATURE:
<223> OTHER INFORMATION: 1H2 LC-FR1

<400> SEQUENCE: 168

Asp Ile Val Met Thr Gln Ser His Lys Phe Met Ser Thr Ser Val Gly
1               5                   10                  15

Asp Arg Val Asn Ile Thr Cys
            20

<210> SEQ ID NO 169
<211> LENGTH: 15
<212> TYPE: PRT
<213> ORGANISM: Artificial Sequence
<220> FEATURE:
<223> OTHER INFORMATION: 1H2 LC-FR2

<400> SEQUENCE: 169

Trp Tyr Gln Gln Lys Pro Gly Gln Ser Pro Lys Val Leu Ile Tyr
1               5                   10                  15

<210> SEQ ID NO 170
<211> LENGTH: 32
<212> TYPE: PRT

```
<213> ORGANISM: Artificial Sequence
<220> FEATURE:
<223> OTHER INFORMATION: 1H2 LC-FR3

<400> SEQUENCE: 170

Gly Val Pro Asp Arg Phe Thr Gly Ser Gly Ser Gly Thr Asp Phe Thr
1               5                   10                  15

Leu Thr Ile Ser Asn Val Gln Ser Glu Asp Leu Ala Asp Tyr Phe Cys
            20                  25                  30

<210> SEQ ID NO 171
<211> LENGTH: 10
<212> TYPE: PRT
<213> ORGANISM: Artificial Sequence
<220> FEATURE:
<223> OTHER INFORMATION: 1H2 LC-FR4

<400> SEQUENCE: 171

Phe Gly Gly Gly Thr Lys Leu Glu Ile Lys
1               5                   10

<210> SEQ ID NO 172
<211> LENGTH: 354
<212> TYPE: DNA
<213> ORGANISM: Artificial Sequence
<220> FEATURE:
<223> OTHER INFORMATION: 1H2 VH

<400> SEQUENCE: 172
caggctcagc tgcagcagtc tggagctgag ctggcgaggc ctggggcttc agtgaagctg     60
tcctgcaagg cttctggcta ccttcacaa gctatggta taacctgggt gaagcagaga    120
actggacagg ccttgagtg gattggagat atttatccta gaagtggtaa tatttattac    180
aatgagaact caagggcga ggccacattg actgcagaca atcctccag cacagcctat    240 atgcagctca gcagactgac atctgaggac tctgcagtct attctgtgc aagatccggg    300 tgggaaggct ggtttgctta ttggggccaa gggactctgg tcactgtctc tgta         354

<210> SEQ ID NO 173
<211> LENGTH: 318
<212> TYPE: DNA
<213> ORGANISM: Artificial Sequence
<220> FEATURE:
<223> OTHER INFORMATION: 1H2 VL

<400> SEQUENCE: 173
gacattgtga tgacccagtc tcacaaattc atgtccacat cagtaggaga cagggtcaac     60
atcacctgca aggccagtca ggatgtgggt agtgctgtag tctggtatca acagaaacca    120
gggcaatctc ctaaagtact gatttactgg gcatccaccc ggcacactgg agtccctgat    180
cgcttcacag gcagtggctc tgggacagat ttcactctca ccattagcaa tgtgcagtct    240
gaagacttgg cagattattt ctgtcagcaa tatagcagtt atcggacgtt cggtggaggc    300
accaagctgg aaatcaaa                                                  318

<210> SEQ ID NO 174
<211> LENGTH: 119
<212> TYPE: PRT
<213> ORGANISM: Artificial Sequence
<220> FEATURE:
<223> OTHER INFORMATION: 7D4 VH

<400> SEQUENCE: 174
```

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Asn Met Asp Trp Val Lys Gln Ser Gln Gly Lys Arg Leu Glu Trp Ile
            35                  40                  45

Gly Asp Ile Asn Pro Asn Tyr Gly Gly Thr Ile Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Thr Thr Val Tyr Tyr Cys
                85                  90                  95

Thr Arg Gly Glu Leu Gly His Trp Tyr Phe Asp Val Trp Gly Thr Gly
            100                 105                 110

Thr Thr Val Thr Val Ser Ser
            115
```

<210> SEQ ID NO 175
<211> LENGTH: 111
<212> TYPE: PRT
<213> ORGANISM: Artificial Sequence
<220> FEATURE:
<223> OTHER INFORMATION: 7D4 VL

<400> SEQUENCE: 175

```
Asp Ile Val Leu Thr Gln Ser Pro Pro Ser Leu Thr Val Ser Leu Gly
1               5                   10                  15

Gln Arg Ala Thr Ile Ser Cys Arg Ala Ser Lys Ser Val Ser Ala Ser
                20                  25                  30

Gly Tyr Ser Tyr Met His Trp Tyr Gln Gln Lys Pro Gly Gln Pro Pro
            35                  40                  45

Lys Leu Leu Ile Tyr Leu Thr Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Trp
                85                  90                  95

Asp Leu Pro Pro Thr Phe Gly Gly Gly Thr Lys Leu Glu Ile Lys
            100                 105                 110
```

<210> SEQ ID NO 176
<211> LENGTH: 5
<212> TYPE: PRT
<213> ORGANISM: Artificial Sequence
<220> FEATURE:
<223> OTHER INFORMATION: 7D4  HC-CDR1

<400> SEQUENCE: 176

```
Asp Tyr Asn Met Asp
1               5
```

<210> SEQ ID NO 177
<211> LENGTH: 17
<212> TYPE: PRT
<213> ORGANISM: Artificial Sequence
<220> FEATURE:
<223> OTHER INFORMATION: 7D4 HC-CDR2

<400> SEQUENCE: 177

```
Asp Ile Asn Pro Asn Tyr Gly Gly Thr Ile Tyr Asn Gln Lys Phe Lys
```

```
1               5                  10                 15

Gly

<210> SEQ ID NO 178
<211> LENGTH: 10
<212> TYPE: PRT
<213> ORGANISM: Artificial Sequence
<220> FEATURE:
<223> OTHER INFORMATION: 7D4 HC-CDR3

<400> SEQUENCE: 178

Gly Glu Leu Gly His Trp Tyr Phe Asp Val
1               5                  10

<210> SEQ ID NO 179
<211> LENGTH: 15
<212> TYPE: PRT
<213> ORGANISM: Artificial Sequence
<220> FEATURE:
<223> OTHER INFORMATION: 7D4 LC-CDR1

<400> SEQUENCE: 179

Arg Ala Ser Lys Ser Val Ser Ala Ser Gly Tyr Ser Tyr Met His
1               5                  10                 15

<210> SEQ ID NO 180
<211> LENGTH: 7
<212> TYPE: PRT
<213> ORGANISM: Artificial Sequence
<220> FEATURE:
<223> OTHER INFORMATION: 7D4 LC-CDR2

<400> SEQUENCE: 180

Leu Thr Ser Asn Leu Glu Ser
1               5

<210> SEQ ID NO 181
<211> LENGTH: 9
<212> TYPE: PRT
<213> ORGANISM: Artificial Sequence
<220> FEATURE:
<223> OTHER INFORMATION: 7D4 LC-CDR3

<400> SEQUENCE: 181

Gln His Ser Trp Asp Leu Pro Pro Thr
1               5

<210> SEQ ID NO 182
<211> LENGTH: 30
<212> TYPE: PRT
<213> ORGANISM: Artificial Sequence
<220> FEATURE:
<223> OTHER INFORMATION: 7D4 HC-FR1

<400> SEQUENCE: 182

Glu Val Gln Leu Gln Gln Ser Gly Pro Glu Leu Val Lys Pro Gly Ala
1               5                  10                 15

Ser Val Lys Ile Ser Cys Lys Ala Ser Gly Tyr Thr Phe Thr
            20                  25                 30

<210> SEQ ID NO 183
<211> LENGTH: 14
<212> TYPE: PRT
<213> ORGANISM: Artificial Sequence
<220> FEATURE:
<223> OTHER INFORMATION: 7D4  HC-FR2
```

<400> SEQUENCE: 183

Trp Val Lys Gln Ser Gln Gly Lys Arg Leu Glu Trp Ile Gly
1               5                   10

<210> SEQ ID NO 184
<211> LENGTH: 32
<212> TYPE: PRT
<213> ORGANISM: Artificial Sequence
<220> FEATURE:
<223> OTHER INFORMATION: 7D4 HC-FR3

<400> SEQUENCE: 184

Lys Ala Thr Leu Thr Val Asp Lys Ser Ser Thr Ala Tyr Met Glu
1               5                   10                  15

Leu Arg Ser Leu Thr Ser Glu Asp Thr Thr Val Tyr Tyr Cys Thr Arg
            20                  25                  30

<210> SEQ ID NO 185
<211> LENGTH: 11
<212> TYPE: PRT
<213> ORGANISM: Artificial Sequence
<220> FEATURE:
<223> OTHER INFORMATION: 7D4 HC-FR4

<400> SEQUENCE: 185

Trp Gly Thr Gly Thr Thr Val Thr Val Ser Ser
1               5                   10

<210> SEQ ID NO 186
<211> LENGTH: 23
<212> TYPE: PRT
<213> ORGANISM: Artificial Sequence
<220> FEATURE:
<223> OTHER INFORMATION: 7D4 LC-FR1

<400> SEQUENCE: 186

Asp Ile Val Leu Thr Gln Ser Pro Pro Ser Leu Thr Val Ser Leu Gly
1               5                   10                  15

Gln Arg Ala Thr Ile Ser Cys
            20

<210> SEQ ID NO 187
<211> LENGTH: 15
<212> TYPE: PRT
<213> ORGANISM: Artificial Sequence
<220> FEATURE:
<223> OTHER INFORMATION: 7D4 LC-FR2

<400> SEQUENCE: 187

Trp Tyr Gln Gln Lys Pro Gly Gln Pro Pro Lys Leu Leu Ile Tyr
1               5                   10                  15

<210> SEQ ID NO 188
<211> LENGTH: 32
<212> TYPE: PRT
<213> ORGANISM: Artificial Sequence
<220> FEATURE:
<223> OTHER INFORMATION: 7D4 LC-FR3

<400> SEQUENCE: 188

Gly Val Pro Ala Arg Phe Ser Gly Ser Gly Ser Gly Thr Asp Phe Thr
1               5                   10                  15

Leu Asn Ile His Pro Val Glu Glu Glu Asp Ala Ala Thr Tyr Tyr Cys
            20                  25                  30

<210> SEQ ID NO 189
<211> LENGTH: 10
<212> TYPE: PRT
<213> ORGANISM: Artificial Sequence
<220> FEATURE:
<223> OTHER INFORMATION: 7D4 LC-FR4

<400> SEQUENCE: 189

Phe Gly Gly Gly Thr Lys Leu Glu Ile Lys
1               5                   10

<210> SEQ ID NO 190
<211> LENGTH: 357
<212> TYPE: DNA
<213> ORGANISM: Artificial Sequence
<220> FEATURE:
<223> OTHER INFORMATION: 7D4 VH

<400> SEQUENCE: 190
gaggtccagc tgcaacagtc tggacctgag ctggtgaagc ctggggcttc agtgaagata      60
tcctgcaagg cttctggata cacattcact gactacaaca tggactgggt gaagcagagt     120
caaggaaaga gacttgagtg gattggagat attaatccta ctatggtgg tactatctac      180 aaccagaagt tcaagggcaa ggccacattg actgttgaca gtcctccag cacagcctac      240 atggagctcc gcagcctgac atctgaggac actacagtct attactgtac aagaggggaa     300
ctgggtcact ggtacttcga tgtctggggc acagggacca cggtcaccgt ctcctca       357

<210> SEQ ID NO 191
<211> LENGTH: 333
<212> TYPE: DNA
<213> ORGANISM: Artificial Sequence
<220> FEATURE:
<223> OTHER INFORMATION: 7D4 VL

<400> SEQUENCE: 191
gacattgtgc tgacacagtc tcctccttcc ttaactgtgt ctctggggca gagggccacc      60
atctcatgca gggccagtaa aagtgtcagt gcgtctggct atagttatat gcactggtac     120
caacagaaac caggacagcc acccaaactc ctcatctatc ttacatccaa cctagaatct     180
ggggtccctg ccaggttcag tgcagtgggc tctgggacag acttcaccct caacatccat     240
cctgtggagg aggaggatgc tgcaacctat tactgtcagc acagttggga ccttcctccg     300
acgttcggtg gaggcaccaa gctggaaatc aaa                                333

<210> SEQ ID NO 192
<211> LENGTH: 119
<212> TYPE: PRT
<213> ORGANISM: Artificial Sequence
<220> FEATURE:
<223> OTHER INFORMATION: 8H11 VH

<400> SEQUENCE: 192

Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Ile Asp Trp Val Lys Gln Ser His Gly Lys Ser Leu Glu Trp Ile
        35                  40                  45

Gly Asp Ile Asn Pro Asn Tyr Gly Gly Thr Leu Tyr Asn Gln Lys Phe
    50                  55                  60

```
Lys Gly Lys Ala Thr Leu Thr Val Asp Lys Ser Ser Thr Ala Tyr
 65                  70                  75                  80

Met Glu Leu Arg Ser Leu Thr Ser Glu Asp Thr Ala Val Tyr Tyr Cys
                 85                  90                  95

Ala Arg Gly Glu Leu Gly His Trp Tyr Phe Asp Val Trp Gly Thr Gly
            100                 105                 110

Thr Thr Val Thr Val Ser Ser
            115

<210> SEQ ID NO 193
<211> LENGTH: 111
<212> TYPE: PRT
<213> ORGANISM: Artificial Sequence
<220> FEATURE:
<223> OTHER INFORMATION: 8H11 VL

<400> SEQUENCE: 193

Asp Ile Val Leu Thr Gln Ser Pro Ala Ser Leu Ala Val Ser Leu Gly
  1               5                  10                  15

Gln Arg Ala Thr Ile Ser Cys Arg Ala Ser Lys Ser Val Ser Thr Ser
             20                  25                  30

Asp Tyr Ser Tyr Met His Trp Tyr Gln Gln Lys Pro Gly His Pro Pro
         35                  40                  45

Lys Leu Leu Ile Tyr Leu Ala Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Phe Cys Gln His Ser Arg
                 85                  90                  95

Asp Leu Pro Pro Thr Phe Gly Gly Gly Thr Lys Leu Glu Ile Lys
            100                 105                 110

<210> SEQ ID NO 194
<211> LENGTH: 5
<212> TYPE: PRT
<213> ORGANISM: Artificial Sequence
<220> FEATURE:
<223> OTHER INFORMATION: 8H11 HC-CDR1

<400> SEQUENCE: 194

Asp Tyr Asn Ile Asp
  1               5

<210> SEQ ID NO 195
<211> LENGTH: 17
<212> TYPE: PRT
<213> ORGANISM: Artificial Sequence
<220> FEATURE:
<223> OTHER INFORMATION: 8H11 HC-CDR2

<400> SEQUENCE: 195

Asp Ile Asn Pro Asn Tyr Gly Gly Thr Leu Tyr Asn Gln Lys Phe Lys
  1               5                  10                  15

Gly

<210> SEQ ID NO 196
<211> LENGTH: 10
<212> TYPE: PRT
<213> ORGANISM: Artificial Sequence
<220> FEATURE:
<223> OTHER INFORMATION: 8H11 HC-CDR3
```

<400> SEQUENCE: 196

Gly Glu Leu Gly His Trp Tyr Phe Asp Val
1               5                   10

<210> SEQ ID NO 197
<211> LENGTH: 15
<212> TYPE: PRT
<213> ORGANISM: Artificial Sequence
<220> FEATURE:
<223> OTHER INFORMATION: 8H11 LC-CDR1

<400> SEQUENCE: 197

Arg Ala Ser Lys Ser Val Ser Thr Ser Asp Tyr Ser Tyr Met His
1               5                   10                  15

<210> SEQ ID NO 198
<211> LENGTH: 7
<212> TYPE: PRT
<213> ORGANISM: Artificial Sequence
<220> FEATURE:
<223> OTHER INFORMATION: 8H11 LC-CDR2

<400> SEQUENCE: 198

Leu Ala Ser Asn Leu Glu Ser
1               5

<210> SEQ ID NO 199
<211> LENGTH: 9
<212> TYPE: PRT
<213> ORGANISM: Artificial Sequence
<220> FEATURE:
<223> OTHER INFORMATION: 8H11 LC-CDR3

<400> SEQUENCE: 199

Gln His Ser Arg Asp Leu Pro Pro Thr
1               5

<210> SEQ ID NO 200
<211> LENGTH: 30
<212> TYPE: PRT
<213> ORGANISM: Artificial Sequence
<220> FEATURE:
<223> OTHER INFORMATION: 8H11 HC-FR1

<400> SEQUENCE: 200

Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr
            20                  25                  30

<210> SEQ ID NO 201
<211> LENGTH: 14
<212> TYPE: PRT
<213> ORGANISM: Artificial Sequence
<220> FEATURE:
<223> OTHER INFORMATION: 8H11 HC-FR2

<400> SEQUENCE: 201

Trp Val Lys Gln Ser His Gly Lys Ser Leu Glu Trp Ile Gly
1               5                   10

<210> SEQ ID NO 202
<211> LENGTH: 32
<212> TYPE: PRT
<213> ORGANISM: Artificial Sequence

<220> FEATURE:
<223> OTHER INFORMATION: 8H11 HC-FR3

<400> SEQUENCE: 202

Lys Ala Thr Leu Thr Val Asp Lys Ser Ser Thr Ala Tyr Met Glu
1               5                   10                  15

Leu Arg Ser Leu Thr Ser Glu Asp Thr Ala Val Tyr Tyr Cys Ala Arg
            20                  25                  30

<210> SEQ ID NO 203
<211> LENGTH: 11
<212> TYPE: PRT
<213> ORGANISM: Artificial Sequence
<220> FEATURE:
<223> OTHER INFORMATION: 8H11 HC-FR4

<400> SEQUENCE: 203

Trp Gly Thr Gly Thr Thr Val Thr Val Ser Ser
1               5                   10

<210> SEQ ID NO 204
<211> LENGTH: 23
<212> TYPE: PRT
<213> ORGANISM: Artificial Sequence
<220> FEATURE:
<223> OTHER INFORMATION: 8H11 LC-FR1

<400> SEQUENCE: 204

Asp Ile Val Leu Thr Gln Ser Pro Ala Ser Leu Ala Val Ser Leu Gly
1               5                   10                  15

Gln Arg Ala Thr Ile Ser Cys
            20

<210> SEQ ID NO 205
<211> LENGTH: 15
<212> TYPE: PRT
<213> ORGANISM: Artificial Sequence
<220> FEATURE:
<223> OTHER INFORMATION: 8H11 LC-FR2

<400> SEQUENCE: 205

Trp Tyr Gln Gln Lys Pro Gly His Pro Pro Lys Leu Leu Ile Tyr
1               5                   10                  15

<210> SEQ ID NO 206
<211> LENGTH: 32
<212> TYPE: PRT
<213> ORGANISM: Artificial Sequence
<220> FEATURE:
<223> OTHER INFORMATION: 8H11 LC-FR3

<400> SEQUENCE: 206

Gly Val Pro Ala Arg Phe Ser Gly Ser Gly Ser Gly Thr Asp Phe Thr
1               5                   10                  15

Leu Asn Ile His Pro Val Glu Glu Glu Asp Ala Ala Thr Tyr Phe Cys
            20                  25                  30

<210> SEQ ID NO 207
<211> LENGTH: 10
<212> TYPE: PRT
<213> ORGANISM: Artificial Sequence
<220> FEATURE:
<223> OTHER INFORMATION: 8H11 LC-FR4

<400> SEQUENCE: 207

Phe Gly Gly Gly Thr Lys Leu Glu Ile Lys
1               5                  10

<210> SEQ ID NO 208
<211> LENGTH: 357
<212> TYPE: DNA
<213> ORGANISM: Artificial Sequence
<220> FEATURE:
<223> OTHER INFORMATION: 8H11 VH

<400> SEQUENCE: 208
gaggtccagc tgcaacagtc tggacctgag ctggtgaagc ctggggcttc agtgaagata     60
ccctgcaagg cttctggata cacattcact gactacaaca tagactgggt gaagcagagc    120
catggaaaga gccttgagtg gattggagat attaatccta attatggtgg tactctctac    180
aaccagaagt tcaagggcaa ggcaacattg actgtagaca gtcctccag cacagcctac     240 atggaactcc gcagcctgac atctgaggac actgcagtct attactgtgc aagaggggaa    300
ctgggtcact ggtacttcga tgtctggggc acagggacca cggtcaccgt ctcctca       357

<210> SEQ ID NO 209
<211> LENGTH: 333
<212> TYPE: DNA
<213> ORGANISM: Artificial Sequence
<220> FEATURE:
<223> OTHER INFORMATION: 8H11 VL

<400> SEQUENCE: 209
gacattgtgc tgacacagtc tcctgcttcc ttagctgtat ctctggggca gagggccacc     60
atctcatgca gggccagcaa agtgtcagt acatctgact atagttatat gcactggtac     120
caacagaaac caggacaccc acccaaactc ctcatctatc ttgcatccaa cctagaatct    180
ggggtccctg ccaggttcag tggcagtggg tctgggacag acttcaccct caacatccat    240
cctgtggagg aggaggatgc tgcaacctat ttctgtcagc acagtaggga ccttcctccg    300
acgttcggtg gaggcaccaa gctggaaatc aaa                                 333

<210> SEQ ID NO 210
<211> LENGTH: 261
<212> TYPE: PRT
<213> ORGANISM: Artificial Sequence
<220> FEATURE:
<223> OTHER INFORMATION: YU100-G08 VH-02A VL

<400> SEQUENCE: 210

Gln Val Gln Leu Val Gln Ser Gly Gly Gly Val Val Gln Pro Gly Arg
1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Gly Ser Ala Ser Ala Pro Lys Leu Glu Glu

```
            115                 120                 125
Gly Glu Phe Ser Glu Ala Arg Val Gln Ser Ala Leu Thr Gln Pro Arg
        130                 135                 140

Ser Val Ser Gly Ser Pro Gly Gln Ser Val Thr Leu Ser Cys Thr Gly
145                 150                 155                 160

Thr Ser Ser Asp Val Gly Gly Tyr Asn Tyr Val Ser Trp Tyr Gln His
                165                 170                 175

Tyr Pro Gly Lys Ala Pro Lys Leu Met Ile Phe Asp Val Asn Glu Arg
            180                 185                 190

Ser Ser Gly Val Pro Asp Arg Phe Ser Gly Ser Lys Ser Gly Asn Thr
        195                 200                 205

Ala Ser Leu Thr Ile Ser Gly Leu Gln Ala Glu Asp Glu Ala Asp Tyr
    210                 215                 220

Tyr Cys Ala Ser Tyr Ala Gly Arg Tyr Thr Trp Met Phe Gly Gly Gly
225                 230                 235                 240

Thr Lys Val Thr Val Leu Gly Gln Pro Lys Ala Ala Pro Ser Val Thr
                245                 250                 255

Leu Phe Pro Pro Ser
            260

<210> SEQ ID NO 211
<211> LENGTH: 327
<212> TYPE: PRT
<213> ORGANISM: Homo sapiens
<220> FEATURE:
<221> NAME/KEY: misc_feature
<222> LOCATION: (1)..(327)
<223> OTHER INFORMATION: IgG4 constant region (IGHG4; UniProt: P01861,
      v1)

<400> SEQUENCE: 211

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
```

```
                195                 200                 205
Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 212
<211> LENGTH: 98
<212> TYPE: PRT
<213> ORGANISM: Artificial Sequence
<220> FEATURE:
<223> OTHER INFORMATION: CH1 IgG4 (positions 1-98 of P01861, v1)

<400> SEQUENCE: 212

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 213
<211> LENGTH: 12
<212> TYPE: PRT
<213> ORGANISM: Artificial Sequence
<220> FEATURE:
<223> OTHER INFORMATION: Hinge IgG4 (positions 99-110 of P01861, v1)

<400> SEQUENCE: 213

Glu Ser Lys Tyr Gly Pro Pro Cys Pro Ser Cys Pro
1               5                   10

<210> SEQ ID NO 214
<211> LENGTH: 110
<212> TYPE: PRT
<213> ORGANISM: Artificial Sequence
<220> FEATURE:
<223> OTHER INFORMATION: CH2 IgG4 (positions 111-220 of P01861, v1)

<400> SEQUENCE: 214
```

```
Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110
```

<210> SEQ ID NO 215
<211> LENGTH: 107
<212> TYPE: PRT
<213> ORGANISM: Artificial Sequence
<220> FEATURE:
<223> OTHER INFORMATION: CH3 IgG4 (positions 221-327 of P01861, v1)

<400> SEQUENCE: 215

```
Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105
```

<210> SEQ ID NO 216
<211> LENGTH: 327
<212> TYPE: PRT
<213> ORGANISM: Artificial Sequence
<220> FEATURE:
<223> OTHER INFORMATION: Human IgG4 constant region (IGHG4; UniProt:
      P01861, v1; S241P)

<400> SEQUENCE: 216

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
```

```
                    85                  90                  95
Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 217
<211> LENGTH: 12
<212> TYPE: PRT
<213> ORGANISM: Artificial Sequence
<220> FEATURE:
<223> OTHER INFORMATION: Hinge IgG4 (positions 99-110 of P01861, v1;
      S241P)

<400> SEQUENCE: 217

Glu Ser Lys Tyr Gly Pro Pro Cys Pro Pro Cys Pro
1               5                   10

<210> SEQ ID NO 218
<211> LENGTH: 327
<212> TYPE: PRT
<213> ORGANISM: Homo sapiens
<220> FEATURE:
<221> NAME/KEY: misc_feature
<222> LOCATION: (1)..(327)
<223> OTHER INFORMATION: IgG4 constant region (IGHG4; UniProt: P01861,
      v1)

<400> SEQUENCE: 218

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

-continued

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
                100                 105                 110

Glu Phe Glu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 219
<211> LENGTH: 110
<212> TYPE: PRT
<213> ORGANISM: Artificial Sequence
<220> FEATURE:
<223> OTHER INFORMATION: CH2 IgG4 (positions 111-220 of P01861, v1;
      L248E)

<400> SEQUENCE: 219

Ala Pro Glu Phe Glu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
```

50                  55                  60
Gln Phe Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                     85                  90                  95

Gly Leu Pro Ser Ser Ile Glu Lys Thr Ile Ser Lys Ala Lys
                100                 105                 110

<210> SEQ ID NO 220
<211> LENGTH: 448
<212> TYPE: PRT
<213> ORGANISM: Artificial Sequence
<220> FEATURE:
<223> OTHER INFORMATION: YU100-G08 VH - Human IgG1 constant region
      (IGHG1; UniProt:P01857-1, v1)

<400> SEQUENCE: 220

Gln Val Gln Leu Val Gln Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Gly Ala Thr Asp Pro Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

```
Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 221
<211> LENGTH: 445
<212> TYPE: PRT
<213> ORGANISM: Artificial Sequence
<220> FEATURE:
<223> OTHER INFORMATION: YU100-G08 VH - Human IgG4 constant region
      (IGHG4; UniProt: P01861, v1)

<400> SEQUENCE: 221

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Gly Ala Thr Asp Pro Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220
```

```
Pro Ser Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
        260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 222
<211> LENGTH: 445
<212> TYPE: PRT
<213> ORGANISM: Artificial Sequence
<220> FEATURE:
<223> OTHER INFORMATION: YU100-G08 VH - Human IgG4 constant region
      (IGHG4; UniProt: P01861, v1; S241P)

<400> SEQUENCE: 222

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Ile Gly Ala Thr Asp Pro Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
```

```
                130                 135                 140
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Lys Thr Tyr Thr Cys Asn Val Asp His Lys Pro Ser
                195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
                275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly Lys
                435                 440                 445

<210> SEQ ID NO 223
<211> LENGTH: 445
<212> TYPE: PRT
<213> ORGANISM: Artificial Sequence
<220> FEATURE:
<223> OTHER INFORMATION: YU100-G08 VH - Human IgG4 constant region
      (IGHG4; UniProt: P01861, v1; S241P and L248E)

<400> SEQUENCE: 223

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
                35                  40                  45
```

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Gly Ala Thr Asp Pro Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Phe Glu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 224
<211> LENGTH: 217
<212> TYPE: PRT

<213> ORGANISM: Artificial Sequence
<220> FEATURE:
<223> OTHER INFORMATION: 02A VL-Ckappa CL (IGCK; UniProt: P01834-1, v2)

<400> SEQUENCE: 224

```
Gln Ser Ala Leu Thr Gln Pro Arg Ser Val Ser Gly Ser Pro Gly Gln
1               5                   10                  15

Ser Val Thr Leu Ser Cys Thr Gly Thr Ser Ser Asp Val Gly Gly Tyr
            20                  25                  30

Asn Tyr Val Ser Trp Tyr Gln His Tyr Pro Gly Lys Ala Pro Lys Leu
        35                  40                  45

Met Ile Phe Asp Val Asn Glu Arg Ser Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Ala Gly Arg
                85                  90                  95

Tyr Thr Trp Met Phe Gly Gly Gly Thr Lys Val Thr Val Leu Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 225
<211> LENGTH: 449
<212> TYPE: PRT
<213> ORGANISM: Artificial Sequence
<220> FEATURE:
<223> OTHER INFORMATION: 3C6 VH 2.2 - Human IgG1 constant region (IGHG1; UniProt:P01857-1, v1)

<400> SEQUENCE: 225

```
Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ala Pro Gly Gln Arg Leu Glu Trp Ile
        35                  40                  45

Gly Asp Ile Asn Pro His Asn Gly Gly Pro Ile Tyr Asn Gln Lys Phe
    50                  55                  60

Thr Gly Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Glu Leu Gly His Trp Tyr Phe Asp Val Trp Gly Gln Gly
            100                 105                 110
```

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 226
<211> LENGTH: 446
<212> TYPE: PRT
<213> ORGANISM: Artificial Sequence
<220> FEATURE:
<223> OTHER INFORMATION: 3C6 VH 2.2 - Human IgG4 constant region (IGHG4;
      UniProt: P01861, v1)

<400> SEQUENCE: 226

Glu Val Gln Leu Val Gln Ser Gly Ala Glu Val Lys Lys Pro Gly Ala
1               5                   10                  15

```
Ser Val Lys Ile Ser Cys Lys Ala Ser Gly Tyr Thr Phe Thr Asp Tyr
            20                  25                  30

Asn Met Asp Trp Val Lys Gln Ala Pro Gly Gln Arg Leu Glu Trp Ile
        35                  40                  45

Gly Asp Ile Asn Pro His Asn Gly Gly Pro Ile Tyr Asn Gln Lys Phe
    50                  55                  60

Thr Gly Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Glu Leu Gly His Trp Tyr Phe Asp Val Trp Gly Gln Gly
                100                 105                 110

Thr Thr Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
    210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430
```

Asn His Tyr Thr Gln Lys Ser Leu Ser Leu Ser Leu Gly Lys
                435                 440                 445

<210> SEQ ID NO 227
<211> LENGTH: 446
<212> TYPE: PRT
<213> ORGANISM: Artificial Sequence
<220> FEATURE:
<223> OTHER INFORMATION: 3C6 VH 2.2 - Human IgG4 constant region (IGHG4;
      UniProt: P01861, v1; S241P)

<400> SEQUENCE: 227

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ala Pro Gly Gln Arg Leu Glu Trp Ile
        35                  40                  45

Gly Asp Ile Asn Pro His Asn Gly Gly Pro Ile Tyr Asn Gln Lys Phe
    50                  55                  60

Thr Gly Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Glu Leu Gly His Trp Tyr Phe Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

```
Ser Gln Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 228
<211> LENGTH: 446
<212> TYPE: PRT
<213> ORGANISM: Artificial Sequence
<220> FEATURE:
<223> OTHER INFORMATION: 3C6 VH 2.2 - Human IgG4 constant region (IGHG4;
      UniProt: P01861, v1; S241P and L248E)

<400> SEQUENCE: 228

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ala Pro Gly Gln Arg Leu Glu Trp Ile
        35                  40                  45

Gly Asp Ile Asn Pro His Asn Gly Gly Pro Ile Tyr Asn Gln Lys Phe
    50                  55                  60

Thr Gly Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Glu Leu Gly His Trp Tyr Phe Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
```

```
                260                 265                 270
Gln Phe Asn Trp Tyr Val Asp Gly Val Glu Val His Asn Ala Lys Thr
            275                 280                 285
Lys Pro Arg Glu Glu Gln Phe Asn Ser Thr Tyr Arg Val Val Ser Val
        290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Asn His Tyr Thr Gln Lys Ser Leu Ser Leu Ser Leu Gly Lys
        435                 440                 445

<210> SEQ ID NO 229
<211> LENGTH: 218
<212> TYPE: PRT
<213> ORGANISM: Artificial Sequence
<220> FEATURE:
<223> OTHER INFORMATION: 3C6 VL 2.2 - Ckappa CL (IGCK; UniProt: P01834-
      1, v2)

<400> SEQUENCE: 229

Asp Ile Val Leu Thr Gln Ser Pro Ala Ser Leu Ala Leu Ser Pro Gly
1               5                   10                  15
Glu Arg Ala Thr Leu Ser Cys Arg Ala Ser Lys Ser Val Ser Thr Ser
            20                  25                  30
Gly Tyr Ser Tyr Ile His Trp Tyr Gln Gln Lys Pro Gly Gln Ala Pro
        35                  40                  45
Arg Leu Leu Ile Tyr Leu Ala Ser Asn Leu Asp Ser Gly Val Pro Ala
    50                  55                  60
Arg Phe Ser Gly Ser Gly Ser Gly Thr Asp Phe Thr Leu Thr Ile Ser
65                  70                  75                  80
Ser Leu Glu Glu Glu Asp Phe Ala Thr Tyr Tyr Cys Gln His Ser Arg
                85                  90                  95
Asp Leu Pro Pro Thr Phe Gly Gln Gly Thr Lys Leu Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
```

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 230
<211> LENGTH: 218
<212> TYPE: PRT
<213> ORGANISM: Artificial Sequence
<220> FEATURE:
<223> OTHER INFORMATION: 3C6 VL 2.1 - Ckappa CL (IGCK; UniProt: P01834-
      1, v2)

<400> SEQUENCE: 230

Asp Ile Val Leu Thr Gln Ser Pro Ala Ser Leu Ala Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Ile His Trp Tyr Gln Gln Lys Pro Gly Gln Pro Pro
        35                  40                  45

Arg Leu Leu Ile Tyr Leu Ala Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Leu Glu Glu Glu Asp Phe Ala Thr Tyr Tyr Cys Gln His Ser Arg
                85                  90                  95

Asp Leu Pro Pro Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 231
<211> LENGTH: 106
<212> TYPE: PRT
<213> ORGANISM: Artificial Sequence
<220> FEATURE:
<223> OTHER INFORMATION: CL CL (IGLC1; UniProt: P0CG04, v1)

<400> SEQUENCE: 231

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro

```
                35                  40                  45
Val Lys Ala Gly Val Glu Thr Thr Lys Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 232
<211> LENGTH: 106
<212> TYPE: PRT
<213> ORGANISM: Artificial Sequence
<220> FEATURE:
<223> OTHER INFORMATION: CL CL (IGLC2; UniProt: P0DOY2, v1)

<400> SEQUENCE: 232

Gly Gln Pro Lys Ala Ala Pro Ser Val Thr Leu Phe Pro Pro Ser Ser
 1                   5                  10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 233
<211> LENGTH: 106
<212> TYPE: PRT
<213> ORGANISM: Artificial Sequence
<220> FEATURE:
<223> OTHER INFORMATION: CL CL (IGLC3; UniProt: P0DOY3, v1)

<400> SEQUENCE: 233

Gly Gln Pro Lys Ala Ala Pro Ser Val Thr Leu Phe Pro Pro Ser Ser
 1                   5                  10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 234
<211> LENGTH: 106
```

```
<212> TYPE: PRT
<213> ORGANISM: Artificial Sequence
<220> FEATURE:
<223> OTHER INFORMATION: CL CL (IGLC6; UniProt: P0CF74, v1)

<400> SEQUENCE: 234

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105

<210> SEQ ID NO 235
<211> LENGTH: 106
<212> TYPE: PRT
<213> ORGANISM: Artificial Sequence
<220> FEATURE:
<223> OTHER INFORMATION: CL CL (IGLC7; UniProt: A0M8Q6, v3)

<400> SEQUENCE: 235

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Asn Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105

<210> SEQ ID NO 236
<211> LENGTH: 216
<212> TYPE: PRT
<213> ORGANISM: Artificial Sequence
<220> FEATURE:
<223> OTHER INFORMATION: 02A VL-CL CL (IGLC1; UniProt: P0CG04, v1)

<400> SEQUENCE: 236

Gln Ser Ala Leu Thr Gln Pro Arg Ser Val Ser Gly Ser Pro Gly Gln
1               5                   10                  15

Ser Val Thr Leu Ser Cys Thr Gly Thr Ser Ser Asp Val Gly Gly Tyr
            20                  25                  30

Asn Tyr Val Ser Trp Tyr Gln His Tyr Pro Gly Lys Ala Pro Lys Leu
        35                  40                  45

Met Ile Phe Asp Val Asn Glu Arg Ser Ser Gly Val Pro Asp Arg Phe
```

-continued

```
                50                  55                  60
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ala Ser Tyr Ala Gly Arg
                 85                  90                  95

Tyr Thr Trp Met Phe Gly Gly Gly Thr Lys Val Thr Val Leu Gly Gln
                100                 105                 110

Pro Lys Ala Asn Pro Thr Val Thr Leu Phe Pro Pro Ser Ser Glu Glu
                115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
                195                 200                 205

Thr Val Ala Pro Thr Glu Cys Ser
                210                 215
```

<210> SEQ ID NO 237
<211> LENGTH: 216
<212> TYPE: PRT
<213> ORGANISM: Artificial Sequence
<220> FEATURE:
<223> OTHER INFORMATION: 02A VL-CL CL (IGLC2; UniProt: P0DOY2, v1))

<400> SEQUENCE: 237

```
Gln Ser Ala Leu Thr Gln Pro Arg Ser Val Ser Gly Ser Pro Gly Gln
 1               5                  10                  15

Ser Val Thr Leu Ser Cys Thr Gly Thr Ser Ser Asp Val Gly Gly Tyr
                 20                  25                  30

Asn Tyr Val Ser Trp Tyr Gln His Tyr Pro Gly Lys Ala Pro Lys Leu
                 35                  40                  45

Met Ile Phe Asp Val Asn Glu Arg Ser Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ala Ser Tyr Ala Gly Arg
                 85                  90                  95

Tyr Thr Trp Met Phe Gly Gly Gly Thr Lys Val Thr Val Leu Gly Gln
                100                 105                 110

Pro Lys Ala Ala Pro Ser Val Thr Leu Phe Pro Pro Ser Ser Glu Glu
                115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
```

```
                195                 200                 205

Thr Val Ala Pro Thr Glu Cys Ser
    210                 215

<210> SEQ ID NO 238
<211> LENGTH: 216
<212> TYPE: PRT
<213> ORGANISM: Artificial Sequence
<220> FEATURE:
<223> OTHER INFORMATION: 02A VL-CL CL (IGLC3; UniProt: P0DOY3, v1)

<400> SEQUENCE: 238

Gln Ser Ala Leu Thr Gln Pro Arg Ser Val Ser Gly Ser Pro Gly Gln
1               5                   10                  15

Ser Val Thr Leu Ser Cys Thr Gly Thr Ser Ser Asp Val Gly Gly Tyr
            20                  25                  30

Asn Tyr Val Ser Trp Tyr Gln His Tyr Pro Gly Lys Ala Pro Lys Leu
        35                  40                  45

Met Ile Phe Asp Val Asn Glu Arg Ser Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Ala Gly Arg
                85                  90                  95

Tyr Thr Trp Met Phe Gly Gly Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 239
<211> LENGTH: 216
<212> TYPE: PRT
<213> ORGANISM: Artificial Sequence
<220> FEATURE:
<223> OTHER INFORMATION: 02A VL-CL CL (IGLC6; UniProt: P0CF74, v1)

<400> SEQUENCE: 239

Gln Ser Ala Leu Thr Gln Pro Arg Ser Val Ser Gly Ser Pro Gly Gln
1               5                   10                  15

Ser Val Thr Leu Ser Cys Thr Gly Thr Ser Ser Asp Val Gly Gly Tyr
            20                  25                  30

Asn Tyr Val Ser Trp Tyr Gln His Tyr Pro Gly Lys Ala Pro Lys Leu
        35                  40                  45

Met Ile Phe Asp Val Asn Glu Arg Ser Ser Gly Val Pro Asp Arg Phe
    50                  55                  60
```

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Ala Gly Arg
            85                  90                  95

Tyr Thr Trp Met Phe Gly Gly Gly Thr Lys Val Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
            130                 135                 140

Pro Gly Ala Val Lys Val Ala Trp Lys Ala Asp Gly Ser Pro Val Asn
145                 150                 155                 160

Thr Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Ala Glu Cys Ser
            210                 215

<210> SEQ ID NO 240
<211> LENGTH: 216
<212> TYPE: PRT
<213> ORGANISM: Artificial Sequence
<220> FEATURE:
<223> OTHER INFORMATION: 02A VL-CL CL (IGLC7; UniProt: A0M8Q6, v3)

<400> SEQUENCE: 240

Gln Ser Ala Leu Thr Gln Pro Arg Ser Val Ser Gly Ser Pro Gly Gln
1               5                   10                  15

Ser Val Thr Leu Ser Cys Thr Gly Thr Ser Ser Asp Val Gly Gly Tyr
            20                  25                  30

Asn Tyr Val Ser Trp Tyr Gln His Tyr Pro Gly Lys Ala Pro Lys Leu
            35                  40                  45

Met Ile Phe Asp Val Asn Glu Arg Ser Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Ala Gly Arg
            85                  90                  95

Tyr Thr Trp Met Phe Gly Gly Gly Thr Lys Val Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Val Ser Asp Phe Asn
            130                 135                 140

Pro Gly Ala Val Thr Val Ala Trp Lys Ala Asp Gly Ser Pro Val Lys
145                 150                 155                 160

Val Gly Val Glu Thr Thr Lys Pro Ser Lys Gln Ser Asn Asn Lys Tyr
            165                 170                 175

```
-continued

Ala Ala Ser Ser Tyr Leu Ser Leu Thr Pro Glu Gln Trp Lys Ser His
            180                 185                 190

Arg Ser Tyr Ser Cys Arg Val Thr His Glu Gly Ser Thr Val Glu Lys
        195             200                 205

Thr Val Ala Pro Ala Glu Cys Ser
    210             215
```